(12) United States Patent
Sinclair et al.

(10) Patent No.: US 12,274,733 B2
(45) Date of Patent: Apr. 15, 2025

(54) CELLULAR REPROGRAMMING TO REVERSE AGING AND PROMOTE ORGAN AND TISSUE REGENERATION

(71) Applicant: President and Fellows of Harvard College, Cambridge, MA (US)

(72) Inventors: David A. Sinclair, Cambridge, MA (US); Yuancheng Lu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 801 days.

(21) Appl. No.: 17/280,384

(22) PCT Filed: Sep. 27, 2019

(86) PCT No.: PCT/US2019/053545
§ 371 (c)(1),
(2) Date: Mar. 26, 2021

(87) PCT Pub. No.: WO2020/069373
PCT Pub. Date: Apr. 2, 2020

(65) Prior Publication Data
US 2023/0048010 A1 Feb. 16, 2023

Related U.S. Application Data

(60) Provisional application No. 62/880,448, filed on Jul. 30, 2019, provisional application No. 62/865,877, filed on Jun. 24, 2019, provisional application No. 62/792,283, filed on Jan. 14, 2019, provisional application No. 62/738,922, filed on Sep. 28, 2018.

(51) Int. Cl.
*A61K 48/00* (2006.01)
*A61K 31/65* (2006.01)
*A61K 38/17* (2006.01)
*C12N 15/86* (2006.01)

(52) U.S. Cl.
CPC .......... *A61K 38/1709* (2013.01); *A61K 31/65* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,399,363 A | 3/1995 | Liversidge et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,589,362 A | 12/1996 | Bujard et al. |
| 5,641,515 A | 6/1997 | Ramtoola |
| 5,650,298 A | 7/1997 | Bujard et al. |
| 5,738,868 A | 4/1998 | Shinkarenko |
| 5,741,516 A | 4/1998 | Webb et al. |
| 5,795,587 A | 8/1998 | Gao et al. |
| 5,928,941 A | 7/1999 | Lee et al. |
| 6,750,015 B2 | 6/2004 | Horwitz et al. |
| 7,541,446 B2 | 6/2009 | Hillen et al. |
| 8,080,647 B2 | 12/2011 | Gordon-Kamm et al. |
| 8,158,415 B2 | 4/2012 | Jo et al. |

(Continued)

FOREIGN PATENT DOCUMENTS

| | | |
|---|---|---|
| AU | 746850 B2 | 5/2002 |
| CN | 103562376 A | 2/2014 |

(Continued)

OTHER PUBLICATIONS

Chen, et al. (2018) "Targeting oncogenic Myc as a strategy for cancer treatment", Nature: Signal Transduction and Targeted Therapy, 3:5, 7 pages as printed. (Year: 2018).*
Lu, et al. (2020) "Reprogramming to recover youthful epigenetic information and restore vision", Nature, 588: 124-129, and supplementary information, 35 pages long. (Year: 2020).*
Paska, et al. (2015) "Aberrant methylation patterns in cancer: a clinical review", Biochemica Medica, 25(2): 161-76. (Year: 2015).*
Lawther, et al. (2011) "Blood-brain barrier", Continuing Education in Anaesthesia, Critical Care & Pain, 11(4): 128-32. (Year: 2011).*
Crudele, et al. (2018) "Cas9 immunity creates challenges for CRISPR gene editing therapies", Nature Communications, 9: 3497, 3 pages. (Year: 2018).*

(Continued)

*Primary Examiner* — Robert M Kelly
(74) *Attorney, Agent, or Firm* — Wolf, Greenfield & Sacks, P.C.

(57) ABSTRACT

Provided herein are engineered nucleic acids (e.g., expression vectors, including viral vectors, such as lentiviral vectors, adenoviral vectors, AAV vectors, herpes viral vectors, and retroviral vectors) that encode OCT4; KLF4; SOX2; or any combination thereof that are useful, for example, in inducing cellular reprogramming, tissue repair, tissue regeneration, organ regeneration, reversing aging, or any combination thereof. Also provided herein are recombinant viruses (e.g., lentiviruses, alphaviruses, vaccinia viruses, adenoviruses, herpes viruses, retroviruses, or AAVs) comprising the engineered nucleic acids (e.g., engineered nucleic acids), engineered cells, compositions comprising the engineered nucleic acids, the recombinant viruses, engineered cells, engineered proteins, chemical agents that are capable of activating expression of OCT4; KLF4; SOX2; or any combination thereof, an engineered protein selected from the group consisting of OCT4; KLF4; SOX2; or any combination thereof, an antibody capable of activating expression of OCT4; KLF4; SOX2; or any combination thereof, and methods of treating a (e.g., ocular disease), preventing a disease (e.g., ocular disease), regulating (e.g., inducing or inducing and then stopping) cellular reprogramming, regulating tissue repair, regulating tissue regeneration, or any combination thereof).

66 Claims, 154 Drawing Sheets
Specification includes a Sequence Listing.

(56) References Cited

U.S. PATENT DOCUMENTS

| | | | |
|---|---|---|---|
| 8,278,104 B2 | 10/2012 | Yamanaka et al. |
| 8,326,547 B2 | 12/2012 | Liu et al. |
| 8,383,364 B2 | 2/2013 | Berkhout et al. |
| 8,609,373 B2 | 12/2013 | Liu et al. |
| 8,716,465 B2 | 5/2014 | Rossi et al. |
| 8,883,506 B2 | 11/2014 | Rossi et al. |
| 8,957,037 B2 | 2/2015 | Collard et al. |
| 9,127,283 B2 | 9/2015 | Bisgrove et al. |
| 9,175,311 B2 | 11/2015 | Townes et al. |
| 9,228,204 B2 | 1/2016 | Pulst et al. |
| 9,580,689 B2 | 2/2017 | Kikyo et al. |
| 9,862,926 B2 | 1/2018 | Chin et al. |
| 9,862,930 B2 | 1/2018 | Dowdy et al. |
| 9,920,333 B2 | 3/2018 | Pulst et al. |
| 11,058,729 B2* | 7/2021 | Tomarev | A61K 31/5575 |
| 11,525,119 B2* | 12/2022 | Vo | C12N 5/0636 |
| RE49,583 E | 7/2023 | Berkhout et al. |
| 11,692,029 B2* | 7/2023 | Min | A61P 27/06 |
| | | | 424/158.1 |
| 2002/0165180 A1 | 11/2002 | Weaver |
| 2003/0065157 A1 | 4/2003 | Lasek |
| 2003/0138772 A1 | 7/2003 | Gao et al. |
| 2003/0138799 A1 | 7/2003 | Ruppert et al. |
| 2003/0165921 A1 | 9/2003 | Tang et al. |
| 2003/0186281 A1 | 10/2003 | Hillen |
| 2004/0038249 A1 | 2/2004 | Darteil et al. |
| 2004/0219579 A1 | 11/2004 | Aziz et al. |
| 2004/0235073 A1 | 11/2004 | Ruppert et al. |
| 2005/0064454 A1 | 3/2005 | Young et al. |
| 2005/0208496 A1 | 9/2005 | Ohtani et al. |
| 2006/0263774 A1 | 11/2006 | Clark et al. |
| 2007/0042392 A1 | 2/2007 | Tang et al. |
| 2007/0048301 A1 | 3/2007 | Bodary-Winter et al. |
| 2007/0060743 A1 | 3/2007 | Tang et al. |
| 2007/0072175 A1 | 3/2007 | Cooper et al. |
| 2007/0161031 A1 | 7/2007 | Trinklein et al. |
| 2008/0050379 A1 | 2/2008 | Young et al. |
| 2008/0050393 A1 | 2/2008 | Tang et al. |
| 2008/0233648 A1 | 9/2008 | Sugaya et al. |
| 2009/0047263 A1 | 2/2009 | Yamanaka et al. |
| 2010/0040649 A1 | 2/2010 | Berkhout et al. |
| 2010/0048678 A1 | 2/2010 | Smit et al. |
| 2010/0074864 A1 | 3/2010 | Achiron et al. |
| 2010/0099144 A1 | 4/2010 | Jo et al. |
| 2010/0150889 A1 | 6/2010 | Townes et al. |
| 2010/0190250 A1 | 7/2010 | Hu et al. |
| 2010/0273220 A1 | 10/2010 | Yanik et al. |
| 2010/0285589 A1 | 11/2010 | Lowry et al. |
| 2011/0002940 A1 | 1/2011 | Piek et al. |
| 2011/0081708 A1 | 4/2011 | Liu et al. |
| 2012/0064048 A1 | 3/2012 | Collard et al. |
| 2012/0095188 A1 | 4/2012 | Jo et al. |
| 2012/0129254 A1 | 5/2012 | Bisgrove et al. |
| 2012/0196328 A1 | 8/2012 | Liu et al. |
| 2012/0208278 A1 | 8/2012 | Yanik et al. |
| 2012/0225076 A1 | 9/2012 | Peeper et al. |
| 2012/0322864 A1 | 12/2012 | Rossi et al. |
| 2012/0322865 A1 | 12/2012 | Rossi et al. |
| 2013/0017596 A1 | 1/2013 | Townes et al. |
| 2013/0059752 A1 | 3/2013 | Bodary-Winter et al. |
| 2013/0065791 A1 | 3/2013 | Rosenthal et al. |
| 2013/0130387 A1 | 5/2013 | Itskovitz-Eldor et al. |
| 2014/0093486 A1 | 4/2014 | Chiou et al. |
| 2014/0107190 A1 | 4/2014 | Molina et al. |
| 2014/0128277 A1 | 5/2014 | Moller et al. |
| 2014/0170752 A1 | 6/2014 | Pulst et al. |
| 2015/0159143 A1 | 6/2015 | Dowdy et al. |
| 2015/0299701 A1 | 10/2015 | Collard et al. |
| 2016/0032393 A1 | 2/2016 | Achiron et al. |
| 2016/0076000 A1 | 3/2016 | Townes et al. |
| 2016/0102127 A1 | 4/2016 | Thepen et al. |
| 2016/0143951 A1 | 5/2016 | Lawrence et al. |
| 2017/0073639 A1* | 3/2017 | Eilertsen | C12N 5/0619 |
| 2018/0155789 A1 | 6/2018 | Maeder et al. |
| 2018/0161358 A1 | 6/2018 | Arber et al. |
| 2018/0195047 A1 | 7/2018 | Jo |
| 2018/0216079 A1 | 8/2018 | Dowdy et al. |
| 2018/0299430 A1 | 10/2018 | Kuo et al. |
| 2018/0305689 A1 | 10/2018 | Sætrom et al. |
| 2019/0055518 A1 | 2/2019 | Young-Ae |
| 2019/0292250 A1 | 9/2019 | Hinderer et al. |
| 2021/0324414 A1 | 10/2021 | Weiss et al. |
| 2021/0403923 A1 | 12/2021 | Sinclair et al. |
| 2023/0338468 A1 | 10/2023 | Sinclair et al. |
| 2024/0261370 A1 | 8/2024 | Sinclair et al. |
| 2024/0316148 A1 | 9/2024 | Sinclair et al. |

FOREIGN PATENT DOCUMENTS

| | | |
|---|---|---|
| CN | 104837862 A | 8/2015 |
| CN | 104919048 A | 9/2015 |
| DE | 19851415 A1 | 5/2000 |
| EP | 1071776 A2 | 1/2001 |
| EP | 1358349 A2 | 11/2003 |
| EP | 1394274 A2 | 3/2004 |
| EP | 1572987 A2 | 9/2005 |
| EP | 1578367 A2 | 9/2005 |
| EP | 1578996 A2 | 9/2005 |
| EP | 1888627 A2 | 2/2008 |
| EP | 2021499 A2 | 2/2009 |
| EP | 2126135 A2 | 12/2009 |
| EP | 2132225 A1 | 12/2009 |
| EP | 2191018 A2 | 6/2010 |
| EP | 2191840 A1 | 6/2010 |
| EP | 2388336 A1 | 11/2011 |
| EP | 2407488 A2 | 1/2012 |
| EP | 2421563 A1 | 2/2012 |
| EP | 2432881 A2 | 3/2012 |
| EP | 2478101 A1 | 7/2012 |
| EP | 2572000 A2 | 3/2013 |
| EP | 2638163 A1 | 9/2013 |
| EP | 2655621 A1 | 10/2013 |
| EP | 2675903 A1 | 12/2013 |
| EP | 2852671 A2 | 4/2015 |
| EP | 2931914 A1 | 10/2015 |
| EP | 3060237 A1 | 8/2016 |
| EP | 3194623 A1 | 7/2017 |
| EP | 2643459 B1 | 9/2017 |
| EP | 3334755 A1 | 6/2018 |
| EP | 3385373 A1 | 10/2018 |
| JP | 2014-500022 A | 1/2014 |
| WO | WO 9954460 A2 | 10/1999 |
| WO | WO 2000/069450 A1 | 11/2000 |
| WO | WO 2001/094629 A2 | 12/2001 |
| WO | WO 2004/073657 A2 | 9/2004 |
| WO | WO 2005/052164 A1 | 6/2005 |
| WO | WO 2006/123930 A2 | 11/2006 |
| WO | WO 2007/058527 A2 | 5/2007 |
| WO | WO 2007/078599 A2 | 7/2007 |
| WO | WO 2008/051854 A2 | 5/2008 |
| WO | WO 2008/081435 A2 | 7/2008 |
| WO | WO 2009/028945 A2 | 3/2009 |
| WO | WO 2009/061442 A1 | 5/2009 |
| WO | WO 2010/104357 A2 | 9/2010 |
| WO | WO 2010/123501 A1 | 10/2010 |
| WO | WO 2010/135329 A2 | 11/2010 |
| WO | WO 2010/138263 A2 | 12/2010 |
| WO | WO 2011/017910 A1 | 2/2011 |
| WO | WO 2011/034421 A1 | 3/2011 |
| WO | WO 2011/144718 A2 | 11/2011 |
| WO | WO 2012/014207 A2 | 2/2012 |
| WO | WO 2012/065143 A1 | 5/2012 |
| WO | WO 2012/071549 A2 | 5/2012 |
| WO | WO 2012/087983 A2 | 6/2012 |
| WO | WO 2012/120026 A1 | 9/2012 |
| WO | WO 2012/136841 A1 | 10/2012 |
| WO | WO 2013/177133 A2 | 11/2013 |
| WO | WO 2014/053082 A1 | 4/2014 |
| WO | WO 2014/152607 A2 | 9/2014 |
| WO | WO 2014/191391 A1 | 12/2014 |
| WO | WO 2016/170348 A2 | 10/2016 |
| WO | WO 2017/026776 A1 | 2/2017 |
| WO | WO 2017/173354 A2 | 10/2017 |
| WO | WO 2017/180587 A2 | 10/2017 |

(56) References Cited

FOREIGN PATENT DOCUMENTS

| WO | WO 2018/041959 A1 | 3/2018 |
|----|-------------------|--------|
| WO | WO 2018/204764 A1 | 11/2018 |
| WO | WO 2019/023680 A1 | 1/2019 |
| WO | WO 2019/094778 A1 | 5/2019 |
| WO | WO 2019/099552 A2 | 5/2019 |
| WO | WO 2020/012164 A1 | 1/2020 |
| WO | WO 2020/069339 A1 | 4/2020 |
| WO | WO 2020/069373 A1 | 4/2020 |
| WO | WO 2021/183825 A1 | 9/2021 |
| WO | WO 2021/183946 A2 | 9/2021 |
| WO | WO 2022/232327 A2 | 11/2022 |
| WO | WO 2023/004367 A2 | 1/2023 |

OTHER PUBLICATIONS

Yuan, et al. (2011) "Brief Report: Combined Chemical Treatment Enables Oct4-Induced Reprogramming from Mouse Embryonic Fibroblasts", Stem Cells, 29: 549-53. (Year: 2011).*
Lambert, et al. (2019) "Towards A Microbead Occlusion Model of Glaucoma for a Non-Human Primate", Nature: Scientific Reports, 9: article 11572, 15 pages. (Year: 2019).*
Li, et al. (2016) "Epigenectics and Common Opthalmic Diseases", Yale Journal of Biology and Medicine, 89: 597-600. (Year: 2016).*
Khalilpour, et al. (2017) "Ischmeic optic neuropathy as a model of neurodegenerative disorder: A review mechanism of axonal degeneration and the role neuroprotection", Journal of Neurological Sciences, 375: 430-41. (Year 2017).*
International Search Report and Written Opinion for Application No. PCT/US2019/053545, mailed Dec. 19, 2019.
International Preliminary Report on Patentability for Application No. PCT/US2019/053545, mailed Apr. 8, 2021.
International Search Report and Written Opinion for Application No. PCT/US2019/053492, mailed Feb. 2, 2020.
International Preliminary Report on Patentability for Application No. PCT/US2019/053492, mailed Apr. 8, 2021.
Abad et al., Reprogramming in vivo produces teratomas and iPS cells with totipotency features. Nature. Oct. 17, 2013;502(7471):340-5. doi: 10.1038/nature12586. Epub Sep. 11, 2013.
Anokye-Danso et al., Highly efficient miRNA-mediated reprogramming of mouse and human somatic cells to pluripotency. Cell Stem Cell. Apr. 8, 2011;8(4):376-88. doi: 10.1016/j.stem.2011.03.001.
Azte et al., Selecting the optimal Tet-On system for doxycycline-inducible gene expression in transiently transfected and stably transduced mammalian cells. Biotechnol J. Jan. 2016;11(1):71-9. doi: 10.1002/biot.201500236. Epub Sep. 24, 2015.
Bar-Nur et al., Small molecules facilitate rapid and synchronous iPSC generation. Nat Methods. Nov. 2014;11(11):1170-6. doi: 10.1038/nmeth.3142. Epub Sep. 24, 2014.
Behr et al., Gene transfer with synthetic cationic amphiphiles: prospects for gene therapy. Bioconjugate Chem. Sep.-Oct. 1994;5(5):382-9. doi: 10.1021/bc00029a002.
Belin et al., Injury-induced decline of intrinsic regenerative ability revealed by quantitative proteomics. Neuron. May 20, 2015;86(4):1000-1014. doi: 10.1016/j.neuron.2015.03.060. Epub Apr. 30, 2015.
Blackmore et al., Krüppel-like Factor 7 engineered for transcriptional activation promotes axon regeneration in the adult corticospinal tract. Proc Natl Acad Sci USA. May 8, 2012;109(19):7517-22. doi: 10.1073/pnas.1120684109. Epub Apr. 23, 2012.
Blanchard et al., Replacing reprogramming factors with antibodies selected from combinatorial antibody libraries. Nat Biotechnol. Oct. 2017;35(10):960-968. doi: 10.1038/nbt.3963. Epub Sep. 11, 2017.
Borkent et al., A Serial shRNA Screen for Roadblocks to Reprogramming Identifies the Protein Modifier SUMO2. Stem Cell Reports. May 10, 2016;6(5):704-716. doi: 10.1016/j.stemcr.2016.02.004. Epub Mar. 3, 2016.
Brumbaugh et al., Nudt21 Controls Cell Fate by Connecting Alternative Polyadenylation to Chromatin Signaling. Cell. Jan. 11, 2018;172(1-2):106-120.e21. doi: 10.1016/j.cell.2017.11.023. Epub Dec. 14, 2017.
Bussian et al., Clearance of senescent glial cells prevents tau-dependent pathology and cognitive decline. Nature. Oct. 2018;562(7728):578-582. doi: 10.1038/s41586-018-0543-y. Epub Sep. 19, 2018.
Carey et al., Reprogramming of murine and human somatic cells using a single polycistronic vector. Proc Natl Acad Sci U S A. Jan. 6, 2009;106(1):157-62. doi: 10.1073/pnas.0811426106. Epub Dec. 24, 2008.
Cheloufi et al., The histone chaperone CAF-1 safeguards somatic cell identity. Nature. Dec. 10, 2015;528(7581):218-24. doi: 10.1038/nature15749.
Cieślar-Pobuda et al., Transdifferentiation and reprogramming: Overview of the processes, their similarities and differences. Biochim Biophys Acta Mol Cell Res. Jul. 2017;1864(7):1359-1369. doi: 10.1016/j.bbamcr.2017.04.017. Epub Apr. 28, 2017.
Cyranoski, 'Reprogrammed' stem cells approved to mend human hearts for the first time. Nature. May 2018;557(7707):619-620. doi: 10.1038/d41586-018-05278-8.
Das et al., Tet-On Systems For Doxycycline-inducible Gene Expression. Curr Gene Ther. 2016;16(3):156-67. doi: 10.2174/1566523216666160524144041.
Eguchi et al., Reprogramming cell fate with a genome-scale library of artificial transcription factors. Proc Natl Acad Sci USA. Dec. 20, 2016;113(51):E8257-E8266. doi: 10.1073/pnas.1611142114. Epub Dec. 5, 2016.
Encinas et al., Sequential treatment of SH-SY5Y cells with retinoic acid and brain-derived neurotrophic factor gives rise to fully differentiated, neurotrophic factor-dependent, human neuron-like cells. J Neurochem. Sep. 2000;75(3):991-1003. doi: 10.1046/j.1471-4159.2000.0750991.x.
Erahimi, Reprogramming barriers and enhancers: strategies to enhance the efficiency and kinetics of induced pluripotency. Cell Regen. Nov. 11, 2015;4:10. doi: 10.1186/s13619-015-0024-9. eCollection 2015.
Gao et al., Replacement of Oct4 by Tet1 during iPSC induction reveals an important role of DNA methylation and hydroxymethylation in reprogramming. Cell Stem Cell. Apr. 4, 2013;12(4):453-69. doi: 10.1016/j.stem.2013.02.005. Epub Mar. 14, 2013.
Genbank Submission; NCBI, Accession No. NM_001040400.2; *Mus musculus* tet methylcytosine dioxygenase 2 (Tet2), transcript variant 1, mRNA. Yang et al.; Sep. 23, 2018.
Genbank Submission; NCBI, Accession No. NM_001127208.2; *Homo sapiens* Kruppel like factor 4 (KLF4), transcript variant 2, mRNA. Yang et al.; Sep. 23, 2018.
Genbank Submission; NCBI, Accession No. NM_001130823.2; *Homo sapiens* Kruppel like factor 4 (KLF4), transcript variant 2, mRNA. Yang et al.; Sep. 24, 2018.
Genbank Submission; NCBI, Accession No. NM_001173531.2; *Homo sapiens* POU class 5 homeobox 1 (POU5F1), transcript variant 3, mRNA. Miyoshi et al.; Sep. 23, 2018.
Genbank Submission; NCBI, Accession No. NM_001207055.1; *Homo sapiens* DNA methyltransferase 3 beta (DNMT3B), transcript variant 7, mRNA. Nunes et al.; Sep. 23, 2018.
Genbank Submission; NCBI, Accession No. NM_001207056.1; *Homo sapiens* DNA methyltransferase 3 beta (DNMT3B), transcript variant 8, mRNA. Nunes et al.; Sep. 23, 2018.
Genbank Submission; NCBI, Accession No. NM_001253857.2; *Mus musculus* tet methylcytosine dioxygenase 1 (Tet1), transcript variant 1, mRNA. SanMiguel et al.; Jul. 15, 2018.
Genbank Submission; NCBI, Accession No. NM_001285986.1; *Homo sapiens* POU class 5 homeobox 1 (POU5F1), transcript variant 4, mRNA. Miyoshi et al.; Sep. 23, 2018.
Genbank Submission; NCBI, Accession No. NM_001285987.1; *Homo sapiens* POU class 5 homeobox 1 (POU5F1), transcript variant 5, mRNA. Miyoshi et al.; Sep. 23, 2018.
Genbank Submission; NCBI, Accession No. NM_001314052.1; *Homo sapiens* Kruppel like factor 4 (KLF4), transcript variant 1, mRNA. Feng et al.; Sep. 24, 2018.
Genbank Submission; NCBI, Accession No. NM_001318730.1; *Homo sapiens* DNA methyltransferase 1 (DNMT1), transcript variant 3, mRNA. Yang et al.; Sep. 24, 2018.

(56) References Cited

OTHER PUBLICATIONS

Genbank Submission; NCBI, Accession No. NM_001318731.1; *Homo sapiens* DNA methyltransferase 1 (DNMT1), transcript variant 4, mRNA. Yang et al.; Sep. 24, 2018.
Genbank Submission; NCBI, Accession No. NM_001320892.1; *Homo sapiens* DNA methyltransferase 3 alpha (DNMT3A), transcript variant 5, mRNA. Liang et al.; Sep. 2, 2018.
Genbank Submission; NCBI, Accession No. NM_001320893.1; *Homo sapiens* DNA methyltransferase 3 alpha (DNMT3A), transcript variant 6, mRNA. Wozniak et al.; Jun. 13, 2021.
Genbank Submission; NCBI, Accession No. NM_001346736.1; *Mus musculus* tet methylcytosine dioxygenase 2 (Tet2), transcript variant 2, mRNA. Li et al.; May 16, 2021.
Genbank Submission; NCBI, Accession No. NM_002467.5; *Homo sapiens* MYC proto-oncogene, bHLH transcription factor (MYC), transcript variant 1, mRNA. Gong et al.; Sep. 2, 2018.
Genbank Submission; NCBI, Accession No. NM_001354870.1; *Homo sapiens* MYC proto-oncogene, bHLH transcription factor (MYC), transcript variant 2, mRNA. Gong et al.; Sep. 2, 2018.
Genbank Submission; NCBI, Accession No. NM_001379.3; *Homo sapiens* DNA methyltransferase 1 (DNMT1), transcript variant 2, mRNA. Yang et al.; Sep. 24, 2018.
Genbank Submission; NCBI, Accession No. NM_002701.5; *Homo sapiens* POU class 5 homeobox 1 (POU5F1), transcript variant 1, mRNA. Miyoshi et al.; Sep. 23, 2018.
Genbank Submission; NCBI, Accession No. NM_003106.3; *Homo sapiens* SRY-box transcription factor 2 (SOX2), mRNA. Chen et al.; Sep. 22, 2018.
Genbank Submission; NCBI, Accession No. NM_004235.5; *Homo sapiens* Kruppel like factor 4 (KLF4), transcript variant 2, mRNA. Feng et al.; Sep. 24, 2018.
Genbank Submission; NCBI, Accession No. NM_006892.3; *Homo sapiens* DNA methyltransferase 3 beta (DNMT3B), transcript variant 1, mRNA. Nunes et al.; Sep. 23, 2018.
Genbank Submission; NCBI, Accession No. NM_011443.4; *Mus musculus* SRY (sex determining region Y)—box 2 (Sox2), mRNA. Bernardo et al.; Sep. 24, 2018.
Genbank Submission; NCBI, Accession No. NM_013369.3; *Homo sapiens* DNA methyltransferase 3 like (DNMT3L), transcript variant 1, mRNA. Lu et al.; Sep. 22, 2018.
Genbank Submission; NCBI, Accession No. NM_017628.4; *Homo sapiens* tet methylcytosine dioxygenase 2 (TET2), transcript variant 2, mRNA. Yang et al.; Sep. 23, 2018.
Genbank Submission; NCBI, Accession No. NM_022552.4; *Homo sapiens* DNA methyltransferase 3 alpha (DNMT3A), transcript variant 3, mRNA. Zhang et al.; Sep. 23, 2018.
Genbank Submission; NCBI, Accession No. NM_030625.3; *Homo sapiens* tet methylcytosine dioxygenase 1 (TET1), mRNA. Li et al.; Sep. 16, 2018.
Genbank Submission; NCBI, Accession No. NM_153759.3; *Homo sapiens* DNA methyltransferase 3 alpha (DNMT3A), transcript variant 2, mRNA. Zhang et al.; Sep. 23, 2018.
Genbank Submission; NCBI, Accession No. NM_175629.2; *Homo sapiens* DNA methyltransferase 3 alpha (DNMT3A), transcript variant 1, mRNA. Zhang et al.; Sep. 23, 2018.
Genbank Submission; NCBI, Accession No. NM_175630.1; *Homo sapiens* DNA methyltransferase 3 alpha (DNMT3A), transcript variant 4, mRNA. Zhang et al.; Sep. 23, 2018.
Genbank Submission; NCBI, Accession No. NM_175848.1; *Homo sapiens* DNA methyltransferase 3 beta (DNMT3B), transcript variant 2, mRNA. Nunes et al.; Sep. 23, 2018.
Genbank Submission; NCBI, Accession No. NM_175849.1; *Homo sapiens* DNA methyltransferase 3 beta (DNMT3B), transcript variant 3, mRNA. Nunes et al.; Sep. 23, 2018.
Genbank Submission; NCBI, Accession No. NM_175850.2; *Homo sapiens* DNA methyltransferase 3 beta (DNMT3B), transcript variant 6, mRNA. Nunes et al.; Sep. 23, 2018.
Genbank Submission; NCBI, Accession No. NM_175867.2; *Homo sapiens* DNA methyltransferase 3 like (DNMT3L), transcript variant 2, mRNA. Lu et al.; Sep. 23, 2018.
Genbank Submission; NCBI, Accession No. NM_203289.5; *Homo sapiens* POU class 5 homeobox 1 (POU5F1), transcript variant 2, mRNA. Miyoshi et al.; Sep. 23, 2018.
Genbank Submission; NCBI, Accession No. NP_001035490.2; methylcytosine dioxygenase TET2 isoform 1 [*Mus musculus*]. Yang et al.; Sep. 23, 2018.
Genbank Submission; NCBI, Accession No. NP_001120680.1; methylcytosine dioxygenase TET2 isoform a [*Homo sapiens*]. Yang et al.; Sep. 23, 2018.
Genbank Submission; NCBI, Accession No. NP_001124295.1; DNA (cytosine-5)-methyltransferase 1 isoform a [*Homo sapiens*]. Yang et al.; Sep. 24, 2018.
Genbank Submission; NCBI, Accession No. NP_001193984.1; DNA (cytosine-5)-methyltransferase 3B isoform 7 [*Homo sapiens*]. Nunes et al.; Sep. 23, 2018.
Genbank Submission; NCBI, Accession No. NP_001193985.1; DNA (cytosine-5)-methyltransferase 3B isoform 8 [*Homo sapiens*]. Nunes et al.; Sep. 23, 2018.
Genbank Submission; NCBI, Accession No. NP_001240786.1; methylcytosine dioxygenase TET1 isoform 1 [*Mus musculus*]. SanMiguel et al.; Jul. 15, 2018.
Genbank Submission; NCBI, Accession No. NP_001274420.1; methylcytosine dioxygenase TET3 isoform 1 [*Homo sapiens*]. Lasho et al.; Sep. 20, 2018.
Genbank Submission; NCBI, Accession No. NP_001300981.1; Krueppel-like factor 4 isoform 1 [*Homo sapiens*]. Feng et al.; Sep. 24, 2018.
Genbank Submission; NCBI, Accession No. NP_001305659.1; DNA (cytosine-5)-methyltransferase 1 isoform c [*Homo sapiens*]. Yang et al.; Sep. 24, 2018.
Genbank Submission; NCBI, Accession No. NP_001305660.1; DNA (cytosine-5)-methyltransferase 1 isoform d [*Homo sapiens*]. Yang et al.; Sep. 24, 2018.
Genbank Submission; NCBI, Accession No. NP_001307821.1; DNA (cytosine-5)-methyltransferase 3A isoform c [*Homo sapiens*]. Liang et al.; Sep. 2, 2018.
Genbank Submission; NCBI, Accession No. NP_001307822.1; DNA (cytosine-5)-methyltransferase 3A isoform d [*Homo sapiens*]. Liang et al.; Sep. 2, 2018.
Genbank Submission; NCBI, Accession No. NP_001333665.1; methylcytosine dioxygenase TET2 isoform 2 [*Mus musculus*]. Reizel et al.; Jul. 29, 2018.
Genbank Submission; NCBI, Accession No. NP_001334242.1; methylcytosine dioxygenase TET3 isoform 1 [*Mus musculus*]. Reizel et al.; Jul. 28, 2018.
Genbank Submission; NCBI, Accession No. NP_001341799.1; myc proto-oncogene protein isoform 2 [*Homo sapiens*]. Gong et al.; Sep. 2, 2018.
Genbank Submission; NCBI, Accession No. NP_001352951.1; methylcytosine dioxygenase TET3 isoform 2 [*Homo sapiens*]. Lasho et al.; Sep. 20, 2018.
Genbank Submission; NCBI, Accession No. NP_001370.1; DNA (cytosine-5)-methyltransferase 1 isoform b [*Homo sapiens*]. Yang et al.; Sep. 24, 2018.
Genbank Submission; NCBI, Accession No. NP_002458.2; myc proto-oncogene protein isoform 1 [*Homo sapiens*]. Gong et al.; Sep. 2, 2018.
Genbank Submission; NCBI, Accession No. NP_003097.1; transcription factor SOX-2 [*Homo sapiens*]. Wu et al.; Sep. 22, 2018.
Genbank Submission; NCBI, Accession No. NP_004226.3; Krueppel-like factor 4 isoform 2 [*Homo sapiens*]. Feng et al.; Sep. 24, 2018.
Genbank Submission; NCBI, Accession No. NP_008823.1; DNA (cytosine-5)-methyltransferase 3B isoform 1 [*Homo sapiens*]. Nunes et al.; Sep. 23, 2018.
Genbank Submission; NCBI, Accession No. NP_037501.2; DNA (cytosine-5)-methyltransferase 3-like isoform 1 [*Homo sapiens*]. Lu et al.; Sep. 22, 2018.
Genbank Submission; NCBI, Accession No. NP_060098.3; methylcytosine dioxygenase TET2 isoform b [*Homo sapiens*]. Yang et al.; Sep. 23, 2018.
Genbank Submission; NCBI, Accession No. NP_072046.2; DNA (cytosine-5)-methyltransferase 3A isoform a [*Homo sapiens*]. Zhang et al.; Sep. 23, 2018.

(56) References Cited

OTHER PUBLICATIONS

Genbank Submission; NCBI, Accession No. NP_085128.2; methylcytosine dioxygenase TET1 [*Homo sapiens*]. Li et al.; Sep. 16, 2018.
Genbank Submission; NCBI, Accession No. NP_715640.2; DNA (cytosine-5)-methyltransferase 3A isoform b [*Homo sapiens*]. Zhang et al.; Sep. 23, 2018.
Genbank Submission; NCBI, Accession No. NP_783328.1; DNA (cytosine-5)-methyltransferase 3A isoform a [*Homo sapiens*]. Zhang et al.; Sep. 23, 2018.
Genbank Submission; NCBI, Accession No. NP_783329.1; DNA (cytosine-5)-methyltransferase 3A isoform c [*Homo sapiens*]. Zhang et al.; Sep. 23, 2018.
Genbank Submission; NCBI, Accession No. NP_787044.1; DNA (cytosine-5)-methyltransferase 3B isoform 2 [*Homo sapiens*]. Nunes et al.; Sep. 23, 2018.
Genbank Submission; NCBI, Accession No. NP_787045.1; DNA (cytosine-5)-methyltransferase 3B isoform 3 [*Homo sapiens*]. Nunes et al.; Sep. 23, 2018.
Genbank Submission; NCBI, Accession No. NP_787046.1; DNA (cytosine-5)-methyltransferase 3B isoform 6 [*Homo sapiens*]. Nunes et al.; Sep. 23, 2018.
Genbank Submission; NCBI, Accession No. NP_787063.1; DNA (cytosine-5)-methyltransferase 3-like isoform 2 [*Homo sapiens*]. Lu et al.; Sep. 23, 2018.
Genbank Submission; NCBI, Accession No. NP_898961.2; methylcytosine dioxygenase TET3 isoform 2 [*Mus musculus*]. Reizel et al.; Jul. 28, 2018.
Geoffroy et al., Evidence for an Age-Dependent Decline in Axon Regeneration in the Adult Mammalian Central Nervous System. Cell Rep. Apr. 12, 2016;15(2):238-46. doi: 10.1016/j.celrep.2016.03.028. Epub Mar. 31, 2016.
Goldberg et al., Amacrine-signaled loss of intrinsic axon growth ability by retinal ganglion cells. Science. Jun. 7, 2002;296(5574):1860-4. doi: 10.1126/science.1068428.
Gossen et al., Transcriptional activation by tetracyclines in mammalian cells. Science. Jun. 23, 1995;268(5218):1766-9. doi: 10.1126/science.7792603.
Guo et al., Hydroxylation of 5-methylcytosine by TET1 promotes active DNA demethylation in the adult brain. Cell. Apr. 29, 2011;145(3):423-34. doi: 10.1016/j.cell.2011.03.022. Epub Apr. 14, 2011.
Heng et al., The nuclear receptor Nr5a2 can replace Oct4 in the reprogramming of murine somatic cells to pluripotent cells. Cell Stem Cell. Feb. 5, 2010;6(2):167-74. doi: 10.1016/j.stem.2009.12.009. Epub Jan. 21, 2010.
Horvath et al., DNA methylation-based biomarkers and the epigenetic clock theory of ageing. Nat Rev Genet. Jun. 2018;19(6):371-384. doi: 10.1038/s41576-018-0004-3.
Horvath, DNA methylation age of human tissues and cell types. Genome Biol. 2013;14(10):R115. doi: 10.1186/gb-2013-14-10-r115.
Hou et al., Pluripotent Stem Cells Induced from Mouse Somatic Cells by Small-Molecule Compounds. Science. Aug. 9, 2013;341(6146):651-4. doi: 10.1126/science.1239278. Epub Jul. 18, 2013.
Hrit et al., OGT binds a conserved C-terminal domain of TET1 to regulate TET1 activity and function in development. Elife. Oct. 16, 2018;7:e34870. doi: 10.7554/eLife.34870.
Jiang et al., Tetracycline-regulated gene expression mediated by a novel chimeric repressor that recruits histone deacetylases in mammalian cells. J Biol Chem. Nov. 30, 2001;276(48):45168-74.
Kaplun et al., Kaiso Gene Knockout Promotes Somatic Cell Reprogramming. Biochemistry (Mosc). Mar. 2019;84(3):283-290. doi: 10.1134/S0006297919030106.
Koch et al., ROCK2 is a major regulator of axonal degeneration, neuronal death and axonal regeneration in the CNS. Cell Death Dis. May 15, 2014;5(5):e1225. doi: 10.1038/cddis.2014.191.
Koch et al., Viral vector-mediated downregulation of RhoA increases survival and axonal regeneration of retinal ganglion cells. Front Cell Neurosci. Sep. 5, 2014;8:273. doi: 10.3389/fncel.2014.00273. eCollection 2014.
Lavars, Japan moves to fast-track innovative stem cell therapy with first trials on human hearts. New Atlas. Jun. 1, 2018. https://newatlas.com/japan-stem-cell-therapy-hearts/54866/.
Levine et al., An epigenetic biomarker of aging for lifespan and healthspan. Aging (Albany NY). Apr. 18, 2018;10(4):573-591. doi: 10.18632/aging.101414.
Li et al., Small-Molecule-Driven Direct Reprogramming of Mouse Fibroblasts into Functional Neurons. Cell Stem Cell. Aug. 6, 2015;17(2):195-203. doi: 10.1016/j.stem.2015.06.003.
Liao et al., In Vivo Target Gene Activation via CRISPR/Cas9-Mediated Trans-epigenetic Modulation. Cell. Dec. 14, 2017;171(7):1495-1507.e15. doi: 10.1016/j.cell.2017.10.025. Epub Dec. 7, 2017.
Lim et al., Neural activity promotes long-distance, target-specific regeneration of adult retinal axons. Nat Neurosci. Aug. 2016;19(8):1073-84. doi: 10.1038/nn.4340. Epub Jul. 11, 2016.
Liu et al., A Sensitized IGF1 Treatment Restores Corticospinal Axon-Dependent Functions. Neuron. Aug. 16, 2017;95(4):817-833.e4. doi: 10.1016/j.neuron.2017.07.037.
Liu et al., CRISPR-Based Chromatin Remodeling of the Endogenous Oct4 or Sox2 Locus Enables Reprogramming to Pluripotency. Cell Stem Cell. Feb. 1, 2018;22(2):252-261.e4. doi: 10.1016/j.stem.2017.12.001. Epub Jan. 18, 2018.
Long et al., Bromodeoxyuridine promotes full-chemical induction of mouse pluripotent stem cells. Cell Res. Oct. 2015;25(10):1171-4. doi: 10.1038/cr.2015.96. Epub Aug. 7, 2015.
Lu et al., In Vivo Cellular Reprogramming For Tissue Regeneration and Age Reversal. Innov Aging. Nov. 2018;2(Suppl 1): 883. Published online Nov. 16, 2018. doi: 10.1093/geroni/igy031.3294.
Lu et al., Reprogramming to recover youthful epigenetic information and restore vision. Nature. Dec. 2020;588(7836):124-129. doi: 10.1038/s41586-020-2975-4. Epub Dec. 2, 2020.
Lu et al., Reversal of ageing- and injury-induced vision loss by Tet-dependent epigenetic reprogramming. BioRXiv. Jul. 2019; 1-51. doi https://doi.org/10.1101/710210.
Mahmoudi et al., Illuminating microbial species-specific effects on organic matter remineralization in marine sediments. Environ Microbiol. May 2020;22(5):1734-1747. doi: 10.1111/1462-2920.14871. Epub Dec. 10, 2019.
Mai et al., NKX3-1 is required for induced pluripotent stem cell reprogramming and can replace OCT4 in mouse and human iPSC induction. Nat Cell Biol. Aug. 2018;20(8):900-908. doi: 10.1038/s41556-018-0136-x. Epub Jul. 16, 2018.
Mandal et al., Reprogramming human fibroblasts to pluripotency using modified mRNA. Nat Protoc. Mar. 2013;8(3):568-82. doi: 10.1038/nprot.2013.019. Epub Feb. 21, 2013.
Manukyan et al., Epigenome rejuvenation: HP1β mobility as a measure of pluripotent and senescent chromatin ground states. Sci Rep. Apr. 25, 2014;4:4789. doi: 10.1038/srep04789.
Mcdermott et al., Gamma Band Neural Stimulation in Humans and the Promise of a New Modality to Prevent and Treat Alzheimer's Disease. J Alzheimers Dis. 2018;65(2):363-392. doi: 10.3233/JAD-180391.
Meer et al., A whole lifespan mouse multi-tissue DNA methylation clock. Elife. Nov. 14, 2018;7:e40675. doi: 10.7554/eLife.40675.
Miyoshi et al., Reprogramming of mouse and human cells to pluripotency using mature microRNAs. Cell Stem Cell. Jun. 3, 2011;8(6):633-8. doi: 10.1016/j.stem.2011.05.001.
Montana et al., Reprogramming of adult rod photoreceptors prevents retinal degeneration. Proc Natl Acad Sci USA. Jan. 29, 2013;110(5):1732-7. doi: 10.1073/pnas.1214387110. Epub Jan. 14, 2013.
Moore et al., KLF family members regulate intrinsic axon regeneration ability. Science. Oct. 9, 2009;326(5950):298-301. doi: 10.1126/science.1175737.
Mor et al., Neutralizing Gatad2a-Chd4-Mbd3/NuRD Complex Facilitates Deterministic Induction of Naive Pluripotency. Cell Stem Cell. Sep. 6, 2018;23(3):412-425.e10. doi: 10.1016/j.stem.2018.07.004. Epub Aug. 16, 2018.

(56) References Cited

OTHER PUBLICATIONS

Mosteiro et al., Tissue damage and senescence provide critical signals for cellular reprogramming in vivo. Science. Nov. 25, 2016;354(6315):aaf4445. doi: 10.1126/science.aaf4445.
Norsworthy et al., Sox11 Expression Promotes Regeneration of Some Retinal Ganglion Cell Types but Kills Others. Neuron. Jun. 21, 2017;94(6):1112-1120.e4. doi: 10.1016/j.neuron.2017.05.035.
Oberdoerffer et al., SIRT1 redistribution on chromatin promotes genomic stability but alters gene expression during aging. Cell. Nov. 28, 2008;135(5):907-18. doi: 10.1016/j.cell.2008.10.025.
Oberdoerffer et al., The role of nuclear architecture in genomic instability and ageing. Nat Rev Mol Cell Biol. Sep. 2007;8(9):692-702. doi: 10.1038/nrm2238.
Ocampo et al., In Vivo Amelioration of Age-Associated Hallmarks by Partial Reprogramming. Cell. Dec. 15, 2016;167(7):1719-1733. e12. doi: 10.1016/j.cell.2016.11.052.
O'Donovan et al., B-RAF kinase drives developmental axon growth and promotes axon regeneration in the injured mature CNS. J Exp Med. May 5, 2014;211(5):801-14. doi: 10.1084/jem.20131780. Epub Apr. 14, 2014.
Otake, Japan Times. Jun. 14, 2017. https://www.japantimes.co.jp/news/2017/06/14/national/science-health/transplants-using-ips-cells-put-riken-specialist-forefront-regenerative-medicine-research/#.W6UF5y-ZOfQ.
Park et al., Promoting axon regeneration in the adult CNS by modulation of the PTEN/mTOR pathway. Science. Nov. 7, 2008;322(5903):963-6. doi: 10.1126/science.1161566.
Redmer et al., E-cadherin is crucial for embryonic stem cell pluripotency and can replace OCT4 during somatic cell reprogramming. EMBO Rep. Jul. 1, 2011;12(7):720-6. doi: 10.1038/embor.2011.88.
Sarkar et al., Transient non-integrative nuclear reprogramming promotes multifaceted reversal of aging in human cells. Nat Commun. Mar. 24, 2020;11(1):1545. doi: 10.1038/s41467-020-15174-3.
Senis et al., AAV vector-mediated in vivo reprogramming into pluripotency. Nat Commun. Jul. 9, 2018;9(1):2651. doi: 10.1038/s41467-018-05059-x.
Shipley et al., Differentiation of the SH-SY5Y Human Neuroblastoma Cell Line. J Vis Exp. Feb. 17, 2016;(108):53193. doi: 10.3791/53193.
Shu et al., Induction of pluripotency in mouse somatic cells with lineage specifiers. Cell. May 23, 2013;153(5):963-75. doi: 10.1016/j.cell.2013.05.001.
Smalley, First AAV gene therapy poised for landmark approval. Nat Biotechnol. Nov. 9, 2017;35(11):998-999. doi: 10.1038/nbt1117-998.
Smith et al., SOCS3 deletion promotes optic nerve regeneration in vivo. Neuron. Dec. 10, 2009;64(5):617-23. doi: 10.1016/j.neuron.2009.11.021.
Takahashi et al., Induction of pluripotent stem cells from mouse embryonic and adult fibroblast cultures by defined factors. Cell. Aug. 25, 2006;126(4):663-76. doi: 10.1016/j.cell.2006.07.024. Epub Aug. 10, 2006.
Tammam et al., Nuclear delivery of recombinant OCT4 by chitosan nanoparticles for transgene-free generation of protein-induced pluripotent stem cells. Oncotarget. Jun. 21, 2016;7(25):37728-37739. doi: 10.18632/oncotarget.9276.
Tan et al., Inhibition of transforming growth factor β (TGF-β) signaling can substitute for Oct4 protein in reprogramming and maintain pluripotency. J Biol Chem. Feb. 13, 2015;290(7):4500-11. doi: 10.1074/jbc.M114.609016. Epub Dec. 29, 2014.
Thompson et al., A multi-tissue full lifespan epigenetic clock for mice. Aging (Albany NY). Oct. 21, 2018;10(10):2832-2854. doi: 10.18632/aging.101590.
Wang et al., Lin28 Signaling Supports Mammalian PNS and CNS Axon Regeneration. Cell Rep. Sep. 4, 2018;24(10):2540-2552.e6. doi: 10.1016/j.celrep.2018.07.105.
Wang et al., Ribosomal DNA harbors an evolutionarily conserved clock of biological aging. Genome Res. Mar. 2019;29(3):325-333. doi: 10.1101/gr.241745.118. Epub Feb. 14, 2019.
Wang et al., Spatiotemporal control of gene expression by a light-switchable transgene system. Nat Methods. Feb. 12, 2012;9(3):266-9. doi: 10.1038/nmeth.1892.
Wang et al., The lysine demethylase LSD1 (KDM1) is required for maintenance of global DNA methylation. Nat Genet. Jan. 2009;41(1):125-9. doi: 10.1038/ng.268. Epub Dec. 21, 2008.
Warren et al., Highly Efficient Reprogramming to Pluripotency and Directed Differentiation of Human Cells with Synthetic Modified mRNA. Cell Stem Cell. Nov. 5, 2010;7(5):618-30. doi: 10.1016/j.stem.2010.08.012. Epub Sep. 30, 2010.
Weltner et al., Human pluripotent reprogramming with CRISPR activators. Nat Commun. Jul. 6, 2018;9(1):2643. doi: 10.1038/s41467-018-05067-x.
Weng et al., An Intrinsic Epigenetic Barrier for Functional Axon Regeneration. Neuron. Apr. 19, 2017;94(2):337-346.e6. doi: 10.1016/j.neuron.2017.03.034.
Wright et al., Identification of factors that contribute to recombinant AAV2 particle aggregation and methods to prevent its occurrence during vector purification and formulation. Mol Ther. Jul. 2005;12(1):171-8. doi: 10.1016/j.ymthe.2005.02.021.
Xiao et al., Endogenous Reprogramming of Alpha Cells into Beta Cells, Induced by Viral Gene Therapy, Reverses Autoimmune Diabetes. Cell Stem Cell. Jan. 4, 2018;22(1):78-90.e4. doi: 10.1016/j.stem.2017.11.020.
Yang et al., Induced pluripotent stem cell lines derived from human somatic cells. Science. Dec. 21, 2007;318(5858):1917-20. doi: 10.1126/science.1151526. Epub Nov. 20, 2007.
Yao et al., Restoration of vision after de novo genesis of rod photoreceptors in mammalian retinas. Nature. Aug. 2018;560(7719):484-488. doi: 10.1038/s41586-018-0425-3. Epub Aug. 15, 2018.
Yu et al., Tet3 regulates synaptic transmission and homeostatic plasticity via DNA oxidation and repair. Nat Neurosci. Jun. 2015;18(6):836-43. doi: 10.1038/nn.4008. Epub Apr. 27, 2015.
Zahid et al., Protein transduction domains: applications for molecular medicine. Curr Gene Ther. Oct. 2012;12(5):374-80. doi: 10.2174/156652312802762527.
Zhao et al., A XEN-like State Bridges Somatic Cells to Pluripotency during Chemical Reprogramming. Cell. Dec. 17, 2015;163(7):1678-91. doi: 10.1016/j.cell.2015.11.017. Epub Dec. 10, 2015.
Zhou et al., Generation of induced pluripotent stem cells using recombinant proteins. Cell Stem Cell. May 8, 2009;4(5):381-4. doi: 10.1016/j.stem.2009.04.005. Epub Apr. 23, 2009.
Zhou et al., Optimization of the Tet-On system for regulated gene expression through viral evolution. Gene Ther. Oct. 2006;13(19):1382-90. doi: 10.1038/sj.gt.3302780. Epub May 25, 2006.
International Search Report and Written Opinion for Application No. PCT/US2023/065374, mailed Jun. 6, 2023.
Aasen et al., Efficient and rapid generation of induced pluripotent stem cells from human keratinocytes. Nat Biotechnol. Nov. 2008;26(11):1276-84. doi: 10.1038/nbt.1503. Epub Oct. 17, 2008.
Agha-Mohammadi et al., Second-generation tetracycline-regulatable promoter: repositioned tet operator elements optimize transactivator synergy while shorter minimal promoter offers tight basal leakiness. J Gene Med. Jul. 2004;6(7):817-28. doi: 10.1002/jgm.566.
Agrawal et al., Generation of recombinant skin in vitro by adeno-associated virus type 2 vector transduction. Tissue Eng. Nov.-Dec. 2004;10(11-12):1707-15. doi: 10.1089/ten.2004.10.1707.
Aida et al., Cloning-free CRISPR/Cas system facilitates functional cassette knock-in in mice. Genome Biol. Apr. 29, 2015;16(1):87. doi: 10.1186/s13059-015-0653-x.
Alaei et al., An improved reprogrammable mouse model harbouring the reverse tetracycline-controlled transcriptional transactivator 3. Stem Cell Res. Jul. 2016;17(1):49-53. doi: 10.1016/j.scr.2016.05.008. Epub May 25, 2016.
Baron et al., Tet repressor-based system for regulated gene expression in eukaryotic cells: principles and advances. Methods Enzymol. 2000;327:401-21. doi: 10.1016/s0076-6879(00)27292-3.
Chen et al., Reprogramming adipose tissue-derived mesenchymal stem cells into pluripotent stem cells by a mutant adeno-associated viral vector. Hum Gene Ther Methods. Feb. 2014;25(1):72-82. doi: 10.1089/hgtb.2013.011. Epub Dec. 28, 2013.

(56) References Cited

OTHER PUBLICATIONS

Cho et al., Generation of transgenic mice. Curr Protoc Cell Biol. Mar. 2009;Chapter 19:Unit 19.11. doi: 10.1002/0471143030.cb1911s42.
Chtarto et al., A regulatable AAV vector mediating GDNF biological effects at clinically-approved sub-antimicrobial doxycycline doses. Mol Ther Methods Clin Dev. Mar. 30, 2016;5:16027. doi: 10.1038/mtm.2016.27. eCollection 2016.
Danke et al., Adjusting transgene expression levels in lymphocytes with a set of inducible promoters. J Gene Med. Jun. 2010;12(6):501-15. doi: 10.1002/jgm.1461.
Das et al., Selecting the optimal Tet-On system for doxycycline-inducible gene expression in transiently transfected and stably transduced mammalian cells. Biotechnol J. Jan. 2016;11(1):71-9. doi: 10.1002/biot.201500236. Epub Sep. 24, 2015.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Doench et al., Optimized sgRNA design to maximize activity and minimize off-target effects of CRISPR-Cas9. Nat Biotechnol. Feb. 2016;34(2):184-191. doi: 10.1038/nbt.3437. Epub Jan. 18, 2016.
Dong et al., Poly(glycoamidoamine) Brushes Formulated Nanomaterials for Systemic siRNA and mRNA Delivery in Vivo. Nano Lett. Feb. 10, 2016;16(2):842-8. doi: 10.1021/acs.nanolett.5b02428. Epub Jan. 13, 2016.
Dugan et al., Non-Arteritic Anterior Ischemic Optic Neuropathy (NAION). American Academy of Ophthalmology Eyewiki. Apr. 7, 2023. 6 pages.
Genbank Submission; NCBI, Accession No. NM_001173531. *Homo sapiens* POU class 5 homeobox 1 (POU5F1), transcript variant 3, mRNA. Jul. 31, 2023. 4 pages.
Genbank Submission; NCBI, Accession No. NM_001285986. *Homo sapiens* POU class 5 homeobox 1 (POU5F1), transcript variant 4, mRNA. Jul. 31, 2023. 4 pages.
Genbank Submission; NCBI, Accession No. NM_001285987. *Homo sapiens* POU class 5 homeobox 1 (POU5F1), transcript variant 5, mRNA, 4 pages. Jul. 31, 2023.
Genbank Submission; NCBI, Accession No. NM_001314052.1; *Homo sapiens* Kruppel like factor 4 (KLF4), transcript variant 1, mRNA. May 28, 2019. 5 pages.
Genbank Submission; NCBI, Accession No. NM_001354870.1. *Homo sapiens* MYC proto-oncogene, bHLH transcription factor (MYC), transcript variant 2, mRNA. Jul. 31, 2023. 7 pages.
Genbank Submission; NCBI, Accession No. NM_002467.5; *Homo sapiens* MYC proto-oncogene, bHLH transcription factor (MYC), transcript variant 1, mRNA. Dec. 30, 2018. 5 pages.
Genbank Submission; NCBI, Accession No. NM_002701. *Homo sapiens* POU class 5 homeobox 1 (POU5F1), transcript variant 1, mRNA. Jul. 31, 2023. 5 pages.
Genbank Submission; NCBI, Accession No. NM_003106.4. *Homo sapiens* SRY-box transcription factor 2 (SOX2), mRNA.,Jul. 31, 2023. 4 pages.
Genbank Submission; NCBI, Accession No. NM_004235.5; *Homo sapiens* Kruppel like factor 4 (KLF4), transcript variant 2, mRNA. Nov. 18, 2018. 4 pages.
Genbank Submission; NCBI, Accession No. NM_011443.4. *Mus musculus* SRY (sex determining region Y)—box 2 (Sox2), mRNA. Aug. 1, 2023. 4 pages.
Genbank Submission; NCBI, Accession No. NM_203289. *Homo sapiens* POU class 5 homeobox 1 (POU5F1), transcript variant 2, mRNA. Jul. 31, 2023. 4 pages.
Genbank Submission; NCBI, Accession No. NP 002458.2. myc proto-oncogene protein isoform 1 [*Homo sapiens*]. Jul. 31, 2023. 5 pages.
Genbank Submission; NCBI, Accession No. NP_001167002.1. POU domain, class 5, transcription factor 1 isoform 2 [*Homo sapiens*]. Jul. 31, 2023. 3 pages.
Genbank Submission; NCBI, Accession No. NP_001272915.1. POU domain, class 5, transcription factor 1 isoform 4 [*Homo sapiens*]. Jul. 31, 2023. 3 pages.
Genbank Submission; NCBI, Accession No. NP_001272916.1. POU domain, class 5, transcription factor 1 isoform 3 [*Homo sapiens*]. Jul. 31, 2023. 3 pages.
Genbank Submission; NCBI, Accession No. NP_001341799.1. myc proto-oncogene protein isoform 2 [*Homo sapiens*]. Jul. 31, 2023. 5 pages.
Genbank Submission; NCBI, Accession No. NP_002692.2; POU domain, class 5, transcription factor 1 isoform 1 [*Homo sapiens*]. Sep. 23, 2018.
Genbank Submission; NCBI, Accession No. NP_003097.1. transcription factor SOX-2 [*Homo sapiens*]. Jul. 31, 2023. 3 pages.
Genbank Submission; NCBI, Accession No. NP_004226.3. Krueppel-like factor 4 isoform 2 [*Homo sapiens*]. Jul. 13, 2023. 4 pages.
Genbank Submission; NCBI, Accession No. NP_976034.4. POU domain, class 5, transcription factor 1 isoform 2 [*Homo sapiens*]. Jul. 31, 2023. 3 pages.
Genbank Submission; NCBI, Accession No. NP_001300981.1. Krueppel-like factor 4 isoform 1 [*Homo sapiens*]. Jul. 13, 2023. 4 pages.
Gill et al., Multi-omic rejuvenation of human cells by maturation phase transient reprogramming. Elife. Apr. 8, 2022;11:e71624. doi: 10.7554/eLife.71624.
Gomes et al., Induced pluripotent stem cells reprogramming: Epigenetics and applications in the regenerative medicine. Rev Assoc Med Bras (1992). Feb. 2017;63(2):180-189. doi: 10.1590/1806-9282.63.02.180.
Gossen et al., Tight control of gene expression in mammalian cells by tetracycline-responsive promoters. Proc Natl Acad Sci U S A. Jun. 15, 1992;89(12):5547-51. doi: 10.1073/pnas.89.12.5547.
Heinz et al., Retroviral and transposon-based tet-regulated all-in-one vectors with reduced background expression and improved dynamic range. Hum Gene Ther. Feb. 2011;22(2):166-76. doi: 10.1089/hum.2010.099. Epub Dec. 19, 2010.
Hishida et al., In vivo partial cellular reprogramming enhances liver plasticity and regeneration. Cell Rep. Apr. 26, 2022;39(4):110730. doi: 10.1016/j.celrep.2022.110730.
Hosoda et al., Development of a tightly-regulated tetracycline-dependent transcriptional activator and repressor co-expression system for the strong induction of transgene expression. Cytotechnology. May 2011;63(3):211-6. doi: 10.1007/s10616-011-9335-z. Epub Feb. 20, 2011.
Hsu et al., Development and applications of CRISPR-Cas9 for genome engineering. Cell. Jun. 5, 2014;157(6):1262-1278. doi: 10.1016/j.cell.2014.05.010.
Karg et al., Sustained vision recovery by OSK gene therapy in a mouse model of glaucoma. Cell Reprogram. Dec. 2023;25(6):288-299. doi: 10.1089/cell.2023.0074. Epub Dec. 7, 2023.
Lamartina et al., Construction of an rtTA2(s)-m2/tts(kid)-based transcription regulatory switch that displays no basal activity, good inducibility, and high responsiveness to doxycycline in mice and non-human primates. Mol Ther. Feb. 2003;7(2):271-80. doi: 10.1016/s1525-0016(02)00051-5.
Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.
Li et al., Reprogramming induced pluripotent stem cells in the absence of c-Myc for differentiation into hepatocyte-like cells. Biomaterials. Sep. 2011;32(26):5994-6005. doi: 10.1016/j.biomaterials.2011.05.009. Epub Jun. 11, 2011.
Liu et al., Systematic comparison of 2A peptides for cloning multi-genes in a polycistronic vector. Sci Rep. May 19, 2017;7(1):2193. doi: 10.1038/s41598-017-02460-2.
Loew et al., Improved Tet-responsive promoters with minimized background expression. BMC Biotechnol. Nov. 24, 2010:10:81. doi: 10.1186/1472-6750-10-81.
Lozano-Torres et al., An OFF-ON Two-Photon Fluorescent Probe for Tracking Cell Senescence in Vivo. J Am Chem Soc. Jul. 5, 2017;139(26):8808-8811. doi: 10.1021/jacs.7b04985. Epub Jun. 23, 2017.
Macip et al., Gene Therapy-Mediated Partial Reprogramming Extends Lifespan and Reverses Age-Related Changes in Aged Mice. Cellular Reprogram. Feb. 2024;26(1):24-32. doi: 10.1089/cell.2023.0072.

(56) References Cited

OTHER PUBLICATIONS

Matsui et al., Avian adeno-associated virus vector efficiently transduces neurons in the embryonic and post-embryonic chicken brain. PLoS One. 2012;7(11):e48730. doi: 10.1371/journal.pone.0048730. Epub Nov. 7, 2012.

Michalon et al., Inducible and neuron-specific gene expression in the adult mouse brain with the rtTA2S-M2 system. Genesis. Dec. 2005;43(4):205-12. doi: 10.1002/gene.20175.

Mohit et al., Cellular Reprogramming, Transdifferentiation and Alleviation of the Aging Pathology. Res J Biotech. 2024; 19(2): 127-139.

Moreira et al., Assessing Executive Dysfunction in Neurodegenerative Disorders: A Critical Review of Brief Neuropsychological Tools. Front Aging Neurosci. Nov. 9, 2017;9:369. doi: 10.3389/fnagi.2017.00369. eCollection 2017.

Nehlin et al., The Werner syndrome. A model for the study of human aging. Ann N Y Acad Sci. Jun. 2000;908:167-79. doi: 10.1111/j.1749-6632.2000.tb06645.x.

No Author Listed, Tet-On® 3G Inducible Expression System. Clontech Laboratories, Inc. 8 pages.

No Author Listed, Tet-On® 3G Inducible Expression Systems User Manual. Clonetech Laboratories, Inc. 2014. 24 pages. Published online at takarabio.com.

No Author Listed, Tet-One technology overview. Takara Bio USA, Inc. Accessed at: https://www.takarabio.com/learning-centers/gene-function/inducible-systems/tet-inducible-systems/tet-one-technology-overview. Last accessed: May 15, 2024. 3 pages.

O'Connor et al., Genetic medicines: treatment strategies for hereditary disorders. Nat Rev Genet. Apr. 2006;7(4):261-76. doi: 10.1038/nrg1829.

Patel et al., Inhaled Nanoformulated mRNA Polyplexes for Protein Production in Lung Epithelium. Adv Mater. Feb. 2019;31(8):e1805116. doi: 10.1002/adma.201805116. Epub Jan. 4, 2019.

Pico et al., Comparative analysis of mouse strains for in vivo reprogramming. bioRxiv. Mar. 8, 2024. 32 pages. https://doi.org/10.1101/2024.03.08.584074.

Puri et al., Epigenetic rejuvenation by partial reprogramming. Bioessays. Apr. 2023;45(4):e2200208. doi: 10.1002/bies.202200208. Epub Mar. 4, 2023.

Ramamoorth et al., Non viral vectors in gene therapy—an overview. J Clin Diagn Res. Jan. 2015;9(1):GE01-6. doi: 10.7860/JCDR/2015/10443.5394. Epub Jan. 1, 2015.

Randolph et al., An all-in-one, Tet-On 3G inducible PiggyBac system for human pluripotent stem cells and derivatives. Sci Rep. May 8, 2017;7(1):1549. doi: 10.1038/s41598-017-01684-6.

Ribas et al., Gene Manipulation Strategies to Identify Molecular Regulators of Axon Regeneration in the Central Nervous System. Front Cell Neurosci. Aug. 7, 2017;11:231. doi: 10.3389/fncel.2017.00231. eCollection 2017.

Rodda et al., Transcriptional Regulation of Nanog by OCT4 and SOX2. J Biol Chem. Jul. 1, 2005;280(26):24731-7. doi: 10.1074/jbc.M502573200. Epub Apr. 27, 2005.

Roney et al., Improvement of the reverse tetracycline transactivator by single amino acid substitutions that reduce leaky target gene expression to undetectable levels. Sci Rep. Jun. 21, 2016;6:27697. doi: 10.1038/srep27697.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sarin et al., Inhibition of acquired immunodeficiency syndrome virus by oligodeoxynucleoside methylphosphonates. Proc Natl Acad Sci USA. Oct. 1988;85(20):7448-51. Doi 10.1073/pnas.85.20.7448.

Sheng et al., Generation and characterization of a Tet-On (rtTA-M2) transgenic rat. BMC Dev Biol. Feb. 16, 2010:10:17. doi: 10.1186/1471-213X-10-17.

Sichani et al., Partial Reprogramming as a Method for Regenerating Neural Tissues in Aged Organisms. Cell Reprogram. Feb. 2024;26(1):10-23. doi: 10.1089/cell.2023.0123.

Singh et al., Age reprogramming: cell rejuvenation by partial reprogramming. Development. Nov. 15, 2022;149(22):dev200755. doi: 10.1242/dev.200755. Epub Nov. 16, 2022.

Takahashi et al., Induction of pluripotent stem cells from adult human fibroblasts by defined factors. Cell. Nov. 30, 2007;131(5):861-72. doi: 10.1016/j.cell.2007.11.019.

Tyner et al., p53 mutant mice that display early ageing-associated phenotypes. Nature. Jan. 3, 2002;415(6867):45-53. doi: 10.1038/415045a.

Uchida et al., Tight regulation of transgene expression by tetracycline-dependent activator and repressor in brain. Genes Brain Behav. Feb. 2006;5(1):96-106. doi: 10.1111/j.1601-183X.2005.00139.x.

Urlinger et al., Exploring the sequence space for tetracycline-dependent transcriptional activators: novel mutations yield expanded range and sensitivity. Proc Natl Acad Sci U S A. Jul. 5, 2000;97(14):7963-8. doi: 10.1073/pnas.130192197.

Wu et al. Induced pluripotent stem cells Cellular research progress in ophthalmic diseases Exhibition. International Journal of Ophthalmology. 2013; 13(2): 295-298.

Yao et al., Systemic and localized reversible regulation of transgene expression by tetracycline with tetR-mediated transcription repression switch. J Surg Res. Apr. 2007;138(2):267-74. doi: 10.1016/j.jss.2006.05.007. Epub Jan. 24, 2007.

Yilmazer et al., In vivo cell reprogramming towards pluripotency by virus-free overexpression of defined factors. PLoS One. 2013;8(1):e54754. doi: 10.1371/journal.pone.0054754. Epub Jan. 23, 2013.

Zhang et al., Reducing Background Expression of Target Gene with tTS/rtTA System in Cell Model. Journal Of Sun Yat-Sen University (Medical Sciences). Jul. 30, 2006; 27(4): 361-364.

Zhao et al., A coumermycin/novobiocin-regulated gene expression system. Hum Gene Ther. Nov. 20, 2003;14(17):1619-29. doi: 10.1089/104303403322542266.

Zhu et al., Silencing and un-silencing of tetracycline-controlled genes in neurons. PLoS One. Jun. 20, 2007;2(6):e533. doi: 10.1371/journal.pone.0000533.

Bekris et al., The Genertics of Parkin's Disease. J Geriatr Psychiatry Neurol. Dec. 2010;23(4):228-42. doi: 10.1177/0891988710383572. Epub Oct. 11, 2010.

Brennan et al., Ocular Salvage and Vision Preservation Using a Topotecan-Based Regimen for Advanced Intraocular Retinoblastoma. J Clin Oncol. Jan. 2017;35(1):72-77. doi: 10.1200/JCO.2016.692996. Epub Oct. 31, 2016

Fan et al., Transient, Inducible, Placenta-Specific Gene Expression in Mice. Endocrinology. Nov. 2012;153(11):5637-44. doi: 10.1210/en.2012-1556. Epub Sep. 25, 2012.

Li et al., Production of Lentiviral Vectors for Transducing Cells from the Central Nervous System. J Vis Exp. May 24, 2012:(63):e4031. doi: 10.3791/4031.

Reichmuth et al., mRNA vaccine delivery using lipid nanoparticles. Ther Deliv. 2016;7(5):319-34. doi: 10.4155/tde-2016-0006.

Wang et al., 2A self-cleaving peptide-based multi-gene expression system in the silkworm Bombyx mori. Sci Rep. Nov. 5, 2015:5:16273. doi: 10.1038/srep16273.

Chtarto et al., Tetracycline-inductible transgene expression mediated by a single AAV vector. Gene Ther. Jan. 2003;10(1):84-94. doi: 10.1038/sj.gt.3301838.

International Preliminary Report on Patentability for Application No. PCT/US2023/065374, mailed Oct. 17, 2024.

[No Author Listed], Homo sapiens tet methylcytosine dioxygenase 3 (TET3), transcript variant 2, mRNA. NCBI Ref Seq No.: NM_001366022.1. Sep. 20, 2018. Accessible at https://www.ncbi.nlm.nih.gov/nuccore/1478050930?sat=47&satkey=7913.

[No Author Listed], Optic Nerve Crush. EYECRO. 2024. Accessed at: https://eyecro.com/models/optic-nerve-crush/. [last accessed: Sep. 18, 2024].

Bareyre et al., In vivo imaging reveals a phase-specific role STAT3 during central and peripheral nervous system axon regenration. Proc Natl Acad Sci USA. Apr. 12, 2011;108(15):6282-7. doi: 10.1073/pnas.1015239108. Epub Mar. 29, 2011.

Cameron et al., Optic Nerve Crush in Mice to Study Retinal Ganglion Cell Survival and Regeneration. Bio Protoc. Mar. 20, 2020;10(6):e3559. doi: 10.21769/BioProtoc.3559.

(56) References Cited

OTHER PUBLICATIONS

Chan et al., Engineered AAVs for efficient noninvasive gene delivery to the central and peripheral nervous systems. Nat Neurosci. Author manuscript; available in PMC: Dec. 26, 2017. Published in final edited form as: Nat Neurosci. Jun. 26, 2017;20(8):1172-1179. doi: 10.1038/nn.4593.

Choi et al., Optimization of AAV expression cassettes to improve packaging capacity and transgene expression in neurons. Mol Brain. Mar. 11, 2014:7:17. doi: 10.1186/1756-6606-7-17.

Gjoneska et al., Conserved epigenomic signals in mice and humans reveal immune basis of Alzheimer's disease. Nature. Feb. 19, 2015;518(7539):365-9. doi: 10.1038/nature1452.

Goersten et al., AAV capsid variants with brain-wide transgene expression and decreased liver targeting after intravenous delivery in mouse and marmoset. Nat Neurosci. Jan. 2022;25(1):106-115. doi: 10.1038/s41593-021-00969-4. Epub Dec. 9, 2021.

Hager et al., An internal polyadenylation signal substantially increases expression levels of lentivirus-delivered transgenes but has the potential to reduce viral titer in a promoter-dependent manner. Hum Gene Ther. Aug. 2008;19(8):840-50. doi: 10.1089/hum.2007.165.

Krolak et al., A High-Efficiency AAV for Endothelial Cell Transdcution Throughout the Central Nervous System. Nat Cardiovasc Res. Author manuscript; available in PMC: Oct. 13, 2022. Published in final edited form as: Nat Cardiovasc Res. Apr. 13, 2022;1(4):389-400. doi: 10.1038/s44161-022-00046-4.

Mahmoudi et al, Old fibrolasts secrete inflammatory cytokines that drive variability in reprogramming efficiency and may affect wound healing between old individuals. Biorxiv. Oct. 19, 2018. doi: https://doi.org/10.1101/448431.

Mathiesen et al., CNS Transduction Benefits of AAV-PHP.eB over AAV9 Are Dependent on Administration Route and Mouse Strain. Mol Ther Methods Clin Dev. Oct. 20, 2020;19:447-458. doi: 10.1016/j.omtm.2020.10.011.eCollection Dec. 11, 2020.

Mertens et al., Directly Reprogrammed Human Neurons Retain Aging-Associated Transcriptomic Signatures and Reveal Age-Related Nucleocytoplasmic Defects. Cell Stem Cell. Dec. 3, 2015;17(6):705-718. doi: 10.1016/j.stem.2015.09.001. Epub Oct. 8, 2015.

Nakagawa et al., Generation of induced pluripotent stem cells without Myc from mouse and human fibroblasts. Nat Biotechnol. Jan. 2008;26(1):101-6. doi: 10.1038/nbt1374. Epub Nov. 30, 2007.

Olova et al., Partial reprogramming induces a steady decline in epigenetic age before loss of somatic identity. Aging Cell. Feb. 2019;18(1):e12877. doi: 10.1111/acel.12877. Epub Nov. 18, 2018.

Shannon, A Mathematical Theory of Communication. The Bell System Technical Journal. 1948; 1: 379-423. https://doi.org/10.1002/j.1538-7305.1948.tb01338.x.

\* cited by examiner

5′ TTATGCAGTGCTGCCATAACCATGAGTGATAACACTGCGGCCAACTTACTTCTGACAACGATCGGAGGACCGAAGGAGCTAACCG
3′ AATACGTCACGACGGTATTGGTACTCACTATTGTGACGCCGGTTGAATGAAGACTGTTGCTAGCCTCCTGGCTTCCTCGATTGGC      85

RYBxO8mRbwMFOFCf7oNIW1BYMn0.1515186099985.7
Extracted region from pAAV-TRE3G-OSK-WPRE3-SV40pA CTTTTTTGCACAACATGGGGGATCATGTAACTCGCCTTGATCGTTGGGAACCGGAGCTGAATGAAGCCATACCAAACGACGAGCG
GAAAAAACGTGTTGTACCCCCTAGTACATTGAGCGGAACTAGCAACCCTTGGCCTCGACTTACTTCGGTATGGTTTGCTGCTCGC      170

RYBxO8mRbwMFOFCf7oNIW1BYMn0.1515186099985.7
Extracted region from pAAV-TRE3G-OSK-WPRE3-SV40pA TGACACCACGATGCCTGTAGTAATGGTAACAACGTTGCGCAAACTATTAACTGGCGAACTACTTACTCTAGCTTCCCGGCAACAA
ACTGTGGTGCTACGGACATCATTACCATTGTTGCAACGCGTTTGATAATTGACCGCTTGATGAATGAGATCGAAGGGCCGTTGTT      255

RYBxO8mRbwMFOFCf7oNIW1BYMn0.1515186099985.7
Extracted region from pAAV-TRE3G-OSK-WPRE3-SV40pA TTAATAGACTGGATGGAGGCGGATAAAGTTGCAGGACCACTTCTGCGCTCGGCCCTTCCGGCTGGCTGGTTTATTGCTGATAAAT
AATTATCTGACCTACCTCCGCCTATTTCAACGTCCTGGTGAAGACGCGAGCCGGGAAGGCCGACCGACCAAATAACGACTATTTA      340

RYBxO8mRbwMFOFCf7oNIW1BYMn0.1515186099985.7
Extracted region from pAAV-TRE3G-OSK-WPRE3-SV40pA BsrDI
                            |
CTGGAGCCGGTGAGCGTGGGTCTCGCGGTATCATTGCAGCACTGGGGCCAGATGGTAAGCCCTCCCGTATCGTAGTTATCTACAC
GACCTCGGCCACTCGCACCCAGAGCGCCATAGTAACGTCGTGACCCCGGTCTACCATTCGGGAGGGCATAGCATCAATAGATGTG      425

RYBxO8mRbwMFOFCf7oNIW1BYMn0.1515186099985.7
Extracted region from pAAV-TRE3G-OSK-WPRE3-SV40pA GACGGGGAGTCAGGCAACTATGGATGAACGAAATAGACAGATCGCTGAGATAGGTGCCTCACTGATTAAGCATTGGTAACTGTCA
CTGCCCCTCAGTCCGTTGATACCTACTTGCTTTATCTGTCTAGCGACTCTATCCACGGAGTGACTAATTCGTAACCATTGACAGT      510

RYBxO8mRbwMFOFCf7oNIW1BYMn0.1515186099985.7
Extracted region from pAAV-TRE3G-OSK-WPRE3-SV40pA

FIG. 4A

```
GACCAAGTTTACTCATATATACTTTAGATTGATTTAAAACTTCATTTTTAATTTAAAAGGATCTAGGTGAAGATCCTTTTTGATA
++++++++++++++++++++++++++++++++++++++++++++++++++++++++++++++++++++++++++++++++++++     595
CTGGTTCAAATGAGTATATATGAAATCTAACTAAATTTTGAAGTAAAAATTAAATTTTCCTAGATCCACTTCTAGGAAAAACTAT
```
RYBxO8mRbwMFOFCf7oNIW1BYMn0.1515186099985.7

Extracted region from pAAV-TRE3G-OSK-WPRE3-SV40pA

```
ATCTCATGACCAAAATCCCTTAACGTGAGTTTTCGTTCCACTGAGCGTCAGACCCCGTAGAAAAGATCAAAGGATCTTCTTGAGA
++++++++++++++++++++++++++++++++++++++++++++++++++++++++++++++++++++++++++++++++++++     680
TAGAGTACTGGTTTTAGGGAATTGCACTCAAAAGCAAGGTGACTCGCAGTCTGGGGCATCTTTTCTAGTTTCCTAGAAGAACTCT
```
RYBxO8mRbwMFOFCf7oNIW1BYMn0.1515186099985.7

Extracted region from pAAV-TRE3G-OSK-WPRE3-SV40pA pBR322_origin

```
TCCTTTTTTTCTGCGCGTAATCTGCTGCTTGCAAACAAAAAAACCACCGCTACCAGCGGTGGTTTGTTTGCCGGATCAAGAGCTA
++++++++++++++++++++++++++++++++++++++++++++++++++++++++++++++++++++++++++++++++++++     765
AGGAAAAAAAGACGCGCATTAGACGACGAACGTTTGTTTTTTTGGTGGCGATGGTCGCCACCAAACAAACGGCCTAGTTCTCGAT
```
RYBxO8mRbwMFOFCf7oNIW1BYMn0.1515186099985.7

Extracted region from pAAV-TRE3G-OSK-WPRE3-SV40pA pBR322_origin

```
CCAACTCTTTTTCCGAAGGTAACTGGCTTCAGCAGAGCGCAGATACCAAATACTGTCCTTCTAGTGTAGCCGTAGTTAGGCCACC
++++++++++++++++++++++++++++++++++++++++++++++++++++++++++++++++++++++++++++++++++++     850
GGTTGAGAAAAAGGCTTCCATTGACCGAAGTCGTCTCGCGTCTATGGTTTATGACAGGAAGATCACATCGGCATCAATCCGGTGG
```
RYBxO8mRbwMFOFCf7oNIW1BYMn0.1515186099985.7

Extracted region from pAAV-TRE3G-OSK-WPRE3-SV40pA pBR322_origin

```
ACTTCAAGAACTCTGTAGCACCGCCTACATACCTCGCTCTGCTAATCCTGTTACCAGTGGCTGCTGCCAGTGGCGATAAGTCGTG
++++++++++++++++++++++++++++++++++++++++++++++++++++++++++++++++++++++++++++++++++++     935
TGAAGTTCTTGAGACATCGTGGCGGATGTATGGAGCGAGACGATTAGGACAATGGTCACCGACGACGGTCACCGCTATTCAGCAC
```
RYBxO8mRbwMFOFCf7oNIW1BYMn0.1515186099985.7

Extracted region from pAAV-TRE3G-OSK-WPRE3-SV40pA pBR322_origin

FIG. 4B

TCTTACCGGGTTGGACTCAAGACGATAGTTACCGGATAAGGCGCAGCGGTCGGGCTGAACGGGGGGTTCGTGCACACAGCCCAGC
AGAATGGCCCAACCTGAGTTCTGCTATCAATGGCCTATTCCGCGTCGCCAGCCCGACTTGCCCCCAAGCACGTGTGTCGGGTCG

1020

RYBxO8mRbwMFOFCf7oNIW1BYMn0.1515186099985.7
Extracted region from pAAV-TRE3G-OSK-WPRE3-SV40pA
pBR322_origin TTGGAGCGAACGACCTACACCGAACTGAGATACCTACAGCGTGAGCTATGAGAAAGCGCCACGCTTCCCGAAGGGAGAAAGGCGG
AACCTCGCTTGCTGGATGTGGCTTGACTCTATGGATGTCGCACTCGATACTCTTTCGCGGTGCGAAGGGCTTCCCTCTTTCCGCC

1105

RYBxO8mRbwMFOFCf7oNIW1BYMn0.1515186099985.7
Extracted region from pAAV-TRE3G-OSK-WPRE3-SV40pA
pBR322_origin ACAGGTATCCGGTAAGCGGCAGGGTCGGAACAGGAGAGCGCACGAGGGAGCTTCCAGGGGGAAACGCCTGGTATCTTTATAGTCC
TGTCCATAGGCCATTCGCCGTCCCAGCCTTGTCCTCTCGCGTGCTCCCTCGAAGGTCCCCCTTTGCGGACCATAGAAATATCAGG

1190

RYBxO8mRbwMFOFCf7oNIW1BYMn0.1515186099985.7
Extracted region from pAAV-TRE3G-OSK-WPRE3-SV40pA
pBR322_origin TGTCGGGTTTCGCCACCTCTGACTTGAGCGTCGATTTTTGTGATGCTCGTCAGGGGGGCGGAGCCTATGGAAAAACGCCAGCAAC
ACAGCCCAAAGCGGTGGAGACTGAACTCGCAGCTAAAAACACTACGAGCAGTCCCCCCGCCTCGGATACCTTTTTGCGGTCGTTG

1275

RYBxO8mRbwMFOFCf7oNIW1BYMn0.1515186099985.7
Extracted region from pAAV-TRE3G-OSK-WPRE3-SV40pA
pBR322_origin GCGGCCTTTTTACGGTTCCTGGCCTTTTGCTGGCCTTTTGCTCACATGTTCTTTCCTGCGTTATCCCCTGATTCTGTGGATAACC
CGCCGGAAAAATGCCAAGGACCGGAAAACGACCGGAAAACGAGTGTACAAGAAAGGACGCAATAGGGGACTAAGACACCTATTGG

1360

RYBxO8mRbwMFOFCf7oNIW1BYMn0.1515186099985.7
Extracted region from pAAV-TRE3G-OSK-WPRE3-SV40pA pBR322_origin     CGG

FIG. 4C

SapI
BspQI

GTATTACCGCCTTTGAGTGAGCTGATACCGCTCGCCGCAGCCGAACGACCGAGCGCAGCGAGTCAGTGAGCGAGGAAGCGGAAGA
CATAATGGCGGAAACTCACTCGACTATGGCGAGCGGCGTCGGCTTGCTGGCTCGCGTCGCTCAGTCACTCGCTCCTTCGCCTTCT 1445

RYBxO8mRbwMFOFCf7oNIW1BYMn0.1515186099985.7
Extracted region from pAAV-TRE3G-OSK-WPRE3-SV40pA GCGCCCAATACGCAAACCGCCTCTCCCCGCGCGTTGGCCGATTCATTAATGCAGCTGGCACGACAGGTTTCCCGACTGGAAAGCG
CGCGGGTTATGCGTTTGGCGGAGAGGGGCGCGCAACCGGCTAAGTAATTACGTCGACCGTGCTGTCCAAAGGGCTGACCTTTCGC 1530

RYBxO8mRbwMFOFCf7oNIW1BYMn0.1515186099985.7
Extracted region from pAAV-TRE3G-OSK-WPRE3-SV40pA GGCAGTGAGCGCAACGCAATTAATGTGAGTTAGCTCACTCATTAGGCACCCCAGGCTTTACACTTTATGCTTCCGGCTCGTATGT
CCGTCACTCGCGTTGCGTTAATTACACTCAATCGAGTGAGTAATCCGTGGGGTCCGAAATGTGAAATACGAAGGCCGAGCATACA 1615

RYBxO8mRbwMFOFCf7oNIW1BYMn0.1515186099985.7
Extracted region from pAAV-TRE3G-OSK-WPRE3-SV40pA TGTGTGGAATTGTGAGCGGATAACAATTTCACACAGGAAACAGCTATGACCATGATTACGCCAGATTTAATTAAGGCCTTAATTA
ACACACCTTAACACTCGCCTATTGTTAAAGTGTGTCCTTTGTCGATACTGGTACTAATGCGGTCTAAATTAATTCCGGAATTAAT 1700

RYBxO8mRbwMFOFCf7oNIW1BYMn0.1515186099985.7
Extracted region from pAAV-TRE3G-OSK-WPRE3-SV40pA
ITR GGCTGCGCGCTCGCTCGCTCACTGAGGCCGCCCGGGCAAAGCCCGGGCGTCGGGCGACCTTTGGTCGCCCGGCCTCAGTGAGCGA
CCGACGCGCGAGCGAGCGAGTGACTCCGGCGGGCCCGTTTCGGGCCCGCAGCCCGCTGGAAACCAGCGGGCCGGAGTCACTCGCT 1785

RYBxO8mRbwMFOFCf7oNIW1BYMn0.1515186099985.7
Extracted region from pAAV-TRE3G-OSK-WPRE3-SV40pA RYBxO8mRbwMFOFCf7oNIW1BYMn0.1520442556627.0
RYBxO8mRbwMFOFCf7oNIW1BYMn0.1520442556735.1
RYBxO8mRbwMFOFCf7oNIW1BYMn0.1520442824995.16
RYBxO8mRbwMFOFCf7oNIW1BYMn0.1520442825019.17
ITR

TCAGTGATAGAGAACGTATAAGCTTTAGGCGTGTACGGTGGGCGCCTATAAAAGCAGAGCTCGTTTAGTGAACCGTCAGATCGCC
AGTCACTATCTCTTGCATATTCGAAATCCGCACATGCCACCCGCGGATATTTTCGTCTCGAGCAAATCACTTGGCAGTCTAGCGG

2210

Digestion of pAAV-TRE3G-OSK-WPRE3-SV40pA - Frag...
RYBxO8mRbwMFOFCf7oNIW1BYMn0.1513097172637.1

RYBxO8mRbwMFOFCf7oNIW1BYMn0.1515186099985.7
RYBxO8mRbwMFOFCf7oNIW1BYMn0.1520442556735.1
RYBxO8mRbwMFOFCf7oNIW1BYMn0.1520442825019.17
RYBxO8mRbwMFOFCf7oNIW1BYMn0.1515185884933.5
RYBxO8mRbwMFOFCf7oNIW1BYMn0.1499881982184.9
GTACACGCCTACCTCGACCCATCAAGTGCCACCTGACGTCTCCCTAT...
RYBxO8mRbwMFOFCf7oNIW1BYMn0.1515186141081.10
Extracted region from pTRE3G
TRE3G\Promoter
tetO | Modified Minimal CMV Promoter

FIG. 4G

```
CCCGCATACGAGTTCTGCGGAGGGATGGCATACTGTGGACCCTCAGGTTGGACTGGGCCTAGTCCCCCAAGTTGGCGTGGAGACTT
GGGCGTATGCTCAAGACGCCTCCCTACCGTATGACACCTGGAGTCCAACCTGACCCGGATCAGGGGGTTCAACCGCACCTCTGAA
```

2550

60 65 70 75 80 85

Pro Ala Tyr Glu Phe Cys Gly Gly Met Ala Tyr Cys Gly Pro Gln Val Gly Leu Gly Leu Val Pro Gln Val Gly Val Glu Thr

- ORF frame 3
- RYBxO8mRbwMFOFCf7oNIW1BYMn0.1513097172637.1
- RYBxO8mRbwMFOFCf7oNIW1BYMn0.1515186099932.6
- Extracted region from pAAV-TRE3G-OSK-WPRE3-SV40pA
- RYBxO8mRbwMFOFCf7oNIW1BYMn0.1499881537908.1
- Digestion of pAAV-TRE3G-OSK-WPRE3-SV40pA - Frag...
- RYBxO8mRbwMFOFCf7oNIW1BYMn0.1515186141043.9
- RYBxO8mRbwMFOFCf7oNIW1BYMn0.1515185884753.3
- RYBxO8mRbwMFOFCf7oNIW1BYMn0.1520442556735.1
- RYBxO8mRbwMFOFCf7oNIW1BYMn0.1520442825019.17
- Oct4

```
TGCAGCCTGAGGGCCAGGCAGGAGCACGAGTGGAAAGCAACTCAGAGGGAACCTCCTCTGAGCCCTGTGCCGACCGCCCCAATGC
ACGTCGGACTCCCGGTCCGTCCTCGTGCTCACCTTTCGTTGAGTCTCCCTTGGAGGAGACTCGGGACACGGCTGGCGGGGTTACG
```

2635

90 95 100 105 110 115

Leu Gln Pro Glu Gly Gln Ala Gly Ala Arg Val Glu Ser Asn Ser Glu Gly Thr Ser Ser Glu Pro Cys Ala Asp Arg Pro Asn Ala

- ORF frame 3
- RYBxO8mRbwMFOFCf7oNIW1BYMn0.1513097172637.1
- RYBxO8mRbwMFOFCf7oNIW1BYMn0.1515186099932.6
- Extracted region from pAAV-TRE3G-OSK-WPRE3-SV40pA
- RYBxO8mRbwMFOFCf7oNIW1BYMn0.1499881537908.1
- Digestion of pAAV-TRE3G-OSK-WPRE3-SV40pA - Frag...
- RYBxO8mRbwMFOFCf7oNIW1BYMn0.1515186141043.9
- RYBxO8mRbwMFOFCf7oNIW1BYMn0.1515185884753.3
- RYBxO8mRbwMFOFCf7oNIW1BYMn0.1520442556735.1
- RYBxO8mRbwMFOFCf7oNIW1BYMn0.1520442825019.17
- Oct4

FIG. 4I

```
CGTGAAGTTGGAGAAGGTGGAACCAACTCCCGAGGAGTCCCAGGACATGAAAGCCCTGCAGAAGGAGCTAGAACAGTTTGCCAAG
GCACTTCAACCTCTTCCACCTTGGTTGAGGGCTCCTCAGGGTCCTGTACTTTCGGGACGTCTTCCTCGATCTTGTCAAACGGTTC
```
2720

Val Lys Leu Glu Lys Val Glu Pro Thr Pro Glu Glu Ser Gln Asp Met Lys Ala Leu Gln Lys Glu Leu Glu Gln Phe Ala Lys

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
RYBxO8mRbwMFOFCf7oNIW1BYMn0.1520442556735.1
RYBxO8mRbwMFOFCf7oNIW1BYMn0.1520442825019.17
Oct4

```
CTGCTGAAGCAGAAGAGGATCACCTTGGGGTACACCCAGGCCGACGTGGGGCTCACCCTGGGCGTTCTCTTTGGAAAGGTGTTCA
GACGACTTCGTCTTCTCCTAGTGGAACCCCATGTGGGTCCGGCTGCACCCCGAGTGGGACCCGCAAGAGAAACCTTTCCACAAGT
```
2805

Leu Leu Lys Gln Lys Arg Ile Thr Leu Gly Tyr Thr Gln Ala Asp Val Gly Leu Thr Leu Gly Val Leu Phe Gly Lys Val Phe

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
RYBxO8mRbwMFOFCf7oNIW1BYMn0.1520442556735.1
RYBxO8mRbwMFOFCf7oNIW1BYMn0.1520442825019.17
Oct4

FIG. 4J

```
                                         AflII
GCCAGACCACCATCTGTCGCTTCGAGGCCTTGCAGCTCAGCCTTAAGAACATGTGTAAGCTGCGGCCCCTGCTGGAGAAGTGGGT
++++++++++++++++++++++++++++++++++++++++++++++++++++++++++++++++++++++++++++++++++++++    2890
CGGTCTGGTGGTAGACAGCGAAGCTCCGGAACGTCGAGTCGGAATTCTTGTACACATTCGACGCCGGGGACGACCTCTTCACCCA
     175        180        185        190        195        200
Ser Gln Thr Thr Ile Cys Arg Phe Glu Ala Leu Gln Leu Ser Leu Lys Asn Met Cys Lys Leu Arg Pro Leu Leu Glu Lys Trp Val
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| RYBxO8mRbwMFOFCf7oNIW1BYMn0.1520442556735.1 | > |
| RYBxO8mRbwMFOFCf7oNIW1BYMn0.1520442825019.17 | > |
| Oct4 | > |

```
GGAGGAAGCCGACAACAATGAGAACCTTCAGGAGATATGCAAATCGGAGACCCTGGTGCAGGCCCGGAAGAGAAAGCGAACTAGC
++++++++++++++++++++++++++++++++++++++++++++++++++++++++++++++++++++++++++++++++++++++    2975
CCTCCTTCGGCTGTTGTTACTCTTGGAAGTCCTCTATACGTTTAGCCTCTGGGACCACGTCCGGGCCTTCTCTTTCGCTTGATCG
     205        210        215        220        225
Glu Glu Ala Asp Asn Asn Glu Asn Leu Gln Glu Ile Cys Lys Ser Glu Thr Leu Val Gln Ala Arg Lys Arg Lys Arg Thr Ser
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| RYBxO8mRbwMFOFCf7oNIW1BYMn0.1520442556735.1 | > |
| RYBxO8mRbwMFOFCf7oNIW1BYMn0.1520442825019.17 | > |
| Oct4 | > |

FIG. 4K

ATTGAGAACCGTGTGAGGTGGAGTCTGGAGACCATGTTTCTGAAGTGCCCGAAGCCCTCCCTACAGCAGATCACTCACATCGCCA 3060
TAACTCTTGGCACACTCCACCTCAGACCTCTGGTACAAAGACTTCACGGGCTTCGGGAGGGATGTCGTCTAGTGAGTGTAGCGGT 230    235    240    245    250    255

Ile Glu Asn Arg Val Arg Trp Ser Leu Glu Thr Met Phe Leu Lys Cys Pro Lys Pro Ser Leu Gln Gln Ile Thr His Ile Ala

ORF frame 3 >
RYBxO8mRbwMFOFCf7oNIW1BYMn0.1513097172637.1 >
RYBxO8mRbwMFOFCf7oNIW1BYMn0.1515186099932.6 >
Extracted region from pAAV-TRE3G-OSK-WPRE3-SV40pA >
RYBxO8mRbwMFOFCf7oNIW1BYMn0.1499881537908.1 >
Digestion of pAAV-TRE3G-OSK-WPRE3-SV40pA - Frag... >
RYBxO8mRbwMFOFCf7oNIW1BYMn0.1515186141043.9 >
RYBxO8mRbwMFOFCf7oNIW1BYMn0.1515185884753.3 >
RYBxO8mRbwMFOFCf7oNIW1BYMn0.1520442556735.1 >
RYBxO8mRbwMFOFCf7oNIW1BYMn0.1520442825019.17 >
Oct4 >

ATCAGCTTGGGCTAGAGAAGGATGTGGTTCGAGTATGGTTCTGTAACCGGCGCCAGAAGGGCAAAAGATCAAGTATTGAGTATTC 3145
TAGTCGAACCCGATCTCTTCCTACACCAAGCTCATACCAAGACATTGGCCGCGGTCTTCCCGTTTTCTAGTTCATAACTCATAAG 260    265    270    275    280    285

Asn Gln Leu Gly Leu Glu Lys Asp Val Val Arg Val Trp Phe Cys Asn Arg Arg Gln Lys Gly Lys Arg Ser Ser Ile Glu Tyr Ser

ORF frame 3 >
RYBxO8mRbwMFOFCf7oNIW1BYMn0.1513097172637.1 >
RYBxO8mRbwMFOFCf7oNIW1BYMn0.1515186099932.6 >
Extracted region from pAAV-TRE3G-OSK-WPRE3-SV40pA >
RYBxO8mRbwMFOFCf7oNIW1BYMn0.1499881537908.1 >
Digestion of pAAV-TRE3G-OSK-WPRE3-SV40pA - Frag... >
RYBxO8mRbwMFOFCf7oNIW1BYMn0.1515186141043.9 >
RYBxO8mRbwMFOFCf7oNIW1BYMn0.1515185884753.3 >
RYBxO8mRbwMFOFCf7oNIW1BYMn0.1520442556735.1 >
RYBxO8mRbwMFOFCf7oNIW1BYMn0.1520442825019.17 >
Oct4 >

```
TCATGGTATGGTCCCGGGGGCAGCGGCGTAAGATGGCCCAGGAGAACCCCAAGATGCACAACTCGGAGATCAGCAAGCGCCTGGG    3655
++++++++++++++++++++++++++++++++++++++++++++++++++++++++++++++++++++++++++++++++++
AGTACCATACCAGGGCCCCCGTCGCCGCATTCTACCGGGTCCTCTTGGGGTTCTACGTGTTGAGCCTCTAGTCGTTCGCGGACCC
         430       435       440       445       450       455
Phe Met Val Trp Ser Arg Gly Gln Arg Arg Lys Met Ala Gln Glu Asn Pro Lys Met His Asn Ser Glu Ile Ser Lys Arg Leu Gly
```

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
Sox2
RYBxO8mRb... RYBxO8mRbwMFOFCf7oNIW1BYMn0.1520442556822.3
RYBxO8mRb... RYBxO8mRbwMFOFCf7oNIW1BYMn0.1520442825077.19

FIG. 4O
Continued

```
CGCGGAGTGGAAACTTTTGTCCGAGACCGAGAAGCGGCCGTTCATCGACGAGGCCAAGCGGCTGCGCGCTCTGCACATGAAGGAG
GCGCCTCACCTTTGAAAACAGGCTCTGGCTCTTCGCCGGCAAGTAGCTGCTCCGGTTCGCCGACGCGCGAGACGTGTACTTCCTC
         460       465       470       475       480
Ala Glu Trp Lys Leu Leu Ser Glu Thr Glu Lys Arg Pro Phe Ile Asp Glu Ala Lys Arg Leu Arg Ala Leu His Met Lys Glu
```
3740

ORF frame 3
RYBxO8mRbwMFOFCf7oNlW1BYMn0.1513097172637.1
RYBxO8mRbwMFOFCf7oNlW1BYMn0.1515186099932.6
Extracted region from pAAV-TRE3G-OSK-WPRE3-SV40pA
RYBxO8mRbwMFOFCf7oNlW1BYMn0.1499881537908.1
Digestion of pAAV-TRE3G-OSK-WPRE3-SV40pA - Frag...
RYBxO8mRbwMFOFCf7oNlW1BYMn0.1515186141043.9
RYBxO8mRbwMFOFCf7oNlW1BYMn0.1515185884753.3
Sox2
RYBxO8mRbwMFOFCf7oNlW1BYMn0.1520442556822.3
RYBxO8mRbwMFOFCf7oNlW1BYMn0.1520442825077.19

```
                          SacII
CACCCGGATTATAAATACCGGCCGCGGCGGAAAAACCAAGACGCTCATGAAGAAGGATAAGTACACGCTTCCCGGAGGCTTGCTGG
GTGGGCCTAATATTTATGGCCGGCGCCGCCTTTTGGTTCTGCGAGTACTTCTTCCTATTCATGTGCGAAGGGCCTCCGAACGACC
     485       490       495       500       505       510
His Pro Asp Tyr Lys Tyr Arg Pro Arg Arg Lys Thr Lys Thr Leu Met Lys Lys Asp Lys Tyr Thr Leu Pro Gly Gly Leu Leu
```
3825

ORF frame 3
RYBxO8mRbwMFOFCf7oNlW1BYMn0.1513097172637.1
RYBxO8mRbwMFOFCf7oNlW1BYMn0.1515186099932.6
Extracted region from pAAV-TRE3G-OSK-WPRE3-SV40pA
RYBxO8mRbwMFOFCf7oNlW1BYMn0.1499881537908.1
Digestion of pAAV-TRE3G-OSK-WPRE3-SV40pA - Frag...
RYBxO8mRbwMFOFCf7oNlW1BYMn0.1515186141043.9
RYBxO8mRbwMFOFCf7oNlW1BYMn0.1515185884753.3
Sox2
RYBxO8mRbwMFOFCf7oNlW1BYMn0.1520442556822.3
RYBxO8mRbwMFOFCf7oNlW1BYMn0.1520442825077.19

FIG. 4P

```
CCCCCGGCGGGAACAGCATGGCGAGCGGGGTTGGGGTGGGCGCCGGCCTGGGTGCGGGCGTGAACCAGCGCATGGACAGCTACGC
GGGGGCCGCCCTTGTCGTACCGCTCGCCCCAACCCCACCCGCGGCCGGACCCACGCCCGCACTTGGTCGCGTACCTGTCGATGCG
        515        520        525        530        535        540
Ala Pro Gly Gly Asn Ser Met Ala Ser Gly Val Gly Val Gly Ala Gly Leu Gly Ala Gly Val Asn Gln Arg Met Asp Ser Tyr Ala
```
3910

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
Sox2
RYBxO8mRbwMFOFCf7oNIW1BYMn0.1520442556822.3
RYBxO8mRbwMFOFCf7oNIW1BYMn0.1520442825077.19

```
GCACATGAACGGCTGGAGCAACGGCAGCTACAGCATGATGCAGGAGCAGCTGGGCTACCCGCAGCACCCGGGCCTCAACGCTCAC
CGTGTACTTGCCGACCTCGTTGCCGTCGATGTCGTACTACGTCCTCGTCGACCCGATGGGCGTCGTGGGCCCGGAGTTGCGAGTG
        545        550        555        560        565
His Met Asn Gly Trp Ser Asn Gly Ser Tyr Ser Met Met Gln Glu Gln Leu Gly Tyr Pro Gln His Pro Gly Leu Asn Ala His
```
3995

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
Sox2
RYBxO8mRbwMFOFCf7oNIW1BYMn0.1520442556822.3 | RYBxO8mRbwMF...
RYBxO8mRbwMFOFCf7oNIW1BYMn0.1520442825077.19 | RYBxO8mRbwMF...

```
                                                                BclI*
CGAGGCCAGCTCCAGCCCCCCGTGGTTACCTCTTCCTCCCACTCCAGGGCGCCCTGCCAGGCCGGGGACCTCCGGGACATGATC
++++++++++++++++++++++++++++++++++++++++++++++++++++++++++++++++++++++++++++++++++   4250
GCTCCGGTCGAGGTCGGGGGGGCACCAATGGAGAAGGAGGGTGAGGTCCCGCGGGACGGTCCGGCCCCTGGAGGCCCTGTACTAG
       630         635         640         645         650
Glu Ala Ser Ser Ser Pro Pro Val Val Thr Ser Ser Ser His Ser Arg Ala Pro Cys Gln Ala Gly Asp Leu Arg Asp Met Ile
```

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Sox2 |
| RYBxO8mRbwMFOFCf7oNIW1BYMn0.1520442556899.4 |
| RYBxO8mRbwMFOFCf7oNIW1BYMn0.1520442825096.20 |

FIG. 4S

AGCATGTACCTCCCCGGCGCCGAGGTGCCGGAGCCCGCTGCGCCCAGTAGACTGCACATGGCCCAGCACTACCAGAGCGGCCCGG 4335
TCGTACATGGAGGGGCCGCGGCTCCACGGCCTCGGGCGACGCGGGTCATCTGACGTGTACCGGGTCGTGATGGTCTCGCCGGGCC
  655      660      665      670      675      680
Ser Met Tyr Leu Pro Gly Ala Glu Val Pro Glu Pro Ala Ala Pro Ser Arg Leu His Met Ala Gln His Tyr Gln Ser Gly Pro

ORF frame 3 >
RYBxO8mRbwMFOFCf7oNIW1BYMn0.1513097172637.1 >
RYBxO8mRbwMFOFCf7oNIW1BYMn0.1515186099932.6 >
Extracted region from pAAV-TRE3G-OSK-WPRE3-SV40pA >
RYBxO8mRbwMFOFCf7oNIW1BYMn0.1499881537908.1 >
Digestion of pAAV-TRE3G-OSK-WPRE3-SV40pA - Frag... >
RYBxO8mRbwMFOFCf7oNIW1BYMn0.1515186141043.9 >
RYBxO8mRbwMFOFCf7oNIW1BYMn0.1515185884753.3 >
Sox2 >
RYBxO8mRbwMFOFCf7oNIW1BYMn0.1520442556899.4 >
RYBxO8mRbwMFOFCf7oNIW1BYMn0.1520442825096.20 >
sox2-fwd >

FIG. 4S
Continued

```
TGCCCGGCACGGCCATTAACGGCACACTGCCCCTGTCGCACATGGCATGCGGCTCCGGCGAGGGCAGGGGAAGTCTTCTAACATG
ACGGGCCGTGCCGGTAATTGCCGTGTGACGGGGACAGCGTGTACCGTACGCCGAGGCCGCTCCCGTCCCCTTCAGAAGATTGTAC
      685       690       695       700       705       710
Val Pro Gly Thr Ala Ile Asn Gly Thr Leu Pro Leu Ser His Met Ala Cys Gly Ser Gly Glu Gly Arg Gly Ser Leu Leu Thr Cys
```
4420

ORF frame 3

RYBxO8mRbwMFOFCf7oNIW1BYMn0.1513097172637.1

RYBxO8mRbwMFOFCf7oNIW1BYMn0.1515186099932.6

Extracted region from pAAV-TRE3G-OSK-WPRE3-SV40pA

RYBxO8mRbwMFOFCf7oNIW1BYMn0.1499881537908.1

Digestion of pAAV-TRE3G-OSK-WPRE3-SV40pA - Frag...

RYBxO8mRbwMFOFCf7oNIW1BYMn0.1515186141043.9

RYBxO8mRbwMFOFCf7oNIW1BYMn0.1515185884753.3

Sox2

RYBxO8mRbwMFOFCf7oNIW1BYMn0.1520442556899.4

RYBxO8mRbwMFOFCf7oNIW1BYMn0.1520442825096.20

FIG. 4T

```
CCGTCCTTCTCCACGTTCGCGTCCGGCCCGGCGGGAAGGGAGAAGACACTGCGTCCAGCAGGTGCCCCGACTAACCGTTGGCGTG
++++++++++++++++++++++++++++++++++++++++++++++++++++++++++++++++++++++++++++++++++++  4590
GGCAGGAAGAGGTGCAAGCGCAGGCCGGGCCGCCCTTCCCTCTTCTGTGACGCAGGTCGTCCACGGGGCTGATTGGCAACCGCAC
    740       745       750       755       760       765
Pro Ser Phe Ser Thr Phe Ala Ser Gly Pro Ala Gly Arg Glu Lys Thr Leu Arg Pro Ala Gly Ala Pro Thr Asn Arg Trp Arg
```

ORF frame 3 >
RYBxO8mRbwMFOFCf7oNIW1BYMn0.1513097172637.1 >
RYBxO8mRbwMFOFCf7oNIW1BYMn0.1515186099932.6 >
Extracted region from pAAV-TRE3G-OSK-WPRE3-SV40pA >
RYBxO8mRbwMFOFCf7oNIW1BYMn0.1499881537908.1 >
Digestion of pAAV-TRE3G-OSK-WPRE3-SV40pA - Frag... >
RYBxO8mRbwMFOFCf7oNIW1BYMn0.1515186141043.9 >
RYBxO8mRbwMFOFCf7oNIW1BYMn0.1515185884753.3 >
Klf4 >
RYBxO8mRbwMFOFCf7oNIW1BYMn0.1520442556899.4 >
RYBxO8mRbwMFOFCf7oNIW1BYMn0.1520442825096.20 >

< Klf4-rev                                                          BstXI

```
AGGAACTCTCTCACATGAAGCGACTTCCCCCACTTCCCGGCCGCCCCTACGACCTGGCGGCGACGGTGGCCACAGACCTGGAGAG
++++++++++++++++++++++++++++++++++++++++++++++++++++++++++++++++++++++++++++++++++++  4675
TCCTTGAGAGAGTGTACTTCGCTGAAGGGGGTGAAGGGCCGGCGGGGATGCTGGACCGCCGCTGCCACCGGTGTCTGGACCTCTC
    770       775       780       785       790       795
Glu Glu Leu Ser His Met Lys Arg Leu Pro Pro Leu Pro Gly Arg Pro Tyr Asp Leu Ala Ala Thr Val Ala Thr Asp Leu Glu Ser
```

ORF frame 3 >
RYBxO8mRbwMFOFCf7oNIW1BYMn0.1513097172637.1 >
RYBxO8mRbwMFOFCf7oNIW1BYMn0.1515186099932.6 >
Extracted region from pAAV-TRE3G-OSK-WPRE3-SV40pA >
RYBxO8mRbwMFOFCf7oNIW1BYMn0.1499881537908.1 >
Digestion of pAAV-TRE3G-OSK-WPRE3-SV40pA - Frag... >
RYBxO8mRbwMFOFCf7oNIW1BYMn0.1515186141043.9 >
RYBxO8mRbwMFOFCf7oNIW1BYMn0.1515185884753.3 >
Klf4 >
RYBxO8mRbwMFOFCf7oNIW1BYMn0.1520442556899.4 >
RYBxO8mRbwMFOFCf7oNIW1BYMn0.1520442825096.20 >

FIG. 4U

```
TGGCGGAGCTGGTGCAGCTTGCAGCAGTAACAACCCGGCCCTCCTAGCCCGGAGGGAGACCGAGGAGTTCAACGACCTCCTGGAC
++++++++++++++++++++++++++++++++++++++++++++++++++++++++++++++++++++++++++++++++++++++
ACCGCCTCGACCACGTCGAACGTCGTCATTGTTGGGCCGGGAGGATCGGGCCTCCCTCTGGCTCCTCAAGTTGCTGGAGGACCTG
        800       805       810       815       820                                   4760
Gly Gly Ala Gly Ala Ala Cys Ser Ser Asn Asn Pro Ala Leu Leu Ala Arg Arg Glu Thr Glu Glu Phe Asn Asp Leu Leu Asp
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556899.4 | > |
| RYBxO8mRbwMFOFCf7oNIW1BYMn0.1520442825096.20 | > |

```
CTAGACTTTATCCTTTCCAACTCGCTAACCCACCAGGAATCGGTGGCCGCCACCGTGACCACCTCGGCGTCAGCTTCATCCTCGT
++++++++++++++++++++++++++++++++++++++++++++++++++++++++++++++++++++++++++++++++++++++
GATCTGAAATAGGAAAGGTTGAGCGATTGGGTGGTCCTTAGCCACCGGCGGTGGCACTGGTGGAGCCGCAGTCGAAGTAGGAGCA
    825       830       835       840       845       850                              4845
Leu Asp Phe Ile Leu Ser Asn Ser Leu Thr His Gln Glu Ser Val Ala Ala Thr Val Thr Thr Ser Ala Ser Ala Ser Ser Ser
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556899.4 | > |
| RYBxO8mRbwMFOFCf7oNIW1BYMn0.1520442825096.20 | > |

FIG. 4V

```
CTTCCCCAGCGAGCAGCGGCCCTGCCAGCGCGCCCTCCACCTGCAGCTTCAGCTATCCGATCCGGGCCGGGGGTGACCCGGGCGT
GAAGGGGTCGCTCGTCGCCGGGACGGTCGCGCGGGAGGTGGACGTCGAAGTCGATAGGCTAGGCCCGGCCCCCACTGGGCCCGCA
        855       860       865       870       875       880
Ser Ser Pro Ala Ser Ser Gly Pro Ala Ser Ala Pro Ser Thr Cys Ser Phe Ser Tyr Pro Ile Arg Ala Gly Gly Asp Pro Gly Val
```
4930

- ORF frame 3
- RYBxO8mRbwMFOFCf7oNIW1BYMn0.1513097172637.1
- RYBxO8mRbwMFOFCf7oNIW1BYMn0.1515186099932.6
- Extracted region from pAAV-TRE3G-OSK-WPRE3-SV40pA
- RYBxO8mRbwMFOFCf7oNIW1BYMn0.1499881537908.1
- Digestion of pAAV-TRE3G-OSK-WPRE3-SV40pA - Frag...
- RYBxO8mRbwMFOFCf7oNIW1BYMn0.1515186141043.9
- RYBxO8mRbwMFOFCf7oNIW1BYMn0.1515185884753.3
- Klf4
- RYBxO8mRbwMFOFCf7oNIW1BYMn0.1520442556899.4 | RYB...
- RYBxO8mRbwMFOFCf7oNIW1BYMn0.1520442825096.20 | RYB...
- Klf4-mid-fwd

FIG. 4W

```
CATCAGTGTTAGCAAAGGAAGCCCAGACGGCAGCCACCCCGTGGTAGTGGCGCCCTACAGCGGTGGCCCGCCGCGCATGTGCCCC
GTAGTCACAATCGTTTCCTTCGGGTCTGCCGTCGGTGGGGCACCATCACCGCGGGATGTCGCCACCGGGCGGCGCGTACACGGGG
         970       975       980       985       990
 Ile Ser Val Ser Lys Gly Ser Pro Asp Gly Ser His Pro Val Val Val Ala Pro Tyr Ser Gly Gly Pro Pro Arg Met Cys Pro
```
5270

| ORF frame 3 | > |
| RYBxO8mRbwMFOFCf7oNIW1BYMn0.15130971726371 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

FIG. 4Y

```
                                                              AfeI
                                                                |
AAGATTAAGCAAGAGGCGGTCCCGTCCTGCACGGTCAGCCGGTCCCTAGAGGCCCATTTGAGCGCTGGACCCCAGCTCAGCAACG   5355
++++++++++++++++++++++++++++++++++++++++++++++++++++++++++++++++++++++++++++++++++++
TTCTAATTCGTTCTCCGCCAGGGCAGGACGTGCCAGTCGGCCAGGGATCTCCGGGTAAACTCGCGACCTGGGGTCGAGTCGTTGC
   ,995,   ,  ,1000,  ,  ,1005,  ,  ,1010,  ,  ,1015,  ,  ,1020,
 Lys Ile Lys Gln Glu Ala Val Pro Ser Cys Thr Val Ser Arg Ser Leu Glu Ala His Leu Ser Ala Gly Pro Gln Leu Ser Asn
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

FIG. 4Y
Continued

```
GCCACCGGCCCAACACACACGACTTCCCCCTGGGGCGGCAGCTCCCCACCAGGACTACCCCTACACTGAGTCCCGAGGAACTGCT
++++++++++++++++++++++++++++++++++++++++++++++++++++++++++++++++++++++++++++++++++++  5440
CGGTGGCCGGGTTGTGTGTGCTGAAGGGGGACCCCGCCGTCGAGGGGTGGTCCTGATGGGGATGTGACTCAGGGCTCCTTGACGA
        1025       1030       1035       1040       1045       1050
Gly His Arg Pro Asn Thr His Asp Phe Pro Leu Gly Arg Gln Leu Pro Thr Arg Thr Thr Pro Thr Leu Ser Pro Glu Glu Leu Leu
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

```
GAACAGCAGGGACTGTCACCCTGGCCTGCCTCTTCCCCCAGGATTCCATCCCCATCCGGGGCCCAACTACCCTCCTTTCCTGCCA
++++++++++++++++++++++++++++++++++++++++++++++++++++++++++++++++++++++++++++++++++++  5525
CTTGTCGTCCCTGACAGTGGGACCGGACGGAGAAGGGGGTCCTAAGGTAGGGGTAGGCCCCGGGTTGATGGGAGGAAAGGACGGT
        1055       1060       1065       1070       1075
Asn Ser Arg Asp Cys His Pro Gly Leu Pro Leu Pro Pro Gly Phe His Pro His Pro Gly Pro Asn Tyr Pro Pro Phe Leu Pro
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

FIG. 4Z

```
GACCAGATGCAGTCACAAGTCCCCTCTCTCCATTATCAAGAGCTCATGCCACCGGGTTCCTGCCTGCCAGAGGAGCCCAAGCCAA
+++++++++++++++++++++++++++++++++++++++++++++++++++++++++++++++++++++++++++++++++++++    5610
CTGGTCTACGTCAGTGTTCAGGGGAGAGAGGTAATAGTTCTCGAGTACGGTGGCCCAAGGACGGACGGTCTCCTCGGGTTCGGTT
    1080     1085     1090     1095     1100     1105
Asp Gln Met Gln Ser Gln Val Pro Ser Leu His Tyr Gln Glu Leu Met Pro Pro Gly Ser Cys Leu Pro Glu Glu Pro Lys Pro
```

| ORF frame 3 | > |
| RYBxO8mRbwMFOFCf7oNlW1BYMn0.1513097172637.1 | > |
| RYBxO8mRbwMFOFCf7oNlW1BYMn0.1515186099932.6 | > |
| Extracted region from pAAV-TRE3G-OSK-WPRE3-SV40pA | > |
| RYBxO8mRbwMFOFCf7oNlW1BYMn0.1499881537908.1 | > |
| Digestion of pAAV-TRE3G-OSK-WPRE3-SV40pA - Frag... | > |
| RYBxO8mRbwMFOFCf7oNlW1BYMn0.1515186141043.9 | > |
| RYBxO8mRbwMFOFCf7oNlW1BYMn0.1515185884753.3 | > |
| Klf4 | > |
| RYBxO8mRbwMFOFCf7oNlW1BYMn0.1520442556934.5 | > |
| RYBxO8mRbwMFOFCf7oNlW1BYMn0.1520442825118.21 | > |

```
                                              AleI
AGAGGGGAAGAAGGTCGTGGCCCCGGAAAAGAACAGCCACCCACACTTGTGACTATGCAGGCTGTGGCAAAACCTATACCAAGAG
+++++++++++++++++++++++++++++++++++++++++++++++++++++++++++++++++++++++++++++++++++++    5695
TCTCCCCTTCTTCCAGCACCGGGGCCTTTTCTTGTCGGTGGGTGTGAACACTGATACGTCCGACACCGTTTTGGATATGGTTCTC
    1110     1115     1120     1125     1130     1135
Lys Arg Gly Arg Arg Ser Trp Pro Arg Lys Arg Thr Ala Thr His Thr Cys Asp Tyr Ala Gly Cys Gly Lys Thr Tyr Thr Lys Ser
```

| ORF frame 3 | > |
| RYBxO8mRbwMFOFCf7oNlW1BYMn0.1513097172637.1 | > |
| RYBxO8mRbwMFOFCf7oNlW1BYMn0.1515186099932.6 | > |
| Extracted region from pAAV-TRE3G-OSK-WPRE3-SV40pA | > |
| RYBxO8mRbwMFOFCf7oNlW1BYMn0.1499881537908.1 | > |
| Digestion of pAAV-TRE3G-OSK-WPRE3-SV40pA - Frag... | > |
| RYBxO8mRbwMFOFCf7oNlW1BYMn0.1515186141043.9 | > |
| RYBxO8mRbwMFOFCf7oNlW1BYMn0.1515185884753.3 | > |
| Klf4 | > |
| RYBxO8mRbwMFOFCf7oNlW1BYMn0.1520442556934.5 | > |
| RYBxO8mRbwMFOFCf7oNlW1BYMn0.1520442825118.21 | > |

FIG. 4AA

```
TTCTCATCTCAAGGCACACCTGCGAACTCACACAGGCGAGAAACCTTACCACTGTGACTGGGACGGCTGTGGGTGGAAATTCGCC
++++++++++++++++++++++++++++++++++++++++++++++++++++++++++++++++++++++++++++++++++++  5780
AAGAGTAGAGTTCCGTGTGGACGCTTGAGTGTGTCCGCTCTTTGGAATGGTGACACTGACCCTGCCGACACCCACCTTTAAGCGG
     1140      1145      1150      1155      1160
```
Ser His Leu Lys Ala His Leu Arg Thr His Thr Gly Glu Lys Pro Tyr His Cys Asp Trp Asp Gly Cys Gly Trp Lys Phe Ala

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

```
CGCTCCGATGAACTGACCAGGCACTACCGCAAACACACAGGGCACCGGCCCTTTCAGTGCCAGAAGTGCGACAGGGCCTTTTCCA
++++++++++++++++++++++++++++++++++++++++++++++++++++++++++++++++++++++++++++++++++++  5865
GCGAGGCTACTTGACTGGTCCGTGATGGCGTTTGTGTGTCCCGTGGCCGGGAAAGTCACGGTCTTCACGCTGTCCCGGAAAAGGT
     1165      1170      1175      1180      1185      1190
```
Arg Ser Asp Glu Leu Thr Arg His Tyr Arg Lys His Thr Gly His Arg Pro Phe Gln Cys Gln Lys Cys Asp Arg Ala Phe Ser

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

FIG. 4AB

AGCTTATAATGGTTACAAATAAAGCAATAGCATCACAAATTTCACAAATAAAGCATTTTTTTCACTGCATTCTAGTTGTGGTTTG
TCGAATATTACCAATGTTTATTTCGTTATCGTAGTGTTTAAAGTGTTTATTTCGTAAAAAAAGTGACGTAAGATCAACACCAAAC

6035

RYBxO8mRbwMFOFCf7oNIW1BYMn0.1515186099985.7
RYBxO8mRbwMFOFCf7oNIW1BYMn0.1520442556934.5
RYBxO8mRbwMFOFCf7oNIW1BYMn0.1520442825118.21
CGCGCAGCGGCCGACCATGGCCCAACTTGTTTATTGCAGCTTATAAT...
Digestion of SV40pA from pAAV lacZ - Fragment 2...
Extracted region from SV40pA from pAAV lacZ FIG. 4AC
Continued

```
CGTAGATAAGTAGCATGGCGGGTTAATCATTAACTACAAGGAACCCCTAGTGATGGAGTTGGCCACTCCCTCTCTGCGCGCTCGC
++++++++++++++++++++++++++++++++++++++++++++++++++++++++++++++++++++++++++++++++++++
GCATCTATTCATCGTACCGCCCAATTAGTAATTGATGTTCCTTGGGGATCACTACCTCAACCGGTGAGGGAGAGACGCGCGAGCG
```
6205

RYBxO8mRbwMFOFCf7oNIW1BYMn0.1515186099985.7

| Digestion of pAAV-TRE3G-OSK-WPRE3-SV40pA - Frag... |
| RYBxO8mRbwMFOFCf7oNIW1BYMn0.1515185884933.5 |
| RYBxO8mRbwMFOFCf7oNIW1BYMn0.1515186099985.7 |
| RYBxO8mRbwMFOFCf7oNIW1BYMn0.1515186141081.10 |
| RYBxO8mRbwMFOFCf7oNIW1BYMn0.1515186313796.12 |
| RYBxO8mRbwMFOFCf7oNIW1BYMn0.1492697902333.2 |
| RYBxO8mRbwMFOFCf7oNIW1BYMn0.1513097172637.1 |
| Extracted region from pAAV-Ubc-EGFP-WPRE3-SV40L... |
| RYBxO8mRbwMFOFCf7oNIW1BYMn0.1520442556934.5 |
| RYBxO8mRbwMFOFCf7oNIW1BYMn0.1520442825118.21 |
| ITR 3' |

FIG. 4AE

```
TCGCTCACTGAGGCCGGGCGACCAAAGGTCGCCCGACGCCCGGGCTTTGCCCGGGCGGCCTCAGTGAGCGAGCGAGCGCGCAGCC
++++++++++++++++++++++++++++++++++++++++++++++++++++++++++++++++++++++++++++++++++++
AGCGAGTGACTCCGGCCCGCTGGTTTCCAGCGGGCTGCGGGCCCGAAACGGGCCCGCCGGAGTCACTCGCTCGCTCGCGCGTCGG
```
6290

RYBxO8mRbwMFOFCf7oNIW1BYMn0.1515186099985.7

Digestion of pAAV-TRE3G-OSK-WPRE3-SV40pA - Frag...

RYBxO8mRbwMFOFCf7oNIW1BYMn0.1515185884933.5

RYBxO8mRbwMFOFCf7oNIW1BYMn0.1515186099985.7

RYBxO8mRbwMFOFCf7oNIW1BYMn0.1515186141081.10

RYBxO8mRbwMFOFCf7oNIW1BYMn0.1515186313796.12

RYBxO8mRbwMFOFCf7oNIW1BYMn0.1492697902333.2

RYBxO8mRbwMFOFCf7oNIW1BYMn0.1513097172637.1

RYBxO8... RYBxO8mRbwMFOFCf7oNIW1BYMn0.1...

RYBxO8mRbwMFOFCf7oNIW1BYMn0.1520442556934.5

RYBxO8... RYBxO8mRbwMFOFCf7oNIW1BYMn0.1...

RYBxO8mRbwMFOFCf7oNIW1BYMn0.1520442825118.21

Extracted region from pAAV-Ubc-EGFP-WPRE3-SV40L...

ITR 3'

FIG. 4AE
Continued

```
TTAATTAACCTAATTCACTGGCCGTCGTTTTACAACGTCGTGACTGGGAAAACCCTGGCGTTACCCAACTTAATCGCCTTGCAGC
AATTAATTGGATTAAGTGACCGGCAGCAAAATGTTGCAGCACTGACCCTTTTGGGACCGCAATGGGTTGAATTAGCGGAACGTCG
```
6375

RYBxO8mRbwMFOFCf7oNIW1BYMn0.1515186099985.7

Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...

ITR 3'

```
ACATCCCCCTTTCGCCAGCTGGCGTAATAGCGAAGAGGCCCGCACCGATCGCCCTTCCCAACAGTTGCGCAGCCTGAATGGCGAA
TGTAGGGGGAAAGCGGTCGACCGCATTATCGCTTCTCCGGGCGTGGCTAGCGGGAAGGGTTGTCAACGCGTCGGACTTACCGCTT
```
6460

RYBxO8mRbwMFOFCf7oNIW1BYMn0.1515186099985.7

Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...

FIG. 4AF

TGGGACGCGCCCTGTAGCGGCGCATTAAGCGCGGCGGGTGTGGTGGTTACGCGCAGCGTGACCGCTACACTTGCCAGCGCCCTAG 6545
ACCCTGCGCGGGACATCGCCGCGTAATTCGCGCCGCCCACACCACCAATGCGCGTCGCACTGGCGATGTGAACGGTCGCGGGATC

RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
f1_origin CGCCCGCTCCTTTCGCTTTCTTCCCTTCCTTTCTGCCACGTTCGCCGGCTTTCCCCGTCAAGCTCTAAATCGGGGGCTCCCTTT 6630
GCGGGCGAGGAAAGCGAAAGAAGGGAAGGAAAGAGCGGTGCAAGCGGCCGAAAGGGGCAGTTCGAGATTTAGCCCCCGAGGGAAA RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
f1_origin

FIG. 4AG

```
AGGGTTCCGATTTAGTGCTTTACGGCACCTCGACCCCAAAAAACTTGATTAGGGTGATGGTTCACGTAGTGGGCCATCGCCCTGA
TCCCAAGGCTAAATCACGAAATGCCGTGGAGCTGGGGTTTTTTGAACTAATCCCACTACCAAGTGCATCACCCGGTAGCGGGACTa
```
6715

RYBxO8mRbwMFOFCf7oNIW1BYMn0.1515186099985.7

| Digestion of pAAV-TRE3G-OSK-WPRE3-SV40pA - Frag... |
| RYBxO8mRbwMFOFCf7oNIW1BYMn0.1515185884933.5 |
| RYBxO8mRbwMFOFCf7oNIW1BYMn0.1515186099985.7 |
| RYBxO8mRbwMFOFCf7oNIW1BYMn0.1515186141081.10 |
| RYBxO8mRbwMFOFCf7oNIW1BYMn0.1515186313796.12 |
| RYBxO8mRbwMFOFCf7oNIW1BYMn0.1492697902333.2 |
| RYBxO8mRbwMFOFCf7oNIW1BYMn0.1513097172637.1 |
| RYBxO8mRbwMFOFCf7oNIW1BYMn0.1520442557010.7 |
| RYBxO8mRbwMFOFCf7oNIW1BYMn0.1520442825190.23 |
| Extracted region from pAAV-Ubc-EGFP-WPRE3-SV40L... |
| f1_origin |

```
TAGACGGTTTTTCGCCCTTTGACGTTGGAGTCCACGTTCTTTAATAGTGGACTCTTGTTCCAAACTGGAACAACACTCAACCCTA
ATCTGCCAAAAAGCGGGAAACTGCAACCTCAGGTGCAAGAAATTATCACCTGAGAACAAGGTTTGACCTTGTTGTGAGTTGGGAT
```
6800

RYBxO8mRbwMFOFCf7oNIW1BYMn0.1515186099985.7

| Digestion of pAAV-TRE3G-OSK-WPRE3-SV40pA - Frag... |
| RYBxO8mRbwMFOFCf7oNIW1BYMn0.1515185884933.5 |
| RYBxO8mRbwMFOFCf7oNIW1BYMn0.1515186099985.7 |
| RYBxO8mRbwMFOFCf7oNIW1BYMn0.1515186141081.10 |
| RYBxO8mRbwMFOFCf7oNIW1BYMn0.1515186313796.12 |
| RYBxO8mRbwMFOFCf7oNIW1BYMn0.1492697902333.2 |
| RYBxO8mRbwMFOFCf7oNIW1BYMn0.1513097172637.1 |
| RYBxO8mRbwMFOFCf7oNIW1BYMn0.1520442557010.7 |
| RYBxO8mRbwMFOFCf7oNIW1BYMn0.1520442825190.23 |
| Extracted region from pAAV-Ubc-EGFP-WPRE3-SV40L... |
| f1_origin |

FIG. 4AH

```
TCTCGGTCTATTCTTTTGATTTATAAGGGATTTTGCCGATTTCGGCCTATTGGTTAAAAAATGAGCTGATTTAACAAAAATTTAA
++++++++++++++++++++++++++++++++++++++++++++++++++++++++++++++++++++++++++++++++++++++
AGAGCCAGATAAGAAAACTAAATATTCCCTAAAACGGCTAAAGCCGGATAACCAATTTTTTACTCGACTAAATTGTTTTTAAATT
```
6885

RYBxO8mRbwMFOFCf7oNIW1BYMn0.1515186099985.7
- Digestion of pAAV-TRE3G-OSK-WPRE3-SV40pA - Frag...
- RYBxO8mRbwMFOFCf7oNIW1BYMn0.1515185884933.5
- RYBxO8mRbwMFOFCf7oNIW1BYMn0.1515186099985.7
- RYBxO8mRbwMFOFCf7oNIW1BYMn0.1515186141081.10
- RYBxO8mRbwMFOFCf7oNIW1BYMn0.1515186313796.12
- RYBxO8mRbwMFOFCf7oNIW1BYMn0.1492697902333.2
- RYBxO8mRbwMFOFCf7oNIW1BYMn0.1513097172637.1
- RYBxO8mRbwMFOFCf7oNIW1BYMn0.1520442557010.7
- RYBxO8mRbwMFOFCf7oNIW1BYMn0.1520442825190.23
- Extracted region from pAAV-Ubc-EGFP-WPRE3-SV40L...

```
CGCGAATTTTAACAAAATATTAACGTTTATAATTTCAGGTGGCATCTTTCGGGGAAATGTGCGCGGAACCCCTATTTGTTTATTT
++++++++++++++++++++++++++++++++++++++++++++++++++++++++++++++++++++++++++++++++++++++
GCGCTTAAAATTGTTTTATAATTGCAAATATTAAAGTCCACCGTAGAAAGCCCCTTTACACGCGCCTTGGGGATAAACAAATAAA
```
6970

RYBxO8mRbwMFOFCf7oNIW1BYMn0.1515186099985.7
- Digestion of pAAV-TRE3G-OSK-WPRE3-SV40pA - Frag...
- RYBxO8mRbwMFOFCf7oNIW1BYMn0.1515185884933.5
- RYBxO8mRbwMFOFCf7oNIW1BYMn0.1515186099985.7
- RYBxO8mRbwMFOFCf7oNIW1BYMn0.1515186141081.10
- RYBxO8mRbwMFOFCf7oNIW1BYMn0.1515186313796.12
- RYBxO8mRbwMFOFCf7oNIW1BYMn0.1492697902333.2
- RYBxO8mRbwMFOFCf7oNIW1BYMn0.1513097172637.1
- RYBxO8mRbwMFOFCf7oNIW1BYMn0.1520442557010.7
- RYBxO8mRbwMFOFCf7oNIW1BYMn0.1520442825190.23
- Extracted region from pAAV-Ubc-EGFP-WPRE3-SV40L...

AGTAAAAGATGCTGAAGATCAGTTGGGTGCACGAGTGGGTTACATCGAACTGGATCTCAATAGTGGTAAGATCCTTGAGAGTTTT
TCATTTTCTACGACTTCTAGTCAACCCACGTGCTCACCCAATGTAGCTTGACCTAGAGTTATCACCATTCTAGGAACTCTCAAAA
7225

RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
AmpR CGCCCCGAAGAACGTTTTCCAATGATGAGCACTTTTAAAGTTCTGCTATGTGGCGCGGTATTATCCCGTATTGACGCCGGGCAAG
GCGGGGCTTCTTGCAAAAGGTTACTACTCGTGAAAATTTCAAGACGATACACCGCGCCATAATAGGGCATAACTGCGGCCCGTTC
7310

RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
AmpR

FIG. 4AK

ScaI

AGCAACTCGGTCGCCGCATACACTATTCTCAGAATGACTTGGTTGAGTACTCACCAGTCACAGAAAAGCATCTTACGGATGGCAT 7395
TCGTTGAGCCAGCGGCGTATGTGATAAGAGTCTTACTGAACCAACTCATGAGTGGTCAGTGTCTTTTCGTAGAATGCCTACCGTA

RYBxO8mRbwMFOFCf7oNIW1BYMn0.1515186099985.7

Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
AmpR

GACAGTAAGAGAA 3'
CTGTCATTCTCTT 5'   7408

Digestion of...
RYBxO8mRb...
RYBxO8mRb...
RYBxO8mRb...
RYBxO8mRb...
RYBxO8mRb...
RYBxO8mRb...
RYBxO8mRb...
RYBxO8mRb...
Extracted...
AmpR

FIG. 4AL

| Feature | Location | Size | | | Type |
|---|---|---|---|---|---|
| ✓ Extracted region from pAAV-TRE3... | 1 .. 1893 | 1893 bp | | → | misc_feature |
| ✓ pBR322_origin | 659 .. 1278 | 620 bp | | → | rep_origin |
| /direction | = RIGHT | | | | |
| ✓ CGG | 1308 .. 1310 | 3 bp | | ⊢⊣ | misc_feature |
| ✓ ITR | 1692 .. 1832 | 141 bp | | → | repeat_region |
| ✓ RYBxO8mRbwMFOFCf7oNIW1BY... | 1734 .. 1744 | 11 bp | | → | misc_feature |
| ✓ RYBxO8mRbwMFOFCf7oNIW1BY... | 1734 .. 1744 | 11 bp | | → | misc_feature |
| ✓ RYBxO8mRbwMFOFCf7oNIW1BY... | 1745 .. 3410 | 1666 bp | | → | misc_feature |
| ✓ RYBxO8mRbwMFOFCf7oNIW1BY... | 1745 .. 3410 | 1666 bp | | → | misc_feature |
| ✓ EcoRI site | 1893 .. 1897 | 5 bp | | → | misc_feature |
| ✓ RYBxO8mRbwMFOFCf7oNIW1BY... | 1893 .. 1897 | 5 bp | | → | misc_feature |
| ✓ RYBxO8mRbwMFOFCf7oNIW1BY... | 1893 .. 1897 | 5 bp | | → | misc_feature |
| ✓ RYBxO8mRbwMFOFCf7oNIW1BY... | 1893 .. 1893 | 1 bp | | → | misc_feature |
| ✓ Digestion of pAAV-TRE3G-OSK-W... | 1894 .. 5911 | 4018 bp | | → | misc_feature |
| ✓ RYBxO8mRbwMFOFCf7oNIW1BY... | 1894 .. 5907 | 4014 bp | | → | misc_feature |
| ✓ RYBxO8mRbwMFOFCf7oNIW1BY... | 1894 .. 2375 | 482 bp | | → | misc_feature |
| ✓ RYBxO8mRbwMFOFCf7oNIW1BY... | 1894 .. 2282 | 389 bp | | → | misc_feature |
| ✓ GTACACGCCTACCTCGACCCATCAA... | 1894 .. 2279 | 386 bp | | ⊢⊣ | misc_feature |
| ✓ RYBxO8mRbwMFOFCf7oNIW1BY... | 1894 .. 2276 | 383 bp | | → | misc_feature |
| ✓ EcoRI site | 1894 .. 1898 | 5 bp | | → | misc_feature |
| ✓ Extracted region from pAAV-TRE-E... | 1894 .. 1898 | 5 bp | | → | misc_feature |
| ✓ RYBxO8mRbwMFOFCf7oNIW1BY... | 1894 .. 1898 | 5 bp | | → | misc_feature |
| ✓ RYBxO8mRbwMFOFCf7oNIW1BY... | 1894 .. 1898 | 5 bp | | → | misc_feature |
| ✓ Ligation | 1894 .. 1897 | 4 bp | | ⊢⊣ | misc_feature |
| ✓ Extracted region from pTRE3G | 1899 .. 2274 | 376 bp | | → | misc_feature |
| ✓ TRE3G\Promoter | 1899 .. 2274 | 376 bp | | → | misc_feature |

FIG. 5A

| | | | | | | |
|---|---|---|---|---|---|---|
| ✓ tetO | 1904 .. 1922 | 19 bp | ☐ | → | regulatory |
| ✓ tetO | 1940 .. 1958 | 19 bp | ☐ | → | regulatory |
| ✓ tetO | 1976 .. 1994 | 19 bp | ☐ | → | regulatory |
| ✓ tetO | 2012 .. 2030 | 19 bp | ☐ | → | regulatory |
| ✓ tetO | 2048 .. 2066 | 19 bp | ☐ | → | regulatory |
| ✓ qPCR-fwd-TRE3G | 2066 .. 2091 | 26 bp | ▨ | → | primer_bind |
| ✓ tetO | 2084 .. 2102 | 19 bp | ☐ | → | regulatory |
| ✓ tetO | 2120 .. 2138 | 19 bp | ☐ | → | regulatory |
| ✓ Modified Minimal CMV Promoter | 2147 .. 2214 | 68 bp | ☐ | → | promoter |
| ✓ qPCR-rev-TRE3G | 2246 .. 2266 | 21 bp | ▨ | → | primer_bind |
| ✓ NotI site | 2275 .. 2282 | 8 bp | ▨ | → | misc_feature |
| ✓ Extracted region from pAAV-TRE-E... | 2275 .. 2276 | 2 bp | ▨ | → | misc_feature |
| ✓ RYBxO8mRbwMFOFCf7oNIW1BY... | 2275 .. 2276 | 2 bp | ▨ | → | misc_feature |
| ✓ RYBxO8mRbwMFOFCf7oNIW1BY... | 2275 .. 2276 | 2 bp | ▨ | → | misc_feature |
| ✓ RYBxO8mRbwMFOFCf7oNIW1BY... | 2277 .. 5907 | 3631 bp | ▨ | → | misc_feature |
| ✓ RYBxO8mRbwMFOFCf7oNIW1BY... | 2277 .. 2375 | 99 bp | ▨ | → | misc_feature |
| ✓ Extracted region from pAAV-CAG-... | 2277 .. 2282 | 6 bp | ▨ | → | misc_feature |
| ✓ RYBxO8mRbwMFOFCf7oNIW1BY... | 2277 .. 2280 | 4 bp | ▨ | → | misc_feature |
| ✓ RYBxO8mRbwMFOFCf7oNIW1BY... | 2277 .. 2280 | 4 bp | ▨ | → | misc_feature |
| ✓ Extracted region from pAAV-TRE3... | 2283 .. 5907 | 3625 bp | ▨ | → | misc_feature |
| ✓ RYBxO8mRbwMFOFCf7oNIW1BY... | 2283 .. 5907 | 3625 bp | ▨ | → | misc_feature |

FIG. 5B

| Feature | Location | Size | | | Type |
|---|---|---|---|---|---|
| ✓ ORF frame 3 | 2292 .. 5901 | 3610 bp | | → | CDS |
| ✓ Oct4 | 2292 .. 3344 | 1053 bp | | → | exon |
| ✓ Oct reverse | 2349 .. 2382 | 34 bp | | ← | misc_feature |
| ✓ RYBxO8mRbwMFOFCf7oNIW1BY... | 2376 .. 5911 | 3536 bp | | → | misc_feature |
| ✓ RYBxO8mRbwMFOFCf7oNIW1BY... | 2376 .. 5907 | 3532 bp | | → | misc_feature |
| ✓ p2a | 2414 .. 2422 | 9 bp | | ← | modified_base |
| ✓ Oct4-fwd | 3268 .. 3289 | 22 bp | | → | primer_bind |
| ✓ P2A | 3360 .. 3417 | 58 bp | | → | intron |
| ✓ RYBxO8mRbwMFOFCf7oNIW1BY... | 3411 .. 3585 | 175 bp | | → | misc_feature |
| ✓ RYBxO8mRbwMFOFCf7oNIW1BY... | 3411 .. 3585 | 175 bp | | → | misc_feature |
| ✓ Sox2 | 3423 .. 4379 | 957 bp | | → | exon |
| ✓ Sox2-reverse | 3512 .. 3535 | 24 bp | | ← | misc_feature |
| ✓ RYBxO8mRbwMFOFCf7oNIW1BY... | 3586 .. 3979 | 394 bp | | → | misc_feature |
| ✓ RYBxO8mRbwMFOFCf7oNIW1BY... | 3586 .. 3979 | 394 bp | | → | misc_feature |
| ✓ RYBxO8mRbwMFOFCf7oNIW1BY... | 3980 .. 4924 | 945 bp | | → | misc_feature |
| ✓ RYBxO8mRbwMFOFCf7oNIW1BY... | 3980 .. 4924 | 945 bp | | → | misc_feature |
| ✓ sox2-fwd | 4306 .. 4329 | 24 bp | | → | primer_bind |
| ✓ Klf4 | 4455 .. 5901 | 1447 bp | | → | exon |
| ✓ Klf4-rev | 4517 .. 4540 | 24 bp | | ← | misc_feature |
| ✓ Klf4-mid-fwd | 4914 .. 4937 | 24 bp | | → | primer_bind |
| ✓ RYBxO8mRbwMFOFCf7oNIW1BY... | 4925 .. 6246 | 1322 bp | | → | misc_feature |
| ✓ RYBxO8mRbwMFOFCf7oNIW1BY... | 4925 .. 6246 | 1322 bp | | → | misc_feature |
| ✓ Stop codon | 5901 .. 5903 | 3 bp | | → | terminator |
| ✓ TTCTCGAGGGCTCGGGCCAGTGTAC... | 5902 .. 5908 | 7 bp | | ↔ | misc_feature |
| ✓ RYBxO8mRbwMFOFCf7oNIW1BY... | 5908 .. 2276 | 3777 bp | | → | misc_feature |
| ▸ 2 segments | | | | | |
| ✓ CGCGCAGCGGCCGACCATGGCCCA... | 5908 .. 6084 | 177 bp | | ↔ | misc_feature |

FIG. 5C

| Feature | Location | Size | | | Type |
|---|---|---|---|---|---|
| ✓ Digestion of SV40pA from pAAV la... | 5908 .. 6084 | 177 bp | | → | misc_feature |
| ✓ Extracted region from SV40pA fro... | 5908 .. 6080 | 173 bp | | → | misc_feature |
| ✓ Ligation | 5908 .. 5911 | 4 bp | | ↔ | misc_feature |
| ✓ Digestion of pAAV-TRE3G-OSK-W... | 6081 .. 9305 | 3225 bp | | → | misc_feature |
| ✓ RYBxO8mRbwMFOFCf7oNIW1BY... | 6081 .. 9305 | 3225 bp | | → | misc_feature |
| ✓ RYBxO8mRbwMFOFCf7oNIW1BY... | 6081 .. 9305 | 3225 bp | | → | misc_feature |
| ✓ RYBxO8mRbwMFOFCf7oNIW1BY... | 6081 .. 9305 | 3225 bp | | → | misc_feature |
| ✓ RYBxO8mRbwMFOFCf7oNIW1BY... | 6081 .. 9301 | 3221 bp | | → | misc_feature |
| ✓ RYBxO8mRbwMFOFCf7oNIW1BY... | 6081 .. 9300 | 3220 bp | | → | misc_feature |
| ✓ Extracted region from pAAV-Ubc-E... | 6081 .. 7408 | 1328 bp | | → | misc_feature |
| ✓ RYBxO8mRbwMFOFCf7oNIW1BY... | 6081 .. 6098 | 18 bp | | → | misc_feature |
| ✓ Ligation | 6081 .. 6084 | 4 bp | | ↔ | misc_feature |
| ✓ RYBxO8mRbwMFOFCf7oNIW1BY... | 6099 .. 9305 | 3207 bp | | → | misc_feature |
| ✓ ITR 3' | 6159 .. 6298 | 140 bp | | → | misc_feature |
| ✓ RYBxO8mRbwMFOFCf7oNIW1BY... | 6247 .. 6257 | 11 bp | | → | misc_feature |
| ✓ RYBxO8mRbwMFOFCf7oNIW1BY... | 6247 .. 6257 | 11 bp | | → | misc_feature |
| ✓ RYBxO8mRbwMFOFCf7oNIW1BY... | 6258 .. 9141 | 2884 bp | | → | misc_feature |
| ✓ RYBxO8mRbwMFOFCf7oNIW1BY... | 6258 .. 9141 | 2884 bp | | → | misc_feature |
| ✓ f1_origin | 6482 .. 6788 | 307 bp | | → | rep_origin |
| /direction | = RIGHT | | | | |
| ✓ AmpR | 7052 .. 7912 | 861 bp | | → | misc_feature |

FIG. 5D

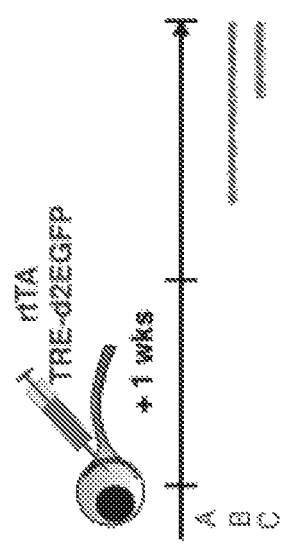
FIG. 11C
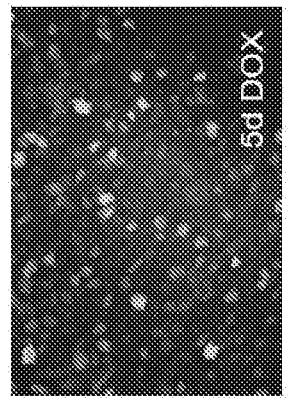
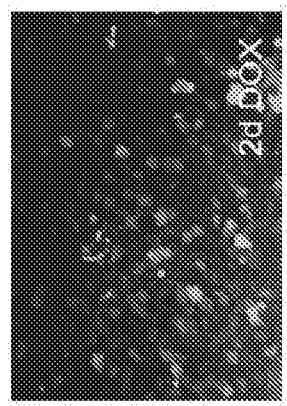
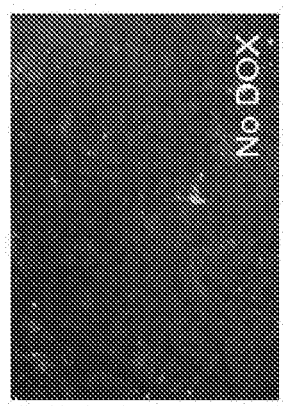
FIG. 11D

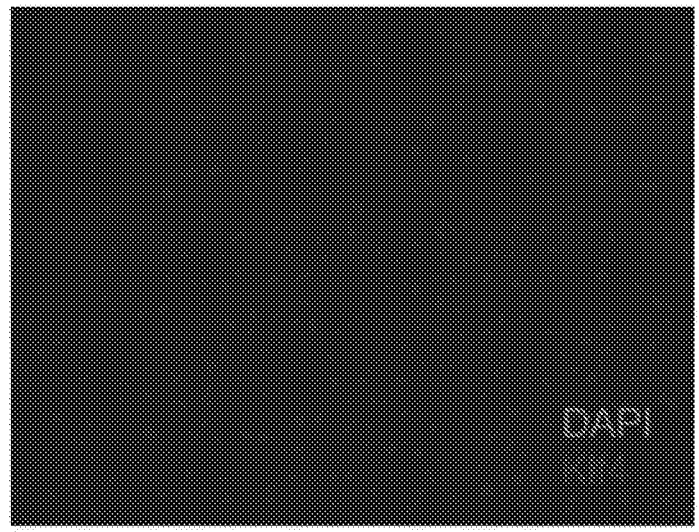
rtTA4 TRE-OSK no DOX
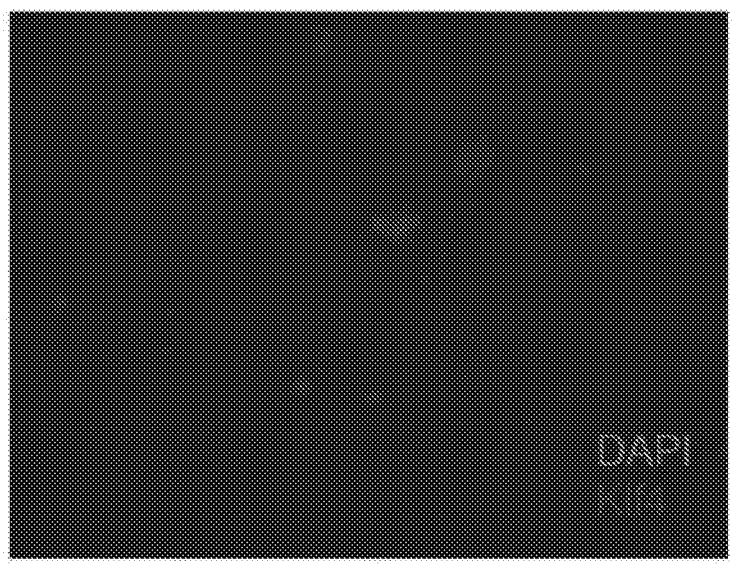
rtTA4 TRE-OSK with DOX
FIG. 13A

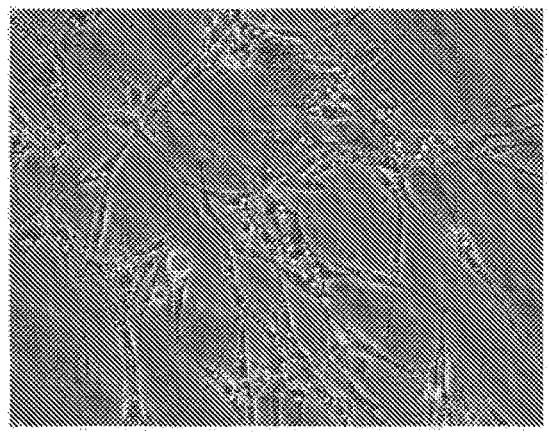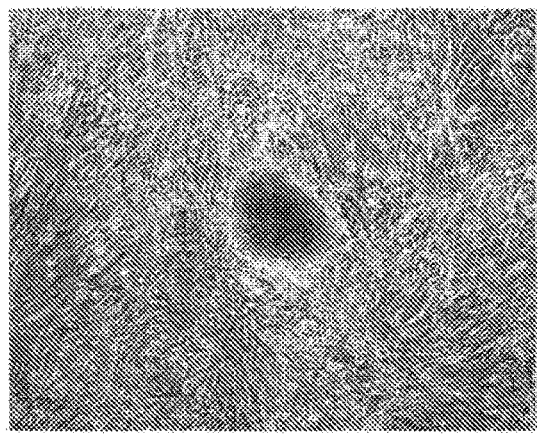
30m FBs after 3d treatment     WT MEFs after 23d treatment
FIG. 21

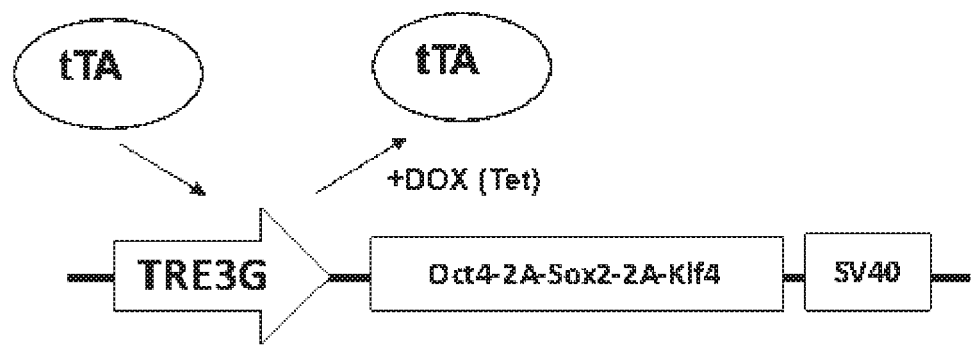
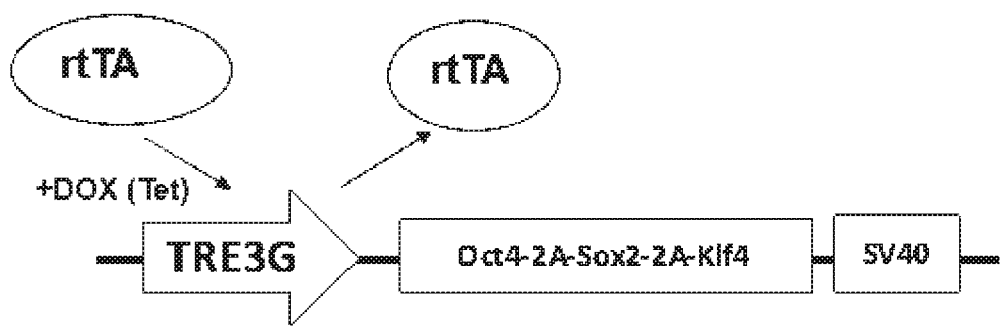
FIG. 22

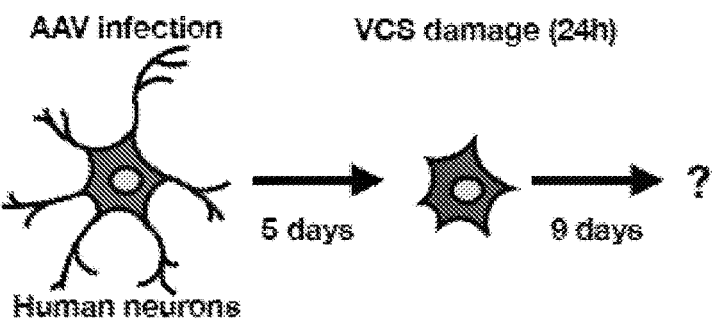
FIG. 33G
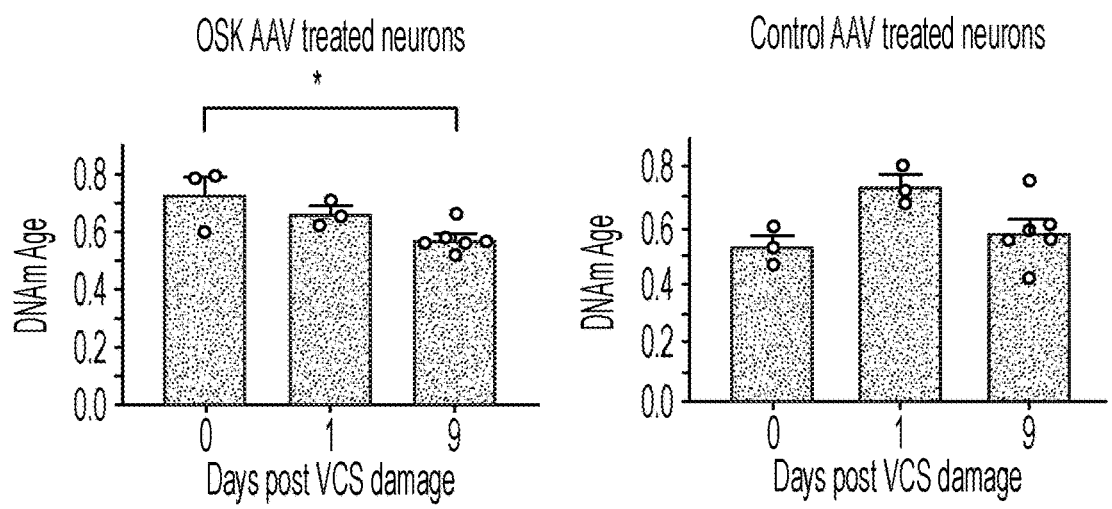
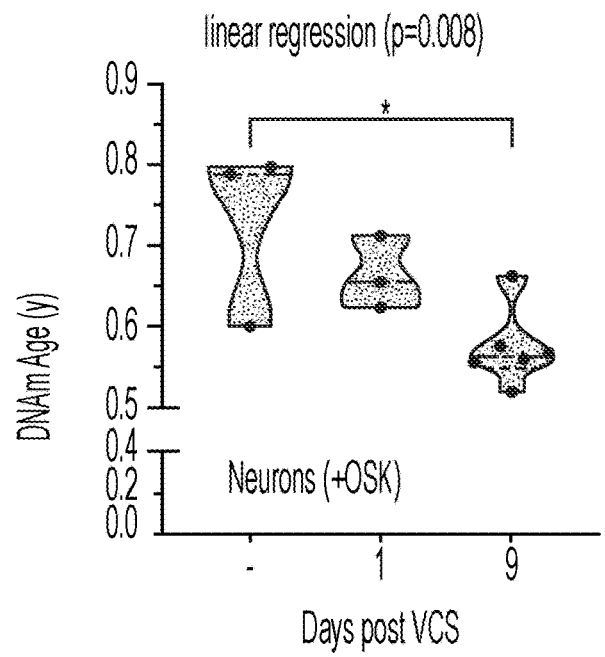
FIG. 33H

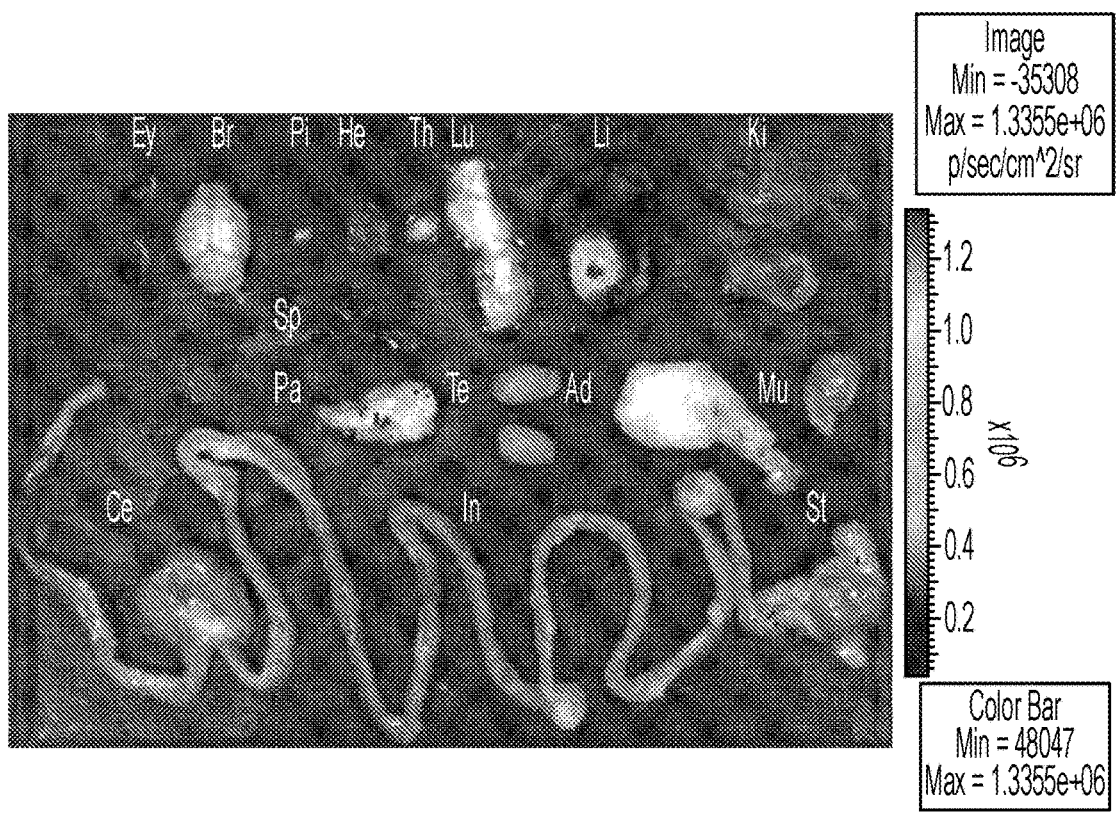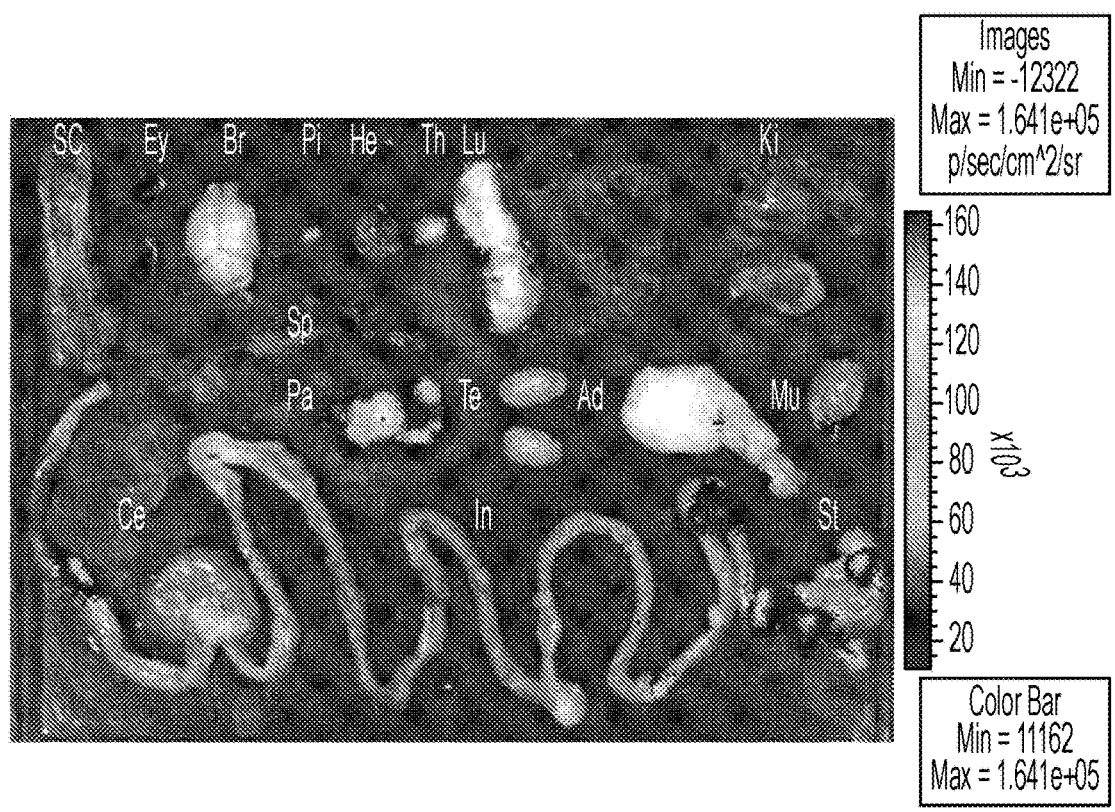
FIG. 36H

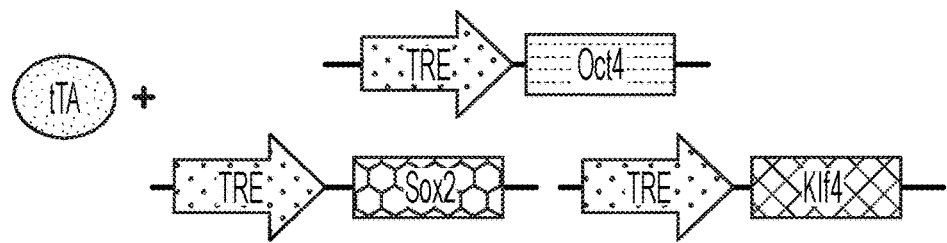
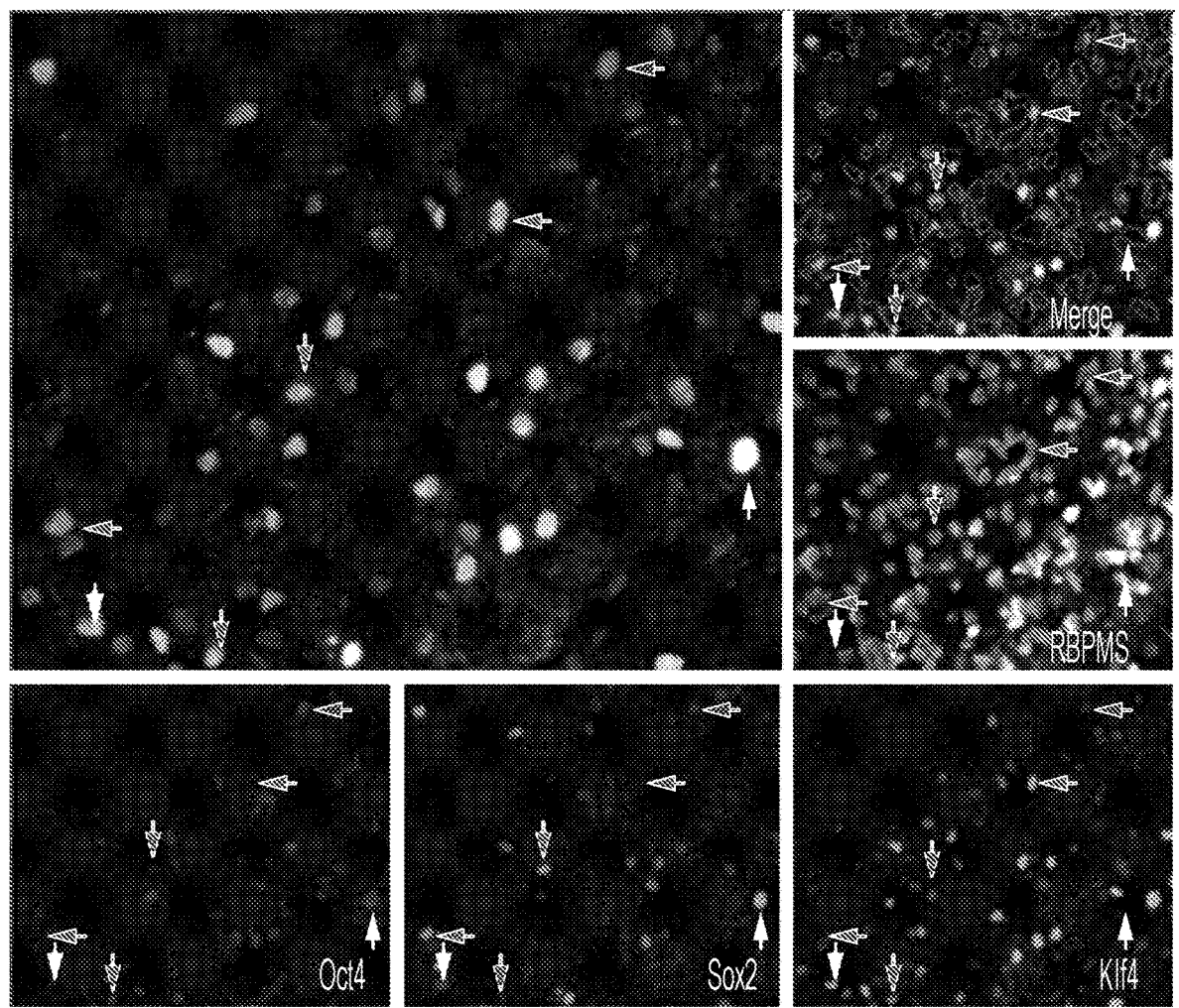
FIG. 37B

SEQUENCE LISTING

```
<160> NUMBER OF SEQ ID NOS: 122

<210> SEQ ID NO 1
<211> LENGTH: 1056
<212> TYPE: DNA
<213> ORGANISM: Mus musculus

<400> SEQUENCE: 1
atggctggac acctggcttc agacttcgcc ttctcacccc caccaggtgg gggtgatggg      60
tcagcagggc tggagccggg ctgggtggat cctcgaacct ggctaagctt ccaagggcct     120
ccaggtgggc ctggaatcgg accaggctca gaggtattgg ggatctcccc atgtccgccc     180
gcatacgagt tctgcggagg gatggcatac tgtggacctc aggttggact gggcctagtc     240
ccccaagttg gcgtggagac tttgcagcct gagggccagg caggagcacg agtggaaagc     300
aactcagagg gaacctcctc tgagccctgt gccgaccgcc ccaatgccgt gaagttggag     360
aaggtggaac caactcccga ggagtcccag gacatgaaag ccctgcagaa ggagctagaa     420
cagtttgcca agctgctgaa gcagaagagg atcaccttgg ggtacaccca ggccgacgtg     480
gggctcaccc tgggcgttct ctttggaaag gtgttcagcc agaccaccat ctgtcgcttc     540
gaggccttgc agctcagcct taagaacatg tgtaagctgc ggcccctgct ggagaagtgg     600
gtggaggaag ccgacaacaa tgagaacctt caggagatat gcaaatcgga gaccctggtg     660
caggcccgga agagaaagcg aactagcatt gagaaccgtg tgaggtggag tctggagacc     720
atgtttctga agtgcccgaa gccctcccta cagcagatca ctcacatcgc caatcagctt     780
gggctagaga aggatgtggt tcgagtatgg ttctgtaacc ggcgccagaa gggcaaaaga     840
tcaagtattg agtattccca acgagaagag tatgaggcta cagggacacc tttcccaggg     900
ggggctgtat cctttcctct gccccaggt ccccactttg gcacccagg ctatggaagc      960 ccccacttca ccacactcta ctcagtccct tttcctgagg gcgaggcctt tccctctgtt    1020
cccgtcactg ctctgggctc tcccatgcat tcaaac                              1056

<210> SEQ ID NO 2
<211> LENGTH: 352
<212> TYPE: PRT
```

<213> ORGANISM: Mus musculus

<400> SEQUENCE: 2

| | | | | | | | | | | | | | | |
|---|---|---|---|---|---|---|---|---|---|---|---|---|---|---|
| Met | Ala | Gly | His | Leu | Ala | Ser | Asp | Phe | Ala | Phe | Ser | Pro | Pro | Gly |
| 1 | | | | 5 | | | | | 10 | | | | | 15 |
| Gly | Gly | Asp | Gly | Ser | Ala | Gly | Leu | Glu | Pro | Gly | Trp | Val | Asp | Pro | Arg |
| | | | 20 | | | | | 25 | | | | | 30 | | |
| Thr | Trp | Leu | Ser | Phe | Gln | Gly | Pro | Gly | Gly | Pro | Gly | Ile | Gly | Pro |
| | | | 35 | | | | | 40 | | | | | 45 | |
| Gly | Ser | Glu | Val | Leu | Gly | Ile | Ser | Pro | Cys | Pro | Ala | Tyr | Glu | Phe |
| 50 | | | | | 55 | | | | | 60 | | | | |
| Cys | Gly | Gly | Met | Ala | Tyr | Cys | Gly | Pro | Gln | Val | Gly | Leu | Gly | Leu | Val |
| 65 | | | | 70 | | | | | 75 | | | | | 80 |
| Pro | Gln | Val | Gly | Val | Glu | Thr | Leu | Gln | Pro | Glu | Gly | Gln | Ala | Gly | Ala |
| | | | | 85 | | | | | 90 | | | | | 95 | |
| Arg | Val | Glu | Ser | Asn | Ser | Glu | Gly | Thr | Ser | Ser | Glu | Pro | Cys | Ala | Asp |
| | | | | 100 | | | | | 105 | | | | | 110 | |
| Arg | Pro | Asn | Ala | Val | Lys | Leu | Glu | Lys | Val | Glu | Pro | Thr | Pro | Glu | Glu |
| | | | 115 | | | | | 120 | | | | | 125 | | |
| Ser | Gln | Asp | Met | Lys | Ala | Leu | Gln | Lys | Glu | Leu | Glu | Gln | Phe | Ala | Lys |
| | 130 | | | | | 135 | | | | | 140 | | | | |
| Leu | Leu | Lys | Gln | Lys | Arg | Ile | Thr | Leu | Gly | Tyr | Thr | Gln | Ala | Asp | Val |
| 145 | | | | | 150 | | | | | 155 | | | | | 160 |
| Gly | Leu | Thr | Leu | Gly | Val | Leu | Phe | Gly | Lys | Val | Phe | Ser | Gln | Thr | Thr |
| | | | | 165 | | | | | 170 | | | | | 175 | |
| Ile | Cys | Arg | Phe | Glu | Ala | Leu | Gln | Leu | Ser | Leu | Lys | Asn | Met | Cys | Lys |
| | | | | 180 | | | | | 185 | | | | | 190 | |
| Leu | Arg | Pro | Leu | Leu | Glu | Lys | Trp | Val | Glu | Glu | Ala | Asp | Asn | Asn | Glu |
| | | | 195 | | | | | 200 | | | | | 205 | | |
| Asn | Leu | Gln | Glu | Ile | Cys | Lys | Ser | Glu | Thr | Leu | Val | Gln | Ala | Arg | Lys |
| | 210 | | | | | 215 | | | | | 220 | | | | |
| Arg | Lys | Arg | Thr | Ser | Ile | Glu | Asn | Arg | Val | Arg | Trp | Ser | Leu | Glu | Thr |
| 225 | | | | | 230 | | | | | 235 | | | | | 240 |
| Met | Phe | Leu | Lys | Cys | Pro | Lys | Pro | Ser | Leu | Gln | Gln | Ile | Thr | His | Ile |
| | | | | 245 | | | | | 250 | | | | | 255 | |
| Ala | Asn | Gln | Leu | Gly | Leu | Glu | Lys | Asp | Val | Val | Arg | Val | Trp | Phe | Cys |
| | | | 260 | | | | | 265 | | | | | 270 | | |
| Asn | Arg | Arg | Gln | Lys | Gly | Lys | Arg | Ser | Ser | Ile | Glu | Tyr | Ser | Gln | Arg |
| | | 275 | | | | | 280 | | | | | 285 | | | |
| Glu | Glu | Tyr | Glu | Ala | Thr | Gly | Thr | Pro | Phe | Pro | Gly | Gly | Ala | Val | Ser |
| | 290 | | | | | 295 | | | | | 300 | | | | |
| Phe | Pro | Leu | Pro | Pro | Gly | Pro | His | Phe | Gly | Thr | Pro | Gly | Tyr | Gly | Ser |
| 305 | | | | | 310 | | | | | 315 | | | | | 320 |
| Pro | His | Phe | Thr | Thr | Leu | Tyr | Ser | Val | Pro | Phe | Pro | Glu | Gly | Glu | Ala |
| | | | | 325 | | | | | 330 | | | | | 335 | |
| Phe | Pro | Ser | Val | Pro | Val | Thr | Ala | Leu | Gly | Ser | Pro | Met | His | Ser | Asn |
| | | | 340 | | | | | 345 | | | | | 350 | | |

<210> SEQ ID NO 3
<211> LENGTH: 957
<212> TYPE: DNA
<213> ORGANISM: Mus musculus

<400> SEQUENCE: 3

```
atgtataaca tgatggagac ggagctgaag ccgccgggcc cgcagcaagc ttcgggggc      60
```

```
ggcggcggag gaggcaacgc cacggcggcg gcgaccggcg gcaaccagaa gaacagcccg      120
gaccgcgtca agaggcccat gaacgccttc atggtatggt cccggggggca gcggcgtaag     180 atggcccagg agaaccccaa gatgcacaac tcggagatca gcaagcgcct gggcgcggag      240
tggaaacttt tgtccgagac cgagaagcgg ccgttcatcg acgaggccaa gcggctgcgc      300
gctctgcaca tgaaggagca cccggattat aaataccggc cgcggcggaa aaccaagacg      360
ctcatgaaga aggataagta cacgcttccc ggaggcttgc tggcccccgg cgggaacagc      420
atggcgagcg gggttggggt gggcgccggc ctgggtgcgg gcgtgaacca gcgcatggac      480
agctacgcgc acatgaacgg ctggagcaac ggcagctaca gcatgatgca ggagcagctg      540
ggctacccgc agcacccggg cctcaacgct cacggcgcgg cacagatgca accgatgcac      600
cgctacgacg tcagcgccct gcagtacaac tccatgacca gctcgcagac ctacatgaac      660
ggctcgccca cctacagcat gtcctactcg cagcagggca cccccggtat ggcgctgggc      720
tccatgggct ctgtggtcaa gtccgaggcc agctccagcc ccccgtggt tacctcttcc       780 tcccactcca gggcgccctg ccaggccggg gacctccggg acatgatcag catgtacctc      840 cccgcgccg aggtgccgga gcccgctgcg cccagtagac tgcacatggc ccagcactac       900
cagagcggcc cggtgcccgg cacggccatt aacggcacac tgcccctgtc gcacatg        957
```

<210> SEQ ID NO 4
<211> LENGTH: 319
<212> TYPE: PRT
<213> ORGANISM: Mus musculus

<400> SEQUENCE: 4

```
Met Tyr Asn Met Met Glu Thr Glu Leu Lys Pro Pro Gly Pro Gln Gln
 1               5                  10                  15

Ala Ser Gly Gly Gly Gly Gly Gly Asn Ala Thr Ala Ala Ala Thr
                20                  25                  30

Gly Gly Asn Gln Lys Asn Ser Pro Asp Arg Val Lys Arg Pro Met Asn
            35                  40                  45

Ala Phe Met Val Trp Ser Arg Gly Gln Arg Arg Lys Met Ala Gln Glu
        50                  55                  60

Asn Pro Lys Met His Asn Ser Glu Ile Ser Lys Arg Leu Gly Ala Glu
 65                  70                  75                  80

Trp Lys Leu Leu Ser Glu Thr Glu Lys Arg Pro Phe Ile Asp Glu Ala
                 85                 90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
        115                 120                 125

Leu Pro Gly Gly Leu Leu Ala Pro Gly Gly Asn Ser Met Ala Ser Gly
    130                 135                 140

Val Gly Val Gly Ala Gly Leu Gly Ala Gly Val Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Asp Val Ser Ala Leu Gln
        195                 200                 205

Tyr Asn Ser Met Thr Ser Ser Gln Thr Tyr Met Asn Gly Ser Pro Thr
```

```
                210                 215                 220
Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Pro Pro Val
                245                 250                 255

Val Thr Ser Ser His Ser Arg Ala Pro Cys Gln Ala Gly Asp Leu
                260                 265                 270

Arg Asp Met Ile Ser Met Tyr Leu Pro Gly Ala Glu Val Pro Glu Pro
            275                 280                 285

Ala Ala Pro Ser Arg Leu His Met Ala Gln His Tyr Gln Ser Gly Pro
            290                 295                 300

Val Pro Gly Thr Ala Ile Asn Gly Thr Leu Pro Leu Ser His Met
305                 310                 315
```

<210> SEQ ID NO 5
<211> LENGTH: 1446
<212> TYPE: DNA
<213> ORGANISM: Mus musculus

<400> SEQUENCE: 5

| | |
|---|---|
| atgaggcagc cacctggcga gtctgacatg gctgtcagcg acgctctgct cccgtccttc | 60 |
| tccacgttcg cgtccggccc ggcgggaagg gagaagacac tgcgtccagc aggtgccccg | 120 |
| actaaccgtt ggcgtgagga actctctcac atgaagcgca ttcccccact tcccggccgc | 180 |
| ccctacgacc tggcggcgac ggtggccaca gacctggaga gtggcggagc tggtgcagct | 240 |
| tgcagcagta caacccggc cctcctagcc cggaggagga ccgaggagtt caacgacctc | 300 |
| ctggacctag actttatcct ttccaactcg ctaacccacc aggaatcggt ggccgccacc | 360 |
| gtgaccacct cggcgtcagc ttcatcctcg tcttccccag cgagcagcgg ccctgccagc | 420 |
| gcgccctcca cctgcagctt cagctatccg atccgggccg ggggtgaccc gggcgtggct | 480 |
| gccagcaaca caggtggagg gctcctctac agcgagaat ctgcgccacc tcccacggcc | 540 |
| cccttcaacc tggcggacat caatgacgtg agccctcgg gcggcttcgt ggctgagctc | 600 |
| ctgcggccgg agttggaccc agtatacatt ccgccacagc agcctcagcc gccaggtggc | 660 |
| gggctgatgg gcaagtttgt gctgaaggcg tctctgacca cccctggcag cgagtacagc | 720 |
| agcccttcgg tcatcagtgt tagcaaagga agcccagacg gcagccaccc cgtggtagtg | 780 |
| gcgccctaca gcggtggccc gccgcgcatg tgccccaaga ttaagcaaga ggcggtcccg | 840 |
| tcctgcacgg tcagccggtc cctagaggcc catttgagcg ctggacccca gctcagcaac | 900 |
| ggccaccggc caacacaca cgacttcccc ctggggcggc agctccccac caggactacc | 960 |
| cctacactga gtcccgagga actgctgaac agcaggact gtcaccctgg cctgcctctt | 1020 |
| cccccaggat ccatcccca tccggggccc aactaccctc ctttcctgcc agaccagatg | 1080 |
| cagtcacaag tccctctct ccattatcaa gagctcatgc caccgggttc ctgcctgcca | 1140 |
| gaggagccca gccaaagag gggaagaagg tcgtggcccc ggaaaagaac agccaccac | 1200 |
| acttgtgact atgcaggctg tgcaaaaacc tataccaaga gttctcatct caaggcacac | 1260 |
| ctgcgaactc acacaggcga gaaaccttac cactgtgact gggacggctg tgggtggaaa | 1320 |
| ttcgcccgct ccgatgaact gaccaggcac taccgcaaac acacagggca ccggcccttt | 1380 |
| cagtgccaga gtgcgacag ggccttttcc aggtcggacc accttgcctt acacatgaag | 1440 |
| aggcac | 1446 |

-continued

```
<210> SEQ ID NO 6
<211> LENGTH: 482
<212> TYPE: PRT
<213> ORGANISM: Mus musculus

<400> SEQUENCE: 6

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Pro Ala Gly Ala Pro Thr Asn Arg Trp Arg Glu Glu Leu
        35                  40                  45

Ser His Met Lys Arg Leu Pro Pro Leu Pro Gly Arg Pro Tyr Asp Leu
    50                  55                  60

Ala Ala Thr Val Ala Thr Asp Leu Glu Ser Gly Gly Ala Gly Ala Ala
65                  70                  75                  80

Cys Ser Ser Asn Asn Pro Ala Leu Leu Ala Arg Arg Glu Thr Glu Glu
                85                  90                  95

Phe Asn Asp Leu Leu Asp Leu Asp Phe Ile Leu Ser Asn Ser Leu Thr
            100                 105                 110

His Gln Glu Ser Val Ala Ala Thr Val Thr Thr Ser Ala Ser Ala Ser
        115                 120                 125

Ser Ser Ser Ser Pro Ala Ser Ser Gly Pro Ala Ser Ala Pro Ser Thr
    130                 135                 140

Cys Ser Phe Ser Tyr Pro Ile Arg Ala Gly Gly Asp Pro Gly Val Ala
145                 150                 155                 160

Ala Ser Asn Thr Gly Gly Gly Leu Leu Tyr Ser Arg Glu Ser Ala Pro
                165                 170                 175

Pro Pro Thr Ala Pro Phe Asn Leu Ala Asp Ile Asn Asp Val Ser Pro
            180                 185                 190

Ser Gly Gly Phe Val Ala Glu Leu Leu Arg Pro Glu Leu Asp Pro Val
        195                 200                 205

Tyr Ile Pro Pro Gln Gln Pro Gln Pro Pro Gly Gly Gly Leu Met Gly
    210                 215                 220

Lys Phe Val Leu Lys Ala Ser Leu Thr Thr Pro Gly Ser Glu Tyr Ser
225                 230                 235                 240

Ser Pro Ser Val Ile Ser Val Ser Lys Gly Ser Pro Asp Gly Ser His
                245                 250                 255

Pro Val Val Val Ala Pro Tyr Ser Gly Gly Pro Pro Arg Met Cys Pro
            260                 265                 270

Lys Ile Lys Gln Glu Ala Val Pro Ser Cys Thr Val Ser Arg Ser Leu
        275                 280                 285

Glu Ala His Leu Ser Ala Gly Pro Gln Leu Ser Asn Gly His Arg Pro
    290                 295                 300

Asn Thr His Asp Phe Pro Leu Gly Arg Gln Leu Pro Thr Arg Thr Thr
305                 310                 315                 320

Pro Thr Leu Ser Pro Glu Glu Leu Leu Asn Ser Arg Asp Cys His Pro
                325                 330                 335

Gly Leu Pro Leu Pro Pro Gly Phe His Pro His Pro Gly Pro Asn Tyr
            340                 345                 350

Pro Pro Phe Leu Pro Asp Gln Met Gln Ser Gln Val Pro Ser Leu His
        355                 360                 365

Tyr Gln Glu Leu Met Pro Pro Gly Ser Cys Leu Pro Glu Glu Pro Lys
    370                 375                 380
```

```
Pro Lys Arg Gly Arg Arg Ser Trp Pro Arg Lys Arg Thr Ala Thr His
385                 390                 395                 400

Thr Cys Asp Tyr Ala Gly Cys Gly Lys Thr Tyr Thr Lys Ser Ser His
                405                 410                 415

Leu Lys Ala His Leu Arg Thr His Thr Gly Glu Lys Pro Tyr His Cys
            420                 425                 430

Asp Trp Asp Gly Cys Gly Trp Lys Phe Ala Arg Ser Asp Glu Leu Thr
        435                 440                 445

Arg His Tyr Arg Lys His Thr Gly His Arg Pro Phe Gln Cys Gln Lys
        450                 455                 460

Cys Asp Arg Ala Phe Ser Arg Ser Asp His Leu Ala Leu His Met Lys
465                 470                 475                 480

Arg His

<210> SEQ ID NO 7
<211> LENGTH: 376
<212> TYPE: DNA
<213> ORGANISM: Artificial Sequence
<220> FEATURE:
<223> OTHER INFORMATION: Synthetic Polynucleotide

<400> SEQUENCE: 7
tttactccct atcagtgata gagaacgtat gaagagttta ctccctatca gtgatagaga      60
acgtatgcag actttactcc ctatcagtga tagagaacgt ataaggagtt tactccctat     120
cagtgataga gaacgtatga ccagtttact ccctatcagt gatagagaac gtatctacag     180
tttactccct atcagtgata gagaacgtat atccagttta ctccctatca gtgatagaga     240
acgtataagc tttaggcgtg tacggtgggc gcctataaaa gcagagctcg tttagtgaac     300
cgtcagatcg cctggagcaa ttccacaaca cttttgtctt ataccaactt ccgtaccac      360 ttcctaccct cgtaaa                                                     376

<210> SEQ ID NO 8
<211> LENGTH: 169
<212> TYPE: DNA
<213> ORGANISM: Artificial Sequence
<220> FEATURE:
<223> OTHER INFORMATION: Synthetic Polynucleotide

<400> SEQUENCE: 8
tgcgcgcagc ggccgaccat ggcccaactt gtttattgca gcttataatg gttacaaata      60
aagcaatagc atcacaaatt tcacaaataa agcatttttt tcactgcatt ctagttgtgg     120
tttgtccaaa ctcatcaatg tatcttatca tgtctggatc tcggtaccg                 169

<210> SEQ ID NO 9
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 9

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 10
<211> LENGTH: 708
```

```
<212> TYPE: DNA
<213> ORGANISM: Artificial Sequence
<220> FEATURE:
<223> OTHER INFORMATION: Synthetic Polynucleotide

<400> SEQUENCE: 10
atgtctaggc tggacaagag caaagtcata acggagctc tggaattact caatggtgtc      60
ggtatcgaag gcctgacgac aaggaaactc gctcaaaagc tgggagttga gcagcctacc     120
ctgtactggc acgtgaagaa caagcgggcc ctgctcgatg ccctgccaat cgagatgctg     180
gacaggcatc ataccactt ctgccccctg aaggcgagt catggcaaga ctttctgcgg       240
aacaacgcca agtcataccg ctgtgctctc ctctcacatc gcgacgggc taaagtgcat      300 ctcggcaccc gcccaacaga gaaacagtac gaaaccctgg aaaatcagct cgcgttcctg     360
tgtcagcaag gcttctccct ggagaacgca ctgtacgctc tgtccgccgt gggccacttt     420
acactgggct gcgtattgga ggaacaggag catcaagtag caaagaggag aagagagaca     480
cctaccaccg attctatgcc cccacttctg agacaagcaa ttgagctgtt cgaccggcag     540
ggagccgaac ctgccttcct tttcggcctg aactaatca tatgtggcct ggagaaacag      600
ctaaagtgcg aaagcggcgg gccgaccgac gcccttgacg attttgactt agacatgctc     660
ccagccgatg cccttgacga ttttgacctt gacatgctcc ccgggtaa                  708

<210> SEQ ID NO 11
<211> LENGTH: 235
<212> TYPE: PRT
<213> ORGANISM: Artificial Sequence
<220> FEATURE:
<223> OTHER INFORMATION: Synthetic Polypeptide

<400> SEQUENCE: 11

Met Ser Arg Leu Asp Lys Ser Lys Val Ile Asn Gly Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Arg Glu Thr
145                 150                 155                 160

Pro Thr Thr Asp Ser Met Pro Pro Leu Leu Arg Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205
```

Thr Asp Ala Leu Asp Asp Phe Asp Leu Asp Met Leu Pro Ala Asp Ala
    210                 215                 220

Leu Asp Asp Phe Asp Leu Asp Met Leu Pro Gly
225                 230                 235

<210> SEQ ID NO 12
<211> LENGTH: 747
<212> TYPE: DNA
<213> ORGANISM: Artificial Sequence
<220> FEATURE:
<223> OTHER INFORMATION: Synthetic Polynucleotide

<400> SEQUENCE: 12
atgtcccgct tggataagag caaggtaata aatagcgcac tcgaactcct caacggcgtg      60
ggcatcgaag gtctgactac tcgaaagctc gcccagaaat gggtgtgga gcaacctaca     120 ttgtattggc atgtcaagaa caaaagagcc ctgctggacg ctcttcctat tgaaatgctt     180
gacaggcatc acactcattc ctgcccccctt gaggtcgaga gttggcaaga ttttctccga     240
aacaatgcaa agtcctaccg ctgcgcactt ttgtcccata gggatggagc aaaagtgcac     300
ctgggaacca ggccaacaga gaaacaatac gagactctcg agaaccagtt ggctttcttg     360
tgccaacagg ggttctcact gaaaatgcc ctttacgcac tgtcagccgt ggacattttt     420
accctggggt gcgttcttga ggagcaagaa catcaggttg ctaaggagga gcgcgagact     480
ccaaccactg attctatgcc acctttgctg aaacaggcca ttgaactttt cgatagacag     540
ggtgctgaac ctgcctttct cttcgggttg gagctgatta tttgtggtct cgaaaaacag     600
ctgaaatgtg aaagtggtgg ccctactgac gccctcgatg atttcgacct ggatatgctg     660
ccagccgatg cacttgatga tttcgatttg gatatgcttc cagccgacgc actggacgac     720
ttcgatttgg acatgcttcc cggttaa                                        747

<210> SEQ ID NO 13
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 13

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Ser Cys Pro Leu Glu Val Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

```
Val Leu Glu Glu Gln Glu His Gln Val Ala Lys Glu Arg Glu Thr
145                 150                 155                 160

Pro Thr Thr Asp Ser Met Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
            245

<210> SEQ ID NO 14
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 14
atgcctttgt atcatgctat tgcttcccgt atggctttca ttttctcctc cttgtataaa      60
tcctggttgc tgtctcttta tgaggagttg tggcccgttg tcaggcaacg tggcgtggtg     120
tgcactgtgt ttgctgacgc aaccccccact ggttggggca ttgccaccac ctgtcagctc    180
ctttccggga cttctcgcttt ccccctccct attgccacgg cggaactcat cgccgcctgc   240
cttgcccgct gctggacagg ggctcggctg ttgggcactg acaattccgt ggtgttgtcg     300
gggaaatcat cgtcctttcc ttggctgctc gcctgtgttg ccacctggat tctgcgcggg     360
acgtccttct gctacgtccc ttcggccctc aatccagcgg accttccttc cgcggcctg     420 ctgccggctc tgcggcctct tccgcgtctt cgccttcgcc ctcagacgag tcggatctcc     480
ctttgggccg cctccccgca tcgataccgt cgacctcgag acctagaaaa acatggagca     540
atcacaagta gcaatacagc agctaccaat gctgattgtg cctggctaga agcacaagag     600
gaggaggagg tgggttttcc agtcacacct caggtacctt taagaccaat gacttacaag     660
gcagctgtag atcttagcca ctttttaaaa gaaaaggggg gactggaagg gctaattcac     720
tcccaacgaa gacaagatat ccttgatctg tggatctacc acacacaagg ctacttccct     780
gattggcaga actacacacc agggccaggg atcagatatc cactgacctt tggatggtgc     840
tacaagctag taccagttga gcaagagaag gtagaagaag ccaatgaagg agagaacacc     900
cgcttgttac accctgtgag cctgcatggg atggatgacc cggagagaga agtattagag     960
tggaggtttg acagccgcct agcatttcat cacatggccc gagagctgca tccggactgt    1020
actgggtctc tctggttaga ccagatctga                                     1050

<210> SEQ ID NO 15
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 15

Met Pro Leu Tyr His Ala Ile Ala Ser Arg Met Ala Phe Ile Phe Ser
```

```
1               5                    10                   15
Ser Leu Tyr Lys Ser Trp Leu Leu Ser Leu Tyr Glu Glu Leu Trp Pro
                20                  25                  30
Val Val Arg Gln Arg Gly Val Val Cys Thr Val Phe Ala Asp Ala Thr
                35                  40                  45
Pro Thr Gly Trp Gly Ile Ala Thr Thr Cys Gln Leu Leu Ser Gly Thr
                50                  55                  60
Phe Ala Phe Pro Leu Pro Ile Ala Thr Ala Glu Leu Ile Ala Ala Cys
65                  70                  75                  80
Leu Ala Arg Cys Trp Thr Gly Ala Arg Leu Leu Gly Thr Asp Asn Ser
                85                  90                  95
Val Val Leu Ser Gly Lys Ser Ser Phe Pro Trp Leu Leu Ala Cys
                100                 105                 110
Val Ala Thr Trp Ile Leu Arg Gly Thr Ser Phe Cys Tyr Val Pro Ser
                115                 120                 125
Ala Leu Asn Pro Ala Asp Leu Pro Ser Arg Gly Leu Leu Pro Ala Leu
                130                 135                 140
Arg Pro Leu Pro Arg Leu Arg Leu Arg Pro Gln Thr Ser Arg Ile Ser
145                 150                 155                 160
Leu Trp Ala Ala Ser Pro His Arg Tyr Arg Pro Arg Asp Leu Glu
                165                 170                 175
Lys His Gly Ala Ile Thr Ser Ser Asn Thr Ala Thr Asn Ala Asp
                180                 185                 190
Cys Ala Trp Leu Glu Ala Gln Glu Glu Glu Val Gly Phe Pro Val
                195                 200                 205
Thr Pro Gln Val Pro Leu Arg Pro Met Thr Tyr Lys Ala Ala Val Asp
                210                 215                 220
Leu Ser His Phe Leu Lys Glu Lys Gly Gly Leu Glu Gly Leu Ile His
225                 230                 235                 240
Ser Gln Arg Arg Gln Asp Ile Leu Asp Leu Trp Ile Tyr His Thr Gln
                245                 250                 255
Gly Tyr Phe Pro Asp Trp Gln Asn Tyr Thr Pro Gly Pro Gly Ile Arg
                260                 265                 270
Tyr Pro Leu Thr Phe Gly Trp Cys Tyr Lys Leu Val Pro Val Glu Gln
                275                 280                 285
Glu Lys Val Glu Glu Ala Asn Glu Gly Glu Asn Thr Arg Leu Leu His
                290                 295                 300
Pro Val Ser Leu His Gly Met Asp Asp Pro Glu Arg Glu Val Leu Glu
305                 310                 315                 320
Trp Arg Phe Asp Ser Arg Leu Ala Phe His His Met Ala Arg Glu Leu
                325                 330                 335
His Pro Asp Cys Thr Gly Ser Leu Trp Leu Asp Gln Ile
                340                 345
```

<210> SEQ ID NO 16
<211> LENGTH: 7408
<212> TYPE: DNA
<213> ORGANISM: Artificial Sequence
<220> FEATURE:
<223> OTHER INFORMATION: Synthetic Polynucleotide

<400> SEQUENCE: 16
ttatgcagtg ctgccataac catgagtgat aacactgcgg ccaacttact tctgacaacg    60
atcggaggac cgaaggagct aaccgctttt ttgcacaaca tgggggatca tgtaactcgc   120

```
cttgatcgtt gggaaccgga gctgaatgaa gccataccaa acgacgagcg tgacaccacg    180
atgcctgtag taatggtaac aacgttgcgc aaactattaa ctggcgaact acttactcta    240
gcttcccggc aacaattaat agactggatg gaggcggata agttgcagg  accacttctg    300 cgctcggccc ttccggctgg ctggtttatt gctgataaat ctggagccgg tgagcgtggg    360
tctcgcggta tcattgcagc actggggcca gatggtaagc cctcccgtat cgtagttatc    420
tacacgacgg ggagtcaggc aactatggat gaacgaaata gacagatcgc tgagataggt    480
gcctcactga ttaagcattg gtaactgtca gaccaagttt actcatatat actttagatt    540
gatttaaaac ttcatttta  atttaaaagg atctaggtga agatcctttt tgataatctc    600
atgaccaaaa tcccttaacg tgagttttcg ttccactgag cgtcagaccc cgtagaaaag    660
atcaaaggat cttcttgaga tcctttttt  ctgcgcgtaa tctgctgctt gcaaacaaaa    720
aaaccaccgc taccagcggt ggtttgtttg ccggatcaag agctaccaac tcttttccg     780 aaggtaactg gcttcagcag agcgcagata ccaaatactg tccttctagt gtagccgtag    840
ttaggccacc acttcaagaa ctctgtagca ccgcctacat acctcgctct gctaatcctg    900
ttaccagtgg ctgctgccag tggcgataag tcgtgtctta ccgggttgga ctcaagacga    960
tagttaccgg ataaggcgca gcggtcgggc tgaacggggg gttcgtgcac acagcccagc   1020
ttggagcgaa cgacctacac cgaactgaga tacctacagc gtgagctatg agaaagcgcc   1080
acgcttcccg aagggagaaa ggcggacagg tatccggtaa gcggcagggt cggaacagga   1140
gagcgcacga gggagcttcc agggggaaac gcctggtatc tttatagtcc tgtcgggttt   1200
cgccacctct gacttgagcg tcgatttttg tgatgctcgt caggggggcg agcctatgg    1260 aaaaacgcca gcaacgcggc ctttttacgg ttcctggcct tttgctggcc ttttgctcac   1320
atgttctttc ctgcgttatc ccctgattct gtggataacc gtattaccgc ctttgagtga   1380
gctgataccg ctcgccgcag ccgaacgacc gagcgcagcg agtcagtgag cgaggaagcg   1440
gaagagcgcc caatacgcaa accgcctctc cccgcgcgtt ggccgattca ttaatgcagc   1500
tggcacgaca ggtttcccga ctggaaagcg ggcagtgagc gcaacgcaat taatgtgagt   1560
tagctcactc attaggcacc ccaggcttta cactttatgc ttccggctcg tatgttgtgt   1620
ggaattgtga gcggataaca atttcacaca ggaaacagct atgaccatga ttacgccaga   1680
tttaattaag gccttaatta ggctgcgcgc tcgctcgctc actgaggccg cccgggcaaa   1740
gcccgggcgt cgggcgacct ttggtcgccc ggcctcagtg agcgagcgag cgcgcagaga   1800
gggagtggcc aactccatca ctaggggttc cttgtagtta atgattaacc cgccatgcta   1860
cttatctacg tagccatgct ctaggaagat cggaattctt tactccctat cagtgataga   1920
gaacgtatga agagtttact ccctatcagt gatagagaac gtatgcagac tttactccct   1980
atcagtgata gagaacgtat aaggagttta ctccctatca gtgatagaga acgtatgacc   2040
agtttactcc ctatcagtga tagagaacgt atctacagtt tactccctat cagtgataga   2100
gaacgtatat ccagtttact ccctatcagt gatagagaac gtataagctt taggcgtgta   2160
cggtgggcgc ctataaaagc agagctcgtt tagtgaaccg tcagatcgcc tggagcaatt   2220
ccacaacact tttgtcttat accaactttc cgtaccactt cctaccctcg taaagcggcc   2280
gcgccaccat ggctggacac ctggcttcag acttcgcctt ctcaccccca ccaggtgggg   2340
gtgatgggtc agcagggctg gagccgggct gggtggatcc tcgaacctgg ctaagcttcc   2400
aagggcctcc aggtgggcct ggaatcggac caggctcaga ggtattgggg atctccccat   2460
gtccgcccgc atacgagttc tgcggaggga tggcatactg tggacctcag gttggactgg   2520
```

```
gcctagtccc ccaagttggc gtggagactt tgcagcctga gggccaggca ggagcacgag   2580
tggaaagcaa ctcagaggga acctcctctg agccctgtgc cgaccgcccc aatgccgtga   2640
agttggagaa ggtggaacca actcccgagg agtcccagga catgaaagcc ctgcagaagg   2700
agctagaaca gtttgccaag ctgctgaagc agaagaggat caccttgggg tacacccagg   2760
ccgacgtggg gctcaccctg ggcgttctct ttggaaaggt gttcagccag accaccatct   2820
gtcgcttcga ggccttgcag ctcagcctta agaacatgtg taagctgcgg ccctgctgg    2880 agaagtgggt ggaggaagcc gacaacaatg agaaccttca ggagatatgc aaatcggaga   2940
ccctggtgca ggcccggaag agaaagcgaa ctagcattga gaaccgtgtg aggtggagtc   3000
tggagaccat gtttctgaag tgcccgaagc cctccctaca gcagatcact cacatcgcca   3060
atcagcttgg gctagagaag gatgtggttc gagtatggtt ctgtaaccgg cgccagaagg   3120
gcaaaagatc aagtattgag tattcccaac gagaagagta tgaggctaca gggacacctt   3180
tcccaggggg ggctgtatcc tttcctctgc ccccaggtcc ccactttggc ccccaggct    3240 atggaagccc ccacttcacc acactctact cagtcccttt tcctgagggc gaggcctttc   3300
cctctgttcc cgtcactgct ctgggctctc ccatgcattc aaacgctagc ggcagcggcg   3360
ccacgaactt ctctctgtta aagcaagcag gagatgttga agaaaacccc gggcctgcat   3420
gcatgtataa catgatggag acggagctga agccgccggg cccgcagcaa gcttcggggg   3480
gcggcggcgg aggaggcaac gccacggcgg cggcgaccgg cggcaaccag aagaacagcc   3540
cggaccgcgt caagaggccc atgaacgcct tcatggtatg gtcccggggg cagcggcgta   3600
agatggccca ggagaacccc aagatgcaca actcggagat cagcaagcgc ctgggcgcgg   3660
agtggaaact tttgtccgag accgagaagc ggccgttcat cgacgaggcc aagcggctgc   3720
gcgctctgca catgaaggag cacccggatt ataaataccg gccgcggcgg aaaaccaaga   3780
cgctcatgaa gaaggataag tacacgcttc ccggaggctt gctggccccc ggcgggaaca   3840
gcatggcgag cggggttggg gtgggcgccg gcctgggtgc gggcgtgaac cagcgcatgg   3900
acagctacgc gcacatgaac ggctggagca acggcagcta cagcatgatg caggagcagc   3960
tgggctaccc gcagcacccg ggcctcaacg ctcacgcgc ggcacagatg caaccgatgc    4020
accgctacga cgtcagcgcc ctgcagtaca actccatgac cagctcgcag acctacatga   4080
acggctcgcc cacctacagc atgtcctact cgcagcaggg caccccggt atggcgctgg    4140 gctccatggg ctctgtggtc aagtccgagg ccagctccag ccccccgtg gttacctctt    4200 cctcccactc cagggcgccc tgccaggccg ggaccttccg ggacatgatc agcatgtacc   4260
tccccggcgc cgaggtgccg gagcccgctg cgcccagtag actgcacatg gcccagcact   4320
accagagcgc cccggtgccc ggcacggcca ttaacgcac actgccctg tcgcacatgg    4380 catgcggctc cggcgagggc aggggaagtc ttctaacatg cggggacgtg gaggaaaatc   4440
ccggcccact cgagatgagg cagccaccctg gcgagtctga catggctgtc agcgacgctc   4500
tgctcccgtc cttctccacg ttcgcgtccg gccggcggg aagggagaag acactgcgtc   4560
cagcaggtgc cccgactaac cgttggcgtg aggaactctc tcacatgaag cgacttcccc   4620
cacttcccgg ccgcccctac gacctggcgg cgacggtggc cacagacctg agagtggcg    4680 gagctggtgc agcttgcagc agtaacaacc cggccctcct agcccggagg gagaccgagg   4740
agttcaacga cctcctggac ctagacttta tccttccaca ctcgctaacc caccaggaat   4800
cggtggccgc caccgtgacc acctcggcgt cagcttcatc ctcgtcttcc ccagcgagca   4860
```

```
gcggccctgc cagcgcgccc tccacctgca gcttcagcta tccgatccgg gccggggtg    4920 acccgggcgt ggctgccagc aacacaggtg gagggctcct ctacagccga gaatctgcgc    4980
cacctcccac ggccccttc aacctggcgg acatcaatga cgtgagcccc tcggcggct     5040 tcgtggctga gctcctgcgg ccggagttgg acccagtata cattccgcca cagcagcctc    5100
agccgccagg tggcgggctg atgggcaagt ttgtgctgaa ggcgtctctg accaccctg     5160 gcagcgagta cagcagccct tcggtcatca gtgttagcaa aggaagccca gacggcagcc    5220
accccgtggt agtggcgccc tacagcggtg gcccgccgcg catgtgcccc aagattaagc    5280
aagaggcggt cccgtcctgc acggtcagcc ggtccctaga ggcccatttg agcgctggac    5340
cccagctcag caacggccac cggcccaaca cacacgactt ccccctgggg cggcagctcc    5400
ccaccaggac tacccctaca ctgagtcccg aggaactgct gaacagcagg gactgtcacc    5460
ctggcctgcc tcttccccca ggattccatc cccatccggg gcccaactac cctcctttcc    5520
tgccagacca gatgcagtca caagtcccct ctctccatta tcaagagctc atgccaccgg    5580
gttcctgcct gccagaggag cccaagccaa agaggggaag aaggtcgtgg ccccggaaaa    5640
gaacagccac ccacacttgt gactatgcag gctgtggcaa aacctatacc aagagttctc    5700
atctcaaggc acacctgcga actcacacag gcgagaaacc ttaccactgt gactgggacg    5760
gctgtgggtg gaaattcgcc cgctccgatg aactgaccag gcactaccgc aaacacacag    5820
ggcaccggcc ctttcagtgc cagaagtgcg acagggcctt ttccaggtcg gaccaccttg    5880
ccttacacat gaagaggcac taaatgacta gtgcgcgcag cggccgacca tggcccaact    5940
tgtttattgc agcttataat ggttacaaat aaagcaatag catcacaaat ttcacaaata    6000
aagcattttt ttcactgcat tctagttgtg gtttgtccaa actcatcaat gtatcttatc    6060
atgtctggat ctcggtaccg gatccaaatt cccgataagg atcttcctag agcatggcta    6120
cgtagataag tagcatggcg ggttaatcat taactacaag gaaccctag tgatggagtt    6180 ggccactccc tctctgcgcg ctcgctgct cactgaggcc gggcgaccaa aggtcgcccg    6240 acgcccggc tttgcccggg cggcctcagt gagcgagcga gcgcgcagcc ttaattaacc    6300
taattcactg gccgtcgttt tacaacgtcg tgactgggaa accctggcg ttacccaact    6360 taatcgcctt gcagcacatc ccccttccgc cagctggcgt aatagcgaag aggcccgcac    6420
cgatcgccct tcccaacagt tgcgcagcct gaatggcgaa tgggacgcgc cctgtagcgg    6480
cgcattaagc gcggcgggtg tggtggttac gcgcagcgtg accgctacac ttgccagcgc    6540
cctagcgccc gctcctttcg ctttcttccc ttcctttctc gccacgttcg ccggctttcc    6600
ccgtcaagct ctaaatcggg ggctcccttt agggttccga tttagtgctt tacggcacct    6660
cgaccccaaa aaacttgatt agggtgatgg ttcacgtagt gggccatcgc cctgatagac    6720
ggtttttcgc cctttgacgt tggagtccac gttctttaat agtggactct tgttccaaac    6780
tggaacaaca ctcaacccta tctcggtcta ttcttttgat ttataaggga ttttgccgat    6840
ttcggcctat tggttaaaaa atgagctgat ttaacaaaaa tttaacgcga atttaacaa     6900 aatattaacg tttataattt caggtggcat ctttcgggga atgtgcgcg gaacccctat     6960 ttgtttattt ttctaaatac attcaaatat gtatccgctc atgagacaat aaccctgata    7020
aatgcttcaa taatattgaa aaaggaagag tatgagtatt caacatttcc gtgtcgccct    7080
tattcccttt tttgcggcat tttgccttcc tgttttgct cacccagaaa cgctggtgaa    7140
agtaaaagat gctgaagatc agttgggtgc acgagtgggt tacatcgaac tggatctcaa    7200
tagtggtaag atccttgaga gttttcgccc cgaagaacgt tttccaatga tgagcacttt    7260
```

```
taaagttctg ctatgtggcg cggtattatc ccgtattgac gccgggcaag agcaactcgg     7320
tcgccgcata cactattctc agaatgactt ggttgagtac tcaccagtca cagaaaagca     7380
tcttacggat ggcatgacag taagagaa                                        7408

<210> SEQ ID NO 17
<211> LENGTH: 5657
<212> TYPE: DNA
<213> ORGANISM: Artificial Sequence
<220> FEATURE:
<223> OTHER INFORMATION: Synthetic Polynucleotide

<400> SEQUENCE: 17
ttatgcagtg ctgccataac catgagtgat aacactgcgg ccaacttact tctgacaacg       60
atcggaggac cgaaggagct aaccgctttt ttgcacaaca tggggggatca tgtaactcgc      120 cttgatcgtt gggaaccgga gctgaatgaa gccataccaa cgacgagcg tgacaccacg       180 atgcctgtag taatggtaac aacgttgcgc aaactattaa ctggcgaact acttactcta      240
gcttcccggc aacaattaat agactggatg gaggcggata agttgcagg accacttctg       300 cgtcggccc ttccggctgg ctggtttatt gctgataaat ctggagccgg tgagcgtggg       360
tctcgcggta tcattgcagc actggggcca gatggtaagc cctcccgtat cgtagttatc      420
tacacgacgg ggagtcaggc aactatggat gaacgaaata gacagatcgc tgagataggt      480
gcctcactga ttaagcattg gtaactgtca gaccaagttt actcatatat actttagatt      540
gatttaaaac ttcatttta atttaaaagg atctaggtga agatccttt tgataatctc       600 atgaccaaaa tcccttaacg tgagttttcg ttccactgag cgtcagaccc cgtagaaaag      660
atcaaaggat cttcttgaga tccttttttt ctgcgcgtaa tctgctgctt gcaaacaaaa      720
aaaccaccgc taccagcggt ggtttgtttg ccggatcaag agctaccaac tcttttttccg     780 aaggtaactg gcttcagcag agcgcagata ccaaatactg tccttctagt gtagccgtag      840
ttaggccacc acttcaagaa ctctgtagca ccgcctacat acctcgctct gctaatcctg      900
ttaccagtgg ctgctgccag tggcgataag tcgtgtctta ccgggttgga ctcaagacga      960
tagttaccgg ataaggcgca gcggtcgggc tgaacgggg gttcgtgcac acagcccagc     1020
ttggagcgaa cgacctacac cgaactgaga tacctacagc gtgagctatg agaaagcgcc     1080
acgcttcccg aagggagaaa ggcggacagg tatccggtaa gcggcagggt cggaacagga     1140
gagcgcacga gggagcttcc agggggaaac gcctggtatc tttatagtcc tgtcgggttt     1200
cgccacctct gacttgagcg tcgattttg tgatgctcgt cagggggcg gagcctatgg      1260 aaaaacgcca gcaacgcggc ctttttacgg ttcctggcct tttgctggcc ttttgctcac     1320 atgttcttc ctgcgttatc ccctgattct gtggataacc gtattaccgc ctttgagtga      1380
gctgataccg ctcgccgcag ccgaacgacc gagcgcagcg agtcagtgag cgaggaagcg     1440
gaagagcgcc caatacgcaa accgcctctc cccgcgcgtt ggccgattca ttaatgcagc     1500
tggcacgaca ggtttcccga ctggaaagcg ggcagtgagc gcaacgcaat taatgtgagt     1560
tagctcactc attaggcacc ccaggcttta cactttatgc ttccggctcg tatgttgtgt     1620
ggaattgtga gcggataaca atttcacaca ggaaacagct atgaccatga ttacgccaga     1680
tttaattaag gccttaatta ggctgcgcgc tcgctcgctc actgaggccg cccgggcaaa     1740
gcccgggcgt cgggcgacct ttggtcgccc ggcctcagtg agcgagcgag cgcgcagaga     1800
gggagtggcc aactccatca ctaggggttc cttgtagtta atgattaacc cgccatgcta     1860
```

-continued

```
cttatctacg tagccatgct ctaggaagat cggaattcct gatctggcct ccgcgccggg    1920
ttttggcgcc tcccgcgggc gccccctcc tcacggcgag cgctgccacg tcagacgaag     1980
ggcgcagcga gcgtcctgat ccttccgccc ggacgctcag acagcggcc cgctgctcat     2040 aagactcggc cttagaaccc cagtatcagc agaaggacat tttaggacgg gacttgggtg    2100
actctagggc actggttttc tttccagaga gcggaacagg cgaggaaaag tagtcccttc    2160
tcggcgattc tgcggaggga tctccgtggg gcggtgaacg ccgatgatta tataaggacg    2220
cgccgggtgt ggcacagcta gttccgtcgc agccgggatt tgggtcgcgg ttcttgtttg    2280
tggatcgctg tgatcgtcac ttggtgagta gcgggctgct gggctggccg ggctttcgt     2340 ggccgccggg ccgctcggtg ggacggaagc gtgtggagag accgccaagg gctgtagtct    2400
gggtccgcga gcaaggttgc cctgaactgg gggttggggg gagcgcagca aaatggcggc    2460
tgttcccgag tcttgaatgg aagacgcttg tgaggcgggc tgtgaggtcg ttgaaacaag    2520 gtgggggca tggtgggcgg caagaaccca aggtcttgag gccttcgcta atgcgggaaa     2580
gctcttattc gggtgagatg ggctggggca ccatctgggg accctgacgt gaagtttgtc    2640
actgactgga gaactcggtt tgtcgtctgt tgcgggggcg gcagttatgc ggtgccgttg    2700
ggcagtgcac ccgtaccttt gggagcgcgc gcctcgtcgt gtcgtgacgt cacccgttct    2760
gttggcttat aatgcagggt ggggccacct gccggtaggt gtgcggtagg ctttctccg     2820 tcgcaggacg caggggttcgg gcctagggta ggctctcctg aatcgacagg cgccggacct   2880
ctggtgaggg gagggataag tgaggcgtca gtttctttgg tcggttttat gtacctatct    2940
tcttaagtag ctgaagctcc ggttttgaac tatgcgctcg gggttggcga gtgtgttttg    3000
tgaagttttt taggcacctt ttgaaatgta atcatttggg tcaatatgta attttcagtg    3060
ttagactagt aaattgtccg ctaaattctg gccgttttg gcttttttgt tagacgaagc     3120
ggccgcatta aacgccacca tgtcccgctt ggataagagc aaggtaataa atagcgcact    3180
cgaactcctc aacggcgtgg gcatcgaagg tctgactact cgaaagctcg cccagaaatt    3240
gggtgtggag caacctacat tgtattggca tgtcaagaac aaaagagccc tgctggacgc    3300
tcttcctatt gaaatgcttg acaggcatca cactcattcc tgccccttg aggtcgagag     3360 ttggcaagat tttctccgaa acaatgcaaa gtcctaccgc tgcgcacttt tgtcccatag    3420
ggatggagca aaagtgcacc tgggaaccag gccaacagag aaacaatacg agactctcga    3480
gaaccagttg gctttcttgt gccaacaggg gttctcactt gaaaatgccc tttacgcact    3540
gtcagccgtt ggacatttta ccctgggggtt cgttcttgag gagcaagaac atcaggttgc    3600
taaggaggag cgcgagactc caaccactga ttctatgcca cctttgctga aacaggccat    3660
tgaacttttc gatagacagg gtgctgaacc tgcctttctc ttcgggttgg agctgattat    3720
ttgtggtctc gaaaaacagc tgaaatgtga aagtggtggc cctactgacg ccctcgatga    3780
tttcgacctg gatatgctgc cagccgatgc acttgatgat ttcgatttgg atatgcttcc    3840
agccgacgca ctggacgact tcgatttgga catgcttccc ggttaaacta gtctagcaat    3900
caacctctgg attacaaaat ttgtgaaaga ttgactggta ttcttaacta tgttgctcct    3960
tttacgctat gtggatacgc tgctttaatg ccttgtatc atgctattgc ttcccgtatg     4020
gctttcattt tctcctcctt gtataaatcc tggttagttc ttgccacggc ggaactcatc    4080
gccgcctgcc ttgcccgctg ctggacaggg gctcggctgt tgggcactga caattccgtg    4140
gtgtttattt gtgaaatttg tgatgctatt gctttatttg taaccattct agctttattt    4200
gtgaaatttg tgatgctatt gctttatttg taaccattat aagctgcaat aaacaagtta    4260
```

| | |
|---|---:|
| acaacaacaa ttgcattcat tttatgtttc aggttcaggg ggagatgtgg gaggtttttt | 4320 |
| aaagcggggg atccaaattc ccgataagga tcttcctaga gcatggctac gtagataagt | 4380 |
| agcatggcgg gttaatcatt aactacaagg aacccctagt gatggagttg gccactccct | 4440 |
| ctctgcgcgc tcgctcgctc actgaggccg ggcgaccaaa ggtcgcccga cgcccgggct | 4500 |
| ttgcccgggc ggcctcagtg agcgagcgag cgcgcagcct taattaacct aattcactgg | 4560 |
| ccgtcgtttt acaacgtcgt gactgggaaa accctggcgt tacccaactt aatcgccttg | 4620 |
| cagcacatcc cctttcgcc agctggcgta atagcgaaga ggcccgcacc gatcgccctt | 4680 |
| cccaacagtt gcgcagcctg aatggcgaat gggacgcgcc ctgtagcggc gcattaagcg | 4740 |
| cggcgggtgt ggtggttacg cgcagcgtga ccgctacact tgccagcgcc ctagcgcccg | 4800 |
| ctcctttcgc tttcttccct tcctttctcg ccacgttcgc cggctttccc cgtcaagctc | 4860 |
| taaatcgggg gctcccttta gggttccgat ttagtgcttt acggcacctc gaccccaaaa | 4920 |
| aacttgatta gggtgatggt tcacgtagtg gccatcgcc ctgatagacg ttttttcgcc | 4980 |
| ctttgacgtt ggagtccacg ttctttaata gtggactctt gttccaaact ggaacaacac | 5040 |
| tcaaccctat ctcggtctat tcttttgatt tataagggat tttgccgatt tcggcctatt | 5100 |
| ggttaaaaaa tgagctgatt taacaaaaat ttaacgcgaa ttttaacaaa atattaacgt | 5160 |
| ttataatttc aggtggcatc tttcggggaa atgtgcgcgg aacccctatt tgtttatttt | 5220 |
| tctaaataca ttcaaatatg tatccgctca tgagacaata accctgataa atgcttcaat | 5280 |
| aatattgaaa aaggaagagt atgagtattc aacatttccg tgtcgccctt attccctttt | 5340 |
| ttgcggcatt ttgccttcct gttttttgctc acccagaaac gctggtgaaa gtaaaagatg | 5400 |
| ctgaagatca gttgggtgca cgagtgggtt acatcgaact ggatctcaat agtggtaaga | 5460 |
| tccttgagag ttttcgcccc gaagaacgtt ttccaatgat gagcactttt aaagttctgc | 5520 |
| tatgtggcgc ggtattatcc cgtattgacg ccgggcaaga gcaactcggt cgccgcatac | 5580 |
| actattctca gaatgacttg gttgagtact caccagtcac agaaaagcat cttacggatg | 5640 |
| gcatgacagt aagagaa | 5657 |

<210> SEQ ID NO 18
<211> LENGTH: 1215
<212> TYPE: DNA
<213> ORGANISM: Artificial Sequence
<220> FEATURE:
<223> OTHER INFORMATION: Synthetic Polynucleotide

<400> SEQUENCE: 18

| | |
|---|---:|
| gatctggcct ccgcgccggg ttttggcgcc tcccgcgggc gcccccctcc tcacggcgag | 60 |
| cgctgccacg tcagacgaag ggcgcagcga gcgtcctgat ccttccgccc ggacgctcag | 120 |
| gacagcggcc cgctgctcat aagactcggc cttagaaccc cagtatcagc agaaggacat | 180 |
| tttaggacgg gacttgggtg actctagggc actggttttc tttccagaga gcggaacagg | 240 |
| cgaggaaaag tagtcccttc tcggcgattc tgcggaggga tctccgtggg gcggtgaacg | 300 |
| ccgatgatta tataaggacg cgccgggtgt ggcacagcta gttccgtcgc agccgggatt | 360 |
| tgggtcgcgg ttcttgtttg tggatcgctg tgatcgtcac ttggtgagta gcgggctgct | 420 |
| gggctggccg gggctttcgt ggccgccggg ccgctcggtg ggacggaagc gtgtggagag | 480 |
| accgccaagg gctgtagtct gggtccgcga gcaaggttgc cctgaactgg gggtgggggg | 540 |
| gagcgcagca aaatggcggc tgttcccgag tcttgaatgg aagacgcttg tgaggcgggc | 600 |

| | |
|---|---|
| tgtgaggtcg ttgaaacaag gtgggggggca tggtgggcgg caagaaccca aggtcttgag | 660 |
| gccttcgcta atgcgggaaa gctcttattc gggtgagatg ggctgggggca ccatctgggg | 720 |
| accctgacgt gaagtttgtc actgactgga gaactcggtt tgtcgtctgt tgcgggggcg | 780 |
| gcagttatgc ggtgccgttg ggcagtgcac ccgtaccttt gggagcgcgc gcctcgtcgt | 840 |
| gtcgtgacgt cacccgttct gttggcttat aatgcagggt ggggccacct gccggtaggt | 900 |
| gtgcggtagg cttttctccg tcgcaggacg cagggttcgg gcctagggta ggctctcctg | 960 |
| aatcgacagg cgccggacct ctggtgaggg gagggataag tgaggcgtca gtttctttgg | 1020 |
| tcggttttat gtacctatct tcttaagtag ctgaagctcc ggttttgaac tatgcgctcg | 1080 |
| gggttggcga gtgtgttttg tgaagttttt taggcacctt ttgaaatgta atcatttggg | 1140 |
| tcaatatgta attttcagtg ttagactagt aaattgtccg ctaaattctg gccgtttttg | 1200 |
| gcttttttgt tagac | 1215 |

<210> SEQ ID NO 19
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 19

| | |
|---|---|
| tccctatcag tgatagaga | 19 |

<210> SEQ ID NO 20
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 20

| | |
|---|---|
| gctttaggcg tgtacggtgg gcgcctataa aagcagagct cgtttagtga accgtcagat | 60 |
| cgcctgga | 68 |

<210> SEQ ID NO 21
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 21

| | |
|---|---|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttag ttcttgccac ggcggaactc | 180 |
| atcgccgcct gccttgcccg ctgctggaca ggggctcggc tgttgggcac tgacaattcc | 240 |
| gtggtgtt | 248 |

<210> SEQ ID NO 22
<211> LENGTH: 141
<212> TYPE: DNA
<213> ORGANISM: Artificial Sequence
<220> FEATURE:
<223> OTHER INFORMATION: Synthetic Polynucleotide

<400> SEQUENCE: 22

| | |
|---|---|
| ccttaattag gctgcgcgct cgctcgctca ctgaggccgc ccgggcaaag cccgggcgtc | 60 |

```
gggcgacctt tggtcgcccg gcctcagtga gcgagcgagc gcgcagagag ggagtggcca    120
actccatcac tagggttcc t                                                141

<210> SEQ ID NO 23
<211> LENGTH: 438
<212> TYPE: DNA
<213> ORGANISM: Artificial Sequence
<220> FEATURE:
<223> OTHER INFORMATION: Synthetic Polynucleotide

<400> SEQUENCE: 23
aattcgtaca cgcctacctc gacccatcaa gtgccacctg acgtctccct atcagtgata     60
gagaagtcga cacgtctcga gctccctatc agtgatagag aaggtacgtc tagaacgtct    120
ccctatcagt gatagagaag tcgacacgtc tcgagctccc tatcagtgat agagaaggta    180
cgtctagaac gtctccctat cagtgataga gaagtcgaca cgtctcgagc tccctatcag    240
tgatagagaa ggtacgtcta gaacgtctcc ctatcagtga tagagaagtc gacacgtctc    300
gagctcccta tcagtgatag agaaggtacc cctatataa gcagagctcg tttagtgaac     360
cgtcagatcg cctggagacg ccatccacgc tgttttgacc tccatagaag acaccgggac    420
cgatccagcc tggatcgc                                                   438

<210> SEQ ID NO 24
<211> LENGTH: 315
<212> TYPE: DNA
<213> ORGANISM: Artificial Sequence
<220> FEATURE:
<223> OTHER INFORMATION: Synthetic Polynucleotide

<400> SEQUENCE: 24
gagtttactc cctatcagtg atagagaacg tatgtcgagt ttactcccta tcagtgatag     60
agaacgatgt cgagtttact ccctatcagt gatagagaac gtatgtcgag tttactccct    120
atcagtgata gagaacgtat gtcgagttta ctccctatca gtgatagaga acgtatgtcg    180
agtttatccc tatcagtgat agagaacgta tgtcgagttt actccctatc agtgatagag    240
aacgtatgtc gaggtaggcg tgtacggtgg gaggcctata taagcagagc tcgtttagtg    300
aaccgtcaga tcgcc                                                      315

<210> SEQ ID NO 25
<211> LENGTH: 618
<212> TYPE: DNA
<213> ORGANISM: Artificial Sequence
<220> FEATURE:
<223> OTHER INFORMATION: Synthetic Polynucleotide

<400> SEQUENCE: 25
atggctagat tagataaaag taaagtgatt aacagcgcat tagagctgct taatgaggtc     60
ggaatcgaag gtttaacaac ccgtaaactc gcccagaagc taggtgtaga gcagcctaca    120
ttgtattggc atgtaaaaaa taagcgggct ttgctcgacg ccttagccat tgagatgtta    180
gataggcacc atactcactt ttgccctttta gaaggggaaa gctggcaaga ttttttacgt    240
aataacgcta aaagttttag atgtgcttta ctaagtcatc gcgatggagc aaaagtacat    300
ttaggtacac ggcctacaga aaacagtat gaaactctcg aaaatcaatt agccttttta    360
tgccaacaag ttttttcact agagaatgca ttatatgcac tcagcgctgt ggggcatttt    420
actttaggtt gcgtattgga agatcaagag catcaagtcg ctaaagaaga aagggaaaca    480
```
cctactactg atagtatgcc gccattatta cgacaagcta tcgaattatt tgatcaccaa    540
ggtgcagagc cagccttctt attcggcctt gaattgatca tatgcggatt agaaaaacaa    600
cttaaatgtg aaagtggg                                                  618

<210> SEQ ID NO 26
<211> LENGTH: 206
<212> TYPE: PRT
<213> ORGANISM: Artificial Sequence
<220> FEATURE:
<223> OTHER INFORMATION: Synthetic Polypeptide

<400> SEQUENCE: 26

```
Met Ala Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly
        195                 200                 205
```

<210> SEQ ID NO 27
<211> LENGTH: 1008
<212> TYPE: DNA
<213> ORGANISM: Artificial Sequence
<220> FEATURE:
<223> OTHER INFORMATION: Synthetic Polynucleotide

<400> SEQUENCE: 27
atggctagat tagataaaag taaagtgatt aacagcgcat tagagctgct taatgaggtc     60
ggaatcgaag gtttaacaac ccgtaaactc gcccagaagc taggtgtaga gcagcctaca    120
ttgtattggc atgtaaaaaa taagcgggct tgctcgacg ccttagccat tgagatgtta    180
gataggcacc atactcactt tgcccctta gaagggaaa gctggcaaga ttttttacgt     240
aataacgcta aagtttag atgtgcttta ctaagtcatc gcgatggagc aaaagtacat     300
ttaggtacac ggcctacaga aaacagtat gaaactctcg aaaatcaatt agcctttta    360 tgccaacaag gttttcact agagaatgca ttatatgcac tcagcgctgt ggggcatttt    420

```
actttaggtt gcgtattgga agatcaagag catcaagtcg ctaaagaaga aagggaaaca    480
cctactactg atagtatgcc gccattatta cgacaagcta tcgaattatt tgatcaccaa    540
ggtgcagagc cagccttctt attcggcctt gaattgatca tatgcggatt agaaaaacaa    600
cttaaatgtg aaagtgggtc gccaaaaaag aagagaaagg tcgacggcgg tggtgctttg    660
tctcctcagc actctgctgt cactcaagga agtatcatca agaacaagga gggcatggat    720
gctaagtcac taactgcctg gtcccggaca ctggtgacct tcaaggatgt atttgtggac    780
ttcaccaggg aggagtggaa gctgctggac actgctcagc agatcgtgta cagaaatgtg    840
atgctggaga actataagaa cctggtttcc ttgggttatc agcttactaa gccagatgtg    900
atcctccggt tggagaaggg agaagagccc tggctggtgg agagagaaat tcaccaagag    960
acccatcctg attcagagac tgcatttgaa atcaaatcat cagtttaa               1008
```

<210> SEQ ID NO 28
<211> LENGTH: 335
<212> TYPE: PRT
<213> ORGANISM: Artificial Sequence
<220> FEATURE:
<223> OTHER INFORMATION: Synthetic Polypeptide

<400> SEQUENCE: 28

```
Met Ala Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Pro
        195                 200                 205

Lys Lys Lys Arg Lys Val Asp Gly Gly Gly Ala Leu Ser Pro Gln His
    210                 215                 220

Ser Ala Val Thr Gln Gly Ser Ile Ile Lys Asn Lys Glu Gly Met Asp
225                 230                 235                 240

Ala Lys Ser Leu Thr Ala Trp Ser Arg Thr Leu Val Thr Phe Lys Asp
                245                 250                 255

Val Phe Val Asp Phe Thr Arg Glu Glu Trp Lys Leu Leu Asp Thr Ala
```

```
                260             265             270
Gln Gln Ile Val Tyr Arg Asn Val Met Leu Glu Asn Tyr Lys Asn Leu
            275             280             285

Val Ser Leu Gly Tyr Gln Leu Thr Lys Pro Asp Val Ile Leu Arg Leu
        290             295             300

Glu Lys Gly Glu Glu Pro Trp Leu Val Glu Arg Glu Ile His Gln Glu
305             310             315             320

Thr His Pro Asp Ser Glu Thr Ala Phe Glu Ile Lys Ser Ser Val
                325             330             335

<210> SEQ ID NO 29
<211> LENGTH: 977
<212> TYPE: DNA
<213> ORGANISM: Artificial Sequence
<220> FEATURE:
<223> OTHER INFORMATION: Synthetic Polynucleotide

<400> SEQUENCE: 29
accttgcttc ctagctgggc ctttccttct cctctataaa taccagctct ggtatttcgc      60
cttggcagct gttgctgcta gggagacggc tggcttgaca tgcatctcct gacaaaacac     120
aaacccgtgg tgtgagtggg tgtgggcggt gtgagtaggg ggatgaatca gagaggggc      180 gagggagaca ggggcgcagg agtcaggcaa aggcgatgcg ggggtgcgac tacacgcagt     240
tggaaacagt cgtcagaaga ttctggaaac tatcttgctg ctataaact tgagggaagc      300 agaaggccaa cattcctccc aagggaaact gaggctcaga gttaaaaccc aggtatcagt     360
gatatgcatg tgccccggcc agggtcactc tctgactaac cggtacctac cctacaggcc     420
tacctagaga ctcttttgaa aggatggtag agacctgtcc gggctttgcc cacagtcgtt     480 ggaaaccctca gcatttctta gcaacttgt gcgaataaaa cacttcgggg gtccttcttg      540
ttcattccaa taacctaaaa cctctcctcg agaaaatag ggggcctcaa acaaacgaaa       600
ttctctagcc cgctttcccc aggataaggc aggcatccaa atggaaaaaa aggggccggc      660 cggggggtctc ctgtcagctc cttgccctgt gaaacccagc aggcctgcct gtcttctgtc    720 ctcttgggc tgtccagggg cgcaggcctc ttgcggggga gctggcctcc cgccccctc      780 gcctgtggcc gcccttttcc tggcaggaca gagggatcct gcagctgtca ggggaggggc     840 gccgggggt gatgtcagga gggctacaaa tagtgcagac agctaagggg ctccgtcacc      900
catcttcaca tccactccag ccggctgccc gcccgctgcc tcctctgtgc gtccgcccag     960
ccagcctcgt ccacgcc                                                     977

<210> SEQ ID NO 30
<211> LENGTH: 5428
<212> TYPE: DNA
<213> ORGANISM: Artificial Sequence
<220> FEATURE:
<223> OTHER INFORMATION: Synthetic Polynucleotide

<400> SEQUENCE: 30
ttatgcagtg ctgccataac catgagtgat aacactgcgg ccaacttact tctgacaacg      60
atcggaggac cgaaggagct aaccgctttt ttgcacaaca tggggatca tgtaactcgc      120 cttgatcgtt gggaaccgga gctgaatgaa gccataccaa acgacgagcg tgacaccacg     180
atgcctgtag taatggtaac aacgttgcgc aaactattaa ctggcgaact acttactcta     240
gcttcccggc aacaattaat agactggatg gaggcggata agttgcagg accacttctg      300 cgctcggccc ttccggctgg ctggtttatt gctgataaat ctggagccgg tgagcgtggg     360
```

```
tctcgcggta tcattgcagc actggggcca gatggtaagc cctcccgtat cgtagttatc      420
tacacgacgg ggagtcaggc aactatggat gaacgaaata gacagatcgc tgagataggt      480
gcctcactga ttaagcattg gtaactgtca gaccaagttt actcatatat actttagatt      540
gatttaaaac ttcatttta atttaaaagg atctaggtga agatccttt tgataatctc       600 atgaccaaaa tcccttaacg tgagttttcg ttccactgag cgtcagaccc cgtagaaaag      660
atcaaaggat cttcttgaga tccttttttt ctgcgcgtaa tctgctgctt gcaaacaaaa      720
aaaccaccgc taccagcggt ggtttgtttg ccggatcaag agctaccaac tctttttccg      780
aaggtaactg gcttcagcag agcgcagata ccaaatactg tccttctagt gtagccgtag      840
ttaggccacc acttcaagaa ctctgtagca ccgcctacat acctcgctct gctaatcctg      900
ttaccagtgg ctgctgccag tggcgataag tcgtgtctta ccgggttgga ctcaagacga      960
tagttaccgg ataaggcgca gcggtcgggc tgaacggggg gttcgtgcac acagcccagc     1020
ttggagcgaa cgacctacac cgaactgaga tacctacagc gtgagctatg agaaagcgcc     1080
acgcttcccg aagggagaaa ggcggacagg tatccggtaa gcggcagggt cggaacagga     1140
gagcgcacga gggagcttcc agggggaaac gcctggtatc tttatagtcc tgtcgggttt     1200
cgccacctct gacttgagcg tcgatttttg tgatgctcgt caggggggcg agcctatgg      1260 aaaaacgcca gcaacgcggc cttttacgg ttcctggcct tttgctggcc ttttgctcac      1320
atgttctttc ctgcgttatc ccctgattct gtggataacc gtattaccgc ctttgagtga     1380
gctgataccg ctcgccgcag ccgaacgacc gagcgcagcg agtcagtgag cgaggaagcg     1440
gaagagcgcc caatacgcaa accgcctctc cccgcgcgtt ggccgattca ttaatgcagc     1500
tggcacgaca ggtttcccga ctggaaagcg ggcagtgagc gcaacgcaat taatgtgagt     1560
tagctcactc attaggcacc ccaggcttta cactttatgc ttccggctcg tatgttgtgt     1620
ggaattgtga gcggataaca atttcacaca ggaaacagct atgaccatga ttacgccaga     1680
tttaattaag gccttaatta ggctgcgcgc tcgctcgctc actgaggccg cccgggcaaa     1740
gcccgggcgt cgggcgacct ttggtcgccc ggcctcagtg agcgagcgag cgcgcagaga     1800
gggagtggcc aactccatca ctaggggttc cttgtagtta atgattaacc cgccatgcta     1860
cttatctacg tagccatgct ctaggaagat cggaattcct agatctacct tgcttcctag     1920
ctgggccttt ccttctcctc tataaatacc agctctggta tttcgccttg gcagctgttg     1980
ctgctaggga cggctggc ttgacatgca tctcctgaca aaacacaaac ccgtggtgtg       2040
agtgggtgtg ggcggtgtga gtaggggat gaatcagaga gggggcgagg gagacagggg      2100
cgcaggagtc aggcaaaggc gatgcggggg tgcgactaca cgcagttgga aacagtcgtc     2160
agaagattct ggaaactatc ttgctggcta taaacttgag ggaagcagaa ggccaacatt     2220
cctcccaagg gaaactgagg ctcagagtta aaacccaggt atcagtgata tgcatgtgcc     2280
ccggccaggt tcactctctg actaaccggt acctacccta caggcctacc tagagactct     2340
tttgaaagga tggtagagac ctgtccgggc tttgcccaca gtcgttggaa acctcagcat     2400
tttctaggca acttgtgcga ataaaacact tcggggtcc ttcttgttca ttccaataac      2460
ctaaaacctc tcctcggaga aaatagggg cctcaaacaa acgaaattct ctagcccgct      2520
ttccccagga taaggcaggc atccaaatgg aaaaaaggg gccggccggg ggtctcctgt      2580
cagctccttg ccctgtgaaa cccagcaggc ctgcctgtct tctgtcctct tggggctgtc     2640
caggggcgca ggcctcttgc gggggagctg gcctccccgc cccctcgcct gtggccgccc     2700
```

```
ttttcctggc aggacagagg gatcctgcag ctgtcagggg aggggcgccg ggggggtgatg    2760 tcaggagggc tacaaatagt gcagacagct aagggcctcc gtcacccatc ttcacatcca    2820
ctccagccgg ctgcccgccc gctgcctcct ctgtgcgtcc gcccagccag cctcgtccac    2880
gccaagcttg cggccgcatt aaacgccacc atgtcccgct tggataagag caaggtaata    2940
aatagcgcac tcgaactcct caacggcgtg ggcatcgaag gtctgactac tcgaaagctc    3000
gcccagaaat tgggtgtgga gcaacctaca ttgtattggc atgtcaagaa caaaagagcc    3060
ctgctggacg ctcttcctat tgaaatgctt gacaggcatc acactcattc ctgccccctt    3120
gaggtcgaga gttggcaaga ttttctccga aacaatgcaa agtcctaccg ctgcgcactt    3180
ttgtcccata gggatggagc aaaagtgcac ctgggaacca ggccaacaga gaaacaatac    3240
gagactctcg agaaccagtt ggctttcttg tgccaacagg ggttctcact tgaaaatgcc    3300
ctttacgcac tgtcagccgt tggacatttt accctggggt gcgttcttga ggagcaagaa    3360
catcaggttg ctaaggagga gcgcgagact ccaaccactg attctatgcc acctttgctg    3420
aaacaggcca ttgaacttt cgatagacag ggtgctgaac ctgcctttct cttcgggttg    3480
gagctgatta tttgtggtct cgaaaaacag ctgaaatgtg aaagtggtgg ccctactgac    3540
gccctcgatg atttcgacct ggatatgctg ccagccgatg cacttgatga tttcgatttg    3600
gatatgcttc cagccgacgc actggacgac ttcgatttgg acatgcttcc cggttaaact    3660
agtctagcaa tcaacctctg gattacaaaa tttgtgaaag attgactggt attcttaact    3720
atgttgctcc ttttacgcta tgtggatacg ctgctttaat gcctttgtat catgctattg    3780
cttcccgtat ggctttcatt ttctcctcct tgtataaatc ctggttagtt cttgccacgg    3840
cggaactcat cgccgcctgc cttgcccgct gctggacagg ggctcggctg ttgggcactg    3900
acaattccgt ggtgttatt tgtgaaattt gtgatgctat tgctttattt gtaaccattc    3960
tagctttatt tgtgaaattt gtgatgctat tgctttattt gtaaccatta taagctgcaa    4020
taaacaagtt aacaacaaca attgcattca ttttatgttt caggttcagg gggagatgtg    4080
ggaggttttt taaagcgggg gatccaaatt cccgataagg atcttcctag agcatggcta    4140
cgtagataag tagcatggcg ggttaatcat taactacaag gaaccctag tgatggagtt    4200 ggccactccc tctctgcgcg ctcgctcgct cactgaggcc gggcgaccaa aggtcgcccg    4260
acgcccgggc tttgcccggg cggcctcagt gagcgagcga gcgcgcagcc ttaattaacc    4320
taattcactg gccgtcgttt tacaacgtcg tgactgggaa aaccctggcg ttacccaact    4380
taatcgcctt gcagcacatc ccccttcgc cagctggcgt aatagcgaag aggcccgcac    4440
cgatcgccct tcccaacagt tgcgcagcct gaatggcgaa tgggacgcgc cctgtagcgg    4500
cgcattaagc gcggcgggtg tggtggttac gcgcagcgtg accgctacac ttgccagcgc    4560
cctagcgccc gctcctttcg ctttcttccc ttcctttctc gccacgttcg ccggctttcc    4620
ccgtcaagct ctaaatcggg ggctcccttt agggttccga tttagtgctt tacggcacct    4680
cgaccccaaa aaacttgatt agggtgatgg ttcacgtagt gggccatcgc cctgatagac    4740
ggtttttcgc cctttgacgt tggagtccac gttctttaat agtggactct tgttccaaac    4800
tggaacaaca ctcaaccta tctcggtcta ttcttttgat ttataaggga ttttgccgat    4860
ttcggcctat tggttaaaaa atgagctgat ttaacaaaaa tttaacgcga attttaacaa    4920
aatattaacg tttataattt caggtggcat ctttcgggga aatgtgcgcg gaacccctat    4980
ttgtttattt ttctaaatac attcaaatat gtatccgctc atgagacaat aaccctgata    5040
aatgcttcaa taatattgaa aaaggaagag tatgagtatt caacatttcc gtgtcgccct    5100
```

| | |
|---|---|
| tattccctttt tttgcggcat tttgccttcc tgtttttgct cacccagaaa cgctggtgaa | 5160 |
| agtaaaagat gctgaagatc agttgggtgc acgagtgggt tacatcgaac tggatctcaa | 5220 |
| tagtggtaag atccttgaga gttttcgccc cgaagaacgt tttccaatga tgagcacttt | 5280 |
| taaagttctg ctatgtggcg cggtattatc ccgtattgac gccgggcaag agcaactcgg | 5340 |
| tcgccgcata cactattctc agaatgactt ggttgagtac tcaccagtca cagaaaagca | 5400 |
| tcttacggat ggcatgacag taagagaa | 5428 |

<210> SEQ ID NO 31
<211> LENGTH: 5332
<212> TYPE: DNA
<213> ORGANISM: Artificial Sequence
<220> FEATURE:
<223> OTHER INFORMATION: Synthetic Polynucleotide

<400> SEQUENCE: 31

| | |
|---|---|
| aaattgtaaa cgttaatatt ttgttaaaat tcgcgttaaa ttttttgttaa atcagctcat | 60 |
| tttttaacca ataggccgaa atcggcaaaa tcccttataa atcaaaagaa tagcccgaga | 120 |
| tagggttgag tgttgttcca gtttggaaca agagtccact attaaagaac gtggactcca | 180 |
| acgtcaaagg gcgaaaaacc gtctatcagg gcgatggccc actacgtgaa ccatcaccca | 240 |
| aatcaagttt ttggggtcg aggtgccgta aagcactaaa tcggaaccct aaagggagcc | 300 |
| cccgatttag agcttgacgg ggaaagccgg cgaacgtggc gagaaaggaa gggaagaaag | 360 |
| cgaaaggagc gggcgctagg gcgctggcaa gtgtagcggt cacgctgcgc gtaaccacca | 420 |
| cacccgccgc gcttaatgcg ccgctacagg gcgcgtacta tggttgcttt gacgtatgcg | 480 |
| gtgtgaaata ccgcacagat gcgtaaggag aaaataccgc atcaggcgcc cctgcaggca | 540 |
| gctgcgcgct cgctcgctca ctgaggccgc ccgggcaaag cccgggcgtc gggcgacctt | 600 |
| tggtcgcccg gcctcagtga gcgagcgagc gcgcagagag ggagtggcca actccatcac | 660 |
| taggggttcc tgcggccgct cggtccgcac gatctcaatt cggccattac ggccggatcc | 720 |
| ggctcgagga gcttggccca ttgcatacgt tgtatccata tcataatatg tacatttata | 780 |
| ttggctcatg tccaacatta ccgccatgtt gacattgatt attgactagt tattaatagt | 840 |
| aatcaattac ggggtcatta gttcatagcc catatatgga gttccgcgtt acataactta | 900 |
| cggtaaatgg cccgcctggc tgaccgccca acgacccccg cccattgacg tcaataatga | 960 |
| cgtatgttcc catagtaacg ccaataggga ctttccattg acgtcaatgg gtggagtatt | 1020 |
| tacgctaaac tgcccacttg gcagtacatc aagtgtatca tatgccaagt acgccccta | 1080 |
| ttgacgtcaa tgacggtaaa tggcccgcct ggcattatgc ccagtacatg accttatggg | 1140 |
| actttcctac ttggcagtac atctacgtat tagtcatcgc tattaccatg gtgatgcggt | 1200 |
| tttggcagta catcaatggg cgtggatagc ggtttgactc acggggattt ccaagtctcc | 1260 |
| accccattga cgtcaatggg agtttgtttt ggcaccaaaa tcaacgggac tttccaaaat | 1320 |
| gtcgtaacaa ctccgcccca ttgacgcaaa tgggcggtag gcgtgtacgg tgggaggtct | 1380 |
| atataagcag agctcgttta gtgaaccgtc agatcgcctg gagacgccat ccacgctgtt | 1440 |
| ttgacctcca tagaagacac cgggaccgat ccagcctccg cggccccgaa ttcaccatgt | 1500 |
| ctagactgga caagagcaaa atcataaaca gcgctctgga attactcaat ggagtcggta | 1560 |
| tcgaaggcct gacgacaagg aaactcgctc aaaagctggg agttgagcag cctaccctgt | 1620 |
| actggcacgt gaagaacaag cgggccctgc tcgatgccct gccaatcgag atgctggaca | 1680 |

```
ggcatcatac ccacagctgc ccccTGGAAG gcgagtcatg gcaagacttt ctgcggaaca    1740
acgccaagtc ataccgctgt gctctcctct cacatcgcga cggggctaaa gtgcatctcg    1800
gcacccgccc aacagagaaa cagtacgaaa ccctggaaaa tcagctcgcg ttcctgtgtc    1860
agcaaggctt ctccctggag aacgcactgt acgctctgtc cgccgtgggc cactttacac    1920
tgggctgcgt attggaggaa caggagcatc aagtagcaaa agaggaaaga gagacaccta    1980
ccaccgattc tatgccccca cttctgaagc aagcaattga gctgttcgac cggcagggag    2040
ccgaacctgc cttcctttc ggcctggaac taatcatatg tggcctggag aaacagctaa    2100
agtgcgaaag cggcgggccg accgacgccc ttgacgattt tgacttagac atgctcccag    2160
ccgatgccct tgacgacttt gaccttgata tgctgcctgc tgacgctctt gacgattttg    2220
accttgacat gctccccggg taactaagta aggatcatct taattaaatc gataaggatc    2280
tggccgcctc ggcctaatca acctctggat tacaaaattt gtgaaagatt gactggtatt    2340
cttaactatg ttgctccttt tacgctatgt ggatacgctg ctttaatgcc tttgtatcat    2400
gctattgctt cccgtatggc tttcattttc tcctccttgt ataaatcctg gttgctgtct    2460
ctttatgagg agttgtggcc cgttgtcagg caacgtggcg tggtgtgcac tgtgtttgct    2520
gacgcaaccc ccactggttg gggcattgcc accacctgtc agctcctttc cgggactttc    2580
gctttccccc tccctattgc cacggcggaa ctcatcgccg cctgccttgc ccgctgctgg    2640 acagggctc ggctgttggg cactgacaat tccgtggtgt tgtcgggaa atcatcgtcc    2700 tttccttggc tgctcgcctg tgttgccacc tggattctgc gcgggacgtc cttctgctac    2760
gtcccttcgg ccctcaatcc agcggacctt ccttcccgcg gcctgctgcc ggctctgcgg    2820
cctcttccgc gtcttcgcct tcgccctcag acgagtcgga tctccctttg ggccgcctcc    2880
ccgccagaca tgataagata cattgatgag tttggacaaa ccacaactag aatgcagtga    2940
aaaaaatgct ttatttgtga aatttgtgat gctattgctt tatttgtaac cattataagc    3000
tgcaataaac aagttaacaa caacaattgc attcatttta tgtttcaggt tcaggggag    3060 atgtgggagg ttttttaaag caagtaaaac ctctacaaat gtggtaacta gcgcgtgcgg    3120
ccgcaggaac ccctagtgat ggagttggcc actccctctc tgcgcgctcg ctcgctcact    3180
gaggccgggc gaccaaaggt cgcccgacgc ccgggctttg cccgggcggc ctcagtgagc    3240
gagcgagcgc gcagctgcct gcaggacatg tgagcaaaag gccagcaaaa ggccaggaac    3300
cgtaaaaagg ccgcgttgct ggcgtttttc cataggctcc gccccctga cgagcatcac    3360 aaaaatcgac gctcaagtca gaggtggcga acccgacag gactataaag ataccaggcg    3420
tttccccctg gaagctccct cgtgcgctct cctgttccga ccctgccgct taccggatac    3480
ctgtccgcct ttctcccttc gggaagcgtg gcgctttctc atagctcacg ctgtaggtat    3540
ctcagttcgg tgtaggtcgt tcgctccaag ctgggctgtg tgcacgaacc cccgttcag    3600 cccgaccgct gcgccttatc cggtaactat cgtcttgagt ccaacccggt aagacacgac    3660
ttatcgccac tggcagcagc cactggtaac aggattagca gagcgaggta tgtaggcggt    3720
gctacagagt tcttgaagtg gtggcctaac tacggctaca ctagaaggac agtatttggt    3780
atctgcgctc tgctgaagcc agttaccttc ggaaaaagag ttggtagctc ttgatccggc    3840
aaacaaacca ccgctggtag cggtggtttt tttgtttgca agcagcagat tacgcgcaga    3900
aaaaaaggat ctcaagaaga tcctttgatc ttttctacgg ggtctgacgc tcagtggaac    3960
gaaaactcac gttaagggat tttggtcatg agattatcaa aaaggatctt cacctagatc    4020
cttttaaatt aaaaatgaag ttttaaatca atctaaagta tatatgagta aacttggtct    4080
```

```
gacagttacc aatgcttaat cagtgaggca cctatctcag cgatctgtct atttcgttca    4140
tccatagttg cctgactccc cgtcgtgtag ataactacga tacggagggg cttaccatct    4200
ggccccagtg ctgcaatgat accgcgagac ccacgctcac cggctccaga tttatcagca    4260
ataaaccagc cagccggaag ggccgagcgc agaagtggtc ctgcaacttt atccgcctcc    4320
atccagtcta ttaattgttg ccgggaagct agagtaagta gttcgccagt taatagtttg    4380
cgcaacgttg ttgccattgc tacaggcatc gtggtgtcac gctcgtcgtt tggtatggct    4440
tcattcagct ccggttccca acgatcaagg cgagttacat gatcccccat gttgtgcaaa    4500
aaagcggtta gctccttcgg tcctccgatc gttgtcagaa gtaagttggc cgcagtgtta    4560
tcactcatgg ttatggcagc actgcataat tctcttactg tcatgccatc cgtaagatgc    4620 tttctgtga ctggtgagta ctcaaccaag tcattctgag aatagtgtat gcggcgaccg    4680
agttgctctt gcccggcgtc aatacgggat aataccgcgc cacatagcag aactttaaaa    4740
gtgctcatca ttggaaaacg ttcttcgggg cgaaaactct caaggatctt accgctgttg    4800
agatccagtt cgatgtaacc cactcgtgca cccaactgat cttcagcatc ttttactttc    4860
accagcgttt ctgggtgagc aaaaacagga aggcaaaatg ccgcaaaaaa gggaataagg    4920
gcgacacgga aatgttgaat actcatactc ttccttttc aatattattg aagcatttat    4980
cagggttatt gtctcatgag cggatacata tttgaatgta tttagaaaaa taaacaaata    5040
ggggttccgc gcacatttcc ccgaaaagtg ccacctgacg tctaagaaac cattattatc    5100
atgacattaa cctataaaaa taggcgtatc acgaggccct ttcgtctcgc gcgtttcggt    5160
gatgacggtg aaaacctctg acacatgcag ctcccggaga cggtcacagc ttgtctgtaa    5220
gcggatgccg ggagcagaca gcccgtcag ggcgcgtcag cgggtgttgg cgggtgtcgg    5280
ggctggctta actatgcggc atcagagcag attgtactga gagtgcacca ta           5332
```

<210> SEQ ID NO 32
<211> LENGTH: 5392
<212> TYPE: DNA
<213> ORGANISM: Artificial Sequence
<220> FEATURE:
<223> OTHER INFORMATION: Synthetic Polynucleotide

<400> SEQUENCE: 32

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtggagc tagttattaa tagtaatcaa     180
ttacggggtc attagttcat agcccatata tggagttccg cgttacataa cttacggtaa     240
atggcccgcc tggctgaccg cccaacgacc cccgcccatt gacgtcaata atgacgtatg     300
ttcccatagt aacgtcaata gggactttcc attgacgtca atgggtggag tatttacggt     360
aaactgccca cttggcagta catcaagtgt atcatatgcc aagtacgccc cctattgacg     420
tcaatgacgg taaatggccc gcctggcatt atgcccagta catgacctta tgggactttc     480
ctacttggca gtacatctac gtattagtca tcgctattac catggtgatg cggttttggc     540
agtacatcaa tgggcgtgga tagcggtttg actcacgggg atttccaagt ctccacccca     600
ttgacgtcaa tgggagtttg ttttgcacca aaatcaacgg gactttccaa aatgtcgtaa     660
caactccgcc ccattgacgc aaatgggcgg taggcgtgta cggtgggagg tctatataag     720
cagagctcgt ttagtgaacc gtcagatcgc ctggagacgc catccacgct gttttgacct     780
```

```
ccatagaaga caccgggacc gatccagcct ccgcggattc gaatcccggc cgggaacggt    840
gcattggaac gcggattccc cgtgccaaga gtgacgtaag taccgcctat agagtctata    900
ggcccacaaa aaatgctttc ttcttttaat atacttttt gtttatctta tttctaatac    960
tttccctaat ctctttcttt cagggcaata atgatacaat gtatcatgcc tctttgcacc   1020
attctaaaga ataacagtga taatttctgg gttaaggcaa tagcaatatt tctgcatata   1080
aatatttctg catataaatt gtaactgatg taagaggttt catattgcta atagcagcta   1140
caatccagct accattctgc ttttatttta tggttgggat aaggctggat tattctgagt   1200
ccaagctagg cccttttgct aatcatgttc atacctctta tcttcctccc acagctcctg   1260
ggcaacgtgc tggtctgtgt gctggcccat cactttggca agaattggg attcgaacat    1320
cgattgaatt catgtctaga ctggacaaga gcaaagtcat aaactctgct ctggaattac   1380
tcaatgaagt cggtatcgaa ggcctgacga caaggaaact cgctcaaaag ctgggagttg   1440
agcagcctac cctgtactgg cacgtgaaga caagcgggc cctgctcgat gccctggcaa    1500
tcgagatgct ggacaggcat catacccact tctgccccct ggaaggcgag tcatggcaag   1560
actttctgcg gaacaacgcc aagtcattcc gctgtgctct cctctcacat cgcgacgggg   1620
ctaaagtgca tctcggcacc cgcccaacag agaaacagta cgaaaccctg gaaaatcagc   1680
tcgcgttcct gtgtcagcaa ggcttctccc tggagaacgc actgtacgct ctgtccgccg   1740
tgggccactt tacactgggc tgcgtattgg aggatcagga gcatcaagta gcaaagagg    1800
aaagagagac acctaccacc gattctatgc ccccacttct gagacaagca attgagctgt   1860
tcgaccatca gggagccgaa cctgccttcc ttttcggcct ggaactaatc atatgtggcc   1920
tggagaaaca gctaaagtgc gaaagcggcg gccggccga cgcccttgac gattttgact    1980
tagacatgct cccagccgat gcccttgacg actttgacct tgatatgctg cctgctgacg   2040
ctcttgacga ttttgacctt gacatgctcc ccggatgagg atcctctaga gtcgacctgc   2100
agaagcttgc ctcgagcagc gctgctcgag agatctacgg gtggcatccc tgtgaccct    2160
ccccagtgcc tctcctggcc ctggaagttg ccactccagt gcccaccagc cttgtcctaa   2220
taaaattaag ttgcatcatt ttgtctgact aggtgtcctt ctataatatt atgggggtgga  2280
ggggggtggt atggagcaag gggcaagttg gaagacaac ctgtagggcc tgcggggtct    2340
attgggaacc aagctggagt gcagtggcac aatcttggct cactgcaatc tccgcctcct   2400
gggttcaagc gattctcctg cctcagcctc ccgagttgtt gggattccag gcatgcatga   2460
ccaggctcag ctaattttg ttttttttggt agagacgggg tttcaccata ttggccaggc    2520
tggtctccaa ctcctaatct caggtgatct acccaccttg gcctcccaaa ttgctgggat   2580
tacaggcgtg aaccactgct cccttccctg tccttctgat tttgtaggta accacgtgcg   2640
gaccgagcgg ccgcaggaac ccctagtgat ggagttggcc actccctctc tgcgcgctcg   2700
ctcgctcact gaggccgggc gaccaaaggt cgcccgacgc ccgggctttg cccgggcggc   2760
ctcagtgagc gagcgagcgc gcagctgcct gcagggcgc ctgatgcggt attttctcct    2820
tacgcatctg tgcggtattt cacaccgcat acgtcaaagc aaccatagta cgcgccctgt   2880
agcggcgcat taagcgcggc gggtgtggtg gttacgcgca gcgtgaccgc tacacttgcc   2940
agcgccctag cgcccgctcc tttcgctttc ttcccttcct ttctcgccac gttcgccggc   3000
tttccccgtc aagctctaaa tcggggggctc ccttttagggt tccgatttag tgctttacgg   3060
cacctcgacc ccaaaaaact tgatttgggt gatggttcac gtagtgggcc atcgccctga   3120
tagacggttt ttcgcccttt gacgttggag tccacgttct ttaatagtgg actcttgttc   3180
```

```
caaactggaa caacactcaa ccctatctcg ggctattctt ttgatttata agggattttg    3240
ccgatttcgg cctattggtt aaaaaatgag ctgatttaac aaaaatttaa cgcgaatttt    3300
aacaaaatat taacgtttac aatttttatgg tgcactctca gtacaatctg ctctgatgcc    3360
gcatagttaa gccagccccg acacccgcca acacccgctg acgcgccctg acgggcttgt    3420
ctgctcccgg catccgctta cagacaagct gtgaccgtct ccgggagctg catgtgtcag    3480
aggttttcac cgtcatcacc gaaacgcgcg agacgaaagg gcctcgtgat acgcctattt    3540
ttataggtta atgtcatgat aataatggtt tcttagacgt caggtggcac ttttcgggga    3600
aatgtgcgcg gaaccctat  ttgtttattt ttctaaatac attcaaatat gtatccgctc    3660
atgagacaat aaccctgata atgcttcaa  taatattgaa aaggaagag  tatgagtatt    3720
caacatttcc gtgtcgccct tattccctt  tttgcggcat tttgccttcc tgttttgct    3780
cacccagaaa cgctggtgaa agtaaaagat gctgaagatc agttgggtgc acgagtgggt    3840
tacatcgaac tggatctcaa cagcggtaag atccttgaga gttttcgccc cgaagaacgt    3900
tttccaatga tgagcacttt taaagttctg ctatgtggcg cggtattatc ccgtattgac    3960
gccgggcaag agcaactcgg tcgccgcata cactattctc agaatgactt ggttgagtac    4020
tcaccagtca cagaaaagca tcttacggat ggcatgacag taagagaatt atgcagtgct    4080
gccataacca tgagtgataa cactgcggcc aacttacttc tgacaacgat cggaggaccg    4140
aaggagctaa ccgcttttttt gcacaacatg ggggatcatg taactcgcct tgatcgttgg    4200
gaaccggagc tgaatgaagc cataccaaac gacgagcgtg acaccacgat gcctgtagca    4260
atggcaacaa cgttgcgcaa actattaact ggcgaactac ttactctagc ttcccggcaa    4320
caattaatag actggatgga ggcggataaa gttgcaggac cacttctgcg ctcggccctt    4380
ccggctggct ggtttattgc tgataaatct ggagccggtg agcgtgggtc tcgcggtatc    4440
attgcagcac tggggccaga tggtaagccc tcccgtatcg tagttatcta cacgacgggg    4500
agtcaggcaa ctatggatga acgaaataga cagatcgctg agataggtgc ctcactgatt    4560
aagcattggt aactgtcaga ccaagtttac tcatatatac tttagattga tttaaaactt    4620
catttttaat ttaaaaggat ctaggtgaag atccttttttg ataatctcat gaccaaaatc    4680
ccttaacgtg agttttcgtt ccactgagcg tcagaccccg tagaaaagat caaaggatct    4740
tcttgagatc ctttttttct gcgcgtaatc tgctgcttgc aaacaaaaaa accaccgcta    4800
ccagcggtgg tttgtttgcc ggatcaagag ctaccaactc ttttttccgaa ggtaactggc    4860
ttcagcagag cgcagatacc aaatactgtc cttctagtgt agccgtagtt aggccaccac    4920
ttcaagaact ctgtagcacc gcctacatac ctcgctctgc taatcctgtt accagtggct    4980
gctgccagtg gcgataagtc gtgtcttacc gggttggact caagacgata gttaccggat    5040
aaggcgcagc ggtcgggctg aacggggggt tcgtgcacac agcccagctt ggagcgaacg    5100
acctacaccg aactgagata cctacagcgt gagctatgag aaagcgccac gcttcccgaa    5160
gggagaaagg cggacaggta tccggtaagc ggcagggtcg gaacaggaga gcgcacgagg    5220
gagcttccag ggggaaacgc ctggtatctt tatagtcctg tcgggtttcg ccacctctga    5280
cttgagcgtc gatttttgtg atgctcgtca gggggcgga  gcctatggaa aaacgccagc    5340
aacgcggcct ttttacggtt cctggccttt tgctggcctt tgctcacat  gt            5392
```

<210> SEQ ID NO 33
<211> LENGTH: 7732
<212> TYPE: DNA

<213> ORGANISM: Artificial Sequence
<220> FEATURE:
<223> OTHER INFORMATION: Synthetic Polynucleotide

<400> SEQUENCE: 33

```
ttatgcagtg ctgccataac catgagtgat aacactgcgg ccaacttact tctgacaacg    60
atcggaggac cgaaggagct aaccgctttt ttgcacaaca tggggatca tgtaactcgc    120
cttgatcgtt gggaaccgga gctgaatgaa gccataccaa acgacgagcg tgacaccacg    180
atgcctgtag taatggtaac aacgttgcgc aaactattaa ctggcgaact acttactcta    240
gcttcccggc aacaattaat agactggatg gaggcggata agttgcagg accacttctg    300
cgctcggccc ttccggctgg ctggtttatt gctgataaat ctggagccgg tgagcgtggg    360
tctcgcggta tcattgcagc actggggcca gatggtaagc cctcccgtat cgtagttatc    420
tacacgacgg ggagtcaggc aactatggat gaacgaaata gacagatcgc tgagataggt    480
gcctcactga ttaagcattg gtaactgtca gaccaagttt actcatatat actttagatt    540
gatttaaaac ttcatttta atttaaaagg atctaggtga agatcctttt tgataatctc    600
atgaccaaaa tcccttaacg tgagttttcg ttccactgag cgtcagaccc cgtagaaaag    660
atcaaaggat cttcttgaga tccttttttt ctgcgcgtaa tctgctgctt gcaaacaaaa    720
aaaccaccgc taccagcggt ggtttgtttg ccggatcaag agctaccaac tcttttccg    780
aaggtaactg gcttcagcag agcgcagata ccaaatactg tccttctagt gtagccgtag    840
ttaggccacc acttcaagaa ctctgtagca ccgcctacat acctcgctct gctaatcctg    900
ttaccagtgg ctgctgccag tggcgataag tcgtgtctta ccgggttgga ctcaagacga    960
tagttaccgg ataaggcgca gcggtcgggc tgaacggggg gttcgtgcac acagcccagc   1020
ttggagcgaa cgacctacac cgaactgaga tacctacagc gtgagctatg agaaagcgcc   1080
acgcttcccg aagggagaaa ggcggacagg tatccggtaa gcggcagggt cggaacagga   1140
gagcgcacga gggagcttcc agggggaaac gcctggtatc tttatagtcc tgtcgggttt   1200
cgccacctct gacttgagcg tcgatttttg tgatgctcgt cagggggggcg agcctatgg    1260
aaaaacgcca gcaacgcggc cttttacgg ttcctggcct tttgctggcc ttttgctcac   1320
atgttctttc ctgcgttatc ccctgattct gtggataacc gtattaccgc ctttgagtga   1380
gctgataccg ctcgccgcag ccgaacgacc gagcgcagcg agtcagtgag cgaggaagcg   1440
gaagagcgcc caatacgcaa accgcctctc cccgcgcgtt ggccgattca ttaatgcagc   1500
tggcacgaca ggtttcccga ctggaaagcg ggcagtgagc gcaacgcaat taatgtgagt   1560
tagctcactc attaggcacc ccaggcttta cactttatgc ttccggctcg tatgttgtgt   1620
ggaattgtga gcggataaca atttcacaca ggaaacagct atgaccatga ttacgccaga   1680
tttaattaag gccttaatta ggctgcgcgc tcgctcgctc actgaggccg cccgggcaaa   1740
gcccgggcgt cgggcgacct ttggtcgccc ggcctcagtg agcgagcgag cgcgcagaga   1800
gggagtggcc aactccatca ctaggggttc cttgtagtta atgattaacc cgccatgcta   1860
cttatctacg tagccatgct ctaggaagat cggaattcgt acacgcctac ctcgacccat   1920
caagtgccac ctgacgtctc cctatcagtg atagagaagt cgacacgtct cgagctccct   1980
atcagtgata gagaaggtac gtctagaacg tctccctatc agtgatagag aagtcgacac   2040
gtctcgagct ccctatcagt gatagagaag gtacgtctag aacgtctccc tatcagtgat   2100
agagaagtcg acacgtctcg agctccctat cagtgataga gaaggtacgt ctagaacgtc   2160
tccctatcag tgatagagaa gtcgacacgt ctcgagctcc ctatcagtga tagagaaggt   2220
```

| | |
|---|---|
| accccctata taagcagagc tcgtttagtg aaccgtcaga tcgcctggag acgccatcca | 2280 |
| cgctgttttg acctccatag aagacaccgg gaccgatcca gcctggatcg cggccgcgcc | 2340 |
| accatggctg gacacctggc ttcagacttc gccttctcac ccccaccagg tgggggtgat | 2400 |
| gggtcagcag ggctggagcc gggctgggtg gatcctcgaa cctggctaag cttccaaggg | 2460 |
| cctccaggtg ggcctggaat cggaccaggc tcagaggtat tggggatctc cccatgtccg | 2520 |
| cccgcatacg agttctgcgg agggatggca tactgtggac ctcaggttgg actgggccta | 2580 |
| gtcccccaag ttggcgtgga gactttgcag cctgagggcc aggcaggagc acgagtggaa | 2640 |
| agcaactcag agggaacctc ctctgagccc tgtgccgacc gccccaatgc cgtgaagttg | 2700 |
| gagaaggtgg aaccaactcc cgaggagtcc caggacatga aagccctgca gaaggagcta | 2760 |
| gaacagtttg ccaagctgct gaagcagaag aggatcacct tggggtacac ccaggccgac | 2820 |
| gtggggctca ccctgggcgt tctctttgga aaggtgttca gccagaccac catctgtcgc | 2880 |
| ttcgaggcct tgcagctcag ccttaagaac atgtgtaagc tgcggcccct gctggagaag | 2940 |
| tgggtggagg aagccgacaa caatgagaac cttcaggaga tatgcaaatc ggagaccctg | 3000 |
| gtgcaggccc ggaagagaaa gcgaactagc attgagaacc gtgtgaggtg gagtctggag | 3060 |
| accatgtttc tgaagtgccc gaagccctcc ctacagcaga tcactcacat cgccaatcag | 3120 |
| cttgggctag agaaggatgt ggttcgagta tggttctgta accggcgcca gaagggcaaa | 3180 |
| agatcaagta ttgagtattc caacgagaa gagtatgagg ctacagggac accttttccca | 3240 |
| gggggggctg tatcctttcc tctgccccca ggtccccact ttggcacccc aggctatgga | 3300 |
| agcccccact tcaccacact ctactcagtc ccttttcctg agggcgaggc ctttccctct | 3360 |
| gttcccgtca ctgctctggg ctctcccatg cattcaaacg ctagcggcag cggcgccacg | 3420 |
| aacttctctc tgttaaagca agcaggagat gttgaagaaa ccccgggcc tgcatgcatg | 3480 |
| tataacatga tggagacgga gctgaagccg ccgggcccgc agcaagcttc ggggggcggc | 3540 |
| ggcggaggag gcaacgccac ggcggcggcg accggcggca accagaagaa cagcccggac | 3600 |
| cgcgtcaaga ggcccatgaa cgccttcatg gtatggtccc gggggcagcg gcgtaagatg | 3660 |
| gcccaggaga accccaagat gcacaactcg gagatcagca agcgcctggg cgcggagtgg | 3720 |
| aaacttttgt ccgagaccga gaagcggccg ttcatcgacg aggccaagcg gctgcgcgct | 3780 |
| ctgcacatga aggagcaccc ggattataaa taccggccgc ggcggaaaac caagacgctc | 3840 |
| atgaagaagg ataagtacac gcttcccgga ggcttgctgg cccccggcgg gaacagcatg | 3900 |
| gcgagcgggg ttggggtggg cgccggcctg ggtgcgggcg tgaaccagcg catggacagc | 3960 |
| tacgcgcaca tgaacggctg gagcaacggc agctacagca tgatgcagga gcagctgggc | 4020 |
| tacccgcagc acccgggcct caacgctcac ggcgcggcac agatgcaacc gatgcaccgc | 4080 |
| tacgacgtca gcgccctgca gtacaactcc atgaccagct cgcagaccta catgaacggc | 4140 |
| tcgcccacct acagcatgtc ctactcgcag caggcacccc ccgtatggc gctgggctcc | 4200 |
| atgggctctg tggtcaagtc cgaggccagc tccagccccc ccgtggttac ctcttcctcc | 4260 |
| cactccaggg cgccctgcca ggccggggac ctccgggaca tgatcagcat gtacctcccc | 4320 |
| ggcgccgagg tgccggagcc cgctgcgccc agtagactgc acatggccca gcactaccag | 4380 |
| agcggcccgg tgcccggcac ggccattaac ggcacactgc ccctgtcgca catggcatgc | 4440 |
| ggctccggcg agggcagggg aagtcttcta acatgcgggg acgtgaggga aaatcccggc | 4500 |
| ccactcgaga tgaggcagcc acctggcgag tctgacatgg ctgtcagcga cgctctgctc | 4560 |

```
ccgtccttct ccacgttcgc gtccggcccg cgggaaggg agaagacact gcgtccagca    4620
ggtgccccga ctaaccgttg gcgtgaggaa ctctctcaca tgaagcgact tccccccactt   4680
cccggccgcc cctacgacct ggcggcgacg gtggccacag acctggagag tggcggagct    4740
ggtgcagctt gcagcagtaa caacccggcc ctcctagccc ggagggagac cgaggagttc    4800
aacgacctcc tggacctaga ctttatcctt tccaactcgc taacccacca ggaatcggtg    4860
gccgccaccg tgaccacctc ggcgtcagct tcatcctcgt cttccccagc gagcagcggc    4920
cctgccagcg cgccctccac ctgcagcttc agctatccga tccgggccgg gggtgacccg    4980
ggcgtggctg ccagcaacac aggtggaggg ctcctctaca gccagagaatc tgcgccacct    5040
cccacggccc ccttcaacct ggcggacatc aatgacgtga gccctcgggg cggcttcgtg    5100
gctgagctcc tgcggccgga gttggaccca gtatacattc cgccacagca gcctcagccg    5160
ccaggtggcg ggctgatggg caagtttgtg ctgaaggcgt ctctgaccac ccctggcagc    5220
gagtacagca gccttcggt catcagtgtt agcaaaggaa gcccagacgg cagccacccc    5280
gtggtagtgg cgccctacag cggtggcccg ccgcgcatgt gccccaagat taagcaagag    5340
gcggtcccgt cctgcacggt cagccggtcc ctagaggccc atttgagcgc tggaccccag    5400
ctcagcaacg gccaccggcc caacacacac gacttccccc tggggcggca gctccccacc    5460
aggactaccc ctacactgag tcccgaggaa ctgctgaaca gcagggactg tcaccctggc    5520
ctgcctcttc ccccaggatt ccatccccat ccggggccca actaccctcc tttcctgcca    5580
gaccagatgc agtcacaagt cccctctctc cattatcaag agctcatgcc accgggttcc    5640
tgcctgccag aggagcccaa gccaaagagg ggaagaaggt cgtggccccg gaaaagaaca    5700
gccacccaca cttgtgacta tgcaggctgt ggcaaaacct ataccaagag ttctcatctc    5760
aaggcacacc tgcgaactca cacaggcgag aaaccttacc actgtgactg ggacggctgt    5820
gggtggaaat cgcccgctc cgatgaactg accaggcact accgcaaaca cacagggcac    5880
cggccctttc agtgccagaa gtgcgacagg gcctttttca ggtcggacca ccttgcctta    5940
cacatgaaga ggcactaaat gactagtcta gcaatcaacc tctggattac aaaatttgtg    6000
aaagattgac tggtattctt aactatgttg ctccttttac gctatgtgga tacgctgctt    6060
taatgccttt gtatcatgct attgcttccc gtatggcttt cattttctcc tccttgtata    6120
aatcctggtt agttcttgcc acggcggaac tcatcgccgc ctgccttgcc cgctgctgga    6180
caggggctcg gctgttgggc actgacaatt ccgtggtgtt tatttgtgaa atttgtgatg    6240
ctattgcttt atttgtaacc attctagctt tatttgtgaa atttgtgatg ctattgcttt    6300
atttgtaacc attataagct gcaataaaca agttaacaac aacaattgca ttcattttat    6360
gtttcaggtt cagggggaga tgtgggaggt tttttaaagc ggggggatcca aattcccgat    6420
aaggatcttc ctagagcatg gctacgtaga taagtagcat ggcgggttaa tcattaacta    6480
caaggaaccc ctagtgatgg agttggccac tccctctctg cgcgctcgct cgctcactga    6540
ggccgggcga ccaaaggtcg cccgacgccc gggctttgcc cgggcggcct cagtgagcga    6600
gcgagcgcgc agccttaatt aacctaattc actggccgtc gttttacaac gtcgtgactg    6660
ggaaaaccct ggcgttaccc aacttaatcg ccttgcagca catccccctt tcgccagctg    6720
gcgtaatagc gaagaggccc gcaccgatcg cccttcccaa cagttgcgca gcctgaatgg    6780
cgaatgggac gcgccctgta gcggcgcatt aagcgcggcg ggtgtggtgg ttacgcgcag    6840
cgtgaccgct acacttgcca gcgccctagc gcccgctcct ttcgctttct tcccttcctt    6900
tctcgccacg ttcgccggct tccccgtca agctctaaat cggggggctcc ctttagggtt    6960
```

```
ccgatttagt gctttacggc acctcgaccc caaaaaactt gattagggtg atggttcacg      7020
tagtgggcca tcgccctgat agacggtttt tcgcccttg acgttggagt ccacgttctt       7080
taatagtgga ctcttgttcc aaactggaac aacactcaac cctatctcgg tctattcttt      7140
tgatttataa gggattttgc cgatttcggc ctattggtta aaaaatgagc tgatttaaca      7200
aaaatttaac gcgaatttta acaaaatatt aacgtttata atttcaggtg gcatctttcg      7260
gggaaatgtg cgcggaaccc ctatttgttt attttctaa atacattcaa atatgtatcc       7320
gctcatgaga caataaccct gataaatgct tcaataatat tgaaaagga agagtatgag       7380 tattcaacat ttccgtgtcg cccttattcc ctttttgcg gcattttgcc ttcctgtttt       7440
tgctcaccca gaaacgctgg tgaaagtaaa agatgctgaa gatcagttgg gtgcacgagt      7500
gggttacatc gaactggatc tcaatagtgg taagatcctt gagagttttc gccccgaaga      7560
acgttttcca atgatgagca cttttaaagt tctgctatgt ggcgcggtat tatcccgtat      7620
tgacgccggg caagagcaac tcggtcgccg catacactat tctcagaatg acttggttga      7680
gtactcacca gtcacagaaa agcatcttac ggatggcatg acagtaagag aa              7732

<210> SEQ ID NO 34
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 34
gaggccagcg gttccggacg ggctgacgca ttggacgatt ttgatctgga tatgctggga        60
agtgacgccc tcgatgattt tgaccttgac atgcttggtt cggatgccct tgatgacttt       120
gacctcgaca tgctcggcag tgacgccctt gatgatttcg acctggacat gctgattaac       180
tctaga                                                                  186

<210> SEQ ID NO 35
<211> LENGTH: 783
<212> TYPE: DNA
<213> ORGANISM: Artificial Sequence
<220> FEATURE:
<223> OTHER INFORMATION: Synthetic Polynucleotide

<400> SEQUENCE: 35
agccagtacc tgcccgacac cgacgaccgg caccggatcg aggaaaagcg gaagcggacc        60
tacgagacat tcaagagcat catgaagaag tccccccttca gcggccccac cgaccctaga      120
cctccaccta gaagaatcgc cgtgcccagc agatccagcg ccagcgtgcc aaaacctgcc       180
ccccagcctt acccccttcac cagcagcctg agcaccatca actacgacga gttccctacc      240
atggtgttcc ccagcggcca gatctctcag gcctctgctc tggctccagc ccctcctcag       300
gtgctgcctc aggctcctgc tcctgcacca gctccagcca tggtgtctgc actggctcag      360
gcaccagcac ccgtgcctgt gctggctcct ggacctccac aggctgtggc tccaccagcc      420
cctaaaccta cacaggccgg cgagggcaca ctgtctgaag ctctgctgca gctgcagttc      480
gacgacgagg atctgggagc cctgctggga aacagcaccg atcctgccgt gttcaccgac      540
ctggccagcg tggacaacag cgagttccag cagctgctga accagggcat ccctgtggcc      600
cctcacacca ccgagcccat gctgatggaa taccccgagg ccatcacccg gctcgtgaca      660
ggcgctcaga ggcctcctga tccagctcct gcccctctgg gagcaccagg cctgcctaat      720
```

```
ggactgctgt ctggcgacga ggacttcagc tctatcgccg atatggattt ctcagccttg    780
ctg                                                                  783

<210> SEQ ID NO 36
<211> LENGTH: 570
<212> TYPE: DNA
<213> ORGANISM: Artificial Sequence
<220> FEATURE:
<223> OTHER INFORMATION: Synthetic Polynucleotide

<400> SEQUENCE: 36
cgggattcca gggaagggat gttttgccg aagcctgagg ccggctccgc tattagtgac      60
gtgtttgagg gccgcgaggt gtgccagcca aaacgaatcc ggccatttca tcctccagga   120
agtccatggg ccaaccgccc actcccgcc agcctcgcac caacaccaac cggtccagta    180
catgagccag tcgggtcact gaccccggca ccagtccctc agccactgga tccagcgccc   240
gcagtgactc ccgaggccag tcacctgttg gaggatcccg atgaagagac gagccaggct   300
gtcaaagccc ttcgggagat ggccgatact gtgattcccc agaaggaaga ggctgcaatc   360
tgtggccaaa tggaccttc ccatccgccc caaggggcc atctggatga gctgacaacc     420
acacttgagt ccatgaccga ggatctgaac ctggactcac ccctgacccc ggaattgaac   480
gagattctgg ataccttcct gaacgacgag tgcctcttgc atgccatgca tatcagcaca   540
ggactgtcca tcttcgacac atctctgttt                                    570

<210> SEQ ID NO 37
<211> LENGTH: 1416
<212> TYPE: DNA
<213> ORGANISM: Artificial Sequence
<220> FEATURE:
<223> OTHER INFORMATION: Synthetic Polynucleotide

<400> SEQUENCE: 37
gcttcaaact ttactcagtt cgtgctcgtg gacaatggtg ggacagggga tgtgacagtg    60
gctccttcta atttcgctaa tggggtggca gagtggatca gctccaactc acggagccag   120
gcctacaagg tgacatgcag cgtcaggcag tctagtgccc agaagagaaa gtataccatc   180
aaggtggagg tccccaaagt ggctacccag acagtgggcg gagtcgaact gcctgtcgcc   240
gcttggaggt cctacctgaa catggagctc actatcccaa ttttcgctac caattctgac   300
tgtgaactca tcgtgaaggc aatgcagggg ctcctcaaag acggtaatcc tatcccttcc   360
gccatcgccg ctaactcagg tatctacagc gctggaggag gtggaagcgg aggaggagga   420
agcggaggag gaggtagcgg acctaagaaa agaggaagg tggcggccgc tggatcccct   480
tcagggcaga tcagcaacca ggccctggct ctggccccta gctccgctcc agtgctggcc   540
cagactatgg tgccctctag tgctatggtg cctctggccc agccacctgc tccagcccct   600
gtgctgaccc caggaccacc ccagtcactg agcgctccag tgcccaagtc tacacaggcc   660
ggcgagggga ctctgagtga agctctgctg cacctgcagt tcgacgctga tgaggacctg   720
ggagctctgc tggggaacag caccgatccc ggagtgttca cagatctggc ctccgtggac   780
aactctgagt tcagcagct gctgaatcag ggcgtgtcca tgtctcatag tacagccgaa   840
ccaatgctga tggagtaccc cgaagccatt acccggctgg tgaccggcag ccagcggccc   900
cccgaccccg ctccaactcc cctgggaacc agcggcctgc ctaatgggct gtccggagat   960
gaagacttct caagcatcgc tgatatggac tttagtgccc tgctgtcaca gatttcctct  1020
agtgggcagg gaggaggtgg aagcggcttc agcgtggaca ccagtgccct gctggacctg  1080
```

```
ttcagcccct cggtgaccgt gcccgacatg agcctgcctg accttgacag cagcctggcc    1140
agtatccaag agctcctgtc tccccaggag ccccccaggc ctcccgaggc agagaacagc    1200
agcccggatt cagggaagca gctggtgcac tacacagcgc agccgctgtt cctgctggac    1260
cccggctccg tggacaccgg gagcaacgac ctgccggtgc tgtttgagct gggagagggc    1320
tcctacttct ccgaaggga cggcttcgcc gaggacccca ccatctccct gctgacaggc    1380
tcggagcctc ccaaagccaa ggaccccact gtctcc                              1416

<210> SEQ ID NO 38
<211> LENGTH: 3594
<212> TYPE: DNA
<213> ORGANISM: Artificial Sequence
<220> FEATURE:
<223> OTHER INFORMATION: Synthetic Polynucleotide

<400> SEQUENCE: 38
atggcgggac acctggcttc ggatttcgcc ttctcgcccc ctccaggtgg tggaggtgat      60
gggccagggg ggccggagcc gggctgggtt gatcctcgga cctggctaag cttccaaggc     120
cctcctggag ggccaggaat cgggccgggg gttgggccag gctctgaggt gtgggggatt     180
cccccatgcc ccccgccgta tgagttctgt gggggatgg cgtactgtgg gccccaggtt     240
ggagtggggc tagtgcccca aggcggcttg gagacctctc agcctgaggg cgaagcagga     300 gtcgggtgg agagcaactc cgatggggcc tccccggagc cctgcaccgt caccctggt     360 gccgtgaagc tggagaagga gaagctggag caaaacccgg aggagtccca ggacatcaaa     420
gctctgcaga agaactcga gcaatttgcc aagctcctga gcagaagag gatcaccctg     480 ggatatacac aggccgatgt ggggctcacc ctgggggttc tatttgggaa ggtattcagc     540
caaacgacca tctgccgctt tgaggctctg cagcttagct tcaagaacat tgtgtaagctg     600 cggcccttgc tgcagaagtg ggtggaggaa gctgacaaca atgaaaatct tcaggagata     660
tgcaaagcag aaaccctcgt gcaggcccga agagaaagc gaaccagtat cgagaaccga     720
gtgagaggca acctggagaa tttgttcctg cagtgcccga aacccacact gcagcagatc     780
agccacatcg cccagcagct tgggctcgag aaggatgtgg tccgagtgtg gttctgtaac     840
cggcgccaga agggcaagcg atcaagcagc gactatgcac aacgagagga ttttgaggct     900
gctgggtctc ctttctcagg gggaccagtg tcctttcctc tggccccagg gccccatttt     960
ggtaccccag gctatgggag ccctcacttc actgcactgt actcctcggt cccctttccct    1020 gaggggggaag cctttccccc tgtctctgtc accactctgg gctctcccat gcattcaaac    1080
gctagcggca gcggcgccac gaacttctct ctgttaaagc aagcaggaga tgttgaagaa    1140 aaccccggc ctgcatgcat gtacaacatg atggagacgg agctgaagcc gccgggcccg    1200
cagcaaactt cgggggggcgg cggcggcaac tccaccgcgg cggcggccgg cggcaaccag    1260
aaaaacagcc cggaccgcgt caagcggccc atgaatgcct tcatggtgtg gtcccgcggg    1320
cagcggcgca agatggccca ggagaacccc aagatgcaca actcggagat cagcaagcgc    1380
ctgggcgccg agtggaaact tttgtcggag acgagaagc ggccgttcat cgacgaggct    1440
aagcggctgc gagcgctgca catgaaggag cacccggatt ataaataccg gcccggcgg    1500 aaaaccaaga cgctcatgaa gaaggataag tacacgctgc ccggcgggct gctggccccc    1560
ggcggcaata gcatggcgag cggggtcggg gtgggcgccg gctgggcgc gggcgtgaac    1620 cagcgcatgg acagttacgc gcacatgaac ggctggagca acggcagcta cagcatgatg    1680
```

| | |
|---|---|
| caggaccagc tgggctaccc gcagcacccg ggcctcaatg cgcacggcgc agcgcagatg | 1740 |
| cagcccatgc accgctacga cgtgagcgcc ctgcagtaca actccatgac cagctcgcag | 1800 |
| acctacatga acggctcgcc cacctacagc atgtcctact cgcagcaggg caccccctggc | 1860 |
| atggctcttg gctccatggg ttcggtggtc aagtccgagg ccagctccag cccccctgtg | 1920 |
| gttacctctt cctcccactc cagggcgccc tgccaggccg ggacctccg ggacatgatc | 1980 |
| agcatgtatc tccccggcgc cgaggtgccg gaacccgccg cccccagcag acttcacatg | 2040 |
| tcccagcact accagagcgg cccggtgccc ggcacggcca ttaacggcac actgcccctc | 2100 |
| tcacacatgg catgcggctc cggcgagggc aggggaagtc ttctaacatg cggggacgtg | 2160 |
| gaggaaaatc ccggcccact cgagatggct gtcagcgacg cgctgctccc atctttctcc | 2220 |
| acgttcgcgt ctggcccggc gggaagggag aagacactgc gtcaagcagg tgccccgaat | 2280 |
| aaccgctggc gggaggagct ctcccacatg aagcgacttc ccccagtgct tcccggccgc | 2340 |
| ccctatgacc tggcggcggc gaccgtggcc acagacctgg agagcggcgg agccggtgcg | 2400 |
| gcttgcggcg gtagcaacct ggcgccccta cctcggagag agaccgagga gttcaacgat | 2460 |
| ctcctggacc tggactttat tctctccaat tcgctgaccc atcctccgga gtcagtggcc | 2520 |
| gccaccgtgt cctcgtcagc gtcagcctcc tcttcgtcgt cgccgtcgag cagcggccct | 2580 |
| gccagcgcgc cctccacctg cagcttcacc tatccgatcc gggccgggaa cgacccgggc | 2640 |
| gtggcgccgg gcggcacggg cggaggcctc ctctatggca gggagtccgc tccccctccg | 2700 |
| acggctccct tcaacctggc ggacatcaac gacgtgagcc cctcgggcgg cttcgtggcc | 2760 |
| gagctcctgc ggccagaatt ggacccggtg tacattccgc cgcagcagcc gcagccgcca | 2820 |
| ggtggcgggc tgatgggcaa gttcgtgctg aaggcgtcgc tgagcgcccc tggcagcgag | 2880 |
| tacggcagcc cgtcggtcat cagcgtcagc aaaggcagcc ctgacggcag ccacccggtg | 2940 |
| gtggtggcgc cctacaacgg cgggccgccg cgcacgtgcc ccaagatcaa gcaggaggcg | 3000 |
| gtctcttcgt gcacccactt gggcgctgga cccccctctca gcaatggcca ccggccggct | 3060 |
| gcacacgact tccccctggg gcggcagctc cccagcagga ctaccccgac cctgggtctt | 3120 |
| gaggaagtgc tgagcagcag ggactgtcac cctgccctgc cgcttcctcc cggcttccat | 3180 |
| ccccacccgg ggcccaatta cccatccttc ctgcccgatc agatgcagcc gcaagtcccg | 3240 |
| ccgctccatt accaagagct catgccaccc ggttcctgca tgccagagga gcccaagcca | 3300 |
| aagagggaa gacgatcgtg gccccggaaa aggaccgcca cccacacttg tgattacgcg | 3360 |
| ggctgcggca aaacctacac aaagagttcc catctcaagg cacacctgcg aacccacaca | 3420 |
| ggtgagaaac cttaccactg tgactgggac ggctgtggat ggaaattcgc ccgctcagat | 3480 |
| gaactgacca ggcactaccg taaacacacg ggcaccgcc cgttccagtg ccaaaaatgc | 3540 |
| gaccgagcat tttccaggtc ggaccacctc gccttacaca tgaagaggca tttt | 3594 |

```
<210> SEQ ID NO 39
<211> LENGTH: 1198
<212> TYPE: PRT
<213> ORGANISM: Artificial Sequence
<220> FEATURE:
<223> OTHER INFORMATION: Synthetic Polypeptide

<400> SEQUENCE: 39

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30
```

Arg Thr Trp Leu Ser Phe Gln Gly Pro Pro Gly Pro Gly Ile Gly
            35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
    195                 200                 205

Glu Glu Ala Asp Asn Asn Glu Asn Leu Gln Glu Ile Cys Lys Ala Glu
            210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn Ala Ser Gly Ser Gly Ala Thr Asn
            355                 360                 365

Phe Ser Leu Leu Lys Gln Ala Gly Asp Val Glu Glu Asn Pro Gly Pro
370                 375                 380

Ala Cys Met Tyr Asn Met Met Glu Thr Glu Leu Lys Pro Pro Gly Pro
385                 390                 395                 400

Gln Gln Thr Ser Gly Gly Gly Gly Asn Ser Thr Ala Ala Ala Ala
                405                 410                 415

Gly Gly Asn Gln Lys Asn Ser Pro Asp Arg Val Lys Arg Pro Met Asn
            420                 425                 430

Ala Phe Met Val Trp Ser Arg Gly Gln Arg Arg Lys Met Ala Gln Glu
            435                 440                 445

```
Asn Pro Lys Met His Asn Ser Glu Ile Ser Lys Arg Leu Gly Ala Glu
    450                 455                 460
Trp Lys Leu Leu Ser Glu Thr Glu Lys Arg Pro Phe Ile Asp Glu Ala
465                 470                 475                 480
Lys Arg Leu Arg Ala Leu His Met Lys Glu His Pro Asp Tyr Lys Tyr
                485                 490                 495
Arg Pro Arg Arg Lys Thr Lys Thr Leu Met Lys Lys Asp Lys Tyr Thr
                500                 505                 510
Leu Pro Gly Gly Leu Leu Ala Pro Gly Gly Asn Ser Met Ala Ser Gly
                515                 520                 525
Val Gly Val Gly Ala Gly Leu Gly Ala Gly Val Asn Gln Arg Met Asp
530                 535                 540
Ser Tyr Ala His Met Asn Gly Trp Ser Asn Gly Ser Tyr Ser Met Met
545                 550                 555                 560
Gln Asp Gln Leu Gly Tyr Pro Gln His Pro Gly Leu Asn Ala His Gly
                565                 570                 575
Ala Ala Gln Met Gln Pro Met His Arg Tyr Asp Val Ser Ala Leu Gln
                580                 585                 590
Tyr Asn Ser Met Thr Ser Ser Gln Thr Tyr Met Asn Gly Ser Pro Thr
            595                 600                 605
Tyr Ser Met Ser Tyr Ser Gln Gln Gly Thr Pro Gly Met Ala Leu Gly
            610                 615                 620
Ser Met Gly Ser Val Val Lys Ser Glu Ala Ser Ser Ser Pro Pro Val
625                 630                 635                 640
Val Thr Ser Ser Ser His Ser Arg Ala Pro Cys Gln Ala Gly Asp Leu
                645                 650                 655
Arg Asp Met Ile Ser Met Tyr Leu Pro Gly Ala Glu Val Pro Glu Pro
                660                 665                 670
Ala Ala Pro Ser Arg Leu His Met Ser Gln His Tyr Gln Ser Gly Pro
                675                 680                 685
Val Pro Gly Thr Ala Ile Asn Gly Thr Leu Pro Leu Ser His Met Ala
                690                 695                 700
Cys Gly Ser Gly Glu Gly Arg Gly Ser Leu Leu Thr Cys Gly Asp Val
705                 710                 715                 720
Glu Glu Asn Pro Gly Pro Leu Glu Met Ala Val Ser Asp Ala Leu Leu
                725                 730                 735
Pro Ser Phe Ser Thr Phe Ala Ser Gly Pro Ala Gly Arg Glu Lys Thr
                740                 745                 750
Leu Arg Gln Ala Gly Ala Pro Asn Asn Arg Trp Arg Glu Glu Leu Ser
                755                 760                 765
His Met Lys Arg Leu Pro Pro Val Leu Pro Gly Arg Pro Tyr Asp Leu
770                 775                 780
Ala Ala Ala Thr Val Ala Thr Asp Leu Glu Ser Gly Gly Ala Gly Ala
785                 790                 795                 800
Ala Cys Gly Gly Ser Asn Leu Ala Pro Leu Pro Arg Arg Glu Thr Glu
                805                 810                 815
Glu Phe Asn Asp Leu Leu Asp Leu Asp Phe Ile Leu Ser Asn Ser Leu
                820                 825                 830
Thr His Pro Pro Glu Ser Val Ala Thr Val Ser Ser Ser Ala Ser
                835                 840                 845
Ala Ser Ser Ser Ser Ser Pro Ser Ser Ser Gly Pro Ala Ser Ala Pro
850                 855                 860
Ser Thr Cys Ser Phe Thr Tyr Pro Ile Arg Ala Gly Asn Asp Pro Gly
```

| | | | | | | | | | | | |
|---|---|---|---|---|---|---|---|---|---|---|---|
| 865 | | | | 870 | | | | 875 | | | 880 |
| Val | Ala | Pro | Gly | Gly | Thr | Gly | Gly | Leu | Leu | Tyr | Gly | Arg | Glu | Ser |

Val Ala Pro Gly Gly Thr Gly Gly Leu Leu Tyr Gly Arg Glu Ser
                          885                            890                        895

Ala Pro Pro Pro Thr Ala Pro Phe Asn Leu Ala Asp Ile Asn Asp Val
            900                            905                        910

Ser Pro Ser Gly Gly Phe Val Ala Glu Leu Leu Arg Pro Glu Leu Asp
            915                            920                        925

Pro Val Tyr Ile Pro Pro Gln Gln Pro Gln Pro Pro Gly Gly Leu
     930                            935                        940

Met Gly Lys Phe Val Leu Lys Ala Ser Leu Ser Ala Pro Gly Ser Glu
945                  950                        955                        960

Tyr Gly Ser Pro Ser Val Ile Ser Val Ser Lys Gly Ser Pro Asp Gly
                965                         970                        975

Ser His Pro Val Val Ala Pro Tyr Asn Gly Gly Pro Arg Thr
              980                         985                        990

Cys Pro Lys Ile Lys Gln Glu Ala  Val Ser Ser Cys Thr  His Leu Gly
           995                          1000                      1005

Ala Gly  Pro Pro Leu Ser Asn  Gly His Arg Pro Ala  Ala His Asp
    1010                      1015                      1020

Phe Pro  Leu Gly Arg Gln Leu  Pro Ser Arg Thr Thr  Pro Thr Leu
    1025                      1030                      1035

Gly Leu  Glu Glu Val Leu Ser  Ser Arg Asp Cys His  Pro Ala Leu
    1040                      1045                      1050

Pro Leu  Pro Pro Gly Phe His  Pro His Pro Gly Pro  Asn Tyr Pro
    1055                      1060                      1065

Ser Phe  Leu Pro Asp Gln Met  Gln Pro Gln Val Pro  Pro Leu His
    1070                      1075                      1080

Tyr Gln  Glu Leu Met Pro Pro  Gly Ser Cys Met Pro  Glu Glu Pro
    1085                      1090                      1095

Lys Pro  Lys Arg Gly Arg Arg  Ser Trp Pro Arg Lys  Arg Thr Ala
    1100                      1105                      1110

Thr His  Thr Cys Asp Tyr Ala  Gly Cys Gly Lys Thr  Tyr Thr Lys
    1115                      1120                      1125

Ser Ser  His Leu Lys Ala His  Leu Arg Thr His Thr  Gly Glu Lys
    1130                      1135                      1140

Pro Tyr  His Cys Asp Trp Asp  Gly Cys Gly Trp Lys  Phe Ala Arg
    1145                      1150                      1155

Ser Asp  Glu Leu Thr Arg His  Tyr Arg Lys His Thr  Gly His Arg
    1160                      1165                      1170

Pro Phe  Gln Cys Gln Lys Cys  Asp Arg Ala Phe Ser  Arg Ser Asp
    1175                      1180                      1185

His Leu  Ala Leu His Met Lys  Arg His Phe
    1190                      1195

<210> SEQ ID NO 40
<211> LENGTH: 1080
<212> TYPE: DNA
<213> ORGANISM: Homo sapiens

<400> SEQUENCE: 40
atggcgggac acctggcttc ggatttcgcc ttctcgcccc ctccaggtgg tggaggtgat    60
gggccagggg ggccggagcc gggctgggtt gatcctcgga cctggctaag cttccaaggc   120
cctcctggag ggccaggaat cgggccgggg gttgggccag gctctgaggt gtggggatt   180

```
cccccatgcc  ccccgccgta  tgagttctgt  gggggggatgg  cgtactgtgg  gccccaggtt       240
ggagtggggc  tagtgcccca  aggcggcttg  gagacctctc  agcctgaggg  cgaagcagga       300
gtcggggtgg  agagcaactc  cgatggggcc  tccccggagc  cctgcaccgt  caccccctggt     360 gccgtgaagc  tggagaagga  gaagctggag  caaaacccgg  aggagtccca  ggacatcaaa       420
gctctgcaga  agaactcga  gcaatttgcc  aagctcctga  agcagaagag  gatcaccctg        480
ggatatacac  aggccgatgt  ggggctcacc  ctggggggttc  tatttgggaa  ggtattcagc      540
caaacgacca  tctgccgctt  tgaggctctg  cagcttagct  tcaagaacat  gtgtaagctg       600
cggcccttgc  tgcagaagtg  ggtggaggaa  gctgacaaca  atgaaaatct  tcaggagata       660
tgcaaagcag  aaaccctcgt  gcaggcccga  aagagaaagc  gaaccagtat  cgagaaccga       720
gtgagaggca  acctggagaa  tttgttcctg  cagtgcccga  aacccacact  gcagcagatc       780
agccacatcg  cccagcagct  tgggctcgag  aaggatgtgg  tccgagtgtg  gttctgtaac      840
cggcgccaga  agggcaagcg  atcaagcagc  gactatgcac  aacgagagga  ttttgaggct       900
gctgggtctc  ctttctcagg  gggaccagtg  tcctttcctc  tggccccagg  gccccatttt       960
ggtaccccag  gctatgggag  ccctcacttc  actgcactgt  actcctcggt  cccttccct     1020 gagggggaag  cctttccccc  tgtctctgtc  accactctgg  gctctcccat  gcattcaaac      1080
```

<210> SEQ ID NO 41
<211> LENGTH: 360
<212> TYPE: PRT
<213> ORGANISM: Homo sapiens

<400> SEQUENCE: 41

```
Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220
```

```
Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
            245                 250                 255

Leu Gln Gln Ile Ser His Ile Ala Gln Gln Leu Gly Leu Glu Lys Asp
        260                 265                 270

Val Val Arg Val Trp Phe Cys Asn Arg Arg Gln Lys Gly Lys Arg Ser
    275                 280                 285

Ser Ser Asp Tyr Ala Gln Arg Glu Asp Phe Glu Ala Ala Gly Ser Pro
        290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
            325                 330                 335

Val Pro Phe Pro Glu Gly Glu Ala Phe Pro Pro Val Ser Val Thr Thr
        340                 345                 350

Leu Gly Ser Pro Met His Ser Asn
        355                 360

<210> SEQ ID NO 42
<211> LENGTH: 951
<212> TYPE: DNA
<213> ORGANISM: Homo sapiens

<400> SEQUENCE: 42
atgtacaaca tgatggagac ggagctgaag ccgccgggcc cgcagcaaac ttcgggggc      60
ggcggcggca actccaccgc ggcggcggcc ggcggcaacc agaaaaacag cccggaccgc    120
gtcaagcggc ccatgaatgc cttcatggtg tggtcccgcg gcagcggcg caagatggcc    180
caggagaacc ccaagatgca caactcggag atcagcaagc gcctgggcgc cgagtggaaa    240
cttttgtcgg agacggagaa gcggccgttc atcgacgagg ctaagcggct gcgagcgctg    300
cacatgaagg agcacccgga ttataaatac cggccccggc ggaaaaccaa gacgctcatg    360
aagaaggata gtacacgct gcccggcggg ctgctggccc ccggcggcaa tagcatggcg    420
agcggggtcg gggtgggcgc cggcctgggc gcgggcgtga accagcgcat ggacagttac    480
gcgcacatga cggctggag caacggcagc tacagcatga tgcaggacca gctgggctac    540
ccgcagcacc cgggcctcaa tgcgcacggc gcagcgcaga tgcagcccat gcaccgctac    600
gacgtgagcg ccctgcagta caactccatg accagctcgc agacctacat gaacggctcg    660
cccacctaca gcatgtccta ctcgcagcag ggcacccctg gcatggctct tggctccatg    720
ggttcggtgg tcaagtccga ggccagctcc agccccctg tggttacctc ttcctcccac    780
tccagggcgc cctgccaggc cggggacctc cgggacatga tcagcatgta tctccccggc    840
gccgaggtgc cggaacccgc cgcccccagc agacttcaca tgtcccagca ctaccagagc    900
ggcccggtgc ccggcacggc cattaacggc acactgcccc tctcacacat g             951

<210> SEQ ID NO 43
<211> LENGTH: 317
<212> TYPE: PRT
<213> ORGANISM: Homo sapiens

<400> SEQUENCE: 43

Met Tyr Asn Met Met Glu Thr Glu Leu Lys Pro Pro Gly Pro Gln Gln
1               5                   10                  15
```

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
                35                  40                  45

Met Val Trp Ser Arg Gly Gln Arg Arg Lys Met Ala Gln Glu Asn Pro
 50                  55                  60

Lys Met His Asn Ser Glu Ile Ser Lys Arg Leu Gly Ala Glu Trp Lys
 65                  70                  75                  80

Leu Leu Ser Glu Thr Glu Lys Arg Pro Phe Ile Asp Glu Ala Lys Arg
                 85                  90                  95

Leu Arg Ala Leu His Met Lys Glu His Pro Asp Tyr Lys Tyr Arg Pro
                100                 105                 110

Arg Arg Lys Thr Lys Thr Leu Met Lys Lys Asp Lys Tyr Thr Leu Pro
            115                 120                 125

Gly Gly Leu Leu Ala Pro Gly Gly Asn Ser Met Ala Ser Gly Val Gly
130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
                180                 185                 190

Gln Met Gln Pro Met His Arg Tyr Asp Val Ser Ala Leu Gln Tyr Asn
            195                 200                 205

Ser Met Thr Ser Ser Gln Thr Tyr Met Asn Gly Ser Pro Thr Tyr Ser
210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
            290                 295                 300

Gly Thr Ala Ile Asn Gly Thr Leu Pro Leu Ser His Met
305                 310                 315

<210> SEQ ID NO 44
<211> LENGTH: 1410
<212> TYPE: DNA
<213> ORGANISM: Homo sapiens

<400> SEQUENCE: 44

```
atggctgtca gcgacgcgct gctcccatct ttctccacgt tcgcgtctgg cccggcggga      60
agggagaaga cactgcgtca agcaggtgcc ccgaataacc gctggcggga ggagctctcc     120
cacatgaagc gacttccccc agtgcttccc ggccgcccct atgacctggc ggcggcgacc     180
gtggccacag acctggagag cggcggagcc ggtgcggctt cggcggtag caacctggcg     240 cccctacctc ggagagagac cgaggagttc aacgatctcc tggacctgga ctttattctc     300
tccaattcgc tgacccatcc tccggagtca gtggccgcca ccgtgtcctc gtcagcgtca     360
gcctcctctt cgtcgtcgcc gtcgagcagc ggccctgcca gcgcgccctc cacctgcagc     420
```

```
ttcacctatc cgatccgggc cgggaacgac ccgggcgtgg cgccgggcgg cacgggcgga      480
ggcctcctct atggcaggga gtccgctccc cctccgacgg ctcccttcaa cctggcggac      540
atcaacgacg tgagcccctc gggcggcttc gtggccgagc tcctgcggcc agaattggac      600
ccggtgtaca ttccgccgca gcagccgcag ccgccaggtg gcgggctgat gggcaagttc      660
gtgctgaagg cgtcgctgag cgcccctggc agcgagtacg gcagcccgtc ggtcatcagc      720
gtcagcaaag gcagccctga cggcagccac ccggtggtgg tggcgcccta caacggcggg      780
ccgccgcgca cgtgccccaa gatcaagcag gaggcggtct cttcgtgcac ccacttgggc      840
gctggacccc ctctcagcaa tggccaccgg ccggctgcac acgacttccc cctggggcgg      900
cagctcccca gcaggactac cccgaccctg ggtcttgagg aagtgctgag cagcagggac      960
tgtcaccctg ccctgccgct tcctcccggc ttccatcccc acccggggcc caattaccca     1020
tccttcctgc ccgatcagat gcagccgcaa gtccgccgc tccattacca agagctcatg      1080
ccacccggtt cctgcatgcc agaggagccc aagccaaaga ggggaagacg atcgtggccc     1140
cggaaaagga ccgccaccca cacttgtgat tacgcgggct gcggcaaaac ctacacaaag     1200
agttcccatc tcaaggcaca cctgcgaacc cacacaggtg agaaaccta ccactgtgac       1260
tgggacggct gtggatggaa attcgcccgc tcagatgaac tgaccaggca ctaccgtaaa     1320
cacacggggc accgcccgtt ccagtgccaa aaatgcgacc gagcattttc caggtcggac     1380
cacctcgcct tacacatgaa gaggcatttt                                      1410
```

<210> SEQ ID NO 45
<211> LENGTH: 470
<212> TYPE: PRT
<213> ORGANISM: Homo sapiens

<400> SEQUENCE: 45

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Ala Thr Val Ala Thr Asp
    50                  55                  60

Leu Glu Ser Gly Gly Ala Gly Ala Ala Cys Gly Gly Ser Asn Leu Ala
65                  70                  75                  80

Pro Leu Pro Arg Arg Glu Thr Glu Glu Phe Asn Asp Leu Leu Asp Leu
                85                  90                  95

Asp Phe Ile Leu Ser Asn Ser Leu Thr His Pro Pro Glu Ser Val Ala
            100                 105                 110

Ala Thr Val Ser Ser Ser Ala Ser Ala Ser Ser Ser Ser Pro Ser
        115                 120                 125

Ser Ser Gly Pro Ala Ser Ala Pro Ser Thr Cys Ser Phe Thr Tyr Pro
    130                 135                 140

Ile Arg Ala Gly Asn Asp Pro Gly Val Ala Pro Gly Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Ser Gly Gly Phe Val Ala
            180                 185                 190

Glu Leu Leu Arg Pro Glu Leu Asp Pro Val Tyr Ile Pro Pro Gln Gln
```

```
                195                 200                 205
Pro Gln Pro Pro Gly Gly Leu Met Gly Lys Phe Val Leu Lys Ala
    210                 215                 220
Ser Leu Ser Ala Pro Gly Ser Glu Tyr Gly Ser Pro Ser Val Ile Ser
225                 230                 235                 240
Val Ser Lys Gly Ser Pro Asp Gly Ser His Pro Val Val Val Ala Pro
                245                 250                 255
Tyr Asn Gly Gly Pro Pro Arg Thr Cys Pro Lys Ile Lys Gln Glu Ala
                260                 265                 270
Val Ser Ser Cys Thr His Leu Gly Ala Gly Pro Pro Leu Ser Asn Gly
                275                 280                 285
His Arg Pro Ala Ala His Asp Phe Pro Leu Gly Arg Gln Leu Pro Ser
    290                 295                 300
Arg Thr Thr Pro Thr Leu Gly Leu Glu Glu Val Leu Ser Ser Arg Asp
305                 310                 315                 320
Cys His Pro Ala Leu Pro Leu Pro Pro Gly Phe His Pro His Pro Gly
                325                 330                 335
Pro Asn Tyr Pro Ser Phe Leu Pro Asp Gln Met Gln Pro Gln Val Pro
                340                 345                 350
Pro Leu His Tyr Gln Glu Leu Met Pro Pro Gly Ser Cys Met Pro Glu
            355                 360                 365
Glu Pro Lys Pro Lys Arg Gly Arg Arg Ser Trp Pro Arg Lys Arg Thr
    370                 375                 380
Ala Thr His Thr Cys Asp Tyr Ala Gly Cys Gly Lys Thr Tyr Thr Lys
385                 390                 395                 400
Ser Ser His Leu Lys Ala His Leu Arg Thr His Thr Gly Glu Lys Pro
                405                 410                 415
Tyr His Cys Asp Trp Asp Gly Cys Gly Trp Lys Phe Ala Arg Ser Asp
                420                 425                 430
Glu Leu Thr Arg His Tyr Arg Lys His Thr Gly His Arg Pro Phe Gln
            435                 440                 445
Cys Gln Lys Cys Asp Arg Ala Phe Ser Arg Ser Asp His Leu Ala Leu
    450                 455                 460
His Met Lys Arg His Phe
465                 470

<210> SEQ ID NO 46
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 46
attttaatct cactagggtt ctgggagcac ccccccccac cgctcccgcc ctccacaaag      60
ctcctgggcc cctcctccct tcaaggattg cgaagagctg gtcgcaaatc ctcctaagcc     120
accagcatct cggtcttcag ctcacaccag ccttgagccc agcctgcggc caggggacca     180
cgcacgtccc acccacccag cgactcccca gccgctgccc actcttcctc actca          235

<210> SEQ ID NO 47
<211> LENGTH: 229
<212> TYPE: DNA
<213> ORGANISM: Artificial Sequence
<220> FEATURE:
<223> OTHER INFORMATION: Synthetic Polynucleotide
```

<400> SEQUENCE: 47

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt    180
gccgcattgc agagatattg tatttaagtg cctagctcga tacataaac                229
```

<210> SEQ ID NO 48
<211> LENGTH: 617
<212> TYPE: DNA
<213> ORGANISM: Artificial Sequence
<220> FEATURE:
<223> OTHER INFORMATION: Synthetic Polynucleotide

<400> SEQUENCE: 48

```
cattgattat tgactagtta ttaatagtaa tcaattacgg ggtcattagt tcatagccca     60
tatatggagt tccgcgttac ataacttacg gtaaatggcc cgcctggctg accgcccaac    120
gacccccgcc cattgacgtc aataatgacg tatgttccca tagtaacgcc aatagggact    180
ttccattgac gtcaatgggt ggactattta cggtaaactg cccacttggc agtacatcaa    240
gtgtatcata tgccaagtac gccccctatt gacgtcaatg acggtaaatg gcccgcctgg    300
cattatgccc agtacatgac cttatgggac tttcctactt ggcagtacat ctacgtatta    360
gtcatcgcta ttaccatggt gatgcggttt tggcagtaca tcaatgggcg tggatagcgg    420
tttgactcac ggggatttcc aagtctccac cccattgacg tcaatgggag tttgttttgg    480
caccaaaatc aacgggactt tccaaaatgt cgtaacaact ccgccccatt gacgcaaatg    540
ggcggtaggc gtgtacggtg ggaggtctat ataagcagag ctggtttagt gaaccgtcag    600
atccgctaga gatccgc                                                   617
```

<210> SEQ ID NO 49
<211> LENGTH: 252
<212> TYPE: DNA
<213> ORGANISM: Artificial Sequence
<220> FEATURE:
<223> OTHER INFORMATION: Synthetic Polynucleotide

<400> SEQUENCE: 49

```
tcgagtggct ccggtgcccg tcagtgggca gagcgcacat cgcccacagt ccccgagaag     60 ttgggggggag gggtcggcaa ttgaaccggt gcctagagaa ggtggcgcgg ggtaaactgg    120
gaaagtgatg tcgtgtactg gctccgcctt tttcccgagg gtgggggaga accgtatata    180
agtgcagtag tcgccgtgaa cgttctttt cgcaacgggt ttgccgccag aacacaggtg    240
tcgtgaccgc gg                                                        252
```

<210> SEQ ID NO 50
<211> LENGTH: 292
<212> TYPE: DNA
<213> ORGANISM: Artificial Sequence
<220> FEATURE:
<223> OTHER INFORMATION: Synthetic Polynucleotide

<400> SEQUENCE: 50

```
gggccccaga agcctggtgg ttgtttgtcc ttctcagggg aaaagtgagg cggccccttg     60
gaggaagggg ccgggcagaa tgatctaatc ggattccaag cagctcaggg gattgtcttt    120
ttctagcacc ttcttgccac tcctaagcgt cctccgtgac cccggctggg atttcgcctg    180
gtgctgtgtc agccccggtc tcccaggggc ttcccagtgg tccccaggaa ccctcgacag    240
```

```
ggcccggtct ctctcgtcca gcaagggcag ggacgggcca caggccaagg gc          292
```

<210> SEQ ID NO 51
<211> LENGTH: 113
<212> TYPE: DNA
<213> ORGANISM: Artificial Sequence
<220> FEATURE:
<223> OTHER INFORMATION: Synthetic Polynucleotide

<400> SEQUENCE: 51

```
gcctgtagcc ttaatctctc ctagcagggg gtttggggga gggaggagga gaaagaaagg    60
gccccttatg gctgagacac aatgacccag ccacaaggag ggattaccgg gcg          113
```

<210> SEQ ID NO 52
<211> LENGTH: 281
<212> TYPE: DNA
<213> ORGANISM: Artificial Sequence
<220> FEATURE:
<223> OTHER INFORMATION: Synthetic Polynucleotide

<400> SEQUENCE: 52

```
aggtaggaag tggcctttaa ctccatagac cctatttaaa cagcttcgga caggtttaaa    60
catctccttg gataattcct agtatccctg ttcccactcc tactcaggga tgatagctct   120
aagaggtgtt aggggattag gctgaaaatg taggtcaccc ctcagccatc tgggaactag   180
aatgagtgag agaggagaga ggggcagaga cacacacatt cgcatattaa ggtgacgcgt   240
gtggcctcga acaccgagcg accctgcagc gacccgctta a                       281
```

<210> SEQ ID NO 53
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 53

```
aacgtatcta cagtttactc cctatc                                        26
```

<210> SEQ ID NO 54
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 54

```
ggtaggaagt ggtacggaaa g                                             21
```

<210> SEQ ID NO 55
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 55

```
cactgacaat tccgtggtgt                                               20
```

<210> SEQ ID NO 56
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 56
gagatccgac tcgtctgagg                                          20

<210> SEQ ID NO 57
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 57
tgggaagaca acctgtaggg                                          20

<210> SEQ ID NO 58
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 58
tgaaaccccg tctctaccaa                                          20

<210> SEQ ID NO 59
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 59
acatcgccaa tcagcttgg                                           19

<210> SEQ ID NO 60
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 60
agaaccatac tcgaaccaca tcc                                      23

<210> SEQ ID NO 61
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 61
acagatgcaa ccgatgcacc                                          20

<210> SEQ ID NO 62
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 62
tggagttgta ctgcagggcg                                          20

```
<210> SEQ ID NO 63
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 63
gtgccccgac taaccgttg                                                 19

<210> SEQ ID NO 64
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 64
gtcgttgaac tcctcggtct                                                20

<210> SEQ ID NO 65
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 65
atgcccctca acgtgaactt c                                              21

<210> SEQ ID NO 66
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 66
cgcaacatag gatggagagc a                                              21

<210> SEQ ID NO 67
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 67
gcgacaacaa gaagacgcgc at                                             22

<210> SEQ ID NO 68
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 68
ctggatgttg ggcaggacgc c                                              21

<210> SEQ ID NO 69
<211> LENGTH: 22
<212> TYPE: DNA
<213> ORGANISM: Artificial Sequence
<220> FEATURE:
<223> OTHER INFORMATION: Synthetic Polynucleotide
```

<400> SEQUENCE: 69
aagaaggacg gcaagaagcg ca                                              22

<210> SEQ ID NO 70
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 70
cgctcgaaga tgtcgttcac ga                                              22

<210> SEQ ID NO 71
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 71
gaagaagcct caccgctacc g                                               21

<210> SEQ ID NO 72
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 72
ggttggtgtc ctcaaacaga ccc                                             23

<210> SEQ ID NO 73
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 73
aacatccagg gcatcaccaa gc                                              22

<210> SEQ ID NO 74
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 74
gttctccagg aacaccttca gc                                              22

<210> SEQ ID NO 75
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 75
ccggcctcaa ggctctcta                                                  19

<210> SEQ ID NO 76
<211> LENGTH: 20

```
<212> TYPE: DNA
<213> ORGANISM: Artificial Sequence
<220> FEATURE:
<223> OTHER INFORMATION: Synthetic Polynucleotide

<400> SEQUENCE: 76
tgccgcctca tactctcgaa                                             20

<210> SEQ ID NO 77
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 77
agtgtgacgt tgacatccgt                                             20

<210> SEQ ID NO 78
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 78
tgctaggagc cagagcagta                                             20

<210> SEQ ID NO 79
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 79
tcttcctggt ccccacagtt t                                           21

<210> SEQ ID NO 80
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 80
gcaagaatag ttctcgggat gaa                                         23

<210> SEQ ID NO 81
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 81
gtgtcttcct caactttctc cttgg                                       25

<210> SEQ ID NO 82
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 82
```

```
cgcggacagc cgcggccgtg gattgc                                          26

<210> SEQ ID NO 83
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 83
ggctccttgc tgtcattcat cttccac                                         27

<210> SEQ ID NO 84
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 84
caccgccgtc aggatctgga agttgg                                          26

<210> SEQ ID NO 85
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 85
ccggcctcaa ggctctcta                                                  19

<210> SEQ ID NO 86
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 86
tgccgcctca tactctcgaa                                                 20

<210> SEQ ID NO 87
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 87
tcaagcaatg gaccactggg                                                 20

<210> SEQ ID NO 88
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 88
tctccatgag ctccctgaca                                                 20

<210> SEQ ID NO 89
<211> LENGTH: 22
<212> TYPE: DNA
<213> ORGANISM: Artificial Sequence
```

```
<220> FEATURE:
<223> OTHER INFORMATION: Synthetic Polynucleotide

<400> SEQUENCE: 89
actcctggtg aacaaagtca ga                                              22

<210> SEQ ID NO 90
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 90
catccctgag agctcttgcc                                                 20

<210> SEQ ID NO 91
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 91
ccaatgtgtc cgtcgtggat ct                                              22

<210> SEQ ID NO 92
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 92
gttgaagtcg caggagacaa cc                                              22

<210> SEQ ID NO 93
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 93
acatcaagac atcgtgcgat att                                             23

<210> SEQ ID NO 94
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 94
ccagcggtac acaaagacca                                                 20

<210> SEQ ID NO 95
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 95
aagcacctcc gaaagtacgt g                                               21
```

<210> SEQ ID NO 96
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 96
ctccagctct accttacagt tga                                        23

<210> SEQ ID NO 97
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 97
gatagaacca accatgttga ggg                                        23

<210> SEQ ID NO 98
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 98
tggagctttg tagccagagg t                                          21

<210> SEQ ID NO 99
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 99
caccattggc aatgagcggt tc                                         22

<210> SEQ ID NO 100
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 100
aggtctttgc ggatgtccac gt                                         22

<210> SEQ ID NO 101
<211> LENGTH: 492
<212> TYPE: DNA
<213> ORGANISM: Homo sapiens

<400> SEQUENCE: 101
gatccggttc caggcctcgg ccctaaatag tctccctggg ctttcaagag aaccacatga      60
gaaaggagga ttcgggctct gagcagtttc accaccacc ccccagtctg caaatcctga     120
cccgtgggtc cacctgcccc aaaggcggac gcaggacagt agaagggaac agagaacaca    180
taaacacaga gagggccaca gcggctccca cagtcaccgc caccttcctg gcggggatgg    240
gtggggcgtc tgagtttggt tcccagcaaa tccctctgag ccgcccttgc gggctcgcct    300
caggagcagg ggagcaagag gtgggaggag gaggtctaag tcccaggccc aattaagaga    360

```
tcaggtagtg tagggtttgg gagcttttaa ggtgaagagg cccgggctga tcccacaggc    420
cagtataaag cgccgtgacc ctcaggtgat gcgccagggc cggctgccgt cggggacagg    480
gctttccata gc                                                       492
```

<210> SEQ ID NO 102
<211> LENGTH: 900
<212> TYPE: DNA
<213> ORGANISM: Homo sapiens

<400> SEQUENCE: 102

```
agttaatgat taacccgcca tgctacttat ctacgtagcc atgctctagg aagatcggaa     60
ttcgccctta agctagcaga tcttccccac ctagccacct ggcaaactgc tccttctctc    120
aaaggcccaa acatggcctc ccagactgca accccaggc agtcaggccc tgtctccaca    180
acctcacagc caccctggac ggaatctgct tcttcccaca tttgagtcct cctcagcccc    240
tgagctcctc tggggcaggc tgtttctttc catctttgta ttcccagggg cctgcaaata    300
aatgtttaat gaacgaacaa gagagtgaat tccaattcca tgcaacaagg attgggctcc    360
tgggccctag gctatgtgtc tggcaccaga aacggaagct gcaggttgca gcccctgccc    420
tcatggagct cctcctgtca gaggagtgtg gggactggat gactccagag gtaacttgtg    480
ggggaacgaa caggtaaggg gctgtgtgac gagatgagag actgggagaa taaaccagaa    540
agtctctagc tgtccagagg acatagcaca gaggcccatg gtccctattt caaacccagg    600
ccaccagact gagctgggac cttgggacag acaagtcatg cagaagttag ggaccttct    660 cctccttttt cctggatgga tcctgagtac cttctcctcc ctgacctcag gcttcctcct    720
agtgtcacct tggcccctct tagaagccaa ttaggccctc agtttctgca gcggggatta    780
atatgattat gaacaccccc aatctcccag atgctgattc agccaggagc ttaggagggg    840
gaggtcactt tataagggtc tggggggtc agaacccaga gtcatcccct gaattctgca    900
```

<210> SEQ ID NO 103
<211> LENGTH: 521
<212> TYPE: DNA
<213> ORGANISM: Mus musculus

<400> SEQUENCE: 103

```
ggttcttccc attttggcta catggtcttt tttttttacct ttttggttcc tttggccttt     60
tggcttttgg cttccagggc ttctggatcc cccccaaccc ctcccataca catacacatg    120
tgcactcgtg cactcaaccc agcacaggat aatgttcatt cttgaccttt ccacatacat    180
ctggctatgt tctctctctt atctacaata aatctcctcc actatactta ggagcagtta    240
tgttcttctt ctttctttct ttttttttttt tttcattcag taacatcatc agaatccct    300 agctctggcc tacctcctca gtaacaatca gctgatccct ggccactaat ctgtactcac    360
taatctgttt tccaaactct tggcccctga gctaattata gcagtgcttc atgccaccca    420
ccccaaccct attcttgttc tctgactccc actaatctac acattcagag gattgtggat    480
ataagaggct gggaggccag cttagcaacc agagctggag g                       521
```

<210> SEQ ID NO 104
<211> LENGTH: 292
<212> TYPE: DNA
<213> ORGANISM: Homo sapiens

<400> SEQUENCE: 104

```
gggcccaga      agcctggtgg   ttgtttgtcc   ttctcagggg   aaaagtgagg   cggcccttg        60 gaggaagggg     ccgggcagaa   tgatctaatc   ggattccaag   cagctcaggg   gattgtcttt      120
ttctagcacc     ttcttgccac   tcctaagcgt   cctccgtgac   cccggctggg   atttagcctg      180
gtgctgtgtc     agcccggtc    tcccagggc    ttcccagtgg   tccccaggaa   ccctcgacag      240
ggcccggtct     ctctcgtcca   gcaagggcag   ggacgggcca   caggccaagg   gc               292

<210> SEQ ID NO 105
<211> LENGTH: 7390
<212> TYPE: DNA
<213> ORGANISM: Homo sapiens

<400> SEQUENCE: 105
ttatgcagtg     ctgccataac   catgagtgat   aacactgcgg   ccaacttact   tctgacaacg       60
atcggaggac     cgaaggagct   aaccgctttt   ttgcacaaca   tggggatca    tgtaactcgc      120 cttgatcgtt     gggaaccgga   gctgaatgaa   gccataccaa   acgacgagcg   tgacaccacg      180
atgcctgtag     taatggtaac   aacgttgcgc   aaactattaa   ctggcgaact   acttactcta      240
gcttcccggc     aacaattaat   agactggatg   gaggcggata   agttgcagg    accacttctg      300 cgctcggccc     ttccggctgg   ctggtttatt   gctgataaat   ctggagccgg   tgagcgtggg      360
tctcgcggta     tcattgcagc   actggggcca   gatggtaagc   cctcccgtat   cgtagttatc      420
tacacgacgg     ggagtcaggc   aactatggat   gaacgaaata   gacagatcgc   tgagataggt      480
gcctcactga     ttaagcattg   gtaactgtca   gaccaagttt   actcatatat   actttagatt      540
gatttaaaac     ttcatttta    atttaaaagg   atctaggtga   agatcctttt   tgataatctc      600
atgaccaaaa     tcccttaacg   tgagttttcg   ttccactgag   cgtcagaccc   cgtagaaaag      660
atcaaaggat     cttcttgaga   tcctttttt   ctgcgcgtaa   tctgctgctt   gcaaacaaaa      720
aaaccaccgc     taccagcggt   ggtttgtttg   ccggatcaag   agctaccaac   tcttttccg       780 aaggtaactg     gcttcagcag   agcgcagata   ccaaatactg   tccttctagt   gtagccgtag      840
ttaggccacc     acttcaagaa   ctctgtagca   ccgcctacat   acctcgctct   gctaatcctg      900
ttaccagtgg     ctgctgccag   tggcgataag   tcgtgtctta   ccgggttgga   ctcaagacga      960
tagttaccgg     ataaggcgca   gcggtcgggc   tgaacggggg   gttcgtgcac   acagcccagc    1020
ttggagcgaa     cgacctacac   cgaactgaga   tacctacagc   gtgagctatg   agaaagcgcc    1080
acgcttcccg     aagggagaaa   ggcggacagg   tatccggtaa   gcggcagggt   cggaacagga    1140
gagcgcacga     gggagcttcc   aggggggaaac  gcctggtatc   tttatagtcc   tgtcgggttt    1200
cgccacctct     gacttgagcg   tcgatttttg   tgatgctcgt   caggggggcg   gagcctatgg    1260
aaaaacgcca     gcaacgcggc   cttttttacgg  ttccctggcct  tttgctggcc   ttttgctcac    1320
atgttctttc     ctgcgttatc   ccctgattct   gtggataacc   gtattaccgc   ctttgagtga    1380
gctgataccg     ctcgccgcag   ccgaacgacc   gagcgcagcg   agtcagtgag   cgaggaagcg    1440
gaagagcgcc     caatacgcaa   accgcctctc   cccgcgcgtt   ggccgattca   ttaatgcagc    1500
tggcacgaca     ggtttcccga   ctggaaagcg   ggcagtgagc   gcaacgcaat   taatgtgagt    1560
tagctcactc     attaggcacc   ccaggcttta   cactttatgc   ttccggctcg   tatgttgtgt    1620
ggaattgtga     gcggataaca   atttcacaca   ggaaacagct   atgaccatga   ttacgccaga    1680
tttaattaag     gccttaatta   ggctgcgcgc   tcgctcgctc   actgaggccg   cccgggcaaa    1740
gcccgggcgt     cggcgacct    ttggtcgccc   ggcctcagtg   agcgagcgag   cgcgcagaga    1800
gggagtggcc     aactccatca   ctaggggttc   cttgtagtta   atgattaacc   cgccatgcta    1860
```

```
cttatctacg tagccatgct ctaggaagat cggaattctt tactccctat cagtgataga    1920
gaacgtatga agagtttact ccctatcagt gatagagaac gtatgcagac tttactccct    1980
atcagtgata gagaacgtat aaggagttta ctccctatca gtgatagaga acgtatgacc    2040
agtttactcc ctatcagtga tagagaacgt atctacagtt tactccctat cagtgataga    2100
gaacgtatat ccagtttact ccctatcagt gatagagaac gtataagctt taggcgtgta    2160
cggtgggcgc ctataaaagc agagctcgtt tagtgaaccg tcagatcgcc tggagcaatt    2220
ccacaacact tttgtcttat accaactttc cgtaccactt cctaccctcg taaagcggcc    2280
gcgccaccat ggcgggacac ctggcttcgg atttcgcctt ctcgccccct ccaggtggtg    2340
gaggtgatgg gccaggggg ccggagccgg ctgggttga tcctcggacc tggctaagct    2400
tccaaggccc tcctggaggg ccaggaatcg ggccggggt tgggccaggc tctgaggtgt    2460
gggggattcc cccatgcccc ccgccgtatg agttctgtgg ggggatggcg tactgtgggc    2520
cccaggttgg agtggggcta gtgccccaag gcggcttgga gacctctcag cctgagggcg    2580
aagcaggagt cggggtggag agcaactccg atggggcctc cccggagccc tgcaccgtca    2640
cccctggtgc cgtgaagctg gagaaggaga agctggagca aaacccggag gagtcccagg    2700
acatcaaagc tctgcagaaa gaactcgagc aatttgccaa gctcctgaag cagaagagga    2760
tcaccctggg atatacacag gccgatgtgg ggctcaccct gggggttcta tttgggaagg    2820
tattcagcca aacgaccatc tgccgctttg aggctctgca gcttagcttc aagaacatgt    2880
gtaagctgcg gcccttgctg cagaagtggg tggaggaagc tgacaacaat gaaaatcttc    2940
aggagatatg caaagcagaa accctcgtgc aggcccgaaa gagaaagcga accagtatcg    3000
agaaccgagt gagaggcaac ctggagaatt tgttcctgca gtgcccgaaa cccacactgc    3060
agcagatcag ccacatcgcc cagcagcttg ggctcgagaa ggatgtggtc cgagtgtggt    3120
tctgtaaccg gcgccagaag ggcaagcgat caagcagcga ctatgcacaa cgagaggatt    3180
ttgaggctgc tgggtctcct ttctcagggg gaccagtgtc ctttcctctg gccccagggc    3240
cccattttgg taccccaggc tatgggagcc ctcacttcac tgcactgtac cctcggtcc    3300
ctttccctga gggggaagcc tttccccctg tctctgtcac cactctgggc tctcccatgc    3360
attcaaacgc tagcggcagc ggcgccacga acttctctct gttaaagcaa gcaggagatg    3420
ttgaagaaaa ccccgggcct gcatgcatgt acaacatgat ggagacgag ctgaagccgc    3480
cgggcccgca gcaaacttcg gggggcggcg gcggcaactc caccgcggcg gcggccggcg    3540
gcaaccagaa aaacagcccg gaccgcgtca agcggcccat gaatgccttc atggtgtggt    3600
cccgcgggca gcggcgcaag atggcccagg agaaccccaa gatgcacaac tcggagatca    3660
gcaagcgcct gggcgccgag tggaaacttt tgtcggagac ggagaagcgg ccgttcatcg    3720
acgaggctaa gcggctgcga gcgctgcaca tgaaggagca cccggattat aaataccggc    3780
cccggcggaa aaccaagacg ctcatgaaga aggataagta cacgctgccc ggcgggctgc    3840
tggcccccgg cggcaatagc atggcgagcg gggtcggggt gggcgccggc ctgggcgcgg    3900
gcgtgaacca gcgcatggac agttacgcgc acatgaacgg ctggagcaac ggcagctaca    3960
gcatgatgca ggaccagctg ggctaccgc agcacccggg cctcaatgcg cacggcgcag    4020
cgcagatgca gcccatgcac cgctacgacg tgagcgccct gcagtacaac tccatgacca    4080
gctcgcagac ctacatgaac ggctcgccca cctacagcat gtcctactcg cagcagggca    4140
cccctggcat ggctcttggc tccatgggtt cggtggtcaa gtccgaggcc agctccagcc    4200
```

```
cccctgtggt tacctcttcc tcccactcca gggcgccctg ccaggccggg gacctccggg    4260
acatgatcag catgtatctc cccggcgccg aggtgccgga accgccgcc cccagcagac     4320
ttcacatgtc ccagcactac cagagcggcc cggtgcccgg cacggccatt aacggcacac    4380
tgcccctctc acacatggca tgcggctccg gcgagggcag gggaagtctt ctaacatgcg    4440
gggacgtgga ggaaaatccc ggcccactcg agatggctgt cagcgacgcg ctgctcccat    4500
ctttctccac gttcgcgtct ggccggcgg gaagggagaa gacactgcgt caagcaggtg     4560
ccccgaataa ccgctggcgg gaggagctct cccacatgaa gcgacttccc ccagtgcttc    4620
ccggccgccc ctatgacctg gcggcggcga ccgtggccac agacctggag agcggcggag    4680
ccggtgcggc ttgcggcggt agcaacctgg cgcccctacc tcggagagag accgaggagt    4740
tcaacgatct cctggacctg gactttattc tctccaattc gctgacccat cctccggagt    4800
cagtggccgc caccgtgtcc tcgtcagcgt cagcctcctc ttcgtcgtcg ccgtcgagca    4860
gcggccctgc cagcgcgccc tccacctgca gcttcaccta tccgatccgg gccgggaacg    4920
acccgggcgt ggcgccgggc ggcacgggcg gaggcctcct ctatggcagg gagtccgctc    4980
cccctccgac ggctcccttc aacctggcgg acatcaacga cgtgagcccc tcgggcggct    5040
tcgtggccga gctcctgcgg ccagaattgg acccggtgta cattccgccg cagcagccgc    5100
agccgccagg tggcgggctg atgggcaagt tcgtgctgaa ggcgtcgctg agcgcccctg    5160
gcagcgagta cggcagcccg tcggtcatca gcgtcagcaa aggcagccct gacggcagcc    5220
acccggtggt ggtggcgccc tacaacggcg ggccgccgcg cacgtgcccc aagatcaagc    5280
aggaggcggt ctcttcgtgc acccacttgg gcgctggacc cctctcagc aatgccacc     5340
ggccggctgc acacgacttc ccctcggggc ggcagctccc cagcaggact accccgaccc    5400
tgggtcttga ggaagtgctg agcagcaggg actgtcaccc tgccctgccg cttcctcccg    5460
gcttccatcc ccacccgggg cccaattacc catccttcct gcccgatcag atgcagccgc    5520
aagtcccgcc gctccattac caagagctca tgccacccgg ttcctgcatg ccagaggagc    5580
ccaagccaaa gagggaaga cgatcgtggc cccggaaaag gaccgccacc cacacttgtg     5640
attacgcggc ctgcggcaaa acctacacaa agagttccca tctcaaggca cacctgcgaa    5700
cccacacagg tgagaaacct taccactgtg actgggacgg ctgtggatgg aaattcgccc    5760
gctcagatga actgaccagg cactaccgta aacacacggg gcaccgcccg ttccagtgcc    5820
aaaaatgcga ccgagcattt tccaggtcgg accacctcgc cttacacatg aagaggcatt    5880
tttaaatgac tagtgcgcgc agcggccgac catggcccaa cttgtttatt gcagcttata    5940
atggttacaa ataaagcaat agcatcacaa atttcacaaa taaagcattt ttttcactgc    6000
attctagttg tggtttgtcc aaactcatca atgtatctta tcatgtctgg atctcggtac    6060
cggatccaaa ttcccgataa ggatcttcct agagcatggc tacgtagata agtagcatgg    6120
cgggttaatc attaactaca aggaaccct agtgatggag ttggccactc cctctctgcg     6180
cgctcgctcg ctcactgagg ccgggcgacc aaaggtcgcc cgacgcccgg ctttgcccg     6240
ggcggcctca gtgagcgagc gagcgcgcag ccttaattaa cctaattcac tggccgtcgt    6300
tttacaacgt cgtgactggg aaaaccctgg cgttacccaa cttaatcgcc ttgcagcaca    6360
tccccctttc gccagctggc gtaatagcga agaggcccgc accgatcgcc cttcccaaca    6420
gttgcgcagc ctgaatggcg aatgggacgc gccctgtagc ggcgcattaa gcgcggcggg    6480
tgtggtggtt acgcgcagcg tgaccgctac acttgccagc gccctagcgc ccgctccttt    6540
cgctttcttc ccttcctttc tcgccacgtt cgccggcttt ccccgtcaag ctctaaatcg    6600
```

```
ggggctccct ttagggttcc gatttagtgc tttacggcac ctcgacccca aaaaacttga    6660
ttagggtgat ggttcacgta gtgggccatc gccctgatag acggtttttc gcccttttgac   6720 gttggagtcc acgttcttta atagtggact cttgttccaa actggaacaa cactcaaccc    6780
tatctcggtc tattcttttg atttataagg gattttgccg atttcggcct attggttaaa    6840
aaatgagctg atttaacaaa aatttaacgc gaattttaac aaaatattaa cgtttataat    6900
ttcaggtggc atctttcggg gaaatgtgcg cggaacccct atttgtttat ttttctaaat    6960
acattcaaat atgtatccgc tcatgagaca ataaccctga taaatgcttc aataatattg    7020
aaaaaggaag agtatgagta ttcaacattt ccgtgtcgcc cttattccct tttttgcggc    7080
attttgcctt cctgtttttg ctcacccaga aacgctggtg aaagtaaaag atgctgaaga    7140
tcagttgggt gcacgagtgg gttacatcga actggatctc aatagtggta agatccttga    7200
gagttttcgc cccgaagaac gttttccaat gatgagcact tttaaagttc tgctatgtgg    7260
cgcggtatta tcccgtattg acgccgggca agagcaactc ggtcgccgca tacactattc    7320
tcagaatgac ttggttgagt actcaccagt cacagaaaag catcttacgg atggcatgac    7380
agtaagagaa                                                            7390

<210> SEQ ID NO 106
<211> LENGTH: 7265
<212> TYPE: DNA
<213> ORGANISM: Homo sapiens

<400> SEQUENCE: 106
ttatgcagtg ctgccataac catgagtgat aacactgcgg ccaacttact tctgacaacg      60
atcggaggac cgaaggagct aaccgctttt ttgcacaaca tgggggatca tgtaactcgc     120
cttgatcgtt gggaaccgga gctgaatgaa gccataccaa acgacgagcg tgacaccacg     180
atgcctgtag taatggtaac aacgttgcgc aaactattaa ctggcgaact acttactcta     240
gcttcccggc aacaattaat agactggatg gaggcggata agttgcagg accacttctg      300 cgctcggccc ttccggctgg ctggtttatt gctgataaat ctggagccgg tgagcgtggg     360
tctcgcggta tcattgcagc actggggcca gatggtaagc cctcccgtat cgtagttatc     420
tacacgacgg ggagtcaggc aactatggat gaacgaaata gacagatcgc tgagataggt     480
gcctcactga ttaagcattg gtaactgtca gaccaagttt actcatatat actttagatt     540
gatttaaaac ttcattttta atttaaaagg atctaggtga agatccttt tgataatctc     600 atgaccaaaa tcccttaacg tgagttttcg ttccactgag cgtcagaccc cgtagaaaag    660
atcaaaggat cttcttgaga tccttttttt ctgcgcgtaa tctgctgctt gcaaacaaaa    720
aaaccaccgc taccagcggt ggtttgtttg ccggatcaag agctaccaac tcttttttccg   780 aaggtaactg gcttcagcag agcgcagata ccaaatactg tccttctagt gtagccgtag    840
ttaggccacc acttcaagaa ctctgtagca ccgcctacat acctcgctct gctaatcctg    900
ttaccagtgg ctgctgccag tggcgataag tcgtgtctta ccgggttgga ctcaagacga    960
tagttaccgg ataaggcgca gcggtcgggc tgaacggggg gttcgtgcac acagcccagc   1020
ttggagcgaa cgacctacac cgaactgaga tacctacagc gtgagctatg agaaagcgcc   1080
acgcttcccg aagggagaaa ggcggacagg tatccggtaa gcggcagggt cggaacagga   1140
gagcgcacga gggagcttcc agggggaaac gcctggtatc tttatagtcc tgtcgggttt   1200
cgccacctct gacttgagcg tcgatttttg tgatgctcgt caggggggcg gagcctatgg   1260
```

```
aaaaacgcca gcaacgcggc cttttttacgg ttcctggcct tttgctggcc ttttgctcac  1320
atgttctttc ctgcgttatc ccctgattct gtggataacc gtattaccgc ctttgagtga  1380
gctgataccg ctcgccgcag ccgaacgacc gagcgcagcg agtcagtgag cgaggaagcg  1440
gaagagcgcc caatacgcaa accgcctctc cccgcgcgtt ggccgattca ttaatgcagc  1500
tggcacgaca ggtttcccga ctggaaagcg ggcagtgagc gcaacgcaat taatgtgagt  1560
tagctcactc attaggcacc ccaggcttta cactttatgc ttccggctcg tatgttgtgt  1620
ggaattgtga gcggataaca atttcacaca ggaaacagct atgaccatga ttacgccaga  1680
tttaattaag gccttaatta ggctgcgcgc tcgctcgctc actgaggccg cccgggcaaa  1740
gcccgggcgt cgggcgacct ttggtcgccc ggcctcagtg agcgagcgag cgcgcagaga  1800
gggagtggcc aactccatca ctaggggttc cttgtagtta atgattaacc cgccatgcta  1860
cttatctacg tagccatgct ctaggaagat cggaattctc gagtggctcc ggtgcccgtc  1920
agtgggcaga gcgcacatcg cccacagtcc ccgagaagtt gggggagggg tcggcaatt  1980 gaaccggtgc ctagagaagg tggcgcgggg taaactggga aagtgatgtc gtgtactggc  2040
tccgcctttt tcccgagggt gggggagaac cgtatataag tgcagtagtc gccgtgaacg  2100 ttcttttcg caacgggttt gccgccagaa cacaggtgtc gtgacgcggg cggccgcgcc  2160
accatggcgg gacacctggc ttcggatttc gccttctcgc cccctccagg tggtggaggt  2220
gatgggccag gggggccgga gccgggctgg gttgatcctc ggacctggct aagcttccaa  2280
ggccctcctg gagggccagg aatcgggccg ggggttgggc caggctctga ggtgtggggg  2340
attcccccat gcccccgcc gtatgagttc tgtgggggga tggcgtactg tgggccccag  2400
gttggagtgg ggctagtgcc ccaaggcggc ttggagacct ctcagcctga gggcgaagca  2460
ggagtcgggg tggagagcaa ctccgatggg gcctccccgg agccctgcac cgtcaccct  2520 ggtgccgtga agctggagaa ggagaagctg gagcaaaacc cggaggagtc ccaggacatc  2580
aaagctctgc agaaagaact cgagcaattt gccaagctcc tgaagcagaa gaggatcacc  2640
ctgggatata cacaggccga tgtggggctc accctggggg ttctatttgg gaaggtattc  2700
agccaaacga ccatctgccg ctttgaggct ctgcagctta gcttcaagaa catgtgtaag  2760
ctgcggccct tgctgcagaa gtgggtggag gaagctgaca caatgaaaaa tcttcaggag  2820
atatgcaaag cagaaaccct cgtgcaggcc gaaagagaa agcgaaccag tatcgagaac  2880
cgagtgagag gcaacctgga gaatttgttc ctgcagtgcc gaaacccac actgcagcag  2940 atcagccaca tcgcccagca gcttgggctc gagaaggatg tggtccgagt gtggttctgt  3000
aaccggcgcc agaagggcaa gcgatcaagc agcgactatg cacaacgaga ggattttgag  3060
gctgctgggt ctcctttctc aggggaccca gtgtcctttc ctctggcccc agggccccat  3120
tttggtaccc caggctatgg gagccctcac ttcactgcac tgtactcctc ggtccctttc  3180
cctgaggggg aagcctttcc ccctgtctct gtcaccactc tgggctctcc catgcattca  3240
aacgctagcg gcagcggcgc cacgaacttc tctctgttaa agcaagcagg agatgttgaa  3300
gaaaaccccg ggcctgcatg catgtacaac atgatggaga cggagctgaa gccgccgggc  3360
ccgcagcaaa cttcgggggg cggcggcggc aactccaccg cggcggcggc cggcggcaac  3420
cagaaaaaca gcccggaccg cgtcaagcgg cccatgaatg ccttcatggt gtggtcccgc  3480
gggcagcggc gcaagatggc ccaggagaac cccaagatgc acaactcgga gatcagcaag  3540
cgcctgggcg ccgagtggaa actttttgtcg gagacggaga gcggccgtt catcgacgag  3600 gctaagcggc tgcgagcgct gcacatgaag gagcacccgg attataaata ccggccccgg  3660
```

```
cggaaaacca agacgctcat gaagaaggat aagtacacgc tgcccggcgg gctgctggcc    3720
cccggcggca atagcatggc gagcggggtc ggggtgggcg ccggcctggg cgcgggcgtg    3780
aaccagcgca tggacagtta cgcgcacatg aacggctgga gcaacggcag ctacagcatg    3840
atgcaggacc agctgggcta cccgcagcac ccgggcctca atgcgcacgg cgcagcgcag    3900
atgcagccca tgcaccgcta cgacgtgagc gccctgcagt acaactccat gaccagctcg    3960
cagacctaca tgaacggctc gcccacctac agcatgtcct actcgcagca gggcaccccct   4020 ggcatggctc tttggctccat gggttcggtg gtcaagtccg aggccagctc cagccccccct  4080 gtggttacct cttcctccca ctccaggcg ccctgccagg ccggggacct ccgggacatg     4140
atcagcatgt atctccccgg cgccgaggtg ccggaacccg ccgcccccag cagacttcac    4200
atgtcccagc actaccagag cggcccggtg cccggcacgg ccattaacgg cacactgccc    4260
ctctcacaca tggcatgcgg ctccggcgag ggcagggaa gtcttctaac atgcggggac     4320
gtggaggaaa atcccggccc actcgagatg gctgtcagcg acgcgctgct cccatctttc    4380
tccacgttcg cgtctggccc ggcgggaagg gagaagacac tgcgtcaagc aggtgccccg    4440
aataaccgct ggcgggagga gctctcccac atgaagcgac ttccccccagt gcttcccggc   4500 cgcccctatg acctggcggc ggcgaccgtg gccacagacc tggagagcgg cggagccggt    4560
gcggcttgcg gcggtagcaa cctggcgccc ctacctcgga gagagaccga ggagttcaac    4620
gatctcctgg acctggactt tattctctcc aattcgctga cccatcctcc ggagtcagtg    4680
gccgccaccg tgtcctcgtc agcgtcagcc tcctcttcgt cgtcgccgtc gagcagcggc    4740
cctgccagcg cgccctccac ctgcagcttc acctatccga tccgggccgg gaacgacccg    4800
ggcgtggcgc cgggcggcac gggcggaggc ctcctctatg gcagggagtc cgctccccct    4860
ccgacggctc ccttcaacct ggcggacatc aacgacgtga gccctcggg cggcttcgtg     4920 gccgagctcc tgcggccaga attggacccg gtgtacattc cgccgcagca gccgcagccg    4980
ccaggtggcg ggctgatggg caagttcgtg ctgaaggcgt cgctgagcgc ccctggcagc    5040
gagtacggca gcccgtcggt catcagcgtc agcaaaggca gccctgacgg cagccacccg    5100
gtggtggtgg cgccctacaa cggcgggccg ccgcgcacgt gccccaagat caagcaggag    5160
gcggtctctt cgtgcaccca cttgggcgct ggaccccctc tcagcaatgg ccaccggccg    5220
gctgcacacg acttccccct ggggcggcag ctccccagca ggactacccc gaccctgggt    5280
cttgaggaag tgctgagcag cagggactgt caccctgccc tgccgcttcc tcccggcttc    5340
catccccacc cggggcccaa ttacccatcc ttcctgcccg atcagatgca gccgcaagtc    5400
ccgccgctcc attaccaaga gctcatgcca cccggttcct gcatgccaga ggagcccaag    5460
ccaaagaggg gaagacgatc gtggccccgg aaaaggaccg ccacccacac ttgtgattac    5520
gcgggctgcg gcaaaaccta cacaaagagt tcccatctca aggcacacct gcgaacccac    5580
acaggtgaga aaccttacca ctgtgactgg gacggctgtg gatggaaatt cgcccgctca    5640
gatgaactga ccaggcacta ccgtaaacac acggggcacc gcccgttcca gtgccaaaaa    5700
tgcgaccgag cattttccag gtcggaccac ctcgccttac acatgaagag gcatttttaa    5760
atgactagtg cgcgcagcgg ccgaccatgg cccaacttgt ttattgcagc ttataatggt    5820
tacaaataaa gcaatagcat cacaaatttc acaaataaag cattttttc actgcattct     5880 agttgtggtt tgtccaaact catcaatgta tcttatcatg tctggatctc ggtaccggat    5940
ccaaattccc gataaggatc ttcctagagc atggctacgt agataagtag catggcgggt    6000
```

```
taatcattaa ctacaaggaa ccectagtga tggagttggc cactccctct ctgcgcgctc      6060
gctcgctcac tgaggccggg cgaccaaagg tcgcccgacg cccgggcttt gcccgggcgg      6120
cctcagtgag cgagcgagcg cgcagccta attaacctaa ttcactggcc gtcgttttac       6180
aacgtcgtga ctgggaaaac cctggcgtta cccaacttaa tcgccttgca gcacatcccc      6240
ctttcgccag ctggcgtaat agcgaagagg cccgcaccga tcgcccttcc caacagttgc      6300
gcagcctgaa tggcgaatgg gacgcgccct gtagcggcgc attaagcgcg gcgggtgtgg      6360
tggttacgcg cagcgtgacc gctacacttg ccagcgccct agcgcccgct cctttcgctt      6420
tcttcccttc ctttctcgcc acgttcgccg gctttccccg tcaagctcta atcgggggc       6480 tccctttagg gttccgattt agtgctttac ggcacctcga ccccaaaaaa cttgattagg      6540
gtgatggttc acgtagtggg ccatcgccct gatagacggt ttttcgccct ttgacgttgg      6600
agtccacgtt ctttaatagt ggactcttgt tccaaactgg aacaacactc aaccctatct      6660
cggtctattc ttttgattta aagggattt tgccgatttc ggcctattgg ttaaaaaatg       6720
agctgattta acaaaaattt aacgcgaatt ttaacaaaat attaacgttt ataatttcag      6780
gtggcatctt tcggggaaat gtgcgcggaa ccccctatttg tttatttttc taaatacatt     6840
caaatatgta tccgctcatg agacaataac cctgataaat gcttcaataa tattgaaaaa      6900
ggaagagtat gagtattcaa catttccgtg tcgcccttat tcccttttt gcggcatttt       6960 gccttcctgt ttttgctcac ccagaaacgc tggtgaaagt aaaagatgct gaagatcagt      7020
tgggtgcacg agtgggttac atcgaactgg atctcaatag tggtaagatc cttgagagtt      7080
ttcgccccga agaacgtttt ccaatgatga gcacttttaa agttctgcta tgtggcgcgg      7140
tattatcccg tattgacgcc gggcaagagc aactcggtcg ccgcatacac tattctcaga      7200
atgacttggt tgagtactca ccagtcacag aaaagcatct tacggatggc atgacagtaa      7260
gagaa                                                                  7265
```

<210> SEQ ID NO 107
<211> LENGTH: 5437
<212> TYPE: DNA
<213> ORGANISM: Artificial Sequence
<220> FEATURE:
<223> OTHER INFORMATION: Synthetic Polynucleotide

<400> SEQUENCE: 107

```
ttatgcagtg ctgccataac catgagtgat aacactgcgg ccaacttact tctgacaacg       60
atcggaggac cgaaggagct aaccgctttt ttgcacaaca tgggggatca tgtaactcgc      120
cttgatcgtt gggaaccgga gctgaatgaa gccataccaa acgacgagcg tgacaccacg      180
atgcctgtag taatggtaac aacgttgcgc aaactattaa ctggcgaact acttactcta     240
gcttcccggc aacaattaat agactggatg gaggcggata agttgcagg accacttctg      300 cgctcggccc ttccggctgg ctggtttatt gctgataaat ctggagccgg tgagcgtggg      360
tctcgcggta tcattgcagc actggggcca gatggtaagc cctcccgtat cgtagttatc      420
tacacgacgg ggagtcaggc aactatggat gaacgaaata gacagatcgc tgagataggt      480
gcctcactga ttaagcattg gtaactgtca gaccaagttt actcatatat actttagatt      540
gatttaaaac ttcattttta atttaaaagg atctaggtga agatcctttt tgataatctc      600
atgaccaaaa tcccttaacg tgagttttcg ttccactgag cgtcagaccc cgtagaaaag      660
atcaaaggat cttcttgaga tcctttttt ctgcgcgtaa tctgctgctt gcaaacaaaa      720
aaaccaccgc taccagcggt ggtttgtttg ccggatcaag agctaccaac tcttttttccg      780
```

```
aaggtaactg gcttcagcag agcgcagata ccaaatactg tccttctagt gtagccgtag    840
ttaggccacc acttcaagaa ctctgtagca ccgcctacat acctcgctct gctaatcctg    900
ttaccagtgg ctgctgccag tggcgataag tcgtgtctta ccgggttgga ctcaagacga    960
tagttaccgg ataaggcgca gcggtcgggc tgaacggggg gttcgtgcac acagcccagc   1020
ttggagcgaa cgacctacac cgaactgaga tacctacagc gtgagctatg agaaagcgcc   1080
acgcttcccg aagggagaaa ggcggacagg tatccggtaa gcggcagggt cggaacagga   1140
gagcgcacga gggagcttcc aggggggaaac gcctggtatc tttatagtcc tgtcgggttt   1200
cgccacctct gacttgagcg tcgattttg tgatgctcgt caggggggcg agcctatgg    1260 aaaaacgcca gcaacgcggc cttttttacgg ttcctggcct tttgctggcc ttttgctcac   1320
atgttctttc ctgcgttatc ccctgattct gtggataacc gtattaccgc ctttgagtga   1380
gctgataccg ctcgccgcag ccgaacgacc gagcgcagcg agtcagtgag cgaggaagcg   1440
gaagagcgcc caatacgcaa accgcctctc ccgcgcgtt ggccgattca ttaatgcagc    1500
tggcacgaca ggtttcccga ctggaaagcg ggcagtgagc gcaacgcaat taatgtgagt   1560
tagctcactc attaggcacc ccaggcttta cactttatgc ttccggctcg tatgttgtgt   1620
ggaattgtga gcggataaca atttcacaca ggaaacagct atgaccatga ttacgccaga   1680
tttaattaag gccttaatta ggctgcgcgc tcgctcgctc actgaggccg cccgggcaaa   1740
gcccgggcgt cgggcgacct ttggtcgccc ggcctcagtg agcgagcgag cgcgcagaga   1800
gggagtggcc aactccatca ctaggggttc cttgtagtta atgattaacc cgccatgcta   1860
cttatctacg tagccatgct ctaggaagat cggaattctt tactccctat cagtgataga   1920
gaacgtatga agagtttact ccctatcagt gatagagaac gtatgcagac tttactccct   1980
atcagtgata gagaacgtat aaggagttta ctccctatca gtgatagaga acgtatgacc   2040
agtttactcc ctatcagtga tagagaacgt atctacagtt tactccctat cagtgataga   2100
gaacgtatat ccagtttact ccctatcagt gatagagaac gtataagctt taggcgtgta   2160
cggtgggcgc ctataaaagc agagctcgtt tagtgaaccg tcagatcgcc tggagcaatt   2220
ccacaacact tttgtcttat accaactttc cgtaccactt cctaccctcg taaagcggcc   2280
gcatggaaga cgccaaaaac ataaagaaag gcccggcgcc attctatccg ctggaagatg   2340
gaaccgctgg agagcaactg cataaggcta tgaagagata cgccctggtt cctggaacaa   2400
ttgcttttac agatgcacat atcgaggtgg acatcactta cgctgagtac ttcgaaatgt   2460
ccgttcggtt ggcagaagct atgaaacgat atgggctgaa tacaaatcac agaatcgtcg   2520
tatgcagtga aaactctctt caattcttta tgccggtgtt gggcgcgtta tttatcggag   2580
ttgcagttgc gcccgcgaac gacatttata atgaacgtga attgctcaac agtatgggca   2640
tttcgcagcc taccgtggtg ttcgtttcca aaaagggggtt gcaaaaaatt ttgaacgtgc   2700
aaaaaaagct cccaatcatc caaaaaatta ttatcatgga ttctaaaacg gattaccagg   2760
gatttcagtc gatgtacacg ttcgtcacat ctcatctacc tcccggtttt aatgaatacg   2820
attttgtgcc agagtccttc gatagggaca agacaattgc actgatcatg aactcctctg   2880
gatctactgg tctgcctaaa ggtgtcgctc tgcctcatag aactgcctgc gtgagattct   2940
cgcatgccag agatcctatt tttggcaatc aaatcattcc ggatactgcg attttaagtg   3000
ttgttccatt ccatcacggt tttggaatgt ttactacact cggatatttg atatgtggat   3060
ttcgagtcgt cttaatgtat agatttgaag aagagctgtt tctgaggagc cttcaggatt   3120
```

```
acaagattca aagtgcgctg ctggtgccaa ccctattctc cttcttcgcc aaaagcactc   3180
tgattgacaa atacgattta tctaatttac acgaaattgc ttctggtggc gctccctct    3240
ctaaggaagt cggggaagcg gttgccaaga ggttccatct gccaggtatc aggcaaggat   3300
atgggctcac tgagactaca tcagctattc tgattacacc cgaggggat gataaaccgg    3360
gcgcggtcgg taaagttgtt ccattttttg aagcgaaggt tgtggatctg ataccggga    3420
aaacgctggg cgttaatcaa agaggcgaac tgtgtgtgag aggtcctatg attatgtccg   3480
gttatgtaaa caatccggaa gcgaccaacg ccttgattga caaggatgga tggctacatt   3540
ctggagacat agcttactgg gacgaagacg aacacttctt catcgttgac cgcctgaagt   3600
ctctgattaa gtacaaaggc tatcaggtgg ctcccgctga attggaatcc atcttgctcc   3660
aacaccccaa catcttcgac gcaggtgtcg caggtcttcc cgacgatgac gccggtgaac   3720
ttcccgccgc cgttgttgtt ttggagcacg aaagacgat gacggaaaaa gagatcgtgg    3780
attacgtcgc cagtcaagta acaaccgcga aaaagttgcg cggaggagtt gtgtttgtgg   3840
acgaagtacc gaaaggtctt accggaaaac tcgacgcaag aaaaatcaga gagatcctca   3900
taaaggccaa aagggcgga aagatcgccg tgtaaactag tgcgcgcagc ggccgaccat    3960
ggcccaactt gtttattgca gcttataatg gttacaaata aagcaatagc atcacaaatt   4020
tcacaaataa agcatttttt tcactgcatt ctagttgtgg tttgtccaaa ctcatcaatg   4080
tatcttatca tgtctggatc tcggtaccgg atccaaattc ccgataagga tcttcctaga   4140
gcatggctac gtagataagt agcatggcgg gttaatcatt aactacaagg aaccccctagt  4200
gatggagttg gccactccct ctctgcgcgc tcgctcgctc actgaggccg ggcgaccaaa   4260
ggtcgcccga cgcccgggct tgcccgggc ggcctcagtg agcgagcgag cgcgcagcct    4320
taattaacct aattcactgg ccgtcgtttt acaacgtcgt gactgggaaa accctggcgt   4380
tacccaactt aatcgccttg cagcacatcc ccctttcgcc agctggcgta atagcgaaga   4440
ggcccgcacc gatcgccctt cccaacagtt gcgcagcctg aatggcgaat gggacgcgcc   4500
ctgtagcggc gcattaagcg cggcgggtgt ggtggttacg cgcagcgtga ccgctacact   4560
tgccagcgcc ctagcgcccg ctcctttcgc tttcttccct cctttctcg ccacgttcgc    4620
cggctttccc cgtcaagctc taaatcgggg gctcccttta gggttccgat ttagtgcttt   4680
acggcacctc gaccccaaaa aacttgatta gggtgatggt tcacgtagtg gccatcgcc    4740
ctgatagacg gttttcgcc ctttgacgtt ggagtccacg ttctttaata gtggactctt    4800
gttccaaact ggaacaacac tcaaccctat ctcggtctat tcttttgatt tataagggat   4860
tttgccgatt tcggcctatt ggttaaaaaa tgagctgatt taacaaaaat ttaacgcgaa   4920
ttttaacaaa atattaacgt ttataattc aggtggcatc tttcggggaa atgtgcgcgg    4980
aaccoctatt tgtttatttt tctaaataca ttcaaatatg tatccgctca tgagacaata   5040
accctgataa atgcttcaat aatattgaaa aaggaagagt atgagtattc aacatttccg   5100
tgtcgccctt attcccttt ttgcggcatt ttgccttcct gttttgctc acccagaaac     5160
gctggtgaaa gtaaaagatg ctgaagatca gttgggtgca cgagtgggtt acatcgaact   5220
ggatctcaat agtggtaaga tccttgagag ttttcgcccc gaagaacgtt ttccaatgat   5280
gagcactttt aaagttctgc tatgtggcgc ggtattatcc cgtattgacg ccgggcaaga   5340
gcaactcggt cgccgcatac actattctca gaatgacttg gttgagtact caccagtcac   5400
agaaaagcat cttacggatg gcatgacagt aagagaa                            5437
```

```
<210> SEQ ID NO 108
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 108
cacaagtcaa acctttatt                                                   19

<210> SEQ ID NO 109
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 109
ggacgtaatc cagaaagaag a                                                21

<210> SEQ ID NO 110
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 110
ttgtgcctct ggaggttata a                                                21

<210> SEQ ID NO 111
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 111
ggaaataaag gctggtgaag g                                                21

<210> SEQ ID NO 112
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 112
gaaagatgaa ggtccatatt a                                                21

<210> SEQ ID NO 113
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 113
gcagatggcc gtgacacaaa t                                                21

<210> SEQ ID NO 114
<211> LENGTH: 21
<212> TYPE: DNA
<213> ORGANISM: Artificial Sequence
<220> FEATURE:
<223> OTHER INFORMATION: Synthetic Polynucleotide
```

<400> SEQUENCE: 114
gctcatggag actaggtttg g                                                    21

<210> SEQ ID NO 115
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 115
ggatgtaagt ttgccagaag c                                                    21

<210> SEQ ID NO 116
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 116
gctccaacga aagctatttg                                                      21

<210> SEQ ID NO 117
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 117
gttcagatgt gcggcgagt                                                       19

<210> SEQ ID NO 118
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 118

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 119
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 119
ggcagcggcg ccacgaactt ctctctgtta aagcaagcag gagatgttga agaaaacccc         60
gggcct                                                                    66

<210> SEQ ID NO 120
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 120

```
ggctccggcg agggcagggg aagtcttcta acatgcgggg acgtggagga aaatcccggc    60
cca                                                                  63

<210> SEQ ID NO 121
<211> LENGTH: 7390
<212> TYPE: DNA
<213> ORGANISM: Artificial Sequence
<220> FEATURE:
<223> OTHER INFORMATION: Synthetic Polynucleotide

<400> SEQUENCE: 121
ttatgcagtg ctgccataac catgagtgat aacactgcgg ccaacttact tctgacaacg    60
atcggaggac cgaaggagct aaccgctttt ttgcacaaca tggggatca tgtaactcgc    120 cttgatcgtt gggaaccgga gctgaatgaa gccataccaa acgacgagcg tgacaccacg    180
atgcctgtag taatggtaac aacgttgcgc aaactattaa ctggcgaact acttactcta    240
gcttcccggc aacaattaat agactggatg gaggcggata agttgcagg accacttctg    300 cgctcggccc ttccggctgg ctggtttatt gctgataaat ctggagccgg tgagcgtggg    360
tctcgcggta tcattgcagc actggggcca gatggtaagc cctcccgtat cgtagttatc    420
tacacgacgg ggagtcaggc aactatggat gaacgaaata gacagatcgc tgagataggt    480
gcctcactga ttaagcattg gtaactgtca gaccaagttt actcatatat actttagatt    540
gatttaaaac ttcattttta atttaaaagg atctaggtga agatcctttt tgataatctc    600
atgaccaaaa tcccttaacg tgagttttcg ttccactgag cgtcagaccc cgtagaaaag    660
atcaaaggat cttcttgaga tccttttttt ctgcgcgtaa tctgctgctt gcaaacaaaa    720
aaaccaccgc taccagcggt ggtttgtttg ccggatcaag agctaccaac tcttttttccg    780 aaggtaactg gcttcagcag agcgcagata ccaaatactg tccttctagt gtagccgtag    840
ttaggccacc acttcaagaa ctctgtagca ccgcctacat acctcgctct gctaatcctg    900
ttaccagtgg ctgctgccag tggcgataag tcgtgtctta ccgggttgga ctcaagacga    960
tagttaccgg ataaggcgca gcggtcgggc tgaacggggg gttcgtgcac acagcccagc    1020
ttggagcgaa cgacctacac cgaactgaga tacctacagc gtgagctatg agaaagcgcc    1080
acgcttcccg aagggagaaa ggcggacagg tatccggtaa gcggcagggt cggaacagga    1140
gagcgcacga gggagcttcc agggggaaac gcctggtatc tttatagtcc tgtcgggttt    1200
cgccacctct gacttgagcg tcgatttttg tgatgctcgt caggggggcg gagcctatgg    1260
aaaaacgcca gcaacgcggc ctttttacgg ttcctggcct tttgctggcc ttttgctcac    1320
atgttctttc ctgcgttatc ccctgattct gtggataacc gtattaccgc ctttgagtga    1380
gctgataccg ctcgccgcag ccgaacgacc gagcgcagcg agtcagtgag cgaggaagcg    1440
gaagagcgcc caatacgcaa accgcctctc cccgcgcgtt ggccgattca ttaatgcagc    1500
tggcacgaca ggtttcccga ctggaaagcg ggcagtgagc gcaacgcaat taatgtgagt    1560
tagctcactc attaggcacc ccaggcttta cactttatgc ttccggctcg tatgttgtgt    1620
ggaattgtga gcggataaca atttcacaca ggaaacagct atgaccatga ttacgccaga    1680
tttaattaag gccttaatta ggctgcgcgc tcgctcgctc actgaggccg cccgggcaaa    1740
gcccgggcgt cgggcgacct ttggtcgccc ggcctcagtg agcgagcgag cgcgcagaga    1800
gggagtggcc aactccatca ctaggggttc cttgtagtta atgattaacc cgccatgcta    1860
cttatctacg tagccatgct ctaggaagat cggaattctt tactccctat cagtgataga    1920
```

```
gaacgtatga agagtttact ccctatcagt gatagagaac gtatgcagac tttactccct   1980
atcagtgata gagaacgtat aaggagttta ctccctatca gtgatagaga acgtatgacc   2040
agtttactcc ctatcagtga tagagaacgt atctacagtt tactccctat cagtgataga   2100
gaacgtatat ccagtttact ccctatcagt gatagagaac gtataagctt taggcgtgta   2160
cggtgggcgc ctataaaagc agagctcgtt tagtgaaccg tcagatcgcc tggagcaatt   2220
ccacaacact tttgtcttat accaactttc cgtaccactt cctaccctcg taaagcggcc   2280
gcgccaccat ggcgggacac ctggcttcgg atttcgcctt ctcgcccct ccaggtggtg    2340
gaggtgatgg gccagggggg ccggagccgg gctgggttga tcctcggacc tggctaagct   2400
tccaaggccc tcctggaggg ccaggaatcg ggccggggt tgggccaggc tctgaggtgt    2460
gggggattcc cccatgcccc ccgccgtatg agttctgtgg ggggatggcg tactgtgggc   2520
cccaggttgg agtgggcta gtgccccaag gcggcttgga gacctctcag cctgagggcg    2580
aagcaggagt cggggtggag agcaactccg atggggcctc ccggagccc tgcaccgtca    2640
cccctggtgc cgtgaagctg gagaaggaga agctggagca aaacccggag gagtcccagg   2700
acatcaaagc tctgcagaaa gaactcgagc aatttgccaa gctcctgaag cagaaggaga   2760
tcaccctggg atatacacag gccgatgtgg ggctcaccct gggggttcta tttgggaagg   2820
tattcagcca aacgaccatc tgccgctttg aggctctgca gcttagcttc aagaacatgt   2880
gtaagctgcg gcccttgctg cagaagtggg tggaggaagc tgacaacaat gaaaatcttc   2940
aggagatatg caaagcagaa accctcgtgc aggcccgaaa gagaaagcga accagtatcg   3000
agaaccgagt gagaggcaac ctggagaatt tgttcctgca gtgcccgaaa cccacactgc   3060
agcagatcag ccacatcgcc cagcagcttg ggctcgagaa ggatgtggtc cgagtgtggt   3120
tctgtaaccg gcgccagaag ggcaagcgat caagcagcga ctatgcacaa cgagaggatt   3180
ttgaggctgc tgggtctcct ttctcagggg gaccagtgtc cttcctctg gccccagggc    3240
cccattttgg taccccaggc tatgggagcc tcacttcac tgcactgtac tcctcggtcc    3300
cttccctga ggggaagcc ttcccctg tctctgtcac cactctgggc tctcccatgc       3360
attcaaacgc tagcggcagc ggcgccacga acttctctct gttaaagcaa gcaggagatg   3420
ttgaagaaaa ccccgggcct gcatgcatgt acaacatgat ggagacggag ctgaagccgc   3480
cgggcccgca gcaaacttcg ggggcggcg cggcaactc caccgcgcg gcggccggcg      3540
gcaaccagaa aaacagcccg gaccgcgtca gcggcccat gaatgccttc atggtgtggt    3600
cccgcgggca gcgcgcaag atgggcccagg agaaccccaa gatgcacaac tcggagatca   3660
gcaagcgcct gggcgccgag tggaaacttt tgtcggagac ggagaagcgg ccgttcatcg   3720
acgaggctaa gcggctgcga gcgctgcaca tgaaggagca cccggattat aaataccggc   3780
cccggcggaa aaccaagacg ctcatgaaga aggataagta cacgctgccc ggcgggctgc   3840
tggcccccgg cggcaatagc atggcgagcg ggtcggggt gggcgccggc ctgggcgcgg   3900
gcgtgaacca gcgcatggac agttacgcgc acatgaacgg ctggagcaac ggcagctaca   3960
gcatgatgca ggaccagctg ggctacccgc agcacccggg cctcaatgcg cacggcgcag   4020
cgcagatgca gcccatgcac cgctacgacg tgagcgccct gcagtacaac tccatgacca   4080
gctcgcagac ctacatgaac ggctcgccca cctacagcat gtcctactcg cagcagggca   4140
cccctggcat ggctcttggc tccatgggtt cggtggtcaa gtccgaggcc agctccagcc   4200
cccctgtggt tacctcttcc tcccactcca gggcgcctg caggccggg gacctccggg     4260
acatgatcag catgtatctc cccggcgccg aggtgccgga acccgccgcc cccagcagac   4320
```

```
ttcacatgtc ccagcactac cagagcggcc cggtgcccgg cacgccatt  aacggcacac   4380
tgcccctctc acacatggca tgcggctccg gcgagggcag gggaagtctt ctaacatgcg   4440
gggacgtgga ggaaaatccc ggcccactcg agatggctgt cagcgacgcg ctgctcccat   4500
ctttctccac gttcgcgtct ggcccggcgg aagggagaa  gacactgcgt caagcaggtg   4560
ccccgaataa ccgctggcgg gaggagctct cccacatgaa gcgacttccc ccagtgcttc   4620
ccggccgccc ctatgacctg gcggcggcga ccgtggccac agacctggag agcggcggag   4680
ccggtgcggc ttgcggcggt agcaacctgg cgccctacc  tcggagagag accgaggagt   4740
tcaacgatct cctggacctg gactttattc tctccaattc gctgacccat cctccggagt   4800
cagtggccgc caccgtgtcc tcgtcagcgt cagcctcctc ttcgtcgtcg ccgtcgagca   4860
gcggccctgc cagcgcgccc tccacctgca gcttcaccta tccgatccgg gccgggaacg   4920
acccgggcgt ggcgccgggc ggcacgggcg gaggcctcct ctatggcagg gagtccgctc   4980
cccctccgac ggctcccttc aacctggcgg acatcaacga cgtgagcccc tcgggcggct   5040
tcgtggccga gctcctgcgg ccagaattgg accggtgta  cattccgccg cagcagccgc   5100
agccgccagg tggcgggctg atgggcaagt tcgtgctgaa ggcgtcgctg agcgcccctg   5160
gcagcgagta cggcagcccg tcggtcatca gcgtcagcaa aggcagccct gacggcagcc   5220
acccggtggt ggtggcgccc tacaacgcg  ggccgccgcg cacgtgcccc aagatcaagc   5280
aggaggcggt ctcttcgtgc acccacttgg gcgctggacc ccctctcagc aatggccacc   5340
ggccggctgc acacgacttc cccctggggc ggcagctccc cagcaggact accccgaccc   5400
tgggtcttga ggaagtgctg agcagcaggg actgtcaccc tgccctgccg cttcctcccg   5460
gcttccatcc ccaccggggg cccaattacc catccttcct gcccgatcag atgcagccgc   5520
aagtcccgcc gctccattac caagagctca tgccacccgg ttcctgcatg ccagaggagc   5580
ccaagccaaa gaggggaaga cgatcgtggc cccggaaaag gaccgccacc cacacttgtg   5640
attacgcggg ctgcggcaaa acctacacaa agagttccca tctcaaggca cacctgcgaa   5700
cccacacagg tgagaaacct taccactgtg actgggacgg ctgtggatgg aaattcgccc   5760
gctcagatga actgaccagg cactaccgta acacacggg  gcaccgcccg ttccagtgcc   5820
aaaaatgcga ccgagcattt tccaggtcgg accacctcgc cttacacatg aagaggcatt   5880
tttaaatgac tagtgcgcgc agcggccgac catggcccaa cttgtttatt gcagcttata   5940
atggttacaa ataaagcaat agcatcacaa atttcacaaa taaagcattt ttttcactgc   6000
attctagttg tggtttgtcc aaactcatca atgtatctta tcatgtctgg atctcggtac   6060
cggatccaaa ttcccgataa ggatcttcct agagcatggc tacgtagata agtagcatgg   6120
cgggttaatc attaactaca aggaaccct  agtgatggag ttggccactc cctctctgcg   6180
cgctcgctcg ctcactgagg ccgggcgacc aaaggtcgcc cgacgcccgg gctttgcccg   6240
ggcggcctca gtgagcgagc gagcgcgcag ccttaattaa cctaattcac tggccgtcgt   6300
tttacaacgt cgtgactggg aaaaccctgg cgttacccaa cttaatcgcc ttgcagcaca   6360
tccccctttc gccagctggc gtaatagcga agaggcccgc accgatcgcc cttcccaaca   6420
gttgcgcagc ctgaatggcg aatgggacgc gccctgtagc ggcgcattaa gcgcggcggg   6480
tgtggtggtt acgcgcagcg tgaccgctac acttgccagc gccctagcgc ccgctccttt   6540
cgctttcttc ccttcctttc tcgccacgtt cgccggcttt cccc gtcaag ctctaaatcg   6600
ggggctccct ttagggttcc gatttagtgc tttacggcac ctcgacccca aaaaacttga   6660
```

```
ttagggtgat ggttcacgta gtgggccatc gccctgatag acggtttttc gcccttgac      6720
gttggagtcc acgttcttta atagtggact cttgttccaa actggaacaa cactcaaccc      6780
tatctcggtc tattcttttg atttataagg gattttgccg atttcggcct attggttaaa      6840
aaatgagctg atttaacaaa aatttaacgc gaattttaac aaaatattaa cgtttataat      6900
ttcaggtggc atctttcggg gaaatgtgcg cggaacccct atttgtttat ttttctaaat      6960
acattcaaat atgtatccgc tcatgagaca ataaccctga taaatgcttc aataatattg      7020
aaaaaggaag agtatgagta ttcaacattt ccgtgtcgcc cttattccct ttttgcggc       7080
attttgcctt cctgtttttg ctcacccaga acgctggtg aaagtaaaag atgctgaaga      7140
tcagttgggt gcacgagtgg gttacatcga actggatctc aatagtggta agatccttga      7200
gagttttcgc cccgaagaac gttttccaat gatgagcact tttaaagttc tgctatgtgg      7260
cgcggtatta tcccgtattg acgccgggca agagcaactc ggtcgccgca tacactattc      7320
tcagaatgac ttggttgagt actcaccagt cacagaaaag catcttacgg atggcatgac      7380
agtaagagaa                                                             7390

<210> SEQ ID NO 122
<211> LENGTH: 6586
<212> TYPE: DNA
<213> ORGANISM: Artificial Sequence
<220> FEATURE:
<223> OTHER INFORMATION: Synthetic polynucleotide

<400> SEQUENCE: 122
aattcagaga ccgggaacca aactagcctt taaaaaacat aagtacagga gccagcaaga      60
tggctcagtg ggtaaaggtg cctaccagca agcctgacag cctgagttca gtccccacga     120
actacgtggt aggagaggac caaccaactc tggaaatctg ttctgcaaac acatgctcac     180
acacacacac acaaatagta taaacaattt taaatttcat ttaaaaataa tttgtaaaca     240
aaatcattag cacaggtttt agaaagagcc tcttggtgac atcaagttga tgctgtagat     300
ggggtatcat tcctgaggac ccaaaaccgg gtctcagcct ttccccattc tgagagttct     360
ctcttttctc agccactagc tgaagagtag agtggctcag cactgggctc ttgagttccc     420
aagtcctaca actggtcagc ctgactacta accagccatg aagaaacaag gagtggatgg     480
gctgagtctg ctgggatggg agtggagtta gtaagtggcc atggatgtaa tgaccccagc     540
aatgctggct agaaggcatg cctccttttcc ttgtctggag acggaacggg agggatcatc     600
ttgtactcac agaagggaga acattctagc tggttgggcc aaaatgtgca agttcacctg     660
gaggtggtgg tgcatgcttt taactccagt actcaggagg cagggccagg tggatctctg     720
tgagttcaag accagcctgc actatggaga gagttttggg acagccagag ttacacagaa     780
aaatcctggt ggaaaatctg aaagaaagag agaagaaag aaagaaagaa aggaagaaag      840
aaagaaagag tggcaggcag gcaggcagga ggaaggaagg aaggaaggaa ggaaggaagg     900
aaggaaggaa ggaaaatagg tgcgacttca agatccggag ttacaagcag aatgcactgt     960
ttccctaaca gggccaagtg ttttgagtaa ctgaaggtgg gcatgatgcc tgggaagcag    1020
aaacaagcca ggcagatgca cccttgcct tgcttccgaa gggctgcagt agcatggaaa      1080
acatggaaaa caaccaatcc attccctttg ctgatataac aggctccaaa gccaaaacct    1140
gtcactggag gctcaagagc agatctccag ccaagaggca aggaatggg ggaagctgga      1200
gggcctccct ctggttatcc aggcttctga aggttcaagc aaagaaaggg ttacaacctt    1260
aaaaggagag cgtcccgggg tatgggtaga agactgctcc accccgaccc ccagggtccc    1320
```

```
taaccgtctt ttccctgggc gagtcagccc aatcacagga ctgagagtgc ctctttagta    1380
gcagcaagcc acttcggaca cccaaatgga acacctccag tcagccctcg ccgaccaccc    1440
cacccctcc atccttttcc ctcagcctcc gattggctga atctagagtc cctccctgct    1500
cccccctctc tccccacccc tggtgaaaac tgcgggcttc agcgctgggt gcagcaactg    1560
gaggcgttgg cgcaccagga ggaggctgca gctagggag tccaggtgag agcaggccga     1620
cgggagggac ccgcacatgc aaggaccgcc gcagggcgag gatgcaagcc ttccccagct    1680
acagttttgg gaaaggatac cagggcgctc ctatatgggg gcgcgggaac tggggaaaga    1740
aggtgctccc aggtcgaggt gggagaggaa ggcagtgcgg ggtcacgggc tttctccctg    1800
ctaacggacg ctttcgaaga gtgggtgccg gaggagaacc atgaggaagg acatcaagga    1860
cagcctttgg tccccaagct caaatcgctt tagtggtgcg aatagaggga ggaggtgggt    1920
ggcaaactgg agggagtccc cagcgggtga cctcgtggct ggctgggtgc ggggcaccgc    1980
aggtaagaaa accgcaatgt tgcgggaggg gactgggtgg caggcgcggg ggaggggaaa    2040
gctagaaagg atgcgaggga gcggaggggg gagggagcgg gagaatctca actggtagag    2100
gaagattaaa atgaggaaat agcatcaggg tggggttagc caagccgggc ctcagggaaa    2160
gggcgcaaag tttgtctggg tgtgggctta ggtgggctgg gtatgagatt cggggcgccg    2220
aaaacactgc tgcgcctctg ccaaatcacg ctaccctgt atctagttct gccaggcttc     2280
tccagcccca gccccaattc ttttctctag tgttccccct tccctcccct gaatctcaag    2340
cccacactcc ctcctccata acccactgtt atcaaatcta agtcatttgc cacccaacaa    2400
ccatcaggag gcggaagcag acgggaggag tttgagatca acttgggcta catcacgagt    2460
tccaggctca ccaaggcttc ttaaggagac cttgtctcta aaattaatta attaattaat    2520
taatagtccc ctttctctgc cacagaacct tgggatctgg ctcctggtcg cagctccccc    2580
cacccccaggc tgacattcac tgccatagcc catccggaaa tcctagtcta tttccccatg    2640
gatcttgaac tgcagagaga atggcagagt ggcccgccct gtgcaaagga tgttcctagc    2700
ctaggtggag ctcgcgaact cgcagactgt gcctctcttg ggcaaggaca ggctagacag    2760
cctgccggtg tgttgagcta gggcactgtg gggaaggcag agaacctgtg cagggcagca    2820
atgaacacag gaccagaaaa ctgcagcccct aggaacactc aagagctggc catttgcaag   2880
catctctggc ctccgtgctt tcactcatg tcccatgtct tatacaggcc tctgtggcac     2940
ctcgcttgcc tgatctcatc cctagccgtt aagctttctg catgacttat cacttggggc    3000
ataatgctgg ataccacca ttttcttaga ccccatcaaa atcctatttg agtgtacggt     3060
tcggagaacc tcatttatcc ggtaaatgtc ttttactctg ctctcaggga gctgaggcag    3120
gacatcctga gatacattgg gagaggagat acagtttcaa taaataata ggttgggtgg     3180
aggtacatgc ctataatgcc accactcagg aaatggtggc agcttcgtga gtttgaggcc    3240
aacccaagaa acatagtgaa accctgtcag taaataagta agcaagtatt tgagtatcta    3300
ctatatgcta gggctgacct ggacattagg ggtcatcttc tgaacaaact agtgcttgag    3360
ggaggtattt ggggttttg tttgtttaat ggatctgaat gagttccaga gactggctac     3420
acagcgatat gactgagctt aacacccta aagcatacag tcagaccaat tagacaataa     3480
aaggtatgta tagcttacca aataaaaaaa ttgtattttc aagagagtgt ctgtctgtgt    3540
agccctggct gttcttgaac tcactctgta gaccaggctg gcctggaaat ccatctgcct    3600
gcctctgcct ctctgcctct ctgcctctct gcctctctct ctgcctctct ctgcctctct    3660
```

```
ctgcccctct ctgcccctct ctgcccctct ctgccgccct ctgccttttg ccctctgccc    3720
tctgttctct ggcctctgcc ctctgccctc tggcctctgg cctctgcctc tgcctcttga    3780
gtgctggaat caaggtgtg agctctgtag gtcttaagtt ccagaagaaa gtaatgaagt    3840
cacccagcag ggaggtgctc agggacagca cagacacaca cccaggacat aggctcccac    3900
ttccttggct ttctctgagt ggcaaaggac cttaggcagt gtcactccct aagagaaggg    3960
gataaagaga ggggctgagg tattcatcat gtgctccgtg gatctcaagc cctcaaggta    4020
aatggggacc cacctgtcct accagctggc tgacctgtag cttccccac cacagaatcc    4080 aagtcggaac tcttggcacc tagaggatct cgaggtcctt cctctgcaga ggtcttgctt    4140
ctcccggtca gctgactccc tccccaagtc cttcaaatat ctcagaacat ggggagaaac    4200
ggggaccttg tccctcctaa ggaaccccag tgctgcatgc catcatcccc cccaccctcg    4260
cccccacccc cgccacttct ccctccatgc ataccactag ctgtcatttt gtactctgta    4320
tttattccag ggctgcttct gattatttag tttgttcttt ccctggagac ctgttagaac    4380
ataagggcgt atggtgggta ggggaggcag gatatcagtc cctggggcga gttcctccct    4440
gccaaccaag ccagatgcct gaaagagata tggatgaggg aagttggact gtgcctgtac    4500
ctggtacagt catactctgt tgaaagaatc atcggggagg ggggggggct caagagggga    4560
gagctctgct gagcctttgt ggaccatcca atgaggatga gggcttagat tctaccaggt    4620
cattctcagc caccacacac aagcgctctg ccatcactga agaagccccc tagggctctt    4680
gggccagggc acactcagta aagatgcagg ttcagtcagg gaatgatggg gaaaggggta    4740
ggaggtgggg gagggatcac cccctcctct aaaacgagag cctgctgtct ccaaaggcct    4800
ctgcctgtag tgagggtggc agaagaagac aaggagccag aactctgact ccaggatcta    4860
agtccgtgca ggaaggggat cctagaacca tctggttgga cccagcttac caaggggagag   4920 cctttattct tctttcccctt gcccctctgt gccagcccct cttgctgtcc ctgatccccc    4980
agacagcgag agtcttgcaa cctgcctctt ccaagacctc ctaatctcag gggcaggcgg    5040
tggagtgaga tccggcgtgc acacttttttg gaagatagct ttcccaagga tcctctcccc    5100
cactggcagc tctgcctgtc ccatcaccat gtataatacc accactgcta cagcatctca    5160
ccgaggaaag aaaactgcac aataaaaacca agcctctgga gtgtgtcctg gtgtctgtct    5220
cttctgtgtc ctggcgtctg tctcttctgt gttcttccaa ggtcagaaac aaaaaccaca    5280
cacttcaacc tggatggctc ggctgagcac ttctgtgtgc agaaggtcca accagactct    5340
ggggtacccc ggccctccct attccccttgc ctcctgtctc ccgctttttta tagctcccta    5400 tgctgggctt ctctggagag tgaaatcttt gcccaaatca atgcgcattc tctctgctga    5460
gtcatctggc gacagcagtt gagttcaccc gccaacacat gggcccagct atgtagccga    5520
accctggctc tggaagtgcc agggactttg tgcataagta tgtaccatgc cctttttttca    5580 cagtcctagc tctgcagaag tgcagcctga aggcctgtct gctgagagga catgccctgg    5640
agccctgaaa caggcacagt gggaggagga acggaggatg acaggcatca ggccctcagt    5700
ccaaaagcaa ccacttgaga atgggctgga gtacgaaaca tggggtcccg tccctggatc    5760
cctcctcaaa gagtaataag taaaatataa acaggtaccc caggccgttc tgggtttggg    5820
ttgtaatggg atccatttgc agagaactat tgagacagcc cagccgtact gtgacaggca    5880
atgtggggga ggaggttgaa tcacttggta tttagcatga atagaataat tccctgaaca    5940
tttttcttaa acatccatat ctaaattacc accactcgct cccagtcttc ctgcctttgc    6000
gccagcctcc tgtctggcca tgcctgaaga aggctggaga agccacccac ctcaggccat    6060
```

```
gacactgcca gccacttggc aggtgcagcc aaacctgagc tgtcccagaa agggacattc    6120
tcaagaccca ggcaccctga tcagcactga cttggagcta caagtgtcat gccagaaaag    6180
tctctaagaa aaccttttca gggaaaaggg ggtgactcaa caccgggcaa gtttgggaag    6240
ccccaccctt cgagtgatgg aagagcagat aggaagcctc agaagagaga caccggcacc    6300
caggtaacgt tcctcatgtg gtctctgtca cactaggtgc tcttccctgg acatctccgt    6360
gaccacactc tcagttctta gggagatgcg ggtgctctct gaggctatct cagagttgca    6420
gattctgagg cctagagtga ctacagtcag cctaggaagc cacagaggac tgtggaccag    6480
gagggcagaa gaggagaagg gaagaaaaac catcagatag gacttgcaat gaaactaacc    6540
caagacaatc ataatgcaga caggaatgtt aaaggcgttc agcagc                   6586
```

CELLULAR REPROGRAMMING TO REVERSE AGING AND PROMOTE ORGAN AND TISSUE REGENERATION

RELATED APPLICATIONS

This application is a national stage filing under 35 U.S.C. § 371 of international PCT application number PCT/US2019/053545, filed Sep. 27, 2019, which claims priority under 35 U.S.C. § 119 (e) of U.S. provisional application No. 62/738,922, filed Sep. 28, 2018, U.S. provisional application No. 62/792,283, filed Jan. 14, 2019, U.S. provisional application No. 62/865,877, filed Jun. 24, 2019, and U.S. provisional application No. 62/880,488, filed Jul. 30, 2019, each of which is incorporated by reference herein in its entirety.

GOVERNMENT SUPPORT

This invention was made with government support under DK100263 and AG019719 awarded by the National Institutes of Health. The government has certain rights in the invention.

BACKGROUND OF THE INVENTION

In many animals, including vertebrates, vital organs have a limited intrinsic capacity for regeneration and repair. Acute injury and chronic disorders can damage vital organs and tissues, including the heart, pancreas, brain, kidney, muscles, skin and neuronal tissue, among others. Mature somatic cells, however, often cannot survive these insults, and even if they do, they are unable to self-renew and transdifferentiate to replace damaged cells. Furthermore, cells that are capable of self-renewal can be limited in quantity, have limited capacity and are susceptible to damage, especially with age. In contrast to somatic cells from adults, cells from individuals that are chronologically closer to fertilization, such as those from embryos and infants, display cellular youthfulness and have a greater capacity to resist injury and stress, to heal, renew, and regenerate organs and tissues. Thus, compositions and methods directed at rejuvenating cells, thereby restoring them from an aged, mature state to a younger, more vital state, have long been sought to treat certain injuries and diseases, as well as generally reverse and prevent aging in entire organisms.

There are two types of information in the body: digital and analog. DNA is digital information and the epigenome is analog information. Analog information never lasts as long as digital, nor can analog information be copied with high fidelity compared to digital information. This has consequences for how long organisms live and thrive. Aging was once thought of as a process driven by mutations in the genetic material of a cell. This has largely been abandoned as an explanation. A major cause of aging is now thought to be due to epigenetic changes that cause cells to transcribe the wrong genes at the wrong time for optimal function, a process that becomes more dysfunctional over time, leading to diseases, an inability to heal and eventually to death. The Yamanaka factors (OCT4, SOX2, c-Myc, and KLF4) have previously been shown to induce pluripotency in vitro (Takahashi et al., Cell. 2006 Aug. 25; 126(4):663-76) and reverse the DNA methlylation clock of aging (Horvath, Genome Biol. 2013). Nanog and Lin28 can help induce pluoripotency together with Yamanaka factors. And Tet1, NR5A-2, Sall4, NKX3-1 can replace Oct4 (Gao et al., Cell Stem Cell 12, 1-17, Apr. 4, 2013 and Mai et al., Nature Cell Biology 20, 900-908, 2018). Expression of original four transcription factors in transgenic mice, however, induce teratomas in vivo, along with other acute toxicities like dysplasia in the intestinal epithelium, that can kill an animal in a few days (Abad et al., Nature. 2013 Oct. 17; 502(7471): 340-5). Therefore, non-toxic and efficient methods of cellular reprogramming are needed.

SUMMARY OF THE INVENTION

The cellular aging process has been postulated to be caused by the loss of both genetic and epigenetic information. While previous studies have hypothesized that aging is caused primarily by the loss of genetic information (most commonly in the form of genetic mutations such as substitutions, and deletions in an organism's genome), the compositions and methods of the present disclosure are informed by the unexpected finding that aging is primarily driven by a loss in the particular epigenetic information that is established closer to fertilization and final differentiation of particular cells. Epigenetic information, which commonly takes the form of covalent modifications to DNA, such as 5-methylcytosine (5mC), hydroxymethylcytosine (5hmeC), 5-formylcytosine (fC), and 5-carboxylcytosine (caC) and adenine methylation, and to certain proteins, such as lysine acetylation, lysine and arginine methylation, serine and threonine phosphorylation, and lysine ubiquitination and sumoylation of histone proteins, is sometimes referred to as the "analog" information of the cell. The loss of this analog information can result in dysregulation of vital cellular processes, such as the processes that maintain cell identity, causing cells to exhibit traits that are typically associated with aging such as senescence.

The methods, compositions, and kits of the present disclosure rejuvenate cells by preventing and reversing the cellular causes of aging. Without being bound by a particular theory, more specifically, the methods, compositions and kits of the present disclosure rejuvenate cells by restoring epigenetic information that has been lost due to the aging process, injury or disease. The methods compositions and kits of the present disclosure comprise the transcription factors OCT4, SOX2 and KLF4. OCT4, SOX2 and KLF4 are three of the four "Yamanaka Factors", with the fourth being c-Myc. The Yamanaka Factors have traditionally been used to reprogram cells to a pluripotent state. However, the induction of expression of the four transcription factors in transgenic mice resulted in the formation of teratomas in vivo, along with other acute toxicities like dysplasia in the intestinal epithelium, which can kill the animal in a few days. Moreover, the fact that the four Yamanaka Factors are typically used to reprogram cells to a completely pluripotent state, wherein the cell loses its pre-established cellular identity, can be dangerous for in vivo applications where the cellular identity of target cells must be maintained for tissue and/or organ integrity. In contrast, in some embodiments, the methods described herein, allow incomplete reprogramming and do not result in global changes in demethylation. In some embodiments, the methods described herein do not require complete de-differentiation of cells. For example, while expression of OCT4, SOX2, and KLF4 promoted regeneration following injury in young and old mice and following vincristine-induced injury in human neurons, expression of OCT4, SOX2, and KLF4 did not induce a global reduction of DNA methylation (see e.g., FIGS. 45B-45C).

In some embodiments, the results disclosed herein suggest that expression of OCT4, SOX2, and KLF4 can allow diseased cells to revert to a healthier state without inducing complete reprogramming. Without being bound by a particular theory, the results disclosed herein suggest that cells maintain a backup epigenome that can be restored using the methods described herein.

The methods, compositions and kits of the present disclosure are in part informed by the surprising and unexpected discovery that the spatially and temporally specific induction of OCT4, SOX2, and KLF4 expression in the absence of the induction of c-Myc expression can rejuvenate a cell without reprogramming the cell to a pluripotent state. Using inducible promoters, the expression of OCT4, SOX2 and KLF4 can be carefully controlled to decrease and reverse epigenetic marks associated with aging, increase the epigenetic marks associated with cellular youthfulness, decrease the expression of aging related proteins, increase the expression of proteins associated with a youthful cellular state, restore the balance between euchromatin and heterochromatin, prevent loss of cellular identity, restore cellular identity, reversing the aging related changes in DNA methylation, thereby rejuvenating the cell without reprogramming the cell to a pluripotent state.

Thus, in various embodiments the methods of the invention rejuvenates a cell by restoring the cellular identity of the cell by reversing the effects of or preventing of one or more dysregulated developmental pathways. For example, the methods:
  (i) increase the abundance of at least one of histone H2A, histone H2B, histone H3, histone H4, or any combination thereof in the cell;
  (ii) increase the abundance of at least one of CHAF1a, CHAF1b, HP1α, NuRD or any combination thereof in the cell;
  (iii) increase at least one heterochromatin mark in the cell such as for example H3K9me3, H3K27me3 or any combination thereof; or decrease one heterochromatin mark such as H4K20me3 or euchromatin mark H3K4me3;
  (iv) increase/decrease DNA methylation of at least one age-related CpG site in the cell towards young level;
  (v) increase the abundance of lamin B1 in the cell;
  (vi) increase acetylation of histone H3 at lysine 27 (H3K27ac), increase acetylation of histone H3 at lysine 56 (H3K56ac) or any combination thereof in the cell;
  (vii) decrease acetylation of histone H3 at lysine 122 (H3K122Ac) or histone H4 at lysine 16 (H4K16ac), or any combination thereof in the cell
  (viii) decrease the abundance of IL6, Ccl2, Ccl20, Apob, p16, LINE-1 repeats, Sat III repeats, Alu elements, IAP or any combination thereof;
  (ix) restores the balance between euchromatin epigenetic marks such as H3K4me3 and heterochromatin epigenetic marks such as for example H3K9me3 or H3K27me3
  (x) induces the formation of euchromatin;
  (xi) restores youthful levels of at least one repressive heterochromatin epigenetic mark; and/or
  (xii) restores the expression of at least one of the genes recited in Table 5 to youthful levels.

The present disclosure stems from the unexpected discovery that, in some embodiments, precise expression of OCT4, SOX2, and KLF4 in the absence of exogenous c-Myc expression can be used to promote reprogramming and tissue regeneration in vivo without acute toxicity. The expression vectors provided herein, in certain embodiments, allow for precise control of OCT4, SOX2, and KLF4 (OSK) expression, incorporation into viruses (e.g., adeno-associated virus (AAV) at a high viral titer (e.g., more than $2\times10^{12}$ particles per preparation, $1\times10^{13}$ particles per mL), reversing aging, treating diseases, including ocular diseases, and/or tissue regeneration (e.g. optic nerve regeneration) in vivo following damage.

As shown in FIG. 14, mice with inducible transgene expression of OCT4, SOX2, and KLF4 (OSK) died two days after induction of OSK expression, due to generalized cytological and architectural dysplasia in the intestinal epithelium. A similar finding has been reported in mice with transgene of OCT4, SOX2, and KLF4 plus c-Myc (Abad et al., Nature. 2013 Oct. 17; 502(7471):340-5; Ocampo et al., Cell. 2016 Dec. 16; 167:1719-33). Surprisingly, in some embodiments as shown in FIG. 14, expression of OCT4, SOX2, and KLF4 did not cause toxicity or cancer in vivo. Continuous expression (e.g., induction by doxycycline administration) of OCT4, SOX2, and KLF4 through AAV9 delivery (TRE-OSK with UBC-rtTA4) did not result in teratoma formation in vivo. No teratoma or body weight loss was detected for three months when AAV9 viruses encoding these three transcription factors were delivered to the entire body of mice (FIG. 14).

Accordingly, provided herein, in certain embodiments, are nucleic acids (e.g., engineered nucleic acid) capable of inducing expression of OCT4, KLF4, inducing agent, and/or SOX2 and/or recombinant viruses (e.g., lentivirus, adenovirus, alphavirus, vaccinia virus, retrovirus, herpes virus, or AAV) comprising the same. The nucleic acids may encode OCT4, KLF4, and/or SOX2. The nucleic acids may encode a transcription factor selected from the group consisting of OCT4; KLF4; SOX2; and any combinations thereof. In certain embodiments, a nucleic encodes two or more transcription factors selected from the group consisting of OCT4, KLF4, and SOX2. In certain embodiments, a nucleic acid encodes OCT4 and SOX2, OCT4 and KLF4. In certain embodiments, a nucleic acid encodes SOX2 and KLF4. In certain embodiments, a nucleic encodes OCT4, KLF4, and SOX2. In certain embodiments, a nucleic acid encodes four or more transcription factors (e.g., OCT4, SOX2, KLF4, and another transcription factor). In some embodiments, the present disclosure provides nucleic acids encoding an inducing agent (e.g., an inducing agent that is capable of inducing expression of OCT4, KLF4, SOX2, or a combination thereof). In some embodiments, the nucleic acids encode a Cas9 fusion protein (CRISPR activator) and a guide RNA sequence targeting a promoter or enhancer at the endogenous locus of OCT4, KLF4, and/or SOX2. In some embodiments, the nucleic acids encode a Cas9 fusion protein (CRISPR activator) and a guide RNA sequence targeting a promoter or enhancer at the endogenous locus of OCT4, SOX2, KLF4, or any combination thereof.

Aspects of the present disclosure also provide methods of regulating cellular reprogramming, promoting tissue repair, promoting tissue survival, promoting tissue regeneration, promoting tissue growth, regulating tissue function, promoting organ regeneration, promoting organ survival, regulating organ function, treating and/or preventing disease, or any combination thereof. Regulating may comprise inducing cellular reprogramming, reversing aging, improving tissue function, improving organ function, tissue repair, tissue survival, tissue regeneration, tissue growth, promoting angiogenesis, reducing scar formation, reducing the appearance of aging, promoting organ regeneration, promoting organ survival, altering the taste and quality of agricultural products derived from animals, treating a disease, or any combination thereof, in vivo or in vitro. The methods may comprise administering any of the nucleic acids described herein (e.g., DNA and/or RNA), any of the engineered proteins encoding KLF4, OCT4, an inducing agent, and/or SOX2, any of the chemical agents activating (e.g., inducing expression of) OCT4, KLF4, an inducing agent, and/or SOX2, antibodies activating (e.g., inducing expression of) OCT4, KLF4, an inducing agent, and/or SOX2, and/or any of the recombinant viruses described herein. The methods may comprise administering any of the nucleic acids described herein (e.g., DNA and/or RNA), any of the engineered proteins encoding KLF4, SOX2, OCT4, or any combination thereof, any of the chemical agents activating (e.g., inducing expression of) OCT4; KLF4; SOX2; or any combination thereof, antibodies activating (e.g., inducing expression of) OCT4; KLF4; SOX2; or any combination thereof and/or any of the recombinant viruses described herein. In certain embodiments, the engineered nucleic acids comprise DNA and/or RNA. The engineered nucleic acid may be an expression vector or not an expression vector. For example, the engineered nucleic acid may be mRNA or plasmid DNA. In certain embodiments, the method further comprises administering a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent. For example, the engineered nucleic acid may be mRNA or plasmid DNA.

One aspect of the present disclosure provide vectors (e.g., expression vectors) comprising a first nucleic acid (e.g., engineered nucleic acid) encoding OCT4, a second nucleic acid (e.g., engineered nucleic acid) encoding SOX2, a third nucleic acid (e.g., engineered nucleic acid) encoding KLF4, alone or in combination and in the absence of an exogenous nucleic acid (e.g., engineered nucleic acid) capable of expressing c-Myc. In certain embodiments, a vector (e.g., expression vector) comprising a first nucleic acid (e.g., engineered nucleic acid) encoding OCT4, a second nucleic acid (e.g., engineered nucleic acid) encoding SOX2, a third nucleic acid (e.g., engineered nucleic acid) encoding KLF4, or any combination thereof. In certain embodiments, the first, second, and third nucleic acids (e.g., engineered nucleic acids) are present on separate expression vectors. In certain embodiments, two of the first, second, and third nucleic acids (e.g., engineered nucleic acids) are present on the same expression vector. In some embodiments, all three nucleic acids (e.g., engineered nucleic acids) are present on the same expression vector. In certain embodiments, the sequence encoding OCT4 is at least 70% (e.g., at least 75%, 80%, 85%, 90%, 95%, 98%, 99%, or 100%) identical to SEQ ID NO: 2 or 41. In certain embodiments, the sequence encoding SOX2 is at least 70% (e.g., at least 75%, 80%, 85%, 90%, 95%, 98%, 99%, or 100%) identical to SEQ ID NO: 4 or 43. In certain embodiments, the sequence encoding KLF4 is at least 70% identical to SEQ ID NO: 6 or 45. In certain embodiments, OCT4, SOX2, KLF4, or any combination thereof is a human protein. In certain embodiments, OCT4, SOX2, KLF4, or any combination thereof is a non-human protein (for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). If two or more of OCT4, SOX2, and KLF4 are on one vector, they may be in any order. The words "first," "second," and "third" are not meant to imply an order of the genes on the vector.

An expression vector of the present disclosure may further comprise an inducible promoter. An expression vector may only have one inducible promoter. In such instances, the expression of OCT4, SOX2, and KLF4 are under the control of the same inducible promoter. In some instances, an expression vector comprises more than one inducible promoter. The inducible promoter may comprise a tetracycline-responsive element (TRE) (e.g., a TRE3G promoter, a TRE2 promoter, or a P tight promoter), mifepristone-responsive promoters (e.g., GAL4-E1b promoter), or a coumermycin-responsive). As an example, a TRE (e.g., TRE3G) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 7. As an example, a TRE (e.g., TRE2) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 23. As an example, a TRE (e.g., P tight) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 24. See, e.g., U.S. Provisional Application, U.S. Ser. No. 62/738,894, entitled MUTANT REVERSE TETRACYCLINE TRANSACTIVATORS FOR EXPRESSION OF GENES, which was filed on Sep. 28, 2018, and the International Patent Application titled MUTANT REVERSE TETRACYCLINE TRANSACTIVATORS FOR EXPRESSION OF GENES, which was filed on the same day as the instant application, each of which is herein incorporated by reference in its entirety.

In certain embodiments, an inducing agent is capable of inducing expression of the first (e.g., OCT4), second (e.g., SOX2), third (e.g., KLF4) nucleic acids (e.g., engineered nucleic acids), or any combination thereof from the inducible promoter in the presence of a tetracycline (e.g., doxycycline). In certain embodiments, the inducing agent is reverse tetracycline-controlled transactivator (rtTA) (e.g., M2-rtTA, rtTA3 or rtTA4). In certain embodiments, the rtTA is rtTA3 comprising an amino acid sequence that is at least 70% (e.g., at least 75%, 80%, 85%, 90%, 95%, 98%, 99%, or 100%) identical to SEQ ID NO: 11. In certain embodiments, the rtTA is rtTA4 and comprises a sequence that is at least 70% (e.g., at least 75%, 80%, 85%, 90%, 95%, 98%, 99%, or 100%) identical to SEQ ID NO: 13. In certain embodiments, the rtTA is M2-rtTA and comprises a sequence that is at least 70% % (e.g., at least 75%, 80%, 85%, 90%, 95%, 98%, 99%, or 100%) identical to SEQ ID NO: 15.

In certain embodiments, an inducing agent is capable of inducing expression of expression of the first nucleic acid (e.g., engineered nucleic acid) (e.g., OCT4), second nucleic acid (e.g., engineered nucleic acid) (e.g., SOX2), third nucleic (e.g., KLF4), or any combination thereof from the inducible promoter in the absence of tetracycline (e.g., doxycycline). In certain embodiments, the inducing agent is tetracycline-controlled transactivator (tTA).

In certain embodiments, an expression vector of the present disclosure comprises a constitutive promoter (e.g., CP1, CMV, EF1 alpha, SV40, PGK1, Ubc, human beta actin, CAG, Ac5, polyhedrin, TEF1, GDS, CaM3 5S, Ubi, H1, and U6 promoter). A constitutive promoter may be operably linked to nucleic acid (e.g., engineered nucleic acid) sequences encoding OCT4, KLF4, SOX2, an inducing agent, or a combination thereof. In some embodiments, an expression vector comprises one constitutive promoter. In some embodiments, an expression vector comprises more than one constitutive promoter.

In certain embodiments, an expression vector of the present disclosure comprises an SV40-derived terminator sequence. In certain embodiments, the SV40-derived sequence is at least 70% (e.g., at least 75%, 80%, 85%, 90%, 95%, 98%, 99%, or 100%) identical to SEQ ID NO: 8.

In certain embodiments, an expression vector of the present disclosure comprises a separator sequence, which may be useful in producing two separate amino acid sequences from one transcript. The separator sequence may encode a self-cleaving peptide (e.g., 2A peptide, including a 2A peptide sequence that is at least 70% (e.g., at least 75%, 80%, 85%, 90%, 95%, 98%, 99%, or 100%) identical to SEQ ID NO: 9). In certain embodiments, the separator sequence is an Internal Ribosome Entry Site (IRES).

In certain embodiments, the expression vector is a viral vector (e.g., a lentiviral, a retroviral, or an adeno-associated virus (AAV) vector) (e.g., FIGS. 2-3). An AAV vector of the present disclosure generally comprises inverted terminal repeats (ITRs) flanking a transgene of interest (e.g., a nucleic acid (e.g., engineered nucleic acid) encoding OCT4, SOX2, KLF4, an inducing agent, or a combination thereof). In some embodiments, the distance between two inverted terminal repeats is less than 5.0 kilobases (kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb).

In certain embodiments, an expression vector (e.g., an expression vector encoding OCT4, KLF4, SOX2, an inducing agent, or a combination thereof) of the present disclosure may further comprise a selection agent (e.g., an antibiotic, including blasticidin, geneticin, hygromycin B, mycophenolic acid, puromycin, zeocin, actinomycin D, ampicillin, carbenicillin, kanamycin, and neomycin) and/or detectable marker (e.g., GFP, RFP, luciferase, CFP, mCherry, DsRed2FP, mKate, biotin, FLAG-tag, HA-tag, His-tag, Myc-tag, V5-tag, etc.).

In some embodiments, the expression vector (e.g., viral vector) encoding OCT4, KLF4, and SOX2 comprises the sequence provided in SEQ ID NO: 16, SEQ ID NO: 105, or SEQ ID NO: 121. In some embodiments, the expression vector encoding OCT4, KLF4, and SOX2 comprise the elements depicted in FIG. 2, FIG. 3, FIGS. 4A-4AL, FIGS. 5A-5D, or a combination thereof. Viral vectors include adeno-associated virus (AAV) vectors, retroviral vectors, lentiviral vectors, and herpes viral vectors.

In another aspect, the present disclosure provides recombinant viruses (e.g., lentivirus, adenovirus, retrovirus, herpes virus, alphavirus, vaccinia virus or adeno-associated virus (AAV)) comprising any of the expression vectors described herein. In certain embodiments, a recombinant virus encodes a transcription factor selected from OCT4; KLF4; SOX2; and any combinations thereof. In certain embodiments, a recombinant virus encodes two or more transcription factors selected from the group consisting of OCT4, KLF4, and SOX2. In certain embodiments, a recombinant virus encodes OCT4 and SOX2, OCT4 and KLF4, OCT4, KLF4, and SOX2, or SOX2 and KLF4. In certain embodiments, a recombinant virus encodes OCT4, KLF4, and SOX2. In certain embodiments, a four or more transcription factors encodes four or more transcription factors (e.g., OCT4, SOX2, KLF4, and another transcription factor).

In yet another aspect, the present disclosure provides methods of regulating (e.g., inducing) cellular reprogramming, tissue repair, tissue regeneration, organ regeneration, reversing aging, or any combination thereof comprising administering to a cell a first nucleic acid (e.g., engineered nucleic acid) encoding OCT4, a second nucleic acid (e.g., engineered nucleic acid) encoding SOX2, and a third nucleic acid (e.g., engineered nucleic acid) encoding KLF4 in the absence of an exogenous nucleic acid (e.g., engineered nucleic acid) capable of expressing c-Myc. In certain embodiments, the first nucleic acid (e.g., engineered nucleic acid) encoding OCT4, the second nucleic acid (e.g., engineered nucleic acid) encoding SOX2, and the third nucleic acid (e.g., engineered nucleic acid) encoding KLF4 is administered to a subject. The subject may be human or non-human. Non-human subjects include, for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). In certain embodiments, the three nucleic acids (e.g., engineered nucleic acids) are administered simultaneously. In certain embodiments, the three nucleic acids (e.g., engineered nucleic acids) are administered simultaneously on the same vector.

In yet another aspect, the present disclosure provides methods of regulating (e.g., inducing) cellular reprogramming, tissue repair, tissue regeneration, organ regeneration, reversing aging, or any combination thereof comprising administering to a cell a first nucleic acid (e.g., engineered nucleic acid) encoding OCT4, a second nucleic acid (e.g., engineered nucleic acid) encoding SOX2, a third nucleic acid (e.g., engineered nucleic acid) encoding KLF4, or any combination thereof. In certain embodiments, the first nucleic acid (e.g., engineered nucleic acid) encoding OCT4, the second nucleic acid (e.g., engineered nucleic acid) encoding SOX2, the third nucleic acid (e.g., engineered nucleic acid) encoding KLF4, or any combination thereof is administered to a subject.

The expression vector comprising one or more of the first, second, and third nucleic acids (e.g., engineered nucleic acids) may be any of the expression vectors described above and herein. In some embodiments, the first nucleic acid, the second nucleic acid, the third nucleic acid, or any combination thereof are present on separate expression vectors. In certain embodiments, two of the first nucleic acid, the second nucleic acid, the third nucleic acid, or any combination thereof are present on the same expression vector. In certain embodiments, all three nucleic acids (e.g., engineered nucleic acids) are present on the same expression vector. In certain embodiments, at least two of the first, second, or third nucleic acids (e.g., engineered nucleic acids) are operably linked to the same promoter. In certain embodiments, all three of the first, second, and third nucleic acids (e.g., engineered nucleic acids) are operably linked to the same promoter.

In some embodiments, the expression vector (e.g., viral expression vector, including lentiviral, retroviral, adeno-associated viral vectors) comprises an inducible promoter (e.g., a promoter comprising a tetracycline-responsive element (TRE) including a TRE3G sequence, a TRE2 sequence, or a P tight sequence), and the method further comprises administering an inducing agent (e.g., a chemical agent, a nucleic acid (e.g., engineered nucleic acid) (e.g., nucleic acid (e.g., engineered nucleic acid) encoding an inducing agent), a protein, light, or temperature). In some embodiments, a pH is used to induce expression of a nucleic acid operably linked to a promoter. In certain embodiments, a chemical agent capable of modulating the activity of an inducing agent is tetracycline (e.g., doxycycline). As a non-limiting example, tetracycline-controlled transactivator (tTA) is an inducing agent whose activity is inhibited by tetracycline. As a non-limiting example, reverse tetracycline-controlled transactivator (rtTA) is an inducing agent whose activity is activated by tetracycline. The inducing agent (e.g., rtTA or tTA) may be encoded by a fourth nucleic acid (e.g., engineered nucleic acid) that is administered nucleic acid. In certain embodiments, the inducing agent (e.g., a chemical agent, a nucleic acid (e.g., engineered nucleic acid) (e.g., a nucleic acid comprising RNA and/or DNA encoding an inducing agent), a protein, light, a particular pH, or temperature) is introduced simultaneously with the nucleic acids (e.g., engineered nucleic acids) encoding OCT4, SOX2, and KLF4. In certain embodiments, the inducing agent (e.g., a chemical agent, a nucleic acid (e.g., engineered nucleic acid) (e.g., a nucleic acid comprising RNA and/or DNA encoding an inducing agent), a protein, light, a particular pH, or temperature) is introduced simultaneously with the nucleic acids (e.g., engineered nucleic acids) encoding one or more (e.g., two or more or three or more) transcription factors selected from OCT4; SOX2; KLF4; and any combinations thereof. A promoter (e.g., constitutive promoter, including CAG and Ubc, or an inducible promoter) may be operably linked to the nucleic acid (e.g., engineered nucleic acid) encoding the inducing agent. In certain embodiments, the promoter operably linked to the nucleic acid (e.g., engineered nucleic acid) encoding the inducing agent is a tissue-specific promoter.

In certain embodiments, the nucleic acid (e.g., engineered nucleic acid) encoding the inducing agent is present on the same expression vector as at least one of the nucleic acids (e.g., engineered nucleic acids) encoding OCT4, SOX2, KLF4, or a combination thereof. In certain embodiments, the nucleic acid (e.g., engineered nucleic acid) encoding the inducing agent is present on a separate expression vector from the nucleic acid (e.g., engineered nucleic acid) encoding OCT4, the nucleic acid (e.g., engineered nucleic acid) SOX2, and the nucleic acid (e.g., engineered nucleic acid) encoding KLF4. In certain embodiments, the nucleic acids (e.g., engineered nucleic acids) encoding OCT4, SOX2, and KLF4 are present on a first expression vector, and the fourth nucleic acid (e.g., engineered nucleic acid) is present on a second expression vector.

In some embodiments, a nucleic acid encoding OCT4, SOX2, KLF4, and/or an inducing agent is not present on a viral vector. In some embodiments, a nucleic acid encoding one or more (e.g., two or more or three or more) transcription factors selected from the group consisting of OCT4; SOX2; KLF4; and any combinations thereof is not present on a viral vector. In some embodiments, the nucleic acid is delivered without a viral vector. In some embodiments, delivery of the nucleic acid that is not on a viral vector comprises administration of a naked nucleic acid, electroporation, use of a nanoparticle, and/or use of a liposome.

The expression vectors may be viral vectors (e.g., lentivirus vectors, adenovirus vectors, retrovirus vectors, herpes virus vectors, alphavirus, vaccinia virus, or AAV vectors). For example, the first expression vector encoding OCT4, SOX2, and KLF4 may comprise the nucleic acid (e.g., engineered nucleic acid) sequence set forth in SEQ ID NO: 16. In some embodiments, the expression vector encoding an inducing agent comprises the sequence provided in SEQ ID NO: 17 (e.g., FIG. 12), SEQ ID NO: 31 (e.g., FIG. 18), or SEQ ID NO: 32 (e.g., FIG. 19).

In certain embodiments, the fourth nucleic acid (e.g., engineered nucleic acid) encoding the inducing agent further comprises an SV-40-derived terminator sequence, including a sequence that is at least 70% identical to SEQ ID NO: 8.

In certain embodiments, the inducing agent is capable of inducing expression from the inducible promoter in the presence of tetracycline (e.g., doxycycline). In certain embodiments, the inducing agent is rtTA (e.g., rtTA3, including rtTA3 with a sequence that is at least 70% identical to SEQ ID NO: 11, and rtTA4, including rtTA4 with a sequence that is at least 70% identical to SEQ ID NO: 13). In certain embodiments, the method further comprises administering tetracycline (e.g., doxycycline) to the cell, tissue, or subject. In certain embodiments, the method comprises removing tetracycline (e.g., doxycycline) from the cell, tissue, or subject.

In certain embodiments, the inducing agent is capable of inducing expression from the inducible promoter in the absence of tetracycline (e.g., doxycycline). In certain embodiments, the inducing agent is a tetracycline transactivator (tTA). Without being bound by a particular theory, tetracycline (e.g., doxycycline) may bind to the tTA and prevent tTA from binding its cognate promoter (e.g., a promoter comprising a tetracycline response element (TRE)) and driving expression of an operably linked nucleic acid. Without being bound by a particular theory, a nucleic acid (e.g., engineered nucleic acid) encoding an inducing agent may not be on the same vector as any of the nucleic acids (e.g., engineered nucleic acids) encoding OCT4, KLF4, and SOX2 to reduce the size of a viral vector and improve viral titer.

In certain embodiments, one or more expression vectors (e.g., AAV comprising an expression vector) is administered to a cell, tissue, or a subject in need thereof. The subject may have an injury or condition, is suspected of having a condition or injury, or is at risk for a condition or injury. Without being bound by a particular theory, expression of the transcription factors OCT4, SOX2, and KLF4 induces cellular reprogramming. In some embodiments, when the nucleic acid (e.g., engineered nucleic acid) encoding OCT4, SOX2, KLF4, or a combination thereof is operably linked to an inducible promoter, administration of an inducing agent (e.g., chemical, a protein, a nucleic acid (e.g., engineered nucleic acid) (e.g., a nucleic acid (e.g., engineered nucleic acid) encoding an inducing agent) under the appropriate conditions (e.g., in the presence or absence of tetracycline). In certain embodiments, an inducing agent (e.g., rtTA) is capable of binding a promoter and driving expression of an operably linked nucleic acid (e.g., engineered nucleic acid) only when the inducing agent is bound to tetracycline. In certain embodiments, an inducing agent (e.g., tTA) cannot bind a promoter and drive expression of an operably linked nucleic acid (e.g., engineered nucleic acid) when the inducing agent is bound to tetracycline. The condition may be an ocular disease, (e.g., a retinal disease, a corneal disease, or any disease affecting the eye), cancer, aging, an age-related disease, injury, or a neurodegenerative disease. In certain embodiments, the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine.

In certain embodiments, the tissue is damaged (e.g., due to an injury, an accident, or an iatrogenic injury) and/or is aged tissue. In certain embodiments, the tissue may be considered healthy but suboptimal for performance or survival in current or future conditions (e.g., in agriculture or adverse conditions including toxic therapies, sun exposure, or travel outside the earth's atmosphere).

In certain embodiments, the method comprises further comprises regulation of a biological process. In some embodiments, the methods described herein comprise regulating any biological process, including, cellular reprogramming, tissue repair, tissue survival, tissue regeneration, tissue growth, tissue function, organ regeneration, organ survival, organ function, or any combination thereof. In some embodiments, the methods comprise inducing cellular reprogramming, reversing aging, improving tissue function, improving organ function, promoting tissue repair, promoting tissue survival, promoting tissue regeneration, promoting tissue growth, promoting angiogenesis, reducing scar formation, reducing the appearance of aging including alopecia, hair thinning, hair greying, sagging skin, and skin wrinkles, promoting organ regeneration, promoting organ survival, altering the taste and quality of agricultural products derived from animals, treating a disease, or any combination thereof, in vivo or in vitro. For example, the method may induce cellular reprogramming, cell survival, organ regeneration, tissue regeneration, or a combination thereof. In certain embodiments, the method comprises inducing and then stopping cellular reprogramming, cell survival, tissue regeneration, organ regeneration, aging, or a combination thereof. In certain embodiments, the method reverses aging of a cell, tissue, organ, or subject. In some embodiments, the method does not induce teratoma formation. In some embodiments, the method does not induce unwanted cell proliferation. In some embodiments, the method does not induce malignant cell growth. In some embodiments, the method does not induce cancer. In some embodiments, the method does not induce tumor growth or tumor formation. In some embodiments, the method does not induce glaucoma.

In some embodiments, a method described herein reverses the epigenetic clock of a cell, a tissue, an organ, a subject, or any combination thereof. In some embodiments, the epigenetic clock is determined using a DNA methylation-based (DNAm) age estimator. In some embodiments, the method alters the expression of one or more genes associated with ageing. In some embodiments, the method reduces expression of one or more genes associated with ageing. In some embodiments, the method alters the expression of one or more genes associated with ageing. In some embodiments, the one or more genes is one or more sensory genes.

In some embodiments, the method reduces expression of one or more genes associated with ageing. In some embodiments, the method reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Ccl9, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnaja1-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galnt18, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg1l2, Hapln4, Hcn3, Hcn4, Hhatl, Hs6st2, Htr3a, Il1rap, Il1rap12, Inka1, Kbtbd12, Kcnj11, Kcnk4, Kdelc2, Klhl33, Lamc3, Lilra5, Lman11, Lrfn2, Lrrc38, Lrrn4cl, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec14l5, Sel1l3, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof. In some embodiments, the method reduces expression of Ace, Kcnk4, Lamc3, Edn1, Syt10, Ngfr, Gprc5c, Cd36, Chrna4, Ednrb, Drd2, or a combination thereof.

In some embodiments, the method increases expression of one or more genes associated with ageing. In some embodiments, the method increases expression of 1700031P21Rik, 1810053B23Rik, 2900045020Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1cl, Ankrd1, Asb15, Atp2c2, AU018091, AW822073, Btnl10, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps8l1, EU599041, Fam90a1a, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2al2a, Ido2, Igfbp1, Kif7, Klhl31, Lrrc31, Mc5r, Mgam, Msh4, Mucl2, Mug1, Mybl2, Myhl5, Nek10, Neurod6, Nr1h5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otogl, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof. In some embodiments, the method increases expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otogl, Olfr943, Olfr1406, Olfr273, Olfr466, Olfr1043, Olfr427, Olfr890, Rbp4, or any combination thereof.

Further aspects of the disclosure relate to methods of reprogramming comprising rejuvenating the epigenetic clock of a cell, tissue, organ, subject, or any combination thereof.

Further aspects of the disclosure relate to methods of reprogramming comprising altering the expression of one or more genes associated with ageing.

Further aspects of the disclosure relate to methods comprising resetting the transcriptional profile of an old cell, an old organ, an old tissue, and/or any combination thereof in vitro.

Further aspects of the disclosure relate to methods comprising resetting the transcriptional profile of an old cell, an old organ, an old tissue, an old subject and/or any combination thereof in vivo.

Further aspects of the disclosure relate to methods of transdifferentiating cells.

Another aspect of the present disclosure provides engineered cells generated by any of the methods described herein. The methods described herein may be useful in the production of any engineered cell, including induced pluripotent stem cells. The engineered cells of the present disclosure may be produced ex vivo and the methods may further comprise generating an engineered tissue or engineered organ. In some embodiments, the methods of the present disclosure comprise administering an engineered cell, engineered tissue, and/or engineered organ of the present disclosure to a subject in need thereof. In some embodiments, the method further comprises treating a disease.

Aspects of the present disclosure also provide compositions comprising any of the nucleic acids (e.g., engineered nucleic acid) capable of inducing OCT4, KLF4, inducing agent, and/or SOX2 expression (e.g., expression vector), any of the engineered proteins described herein, any of the chemical agents activating (e.g., inducing expression of) OCT4, KLF4, an inducing agent, and/or SOX2, any of the antibodies activating (e.g., inducing expression of) OCT4, KLF4, an inducing agent, and/or SOX2, and/or any of the recombinant viruses (e.g., lentivirus, adenovirus, alphavirus, vaccinia virus, retrovirus, herpes virus, or AAV) described herein, alone, or in combination. In some embodiments, the pharmaceutical compositions of the present disclosure further comprise a pharmaceutically acceptable carrier. In some embodiments, the pharmaceutical composition further comprises a second engineered nucleic acid (e.g., engineered nucleic acid) (e.g., expression vector including viral vector) encoding an inducing agent (e.g., rtTA or tTA).

Aspects of the present disclosure also provide compositions comprising any of the nucleic acids (e.g., engineered nucleic acid) acids capable of inducing OCT4, KLF4, and/or SOX2 (e.g., expression vector, including an inducible expression vector), any of the engineered proteins described herein, any of the chemical agents capable of activating (e.g., inducing expression of) OCT4, KLF4, and/or SOX2, any of the antibodies capable of activating (e.g., inducing expression of) OCT4, KLF4, and/or SOX2, and/or any of the recombinant viruses (e.g., lentivirus, adenovirus, alphavirus, vaccinia virus, retrovirus, herpes virus, or AAV) described herein, alone or in combination. In some embodiments, the composition further comprises a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent. In some embodiments, the pharmaceutical compositions of the present disclosure further comprise a pharmaceutically acceptable carrier. In some embodiments, the pharmaceutical composition further comprises a second engineered nucleic acid (e.g., engineered nucleic acid) (e.g., expression vector including viral vector) encoding an inducing agent (e.g., rtTA or tTA).

Aspects of the present disclosure also provide compositions comprising any of the nucleic acids (e.g., engineered nucleic acid) (e.g., expression vector) capable of inducing expression of one or more transcription factors selected from OCT4; SOX2; KLF4; and any combination thereof, any of the engineered proteins described herein, any of the chemical agents activating (e.g., inducing expression of) one or more transcription factors selected from the group consisting of OCT4; SOX2; KLF4; and any combinations thereof, any of the antibodies activating (e.g., inducing expression of) one or more transcription factors selected from the group consisting of OCT4; SOX2; KLF4; and any combinations thereof, and/or any of the recombinant viruses (e.g., lentivirus, adenovirus, alphavirus, vaccinia virus, retrovirus, herpes virus, or AAV) described herein, alone or in combination. In certain embodiments, a composition comprises any of the nucleic acids (e.g., engineered nucleic acid) (e.g., expression vector) capable of inducing expression of two or more transcription factors selected from OCT4; SOX2; KLF4; and any combination thereof, any of the engineered proteins described herein, any of the chemical agents activating (e.g., inducing expression of) two or more transcription selected from the group consisting of OCT4; SOX2; KLF4; and any combinations thereof, any of the antibodies activating (e.g., inducing expression of) two or more transcription factors selected from the group consisting of OCT4; SOX2; KLF4; and any combinations thereof, and/or any of the recombinant viruses (e.g., lentivirus, adenovirus, alphavirus, vaccinia virus, retrovirus, herpes virus, or AAV) described herein, alone or in combination. The two or more transcription factors may comprise OCT4 and SOX2, OCT4 and KLF4, OCT4, KLF4, and SOX2, or SOX2 and KLF4. In certain embodiments, a composition comprises any of the nucleic acids (e.g., engineered nucleic acid) (e.g., expression vector) capable of inducing expression of three or more transcription factors selected from OCT4, SOX2, KLF4, and combinations thereof expression, any of the engineered proteins described herein, any of the chemical agents activating (e.g., inducing expression of) three or more transcription selected from the group consisting of OCT4; SOX2; KLF4; and any combinations thereof, any of the antibodies activating (e.g., inducing expression of) three or more transcription factors selected from the group consisting of OCT4; SOX2; KLF4; and any combinations thereof, and/or any of the recombinant viruses (e.g., lentivirus, adenovirus, alphavirus, vaccinia virus, retrovirus, herpes virus, or AAV) described herein, alone or in combination. In certain embodiments, the three or more transcription factors may comprise OCT4, SOX2, and KLF4. In some embodiments, a pharmaceutical composition further comprises a nucleic acid (e.g., engineered nucleic acid) (e.g., expression vector) encoding an inducing agent (e.g., rtTA or tTA), any of the engineered proteins encoding an inducing agent, any of the chemical agents capable of activating (e.g., inducing expression of) an inducing agent, and/or any of the recombinant viruses (e.g., lentivirus, adenovirus, alphavirus, vaccinia virus, retrovirus, herpes virus, or AAV) encoding an inducing agent. In some embodiments, the pharmaceutical compositions of the present disclosure further comprise a pharmaceutically acceptable carrier.

In yet another aspect, the present disclosure provides kits comprising any of the nucleic acids (e.g., engineered nucleic acid) capable of inducing OCT4, KLF4, inducing agent, and/or SOX2 expression (e.g., expression vector), any of the engineered proteins described herein, any of the chemical agents activating (e.g., inducing expression of) OCT4, KLF4, an inducing agent, and/or SOX2, any of the antibodies activating (e.g., inducing expression of) OCT4, KLF4, an inducing agent, and/or SOX2, and/or any of the recombinant viruses (e.g., lentivirus, adenovirus, alphavirus, vaccinia virus, retrovirus, herpes virus, or AAV) described herein.

In yet another aspect, the present disclosure provides kits comprising any of the nucleic acids (e.g., engineered nucleic acid) acids capable of inducing OCT4, KLF4, and/or SOX2 expression (e.g., expression vector), any of the engineered proteins described herein, any of the chemical agents activating (e.g., inducing expression of) OCT4, KLF4, and/or SOX2, any of the antibodies activating (e.g., inducing expression of) OCT4, KLF4, and/or SOX2, and/or any of the recombinant viruses (e.g., lentivirus, adenovirus, alphavirus, vaccinia virus, retrovirus, herpes virus, or AAV) described herein. In some embodiments, the kit further comprises a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent.

In yet another aspect, the present disclosure provides kits comprising any of the nucleic acids (e.g., engineered nucleic acid) (e.g., expression vector) capable of inducing expression of one or more transcription factors selected from the group consisting of OCT4; SOX2; KLF4; and any combinations thereof, any of the engineered proteins described herein, any of the chemical agents activating (e.g., inducing expression of) one or more transcription factors selected from the group consisting of OCT4; SOX2; KLF4; and any combinations thereof, any of the antibodies activating (e.g., inducing expression of) OCT4; SOX2; KLF4; and any combinations thereof, and/or any of the recombinant viruses (e.g., lentivirus, adenovirus, alphavirus, vaccinia virus, retrovirus, herpes virus, or AAV) described herein. In certain embodiments, a kit further comprises a nucleic acid (e.g., engineered nucleic acid) (e.g., expression vector) encoding an inducing agent (e.g., rtTA or tTA), any of the engineered proteins encoding an inducing agent, any of the chemical agents capable of activating (e.g., inducing expression of) an inducing agent, and/or any of the recombinant viruses (e.g., lentivirus, adenovirus, alphavirus, vaccinia virus, retrovirus, herpes virus, or AAV) encoding an inducing agent.

The details of one or more embodiments of the invention are set forth herein. Other features, objects, and advantages of the invention will be apparent from the Detailed Description, Examples, Figures, and Claims.

References cited in this application are incorporated herein by reference.

Definitions

Definitions of specific terms are described in more detail below. The disclosure is not intended to be limited in any manner by the exemplary listing of substituents described herein.

"AAV" or "adeno-associated virus" is a nonenveloped virus that is capable of carrying and delivering nucleic acids (e.g., engineered nucleic acids) (e.g., nucleic acids (e.g., engineered nucleic acids) encoding OCT4; KLF4; SOX2; or any combination thereof) and belongs to the genus *Dependoparvovirus*. In some instances, an AAV is capable of delivering a nucleic acid encoding an inducing agent. In general, AAV does not integrate into the genome. The tissue-specific targeting capabilities of AAV is often determined by the AAV capsid serotype (see, e.g., Table 1 below for examples of AAV serotypes and their utility in tissue-specific delivery). Non-limiting serotypes of AAV include AAV1, AAV2, AAV3, AAV4, AAV5, AAV6, AAV7, AAV8, AAV9, AAV10, AAV11, and variants thereof. In certain embodiments, the AAV serotype is a variant of AAV9 (e.g., AAV PHP.b).

A "recombinant virus" is a virus (e.g., lentivirus, adenovirus, retrovirus, herpes virus, alphavirus, vaccinia virus or adeno-associated virus (AAV))) that has been isolated from its natural environment (e.g., from a host cell, tissue, or a subject) or is artificially produced.

The term "AAV vector" as used herein is a nucleic acid (e.g., engineered nucleic acid) that comprises AAV inverted terminal repeats (ITRs) flanking an expression cassette (e.g., an expression cassette comprising a nucleic acid (e.g., engineered nucleic acid) encoding OCT4, KLF4, and SOX2, each alone or in combination, or an expression cassette encoding rtTA or tTA). An AAV vector may further comprise a promoter sequence.

The terms "administer," "administering," or "administration," as used herein refers to introduction of any of the compositions described herein, any of the nucleic acids (e.g., engineered nucleic acid) capable of inducing OCT4, KLF4, and/or SOX2 expression (e.g., expression vector), any of the nucleic acids (e.g., engineered nucleic acid) (e.g., expression vector) capable of inducing expression of one or more transcription factors selected from the group consisting of OCT4; KLF4; SOX2; and any combinations thereof, any of the engineered proteins described herein, any of the chemical agents activating (e.g., inducing expression of) OCT4, KLF4, and/or SOX2, any of the chemical agents activating (e.g., inducing expression of) one or more transcription factors selected from OCT4; KLF4; SOX2; and any combinations thereof, any of the antibodies activating (e.g., inducing expression of) OCT4, KLF4, and/or SOX2, any of the antibodies activating (e.g., inducing expression of) one or more transcription factors selected from OCT4; KLF4; SOX2; and any combinations thereof, and/or any of the recombinant viruses (e.g., lentivirus, adenovirus, alphavirus, vaccinia virus, retrovirus, herpes virus, or AAV) described herein, alone, or in combination to any cell, tissue, organ, and/or subject. In some embodiments, a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent is also administered to the cell, tissue, organ and/or subject. Any of the compositions described herein, comprising any of the nucleic acids (e.g., engineered nucleic acid) capable of inducing OCT4, KLF4, and/or SOX2 expression (e.g., expression vector), comprising any of the nucleic acids (e.g., engineered nucleic acid) (e.g., expression vector) capable of inducing expression of one or more transcription factors selected from OCT4; KLF4; SOX2; and any combinations thereof, any of the engineered proteins described herein, any of the chemical agents activating (e.g., inducing expression of) OCT4, KLF4, and/or SOX2, any of the engineered proteins encoding OCT4, SOX2, KLF4, or any combinations thereof, any of the chemical agents activating (e.g., inducing expression of) OCT4; KLF4; SOX2; or any combination thereof, any of the antibodies activating (e.g., inducing expression of) OCT4, KLF4, and/or SOX2, any of the antibodies activating (e.g., inducing expression of) OCT4; KLF4; SOX2; or any combination thereof, and/or any of the recombinant viruses (e.g., lentivirus, adenovirus, alphavirus, vaccinia virus, retrovirus, herpes virus, or AAV) described herein, alone, or in combination may be administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art (see, for example, Remington's Pharmaceutical Sciences (1990), incorporated herein by reference). In some embodiments, a composition comprising a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent is also administered to the cell, tissue, organ and/or subject is administered using any suitable method.

The term "epigenome" or "epigenetics" refers to the modification and structural changes within a cell that control the expression of nucleic acids (e.g., engineered nucleic acids) or genomic information in a cell. Changes to the epigenome occur during, and drive the processes of embryonic development, disease progression, and aging.

The term "epigenetic clock" may refer to an age estimator or an innate biological process. In some embodiments, rejuvenating or reversing the epigenetic clock refers to reducing the estimated age of a cell, tissue, organ, or a subject. The epigenetic clock may be partially or fully reversed or rejuvenated by any of the methods described herein. In some embodiments, an age estimator is an epigenetic age estimator. For example, an epigenetic age estimator may be sets of CpG dinucleotides that when used in combination with a mathematical algorithm may be used to estimate age of a DNA source, including cells, organs, or tissues. In some embodiments, an age estimator is a DNA methylation-based (DNAm) age estimator. In some embodiments, a DNAm age estimator is calculated as an age correlation using Pearson correlation coefficient r, between DNA methylation-based (DNam) age (also known as estimated age) and chronological age. In some embodiments, the DNA methylation-based (DNAm) age estimator is a single-tissue DNA methylation-based age estimator. In some embodiments, the DNA methylation-based age estimator is a multi-tissue DNA methylation-based age estimator. In some embodiments, the DNAm age estimator is DNAm PhenoAge. See, e.g., Horvath and Raj, Nat Rev Genet. 2018 June; 19(6):371-384; Levine et al., Aging (Albany NY). 2018 Apr. 18; 10(4):573-591; and the Examples below.

"Epigenetic information" as used herein includes covalent modifications to DNA, such as 5-methylcytosine (5mC), hydroxymethylcytosine (5hmeC), 5-formylcytosine (fC), and 5-carboxylcytosine (caC), and to certain proteins, such as lysine acetylation, lysine and arginine methylation, serine and threonine phosphorylation, and lysine ubiquitination and sumoylation of histone proteins, and the 3D architecture of cells, including TADs (topologically associated domains) and compartments. Epigenetic information is sometimes referred to as the "analog" information of the cell.

"Restoring the expression" of at least one gene in Table 5 to youthful levels is meant to include increasing the expression of a downregulated gene or decreasing the expression of an upregulated gene that changes during aging.

As used herein, the term "cell" is meant not only to include an individual cell but refers also to the particular tissue or organ from which it originates.

The term "cellular senescence" refers to a cell that has exited the cell cycle, displays epigenetic markers consistent with senescence, or expressing senescence cell markers (e.g. senescence-associated beta-galactosidase, or inflammatory cytokines). Cellular senescence may be partial or complete.

The term "gene expression" refers to the degree to which certain genes or all genes in a cell or tissue are transcribed into RNA. In some instances, the RNA is translated by the cell into a protein. The epigenome dictates gene expression patterns.

The term "cellular reprogramming" refers to the process of altering the epigenome of a cell using reprogramming factors (e.g. reversing or preventing epigenetic changes in cells that are causes of dysfunction, deterioration, cell death, senescence or aging). Cellular reprogramming may be complete reprogramming, such that a differentiated cell (e.g., somatic cell) is reprogrammed to a pluripotent stem cell. Cellular reprogramming may be incomplete, such that a differentiated cell (e.g., somatic cell) retains its cellular identity (e.g., lineage-specific stem cell). Cellular reprogramming may be incomplete, e.g., a stem cell is not created, such that a cell is rejuvenated, or takes on more youthful attributes (e.g. increased survival, reduced inflammation, or ability to divide). Cellular reprogramming may provide additional cellular functions, or prevent cellular aging (e.g., transdifferentiation, or transition into cellular senescence). Cellular reprogramming may induce temporary or permanent gene expression changes. In some embodiments, incomplete cellular reprogramming is shown by the lack of Nanog expression. In some embodiments, cellular reprogramming prevents senescence from occurring.

The term "rejuvenating a cell" as used herein is meant to include preventing or reversing the cellular causes of aging without inducing a pluripotent state. A rejuvenated cell as used herein includes for example a retinal ganglion cell that expresses RBPMS and or Brn3a.

A "pluripotent state" as used herein is meant to include a state in which the cell expresses at least one stem cell marker such as but not limited to Esrrb, Nanog, Lin28, TRA-1-60/TRA-1-81/TRA-2-54, SSEA1, or SSEA4. Methods of measuring the expression of stem cell markers on the cell are known in the art and include the methods described herein.

The term "transdifferentiation" refers to a process in which one cell type is changed into another cell type without entering a pluripotent state. Transdifferentiation may also be referred to as lineage reprogramming or lineage conversion. See, e.g., Cieslar-Pobuda et al., Biochim Biophys Acta Mol Cell Res. 2017 July; 1864(7):1359-1369, which is herein incorporated by reference in its entirety.

The terms "condition," "disease," and "disorder" are used interchangeably. Non-limiting examples of conditions, diseases, and disorders include acute injuries, neurodegenerative diseases, chronic diseases, proliferative diseases, cardiovascular diseases, genetic diseases, inflammatory diseases, autoimmunue diseases, neurological diseases, hematological diseases, painful conditions, psychiatric disorders, metabolic disorders, chronic diseases, cancers, aging, age-related diseases, and diseases affecting any tissue in a subject. For example, age-related conditions include, heart failure, stroke, heart disease, atherosclerosis, neurodegenerative diseases (e.g., Parkinson's disease and Alzheimer's disease), cognitive decline, memory loss, diabetes, osteoporosis, arthritis, muscle loss, hearing loss (partial or total), eye-related conditions (e.g., poor eye sight or retinal disease), glaucoma, a progeroid syndrome (e.g., Hutchinson-Gilford progeria syndrome), and cancer. In certain embodiments, the disease is a retinal disease (e.g., macular degeneration). In some embodiments, an age-related condition is senescence. As a non-limiting example, senescence of glial cells may be a cause of Alzheimer's disease. See e.g., Bussian, et al., Nature. 2018 Sep. 19. In some instances, the condition is nerve damage. In some instances, the condition is damage in the central nervous system (CNS). In some instances, the nerve damage is peripheral nerve damage. In some instances, the nerve damage is neurapraxia, axonotmesis, or neurotmesis.

In some instances, a condition increases the DNA methylation-based age of a cell, a tissue, an organ, and/or a subject relative to a control. In some instances, a condition increases the DNA methylation-based age of a cell, a tissue, an organ, and/or a subject by at least 1%, at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1,000% relative to a control. In some instances, the control is a cell, a tissue, an organ, and/or a subject that does not have the condition. In some instances, the control is the same cell, tissue, organ, and/or subject prior to having the condition. Without being bound by a particular theory, any of the methods described herein may be useful in decreasing the DNA methylation-based age of a diseased cell, a diseased tissue, a diseased organ, and/or a subject who has, is at risk for, or is suspected of having a disease. In some instances, the disease increases the DNA-methylation-based age of the cell, tissue, organ, and/or subject. In some instances, the disease is an injury.

In some instances, the condition is ageing. In some instances, aging is driven by epigenetic noise. See, e.g., Oberdoerffer and Sinclair. Nat Rev Mol Cell Biol 8, 692-702, doi:10.1038/nrm2238 (2007); Oberdoerffer et al. Cell 135, 907-918, doi:10.1016/j.cell.2008.10.025 (2008). Without being bound by a particular theory, mammalian cells may retain a faithful copy of epigenetic information from earlier in life, analogous to Shannon's "observer" system in Information Theory, essentially a back-up copy of the original signal to allow for its reconstitution at the receiving end if information is lost or noise is introduced during transmission. See, e.g., Shannon, The Bell System Technical Journal 27, 379-423 (1948) for a description of the observer system.

As used herein, an "ocular disease" or "eye disease" is a disease or condition of the eye. Non-limiting examples of conditions that affect the eye include Ectropion, Lagophthalmos, Blepharochalasis, Ptosis, Stye, Xanthelasma, Dermatitis, Demodex, leishmaniasis, loiasis, onchocerciasis, phthiriasis, (herpes simplex), leprosy, molluscum contagiosum, tuberculosis, yaws, zoster, impetigo, Dacryoadenitis, Epiphora, exophthalmos, Conjunctivitis, Scleritis, Keratitis, Corneal ulcer/Corneal abrasion, Snow blindness/Arc eye, Thygeson's superficial punctate keratopathy, Corneal neovascularization, Fuchs' dystrophy, Keratoconus, Keratoconjunctivitis sicca, Iritis, iris, Uveitis, Sympathetic ophthalmia, Cataract, lens, Chorioretinal inflammation, Focal chorioretinal inflammation, chorioretinitis, choroiditis, retinitis, retinochoroiditis, Disseminated chorioretinal inflammation, exudative retinopathy, Posterior cyclitis, Pars planitis, chorioretinal inflammations, Harada's disease, Chorioretinal inflammation, choroid, Chorioretinal scars, Macula scars, posterior pole (postinflammatory) (post-traumatic), Solar retinopathy, Choroidal degeneration, Atrophy, Sclerosis, angioid streaks, choroidal dystrophy, Choroideremia, choroidal, areolar, (peripapillary), Gyrate atrophy, choroid, ornithinaemia, Choroidal haemorrhage, Choroidal detachment, Chorioretinal, Chorioretinal inflammation, infectious and parasitic diseases, Chorioretinitis, syphilitic, toxoplasma, tuberculosis, chorioretinal, Retinal detachment, retina, choroid, distorted vision, Retinoschisis, Hypertensive retinopathy, Diabetic retinopathy, Retinopathy, Retinopathy of prematurity, Age-related macular degeneration, macula, Macular degeneration, Bull's Eye Maculopathy, Epiretinal membrane, Peripheral retinal degeneration, Hereditary retinal dystrophy, Retinitis pigmentosa, Retinal haemorrhage, retinal layers, Central serous retinopathy, Retinal detachment, retinal disorders, Macular edema, macula, Retinal disorder, Diabetic retinopathy, Glaucoma, optic neuropathy, ocular hypertension, open-angle glaucoma, angle-closure glaucoma, Normal Tension glaucoma, open-angle glaucoma, angle-closure glaucoma, Floaters, Leber's hereditary optic neuropathy, Optic disc drusen, Strabismus, Ophthalmoparesis, eye muscles, Progressive external ophthalmoplegia, Esotropia, Exotropia, Disorders of refraction, accommodation, Hypermetropia, Myopia, Astigmatism, Anisometropia, Presbyopia, ophthalmoplegia, Amblyopia, Leber's congenital amaurosis, Scotoma, Anopsia, Color blindness, Achromatopsia/Maskun, cone cells, Nyctalopia, Blindness, River blindness, Micropthalmia/coloboma, optic nerve, brain, spinal cord, Red eye, Argyll Robertson pupil, pupils, Keratomycosis, Xerophthalmia, and Aniridia. In some embodiments, the ocular disease is acute or chronic eye injury.

In some embodiments, the ocular disease is a scratched cornea.

In some embodiments, the ocular disease is glaucoma.

In some embodiments, an ocular disease is a corneal disease (e.g., a disease affecting the cornea or corneal cells). In some embodiments, an ocular disease is *Acanthamoeba keratitis*, ectropion, lagoph amblyopia, anisocoria, astigmatism, Bell's Palsy, blepharitis, blurry vision, burning eyes, cataracts, macular degeneration, age-related macular degeneration, diabetic eye disease, glaucoma, dry eye, poor vision (e.g., low vision), astigmatism, blepharitis, cataract, chalazion, conjunctivitis, diabetic retinopathy, dry eye, glaucoma, keratitis, keratonconus, macular degeneration, ocular hypertension, pinquecula, pterygium, retinitis pigmentosa, or ocular cancer (e.g., retinoblastoma, melanoma of the eye, lymphoma of the eye, medulloepithelioma, squamous cell cancer of the conjunctiva). Examples of corneal diseases include, but are not limited to, corneal neovascularization (NV), corneal dystrophy, corneal inflammation, corneal abrasion, and corneal fibrosis. In some embodiments, the ocular disease is Keritaconus. In some embodiments, an ocular disease is macular degeneration. Additional non-limiting examples of eye diseases may be found in the International Statistical Classification of Diseases and Related Health Problems (e.g., VII Diseases of the eye and adnexa).

An ocular disease may affect any part of the eye and/or adnexa. In some embodiments, the ocular disease is a disorder of the eyelid, lacrimal system and/or orbit. In some embodiments, the ocular disease is a disorders of conjunctiva. In some embodiments, the ocular disease is a disorder of sclera, cornea, iris, and/or ciliary body. In some embodiments, the ocular disease is a disorder of the lens. In some embodiments, the ocular disease is a disorder of choroid and/or retina. In some embodiments, the ocular disease is glaucoma. In some embodiments, the ocular disease is a disorder of vitreous body and/or globe. In some embodiments, the ocular disease is a disorder of optic nerve and/or visual pathways. In some embodiments, the ocular disease is a disorder of ocular muscles, binocular movement, accommodation, and/or refraction. In some embodiments, the ocular disease is a visual disturbance and/or blindness. In some embodiments, the ocular disease is associated with aging, for example, vision loss associated with aging, decline in visual acuity associated with aging, and/or decline in retinal function.

Any suitable method may be used to measure ocular function. Non-limiting examples include visual acuity tests, pattern electroretinograms, and pathology.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, a progeroid syndrome (e.g., Hutchinson-Gilford progeria syndrome), and Zellweger syndrome.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstram's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma); pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, postsurgical inflammation. In some embodiments, the inflammatory disease is inflammaging (e.g., inflammation that is a side effect of aging).

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases and injuries that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, vascular dementias, stroke, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illnesses include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "musculoskeletal disease" or "MSD" refers to an injury and/or pain in a subject's joints, ligaments, muscles, nerves, tendons, and structures that support limbs, neck, and back. In certain embodiments, an MSD is a degenerative disease. In certain embodiments, an MSD includes an inflammatory condition. Body parts of a subject that may be associated with MSDs include upper and lower back, neck, shoulders, and extremities (arms, legs, feet, and hands). In certain embodiments, an MSD is a bone disease, such as achondroplasia, acromegaly, bone callus, bone demineralization, bone fracture, bone marrow disease, bone marrow neoplasm, dyskeratosis congenita, leukemia (e.g., hairy cell leukemia, lymphocytic leukemia, myeloid leukemia, Philadelphia chromosome-positive leukemia, plasma cell leukemia, stem cell leukemia), systemic mastocytosis, myelodysplastic syndromes, paroxysmal nocturnal hemoglobinuria, myeloid sarcoma, myeloproliferative disorders, multiple myeloma, polycythemia vera, pearson marrow-pancreas syndrome, bone neoplasm, bone marrow neoplasm, Ewing sarcoma, osteochondroma, osteoclastoma, osteosarcoma, brachydactyly, Camurati-Engelmann syndrome, Craniosynostosis, Crouzon craniofacial dysostosis, dwarfism, achondroplasia, bloom syndrome, Cockayne syndrome, Ellis-van Creveld syndrome, Seckel syndrome, spondyloepiphyseal dysplasia, spondyloepiphyseal dysplasia congenita, Werner syndrome, hyperostosis, osteophyte, Klippel-Trenaunay-Weber syndrome, Marfan syndrome, McCune-Albright syndrome, osteitis, osteoarthritis, osteochondritis, osteochondrodysplasia, Kashin-Beck disease, Leri-Weill dyschondrosteosis, osteochondrosis, osteodystrophy, osteogenesis imperfecta, osteolysis, Gorham-Stout syndrome, osteomalacia, osteomyelitis, osteonecrosis, osteopenia, osteopetrosis, osteoporosis, osteosclerosis, otospondylomegaepiphyseal dysplasia, pachydermoperiostosis, Paget disease of bone, Polydactyly, Meckel syndrome, rickets, Rothmund-Thomson syndrome, Sotos syndrome, spondyloepiphyseal dysplasia, spondyloepiphyseal dysplasia congenita, syndactyly, Apert syndrome, syndactyly type II, or Werner syndrome. In certain embodiments, an MSD is a cartilage disease, such as cartilage neoplasm, osteochondritis, osteochondrodysplasia, Kashin-Beck disease, or Leri-Weill dyschondrosteosis. In certain embodiments, an MSD is hernia, such as intervertebral disk hernia. In certain embodiments, an MSD is a joint disease, such as arthralgia, arthritis (e.g., gout (e.g., Kelley-Seegmiller syndrome, Lesch-Nyhan syndrome), Lyme disease, osteoarthritis, psoriatic arthritis, reactive arthritis, rheumatic fever, rheumatoid arthritis, Felty syndrome, synovitis, Blau syndrome, nail-patella syndrome, spondyloarthropathy, reactive arthritis, Stickler syndrome, synovial membrane disease, synovitis, or Blau syndrome. In certain embodiments, an MSD is Langer-Giedion syndrome. In certain embodiments, an MSD is a muscle disease, such as Barth syndrome, mitochondrial encephalomyopathy, MELAS syndrome, MERRF syndrome, MNGIE syndrome, mitochondrial myopathy, Kearns-Sayre syndrome, myalgia, fibromyalgia, polymyalgia rheumatica, myoma, myositis, dermatomyositis, neuromuscular disease, Kearns-Sayre syndrome, muscular dystrophy, myasthenia, congenital myasthenic syndrome, Lambert-Eaton myasthenic syndrome, myasthenia gravis, myotonia, myotonia congenita, spinal muscular atrophy, tetany, ophthalmoplegia, or rhabdomyolysis. In certain embodiments, an MSD is Proteus syndrome. In certain embodiments, an MSD is a rheumatic diseases, such as arthritis (e.g., gout (e.g., Kelley-Seegmiller syndrome, Lesch-Nyhan lyme disease)), osteoarthritis, psoriatic arthritis, reactive arthritis, rheumatic fever, rheumatoid arthritis, Felty syndrome, synovitis, Blau syndrome, gout (e.g., Kelley-Seegmiller syndrome, Lesch-Nyhan syndrome), polymyalgia rheumatica, rheumatic fever, rheumatic heart disease, or Sjogren syndrome. In certain embodiments, an MSD is Schwartz-Jampel syndrome. In certain embodiments, an MSD is a skeleton disease, such as Leri-Weill dyschondrosteosis, skeleton malformations, Melnick-Needles syndrome, pachydermoperiostosis, Rieger syndrome, spinal column disease, intervertebral disk hernia, scoliosis, spina bifida, spondylitis, ankylosing spondylitis, spondyloarthropathy, reactive arthritis, spondyloepiphyseal dysplasia, spondyloepiphyseal dysplasia congenita, or spondylosis. In some embodiments, the disease is a musculoskeletal disease.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

In some embodiments, a disease is characterized by cellular dysfunction. For example, a disease may be a mitochondrial disease. Non-limiting mitochondrial diseases include Freidrich's ataxia, alphers disease, barth syndrome, beta-oxidation defects, carnitine deficiency, CPT I deficiency, and mitochondrial DNA depletion. Cellular dysfunction may include mitochondria dysfunction, RNA replication dysfunction, DNA replication dysfunction, translation dysfunction, and/or protein folding dysfunction.

In some embodiments, the disease or condition by a wood, bleeding out, injuries (e.g., broken bones, gunshot wound, cut, scarring during surgery (e.g., cesarean).

In some embodiments, the disease is an infectious disease (e.g., a disease caused by a pathogen and/or virus). Non-limiting examples of infectious diseases include tuberculosis, HIV/AIDS, rabies, plague, cholera, dengue fever, measles, malaria, meningitis, whooping cough, Lyme disease, influenza, hepatitis C, typhoid fever, and poliomyelitis.

"Cellular causes of aging" as used herein include loss or modification of epigenetic information.

The terms "c-Myc" or "Myc" refer to a nuclear phosphoprotein that has been implicated in cell cycle progression. c-Myc is capable of forming a heterodimer with the transcription factor MAX and the heterodimer is capable of binding to an E box consequence sequence on nucleic acids (e.g., engineered nucleic acids) to regulate transcription of target genes. In certain embodiments, a nucleotide sequence encoding c-Myc comprises a sequence that is at least 70% (e.g., at least 75%, 80%, 85%, 90%, 95%, 98%, 99%, or 100%) identical to a sequence as described in the NCBI RefSeq database under accession number NM_001354870.1 or NM_002467.5. In certain embodiments, an amino acid sequence encoding c-Myc comprises a sequence that is at least 70% (e.g., at least 75%, 80%, 85%, 90%, 95%, 98%, 99%, or 100%) identical to NP_002458.2 or NP_001341799.1. In certain embodiments, the methods comprise inducing expression of OCT4; KLF4; SOX2; or any combination thereof in the absence of inducing c-Myc expression or in the absence of activating c-Myc. Absence of inducing c-Myc expression may refer to absence of substantial induction of c-Myc expression over endogenous levels of c-Myc expression in a cell, tissue, subject, or any combination thereof. Absence of substantial induction of c-Myc expression as compared to endogenous levels of c-Myc expression in a cell, tissue, subject, or any combination thereof, may refer to increasing c-Myc expression by less than 70%, less than 60%, less than 50%, less than 40%, less than 30%, less than 20%, less than 10%, or any values in between as compared to endogenous levels of c-Myc expression in the cell, tissue, subject, or any combination thereof. Absence of activating c-Myc expression may refer to absence of substantial activation of c-Myc (e.g., activity) over endogenous c-Myc activity in a cell, tissue, subject, or any combination thereof. Absence of substantial induction of c-Myc activity as compared to endogenous c-Myc activity in a cell, tissue, subject, or any combination thereof, may refer to increasing c-Myc activity by less than 70%, less than 60%, less than 50%, less than 40%, less than 30%, less than 20%, less than 10%, or any values in between as compared to endogenous c-Myc activity in the cell, tissue, subject, or any combination thereof.

The terms "effective amount" and "therapeutically effective amount," as used herein, refer to the amount or concentration of an inventive compound, that, when administered to a subject, is effective to at least partially treat a condition from which the subject is suffering.

As used herein, a protein that is "functional" or "active" is one that retains its biological activity (e.g., capable of acting as a transcription factor or as an inducing agent). Conversely, a protein that is not functional or is inactive is one that is not capable of performing one or more of its wild-type functions.

The term "gene" refers to a nucleic acid (e.g., engineered nucleic acid) fragment that expresses a protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Homolog" or "homologous" refers to sequences (e.g., nucleic acid (e.g., engineered nucleic acid) or amino acid sequences) that share a certain percent identity (e.g., at least 5%, at least 10%, at least 15%, at least 20%, at least 25%, at least 30%, at least 35%, at least 40%, at least 45%, at least 50%, at least 55%, at least 60%, at least 65%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% percent identity). Homologous sequences include but are not limited to paralogous or orthologous sequences. Paralogous sequences arise from duplication of a gene within a genome of a species, while orthologous sequences diverge after a speciation event. A functional homolog retains one or more biological activities of a wild-type protein. In certain embodiments, a functional homolog of OCT4, KLF4, or SOX2 retains at least 10%, at least 20%, at least 30%, at least 40%, at least 50%, at least 60%, at least 70%, at least 80%, at least 90%, or at least 100% of the biological activity (e.g., transcription factor activity) of a wild-type counterpart.

"KLF4" may also be referred to as Kruppel-like factor 4, EZF, or GKLF and is a zinc-finger transcription factor. KLF4 has been implicated in regulation of differentiation and proliferation and is capable of interacting with co-activators, including members of the p300-CBP coactivator family. A KLF4 transcription factor, homolog (e.g., functional homolog), or variant thereof, as used herein, may be derived from any species, including humans. In certain embodiments, the nucleic acid (e.g., engineered nucleic acid) encoding human KLF4 comprises a sequence that is at least 70% (e.g., at least 75%, 80%, 85%, 90%, 95%, 98%, 99%, or 100%) identical to a nucleic acid (e.g., engineered nucleic acid) described in the NCBI RefSeq database under accession number NM_004235.5 or NM_001314052.1. Non-limiting examples of KLF4 variants include Krueppel-like factor 4 transcript variant 1 and Krueppel-like factor 4 transcript variant 2. In certain embodiments, KLF4 comprises a nucleic acid (e.g., engineered nucleic acid) sequence that is at least 70% (e.g., at least 75%, 80%, 85%, 90%, 95%, 98%, 99%, or 100%) identical to SEQ ID NO: 5 or SEQ ID NO: 44. SEQ ID NO: 5 is a non-limiting example of a nucleotide sequence encoding KLF4 from *Mus musculus*. SEQ ID NO: 44 is a non-limiting example of a nucleotide sequence encoding human KLF4. In certain embodiments, KLF4 comprises an amino acid sequence that is at least 70% (e.g., at least 75%, 80%, 85%, 90%, 95%, 98%, 99%, or 100%) identical to NP_001300981.1 or NP_004226.3. In certain embodiments, KLF4 comprises an amino acid sequence that is at least 70% (e.g., at least 75%, 80%, 85%, 90%, 95%, 98%, 99%, or 100%) identical to SEQ ID NO: 6. In certain embodiments, KLF4 comprises an amino acid sequence that is at least 70% (e.g., at least 75%, 80%, 85%, 90%, 95%, 98%, 99%, or 100%) identical to SEQ ID NO: 45. SEQ ID NO: 6 is a non-limiting example of an amino acid sequence encoding KLF4 from *Mus musculus*. SEQ ID NO: 45 is a non-limiting example of an amino acid sequence encoding human KLF4.

"Inverted terminal repeats" or "ITRs" are nucleic acid (e.g., engineered nucleic acid) sequences that are reverse complements of one another. In general, in an AAV vector, ITRs are found on either side of a cassette (e.g., an expression cassette comprising a nucleic acid (e.g., engineered nucleic acid) encoding OCT4; KLF4; SOX2; or any combination thereof). In some instances, the cassette encodes an inducing agent. AAV ITRs include ITRs from AAV1, AAV2, AAV3, AAV4, AAV5, AAV6, AAV7, AAV8, AAV9, AAV10, AAV11, and AAV variants thereof.

The terms "nucleic acid," "polynucleotide", "nucleotide sequence", "nucleic acid (e.g., engineered nucleic acid) molecule", "nucleic acid (e.g., engineered nucleic acid) sequence", and "oligonucleotide" refer to a series of nucleotide bases (also called "nucleotides") in DNA and RNA, and mean any chain of two or more nucleotides. The terms "nucleic acid" or "nucleic acid (e.g., engineered nucleic acid) sequence", "nucleic acid (e.g., engineered nucleic acid) molecule", "nucleic acid (e.g., engineered nucleic acid) fragment" or "polynucleotide" may be used interchangeably with "gene", "mRNA encoded by a gene" and "cDNA".

The nucleic acids (e.g., engineered nucleic acids) can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids (e.g., engineered nucleic acids)" (PNAs) formed by conjugating bases to an amino acid backbone. This also includes nucleic acids (e.g., engineered nucleic acids) containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

The nucleic acids (e.g., engineered nucleic acids) described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The nucleic acids (e.g., engineered nucleic acids) may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids (e.g., engineered nucleic acids) may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly.

Exemplary labels include radioisotopes, fluorescent molecules, epitope tags, isotopes (e.g., radioactive isotopes), biotin, and the like.

A "recombinant nucleic acid (e.g., engineered nucleic acid) molecule" or "engineered nucleic acid" is a nucleic acid (e.g., engineered nucleic acid) molecule that has undergone a molecular biological manipulation, i.e., non-naturally occurring nucleic acid (e.g., engineered nucleic acid) molecule or genetically engineered nucleic acid (e.g., engineered nucleic acid) molecule. Furthermore, the terms "recombinant DNA molecule" or "engineered nucleic acid" refer to a nucleic acid (e.g., engineered nucleic acid) sequence which is not naturally occurring, or can be made by the artificial combination of two otherwise separated segments of nucleic acid (e.g., engineered nucleic acid) sequence, i.e., by ligating together pieces of DNA that are not normally continuous. By "recombinantly produced" is meant artificial combination often accomplished by either chemical synthesis means, or by the artificial manipulation of isolated segments of nucleic acids (e.g., engineered nucleic acids), e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al., *Current Protocols in Molecular Biology*, Current Protocols (1989), and *DNA Cloning: A Practical Approach*, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid (e.g., engineered nucleic acid) segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design.

"OCT4" may also be referred to as Octamer-binding transcription factor 4, OCT3, OCT3/4, POU5F1, or POU class 5 homeobox 1 and is a transcription factor that has been implicated in embryonic development and determination of cell fate. Similar to other OCT transcription factors, OCT4 is characterized by a bipartite DNA binding domain called a POU domain. An OCT4 transcription factor, homolog, or variant thereof, as used herein, may be derived from any species, including humans. In certain embodiments, the nucleic acid (e.g., engineered nucleic acid) encoding human OCT4 is at least 70% (e.g., at least 75%, 80%, 85%, 90%, 95%, 98%, 99%, or 100%) identical to a nucleic acid (e.g., engineered nucleic acid) described in the NCBI RefSeq under accession number NM_002701, NM_203289, NM_001173531, NM_001285986, or NM_001285987. In certain embodiments, the nucleic acid (e.g., engineered nucleic acid) encoding an OCT4 comprises a sequence that is at least 70% (e.g., at least 75%, 80%, 85%, 90%, 95%, 98%, 99%, or 100%) identical to a nucleic acid (e.g., engineered nucleic acid) sequence provided as SEQ ID NO: 1. SEQ ID NO: 1 is a non-limiting example of a nucleotide sequence encoding OCT4 from *Mus musculus*. In certain embodiments, the nucleic acid (e.g., engineered nucleic acid) encoding a human OCT4 comprises a sequence that is at least 70% (e.g., at least 75%, 80%, 85%, 90%, 95%, 98%, 99%, or 100%) identical to a nucleic acid (e.g., engineered nucleic acid) sequence provided as SEQ ID NO: 40. SEQ ID NO: 40 is a non-limiting example of a nucleotide sequence encoding human OCT4. Non-limiting examples of OCT4 variants encompassed herein include POU5F1, transcript variant 1, POU5F1, transcript variant 2, POU5F1, transcript variant 3, POU5F1, transcript variant 4, and POU5F1 transcript variant 5. In certain embodiments, the amino acid sequence encoding human OCT4 is at least 70% (e.g., at least 75%, 80%, 85%, 90%, 95%, 98%, 99%, or 100%) identical to a nucleic acid (e.g., engineered nucleic acid) described in the NCBI RefSeq under accession number NP_001167002.1, NP_001272915.1, NP_001272916.1, NP_002692.2, or NP_976034.4. In certain embodiments, an OCT4 comprises an amino acid sequence that is at least 70% (e.g., at least 75%, 80%, 85%, 90%, 95%, 98%, 99%, or 100%) identical to SEQ ID NO: 2. SEQ ID NO: 2 is a non-limiting example of an amino acid sequence encoding OCT4 from *Mus musculus*. In certain embodiments, an OCT4 comprises an amino acid sequence that is at least 70% (e.g., at least 75%, 80%, 85%, 90%, 95%, 98%, 99%, or 100%) identical to SEQ ID NO: 41. SEQ ID NO: 41 is a non-limiting example of an amino acid sequence encoding human OCT4. Other OCT4 transcription factors (e.g., from other species) are known and nucleic acids (e.g., engineered nucleic acids) encoding OCT4 transcription factors can be found in publically available databases, including GenBank.

The term "promoter" refers to a control region of a nucleic acid (e.g., engineered nucleic acid) sequence at which initiation and rate of transcription of the remainder of a nucleic acid (e.g., engineered nucleic acid) sequence are controlled. A promoter may also contain sub-regions at which regulatory proteins and molecules may bind, such as RNA polymerase and other transcription factors. Promoters may be constitutive, inducible, activatable, repressible, tissue-specific, or any combination thereof. A promoter drives expression or drives transcription of the nucleic acid (e.g., engineered nucleic acid) sequence that it regulates. Herein, a promoter is considered to be "operably linked" when it is in a correct functional location and orientation in relation to a nucleic acid (e.g., engineered nucleic acid) sequence it regulates to control ("drive") transcriptional initiation of that sequence, expression of that sequence, or a combination thereof.

A promoter may promote ubiquitous expression or tissue-specific expression of an operably linked nucleic acid (e.g., engineered nucleic acid) sequence from any species, including humans. In some embodiments, the promoter is a eukaryotic promoter. Non-limiting examples of eukaryotic promoters include TDH3, PGK1, PKC1, TDH2, PYK1, TPI1, AT1, CMV, EF1 alpha, SV40, PGK1 (human or mouse), Ubc, human beta actin, CAG, TRE, UAS, Ac5, Polyhedrin, CaMKIIa, GAL1, GAL10, TEF1, GDS, ADH1, CaMV35S, Ubi, H1, and U6, as would be known to one of ordinary skill in the art (see, e.g., Addgene website: blog.addgene.org/plasmids-101-the-promoter-region).

Non-limiting examples of ubiquitous promoters include tetracycline-responsive promoters (under the relevant conditions), CMV (e.g., SEQ ID NO: 48), EF1 alpha, a SV40 promoter, PGK1, Ubc, CAG, human beta actin gene promoter, a RSV promoter (e.g., SEQ ID NO: 47), an EFS promoter (e.g., SEQ ID NO: 49), and a promoter comprising an upstream activating sequence (UAS). In certain embodiments, the promoter is a mammalian promoter.

Non-limiting examples of tissue-specific promoters include brain-specific, liver-specific, muscle-specific, nerve cell-specific, lung-specific, heart-specific, bone-specific, intestine-specific, skin-specific promoters, brain-specific promoters, and eye-specific promoters. As an example, a muscle-specific promoter is a desmin promoter (e.g., a sequence that is at least 70% (e.g., at least 75%, 80%, 85%, 90%, 95%, 98%, 99%, or 100%) identical to SEQ ID NO: 29). Non-limiting examples of eye-specific promoters include human GRK1 (rhodopsin kinase) promoter (e.g., SEQ ID NO: 50), human CRX (cone rod homeobox transcription factor) promoter (e.g., SEQ ID NO: 51), and human NRL promoter (neural retina leucine zipper transcription factor enhancer upstream of the human TK terminal promoter).

In some embodiments, a promoter is specific for senescent cells. For example, a promoter may specifically induce expression of an operably linked nucleic acid in a senescent cell and not in non-senescent cells. As a non-limiting example, the p16 promoter may be used to promote expression of a operably linked nucleic acid in senescent cells.

In some embodiments, a promoter of the present disclosure is suitable for use in AAV vectors. See, e.g., U.S. Patent Application Publication No. 2018/0155789, which is hereby incorporated by reference in its entirety for this purpose.

Non-limiting examples of constitutive promoters include CP1, CMV, EF1 alpha, SV40, PGK1, Ubc, human beta actin, beta tubulin, CAG, Ac5, Rosa26 promoter, COL1A1 promoter, polyhedrin, TEF1, GDS, CaM3 5S, Ubi, H1, U6, red opsin promoter (red promoter), rhodopsin promoter (rho promoter), cone arrestin promoter (car promoter), rhodopsin kinase promoter (rk promoter). An Ubc promoter may comprise a sequence that is at least 70% (e.g., at least 75%, 80%, 85%, 90%, 95%, 98%, 99%, or 100%) identical to SEQ ID NO: 18. In some instances, the constitutive promoter is a Rosa26 promoter. In some instances, the constitutive promoter is a COL1A1 promoter. A red opsin promoter may comprise a sequence that is at least 70% (e.g., at least 75%, 80%, 85%, 90%, 95%, 98%, 99%, or 100%) identical to SEQ ID NO: 101. A rho promoter may comprise a sequence that is at least 70% (e.g., at least 75%, 80%, 85%, 90%, 95%, 98%, 99%, or 100%) identical to SEQ ID NO: 102. A cone arrestin promoter may comprise a sequence that is at least 70% (e.g., at least 75%, 80%, 85%, 90%, 95%, 98%, 99%, or 100%) identical to SEQ ID NO: 103. A rhodopsin kinase promoter may comprise a sequence that is at least 70% (e.g., at least 75%, 80%, 85%, 90%, 95%, 98%, 99%, or 100%) identical to SEQ ID NO: 104. A tissue-specific promoter may be used to drive expression of an engineered nucleic acid, including e.g., a nucleic acid encoding a rtTA, tTA, OCT4, KLF4, SOX2, or any combination thereof. In some embodiments, a tissue-specific promoter is used to drive expression of a rtTA or a rTA. In some embodiments, a tissue-specific promoter is used to drive expression of OCT4, KLF4, and SOX2. In some embodiments, the tissue-specific promoter is selected from the group consisting of SEQ ID NOS: 101-104. In some embodiments, the hRK promoter is used to drive expression of OCT4, KLF4, and SOX2.

An "inducible promoter" is one that is characterized by initiating or enhancing transcriptional activity when in the presence of, influenced by, or contacted by an inducing agent. An inducing agent may be endogenous or a normally exogenous condition, compound, agent, or protein that contacts an engineered nucleic acid (e.g., engineered nucleic acid) in such a way as to be active in inducing transcriptional activity from the inducible promoter. In certain embodiments, an inducing agent is a tetracycline-sensitive protein (e.g., tTA or rtTA, TetR family regulators).

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (TetR, e.g., SEQ ID NO: 26, or TetRKRAB, e.g., SEQ ID NO: 27), a tetracycline operator sequence (tetO) and a tetracycline transactivator fusion protein (tTA), and a tetracycline operator sequence (tetO) and a reverse tetracycline transactivator fusion protein (rtTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), pH-regulated promoters, and light-regulated promoters. A non-limiting example of an inducible system that uses a light-regulated promoter is provided in Wang et al., Nat. Methods. 2012 Feb. 12; 9(3):266-9.

In certain embodiments, an inducible promoter comprises a tetracycline (Tet)-responsive element. For example, an inducible promoter may be a TRE3G promoter (e.g., a TRE3G promoter that comprises a sequence that is at least 70% (e.g., at least 75%, 80%, 85%, 90%, 95%, 98%, 99%, or 100%) identical to SEQ ID NO: 7). As an example, a TRE (e.g., TRE2) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 23. As an example, a TRE (e.g., P tight) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 24.

Additional non-limiting examples of inducible promoters include mifepristone-responsive promoters (e.g., GAL4-E1b promoter) and coumermycin-responsive promoters. See, e.g., Zhao et al., Hum Gene Ther. 2003 Nov. 20; 14(17): 1619-29.

A "reverse tetracycline transactivator" ("rtTA"), as used herein, is an inducing agent that binds to a TRE promoter (e.g., a TRE3G, a TRE2 promoter, or a P tight promoter) in the presence of tetracycline (e.g., doxycycline) and is capable of driving expression of a transgene that is operably linked to the TRE promoter. rtTAs generally comprise a mutant tetracycline repressor DNA binding protein (TetR) and a transactivation domain (see, e.g., Gossen et al., Science. 1995 Jun. 23; 268(5218):1766-9 and any of the transactivation domains listed herein). The mutant TetR domain is capable of binding to a TRE promoter when bound to tetracycline. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

"SRY-box 2" or "SOX2" is a member of the SRY-related HMG-box (SOX) family of transcription factors. SOX2 has been implicated in promoting embryonic development. Members of the SOX (SRY-related HMG-box) family of transcription factors are characterized by a high mobility group 5 (HMG)-box DNA sequence. This HMG box is a DNA binding domain that is highly conserved throughout eukaryotic species. A SOX2 transcription factor, homolog or variant thereof, as used herein, may be derived from any species, including humans. In certain embodiments, the nucleic acid (e.g., engineered nucleic acid) encoding SOX2 comprises a sequence that is at least 70% (e.g., at least 75%, 80%, 85%, 90%, 95%, 98%, 99%, or 100%) identical to a nucleic acid (e.g., engineered nucleic acid) described in the NCBI RefSeq under accession number NM_011443.4. In certain embodiments, the nucleic acid (e.g., engineered nucleic acid) encoding a human SOX2 comprises a sequence that is at least 70% (e.g., at least 75%, 80%, 85%, 90%, 95%, 98%, 99%, or 100%) identical to a nucleic acid (e.g., engineered nucleic acid) described in the NCBI RefSeq under accession number NM_003106.4. In certain embodiments, SOX2 comprises a nucleic acid (e.g., engineered nucleic acid) sequence that is at least 70% (e.g., at least 75%, 80%, 85%, 90%, 95%, 98%, 99%, or 100%) identical to SEQ ID NO: 3 or SEQ ID NO: 42. SEQ ID NO: 3 is a non-limiting example of a nucleotide sequence encoding SOX2 from Mus musculus. SEQ ID NO: 42 is a non-limiting example of a nucleotide sequence encoding human SOX2. In certain embodiments, the nucleic acid (e.g., engineered nucleic acid) encoding human SOX2 comprises a sequence that is at least 70% (e.g., at least 75%, 80%, 85%, 90%, 95%, 98%, 99%, or 100%) identical to the amino acid sequence described in the NCBI RefSeq under accession number NP_003097.1. In some instances, SOX2 comprises an amino acid sequence that is at least 70% (e.g., at least 75%, 80%, 85%, 90%, 95%, 98%, 99%, or 100%) identical to SEQ ID NO: 4. In some instances, SOX2 comprises an amino acid sequence that is at least 70% (e.g., at least 75%, 80%, 85%, 90%, 95%, 98%, 99%, or 100%) identical to SEQ ID NO: 43. SEQ ID NO: 4 is a non-limiting example of an amino acid sequence encoding SOX2 from Mus musculus. SEQ ID NO: 43 is a non-limiting example of an amino acid sequence encoding human SOX2.

A "multicistronic vector" is a vector that encodes more than one amino acid sequence (e.g., a vector encoding OCT4 and KLF4, OCT4 and SOX2, KLF4 and SOX2, or OCT4, SOX2, and KL4 (OSK)). A multicistronic vector allows for expression of multiple amino acid sequences from a nucleic acid (e.g., engineered nucleic acid) sequence. Nucleic acid (e.g., engineered nucleic acid) sequences encoding each transcription factor (e.g., OCT4, KLF4, or SOX2) may be connected or separated such that they produce unconnected proteins. For example, internal ribosome entry sites (IRES) or polypeptide cleavage signals may be placed between nucleic acid (e.g., engineered nucleic acid) sequences encoding each transcription factor in a vector. Exemplary polypeptide cleavage signals include 2A peptides (e.g., T2A, P2A, E2A, and F2A). A 2A peptide may comprise a sequence that is at least 70% (e.g., at least 75%, 80%, 85%, 90%, 95%, 98%, 99%, or 100%) identical to SEQ ID NO: 9. In some embodiments, an expression vector of the present disclosure is a multicistronic expression vector.

"Reversing aging" or "reversing ageing" as used herein refers to modifying the physical characteristics associated with aging. All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). In certain embodiments, the animal is a mammal. The animal may be a male or female and at any stage of development. A non-human animal may be a transgenic animal.

One of ordinary skill in the art would recognize that the biological age of a pediatric subject or adult subject may vary depending on the type of animal. As a non-limiting example, an adult mouse may be 1 year of age, while an adult human may be more than 21 years of age. In some embodiments, a pediatric subject is less than 21 years of age, less than 20 years of age, less than 15 years of age, less than 10 years of age, less than 9 years of age, less than 8 years of age, less than 7 years of age, less than 6 years of age, less than 5 years of age, less than 4 years of age, less than 3 years of age, less than 2 years of age, less than 1 year of age, less than 10 months of age, less than 9 months of age, less than 8 months of age, less than 7 months of age, less than 6 months of age, less than 5 months of age, less than 4 months of age, less than 2 months of age, or less than 1 month of age. In some embodiments, an adult subject is at least 3 weeks of age, 1 month of age, at least 2 months of age, at least 3 months of age, at least 4 months of age, at least 5 months of age, at least 6 months of age, at least 7 months of age, at least 8 months of age, at least 9 months of age, at least 10 months of age, at least 11 months of age, at least 1 year of age, at least 2 years of age, at least 3 years of age, at least 5 years of age, at least 10 years of age, at least 15 years of age, at least 20 years of age, at least 25 years of age, at least 30 years of age, at least 40 years of age, at least 50 years of age, at least 55 years of age, at least 60 years of age, at least 65 years of age, at least 70 years of age, at least 75 years of age, at least 80 years of age, at least 90 years of age, or at least 100 years of age. In some embodiments, a middle-aged adult subject is between 1 and 6 months of age, between 6 and 12 months of age, between 1 year and 5 years of age, between 5 years and 10 years of age, between 10 and 20 years of age, between 20 and 30 years of age, between 30 and 50 years of age, between 50 and 60 years of age, between 40 and 60 years of age, between 40 and 50 years of age, or between 45 and 65 years of age. In some embodiments, a senior adult subject is at least 1 month of age, at least 2 months of age, at least 3 months of age, at least 4 months of age, at least 5 months of age, at least 6 months of age, at least 7 months of age, at least 8 months of age, at least 9 months of age, at least 10 months of age, at least 11 months of age, at least 1 year of age, at least 2 years of age, at least 3 years of age, at least 5 years of age, at least 10 years of age, at least 15 years of age, at least 20 years of age, at least 25 years of age, at least 30 years of age, at least 40 years of age, at least 50 years of age, at least 55 years of age, at least 60 years of age, at least 65 years of age, at least 70 years of age, at least 75 years of age, at least 80 years of age, at least 90 years of age, or at least 100 years of age.

A "terminator" or "terminator sequence," as used herein, is a nucleic acid (e.g., engineered nucleic acid) sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid (e.g., engineered nucleic acid) sequences by upstream promoters. Thus, in certain embodiments, a terminator that ends the production of an RNA transcript is contemplated.

The most commonly used type of terminator is a forward terminator. When placed downstream of a nucleic acid (e.g., engineered nucleic acid) sequence that is usually transcribed, a forward transcriptional terminator will cause transcription to abort. In some embodiments, bidirectional transcriptional terminators may be used, which usually cause transcription to terminate on both the forward and reverse strand. In some embodiments, reverse transcriptional terminators may be used, which usually terminate transcription on the reverse strand only.

Non-limiting examples of mammalian terminator sequences include bovine growth hormone terminator, and viral termination sequences such as, for example, the SV40 terminator, spy, yejM, secG-leuU, thrLABC, rrnB Ti, hisLGDCBHAFI, metZWV, rrnC, xapR, aspA, and arcA terminator. In certain embodiments, the terminator sequence is SV40 and comprises a sequence that is at least 70% (e.g., at least 75%, 80%, 85%, 90%, 95%, 98%, 99%, or 100%) identical to SEQ ID NO: 8.

A "Tet-Off" system, as used herein, is a type of inducible system that is capable of repressing expression of a particular transgene in the presence of tetracycline (e.g., doxycycline (DOX)). Conversely, a Tet-Off system is capable of inducing expression of a particular transgene in the absence of tetracycline (e.g., doxycycline, DOX). In certain embodiments, a Tet-Off system comprises a tetracycline-responsive promoter operably linked to a transgene (e.g., encoding OCT4; KLF4; SOX2; or any combination thereof) and a tetracycline-controlled transactivator (tTA). The transgene with the tetracycline-responsive promoter (e.g., TRE3G, P tight, or TRE2) and the tetracycline-controlled transactivator may be encoded on the same vector or be encoded on separate vectors. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

A "Tet-On" system, as used herein, is a type of inducible system that is capable of inducing expression of a particular transgene in the presence of tetracycline (e.g., doxycycline (DOX)). In certain embodiments, a Tet-On system comprises a tetracycline-responsive promoter operably linked to a transgene (e.g., encoding OCT4; KLF4; SOX2; or any combination thereof) and a reverse tetracycline-controlled transactivator (rtTA). For example, the rtTA may be rtTA3, rtTA4, or variants thereof. In certain embodiments, a nucleic acid (e.g., engineered nucleic acid) encoding rtTA3 comprises a sequence that is at least 70% (e.g., at least 75%, at least 80%, at least 85%, at least 90%, at least 95%, or at least 100%) identical to SEQ ID NO: 10. In certain embodiments, an amino acid sequence encoding rtTA3 comprises a sequence that is at least 70% (e.g., at least 75%, at least 80%, at least 85%, at least 90%, at least 95%, at least 98%, at least 99%, or at least 100%) identical to (SEQ ID NO: 11). In certain embodiments, a nucleic acid (e.g., engineered nucleic acid) encoding rtTA4 comprises a sequence that is at least 70% (e.g., at least 75%, at least 80%, at least 85%, at least 90%, at least 95%, at least 98%, at least 99%, or at least 100%) identical to SEQ ID NO: 12. In certain embodiments, an amino acid sequence encoding rtTA4 comprises a sequence that is at least 70% (e.g., at least 75%, at least 80%, at least 85%, at least 90%, at least 95%, at least 98%, at least 99%, or at least 100%) identical to (SEQ ID NO: 13). The expression cassette encoding a tetracycline-responsive promoter (e.g., a promoter comprising a TRE, including TRE3G, P tight, and TRE2) and a reverse tetracycline-controlled transactivator may be encoded on the same vector or be encoded on separate vectors. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal, damaged, or unhealthy tissue, which may need to be treated. A tissue may also be a normal or healthy tissue that is under a higher than normal risk of becoming abnormal or unhealthy, which may need to be prevented. In certain embodiments, the tissue is considered healthy but suboptimal for performance or survival in current or future conditions. For example, in agricultural practice, environmental conditions including weather and growing conditions (e.g., nutrition) may benefit from any of the methods described herein. In certain embodiments, the tissue is the central nervous system. In certain embodiments, the tissue refers to tissue from the In certain embodiments, the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine. In certain embodiments, the tissue is damaged (e.g., due to a congenital defect, an injury, an accident, or an iatrogenic injury) and/or is aged tissue. In certain embodiments, the tissue is a deep tissue that is reachable with a fiber optic probe.

The term "tetracycline repressor" or "TetR" refers to a protein that is capable of binding to a Tet-O sequence (e.g., a Tet-O sequence in a TRE, e.g., a Tet-O sequence may comprise SEQ ID NO: 19) in the absence of tetracycline (e.g., doxycycline) and prevents binding of rtTA (e.g., rtTA3, rtTA4, or variants thereof) in the absence of tetracycline (e.g., doxycycline). TetRs prevent gene expression from promoters comprising a TRE in the absence of tetracycline (e.g., doxycycline). In the presence of tetracycline, TetRs cannot bind promoters comprising a TRE, and TetR cannot prevent transcription. Non-limiting examples of TetRs include tetR (e.g., SEQ ID NO: 26), tetRKRAB (e.g., SEQ ID NO: 28). In some embodiments, a TetR is a TetR fusion (e.g., TRSID, which may be created by fusing TetR to a mSIN30interacting domain (SID) of Mad1). See, e.g., Zhang et al., J Biol Chem. 2001 Nov. 30; 276(48):45168-74.

As used herein, a "TRE promoter" is a promoter comprising a tetracycline-responsive element (TRE). As used herein, a TRE comprises at least one (e.g., at least 2, 3, 4, 5, 6, 7, 8, 9, 10, 11, 12, 13, 14, 15, 16, 17, 18, 19, or 20) Tet-O sequences. A non-limiting example of a Tet-O sequence is sequence that is at least 70% (e.g., 75%, 80%, 85%, 90%, 95%, 98%, 99%, or 100%) identical to SEQ ID NO: 19. In some embodiments, a TRE promoter further comprises a minimal promoter located downstream of a tet-O sequence. A minimal promoter is a promoter that comprises the minimal elements of a promoter (e.g., TATA box and transcription initiation site), but is inactive in the absence of an upstream enhancer (e.g., sequences comprising Tet-O). As an example, a minimal promoter may be a minimal CMV promoter that comprises a sequence that is at least 70% (e.g., at least 75%, 80%, 85%, 90%, 95%, 98%, 99%, or 100%) identical to SEQ ID NO: 20. For example, a TRE promoter may be a TRE3G promoter (e.g., a TRE3G promoter that comprises a sequence that is at least 70% (e.g., at least 75%, 80%, 85%, 90%, 95%, 98%, 99%, or 100%) identical to SEQ ID NO: 7. In some embodiments, a TRE promoter is a TRE2 promoter comprising a sequence that is at least 70% (e.g., at least 75%, 80%, 85%, 90%, 95%, 98%, 99%, or 100%) identical to SEQ ID NO: 23. In some embodiments, a TRE promoter is a P tight promoter comprising a sequence that is at least 70% (e.g., at least 75%, 80%, 85%, 90%, 95%, 98%, 99%, or 100%) identical to SEQ ID NO: 24.

The term "tissue repair" in the context of damaged tissue refers to restoration of tissue architecture, function following tissue damage, or a combination thereof. Tissue repair includes tissue regeneration, cell growth, tissue replacement, and/or rewiring of existing tissue (reprogramming).

The term "tissue regeneration" refers to production of new tissue or cells within a tissue that are the same type as the tissue of interest (e.g., same type as the damaged tissue or cell). In some embodiments, the methods provided herein promote organ regeneration.

The term "tissue replacement" refers to production of a different type of tissue compared to the tissue of interest (e.g., connective tissue to replace damaged tissue).

As used herein, the terms "treatment," "treat," and "treating" refer to reversing, alleviating, delaying the onset of, or inhibiting the progress of a disease or disorder, or one or more symptoms thereof, as described herein. In certain embodiments, treatment may be administered after one or more symptoms have developed. In other embodiments, treatment may be administered in the absence of symptoms. For example, treatment may be administered to a susceptible individual prior to the onset of symptoms or may be treated with another damaging agent (e.g., in light of a history of symptoms, in light of genetic or other susceptibility factors, a disease therapy, or any combination thereof). Treatment may also be continued after symptoms have resolved, for example, to prevent or delay their recurrence.

The term "variant" refers to a sequence that comprises a modification relative to a wild-type sequence. Non-limiting modifications in an amino acid sequence include insertions, deletions, and point mutations. Non-limiting modifications to nucleic acid (e.g., engineered nucleic acid) sequences include frameshift mutations, nucleotide insertions, and nucleotide deletions.

The term "WPRE" refers to a Woodchuck Hepatitis Virus (WHP) Posttranscriptional Regulatory Element (WPRE). WPREs create tertiary structures in nucleic acids (e.g., expression vectors) and are capable of enhancing transgene expression (e.g., from a viral vector). In certain embodiments, a WPRE sequence is at least 70% (e.g., at least 75%, at least 80%, at least 85%, at least 90%, at least 95%, at least 98%, at least 99%, or at least 100%) identical to SEQ ID NO: 21.

These and other exemplary substituents are described in more detail in the Detailed Description, Examples, and claims. The invention is not intended to be limited in any manner by the above exemplary listing of substituents.

BRIEF DESCRIPTION OF THE DRAWINGS

FIGS. 5A-5D show the nucleotide positions and lengths of the nucleic acid (e.g., engineered nucleic acid) sequences of the features shown in FIGS. 4A-4AL.

FIG. 6A shows the effect of doxycycline on protein expression in cells infected with AAV9 virus harboring the TRE3G-OSK-SV40 pA vector and with AAV9 virus harboring a vector that encodes rtTA3 (tetracycline (Tet)-on system). FIG. 6B shows the effect of DOX on protein expression in cells infected with AAV2 virus harboring the TRE3G-OSK-SV40 pA vector and with AAV2 virus harboring a vector that encodes tTA (Tet-Off system). FIG. 6C shows the effect of DOX treatment and DOX removal on protein expression in cells infected with AAV.PHP.b virus harboring the TRE3G-OSK-SV40 pA vector and with AAV.PHP.b virus harboring a vector that encodes rtTA3 (Tet-On system). The length of DOX treatment (+DOX) or DOX removal (−DOX) in days is indicated in parenthesis.

FIG. 7A includes a series of photos showing that injection of TRE-OSK-SV40 AAV virus and CAG-tTA AAV virus into mouse retina resulted in expression of KLF4 in mouse retina ganglion cells (RGCs). RBPMS (RGC marker) and KLF4 staining of an optical coherence tomography (OCT) section from mouse retina is shown. FIG. 7B includes a series of photos showing that injection of TRE-OSK-SV40 AAV virus and CAG-tTA AAV virus resulted in inducible expression of KLF4 and OCT4 in mouse retina. OCT4 and KLF4 staining of a whole retina mount in the absence of doxycycline treatment (top two photos) and after four days of DOX treatment (bottom two photos) is shown. FIG. 7C shows an experimental timeline to determine the effect of TRE-OSK-SV40 AAV virus alone or in combination with CAG-tTA AAV virus on optical nerve regeneration following optic nerve crush damage. CTB stands for cholera toxin β-subunit and allows for fluorescence imaging of axons. FIG. 7D shows the co-localization staining of OCT4 and KLF4 from a whole mount retina with TRE-OSK-SV40 AAV virus injected in combination with CAG-tTA, RBPMS stains retina ganglion cells specifically. FIG. 7E shows fluorescence imaging of CTB-labeled axons in an optical nerve after crush damage in mouse retina injected with TRE-OSK-SV40 AAV virus alone (left) or TRE-OSK-SV40 AAV in combination with CAG-tTA AAV (right). Stars represent the site of the lesion. FIG. 7F shows additional fluorescence images of optical nerves treated as in FIG. 7E with viruses as indicated.

FIG. 8A shows the effect of virus encoding tTA in combination with virus encoding TRE-OSK-SV40 in the absence of DOX (circles, n=9), with virus encoding TRE-OSK-SV40 in the presence of dox (triangles, n=5), or with virus encoding d2EGFP (squares, control, n=5) on RGC axon regeneration. The number of estimated axons per nerve is shown as a function of the distance from the site of injury (μm). FIG. 8B is an experimental timeline to determine the effect of d2EGFP expression on RGC axon regeneration. FIG. 8C is a series of images showing CTB-labeled axons from the experiment outlined in FIG. 8B. FIG. 8D is an experimental timeline to determine the effect of uninduced OSK expression on axon regeneration. FIG. 8E is a series of images showing CTB-labeled axons from the experiment outlined in FIG. 4D. FIG. 8F is an experimental timeline to determine the effect of induced OSK expression on axon regeneration. FIG. 8G is a series of images showing CTB-labeled axons from the experiment outlined in FIG. 8F. Stars indicate the site of the lesion.

FIG. 9A shows staining for RBPMS and GFP in GFP AAV-infected uncrushed RGCs (upper left) and in crushed RGCs (upper right). staining for RBPMS and KLF4 in OSK AAV-infected uncrushed RGCs (lower left) and in crushed RGCs (lower right). FIG. 9B shows the ratio of RBPMS (RNA binding protein with multiple splicing)-positive (+) cells for uncrushed and crushed RGCs infected with a destabilized form of GFP (d2EGFP) virus or OSK virus. GFP infected RGCs has the same survival rate as uninfected RGCs, therefore GFP+RBPMs+% remains the same after crush injury. OSK infected RGCs had triple the survival rate compared to uninfected RGC, therefore, KLF4+ RBPMS+% increased after crush injury. FIG. 9C shows survived RGCs under uncrushed (left) and crushed (right) condition, with OSK virus infection. FIG. 9D shows the survival of RGCs (RBPMS+) under uncrushed and crushed condition, when they were infected with d2EGFP virus or OSK virus.

FIG. 10A is a series of images showing RBPMS and pS6 staining of control and OSK-infected RGCs that were uncrushed or crushed. FIG. 10B is a graph quantifying the percentage of pS6 positive cells from series of pictures like FIG. 10A.

FIGS. 11A-11D show that an AAV Tet-On system comprising a CMV-rtTA vector (SEQ ID NO: 31) induces faster gene expression compared to an AAV Tet-Off system in retinal cells after nerve crush. FIG. 11A shows an experimental timeline to test the effect of doxycycline removal on GFP expression in an AAV Tet-Off system. Lines indicate the length of DOX treatment. Treatments A-D as indicated correspond to photographs 1-4 of FIG. 7B, respectively. FIG. 11B is a series of photos showing results of the experiment outlined in FIG. 11A. GFP-positive cells from mouse retina that was infected with virus encoding tTA and virus encoding TRE-d2EGFP at indicated days of DOX removal are shown. FIG. 11C shows an experimental timeline to test the effect of doxycycline treatment on GFP expression in an AAV Tet-On system comprising a CMV-rtTA vector (SEQ ID NO: 31). Lines indicate the length of DOX treatment. Treatments A-C as indicated correspond to photographs 1-3 of FIG. 11D, respectively. FIG. 11D is a series of photos showing results of the experiment outlined in FIG. 11C. GFP-positive cells from mouse retina that was infected with virus encoding rtTA and virus encoding TRE-d2EGFP at the indicated days of DOX treatment are shown.

FIGS. 13A-13C include data showing that a Tet-On system comprising rtTA4 (SEQ ID NO: 13) has low leakiness in the liver of mice. FIG. 13A is a series of immunofluorescence images showing expression of KLF4 in the livers of mice that have been administered AAVs harboring nucleic acids (e.g., engineered nucleic acids) shown in FIG. 13B in the absence of doxycycline (no DOX) and in the presence of doxycycline (with DOX). DAPI is a nuclear stain that was used to visualize cells. FIG. 13B is a schematic depicting the two nucleic acids (e.g., engineered nucleic acids) that were administered to mice in AAV9 viruses. FIG. 13C is a western blot of liver samples from mice that received the constructs depicted in FIG. 13B and were treated with no doxycycline or with doxycycline. OCT4, KLF4, and SOX2 levels were detected as indicated using antibodies. Actin is shown as a loading control.

FIG. 21 is a series of images showing successful chemical reprogramming of mouse embryonic fibroblasts.

FIG. 22 includes a schematic showing a non-limiting example of a Tet-Off system to express OCT4, SOX2, and KLF4 in the absence of tetracycline (top panel) and a schematic showing a non-limiting example of a Tet-ON system to express OCT4, SOX2, and KLF4 (OSK) in the presence of tetracycline (bottom panel).

FIG. 23A is a series of images showing CTB-labeled axons from mice at indicated ages (in months) and comparing the effect of AAV2 virus encoding TRE-OSK-SV40 with the effect of AAV2 virus encoding GFP. Experiments were conducted in the absence of DOX using the Tet-Off system depicted in FIG. 22, top panel. FIG. 23B quantifies the number of estimated axons per nerve for mice with the indicated ages and treatments as a function of the distance from the site of injury (μm). FIG. 23C is a chart showing that OSK increased the survival of RGCs after optic nerve injury in adult (3 month old) and aged (12 month old) mice compared to control GFP. The survival of RGCs (RBPMS+) is shown for mice of the indicated ages receiving virus encoding d2EGFP or OSK.

FIG. 24A is a series of photos showing CTB-labeled axons from 12 month old mice five weeks after optic nerve crush injury. Mice were administered virus encoding GFP or encoding TRE-SV40-OSK and virus encoding tTA prior to nerve crush injury. FIG. 24B is a graph quantifying the number of estimated axons per nerve as a function of the distance from the site of injury (μm) from FIG. 24A.

FIG. 25A includes schematics showing treatment timelines to determine the effect of OSK expression before or after optic nerve crush. In the Tet-On system, induction of OSK expression prior to optic nerve crush injury (pre-injury induction) and induction of OSK expression after optic nerve crush injury (post-injury induction) are shown (top panel). Doxycycline treatment was used to induce OSK expression. In the Tet-Off system, suppression of OSK induction with doxycycline treatment prior to optic nerve crush (pre-injury suppression) and suppression of OSK induction with doxycycline treatment after optic nerve crush (post-injury suppression) are shown (bottom panel). The shaded lines on the timeline indicate the length of doxycycline (DOX) treatment. Cholera toxin β-subunit (CTB) injection for imaging of axons is also shown. FIG. 25B is a chart quantifying the number of estimated axons per nerve as a function of the distance from the site of injury (μm) for four-week old (young) mice with no OSK induction (n=4), OSK induction pre-injury only (n=5), OSK expression suppressed from injury (n=5), and OSK induction post injury (n=5). The protocols for pre-injury and post-injury induction used were as shown in FIG. 25A. FIG. 25C is a chart quantifying the number of RBPMS+ cells from four-week old (young) mice with no OSK induction, OSK induction pre-injury only, OSK suppressed from injury, and OSK induction post injury.

FIG. 26A is a schematic showing the AAV combinations injected in each group two weeks before the crush injury and non-limiting exemplary expression cassettes in Tet-Off systems encoding OCT4, SOX2, and/or KLF4. FIG. 26B is a chart showing that expression of OSK from a single transcript improved axon regeneration relative to expression of OCT4, SOX2, and KLF4 from separate transcripts. The number of estimated axons per nerve after optic nerve crush injury as a function of the distance from the site of injury (μm) was quantified for mice receiving tTA virus and one of the following (1) OCT4 virus, (2) SOX2 virus, (3) KLF4 virus, (4) virus with a vector encoding OCT4 and SOX2 under one promoter (OCT4-SOX2), (5) separate OCT4, SOX2, and KLF4 viruses (Oct4, Sox2, KLF4 or O,S,K), or (6) virus with a vector encoding OCT4, KLF4, and SOX2 under one promoter (Oct4-Sox2-KLF4 or OSK). The various vectors used are depicted in FIG. 26A. FIG. 26C is a chart showing that expression of OSK from a single transcript improved RGC survival relative to expression of OCT4, SOX2, and KLF4 from separate transcripts. FIG. 26D includes whole mount staining of mouse retina showing that a heterogeneous population of cells with few RBPMS+ cells were detected when separate viral vectors encoding OCT4, SOX2, and KLF4 in separate viruses were delivered to the eye of mice. Arrows point to seven different types of cells expressing OCT4, SOX2, KLF4, and/or RBPMS in the upper left image under the schematic of the vectors. FIG. 26E includes data showing that a more homogenous population of cells was detected when virus comprising a viral vector encoding OSK under one promoter was delivered to the eye of mice as compared to FIG. 26D. More OSK-expressing cells that were also RBPMS+ were detected as compared to FIG. 26D. In the upper left image under the schematic of the vector used, the long white arrow points to RBPMS+ cells expressing OCT4, SOX2, and KLF4 and the shorter arrow indicates even some cells that did not express RBPMS expressed OSK.

FIG. 28 is a chart showing that intravitreal injection of mice with virus encoding tTA and virus encoding TRE-OSK in the absence of doxycycline (OSK induction condition) reversed the age-related decrease in the spatial frequency threshold (cycles/degree, visual acuity test) observed in aged mice (12 month old (12 m) and 18 month old (18 m) mice). A visual acuity test based on optomotor response (OMR) was used. As controls, age-matched mice received virus encoding virus encoding rtTA and virus TRE-OSK in the absence of doxycycline (uninduced control). Adult mice (3 month old (3 m)) were also used as a control.

FIG. 29 is a chart showing the measurement of electrical waves generated from RGCs from adult (3 month old (3 m)) and aged (12 month old (12 m) and 18 month old (18 m)) mice. A pattern electroretinogram (pattern ERG) was used. Mice were injected with rtTA virus and TRE-OSK virus without doxycycline (uninduced control (ctl)) or with tTA virus and TRE-OSK virus (induced, OSK) without doxycycline. Results were obtained one month after virus injection.

FIG. 30A is a chart showing that polystyrene microbeads induced glaucoma as measured by an increase in intraocular pressure (IOP) compared to saline treatment in adult C57BL/6J mice. The IOP measurements are shown in the first four weeks after microbead injection. FIGS. 30B-30C show that 4 weeks after microbeads injection into the anterior chamber of the eye, there was significant loss of axon density and RGC density. AAVs were intravitreally injected at 3 weeks post microbeads and it took another week before OSK expression was observed. FIG. 30B includes a chart quantifying axon density (left panel) using p-phenylenediamine (PPD) staining (shown, for example, on the right). FIG. 30C includes a chart quantifying RGC cell density (left panel) using Brn3a staining (shown, for example, on the right). FIG. 30D is a chart showing visual acuity improvement by OSK AAV treatment in glaucoma-induced mice. Mice were intravitreally injected with microbeads to induce glaucoma or saline without microbeads (no glaucoma control; saline). Three weeks after microbeads injection, mice are then treated with (1) virus encoding rtTA and virus TRE-OSK in the absence of doxycycline (beads (OSK AAV OFF)); (2) virus encoding tTA and virus encoding TRE-OSK in the absence of doxycycline (beads (OSK AAV ON)). Results at 3 weeks after saline or microbead injection (pre-AAV injection) and 4 weeks after AAV injection (7 week post microbeads) are shown. FIG. 30E is a chart showing RGC function results by pattern electroretinogram in mice treated as in FIG. 30B.

FIG. 31A includes a series of images showing the effect of inducing OSK expression (OSK On) compared to no induction of OSK expression (OSK Off) on the structure of neurons. Images were taken at day 3 and at day 9 after 24 hours of VCS treatment. The outlines of the neuronal cell area are shown at Day 9. FIG. 31B is a chart quantifying neuron cell area ($\mu m^2$) at indicated days after 24 hours of VCS treatment for cells in which OSK expression was induced (OSK On) and for cells in which OSK expression was not induced (OSK Off). FIG. 31C is a chart quantifying neuron cell area ($\mu m^2$) at indicated days after 48 hours of VCS treatment for cells in which OSK expression was induced (OSK On) and for cells in which OSK expression was not induced (OSK Off).

FIG. 32A is a schematic of the Tet-On and Tet-Off AAV vectors used in the study to control OSK expression. FIG. 32B shows body weight of WT mice, OSK transgenic mice, and AAV-mediated OSK-expressing mice ($1.0 \times 10^{12}$ gene copies) with or without doxycycline induction in the first 4 weeks (n=5, 3, 6, 4, 6, 3, respectively). FIG. 32C is a schematic showing intravitreal AAV injection to target retina ganglion cells. Immunofluorescence of the whole-mounted display and cross section of retina, showing the infection rate and targeted retina layer. The scale bars represent 1 mm and 100 μm, respectively. FIG. 32D shows an experimental outline of the optic nerve crush study using the Tet-Off system. FIG. 32E shows quantification of the regenerating fibers by to d2EGFP, Oct4, Sox2, Klf4, OS, O+S+K, or OSK AAV at different distances distal to the lesion site. Error bars indicate s.e.m. (n=4-7). **, P<0.0001, ANOVA with Bonferroni posttests. FIG. 32F shows the survival of RBPMS-positive cells in the RGC layer transduced with different AAV vectors at day 14 post crush injury (n=4-8). *, P<0.001, ****, P<0.0001, one-way ANOVA with Bonferroni post-tests, relative to d2EGFP.

FIG. 32G shows representative images of optic nerve sections showing CTB-labeled axons in wild-type mice with intravitreal injection of AAV2-tTA and TRE-OSK in the presence and absence of DOX at 2 weeks after optic nerve injury. The crush site is indicated by asterisks. The scale bars represent 200 µm.

FIGS. 33A-33K show that OSK expression promotes axon regeneration and neuronal survival through a Tet-dependent mechanism. FIG. 33A shows experimental strategies for pre- and post-injury induction of OSK expression. FIG. 33B shows RGC survival in retinas with pre- and post-injury OSK expression. FIG. 33C shows the quantification of regenerating fibers from pre- and post-injury OSK expression models. FIG. 33D shows representative images of optic nerves showing regenerating axons at 4 weeks after injury, with or without post injury OSK expression. The crush site is indicated with asterisks. The scale bars represent 200 µm. FIGS. 33E-33F show the quantification of regenerating fibers and RGC survival in retinas co-transduced with AAV2 vectors encoding polycistronic OSK, tTA, and shRNA vectors with a scrambled sequence (Scr), Tet1, or Tet2 sequences to knockdown Tet DNA dioxygenases/demethylases. FIG. 33G shows experimental outlines for examining axon regeneration in human neurons post vincristine (VCS) damage. FIG. 33H shows that OSK rejuvenates human neurons according to the skin & blood clock. In the top panel of FIG. 33H, P value is calculated by linear regression model to see if DNAmAge decrease with time. In the bottom panel of FIG. 33H, DNA methylation age of human neurons with OSK expression pre (Day −) or after VCS damage (Day 1 and 9), estimated by skin and blood cell clocks is shown. FIG. 33I shows the neurite area in each AAV treatment group. $*p<0.05$, $p<0.01$, $**p<0.0001$, one-way ANOVA with Tukey's multiple comparison test. FIG. 33J shows representative images of human neurons and the neurite area after 9 days of recovery from VCS damage. FIG. 33K shows rDNA methylation age of 1-month-old RGCs isolated from axon-intact retina infected with or without GFP, or from axon-injured retinas infected with GFP-AAV or OSK-AAV 4 days after nerve crush.

FIG. 34A is a schematic showing the experimental outline. FIG. 34B shows Intraocular pressure measured weekly by rebound tonometry for the first 4 weeks post-microbead injection. FIG. 34C shows Representative micrographs of PPD-stained optic nerve cross-sections at 4 wks post AAV2 or PBS injection. Scale bars, 50 µm. OSK Off (rtTA+TRE-OSK); OSK On (tTA+TRE-OSK). FIG. 34D shows a quantification of healthy axons of the optic nerve at 4 weeks post PBS or AAV injection. FIG. 34E is a Schematic of High-contrast visual stimulation assay to measure optomotor response. A reflexive head movement in response to the rotation of a moving stripe pattern that increases in spatial frequency was used to assess vision. FIG. 34F shows Spatial frequency threshold response of each mouse measured before treatment and 4 weeks after intravitreal injection of AAV vectors. FIG. 34G shows Representative pERG waveforms recorded from the same eye at baseline before treatment and four weeks later after treatment with OSK-OFF AAV (top graph) or OSK-ON AAV (bottom graph). FIG. 34H shows the Mean pERG amplitudes of recordings measured from each mouse at baseline before treatment and 4 weeks after intravitreal injection of AAVs. $*P<0.05$; $P<0.01$; $*P<0.001$, $****P<0.0001$ Two-way ANOVA with Turkey posttests between groups was used for the overall effect of time and treatment. A paired t-test was used to compare before and after treatments.

FIG. 35A shows an Experimental outline for testing the effects of OSK AAV treatment in aged mice on axon regeneration following optic nerve crush and restoration of vision loss associated with physiological aging. FIG. 35B shows Axon regeneration in 12-month-old mice with OSK AAV or control AAV (d2EGFP) treatment following 2 or 5 weeks post optic nerve crush. FIG. 35C Representative confocal images of longitudinal sections through the optic nerve showing CTB-labeled axons after 5 weeks of OSK treatment. Scale bar represents 200 µm. FIG. 35D The spatial frequency threshold in young mice (4 months) and old mice (12 months) treated with OSK-Off or OSK-On AAVs. FIGS. 35E-35F show Spatial frequency threshold and pERG amplitudes in old mice (12 months) treated with: (i) OSK-Off, (ii) OSK-On, or (iii) OSK-On plus either: sh-Scr, sh-Tet1- or sh-Tet2-mediated knockdown of DNA demethylases. OSK-Off, (rtTA+TRE-OSK); OSK-On, (tTA+OSK). FIG. 35G is hierarchical clustered heatmap showing RNA-Seq expression of 464 differentially expressed genes in cell sorted purified RGCs from intact young mice (5 months) or intact old mice (12 months), or old mice treated with either control AAV (TRE-OSK) or OSK-On AAV. FIG. 35H is a scatter plot of OSK-induced changes in RNA levels versus age-associated changes in mRNA levels. Dots represent differentially expressed genes in RGCs. FIG. 35I shows rDNA methylation age of 12-month-old RGCs FACS isolated from retinas infected for 4 weeks with −OSK or +OSK AAV together with short-hairpin DNAs with a scrambled sequence (sh-Scr) or targeted to Tet1 or Tet2 (sh-Tet1/sh-Tet2). Gene exclusion criteria for FIG. 35G and FIG. 35H: genes with low overall expression (log 2(CPM)<2), genes that did not significantly change with age (absolute log 2 fold-change<1) or genes altered by the virus (differentially expressed between intact old and old treated with TRE-OSK AAV). $*P<0.05$; $P<0.01$; $*P<0.001$, $****P<0.0001$. Two-way ANOVA in FIG. 35D; One-way ANOVA in FIGS. 35B, 35E and 35F.

FIGS. 36A-36H show an exploration of OSK (no Myc) effects on ageing and the safety of OSK AAV. FIG. 36A is a schematic of an experimental outline of testing reprogramming effect in young and old transgenic mouse fibroblasts. FIG. 36B shows OSKM expression rescues age-associated transcriptional changes without inducing pluripotency. For example, Nanog expression is not induced. FIG. 36C shows OSK expression rescues age-associated transcriptional changes without inducing pluripotency. For example, Nanog expression is not induced. FIG. 36D shows OSK AAV9 expression in the liver compared to transgenic mice. FIG. 36E shows the body weight of WT mice and AAV-mediated OSK-expressing mice ($1.0 \times 10^{12}$ gene copies total) with or without doxycycline in the following 9 months after first 4 weeks (n=5, 3, 6, 4, respectively). FIG. 36F shows AAV-UBC-rtTA and AAV-TRE-Luc vectors used for measuring tissue distribution. FIG. 36G shows luciferase imaging of WT mice at 2 months after retro-orbital injections of AAV9-UBC-rtTA and AAV9-TRE-Luc ($1.0 \times 10^{12}$ gene copies total). Doxycycline was delivered in drinking water (1 mg/mL) for 7 days to the mouse shown on the right. FIG. 36H shows luciferase imaging of eye (Ey), brain (Br), pituitary gland (Pi), heart (He), thymus (Th), lung (Lu), liver (Li), kidney (Ki), spleen (Sp), pancreas (Pa), testis (Te), adipose (Ad), muscle (Mu), spinal cord (SC), stomach (St), small intestine (In), and cecum (Ce) 2 months after retro-orbital injection of AAV9-UBC-rtTA and AAV9-TRE-Luc followed by treatment with doxycycline for 7 days. The luciferase signal is primarily in liver. Imaging the same tissues with a longer exposure time (FIG. 36H, lower panel) revealed lower levels of luciferase signal in pancreas (liver was removed).

FIGS. 37A-37D show the characterization of an inducible polycistronic AAV system. FIG. 37A shows an Immunofluorescence analysis of the whole-mounted retina transduced with a polycistronic AAV vector expressing OCT4, SOX2, and KLF4 in the same cell. Arrows point at triple positive cells. FIG. 37B shows an immunofluorescence analysis of the whole-mounted retina transduced with AAVs separately encoding OCT4, SOX2, and KLF4. Dotted arrows point to double-positive cells. Solid arrows point at single-positive cells, except for arrow in lower right corner of each image, which points at a triple positive cell. FIGS. 37C-37D are images showing whole-mounted retina display of RBPMS and Klf4 immunofluorescence. FIG. 37C shows that expression from AAV2 Tet-Off system can be turned off by Dox drinking water (2 mg/mL 3 days). FIG. 37D shows that expression from AAV2 Tet-On system can be turned on by Dox drinking water (2 mg/mL 2 days). Scale bars represent 1 mm.

FIG. 38A shows retina whole-mount staining showing OSK infected RGCs have no proliferation marker Ki67 (left), while proliferating 293T cells have Ki67 signal (right). The scale bars represent 100 μm. FIG. 38B shows whole nerve imaging of optic nerves showing regenerating axons from control (no AAV) or OSK AAV treatment at 3 months after injury. The scale bars represent 200 μm. FIG. 38C shows whole nerve imaging showing CTB-labeled regenerative axons at 16 weeks post-injury (wpc) in wild-type mice with intravitreal injection of AAV2-tTA and TRE-OSK. Scale bars represent 200 m.

FIG. 39A shows Representative images showing the d2EGFP expression in retina from Tet-Off AAV system with different Dox treatment. When pre-treated with DOX to suppress expression (on DOX), the GFP expression only showed up sparsely after DOX been withdrawal for 8 days, much weaker compared to peak expression (Never DOX). FIG. 39B are representative images showing the d2EGFP in retina from Tet-On AAV system. No GFP expression was observed in the absence of DOX, and GFP expression reached peak in 2 days after Dox induction and didn't get stronger with 5 days of DOX induction. FIG. 39C shows representative Immunofluorescence image of GFP-positive or KLF4-positive RGCs in intact and crushed samples. FIG. 39D shows quantification of GFP- or KLF4-positive cells indicating higher survival rate of OSK expressing RGCs after crush. Scale bars represent 200 μm in FIG. 39A, FIG. 39B, and FIG. 39C.

FIG. 40A Representative images of retinal whole mounts transduced with d2EGFP- or OSK-encoding AAV2 in the presence or absence of crush injury. The retinal whole mounts were immunostained for RGC marker RBPMS and mTOR activation marker pS6. FIG. 40B shows the quantification of pS6 positive RGC % in intact and crushed samples. FIG. 40C quantification of transduction rate of shRNA-YFP AAV in the OSK expressed RGCs. FIG. 40D shows representative images of retinal whole mounts transduced with OSK-encoding AAV2 in the combination with sh-Scr, sh-Tet1 or sh-Tet2 YFP AAV. The retinal whole mounts were immunostained for Klf4. Scale bars represent 100 μm in FIG. 40A and FIG. 40D. FIG. 40E shows Tet1 versus GAPDH mRNA level with sh-Scr or sh-Tet1 treatment in mouse RGCs in the presence of OSK expression. FIG. 40F shows Tet2 versus GAPDH mRNA level with sh-Scr or sh-Tet2 AAV in mouse RGCs in the presence of OSK expression.

FIG. 41A shows immunofluorescence of differentiated human neurons with transduction of AAV-DJ vectors encoding TRE-OSK and tTA (OSK On) or TRE-OSK alone (OSK Off). FIG. 41B shows mRNA level of Oct4, Sox2 and Klf4 of human neurons transduced with AAV-DJ vectors as in FIG. 41A. FIG. 41C shows the FACS profile of G1, S, and G2 phases in undifferentiated cells and differentiated cells with OSK On or Off. FIG. 41D shows the quantification of cell population that are in proliferating S phase. FIG. 41E shows representative images and the neurite area of human neurons post vincristine damage with or without OSK expression. FIG. 41F shows the quantification of neurite area at different time points post vincristine damage. FIG. 41G shows Tet2 mRNA level with sh-Scr and sh-Tet2 AAV treatment in human neurons. FIG. 41H shows the phosphorylation level of S6 in human neurons with Rapamycin treatment (10 nM) for 5 days. FIG. 41I shows the effect of mTOR inhibition on axon regeneration of differentiated neurons with OSK Off or OSK On. FIG. 41J shows DNA methylation age of human neurons before vincristine (VCS) damage (Day –) or 1 and 9 days post-damage in the absence of OSK expression, estimated using a skin or a blood cell clock. FIG. 41K shows mouse Oct4 mRNA level with sh-Scr or sh-Tet2 AAV in human neurons in the absence or presence of OSK expression.

FIG. 42A shows the quantification of RGCs and representative confocal microscopic images from retinal flat-mounts stained with anti-Brn3a, an RGC-specific marker, and DAPI, a nuclear stain, at 4 weeks post-microbead or post-saline injection. The scale bar represents 75 mm. FIG. 42B shows the quantification of healthy axons of optic nerve and representative photomicrographs of PPD-stained optic nerve cross-sections, at 4 weeks post-microbead or post-saline injection. The scale bars represent 10 μm. FIG. 42C shows the quantification of RGCs and representative confocal microscopic images at 4 weeks post AAV injection and 8 weeks post-microbead or post-saline injection.

FIG. 43A shows the effect of OSK expression on RGC survival in young, adult, and aged mice after optic nerve crush. FIG. 43B shows the axon regeneration promoted by OSK expression compared to the d2EGFP controls in young (1 month old), adult (3 months old), and aged (12 months old) mice at 2 weeks post injury. FIG. 43C shows a comparison of pERG measurements in different ages at one month post OSK off or OSK On treatment. OSK Off, rtTA+TRE=OSK AAV; OSK On, tTA+OSK AAV. FIG. 43D shows comparison of RGC cell density in 4 m- and 12 m-old mice at one month post OSK off or OSK On treatment. FIG. 43E shows a comparison of axon density in 4 m- and 12 m-old-mice at one month post OSK off or OSK On treatment. FIG. 43F shows comparison of pERG measurement in different ages at one-month after –OSK or +OSK treatment. –OSK: AAV-rtTA+AAV-TRE-OSK; +OSK: AAVtTA+AAV-TRE-OSK.

FIG. 43G shows spatial frequency threshold in 18-month-old mice treated with −OSK or +OSK AAV for 4 weeks.

FIG. 44A is a scatter plot of OSK-induced changes in RNA levels versus age-associated changes in mRNA levels. Dots represent differentially expressed genes in RGCs are shown. Gene exclusion criteria: genes with low overall expression (log 2(CPM)<2), genes that did not significantly change with age (absolute log 2 fold-change<1) or genes altered by the virus (differentially expressed between intact old and old treated with TRE-OSK AAV). FIG. 44B is a hierarchical clustered heatmap showing RNA-Seq expression of sensory genes in cell sorted purified RGCs from intact young mice (5 months) or intact old mice (12 months), or old mice treated with either control AAV (TRE-OSK) or OSK-On AAV. FIG. 44C shows the top 10 biological process that are lower in old compared to young and restored by OSK. FIG. 44D shows the top 10 biological process that are higher in old compared to young and reduced by OSK.

FIG. 45A shows correlation between rDNA methylation age and chronological age of sorted mouse RGCs. FIG. 45B shows average DNA methylation levels of RGCs from different ages and treatments. FIG. 45C shows average DNA methylation levels of human neurons treated with OSK before treatment with vincristine (VCS) (−) or days post-VCS damage (1 and 9).

FIG. 46A are representative optic nerve images. FIG. 46B is a graph quantifying axon numbers.

DETAILED DESCRIPTION OF CERTAIN EMBODIMENTS OF THE INVENTION

Figure 1:
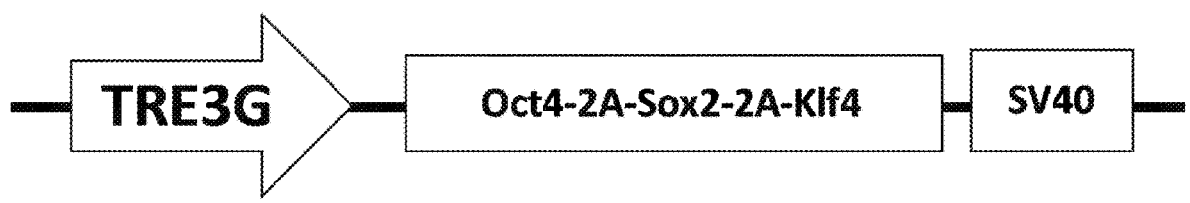
FIG. 1 is a schematic with a linear representation of an expression vector encoding OCT4, SOX2, and KLF4. TRE3G is shown as an exemplary inducible promoter, and SV40 is shown as an exemplary terminator sequence.

The present disclosure is based, at least in part, on the unexpected results demonstrating that expression of OCT4, SOX2, and KLF4 in the absence of exogenous c-Myc expression can be used to promote partial reprogramming and tissue regeneration in vivo. Surprisingly, using the eye as a model tissue, as described herein, in some embodiments, it was determined that the combination of OCT4, SOX2, and KLF4 (OSK) could be used to reset the youthful gene expression patterns and epigenetic age of retinal ganglion cells to promote optic nerve regrowth and the restoration of vision in a rodent model of glaucoma and in old animals. In some embodiments, the DNA demethylases Tet1 and Tet2 are required for these restorative activities, which without being bound by a particular theory, suggests that the DNA methylation clock is not just a correlate of age but a regulator of it.

Provided herein, in certain embodiments, are engineered nucleic acids (e.g., expression vectors, including viral vectors) encoding OCT4, SOX2, and KLF4, each alone or in combination, recombinant viruses (e.g., lentivirus, alphavirus, vaccinia virus, retrovirus, adenovirus, herpes virus, or AAV) comprising the same, pharmaceutical compositions comprising the engineered nucleic acids and/or recombinant viruses, kits comprising the engineered nucleic acids and/or recombinant viruses, and methods of regulating (e.g., inducing, inducing and then stopping, etc.) cellular reprogramming, reversing aging, tissue repair, organ regeneration, and tissue regeneration.

In certain embodiments, the expression of one of more of the genes is transient (e.g., using an inducible promoter to regulate gene expression). Expression of one or more of the genes (e.g., OCT4, SOX2, KLF4, or a combination thereof) may be modulated by altering the activity of an inducing agent. As a non-limiting example, tetracycline transactivator (tTA) is capable of inducing expression from a tetracycline-responsive promoter in the absence of tetracycline. When tetracycline is added, tTA can no longer bind to the promoter and induce cannot expression. As another non-limiting example, reverse tetracycline transactivator (rtTA) is capable of inducing expression from a tetracycline-responsive promoter in the presence of tetracycline. When tetracycline is removed, rtTA can no longer bind to the promoter and cannot induce expression. As described herein, an inducible AAV vector encoding OCT4, SOX2, and KLF4 (OSK) promoted optic regeneration in vivo following damage. Therefore, the expression of these three genes may be useful in tissue and organ regeneration, tissue and organ repair, reversing aging, treating neurodegenerative diseases and conditions, cellular reprogramming, As described below, the vectors described herein may be packaged, in some instances, into viruses with a titer of more than $2\times10^{12}$ particles per preparation and allow for precise control of OSK expression in mammalian cells in vitro and in vivo.

Cellular reprograming allows for the production of numerous cell types from existing somatic cells. Although the Yamanaka factors (OCT4, SOX2, KLF4 and c-Myc, also known collectively as OSKM) have been shown to induce pluripotency in differentiated cells, administration of these factors may induce teratomas or other cancers in vivo (Takahashi et al., Cell. 2006 Aug. 25; 126(4):663-76); (Abad et al., Nature. 2013 Oct. 17; 502(7471):340-5). As a result of these safety concerns, use of the Yamanaka factors has largely been limited to in vitro applications. Furthermore, existing methods of gene therapy are plagued by inefficient and inconsistent gene transduction of target cells. The engineered nucleic acids, recombinant viruses comprising the same, pharmaceutical compositions thereof and kits provided herein overcome many of these limitations.

Engineered Nucleic Acids

The engineered nucleic acids of the present disclosure may encode OCT4, SOX2, KLF4, and homologs or variants (e.g., functional variants) thereof, each alone or in combination. In certain embodiments, an engineered nucleic acid (e.g., engineered nucleic acid) does not encode c-Myc. In certain embodiments, an engineered nucleic acid (e.g., engineered nucleic acid) does not encode a functional c-Myc because it lacks a c-Myc sequence. Assays to determine transcription factor (e.g., OCT4, SOX2, KLF4, or any combination thereof) activity are known in the art and include cell-based transcription assays and in vitro transcription assays. Transcription factor expression may also be determined using other methods including enzyme-linked immunosorbent assays (ELISAs), western blots, and quantification of RNA (e.g., using reverse transcription polymerase chain reaction).

A transcription factor (e.g., OCT4, SOX2, KLF4, or homologs or variants thereof, including mammalian OCT4, mammalian SOX2, and mammalian KLF4) may be encoded by a single nucleic acid, or a single nucleic acid (e.g., engineered nucleic acid) may encode two or more transcription factors (e.g., each operably linked to a different promoter, or both operably linked to the same promoter). For example, in certain embodiments, a nucleic acid (e.g., engineered nucleic acid) may encode OCT4; SOX2; KLF4; OCT4 and SOX2; OCT4 and KLF4; SOX2 and KLF4; or OCT4, SOX2, and KLF4, in any order.

In certain embodiments, an engineered nucleic acid (e.g., engineered nucleic acid) encodes an inducing agent (e.g., tTA or rtTA). In certain embodiments, a nucleic acid (e.g., engineered nucleic acid) may encode one or more transcription factors (e.g., one, two or three transcription factors) and an inducing agent. In certain embodiments, an inducing agent is encoded by a separate nucleic acid (e.g., engineered nucleic acid) that does not also encode a transcription factor (e.g., OCT4, SOX2, or KLF4). In certain embodiments, an inducing agent is encoded by a the nucleic acid (e.g., engineered nucleic acid) that also encodes a transcription factor (e.g., OCT4, SOX2, and/or KLF4). In certain embodiments, an inducing agent is encoded by a nucleic acid (e.g., engineered nucleic acid) that also encodes one or more transcription factors selected from the group consisting of OCT4; SOX2; KLF4; and any combinations thereof (e.g., OCT4; SOX2; KLF4; OCT4 and SOX2; OCT4 and KLF4; SOX2 and KLF4; or OCT4, SOX2, and KLF4).

The transcription factors described herein (e.g., OCT4, SOX2, KLF4, or any combination thereof) or inducing agents may comprise one or more amino acid substitutions. Variants can be prepared according to methods for altering polypeptide sequences known to one of ordinary skill in the art such as those found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In certain embodiments, the engineered nucleic acids of the present disclosure comprise RNA (e.g., mRNA) and/or DNA. In some embodiments, the RNA and/or DNA is further modified. As a non-limiting example, an nucleic acid (e.g., engineered nucleic acid) of the present disclosure, may be modified RNA (e.g., mRNA) encoding OCT4, KLF4, SOX2, an inducing, or any combination thereof. See, e.g., Warren et al., Cell Stem Cell. 2010 Nov. 5; 7(5):618-30. As a non-limiting example, the engineered nucleic acids (e.g., RNA, including mRNA, or DNA) of the present disclosure may be formulated in a nanoparticle for delivery. See, e.g., Dong et al., Nano Lett. 2016 Feb. 10; 16(2):842-8. In some embodiments, the nanoparticle comprises acetylated galactose. See, e.g., Lozano-Torres et al., J Am Chem Soc. 2017 Jul. 5; 139(26):8808-8811. In some embodiments, the engineered nucleic acids (e.g., RNA, including mRNA, or DNA) is electroporated or transfected into a cell. In certain embodiments, the engineered nucleic acids are delivered as a naked nucleic acid (e.g., naked DNA or naked RNA).

In some embodiments, an engineered nucleic acid that is formulated in a nanoparticle for delivery is not an AAV vector. Suitable vector backbones for formulation in a nanoparticle include, but are not limited to, NANOPLASMID™ vectors and NTC '8' Series Mammalian Expression Vectors. Non-limiting examples of vector backbones for formulation in a nanoparticle include NTC9385R and NTC8685. Without being bound by a particular theory, NTC '8' Series Mammalian Expression Vectors may be useful as they are generally cleared by cells within weeks. The NTC '8' Series Mammalian Expression Vector comprises a CMV promoter, which can be operably linked to a sequence encoding OCT4, KLF4, SOX2, or a combination thereof. Without being bound by a particular theory, the NANOPLASMID™ vector may be less immunogenic than other vectors and express at a higher level and may express for a long time, which could be useful in long-term expression of an operably linked nucleic acid. In some embodiments, the NANOPLASMID™ vector may be useful in long term expression of OCT4, KLF4, SOX2, or a combination thereof.

In some embodiments, engineered nucleic acids encoding OSK may be useful in making induced pluripotent stem cells). Without being bound by a particular theory, modified RNA (e.g., mRNA) may have an advantage of minimal activation of innate immune responses and limited cytotoxicity, thereby allowing robust and sustained protein expression. In some embodiments, the RNA (e.g., mRNA) comprises modifications including complete substitution of either 5-methylcytidine (5mC) for cytidine or pseudouridine (psi) for uridine.

In some embodiments, OCT4, KLF4, and/or SOX2 expression may be activated using a CRISPR-activating system. In some embodiments, expression of one or more transcription factors selected from the group consisting of OCT4, KLF4, SOX2, and combinations thereof may be activated using a CRISPR-activating system. See, e.g., Liao et al., Cell. 2017 Dec. 14; 171(7):1495-1507.e15; Liu et al., 2018, Cell Stem Cell 22, 1-10 Feb. 1, 2018. In general, a CRISPR-activating system comprises an enzymatically dead Cas9 nuclease (or nuclease-deficient Cas9 (dCas9)) fused to a transcription activation complex (e.g., comprising VP64, P65, Rta, and/or MPH). Non-limiting examples of sequences encoding VP64, P65, Rta, and/or MPH are provided below. A VP64, P65, Rta, or MPH may be encoded by a sequence that comprises a sequence that is at least 70% (e.g., 75%, 80%, 85%, 90%, 95%, 98%, 99%, or 100%) identical to any of the VP64, P65, Rta, and/or MPH sequences described herein. This Cas9 fusion protein may be referred to as a CRISPR activator. A guide RNA targeting the promoter and/or enhancer region of a gene of interest is used in a CRISPR-activating system to target the dCas9-transcription activation complex and drive expression of the endogenous gene.

In some embodiments, expression of OCT4; KLF4; SOX2; or any combination thereof may be activated using a transcription activator-like effector nucleases (TALEN) or a Zinc-finger nuclease (ZFN) system.

The engineered nucleic acids of the present disclosure may encode sgRNA to target and the promoter and/or enhancer region of the endogenous locus of OCT4, SOX2, and/or KLF4 in a cell. The engineered nucleic acids of the present disclosure may encode sgRNA to target and the promoter and/or enhancer region of the endogenous locus of one or more transcription factors selected from OCT4; SOX2; KLF4; and any combinations thereof in a cell. In some embodiments, the engineered nucleic acid (e.g., expression vector) further encodes a dCas9 (dead Cas9) and a transcriptional activation complex (e.g., VP64, P65, Rta, MPH). In some embodiments, the dCas9 (dead Cas9) and a transcriptional activation complex (e.g., VP64, P65, Rta, MPH) is administered to a cell on a engineered nucleic acid (e.g. expression vector). In some embodiments, the vector encoding the sgRNA and/or a dCas9 (dead Cas9) and a transcriptional activation complex (e.g., VP64, P65, Rta, MPH) is a viral vector (e.g., AAV vector). In some embodiments, dCas9 (dead Cas9) and a transcriptional activation complex (e.g., VP64, P65, Rta, MPH) is introduced into a cell as protein.

In some embodiments, guide RNA targeting the enhancer and/or promoter region of OCT4, SOX2, and/or KLF4 is formulated in a nanoparticle and injected with dCas9-VP64 protein. In some embodiments, guide RNA targeting the enhancer and/or promoter region of OCT4, SOX2, KLF4, or any combination thereof is formulated in a nanoparticle and injected with dCas9-VP64 protein. In some embodiments, the guide RNA and/or nucleic acid encoding dCas9 (dead Cas9) and a transcriptional activation complex (e.g., VP64, P65, Rta, MPH) is administered as naked nucleic acid (e.g., naked DNA formulated in a nanoparticle). In some embodiments, the guide RNA and/or nucleic acid encoding dCas9 (dead Cas9) and a transcriptional activation complex (e.g., VP64, P65, Rta, MPH) is delivered via a recombinant virus (e.g., lentivirus, adenovirus, retrovirus, herpes virus, alphavirus, vaccinia virus or adeno-associated virus (AAV)).

Non-limiting example, sequences of guide RNAs targeting the endogenous OCT4 locus or SOX2 locus are provided in Liu et al., Cell Stem Cell. 2018 Feb. 1; 22(2):252-261.e4. Non-limiting examples of guide RNAs targeting OCT4, SOX2, and/or KLF4 are also provided in Weltner et al., Nat Commun. 2018 Jul. 6; 9(1):2643.

Without being bound by a particular theory, use of a CRISPR-CAS9 system to activation endogenous expression of OCT4, KLF4, and/or SOX2 in the absence of c-Myc expression may obviate potential toxicity associated with exogenous gene expression and/or superphysiological gene expression.

Nucleic acids (e.g., engineered nucleic acids) encoding a transcription factor (OCT4, SOX2, KLF4, or any combination thereof) or encoding an inducing agent) may be introduced into an expression vector using conventional cloning techniques. Suitable expression vectors include vectors with a promoter (e.g., a constitutive or inducible promoter, including a TRE promoter) operably-linked to a nucleic acid (e.g., engineered nucleic acid) encoding OCT4, SOX2, KLF4, or any combination thereof, and a terminator sequence (e.g., a SV40 sequence as described herein). In some embodiments, a nucleic acid (e.g., engineered nucleic acid) encodes a promoter operably linked to a nucleic acid encoding an inducing agent. In some embodiments, a vector comprises a WPRE sequence. Expression vectors containing the necessary elements for expression are commercially available and known to one of ordinary skill in the art (see, e.g., Sambrook et al., Molecular Cloning: A Laboratory Manual, Fourth Edition, Cold Spring Harbor Laboratory Press, 2012).

Vectors of the invention may further comprise a marker sequence for use in the identification of cells that have or have not been transformed or transfected with the vector, or have been reprogrammed. Markers include, for example, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds, genes encoding enzymes with activities detectable by standard assays known in the art (e.g., 0-galactosidase, senescence-associated beta-galactosidase, luciferase or alkaline phosphatase), and genes that visibly affect the phenotype of transformed or transfected cells, hosts, colonies or plaques (e.g., green fluorescent protein). In some embodiments, the vectors used herein are capable of autonomous replication and expression of the structural gene products present in the DNA segments to which they are operably linked.

In certain embodiments, the expression vector comprises an inducible promoter (e.g., a tetracycline-responsive promoter) operably linked to a sequence encoding a transcription factor (e.g., OCT4, SOX2, KLF4, or any combination thereof). In certain embodiments, the promoter operably linked to a sequence encoding a transcription factor (e.g., OCT4, SOX2, KLF4, or any combination thereof) is a tissue-specific or cell type-specific promoter (e.g., brain-specific, liver-specific, muscle-specific, nerve cell-specific, glial cell-specific, endothelial cell-specific, lung-specific, heart-specific, bone-specific, intestine-specific, skin-specific promoters, or eye-specific promoter). As an example, the muscle-specific promoter may be a desmin promoter (e.g., a sequence that is at least 70% (e.g., at least 75%, 80%, 85%, 90%, 95%, 98%, 99%, or 100%) identical to SEQ ID NO: 29). In some embodiments, an eye-specific promoter may be a promoter that is at least 70% (e.g., at least 75%, 80%, 85%, 90%, 95%, 98%, 99%, or 100%) identical to a sequence selected from SEQ ID NOs: 101-104.

In certain embodiments, the promoter operably linked to a sequence encoding a transcription factor (e.g., OCT4, SOX2, KLF4, or any combination thereof) is age- or senescence-specific (e.g. the age- or senescence-specific promoter may be a p16 promoter or a Cas9-directed transcription factor that binds to methylated DNA, which is known to accumulate with age).

In certain embodiments, an expression vector comprises a constitutive promoter operably linked to a nucleic acid (e.g., engineered nucleic acid) encoding OCT4, SOX2, KLF4, or any combination thereof. In some embodiments, such a vector may be inactivated using a Clustered Regularly Interspaced Short Palindromic Repeats (CRISPR)/guide RNA system. For example, a guide RNA may be complementary to the vector and is capable of targeting a Cas9 nuclease to the vector. In some embodiments, the guide RNA is complementary to a transgene (e.g. transgene encoding OCT4, KLF4, SOX2, or a combination thereof) in any of the expression vectors described herein. Cas9 may then generate double-stranded breaks in the vector and/or mutate the vector, rendering the vector inactive.

In certain embodiments, the promoter operably linked to a sequence encoding an inducing agent is a constitutive promoter (e.g., CMV, EF1 alpha, a SV40 promoter, PGK1, UBC, CAG, human beta actin gene promoter, or UAS). In certain embodiments, the promoter operably linked to a sequence encoding an inducing agent is a tissue-specific promoter (e.g., brain-specific, liver-specific, muscle-specific, nerve cell-specific, lung-specific, heart-specific, bone-specific, intestine-specific, skin-specific promoters, or eye-specific promoter). As an example, the muscle-specific promoter may be a desmin promoter (e.g., a sequence that is at least 70% (e.g., at least 75%, 80%, 85%, 90%, 95%, 98%, 99%, or 100%) identical to SEQ ID NO: 29).

A nucleic acid (e.g., engineered nucleic acid) (e.g., an expression vector) may further comprise a separator sequence (e.g., an IRES or a polypeptide cleavage signal). Exemplary polypeptide cleavage signals include 2A peptides (e.g., T2A, P2A, E2A, and F2A). A 2A peptide may comprise a sequence that is at least 70% (e.g., at least 75%, 80%, 85%, 90%, 95%, 98%, 99%, or 100%) identical to SEQ ID NO: 9. For nucleic acids (e.g., engineered nucleic acids) (e.g., expression vectors) encoding more than one transcription factor (e.g., OCT4, SOX2, KLF4, or any combination thereof), each transcription factor may be operably linked to a different promoter or to the same promoter. The transcription factors may be separated (e.g., by peptide separator sequence) on the nucleic acid. Expression of the nucleic acid (e.g., engineered nucleic acid) results in separate amino acid sequences encoding each transcription factor.

In certain embodiments, an expression vector (e.g., an expression vector encoding OCT4, KLF4, SOX2, or a combination thereof) of the present disclosure may further comprise a selection agent (e.g., an antibiotic, including blasticidin, geneticin, hygromycin B, mycophenolic acid, puromycin, zeocin, actinomycin D, ampicillin, carbenicillin, kanamycin, and neomycin) and/or detectable marker (e.g., GFP, RFP, luciferase, CFP, mCherry, DsRed2FP, mKate, biotin, FLAG-tag, HA-tag, His-tag, Myc-tag, V5-tag, etc.).

In certain embodiments, an expression vector encoding an inducing agent of the present disclosure may further comprise a selection agent (e.g., an antibiotic, including blasticidin, geneticin, hygromycin B, mycophenolic acid, puromycin, zeocin, actinomycin D, ampicillin, carbenicillin, kanamycin, and neomycin) and/or detectable marker (e.g., GFP, RFP, luciferase, CFP, mCherry, DsRed2FP, mKate, biotin, FLAG-tag, HA-tag, His-tag, Myc-tag, V5-tag, etc.).

In certain embodiments, an expression vector (e.g., encoding OCT4, SOX2, KLF4, or any combination thereof) is present on a viral vector (e.g., AAV vector). In certain embodiments, an expression vector encoding an inducing agent is present on a viral vector (e.g., AAV vector). An AAV vector, as used herein, generally comprises ITRs flanking an expression cassette (e.g., a nucleic acid (e.g., engineered nucleic acid) comprising a promoter sequence operably linked to a sequence encoding OCT4, SOX2, KLF4, or any combination thereof and a terminator sequence, a nucleic acid (e.g., engineered nucleic acid) comprising a promoter sequence operably linked to a sequence encoding an inducing agent, or a combination thereof).

In certain embodiments, the number of base pairs between two ITRs in an AAV vector of the present disclosure is less than 5 kilobases (kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb). In certain embodiments, an AAV vector with a distance of less than 4.7 kb between two ITRs is capable of being packaged into virus at a titer of at least $0.5\times10^{10}$ particle forming units per ml (pfu/ml), at least $1\times10^{10}$ pfu/ml, at least $5\times10^{10}$ pfu/ml, at least $1\times10^{11}$ pfu/ml, at least $5\times10^{11}$ pfu/ml, at least $1\times10^{12}$ pfu/ml, at least $2\times10^{12}$ pfu/ml, at least $3\times10^{12}$ pfu/ml, at least $4\times10^{12}$ pfu/ml, at least $5\times10^{12}$ pfu/ml, at least $6\times10^{12}$ pfu/ml, at least $7\times10^{12}$ pfu/ml, at least $8\times10^{12}$ pfu/ml, at least $9\times10^{12}$ pfu/ml, or at least $1\times10^{13}$ pfu/ml.

In certain embodiments, an expression vector of the present disclosure is at least 1 kilobase (kb) (e.g., at least 1 kb, 2 kb, 3 kb, 4 kb, 5 kb, 6 kb, 7 kb, 8 kb, 9 kb, 10 kb, 50 kb, or 100 kb). In certain embodiments, an expression vector of the present disclosure is less than 10 kb (e.g., less than 9 kb, less 8 kb, less than 7 kb, less than 6 kb, less than 5 kb, less than 4 kb, less than 3 kb, less than 2 kb, or less than 1 kb).

Without being bound by a particular theory, an expression vector (e.g., an AAV vector) that encodes OCT4, SOX2, and KLF4 under one promoter results in more efficient transduction of all three transcription factors in vivo compared to separate nucleic acids (e.g., engineered nucleic acids) encoding one or two of the transcription factors. In certain embodiments, the infection efficiency of a recombinant virus (e.g., lentivirus, alphavirus, vaccinia virus, retrovirus, adenovirus, herpes virus, or AAV) harboring a vector of the present disclosure in cells (e.g., animal cells, including mammalian cells) is at least 20% (e.g., at least 30%, at least 40%, at least 50%, at least 60%, at least 70%, at least 80%, or at least 90%, or 100%).

Recombinant Viruses

Aspects of the present disclosure provide recombinant viruses (e.g., lentiviruses, alphaviruses, vaccinia viruses, adenoviruses, herpes viruses, retroviruses, or AAVs). The recombinant viruses (e.g., lentiviruses, alphaviruses, vaccinia viruses, adenoviruses, herpes viruses, retroviruses, or AAVs) may harbor a nucleic acid (e.g., engineered nucleic acid) (e.g., expression vector) encoding a transcription factor (e.g., OCT4, SOX2, KLF4, or any combination thereof), or a combination thereof. In some embodiments, a recombinant virus harbors a nucleic acid encoding at least two transcription factors selected from OCT4, SOX2, and KLF4 (e.g., OCT4 and SOX2; KLF4 and SOX2; OCT4, KLF4, and SOX2; or OCT4 and KLF4). In some embodiments, a recombinant virus harbors a nucleic acid encoding at least three transcription factors selected from OCT4, SOX2, and KLF4 (e.g., OCT4, SOX2, and KLF4). In some instances, a recombinant virus of the present disclosure comprises a nucleic acid encoding an inducing agent.

In certain embodiments, recombinant virus is a recombinant AAV. In some embodiments, a recombinant AAV has tissue-specific targeting capabilities, such that a transgene of the AAV will be delivered specifically to one or more predetermined tissue(s). Generally, the AAV capsid is a relevant factor in determining the tissue-specific targeting capabilities of an AAV. An AAV capsid may comprise an amino acid sequence derived from AAV1, AAV2, AAV3, AAV4, AAV5, AAV6, AAV7, AAV8, AAV9, AAV10, AAV11, and variants thereof. Non-limiting examples of the tissue-specificity of AAV serotypes are provided in Table 1. An "x" indicates that the indicated AAV serotype is capable of delivering a transgene to a specific tissue.

TABLE 1

Non-limiting examples of AAV serotypes and their utility in specific tissues.

| AAV serotype | Relevant Tissue | | | | | | | | |
|---|---|---|---|---|---|---|---|---|---|
| | Liver | Heart | Muscle (e.g; Skeletal Muscle) | Eye | Central Nervous System (CNS) | Central Nervous System (Blood-brain barrier) | Pancreas | Lung | Immune System (T-cells, B-cells and Dendritic Cells) |
| AAV1 | | x | x | | x | | | | |
| AAV2 | x | | x | x | x | | | | |
| AAV3 | x | | x | x | | | | x | |

TABLE 1-continued

Non-limiting examples of AAV serotypes and their utility in specific tissues.

| AAV serotype | Relevant Tissue | | | | | | | | |
|---|---|---|---|---|---|---|---|---|---|
| | Liver | Heart | Muscle (e.g; Skeletal Muscle) | Eye | Central Nervous System (CNS) | Central Nervous System (Blood-brain barrier) | Pancreas | Lung | Immune System (T-cells, B-cells and Dendritic Cells) |
| AAV4 | | | x | x | x | | | | |
| AAV5 | | | | x | x | | x | x | |
| AAV6 (e.g., AAV6.2) | | x | x | | | | | x | x |
| AAV7 | x | | x | | | | | | |
| AAV8 | x | | x | | x | | x | | |
| AAV9 | x | x | x | x | x | x | x | x | |
| AAV10 (e.g., AAVrh10) | x | x | x | x | x | x | x | x | |
| AAVDJ | x | | x | | x | | | | |
| AAVPHP.B | | | | | x | x | | | |

Recombinant AAVs comprising a particular capsid protein may be produced using any suitable method. See, e.g., U.S. Patent Application Publication, US 2003/0138772, which is incorporated herein by reference. AAV capsid protein sequences also known in the art. See, e.g., Published PCT Application, WO 2010/138263, which is incorporated herein by reference. Generally, recombinant AAV is produced in a host cell with the following components: (1) a nucleic acid (e.g., engineered nucleic acid) sequence encoding an AAV capsid protein or a fragment thereof, (2) a nucleic acid (e.g., engineered nucleic acid) encoding a functional rep gene, (3) a recombinant AAV vector comprising AAV inverted terminal repeats flanking a transgene (e.g., nucleic acids (e.g., engineered nucleic acids) encoding OCT4, KLF4, SOX2, or a combination thereof), and (4) helper functions that allow for packaging of the recombinant AAV vector into AAV capsid proteins. In some instances, a recombinant AAV vector comprises a nucleic acid encoding an inducing agent. In certain embodiments, the helper functions are introduced via a helper vector that is known in the art.

In some instances, a suitable host cell line (e.g., HEK293T cells) may be used for producing a recombinant AAV disclosed herein following routine practice. One or more expression vectors encoding one or more of the components described above may be introduced into a host cell by exogenous nucleic acids (e.g., engineered nucleic acids), which can be cultured under suitable conditions allowing for production of AAV particles. When needed, a helper vector can be used to facilitate replication, to facilitate assembly of the AAV particles, or any combination thereof. In certain embodiments, the recombinant AAV vector is present on a separate nucleic acid (e.g., engineered nucleic acid) from the other components (e.g., a nucleic acid (e.g., engineered nucleic acid) sequence encoding an AAV capsid protein or a fragment thereof, a nucleic acid (e.g., engineered nucleic acid) encoding a functional rep gene, and helper functions that allow for packaging of the recombinant AAV vector into AAV capsid proteins. In certain embodiments, a host cell may stably express one or more components needed to produce AAV virus. In that case, the remaining components may be introduced into the host cell. The supernatant of the cell culture may be collected, and the viral particles contained therein can be collected via routine methodology.

Methods of Activating OCT4, SOX2, and KLF4, Each Alone or in Combination, and Replacements Thereof Aspects of the present disclosure, in some embodiments, relate to activating OCT4, SOX2, and KLF4, each alone or in combination, in a cell, tissue and/or organ. In some embodiments, OCT4, SOX2, and KLF4, each alone or in combination, is activated in the absence of c-Myc activation. The cell, tissue, and/or organ may be in vivo (e.g., in a subject) or be ex vivo. As used herein, activation includes any nucleic acid (e.g., nucleic acid comprising RNA, comprising DNA, or any combination thereof), protein, antibody, chemical agent, or any combination thereof that is capable of increasing the biological activity of a protein of interest (e.g., OCT4, SOX2, and/or KLF4). Biological activity (e.g., gene expression, reprogramming ability, transcription factor activity, etc.) may be measured using any routine method known in the art. In some embodiments, any nucleic acid (e.g., nucleic acid comprising RNA, comprising DNA, or any combination thereof), protein, antibody, chemical agent, or any combination thereof described herein replaces OCT4, SOX2 and/or KLF4. In some embodiments, any nucleic acid (e.g., nucleic acid comprising RNA, comprising DNA, or any combination thereof), protein, antibody, chemical agent, or any combination thereof described herein replaces OCT4, SOX2, KLF4, or any combination thereof. In some embodiments, any of the nucleic acids (e.g., engineered nucleic acid) encoding an inducing agent, engineered proteins encoding an inducing agent, chemical agents capable of modulating (e.g., activating or inhibiting) the activity of an inducing agent, and/or recombinant viruses encoding an inducing agent described herein is used to activate an inducing agent.

Activation of OCT4, SOX2, and KLF4, each alone or in combination includes increasing expression (e.g., RNA and/or protein expression) of OCT4, SOX2, and KLF4, each alone or in combination. In some embodiments, the expression of OCT4, SOX2, and KLF4, each alone or in combination is increased by at least 1%, 5%, 10%, 20%, 30%, 40%, 50%, 60%, 70%, 80%, 90%, 100%, 200%, 300%, 400%, 500%, 600%, 700%, 800%, 900%, or 1000% after administration of a nucleic acid (e.g., nucleic acid comprising RNA, comprising DNA, or any combination thereof) encoding OCT4, SOX2, and/or KLF4, protein encoding OCT4, SOX2, and/or KLF4, antibody capable of activating encoding OCT4, SOX2, and/or KLF4, chemical agent capable of activating encoding OCT4, SOX2, and/or KLF4, or any combination thereof to a cell, tissue, organ, and/or subject compared to before administration. In some embodiments, the expression of OCT4, SOX2, and KLF4, each alone or in combination is increased by at least 1%, 5%, 10%, 20%, 30%, 40%, 50%, 60%, 70%, 80%, 90%, 100%, 200%, 300%, 400%, 500%, 600%, 700%, 800%, 900%, or 1000% after administration of a nucleic acid (e.g., nucleic acid comprising RNA, comprising DNA, or any combination thereof) encoding OCT4, SOX2, KLF4, or any combination thereof, protein encoding OCT4, SOX2, KLF4, or any combination thereof, antibody capable of activating encoding OCT4, SOX2, KLF4, or any combination thereof, chemical agent capable of activating encoding OCT4, SOX2, KLF4, or any combination thereof, or any combination thereof to a cell, tissue, organ, and/or subject compared to before administration.

Activation of a inducing agent includes increasing expression (e.g., RNA and/or protein expression) of an inducing agent. In some embodiments, the expression of an inducing agent, is increased by at least 1%, 5%, 10%, 20%, 30%, 40%, 50%, 60%, 70%, 80%, 90%, 100%, 200%, 300%, 400%, 500%, 600%, 700%, 800%, 900%, or 1000% after administration of a nucleic acid (e.g., nucleic acid comprising RNA, comprising DNA, or any combination thereof) encoding the inducing agent, protein encoding the inducing agent, chemical agent capable of modulating the activity of the inducing agent, or any combination thereof to a cell, tissue, organ, and/or subject compared to before administration.

Expression may be measured by any routine method known in the art, including quantification of the level of a protein of interest (e.g., using an ELISA, and/or western blot analysis with antibodies that recognize a protein of interest) or quantification of RNA (e.g., mRNA) levels for a gene of interest (e.g., using reverse transcription polymerase chain reaction).

In addition to the engineered nucleic acids discussed herein, OCT4, SOX2, KLF4, alone or in combination may be activated in a cell, tissue, organ, and/or subject through the use of engineered proteins. For example, protein encoding OCT4, SOX2, and/or KLF4 may be generated (e.g., recombinantly or synthetically) and administered to a cell, tissue, organ, and/or subject through any suitable route. For example, protein encoding one or more transcription factors selected from the group consisting of OCT4; SOX2; KLF4; and any combinations thereof may be generated (e.g., recombinantly or synthetically) and administered to a cell, tissue, organ, and/or subject through any suitable route.

In some embodiments, activating expression of OCT4; SOX2; KLF4; a replacement thereof; or any combination thereof from a tetracycline-inducible expression vector comprises administering a tetracycline (e.g., doxycycline) to a cell, organ, tissue, or a subject. As one of ordinary skill in the art would appreciate, the route of tetracycline administration may be dependent on the type of cell, organ, tissue, and/or characteristics of a subject. In some embodiments, tetracycline is administered directly to a cell, organ, and/or tissue. As a non-limiting example, tetracycline may be administered to the eye of a subject through any suitable method, including eye drops comprising tetracycline, sustained release devices (e.g., micropumps, particles, and/or drug depots), and medicated contact lenses comprising a tetracycline). In some embodiments, tetracycline is administered systemically (e.g., through drinking water or intravenous injection) to a subject. Tetracycline may be administered topically (e.g., in a cream) or through a subcutaneous pump (e.g., to deliver tetracycline to a particular tissue). Tetracycline may be administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in particles (e.g., nanoparticles, microparticles), in lipid compositions (e.g., liposomes), or by other method or any combination of the forgoing as would be known to one of ordinary skill in the art (see, for example, Remington's Pharmaceutical Sciences (1990), incorporated herein by reference).

As a non-limiting example, an engineered protein may be further modified or formulated for delivery to a cell, tissue, organ, and/or subject. For example, protein transduction domains (i.e., PTD or cell-penetrating peptides) may be attached to an engineered protein (e.g., OCT4, SOX2, and/or KLF4). As a non-limiting example, a protein transduction domain (i.e., PTD or cell-penetrating peptide) may be attached to an engineered protein encoding an inducing agent. Without being bound by a particular theory, a protein transduction domain facilitate delivery of a cargo (e.g., a protein, nucleic acids, nanoparticles, viral particles, etc.) across cellular membranes. Protein transduction domains include cationic peptides, hydrophobic peptides, and/or a cell specific peptides. See, e.g., Zhou et al., Cell Stem Cell. 2009 May 8; 4(5):381-4; Zahid et al., Curr Gene Ther. 2012 October; 12(5):374-80.

In some embodiments, a protein encoding OCT4, SOX2, and/or KLF4, and/or an inducing agent is formulated in a nanoparticle (e.g., for nuclear delivery). In some embodiments, a protein encoding OCT4, SOX2, KLF4, or any combination thereof (e.g., OCT4 and SOX2; KLF4 and SOX2; OCT4 and KLF4; or KLF4, SOX2, and OCT4) is formulated in a nanoparticle (e.g., for nuclear delivery). In certain embodiments, a nanoparticle further comprises a protein encoding an inducing agent. For example, chitosan [poly(N-acetyl glucosamine)] is a biodegradable polysaccharide and may be used to formulate nanoparticles by several methods. In some embodiments, a chitosan polymeric nanoparticle is loaded with protein encoding OCT4, SOX2, and/or KLF4, and/or an inducing agent and is delivered to the nucleus of a cell. See, e.g., Tammam et al., Oncotarget. 2016 Jun. 21; 7(25):37728-37739.

In some embodiments, a chemical agent, antibody and/or protein replaces OCT4, SOX2, and/or KLF4. In some embodiments, a chemical agent, antibody, a protein, or any combination thereof replaces OCT4, SOX2, KLF4, or any combination thereof (e.g., OCT4 and SOX2; OCT4 and KLF4; KLF4 and SOX2; or KLF4, SOX2, and OCT4). For example, a chemical agent, antibody and/or protein may promote expression of OCT4, SOX2, and/or KLF4. In certain instances, a chemical agent, antibody and/or protein may promote expression of one or more transcription factors selected from OCT4; SOX2; KLF4; and any combinations thereof. In some embodiments, a chemical agent, antibody and/or protein may activate target genes downstream of OCT4, SOX2, and/or KLF4. In some embodiments, a chemical agent, antibody, a protein, or any combination thereof may activate target genes downstream of one or more transcription factors selected from the group consisting of OCT4; SOX2; KLF4; and any combinations thereof. In some embodiments, a chemical agent, antibody and/or protein is said to replace OCT4, SOX2, and/or KLF4 if the chemical agent, antibody and/or protein may be used together with the other two transcription factors and promote cellular reprogramming. In some embodiments, a chemical agent, antibody, protein, or any combination thereof is said to replace OCT4, SOX2, KLF4, or any combination thereof if the chemical agent, antibody, protein or any combination thereof may be used together with the other two transcription factors and promote cellular reprogramming. For example, cellular reprogramming may be determined by measuring gene expression (e.g., expression of embryonic markers and/or pluripotency markers). In some embodiments, pluripotency markers include AP, SSEA1, and/or Nanog.

In some embodiments, an antibody is used to activate OCT4, SOX2, and/or KLF4. In some embodiments, an antibody is used to activate one or more transcription factors selected from OCT4, SOX2, KLF4, or any combination thereof. In some embodiments, the antibody does not target OCT4, SOX2, and/or KLF4. In some embodiments, the antibody does not target OCT4, SOX2, KLF4, or any combination thereof. In some embodiments, the antibody increases expression of OCT4, SOX2, and/or KLF4. In some embodiments, the antibody increases expression of OCT4, SOX2, KLF4, or any combination thereof. In some embodiments, the antibody does not increase expression of OCT4, SOX2, and/or KLF4. In some embodiments, an antibody replaces OCT4, SOX2, and/or KLF4. In some embodiments, the antibody does not increase expression of OCT4, SOX2, KLF4, or any combination thereof. In some embodiments, an antibody replaces OCT4, SOX2, KLF4, or any combination thereof. Any suitable method of identifying antibodies that can replace a transcription factor (e.g., OCT4, SOX2, and/or KLF4) may be used. Any suitable method of identifying antibodies that can replace a transcription factor (e.g., OCT4, SOX2, KLF4, or any combination thereof) may be used. See, e.g., Blanchard et al., Nat Biotechnol. 2017 October; 35(10):960-968.

In some embodiments, another protein (e.g., a nucleic acid encoding the protein or a polypeptide encoding the protein) may be used to replace OCT4, SOX2, and/or KLF4. In some embodiments, another protein (e.g., a nucleic acid encoding the protein or a polypeptide encoding the protein) may be used to replace OCT4, SOX2, KLF4, or a combination thereof. For example, OCT4 may be replaced by Tet1, NR5A-2, Sall4, E-cadherin, NKX3-1, or any combination thereof. In some embodiments, OCT4, SOX2, and/or KLF4 may be replaced by NANOG and/or TET2. In some embodiments, OCT4, SOX2, KLF4, or any combination thereof may be replaced by NANOG and/or TET2. See, e.g., Nat Cell Biol. 2018 August; 20(8):900-908; Gao et al., Cell Stem Cell. 2013 Apr. 4; 12(4):453-69. Nanog and Lin28 can replace Klf4. See, e.g., Yu et al, Science. 318, 1917-1920, 2007). In some embodiments, OCT4, SOX2, and/or KLF4 is replaced by Tet3 (tet methylcytosine dioxygenase 3). In some embodiments, OCT4, SOX2, KLF4, or any combination thereof is replaced by Tet3 (tet methylcytosine dioxygenase 3). In some embodiments, a nucleic acid encoding a Tet1 DNA demethylase comprises a sequence that is at least 70% (e.g., at least 75%, 80%, 85%, 90%, 95%, 98%, 99%, or 100%) identical to NM_030625.3 or NM_001253857.2. In some embodiments, an amino acid encoding a Tet1 DNA demethylase comprises a sequence that is at least 70% (e.g., at least 75%, 80%, 85%, 90%, 95%, 98%, 99%, or 100%) identical to NP_085128.2 or NP_001240786.1. In some embodiments, a nucleic acid encoding a Tet2 DNA demethylase comprises a sequence that is at least 70% (e.g., at least 75%, 80%, 85%, 90%, 95%, 98%, 99%, or 100%) identical to NM_001127208.2, NM_001040400.2, NM_001346736.1, or NM_017628.4. In some embodiments, an amino acid encoding a Tet2 DNA demethylase comprises a sequence that is at least 70% (e.g., at least 75%, 80%, 85%, 90%, 95%, 98%, 99%, or 100%) identical to NP_060098.3, NP_001035490.2, NP_001333665.1, or NP_001120680.1. In some embodiments, a nucleic acid encoding a Tet3 DNA demethylase comprises a sequence that is at least 70% (e.g., at least 75%, 80%, 85%, 90%, 95%, 98%, 99%, or 100%) identical to NM_001287491.2, NM_001347313.1, NM_183138.2, or NM_001366022.1. In some embodiments, an amino acid encoding a Tet3 DNA demethylase comprises a sequence that is at least 70% (e.g., at least 75%, 80%, 85%, 90%, 95%, 98%, 99%, or 100%) identical to NP_001274420.1, NP_001334242.1, NP_898961.2, or NP_001352951.1. Tet1, Tet2, and/or Tet3 may be derived from any species. In some embodiments, Tet1, Tet2, and/or Tet3 is a truncated form of a wild-type counterpart. As a non-limiting example, Tet1, Tet2, and/or Tet3 is N-terminally truncated compared to a wild-type Tet1, Tet2, and/or Tet3 counterpart and is catalytically active. In some embodiments, Tet1, Tet2, and/or Tet3 only comprises the catalytic domain of Tet1, Tet2, and/or Tet3. In some embodiments, Tet1, Tet2, and/or Tet3 comprises the catalytic domain of Tet1, Tet2, Tet3, or any combination thereof. Non-limiting examples of functional truncated Tet1 may be found in Hrit et al., Elife. 2018 Oct. 16; 7. pii: e34870.

Additional methods of replacing OCT4, SOX2, and/or KLF4 to promote cellular reprogramming are known in the art. See, e.g., Heng et al., Cell Stem Cell 6, 167-174 (2010); Eguchi et al., Proc. Natl Acad. Sci. USA 113, E8257-E8266 (2016); Gao et al., Cell Stem Cell 12, 453-469 (2013); Long et al., Cell Res. 25, 1171-1174 (2015); Hou et al., Science 341, 651-654 (2013); Redmer et al., EMBO Rep. 12, 720-726 (2011); Tan et al., J. Biol. Chem. 290, 4500-4511 (2014); Anokye-Danso et al., Cell Stem Cell 8, 376-388 (2011); Miyoshi et al., Cell Stem Cell 8, 633-638 (2011); Shu et al., Cell 153, 963-975 (2013); Yu, J. et al., Science 318, 1917-1920 (2007).

In some embodiments, a chemical agent replaces OCT4, SOX2, and/or KLF4 (e.g., can be used in place of OCT4, SOX2, and/or KLF4 along with the other two transcription factors to promote cellular reprogramming). In some embodiments, a chemical agent replaces OCT4, SOX2, KLF4, or any combination thereof (e.g., can be used in place of OCT4, SOX2, KLF4, or any combination thereof, along with the other two transcription factors to promote cellular reprogramming). For example, SOX2 may be replaced by CHIR, FSK, or 616452. OCT4 may be replaced by DZNep. Since Sall4 may be used to replace OCT4 as mentioned above, any compound that replaces Sall4 may also be used to replace OCT4. For example, CHIR, FSK, and 616452 may be used to replace Sall4. Nanog may be replaced with 2i medium. See, e.g., Hou et al., Science. 2013 Aug. 9; 341(6146):651-4. See, also, e.g., Zhao et al., Cell. 2015 Dec. 17; 163(7):1678-91.

In some embodiments, chemical reprogramming comprises using chemicals that reduce the toxicity of chemical agents that induce reprogramming. Non-limiting examples of chemicals that reduce the toxicity of chemical reprogramming include ROCK inhibitors (e.g., Y27632 and Fasudil) and P38 MAPK inhibitors (e.g., SB203580 and BIRB796). See, e.g., Li et al., Cell Stem Cell. 2015 Aug. 6; 17(2):195-203.

OCT4, KLF4, SOX2, replacements, or any combination thereof may be activated (e.g., expression may be induced) in combination with activating an enhancer of reprogramming and/or inhibiting a barrier of reprogramming. An enhancer of reprogramming may be activated using any suitable method known in the art, including overexpression of the enhancer, increasing expression of an endogenous gene encoding the enhancer (e.g., using CRISPR technology), use of a chemical agent and/or antibody to increase the biological activity of the enhancer, and use a chemical agent and/or antibody to promote expression of the enhancer. A barrier of reprogramming may be inhibited using any suitable method known in the art, including knocking down expression of the inhibitor (e.g., with siRNAs, miRNAs, shRNAs), knocking out an endogenous copy of the inhibitor (e.g., using CRISPR technology, TALENs, zinc finger nucleases, etc.), using a chemical agent and/or antibody to decrease the biological activity of the inhibitor, and using a chemical agent and/or antibody to decrease expression of the inhibitor.

Non-limiting examples of enhancers and barriers of reprogramming are provided in Table 2. See also, e.g., Ebrahimi, Cell Regen (Lond). 2015 Nov. 11; 4:10, which is incorporated by reference in its entirety for this purpose.

In some embodiments, OCT4, SOX2, KLF4, replacements thereof, or any combination thereof are activated in a cell, tissue, organ and/or a subject in combination with a cytokine that facilitates reprogramming. IL6 is a non-limiting example of a cytokine. See, e.g., Mosteiro et al, Science. 2016 Nov. 25; 354(6315), which is hereby incorporated by reference in its entirety for this purpose.

In some embodiments, OCT4, SOX2, KLF4, replacements thereof, or any combination thereof are activated in a cell, tissue, organ and/or a subject in combination with activation of a miRNA (e.g., administration of a miRNA and/or expression of a miRNA). For example, a miRNA that promotes cell cycle progression may be introduced to a cell, tissue, organ, and/or subject. Non-limiting examples of miRNAs that promote cell cycle progression include miR 302-367, miR 371-373, miR-200b, miR-200c, miR-205, miR 290-295, miR-93, miR-106, and miR 135b.

As a non-limiting example, nerve regeneration may be enhanced by combining activation of OCT4, SOX2, KLF4, replacements thereof, or any combination thereof with activation of an enhancer. Non-limiting activation of enhancers

TABLE 2

Non-limiting examples of strategies to enhance reprogramming.

| Reprogramming Enhancing Strategy | |
|---|---|
| | Enhancers |
| Activation of Enhancers | C/EBPα; UTF1; Mef2c; Tdgf1; FOXH1; GLIS1; mutated reprogramming factors, MDM2; Bcl-2; CCL2; Kdm3a, Kdm3b, Kdm4c, and Kdm4b/2b; Jhdm1a/1b; MOF; Mbd1-4 (or their small molecule activators); Wnt/β-catenin signaling; small molecule Pitstops 1 and 2; vitamin C, palbiociclib; cytokines, e.g. IL-6; CDK4, CDK8, CDK19; lincU |
| | Barriers |
| Inhibition of Barriers | p53, p57, p38, p16$^{Ink4a}$/p19$^{Arf}$, p21$^{Cip1}$, Rb<br>TGF-β, MAP kinase, Aurora A kinase, MEK/ERK, Gsk3, Wnt/β-catenin signaling pathways, LATS2, PKC, IP3K, CDK8, CDK19.<br>Native/somatic gene or transcriptional regulatory network (GRN/TRN).<br>Specific members of ADAM family (e.g., ADAM7, ADAM21, ADAM29), endocytosis: (e.g., DRAM1, SLC17A5, ARSD), phosphatase: (e.g., PTPRJ, PTPRK, PTPN11).<br>Chromatin regulators: (e.g., ATF7IP, MacroH2A, Mbd1-4, Setdb1a.<br>Transcription factors: (e.g., TTF1, TTF2, TMF1, T), Bright.<br>Fbxw7 (a member of ubiquitin-proteasome system (UPS))<br>Lzts1, Ssbp3, Arx, Tfdp1, Nfe2, Ankrd22, Msx3, Dbx1, Lasp1, and Hspa8.<br>Cytokines e.g., TNFα<br>Cells (e.g., senescent cells and NK cells) (e.g., navitoclax, BAY117082)<br>NuRD, Mbd1-4, Gatad2a, Chd4 (see, e.g., Mor et al., Cell Stem Cell. 2018 Sep. 6; 23(3): 412-425.e10)<br>KDM1a<br>Kaiso (see, e.g., Kaplun et al., Biochemistry (Mosc). 2019 March; 84(3): 283-290) |

Additional reprogramming enhancers that may be activated in combination with activation of OCT4, KLF4, SOX2, replacements thereof, or any combination thereof, include histone lysine demethylases (e.g., KDM2, KDM3, and KDM4). Histone lysine demethylases may be activated by being overexpressed in a cell, tissue, organ, and/or a subject. Chemical activators of histone lysine demethylases are also encompassed by the present disclosure. For example, vitamin C may be used to activate KDM3 and/or KDM4.

In some embodiments, OCT4, SOX2, KLF4, replacements thereof, or any combination thereof, is activated along with activation of C/EBPα and Tfcp2l1. Without being bound by a particular theory, C/EBPα, and Tfcp2l1 together with Klf4 may drive Tet2-mediated enhancer demethylation and activation during reprogramming.

include overexpression of a member of the KLF family (e.g., KLF7), overexpression of c-Myc, STAT3 activation, SOX11 overexpression, overexpression of Lin28, overexpression of or delivery of soluble protein encoding insulin-like growth factor 1 (IGF1) and osteopontin (OPN), and activation of B-RAF (e.g., introduction of a gain of function mutation). See also, e.g., Blackmore et al., Proc Natl Acad Sci USA. 2012 May 8; 109(19):7517-22; Belin et al., Neuron. 2015 May 20; 86(4):1000-1014; Bareyre et al., Proc Natl Acad Sci USA. 2011 Apr. 12; 108(15):6282-7; Norsworthy et al., Neuron. 2017 Jun. 21; 94(6):1112-1120.e4; Wang et al., Cell Rep. 2018 Sep. 4; 24(10):2540-2552.e6; Liu et al., Neuron. 2017 Aug. 16; 95(4):817-833; O'Donovan et al., J Exp Med, 2014. 211(5): p. 801-14, which is each hereby incorporated by reference in its entirety for this purpose.

In some embodiments, OCT4, SOX2, KLF4, replacements thereof, or any combination thereof, are activated in a cell, tissue, organ, and/or a subject in combination with suppression or knockdown of reprogramming barriers. Non-limiting examples of reprogramming barriers include Chaf1a, Chaf1b, Ube2i, sumo2, and/or Nudt21. See, e.g., Brumbaugh et al., Cell. 2018 Jan. 11; 172(1-2):106-120.e21; Cheloufi et al., Nature. 2015 Dec. 10; 528(7581):218-24; and Borkent et al., Stem Cell Reports, 2016. 6(5): p. 704-716, which is each hereby incorporated by reference in its entirety for this purpose.

As a non-limiting example, a reprogramming barrier may be a DNA methyltransferase (DNMT) may be and a DNMT may be inhibited to promote reprogramming of a tissue, cell, and/or organ. Most DNA methyltransferases use S-adenosyl-L-methionine as a methyl donor. DNMT may be from any species. There are at least three different types of methyltransferases. m6A methyltransferases are capable of methylating the amino group at the c-6 position of adenines in DNA (e.g., Enzyme Commission (EC) No. 2.1.1.72). m4C methyltransferases are capable of generating N4-methylcytosine (e.g., Enzyme Commission (EC) No. 2.1.1.113). M5C methyltransferases are capable of generating C5-methylcytosine (e.g., Enzyme Commission (EC) No. 2.1.1.37).

Non-limiting examples of mammalian DNA methyltransferases (DNMTs) include DNMT1 and its isoforms DNMT1b and DNMT1o (oocytes-specific), DNMT3a, DNMT3b, DNMT3L. GenBank Accession Nos. NM_001130823.3 (isoform a), NM_001318730.1 (isoform c), NM_001318731.1 (isoform d), and NM_001379.3 (isoform b) are non-limiting examples of nucleotide sequences encoding human DNMT1. A nucleic acid encoding a DNMT1 may comprise a sequence that is at least 70% (e.g., at least 75%, 80%, 85%, 90%, 95%, 98%, 99%, or 100%) identical to a sequence set forth in GenBank Accession Nos. NM_001130823.3 (isoform a), NM_001318730.1 (isoform c), NM_001318731.1 (isoform d), and/or NM_001379.3 (isoform b). GenBank Accession Nos. NP_001124295.1 (isoform a), NP_001305659.1 (isoform c), NP_001305660.1 (isoform d), and NP_001370.1 (isoform b) are non-limiting examples of amino acid sequences encoding human DNMT1. An amino acid sequence encoding a DNMT1 may comprise a sequence that is at least 70% (e.g., at least 75%, 80%, 85%, 90%, 95%, 98%, 99%, or 100%) identical to a sequence set forth in GenBank Accession Nos. NP_001124295.1 (isoform a), NP_001305659.1 (isoform c), NP_001305660.1 (isoform d), and/or NP_001370.1 (isoform b). A nucleic acid encoding human DNMT3A includes GenBank Accession No. NM_001320892.1, NM_001320893.1, NM_022552.4, NM_153759.3, NM_175629.2, and NM_175630.1. A nucleic acid encoding a DNMT3A may be at least 70% (e.g., at least 75%, 80%, 85%, 90%, 95%, 98%, 99%, or 100%) identical to a sequence set forth in GenBank Accession Nos. NM_001320892.1, NM_001320893.1, NM_022552.4, NM_153759.3, NM_175629.2, and/or NM_175630.1. An amino acid sequence encoding human DNMT3A includes GenBank Accession Nos. NP_001307821.1, NP_001307822.1, NP_072046.2, NP_715640.2, NP_783328.1, and NP_783329.1. An amino acid sequence encoding a DNMT3A may be at least 70% (e.g., at least 75%, 80%, 85%, 90%, 95%, 98%, 99%, or 100%) identical to a sequence set forth in GenBank Accession Nos. NP_001307821.1, NP_001307822.1, NP_072046.2, NP_715640.2, NP_783328.1, and/or NP_783329.1. A nucleic acid encoding human DNMT3B includes GenBank Accession No. NM_001207055.1, NM_001207056.1, NM_006892.3, NM_175848.1, NM_175849.1, and NM_175850.2. A nucleic acid encoding a DNMT3B may be at least 70% (e.g., at least 75%, 80%, 85%, 90%, 95%, 98%, 99%, or 100%) identical to a sequence set forth in GenBank Accession Nos. NM_001207055.1, NM_001207056.1, NM_006892.3, NM_175848.1, NM_175849.1, and/or NM_175850.2. An amino acid sequence encoding human DNMT3B includes GenBank Accession Nos. NP_001193984.1, NP_001193985.1, NP_008823.1, NP_787044.1, NP_787045.1, and NP_787046.1. An amino acid sequence encoding a DNMT3B may be at least 70% (e.g., at least 75%, 80%, 85%, 90%, 95%, 98%, 99%, or 100%) identical to a sequence set forth in GenBank Accession Nos. NP_001193984.1, NP_001193985.1, NP_008823.1, NP_787044.1, NP_787045.1, and/or NP_787046.1. A nucleic acid encoding human DNMT3L includes GenBank Accession No. NM_013369.3 and NM_175867.2. A nucleic acid encoding a DNMT3L may be at least 70% (e.g., at least 75%, 80%, 85%, 90%, 95%, 98%, 99%, or 100%) identical to a sequence set forth in GenBank Accession Nos. NM_013369.3 and/or NM_175867.2. An amino acid sequence encoding human DNMT3L includes GenBank Accession Nos. NP_037501.2 and NP_787063.1. An amino acid sequence encoding a DNMT3L may be at least 70% (e.g., at least 75%, 80%, 85%, 90%, 95%, 98%, 99%, or 100%) identical to a sequence set forth in GenBank Accession Nos. NP_037501.2 and/or NP_787063.1.

A DNMT may be inhibited using any suitable method known in the art. Suitable methods include knockdown of a DNMT mRNA, genetically knocking out a DNMT, and use of a DNMT inhibitor (e.g., chemical inhibitors). DNMT inhibitors are being investigated in clinical trials (e.g., phase III clinical trials) in the United States of America and beyond. Non-limiting examples of DNMT inhibitors include VIDAZA™ (azacitidine) (e.g., for the treatment of Myelodysplastic Syndromes and treatment of acute myeloid leukemia (AML)), DACOGEN™ (decitabine) (e.g., for treatment of AML and treatment of Chronic myeloid leukemia (CML)), and Guadecitabine (SGI-110) (e.g., for treatment of AML). In 2012, the European Union approved DACOGEN™ (decitabine) for use in patients with AML.

A DNMT may be inhibited by inhibiting a DNMT stabilizer. Suitable methods of inhibiting a DNMT stabilizer include knockdown of the mRNA encoding the stabilizer, genetically knocking out the gene that encodes the stabilizer and use of an inhibitor (e.g., chemical inhibitors). As a non-limiting example, KDM1a, which is also referred to as Lsd1 or Aof2, is a stabilizer of DNMT1. See, e.g., Wang et al., Nat Genet. 2009 January; 41(1):125-9. In some embodiments, KDM1a expression is knocked down using a shRNA disclosed herein or known in the art. In some embodiments, KDM1a is inhibited to prevent injury induced by hypermethylation from DNMTs, which could be useful in promoting reprogramming.

In some embodiments, a histone methyltransferase is a reprogramming barrier and is inhibited to facilitate reprogramming of a cell, tissue and/or organ. Histone methyltransferases may be inhibited by any suitable method, including use of chemical inhibitors. For example, 3-deazaneplanocin A (Dznep), epz004777, and BIX-01294 are examples of histone methyltransferase inhibitors.

In some embodiments, a reprogramming barrier is a histone deacetylase (HDAC) and a HDAC is inhibited to facilitate reprogramming of a cell, tissue, and/or organ. Non-limiting examples of HDAC inhibitors include valproic acid (VPA), trichostatin A (TSA), suberoylanilide hydroxamic Acid (SAHA), sodium butyrate (SB), Belinostat (PXD101), Panobinostat (LBH589), Quisinostat (JNJ-26481585), Abexinostat (PCI-24781), Givinostat (ITF2357), Resminostat (4SC-201), Phenylbutyrate (PBA), Depsipeptide (romidepsin), Entinostat (MS-275), Mocetinostat (MGCD0103), and Tubastatin A (TBA).

In some embodiments, a reprogramming barrier is a NF-1B, and it is inhibited to facilitate reprogramming of a cell, tissue, and/or organ. Non-limiting examples of NF-κB inhibitor includes BAY 11-7082, TPCA 1, and p65 siRNA. See, e.g., the NF-κB small molecule guide compiled by Abcam, which is available on the Abcam website (www.abcam.com/reagents/nf-kb-small-molecule-guide).

In some embodiments, a reprogramming barrier is a cytokine secreted from senescent cells in which a cytokine is inhibited to facilitate reprogramming of a cell, tissue, and/or organ. None limiting examples of cytokines inhibitors include Anti-TNFα (Mahmoudi et al, Biorxiv, 2018) and drugs, including Navitoclax, that kill senescence cells.

In some embodiments, a reprogramming barrier is a microRNA (miRNA) and a microRNA is inhibited to facilitate reprogramming of a cell, tissue, and/or organ. Non-limiting examples of microRNAs that are reprogramming barriers include miR Let-7 and miR-34. Without being bound by a particular theory, inhibition of miR Let-7 may increase the efficiency of reprogramming because miR Let-7 inhibits the cell cycle and inhibition of miR-34 may facilitate reprogramming because miR-34 inhibits the translation of p53.

In some embodiments, OCT4, SOX2, KLF4, replacements thereof, or any combination thereof is activated in a cell, tissue, organ and/or a subject in combination with inhibition of PTEN, SOCS3, RhoA, and/or ROCK to enhance nerve regeneration. In some embodiments, PTEN is deleted, SOCS3 is deleted, RhoA is knocked down, and/or ROCK is knocked down in a cell, tissue, organ and/or subject. See, e.g., Park et al., Science. 2008 Nov. 7; 322 (5903):963-6; Smith et al., Neuron. 2009 Dec. 10; 64(5): 617-23; Koch et al., Front Cell Neurosci. 2014 Sep. 5; 8:273; Koch et al., Cell Death Dis. 2014 May 15; 5:e1225 for descriptions of inhibition of PTEN, SOCS3, RhoA, and/or ROCK. Each reference is hereby incorporated by reference in its entirety for this purpose.

In some embodiments, OCT4, SOX2, KLF4, replacements thereof, or any combination thereof is activated in a cell, tissue, organ and/or a subject in combination with neuronal electrical stimulation (e.g., high-contrast visual stimulation) to promote nerve regeneration. See, e.g., Lim et al., Nat Neurosci. 2016 August; 19(8):1073-84 for a description of high-contrast visual stimulation. This reference is hereby incorporated by reference in its entirety for this purpose.

In some embodiments, OCT4, SOX2, KLF4, replacements thereof, or any combination thereof is activated in a cell, tissue, organ and/or a subject in combination with gamma band light stimulation to promote nerve regeneration. See, e.g., McDermott et al., J Alzheimers Dis. 2018; 65(2): 363-392 for a description of gamma band light stimulation. This reference is hereby incorporated by reference in its entirety for this purpose.

Engineered Cells

Engineered cells and method of producing engineered cells are also encompassed by the present disclosure. The engineered cells, for example, may be useful in cell-based therapies (e.g., stem cell therapies). Although stem cell therapy is currently in clinical trials (see, e.g., David Cyranoski, Nature 557, 619-620 (2018), toxicity (e.g., off-target toxicity) is a concern, Without being bound by a particular theory, the engineered cells of the present disclosure (e.g., cells engineered using AAV vectors encoding OCT4, KLF4, and/or SOX2, and/or an inducing agent) may have a lower toxicity because AAV is does not integrate into the genome of host cells and use of the inducible systems described herein to control expression of OCT4, KLF4, and/or SOX2 may allow for precise control (e.g., amount and timing) of gene expression.

Any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced into a host cell, host tissue, or organ to produce an engineered cell, an engineered tissue, or an engineered organ. Any of the nucleic acids (e.g., engineered nucleic acid) (e.g., expression vector) capable of inducing expression of OCT4; KLF4; SOX2; or any combination thereof, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone, or in combination may be introduced into a host cell, host tissue, or organ to produce an engineered cell, an engineered tissue, or an engineered organ. In some embodiments, a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent is also introduced into a host cell, host tissue, or organ to produce an engineered cell, an engineered tissue, or an engineered organ.

In some embodiments, the engineered cell is an induced pluripotent stem cell (iPSC).

In some embodiments, a viral vector (e.g., an AAV vector, including a vector with a TRE promoter operably linked to a nucleic acid encoding OCT4, KLF4, and SOX2) is packaged into a virus with an AAV-DJ capsid. In some embodiments, the AAV-DJ capsid increases the transduction efficiency into cultured cells compared to cells without the AAV-DJ capsid. In some embodiments, the AAV virus encoding OSK is administered to a cell. In some embodiments, an AAV virus (e.g., AAV-DJ virus) encoding the inducing agent or a protein encoding the inducing agent is administered to the same cells. In some embodiments, this system produces an engineered cell (e.g., an induced pluripotent stem cell). In some embodiments, the engineered cell is further differentiated into (e.g., differentiated into an eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine cell). In some embodiments, the differentiated cell is used for transplantation purposes. In some embodiments, the engineered cell is cultured to create an engineered tissue. In some embodiments, the engineered cell is cultured to create an engineered organ. In some embodiments, the engineered cells are retina pigment epithelium cells, neuron cells, pancreatic beta-cells, or cardiac cells.

Compositions

The compositions of the disclosure may comprise at least one of any of the nucleic acids (e.g., engineered nucleic acid) capable of inducing OCT4, KLF4, and/or SOX2 expression (e.g., expression vector), engineered proteins, engineered cells, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein alone, or in combination. In certain embodiments, the compositions of the disclosure comprise at least one of any of the nucleic acids (e.g., engineered nucleic acid) (e.g., expression vector) capable of inducing expression of OCT4; KLF4; SOX2; or any combination thereof, engineered proteins, engineered cells, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein alone, or in combination. In some embodiments, a composition comprises 1, 2, 3, 4, 5, 6, 7, 8, 9, 10, or more different nucleic acids (e.g., engineered nucleic acids) capable of inducing OCT4, KLF4, and/or SOX2 expression (e.g., expression vectors encoding OCT4, KLF4, and/or SOX2). In some embodiments, a composition comprises 1, 2, 3, 4, 5, 6, 7, 8, 9, 10, or more different nucleic acids (e.g., engineered nucleic acids) capable of inducing expression of OCT4; KLF4; SOX2; or any combination thereof (e.g., expression vectors encoding OCT4; KLF4; SOX2; or any combination thereof). In some embodiments, a composition comprises 1, 2, 3, 4, 5, 6, 7, 8, 9, 10, or more different viruses (e.g., lentivirus, alphavirus, vaccinia virus, adenovirus, retrovirus, herpes virus, or AAV) each having one or more different transgenes. In some embodiments, a composition comprises 1, 2, 3, 4, 5, 6, 7, 8, 9, 10, or more different chemical agents activating (e.g., inducing expression of) OCT4, KLF4, and/or SOX2. In some embodiments, a composition comprises 1, 2, 3, 4, 5, 6, 7, 8, 9, 10, or more different chemical agents activating (e.g., inducing expression of) OCT4; KLF4; SOX2; or any combination thereof. In some embodiments, a composition further comprises one or more nucleic acids (e.g., engineered nucleic acids) encoding an inducing agent, one or more engineered proteins encoding an inducing agent, one or more chemical agents capable of modulating (e.g., activating or inhibiting) the activity of an inducing agent, and/or one or more recombinant viruses encoding an inducing agent. In some embodiments, a composition comprises engineered cells (e.g., induced pluripotent stem cells and/or differentiated cells). In some embodiments, a composition comprises an engineered protein encoding OCT4, SOX2, and/or KLF4. In some embodiments, a composition comprises an engineered protein encoding OCT4, SOX2, KLF4, or any combination thereof. In some embodiments, a composition further comprises an engineered protein encoding an inducing agent.

In some embodiments, a composition further comprises a pharmaceutically acceptable carrier. Suitable carriers may be readily selected by one of skill in the art in view of the indication for which the nucleic acids (e.g., engineered nucleic acid) capable of inducing OCT4, KLF4, and/or SOX2 expression (e.g., expression vector), chemical agents activating (e.g., inducing expression of) OCT4, KLF4, and/or SOX2, antibodies activating (e.g., inducing expression of) OCT4, KLF4, and/or SOX2, engineered proteins, engineered cells, and/or recombinant viruses (e.g., lentivirus, adenovirus, alphavirus, vaccinia virus, retrovirus, herpes virus, or AAV) e.g. is directed. Suitable carriers may be readily selected by one of skill in the art in view of the indication for which the nucleic acids (e.g., engineered nucleic acid) (e.g., expression vectors) capable of inducing expression of OCT4; KLF4; SOX2; or any combination thereof, chemical agents activating (e.g., inducing expression of) OCT4; KLF4; SOX2; or any combination thereof, antibodies activating (e.g., inducing expression of) OCT4; KLF4; SOX2; or any combination thereof, engineered proteins, engineered cells, and/or recombinant viruses (e.g., lentivirus, adenovirus, alphavirus, vaccinia virus, retrovirus, herpes virus, or AAV) e.g. is directed. Suitable carriers may also be readily selected by one of skill in the art in view of the indication for which the nucleic acids (e.g., engineered nucleic acids) encoding an inducing agent, engineered proteins encoding an inducing agent, chemical agents capable of modulating (e.g., activating or inhibiting) the activity of an inducing agent, and/or recombinant viruses (e.g., lentivirus, adenovirus, alphavirus, vaccinia virus, retrovirus, herpes virus, or AAV) comprising an inducing agent e.g. is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may comprise, in addition to the nucleic acids (e.g., engineered nucleic acid) capable of inducing OCT4, KLF4, and/or SOX2 expression (e.g., expression vector), engineered cells comprising OCT4, KLF4, and/or SOX2, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) e.g. and carrier(s), other pharmaceutical ingredients, such as preservatives, or chemical stabilizers. Optionally, the compositions of the disclosure may comprise, in addition to the nucleic acids (e.g., engineered nucleic acid) (e.g., expression vector) capable of inducing expression of OCT4; KLF4; SOX2; or any combination thereof, engineered cells comprising OCT4; KLF4; SOX2; or any combination thereof, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) e.g. and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin. The compositions of the present disclosure may further comprise a nucleic acid (e.g., engineered nucleic acids) encoding an inducing agent, an engineered protein encoding an inducing agent, chemical agents capable of modulating (e.g., activating or inhibiting) the activity of an inducing agent, and/or recombinant viruses encoding an inducing agent.

The nucleic acid (e.g., engineered nucleic acid) (e.g., expression vector) capable of inducing expression of OCT4; KLF4; SOX2; or any combination thereof, engineered cells, chemical agents activating (e.g., inducing expression of) OCT4; KLF4; SOX2; or any combination thereof, engineered proteins encoding OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) encoding the same described herein are administered in sufficient amounts to transfect the cells of a desired tissue (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine tissue) and to provide sufficient levels of gene transfer and expression without undue adverse effects. Any of the nucleic acids (e.g., engineered nucleic acids) encoding an inducing agent, an engineered protein encoding an inducing agent, chemical agents capable of modulating (e.g., activating or inhibiting) the activity of an inducing agent, and/or recombinant viruses encoding an inducing agent are administered in sufficient amounts to transfect the cells of a desired tissue (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine tissue) and to provide sufficient levels of gene transfer and expression without undue adverse effects. Examples of pharmaceutically acceptable routes of administration include, but are not limited to, direct delivery to the selected organ (e.g., direct delivery to eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). Any of the nucleic acids (e.g., engineered nucleic acids) capable of inducing OCT4, KLF4, and/or SOX2 expression (e.g., expression vector), engineered cells, chemical agents activating (e.g., inducing expression of) OCT4, KLF4, and/or SOX2, engineered proteins, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein may be delivered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art. Any of the nucleic acids (e.g., engineered nucleic acids) (e.g., expression vectors) capable of inducing expression of OCT4; KLF4; SOX2; or any combination thereof, engineered cells, chemical agents activating (e.g., inducing expression of) OCT4; KLF4; SOX2; or any combination thereof, engineered proteins, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein may be delivered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art. Any of the nucleic acids encoding an inducing agent, chemical agents capable of modulating the activity of an inducing agent, engineered proteins encoding an inducing agent, and/or recombinant viruses encoding an inducing agent may be may be delivered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art. Routes of administration may be combined, if desired.

In some embodiments, a nucleic acid is delivered non-virally (e.g., not on a viral vector and/or not in a virus). In some embodiments, a nucleic acid (e.g., RNA or DNA) encoding OCT4, SOX2, and/or KLF4 and/or an inducing agent is administered in a liposome. In some embodiments, a nucleic acid (e.g., RNA or DNA) encoding OCT4, SOX2, KLF4, or any combination thereof, and/or an inducing agent is administered in a liposome. In some embodiments, a nucleic acid (e.g., RNA or DNA) encoding OCT4, SOX2, and/or KLF4 and/or an inducing agent is administered in a particle. In some embodiments, a nucleic acid (e.g., RNA or DNA) encoding OCT4, SOX2, KLF4, or any combination thereof, and/or an inducing agent is administered in a particle. In some embodiments, the nucleic acid is RNA (e.g., mRNA).

In some embodiments, a pharmaceutical composition comprising an expression vector encoding OCT4, KLF4, and/or SOX2 or a pharmaceutical composition comprising a virus harboring the expression vector is administered to a cell, tissue, organ or a subject. In some embodiments, a pharmaceutical composition comprising an expression vector encoding an inducing agent or a pharmaceutical composition comprising a virus harboring the expression vector is administered to a cell, tissue, organ or a subject. In some embodiments, the virus and/or expression vector encoding OCT4, KLF4, and/or SOX2 is administered systemically. In some embodiments, the virus and/or expression vector encoding an inducing agent is administered systemically. In some embodiments, the virus and/or expression vector encoding OCT4, KLF4, and/or SOX2 is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, a virus and/or expression vector encoding an inducing agent is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered using the same route of administration as the OCT4, KLF4, and/or SOX2 (e.g., nucleic acid encoding OCT4, KLF4, and/or SOX2). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered via a different route of administration as the OCT4, KLF4, and/or SOX2 (e.g., nucleic acid encoding OCT4, KLF4, and/or SOX2).

In some embodiments, a pharmaceutical composition comprising an expression vector encoding OCT4; KLF4; SOX2; or any combination thereof, or a pharmaceutical composition comprising a virus harboring the expression vector is administered to a cell, tissue, organ, or subject. In some embodiments, a pharmaceutical composition comprising an expression vector encoding an inducing agent or a pharmaceutical composition comprising a virus harboring the expression vector is administered to a cell, tissue, organ, or subject. In some embodiments, the virus and/or expression vector encoding OCT4; KLF4; SOX2; or any combination thereof is administered systemically. In some embodiments, the virus and/or expression vector encoding an inducing agent is administered systemically. In some embodiments, the virus and/or expression vector encoding OCT4; KLF4; SOX2; or any combination thereof is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, a virus and/or expression vector encoding an inducing agent is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered using the same route of administration as the OCT4; KLF4; SOX2; or any combination thereof (e.g., nucleic acid encoding OCT4; KLF4; SOX2; OCT4 and SOX2; OCT4 and KLF4; KLF4 and SOX2; or KLF4, OCT4, and SOX2). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered via a different route of administration as the OCT4; KLF4; SOX2; or any combination thereof (e.g., nucleic acid encoding nucleic acid encoding OCT4; KLF4; SOX2; OCT4 and SOX2; OCT4 and KLF4; KLF4 and SOX2; or KLF4, OCT4, and SOX2).

In some embodiments, the expression vector is an inducible vector in which a nucleic acid encoding OCT4, KLF4, and/or SOX2 and/or inducing agent, is operably linked to an inducible TRE promoter (e.g., TRE3G, TRE2, or P tight). In some embodiments, the expression vector is an inducible vector in which a nucleic acid encoding OCT4; KLF4; SOX2; or any combination thereof, and/or inducing agent, is operably linked to an inducible TRE promoter (e.g., TRE3G, TRE2, or P tight). In some embodiments, the virus and/or inducible vector is administered with tetracycline (e.g., doxycycline). In some embodiments, the virus and/or expression vector comprising a TRE promoter is administered separately from tetracycline (e.g., doxycycline). For example, any of the viruses and/or expression vectors comprising a TRE promoter described herein may be administered systemically and the tetracycline may be administered locally (e.g., to an organ or tissue of interest). In some embodiments, any of the viruses and/or expression vectors comprising a TRE promoter described herein may be administered locally (e.g., to directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) and the tetracycline may be administered systemically. As a non-limiting example, a virus and/or expression vector comprising a TRE promoter is administered directly (e.g., injected) into the eye of a subject and the tetracycline (e.g., doxycycline) is administered systemically (e.g., orally as a pill).

In some embodiments, tetracycline is administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, or in lipid compositions. In some embodiments, tetracycline is administered directly to a cell, organ, and/or tissue. As a non-limiting example, tetracycline may be administered to the eye of a subject through any suitable method, including eye drops comprising tetracycline, sustained release devices (e.g., micropumps, particles, and/or drug depots), and medicated contact lenses comprising tetracycline. In some embodiments, tetracycline is administered systemically (e.g., through drinking water or intravenous injection) to a subject. Tetracycline may be administered topically (e.g., in a cream) or through a subcutaneous pump (e.g., to deliver tetracycline to a particular tissue).

As an example, the dose of recombinant virus (e.g., lentivirus, alphaviruses, vaccinia viruses, adenovirus, retrovirus, herpes virus, or AAV) virions required to achieve a particular therapeutic effect, e.g., the units of dose in genome copies/per kilogram of body weight (GC/kg), will vary based on several factors including, but not limited to: the route of recombinant virus (e.g., lentivirus, alphaviruses, vaccinia viruses, adenovirus, retrovirus, herpes virus, or AAV) virion administration, the level of gene or RNA expression required to achieve a therapeutic effect, the specific disease or disorder being treated, and the stability of the gene or RNA product. One of skill in the art can readily determine a recombinant virus (e.g., lentivirus, alphaviruses, vaccinia viruses, adenovirus, retrovirus, herpes virus, or AAV virion) dose range to treat a patient having a particular disease or disorder based on the aforementioned factors, as well as other factors.

An effective amount of a recombinant virus (e.g., lentivirus, alphaviruses, vaccinia viruses, adenovirus, retrovirus, herpes virus, or AAV) is an amount sufficient to target infect an animal, target a desired tissue. In some embodiments, an effective amount of an recombinant virus (e.g., lentivirus, alphavirus, vaccinia virus, adenovirus, retrovirus, herpes virus, or AAV) is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the recombinant virus (e.g., lentivirus, alphavirus, vaccinia virus, adenovirus, retrovirus, herpes virus, or AAV) is generally in the range of from about 1 ml to about 100 ml of solution containing from about $10^9$ to $10^{16}$ genome copies. In some cases, a dosage between about $10^{11}$ to $10^{13}$ recombinant virus (e.g., lentivirus, adenovirus, retrovirus, alphavirus, vaccinia virus, herpes virus, or AAV) genome copies is appropriate. In certain embodiments, $10^{10}$ or $10^{11}$ recombinant virus (e.g., lentivirus, adenovirus, retrovirus, alphavirus, vaccinia virus, herpes virus, or AAV) genome copies is effective to target ocular tissue (e.g., retinal tissue). In some cases, stable transgenic animals are produced by multiple doses of a recombinant virus (e.g., lentivirus, adenovirus, retrovirus, herpes virus, alphavirus, vaccinia virus, or AAV).

In some embodiments, a dose of recombinant virus (e.g., lentivirus, adenovirus, retrovirus, herpes virus, alphavirus, vaccinia virus, or AAV) is administered to a subject no more than once per calendar day (e.g., a 24-hour period). In some embodiments, a dose of recombinant virus (e.g., lentivirus, alphavirus, vaccinia virus, adenovirus, retrovirus, herpes virus, or AAV) is administered to a subject no more than once per 2, 3, 4, 5, 6, or 7 calendar days. In some embodiments, a dose of recombinant virus (e.g., lentivirus, alphavirus, vaccinia virus, adenovirus, retrovirus, herpes virus, or AAV) is administered to a subject no more than once per calendar week (e.g., 7 calendar days). In some embodiments, a dose of recombinant virus (e.g., lentivirus, alphavirus, vaccinia virus, adenovirus, retrovirus, herpes virus, or AAV) is administered to a subject no more than bi-weekly (e.g., once in a two calendar week period). In some embodiments, a dose of recombinant virus (e.g., lentivirus, alphavirus, vaccinia virus, adenovirus, retrovirus, herpes virus, or AAV) is administered to a subject no more than once per calendar month (e.g., once in 30 calendar days). In some embodiments, a dose of recombinant virus (e.g., lentivirus, alphavirus, vaccinia virus, adenovirus, retrovirus, herpes virus, or AAV) is administered to a subject no more than once per six calendar months. In some embodiments, a dose of recombinant virus (e.g., lentivirus, alphavirus, vaccinia virus, adenovirus, retrovirus, herpes virus, or AAV) is administered to a subject no more than once per calendar year (e.g., 365 days or 366 days in a leap year).

In some embodiments, recombinant virus (e.g., lentivirus, alphavirus, vaccinia virus, adenovirus, retrovirus, herpes virus, or AAV) compositions are formulated to reduce aggregation of AAV particles in the composition, particularly where high recombinant virus (e.g., lentivirus, alphavirus, vaccinia virus, adenovirus, retrovirus, herpes virus, or AAV) concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

As a non-limiting example, delivery of transgenes via AAV have been shown to be feasible and non-toxic in humans. For example, AAV may be delivered to the eye. See, e.g., Smalley Nat Biotechnol. 2017 Nov. 9; 35(11):998-999.

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, the nucleic acids (e.g., engineered nucleic acid) capable of inducing OCT4, KLF4, and/or SOX2 expression (e.g., expression vector), engineered cells comprising OCT4, KLF4, and/or SOX2, engineered proteins encoding Oct4, KLF4, and/or SOX2, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) e.g. in suitably formulated pharmaceutical compositions disclosed herein are delivered directly to target tissue, e.g., direct to a tissue of interest (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

In some embodiments, the nucleic acids (e.g., engineered nucleic acid) (e.g., expression vector) capable of inducing expression of OCT4; KLF4; SOX2; or any combination thereof, engineered cells comprising OCT4; KLF4; SOX2; or any combination thereof, engineered proteins encoding Oct4, KLF4, SOX2, or a combination thereof, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) e.g. in suitably formulated pharmaceutical compositions disclosed herein are delivered directly to target tissue, e.g., direct to a tissue of interest (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

In some embodiments, the nucleic acids (e.g., engineered nucleic acid) encoding an inducing agent (e.g., an expression vector), engineered cells comprising an inducing agent, engineered proteins encoding a inducing agent, chemical agents capable of modulating the activity of an inducing agent, and/or recombinant viruses (e.g., lentiviruses, adenoviruses, alphaviruses, vaccinia viruses, retroviruses, herpes viruses, or AAVs) encoding an inducing agent e.g. in suitably formulated pharmaceutical compositions disclosed herein are delivered directly to target tissue, e.g., direct to a tissue of interest (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

However, in certain circumstances it may be desirable to separately or in addition deliver any of the nucleic acids (e.g., engineered nucleic acid) capable of inducing OCT4, KLF4, and/or SOX2 expression (e.g., expression vector) and/or nucleic acid encoding an inducing agent, nucleic acids (e.g., engineered nucleic acid) capable of inducing expression of a combination of transcription factors selected from OCT4, KLF4, and/or nucleic acid encoding an inducing agent, engineered cells, engineered proteins, chemical agents activating (e.g., inducing expression of) OCT4, KLF4, and/or SOX2, chemical agents activating (e.g., inducing expression of) a combination of transcription factors selected from OCT4, KLF4, and SOX2, chemical agents capable of modulating (e.g., inhibiting or activating) the activity of an inducing agent, antibodies activating (e.g., inducing expression of) OCT4, KLF4, and/or SOX2, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver recombinant virus (e.g., lentivirus, alphavirus, vaccinia virus, adenovirus, retrovirus, herpes virus, or AAVs). In some embodiments, a preferred mode of administration is by intrastromal injection.

In some embodiments, a nucleic acid (e.g., mRNA) encoding OCT4, SOX2, KLF4, or any combination thereof is nanoformulated into a polyplex, which may be useful, for example, for noninvasive aerosol inhalation and delivery of the nucleic acid to the lung (e.g., lung epithelium). See, e.g., Patel et al., Adv Mater. 2019 Jan. 4:e1805116. doi: 10.1002/adma.201805116 for description of nanoformulated mRNA polyplexes, which is hereby incorporated by reference in its entirety for this purpose.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the nucleic acid (e.g., engineered nucleic acid) capable of inducing OCT4, KLF4, and/or SOX2 expression (e.g., expression vector), engineered cells, engineered proteins, chemical agents activating (e.g., inducing expression of) OCT4, KLF4, an and/or SOX2, antibodies activating (e.g., inducing expression of) OCT4, KLF4, and/or SOX2, and/or active recombinant viruses (e.g., lentivirus, adenovirus, alphavirus, vaccinia virus, retrovirus, herpes virus, or AAV) e.g. in the required amount in the appropriate solvent with various of the other ingredients enumerated herein, as required, followed by filtered sterilization. Sterile injectable solutions are prepared by incorporating the nucleic acid (e.g., engineered nucleic acid) (e.g., expression vector) capable of inducing expression of OCT4, KLF4, SOX2, or any combination thereof, engineered cells, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or active recombinant viruses (e.g., lentivirus, adenovirus, alphavirus, vaccinia virus, retrovirus, herpes virus, or AAV) e.g. in the required amount in the appropriate solvent with various of the other ingredients enumerated herein, as required, followed by filtered sterilization. In certain embodiments, the sterile injectable solutions are prepared by incorporating a nucleic acid (e.g., engineered nucleic acid) encoding an inducing agent, engineered protein encoding an inducing agent, chemical agents capable of modulating the activity of an inducing agent and/or active recombinant viruses (e.g., lentivirus, adenovirus, alphavirus, vaccinia virus, retrovirus, herpes virus, or AAV) encoding an inducing agent e.g. in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions comprising nucleic acids (e.g., engineered nucleic acids) encoding OCT4, KLF4, and/or SOX2 (e.g., expression vector), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) disclosed herein may also be formulated in a neutral or salt form. The compositions comprising nucleic acids (e.g., engineered nucleic acids) (e.g., expression vector) encoding OCT4; KLF4; SOX2; or any combination thereof, engineered cells, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) disclosed herein may also be formulated in a neutral or salt form. The compositions may comprise an inducing agent (e.g., a nucleic acid encoding an inducing agent or a protein encoding an inducing agent and/or a recombinant virus encoding an inducing agent) and/or a chemical agent capable of modulating the activity of an inducing agent. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

A carrier includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

Delivery vehicles such as liposomes, nanocapsules, microparticles, microspheres, lipid particles, vesicles, and the like, may be used for the introduction of the compositions of the present disclosure into suitable host cells. In particular, any of the nucleic acids (e.g., engineered nucleic acids) capable of inducing OCT4, KLF4, and/or SOX2 expression (e.g., expression vector), any of the engineered proteins, any of the chemical agents activating (e.g., inducing expression of) OCT4, KLF4, and/or SOX2, any of the antibodies activating (e.g., inducing expression of) OCT4, KLF4, and/or SOX2, engineered cells, and/or any of the recombinant viruses (e.g., lentivirus, adenovirus, alphavirus, vaccinia virus, retrovirus, herpes virus, or AAV) may be encapsulated in a lipid particle, a liposome, a vesicle, a nanosphere, or a nanoparticle or the like. In some embodiments, any of the nucleic acids (e.g., engineered nucleic acids) (e.g., expression vector) capable of inducing expression of OCT4; KLF4; SOX2; or any combination thereof, any of the engineered proteins, any of the chemical agents activating (e.g., inducing expression of) OCT4; KLF4; SOX2; or any combination thereof, any of the antibodies activating (e.g., inducing expression of) OCT4; KLF4; SOX2; or any combination thereof, engineered cells, and/or any of the recombinant viruses (e.g., lentivirus, adenovirus, alphavirus, vaccinia virus, retrovirus, herpes virus, or AAV) may be encapsulated in a lipid particle, a liposome, a vesicle, a nanosphere, or a nanoparticle or the like. An inducing agent (e.g., a nucleic acid encoding an inducing agent or a protein encoding an inducing agent and/or a recombinant virus encoding an inducing agent) and/or a chemical agent capable of modulating the activity of an inducing agent may be encapsulated in a lipid particle, a liposome, a vesicle, a nanosphere, or a nanoparticle or the like.

In some embodiments, the delivery vehicle targets the cargo. For example, any of the nucleic acids, engineered proteins, chemical agents, antibodies, and/or recombinant viruses (e.g., lentivirus, adenovirus, alphavirus, vaccinia virus, retrovirus, herpes virus, or AAV) described herein may be delivered via a nanoparticle that delivers the cargo to a certain tissue or cell type. Nanoparticles coated in galactose polymers, for example, are known to release their cargo within senescent cells as a result of their endogenous beta-galactosidase activity. See e.g., Lozano-Torres et al., J Am Chem Soc. 2017 Jul. 5; 139(26):8808-8811.

In some embodiments, any of the nucleic acids, engineered proteins, chemical agents, antibodies, and/or recombinant viruses (e.g., lentivirus, adenovirus, alphavirus, vaccinia virus, retrovirus, herpes virus, or AAV) is formulated in a poly(glycoamidoamine) brush nanoparticles. See, e.g., Dong et al., Nano Lett. 2016 Feb. 10; 16(2):842-8.

In some embodiments, any of the nucleic acids, engineered proteins, chemical agents, antibodies, and/or recombinant viruses (e.g., lentivirus, adenovirus, alphavirus, vaccinia virus, retrovirus, herpes virus, or AAV) is formulated in a lipid nanoparticle. See, e.g., Cullis and Hope Mol Ther. 2017 Jul. 5; 25(7):1467-1475. In some embodiments, the lipid nanoparticle comprises one or more membrane fusion proteins, which deliver plasmids directly into the cytoplasm or the factors OCT4; KLF4; SOX2; or any combination thereof may be fused directly to the targeting protein with or without nanoparticle encapsulation. In some embodiments, the lipid nanoparticle is a Fusogenix lipid nanoparticle. In some embodiments, the lipid nanoparticle is a "Wrapped Liposomes" (WL). See, e.g., Yamauchi et al., Biochim Biophys Acta. 2006 January; 1758(1):90-7. In some embodiments, the lipid nanoparticle is a PEGylated liposome (e.g., DOXIL™) (e.g., Allen & Hansen, Biochim Biophys Acta. 1991 Jul. 1; 1066(1):29-36), 1, 2-dioleoyl-sn-glycerol-3 phosphatidylethanolamine (DOPE), a neutral helper lipid phosphatidylethanolamine (PE), or combinations thereof (e.g., Farhood et al., Biochim Biophys Acta. 1995 May 4; 1235(2):289-95; Zhou & Huang, Biochim Biophys Acta. 1994 Jan. 19; 1189(2):195-203). In some embodiments, the lipid nanoparticle or fusion protein comprises employs a molecule or protein to mimic methods employed by viruses for intracellular delivery of macromolecules (e.g., Kobayashi et al., Bioconjug Chem. 2009 May 20; 20(5):953-9), e.g., using a variety of pH sensitive peptides such as vesicular stomatitis virus proteins (VSV G), phage coat proteins and/or shGALA, and/or Fusion associated small transmembrane (FAST) proteins, e.g., avian reovirus (ARV), nelson bay reovirus (NBV), and baboon reovirus (BBV), aquareovirus reovirus (AQV) and reptilian reovirus (RRV), and/or Bombesin targeting peptide. See, e.g., Peisajovich et al., Eur J Biochem. 2002 September; 269(17):4342-50; Sakurai et al., 2011. See also Nesbitt, Targeted Intracellular Therapeutic Delivery Using Liposomes Formulated with Multifunctional FAST proteins, Western University Thesis, 2012. https://www.google.com/url?sa=t&rct=j&q=&esrc=s&source=web&cd=14&ved=2ahUKEwi X-YW5puzfAhXGTd8KHUmCATOQFjANeg-QIAh- AB&url=http %3A %2F %2Fir.lib.uwo.ca %2 Fcgi %2Fviewcontent.cgi %3Farticle %3D1571%26context %3Detd&usg=AOvVaw3A20aOef HfJISZRR_-kPD In some embodiments, a nucleic acid (e.g., RNA or DNA, including a plasmid) encoding OCT4, KLF4, SOX2, or a combination thereof is encapsulated in a Fusogenix lipid nanoparticle. In some embodiments, a nucleic acid encoding an inducing agent (e.g., rtTA or tTA) is encapsulated in a Fusogenix lipid nanoparticle. In some embodiments, a lipid nanoparticle comprises a viral membrane protein. Without being bound by a particular theory, a lipid nanoparticle may be non-toxic because it comprises a membrane fusion protein that is not a viral membrane fusion protein. Non-limiting examples of membrane fusion proteins include membrane fusion proteins disclosed in U.S. Pat. Nos. 7,851,595, 8,252,901, International Application Publication No. WO 2012/040825, and International Application Publication No. WO 2002/044206.

In some embodiments, a composition of the present disclosure (e.g., comprising a nucleic acid encoding OCT4, KLF4, SOX2, or a combination thereof) is delivered non-virally. Methods of non-viral delivery of nucleic acids include lipofection, nucleofection, microinjection, biolistics, virosomes, liposomes, immunoliposomes, polycation or lipid:nucleic acid conjugates, naked nucleic acid (e.g., RNA or DNA), artificial virions, and agent-enhanced uptake of a nucleic acid (e.g., RNA or DNA).

In some embodiments, a cationic lipid is used to deliver a nucleic acid. A cationic lipid is a lipid which has a cationic, or positive, charge at physiologic pH. Cationic lipids can take a variety of forms including, but not limited to, liposomes or micelles. Cationic lipids useful for certain aspects of the present disclosure are known in the art, and, generally comprise both polar and non-polar domains, bind to polyanions, such as nucleic acid molecules or negatively supercharged proteins, and are typically known to facilitate the delivery of nucleic acids into cells. Examples of useful cationic lipids include polyethylenimine, polyamidoamine (PAMAM) starburst dendrimers, Lipofectin (a combination of DOTMA and DOPE, see, e.g., U.S. Pat. Nos. 5,049,386, 4,946,787; and 4,897,355), Lipofectase, LIPO-FECTAMINE® (e.g., LIPOFECTAMINE® 2000, LIPO-FECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N, N,N-trimethylammonium methylsulfate (DOTAP), 3β-[N-(N',N'-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). Cationic lipids have been used in the art to deliver nucleic acid molecules to cells (see, e.g., U.S. Pat. Nos. 5,855,910; 5,851,548; 5,830,430; 5,780,053; 5,767,099; 8,569,256; 8,691,750; 8,748,667; 8,758,810; 8,759,104; 8,771,728; Lewis et al. 1996. Proc. Natl. Acad. Sci. USA 93:3176; Hope et al. 1998. Molecular Membrane Biology 15:1).

In addition, other lipid compositions are also known in the art and include, e.g., those taught in U.S. Pat. Nos. 4,235,871; 4,501,728; 4,837,028; 4,737,323. Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Polymer-based delivery systems may also be used to deliver a nucleic acid. Polymers including polyethylenimine (PEI), chitosan, Poly (DL-Lactide) (PLA) and Poly (DL-Lactide-co-glycoside) (PLGA), dedrimers, and Polymethacrylate may be used. See, e.g., Yang et al., Macromol Biosci. 2012 December; 12(12):1600-14; Ramamoorth et al., J Clin Diagn Res. 2015 January; 9(1): GE01-GE06. As a non-limiting example, a cationic polymer may be used. A cationic polymer is a polymer having a net positive charge. Cationic polymers are well known in the art, and include those described in Samal et al., Cationic polymers and their therapeutic potential. Chem Soc Rev. 2012 Nov. 7; 41(21): 7147-94; in published U.S. patent applications U.S. 2014/0141487 A1, U.S. 2014/0141094 A1, U.S. 2014/0044793 A1, U.S. 2014/0018404 A1, U.S. 2014/0005269 A1, and U.S. 2013/0344117 A1; and in U.S. Pat. Nos. 8,709,466; 8,728,526; 8,759,103; and 8,790,664; the entire contents of each are incorporated herein by reference. Exemplary cationic polymers include, but are not limited to, polyallylamine (PAH); polyethyleneimine (PEI); poly(L-lysine) (PLL); poly(L-arginine) (PLA); polyvinylamine homo- or copolymer; a poly(vinylbenzyl-tri-C1-C4-alkylammonium salt); a polymer of an aliphatic or araliphatic dihalide and an aliphatic N,N,N',N'-tetra-C1-C4-alkyl-alkylenediamine; a poly(vinylpyridin) or poly(vinylpyridinium salt); a poly(N, N-diallyl-N,N-di-C1-C4-alkyl-ammoniumhalide); a homo- or copolymer of a quaternized di-C1-C4-alkyl-aminoethyl acrylate or methacrylate; POLYQUAD™; a polyaminoamide; and the like.

Such formulations may be preferred for the introduction of pharmaceutically acceptable formulations of any of the nucleic acids, engineered proteins, chemical agents, antibodies, and/or recombinant viruses (e.g., lentivirus, adenovirus, alphavirus, vaccinia virus, retrovirus, herpes virus, or AAV) disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868; and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500.ANG., containing an aqueous solution in the core.

Alternatively, nanocapsule formulations of the recombinant virus (e.g., lentivirus, alphavirus, vaccinia virus, adenovirus, retrovirus, herpes virus, or AAV) may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

Kits and Related Compositions

Any of the nucleic acids, engineered proteins, chemical agents, antibodies, and/or recombinant viruses described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a recombinant virus (e.g., lentivirus, alphavirus, vaccinia virus, adenovirus, retrovirus, herpes virus, or AAV) and/or engineered cells, the kit comprising a container housing an engineered nucleic acid (e.g., engineered nucleic acid) encoding OCT4, KLF4, SOX2, or a combination thereof and/or host cells. In some embodiments, the kit further comprises instructions for producing the recombinant virus (e.g., lentivirus, alphavirus, vaccinia virus, adenovirus, retrovirus, herpes virus, or AAV) and/or instructions for producing engineered cells. In some embodiments, the kit further comprises at least one container housing a recombinant AAV vector, wherein the recombinant AAV vector comprises a transgene (e.g., a gene associated with ocular disease, such as corneal disease).

In some embodiments, the instant disclosure relates to a kit comprising a container housing any of the engineered nucleic acids (e.g., expression vectors), chemical agents, antibodies, engineered cells, or recombinant viruses described herein. For example, an expression vector or recombinant virus encoding KLF4, SOX2, OCT4, or a combination thereof may comprise a sequence that is at least 70% (e.g., at least 75%, 80%, 85%, 90%, 95%, 98%, 99%, or 100%) identical to SEQ ID NO: 16, SEQ ID NO: 105, or SEQ ID NO: 121. In some embodiments, an expression vector or recombinant virus encoding KLF4, SOX2, OCT4, or a combination thereof comprises SEQ ID NO: 16, SEQ ID NO: 105, or SEQ ID NO: 121. In some embodiments, the expression vector encoding these three transcription factors consists of SEQ ID NO: 16, SEQ ID NO: 105, or SEQ ID NO: 121. The kit may further comprise an expression vector or recombinant virus encoding an inducing agent. In some embodiments, an expression vector encoding an inducing agent comprises SEQ ID NO: 17, SEQ ID NO: 31, or SEQ ID NO: 32. In some embodiments, the expression vector encoding an inducing agent consists of SEQ ID NO: 17, SEQ ID NO: 31, or SEQ ID NO: 32. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink-wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

Therapeutic Applications

Any of the nucleic acids (e.g., engineered nucleic acids) capable of inducing OCT4, KLF4, and/or SOX2 expression (e.g., expression vector), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein may be used for regulating (e.g., inducing or inducing and stopping) cellular reprogramming, tissue repair, tissue regeneration, organ regeneration, reversing aging, treating a disease, or any combination thereof. Any of the nucleic acids (e.g., engineered nucleic acids) capable of inducing expression of a combination of transcription factors selected from OCT4, KLF4, and SOX2 (e.g., OCT4 and KLF4, OCT4 and SOX2, SOX2 and KLF4, or KLF4, OCT4, and SOX2), engineered cells, engineered proteins, chemical agents activating (e.g., inducing expression of) a combination of transcription factors selected from OCT4, KLF4, and SOX2 (e.g., OCT4 and KLF4, OCT4 and SOX2, SOX2 and KLF4, or KLF4, OCT4, and SOX2), antibodies activating (e.g., inducing expression of) combination of transcription factors selected from OCT4, KLF4, and SOX2 (e.g., OCT4 and KLF4, OCT4 and SOX2, SOX2 and KLF4, or KLF4, OCT4, and SOX2), and/or recombinant viruses (e.g., lentivirus, adenovirus, alphavirus, vaccinia virus, retrovirus, herpes virus, or AAV) described herein may be used for regulating (e.g., inducing or inducing and stopping) cellular reprogramming, tissue repair, tissue regeneration, organ regeneration, reversing aging, treating a disease, or any combination thereof. In some embodiments, any of the nucleic acid (e.g., engineered nucleic acid) capable of inducing OCT4, KLF4, and/or SOX2 expression (e.g., expression vector), any of the engineered cells, any of the engineered proteins, any of the chemical agents activating (e.g., inducing expression of) OCT4, KLF4, and/or SOX2, any of the antibodies activating (e.g., inducing expression of) OCT4, KLF4, and/or SOX2, and/or any of the recombinant viruses (e.g., lentivirus, adenovirus, alphavirus, vaccinia virus, retrovirus, herpes virus, or AAV) may be useful in regulating cellular reprogramming, tissue repair, tissue survival, tissue regeneration, tissue growth, tissue function, organ regeneration, organ survival, organ function, or any combination thereof, optionally wherein regulating comprises inducing cellular reprogramming, reversing aging, improving tissue function, improving organ function, tissue repair, tissue survival, tissue regeneration, tissue growth, angiogenesis, scar formation, the appearance of aging, organ regeneration, organ survival, altering the taste and quality of agricultural products derived from animals, treating a disease, or any combination thereof, in vivo or in vitro may be administered to a cell, tissue, or organ that is in vivo (e.g., part of a subject), or may be administered to a cell, tissue, or organ ex vivo. In some embodiments, any of the nucleic acid (e.g., engineered nucleic acid) (e.g., expression vector) capable of inducing expression of OCT4; KLF4; SOX2; or any combination thereof, any of the engineered cells, any of the engineered proteins, any of the chemical agents activating (e.g., inducing expression of) OCT4; KLF4; SOX2; or any combination thereof, any of the antibodies activating (e.g., inducing expression of) OCT4, KLF4, SOX2, or a combination thereof, and/or any of the recombinant viruses (e.g., lentivirus, adenovirus, alphavirus, vaccinia virus, retrovirus, herpes virus, or AAV) may be useful in regulating cellular reprogramming, tissue repair, tissue survival, tissue regeneration, tissue growth, tissue function, organ regeneration, organ survival, organ function, or any combination thereof, optionally wherein regulating comprises inducing cellular reprogramming, reversing aging, improving tissue function, improving organ function, tissue repair, tissue survival, tissue regeneration, tissue growth, angiogenesis, scar formation, the appearance of aging, organ regeneration, organ survival, altering the taste and quality of agricultural products derived from animals, treating a disease, or any combination thereof, in vivo or in vitro may be administered to a cell, tissue, or organ that is in vivo (e.g., part of a subject), or may be administered to a cell, tissue, or organ ex vivo. As used herein, regulating may refer to any type of modulation, including inducing or promoting, inhibiting, and/or stopping. Angiogenesis refers to growth of new blood vessels, including capillaries.

In some instances, a viral vector (e.g., lentivirus vector, alphavirus vector, vaccinia virus vector, adenovirus vector, herpes virus vector, retrovirus vector, or AAV vector) is administered in a recombinant virus (e.g., lentivirus, alphavirus, vaccinia virus, adenovirus, herpes virus, retrovirus, or AAV). Without being bound by a particular theory, transient expression of OCT4, SOX2, and KLF4 may result in partial reprogramming of a cell. For example, partial reprogramming may induce a fully differentiated cell to rejuvenate and gain pluripotency. In some embodiments, transient expression of OCT4, SOX2, and/or KLF4 does not induce expression of stem cell markers (e.g., Nanog).

In some embodiments, transient expression of OCT4, SOX2, KLF4, or a combination thereof does not induce expression of stem cell markers (e.g., Nanog). Without being bound by any particular theory, Nanog activation may induce teratomas and cause death of the host. In some embodiments, the method does not induce teratoma formation. In some embodiments, the method does not induce unwanted cell proliferation. In some embodiments, the method does not induce malignant cell growth. In some embodiments, the method does not induce cancer. In some embodiments, the method does not induce glaucoma. In some embodiments, transient expression is at most 1 hour, 5 hours, 24 hours, 2 days, 3 days, 4 days, 5, days, or 1 week. In some instances, prolonged expression (e.g., continued expression for at least 5 days, at least 1 week, or at least 1 month) of OCT4, SOX2, and KLF4, results in full reprogramming of a cell. For example, a cell may be fully reprogrammed into a pluripotent cell (e.g., induced pluripotent cell). In some instances, prolonged expression (e.g., continued expression for at least 5 days, at least 1 week, or at least 1 month) of OCT4, SOX2, KLF4, or a combination thereof, results in full reprogramming of a cell. For example, a cell may be fully reprogrammed into a pluripotent cell (e.g., induced pluripotent cell).

Without being bound by a particular theory, expression of OCT4, SOX2, and KLF4 may promote cellular reprogramming, promote tissue regeneration, promote organ regeneration, reverse aging, treat a disease, or any combination thereof because OCT4, SOX2, and KLF4 induce partial reprogramming. As used herein, partial or incomplete reprogramming of a cell refers to a cell that are not stem cells, but have youthful characteristics. In some embodiments, a youthful characteristic is an epigenome that is similar to a young cell. In some embodiments, a stem cell shows higher levels of Nanog expression compared to a cell that is not a stem cell. In some embodiments, youthful characteristics refers to rejuvenation of a cell without changing cell identity. See, e.g., shown in FIG. 16, in which the expression of histone and Chaf (Chromatin assembly factor) genes decline during aging in ear fibroblasts from aged mice (12 months or 15 months) compared to those from young mice, short term of OSKM (3 days) or OSK expression (5 days) induction can reset their gene expression level to young state, without making the cells into a stem cell (e.g., Nanog expression is not induced in these cells).

To practice this embodiment, an effective amount of any of the nucleic acids (e.g., engineered nucleic acids) capable of inducing OCT4, KLF4, and/or SOX2 expression (e.g., expression vector), engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) are administered to a cell, a tissue, organ, and/or subject. In some embodiments, an effective amount of any of the nucleic acids (e.g., engineered nucleic acids) (e.g., expression vector) capable of inducing expression of OCT4, KLF4, SOX2, or a combination thereof, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) are administered to a cell, a tissue, organ, and/or subject. Engineered cells may be administered to any tissue, organ, and/or subject. When the expression vector comprises an inducible promoter (e.g., a TRE promoter, including a TRE3G, TRE2, or P tight), the inducing agent may also be introduced into the cell (e.g., simultaneously or sequentially with one or more nucleic acids (e.g., engineered nucleic acids) encoding OCT4, SOX2, KLF4, or any combination thereof). In one embodiment, OCT4, SOX2, and KLF4 are encoded by one expression vector that is separate from an expression vector encoding the inducing agent. In some instances, the inducing agent is encoded by the same expression vector that encodes OCT4, SOX2, KLF4, or any combination thereof.

In some instances, an inducing agent (e.g., a nucleic acid encoding an inducing agent, an engineered protein encoding an inducing agent, or a virus encoding an inducing agent) and/or a chemical agent (e.g., tetracycline) that is capable of modulating (e.g., activating or inhibiting) activity of the inducing agent is also introduced into a cell, tissue, organ, and/or subject. In certain embodiments, a cell, tissue, subject, and/or organ is further cultured in the presence or absence of a chemical agent that is capable of modulating the activity of an inducing agent (e.g., tetracycline, which includes doxycycline). For a Tet-On system, the inducing agent may be rtTA (e.g., rtTA3 or rtTA4), and the inducing agent promotes expression of OCT4, SOX2, KLF4, or any combination thereof in the presence of tetracycline. For a Tet-Off system, the inducing agent may be tTA, and the inducing agent promotes expression of OCT4, SOX2, KLF4, or any combination thereof in the absence of tetracycline.

Administration of an expression vector encoding a transcription factor described herein and in some cases the inducing agent (e.g., a nucleic acid (e.g., engineered nucleic acid) encoding an inducing agent or the inducing agent as protein) and/or chemical agent that is capable of modulating the activity of the inducing agent under suitable conditions for expression may increase expression of the transgene by at least 10%, at least 20%, at least 30%, at least 40%, at least 50%, at least 60%, at least 70%, at least 80%, at least 90%, at least 100%, at least 200%, at least 300%, at least 400%, at least 500%, at least 500%, at least 600%, at least 700%, at least 800%, at least 900%, or at least 1,000% in a cell. Gene expression may be determined by routine methods including enzyme-linked immunosorbent assays (ELISAs), western blots, and quantification of RNA (e.g., reverse transcription polymerase chain reaction).

In some embodiments, any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced to a tissue, cell, or organ ex vivo (e.g., not in a subject) and the tissue, cell, and/or organ may be further cultured ex vivo. In some embodiments, any of the nucleic acids (e.g., engineered nucleic acid) (e.g., expression vector) capable of inducing expression of OCT4; KLF4; SOX2; or any combination thereof, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone, or in combination may be introduced to a tissue, cell, or organ ex vivo (e.g., not in a subject) and the tissue, cell, and/or organ may be further cultured ex vivo. In some instances, an inducing agent and/or a chemical agent capable of modulating the activity of the inducing agent is introduced to a tissue, cell, and/or organ ex vivo and the tissue, cell, and/or organ may be further cultured ex vivo. In some embodiments, engineered cells are cultured to produce an engineered tissue. In some embodiments, engineered cells are cultured to produce an engineered organ. In some embodiments, an engineered tissue is cultured to produce an engineered organ. These methods may be useful in producing an engineered (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) cell, engineered (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) tissue or organ (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) for transplantation into a subject. In some embodiments, the engineered cell, tissue, and/or organ is transplanted into a subject.

In some embodiments, cells, tissues, organs, or any combination thereof to be engineered are autologous to the subject, e.g., obtained from a subject in need thereof. Administration of autologous cells, autologous tissues, autologous organs, or any combination thereof may result in reduced rejection of the cells, tissues, organs, or any combination thereof compared to administration of non-autologous cells, non-autologous tissue and/or non-autologous organs. Alternatively, the cells, tissues, or organs to be engineered may be allogenic cells, allogenic tissues, or allogenic organs. For example, allogenic cells, allogenic tissue, allogenic organs, or any combination thereof may be derived from a donor (e.g., from a particular species) and administered to a recipient (e.g., from the same species) who is different from the donor. In some embodiments, allogenic cells, allogenic tissue, allogenic organs, or any combination thereof may be derived from a donor subject from a particular species and administered to a recipient subject from a different species from the donor.

In some embodiments, the engineered cell is a stem cell (iPSC) including naïve iPSC that can different into three germ layers. In some embodiments, the iPSC is further differentiated into another cell type (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). The iPSC may be further differentiated using methods known in the art (e.g., ex vivo)

In some embodiments, engineered cells comprise more than one cell type (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

As a non-limiting example, any of the engineered nucleic acids (e.g., naked nucleic acids or nucleic acids formulated in a delivery vehicle, including a viral vector and/or nanoparticle) encoding OCT4, KLF4, and SOX2, may be delivered to a cell (e.g., a differentiated cell) to produce an induced pluripotent stem cell. In some embodiments, the induced pluripotent stem cell is further differentiated (e.g., differentiated into an eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine cell). In some embodiments, cells are engineered ex vivo and administered to a subject in need thereof. In some embodiments, an organ or a tissue may be regenerated in vitro using iPSCs and the organ or tissue is transplanted into an individual.

As a non-limiting example, the methods described herein may be used to produce engineered skin, an engineered liver, an engineered eye, an engineered liver, any engineered cell, any engineered organ, or any engineered tissue ex vivo. The engineered organ, engineered tissue, engineered organ, or any combination thereof may be administered to a subject. In some embodiments, administration of an engineered cell, engineered tissue, engineered organ, or a combination thereof improves survival of a subject (e.g., increases the lifespan of a subject relative to not receiving the engineered cell, tissue, or organ).

A pharmaceutical composition described herein may be administered to a subject in need thereof. Non-limiting examples of subjects include any animal (e.g., mammals, including humans). A subject may be suspected of having, be at risk for or have a condition. For example, the condition may be an injury or a disease and the condition may affect any tissue (e.g., ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). Non-limiting examples of conditions, diseases, and disorders include acute injuries, neurodegenerative disease, chronic diseases, proliferative diseases, cardiovascular diseases, genetic diseases, inflammatory diseases, autoimmunue diseases, neurological diseases, hematological diseases, painful conditions, psychiatric disorders, metabolic disorders, cancers, aging, age-related diseases, and diseases affecting any tissue in a subject. In some embodiments, the disease is an ocular disease.

In certain embodiments, any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced to a subject prior to the onset of a disease (e.g., to prevent a disease or to prevent damage to a cell, tissue, or organ). In certain embodiments, any of the nucleic acids (e.g., engineered nucleic acid) (e.g., expression vector) capable of inducing expression of OCT4; KLF4; SOX2; or any combination thereof, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone, or in combination may be introduced to a subject prior to the onset of a disease (e.g., to prevent a disease or to prevent damage to a cell, tissue, or organ). In certain embodiments, an inducing agent and/or a chemical agent capable of modulating activity of the inducing agent may be introduced to a subject prior to the onset of a disease. In some embodiments, the subject may be a healthy subject.

In certain embodiments, any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced to a subject following the onset of disease (e.g., to alleviate the damage or symptoms associated with a disease). In certain embodiments, any of the nucleic acids (e.g., engineered nucleic acid) capable of inducing expression of OCT4; KLF4; SOX2; or any combination thereof expression, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone or in combination, may be introduced to a subject following the onset of disease (e.g., to alleviate the damage or symptoms associated with a disease). In some embodiments, OCT4, KLF4, and/or SOX2 expression is induced prior to the onset of a disease. In some embodiments, expression of OCT4; KLF4; SOX2; or any combination thereof is induced prior to the onset of a disease. In some embodiments, OCT4, KLF4, and/or SOX2 expression is induced after the onset of a disease. In some embodiments, expression of OCT4; KLF4; SOX2; or any combination thereof is induced after the onset of a disease. In some embodiments, OCT4, KLF4, and/or SOX2 expression is induced in a young subject, young cell, young tissue, and/or young organ. In some embodiments, OCT4, KLF4, and/or SOX2 expression is induced in an aged subject, aged cell, aged tissue, and/or aged organ. In some embodiments, expression of OCT4; KLF4; SOX2; or any combination thereof is induced in a young subject, young cell, young tissue, and/or young organ. In some embodiments expression of, OCT4; KLF4; SOX2; or any combination thereof is induced in an aged subject, aged cell, aged tissue, and/or aged organ. In certain embodiments, an inducing agent and/or a chemical agent capable of modulating activity of the inducing agent may be introduced to a subject following the onset of a disease.

In certain embodiments, the tissue may be considered healthy but suboptimal for performance or survival in current or future conditions (e.g., in agriculture, or adverse conditions including disease treatments, toxic therapies, sun exposure, or space travel outside the earth's atmosphere).

In certain embodiments, the condition is aging. All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

In some cases, characteristics of aging can be quite obvious. For example, characteristics of older humans include skin wrinkling, graying of the hair, baldness, and cataracts, as well as hypermelanosis, osteoporosis, cerebral cortical atrophy, lymphoid depletion, thymic atrophy, increased incidence of diabetes type II, atherosclerosis, cancer, and heart disease. Nehlin et al. (2000), *Annals NY Acad Sci* 980:176-79. Other aspects of mammalian aging include weight loss, lordokyphosis (hunchback spine), absence of vigor, lymphoid atrophy, decreased bone density, dermal thickening and subcutaneous adipose tissue, decreased ability to tolerate stress (including heat or cold, wounding, anesthesia, and hematopoietic precursor cell ablation), liver pathology, atrophy of intestinal villi, skin ulceration, amyloid deposits, and joint diseases. Tyner et al. (2002), Nature 415:45-53.

Those skilled in the art will recognize that the aging process is also manifested at the cellular level, as well as in mitochondria. Cellular aging is manifested in loss of doubling capacity, increased levels of apoptosis, changes in differentiated phenotype, and changes in metabolism, e.g., decreased levels of protein synthesis and turnover.

Given the programmed nature of cellular and organismal aging, it is possible to evaluate the "biological age" of a cell or organism by means of phenotypic characteristics that are correlated with aging. For example, biological age can be deduced from patterns of gene expression, resistance to stress (e.g., oxidative or genotoxic stress), rate of cellular proliferation, and the metabolic characteristics of cells (e.g., rates of protein synthesis and turnover, mitochondrial function, ubiquinone biosynthesis, cholesterol biosynthesis, ATP levels within the cell, levels of a Krebs cycle intermediate in the cell, glucose metabolism, nucleic acid (e.g., engineered nucleic acid) metabolism, ribosomal translation rates, etc.). As used herein, "biological age" is a measure of the age of a cell or organism based upon the molecular characteristics of the cell or organism. Biological age is distinct from "temporal age," which refers to the age of a cell or organism as measured by days, months, and years.

The rate of aging of an organism, e.g., an invertebrate (e.g., a worm or a fly) or a vertebrate (e.g., a rodent, e.g., a mouse) can be determined by a variety of methods, e.g., by one or more of: a) assessing the life span of the cell or the organism; (b) assessing the presence or abundance of a gene transcript or gene product in the cell or organism that has a biological age-dependent expression pattern; (c) evaluating resistance of the cell or organism to stress, e.g., genotoxic stress (e.g., etoposide, UV irradiation, exposure to a mutagen, and so forth) or oxidative stress; (d) evaluating one or more metabolic parameters of the cell or organism; (e) evaluating the proliferative capacity of the cell or a set of cells present in the organism; and (f) evaluating physical appearance or behavior of the cell or organism. In one example, evaluating the rate of aging includes directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined by measuring an age-related parameter. Examples of age-related parameters include: appearance, e.g., visible signs of age; the expression of one or more genes or proteins (e.g., genes or proteins that have an age-related expression pattern); resistance to oxidative stress; metabolic parameters (e.g., protein synthesis or degradation, ubiquinone biosynthesis, cholesterol biosynthesis, ATP levels, glucose metabolism, nucleic acid (e.g., engineered nucleic acid) metabolism, ribosomal translation rates, etc.); and cellular proliferation (e.g., of retinal cells, bone cells, white blood cells, etc.).

Aging can also be determined by the rate of change of biomarkers (e.g., epigenetic marks including DNA methylation level of CpG island in the genome (known as the "Horvath Clock") beta-galactosidase-positive cells in cells, gene expression changes, or certain changes to the abundance of molecules in the bloodstream). An example is an algorithm from Segterra Inc. that determines "InnerAge" based on blood biomarkers (see InsideTracker.com).

As shown in the Examples herein, recombinant viruses (e.g., AAVs) encoding OCT4, KLF4, and SOX2 promoted regeneration of axons, which may be used to prevent or alleviate neurodegeneration that is often associated with aging. The methods may be used to prevent or alleviate neurodegeneration and peripheral neuropathies associated. Neurodegenerative diseases include Parkinson's disease, Alzheimer's disease, multiple sclerosis, amniotropic lateral sclerosis (ALS), Huntington's disease, and muscular dystrophy. Neurodegeneration may be quantified using any method known in the art. For example, the executive function of an individual may be determined (Moreira et al., Front Aging Neurosci. 2017 Nov. 9; 9:369).

In some embodiments, expression, induction, or activation of OCT4, SOX2, KLF4, or a combination thereof as described herein increases the number of axons per nerve in a tissue, organ, or a subject relative to a control. In some embodiments, a method described herein increases the number of axons per nerve by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the number of axons per nerve in the tissue, organ, or subject prior to expression, induction, or activation of OCT4, SOX2, KLF4, or a combination thereof.

Additional age-related conditions which may be treated include heart failure, stroke, diabetes, liver diseases, fibrotic diseases, osteoporosis, arthritis, hearing loss (partial or total), eye-related conditions (e.g., poor eye sight, retinal disease, any ocular disease (e.g., any condition affecting the eye)), glaucoma, muscle diseases (e.g., sarcopenia and muscular dystrophies), frailty, a progeroid syndrome (e.g., Hutchinson-Gilford progeria syndrome), and cancer. In certain embodiments, the disease is a retinal disease (e.g., macular degeneration).

In some embodiments, expression, induction, or activation of OCT4, SOX2, KLF4, or a combination thereof in a neuron increases neurite area of the neuron by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to the neuron without expression, induction, or activation of OCT4, SOX2, KLF4, or a combination thereof.

In some embodiments, expression, induction, or activation of OCT4, SOX2, KLF4, or a combination thereof as described herein increases the axon density in a tissue, organ, or a subject relative to a control. In some embodiments, a method described herein increases axon density at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the axon density in the tissue, organ, or subject prior to expression, induction, or activation of OCT4, SOX2, KLF4, or a combination thereof.

In some embodiments, expression, induction, or activation of OCT4, SOX2, KLF4, or a combination thereof in a subject increases the visual acuity of the subject relative to a control. In some embodiments, a method described herein increases the visual acuity of a subject by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the visual acuity of the subject prior to expression, induction, or activation of OCT4, SOX2, KLF4, or a combination thereof. In some embodiments, visual acuity is measured by optomotor acuity. In some embodiments, visual acuity is measured using a pattern electroretinogram response. In some embodiments, visual acuity is measured using a distance visual acuity test, which may include the use of a Snellen chart or E chart. See, e.g., Marsden et al., Community Eye Health. 2014; 27(85): 16 and the Examples below.

In some embodiments, expression, induction, or activation of OCT4, SOX2, KLF4, or a combination thereof in a subject decreases the intraocular pressure of the subject relative to a control. In some embodiments, a method described herein decreases the intraocular pressure of a subject by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the intraocular pressure of the subject prior to expression, induction, or activation of OCT4, SOX2, KLF4, or a combination thereof. See, e.g., the Examples below.

In some embodiments, any of the nucleic acids (e.g., engineered nucleic acids) capable of inducing OCT4, KLF4, and/or SOX2 expression (e.g., expression vector), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein may be used to treat and/or prevent any of the diseases described herein. In some embodiments, an inducing agent and/or a chemical agent capable of modulating activity of the inducing agent is also used.

As a non-limiting example, an engineered cell of the present disclosure may be used to replace a dysfunctional cell in a subject in need thereof. As another non-limiting example, any of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) may be used to (e.g., incompletely or fully) reprogram a cell in vivo or in vitro. In some embodiments, an inducing agent and/or a chemical agent capable of modulating activity of the inducing agent is also used. For example, any of the any of the nucleic acids (e.g., engineered nucleic acids) capable of inducing OCT4, KLF4, and/or SOX2 expression (e.g., expression vector), engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) may be used to produce an engineered cell (e.g., an induced pluripotent stem cell). For example, any of the nucleic acids (e.g., engineered nucleic acids) (e.g., expression vector) capable of inducing expression of OCT4, KLF4, SOX2, or a combination thereof, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) may be used to produce an engineered cell (e.g., an induced pluripotent stem cell). The engineered cell (e.g., induced pluripotent stem cell) may then be administered to a subject in need thereof. In some embodiments, the engineered cell is cultured in the presence of an inducing agent and/or a chemical agent capable of modulating activity of the inducing agent. In some embodiments, an inducing agent and/or a chemical agent capable of modulating activity of the inducing agent is also administered to the subject.

Non-limiting uses of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, engineered cells, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) include wound healing, bleed out, injuries, broken bones, gunshot wounds, cuts, scarring during surgery (e.g., cesarean). In some embodiments, an inducing agent and/or a chemical agent capable of modulating activity of the inducing agent is also used.

In some embodiments, any of the of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered cells, engineered proteins, chemical agents activating (e.g., inducing expression of) OCT4, an KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) are used to treat disease that affects a non-human subject (e.g., a disease affecting livestock, domesticated pets, and/or other non-human animals). In some embodiments, an inducing agent and/or a chemical agent capable of modulating activity of the inducing agent is also used. For example, the disease may be a cattle disease, a primate (e.g., cynomolgus monkeys, rhesus monkeys) disease, a disease affecting a commercially relevant animal, such as cattle, pigs, horses, sheep, goats, cats, and/or dogs) and/or a disease affecting birds (e.g., commercially relevant birds, such as chickens, ducks, geese, and/or turkeys).

In some embodiments, any of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered cells, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) described herein are used to promote wound healing (e.g., for a cut), treat an injury (e.g., broken bones, bleeding out, gun shot injury, and/or reduce scarring during surgery). In some embodiments, surgery includes cesarean. In some embodiments, an inducing agent and/or a chemical agent capable of modulating activity of the inducing agent is also used.

In some embodiments, any of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered cells, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) described herein are useful in healing an injury and/or inflammation. In some embodiments, an inducing agent and/or a chemical agent capable of modulating activity of the inducing agent is also used. In some embodiments, the inflammation is hyperinflammation, which may be a side effect of aging. In some embodiments, the hyperinflammation is inflammaging.

In some embodiments, any of the nucleic acids (e.g., engineered nucleic acids) capable of inducing OCT4, KLF4, and/or SOX2 expression (e.g., expression vectors), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein provide a healing capacity.

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein provide a healing capacity.

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein are useful in enhancing or rejuvenating optimal or sub-optimal organs. As a non-limiting example, any of the compositions described herein (e.g., recombinant viruses including recombinant AAV viruses) encoding OCT4, KLF4, SOX2, or a combination thereof may be useful in enhancing or rejuvenating suboptimal organs (e.g., from older individuals) that are used for transplantation or to promote organ survival during transport or to promote organ survival after reimplantation of the organ into a subject.

Any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein may be used to rejuvenate or increase the survival and longevity of cells (e.g., hematopoietic stem cells, T-cells, etc.) that are used for transplantation. In some embodiments, recombinant viruses (e.g., AAV viruses) encoding OCT4, KLF4, SOX2, or a combination thereof are useful in rejuvenating or increasing the survival and longevity of cells (e.g., hematopoietic stem cells, T-cells, etc.) that are used for transplantation.

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein is used to prevent or relieve the side effects of a toxin and/or a drug (e.g., a chemotherapy) in a subject. Non-limiting examples of side effects include hair loss and peripheral neuropathy. Chemotherapies include vincristine (VCS). See, e.g., example 15. In certain embodiments, a composition comprising a recombinant virus (e.g., AAV virus) encoding SOX2, KLF4, OCT4, or a combination thereof, is administered to treat (e.g., recover from) or prevent the side effects induced by a toxin and/or damaging drug therapy (e.g., a chemotherapy drug including VCS).

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein is administered to a subject to prevent or relieve the side effects of a toxin and/or a drug (e.g., a chemotherapy).

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein is administered to a subject to protect a tissue, organ, and/or entire body of the subject from radiation (e.g., prevent the damaging effects of radiation). In certain embodiments, AAV encoding OCT4, SOX2, KLF4, or any combination thereof, is administered to a subject to protect a tissue, organ, and/or entire body of the subject from radiation protect (e.g., prevent the damaging effects of radiation).

Methods for identifying subjects suspected of having a condition may include physical examination, subject's family medical history, subject's medical history, biopsy, genetic testing, DNA sequencing of pathogens or the microbiome, proteomics, or a number of imaging technologies such as ultrasonography, computed tomography, magnetic resonance imaging, magnetic resonance spectroscopy, or positron emission tomography.

Effective amounts of the engineered nucleic acids (e.g., expression vectors, including viral vectors), viruses (e.g., lentiviruses, retroviruses, adenoviruses, retroviruses, alphaviruses, vaccinia viruses, or AAVs) or compositions thereof vary, as recognized by those skilled in the art, depending on route of administration, excipient usage, and co-usage with other active agents. The quantity to be administered depends on the subject to be treated, including, for example, the age of the subject, the gravity of the condition, the weight of the subject, the genetics of the subject, the cells, tissue, or organ to be targeted, or any combination thereof.

Expression of one or more transcription factors of the present disclosure (e.g., OCT4; KLF4; SOX2; or any combination thereof) may result in reprogramming of a cell, tissue repair, tissue regeneration, increase blood flow, organ regeneration, improved immunity, reversal of aging, counter senescence, or any combination thereof. Cellular reprogramming may be determined by determining the extent of differentiation of a cell (e.g., by determining the expression of one or more lineage markers or pluripotency markers, including OCT4, KLF4, SOX2, NANOG, ESRRB, NR4A2, and C/EBPα). The differentiation potential of a cell may also be determined using routine differentiation assays or gene expression patterns. Tissue repair may be determined by tissue replacement and tissue regeneration assays. For example, tissue replacement assays include wound healing assays in cell culture or in mice. Tissue regeneration may be determined by quantifying a particular cell type following expression of one or more transcription factors compared to before expression of OCT4, KLF4, and SOX2 (see, e.g., the Examples provided below). Tissue regeneration may be determined by quantifying a particular cell type following expression of one or more transcription factors compared to before expression of OCT4; KLF4; SOX2; or any combination thereof. In some instances, the methods described herein promote organ regeneration (e.g. liver regeneration or reversal of liver fibrosis and regrowth). In some instances, the methods described herein promote tissue and cell survival. Cell survival in the face of adversity and damage may be determined using assays for cell viability that are standard in the art (e.g., testing neuronal survival with the nano-glo live cell assay from Promega corp.). In some instances, the methods described herein may prevent axonal or Wallerian degeneration, which may be determined by quantifying the rate of axonal degeneration after nerve crush in vitro using nerve cell cultures or in rat and mouse nerve crush models known to those skilled in the art.

In some embodiments, the methods described herein do not induce teratoma formation. In some embodiments, expression of OCT4, SOX2, KLF4, or a combination thereof or activation of OCT4, SOX2, KLF4, or a combination thereof in a subject, tissue, or organ, results in at least 10%, at least 20%, at least 30%, at least 40%, at least 50%, at least 60%, at least 70%, at least 80%, at least 90%, or at least 100% reduction in teratoma formation as compared to expression of OCT4, SOX2, KLF4, or a combination thereof and c-MYC or activation of OCT4, SOX2, KLF4, or a combination thereof and c-MYC in the subject, tissue, or organ. In some embodiments, expression of OCT4, SOX2, and KLF4 or activation of OCT4, SOX2, and KLF4 in a subject, tissue, or organ, results in at least 10%, at least 20%, at least 30%, at least 40%, at least 50%, at least 60%, at least 70%, at least 80%, at least 90%, or at least 100% reduction in teratoma formation as compared to expression of OCT4, SOX2, and KLF4, and c-MYC or activation of OCT4, SOX2, KLF4, and c-MYC in the subject, tissue, or organ. In some embodiments, the number of teratomas or the size of a teratoma in a subject, tissue, or organ is the same or is reduced following expression of OCT4, SOX2, KLF4, or a combination thereof or activation of OCT4, SOX2, KLF4, or a combination thereof in a subject, tissue, or organ as compared to the number of teratomas or the size of a teratoma in the subject, tissue, or organ prior to activation or expression of OCT4, SOX2, KLF4, or a combination thereof.

In some embodiments, the methods described herein do not induce unwanted cell proliferation. In some embodiments, the unwanted cell proliferation is aberrant cell proliferation, which may be benign or cancerous. In some embodiments, expression of OCT4, SOX2, KLF4, or a combination thereof or activation of OCT4, SOX2, KLF4, or a combination thereof in a subject, tissue, or organ reduces unwanted cell proliferation in a subject, tissue, or organ, by at least 10%, at least 20%, at least 30%, at least 40%, at least 50%, at least 60%, at least 70%, at least 80%, at least 90%, or at least 100% as compared to the same method with c-Myc expression or activation. In some embodiments, unwanted cell proliferation in a subject, tissue, or organ is the same or is reduced following expression of OCT4, SOX2, KLF4, or a combination thereof or activation of OCT4, SOX2, KLF4, or a combination thereof in a subject, tissue, or organ as compared to the amount of unwanted cell proliferation in the subject, tissue, or organ prior to activation or expression of OCT4, SOX2, KLF4, or a combination thereof.

In some embodiments, the methods described herein do not induce tumor formation or tumor growth. In some embodiments, expression of OCT4, SOX2, KLF4, or a combination thereof or activation of OCT4, SOX2, KLF4, or a combination thereof in a subject, tissue, or organ reduces the number of tumors or the size of a tumor in a subject, tissue, or organ, by at least 10%, at least 20%, at least 30%, at least 40%, at least 50%, at least 60%, at least 70%, at least 80%, at least 90%, or at least 100% as compared to the same method with c-Myc expression or activation. In some embodiments, the number of tumors or the size of a tumor in a subject, tissue, or organ is the same or is reduced following expression of OCT4, SOX2, KLF4, or a combination thereof or activation of OCT4, SOX2, KLF4, or a combination thereof in a subject, tissue, or organ as compared to the number of tumors or the size of a tumor in the subject, tissue, or organ prior to activation or expression of OCT4, SOX2, KLF4, or a combination thereof. In some embodiments, a method described herein does not induce cancer. In some embodiments, a method described herein does not induce glaucoma.

Methods of reprogramming are also provided herein. In some embodiments, a method of reprogramming described herein comprises reversing or rejuvenating the epigenetic clock of a cell, tissue, organ, or a subject. In some embodiments, the epigenetic clock may be partially or fully reversed. In some embodiments, the epigenetic clock of a cell, tissue, organ, or a subject is measured using DNA methylation-based age (DNAmAGE or DNAm age). In some embodiments, a method described herein reduces the DNAmAge age of a cell by 1%, 5%, 10%, 20%, 30%, 40%, 50%, 60%, 70%, 80%, 90%, or 100%.

In some embodiments, a method of reprogramming described herein comprises altering the expression of one or more genes associated with ageing. In some embodiments, expression of a gene is increased by at least 1%, at least 5%, at least 10%, at least 20%, at least 30%, at least 40%, at least 50%, at least 60%, at least 70%, at least 80%, at least 90%, or at least 100%. In some embodiments, expression of a gene is reduced by at least 1%, at least 5%, at least 10%, at least 20%, at least 30%, at least 40%, at least 50%, at least 60%, at least 70%, at least 80%, at least 90%, or at least 100%. In some embodiments, expression of one or more genes following performance of a method is determined relative to expression of the one or more genes prior to performance of the method. In some embodiments, expression of one or more genes is determined relative to expression of the one or more genes in a young cell, a young subject, a young tissue, a young organ, or any combination thereof. In some embodiments, expression of one or more genes is determined relative to expression of the one or more genes in an old cell, an old subject, an old tissue, an old organ, or any combination thereof.

A gene associated with ageing may be a gene whose expression is altered in an old, an old tissue, an old organ, an old subject, or any combination thereof as compared to a young counterpart. In some embodiments, the gene associated with ageing is 1700031P21Rik, 1810053B23Rik, 2900045020Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1cl, Ankrd1, Asb15, Atp2c2, AU018091, AW822073, Btnl10, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps8l1, EU599041, Fam90a1a, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2al2a, Ido2, Igfbp1, Kif7, Klhl31, Lrrc31, Mc5r, Mgam, Msh4, Mucl2, Mug1, Mybl2, Myhl5, Nek10, Neurod6, Nr1h5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otogl, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Ccl9, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnaja1-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galnt18, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg1l2, Hapln4, Hcn3, Hcn4, Hhatl, Hs6st2, Htr3a, Il1rap, Il1rap12, Inka1, Kbtbd12, Kcnj11, Kcnk4, Kdelc2, Klhl33, Lamc3, Lilra5, Lman11, Lrfn2, Lrrc38, Lrrn4cl, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sel1l3, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof. In some embodiments, the gene is a sensory gene.

In some embodiments, a method described herein reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Ccl9, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnaja1-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galnt18, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg1l2, Hapln4, Hcn3, Hcn4, Hhatl, Hs6st2, Htr3a, Il1rap, Il1rap12, Inka1, Kbtbd12, Kcnj11, Kcnk4, Kdelc2, Klhl33, Lamc3, Lilra5, Lman11, Lrfn2, Lrrc38, Lrrn4cl, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sel1l3, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof. See, e.g., Table 5 for genes associated with ageing.

In some embodiments, a method described herein increases expression of 1700031P21Rik, 1810053B23Rik, 2900045O20Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1cl, Ankrd1, Asb15, Atp2c2, AU018091, AW822073, Btnl10, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps8l1, EU599041, Fam90a1a, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2al2a, Ido2, Igfbp1, Kif7, Klhl31, Lrrc31, Mc5r, Mgam, Msh4, Mucl2, Mug1, Mybl2, Myhl5, Nek10, Neurod6, Nr1h5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otogl, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Aspects of the present disclosure relate to methods comprising resetting the transcriptional profile of an old cell, an old organ, an old tissue, and/or any combination thereof in vitro. Aspects of the present disclosure relate to methods comprising resetting the transcriptional profile of an old cell, an old organ, an old tissue, an old subject and/or any combination thereof in vivo. In some embodiments, resetting the transcriptional profile an old cell, an old organ, an old tissue, an old subject and/or any combination thereof comprises altering the gene expression of one or more genes associated with ageing. In some embodiments, resetting the transcriptional profile an old cell, an old organ, an old tissue, an old subject and/or any combination thereof comprises reversing the epigenetic clock. In some embodiments, the transcription profile of an old cell is reset. In some embodiments, the transcriptional profile of an old cell, an old organ, an old tissue, an old subject, or any combination thereof is reset to that of a young cell, a young tissue, a young organ, a young subject, or any combination thereof. In some embodiments, a method described herein reverses one or more changes in gene expression that are detected between an old cell, an old organ, an old tissue, an old subject, or any combination thereof and a control. In some embodiments, the control is a young cell, a young organ, a young tissue, a young subject, or any combination thereof. In some embodiments, the transcriptional profile of an old cell, an old organ, an old tissue, an old subject, or any combination thereof is changed from a young counterpart. In some embodiments, a method described herein resets at least 10%, at least 20%, at least 30%, at least 40%, at least 50%, at least 60%, at least 70%, at least 80%, at least 90%, or 100% of the gene expression change in an old cell, an old organ, an old tissue, an old subject, or any combination thereof to a young level. In some embodiments, a sensory gene is a sensory receptor gene. Without being bound by a particular theory, resetting of a sensor receptor gene expression level in an aged cell to a young level may be indicative of an improvement of retina ganglion cell function.

In some aspects, the cellular reprogramming methods described herein may be used to promote the transdifferentiation of cells, which may be useful in treatment of disease. In some embodiments, the methods described herein may improve the efficiency of existing methods of transdifferentiation. For example, OCT4, SOX2, KLF4, or a combination thereof may be activated (e.g., expressed) in one cell type along with one or more perturbations of genes that affect cell fate to promote lineage reprogramming or conversion to another cell type. In some embodiments, the perturbation is reducing expression of a lineage determining factor. In some embodiments, the perturbation is expression of a lineage determining factor. In some embodiments, the lineage determining factor is a lineage transcription factor.

As a non-limiting example, night blindness is caused by rod death and daytime blindness is caused by cone death. Cell types including cones, rods, and muller cells could be reprogrammed into another cell type needed to restore vision. For example, loss of Nrl promotes transdifferentiation of adult rods into cone cells. See, e.g., Montana et al., Proc Natl Acad Sci USA. 2013 Jan. 29; 110(5):1732-7. In some embodiments, transcription factors that promote rod cell fate include Otx2, Crx and Nrl. As a non-limiting example, Müller glia (MG) can be reprogrammed into rod cells by expressing β-catenin, Otx2, Crx, and Nrl. See, e.g., Yao et al., Nature. 2018 August; 560(7719):484-488.

As another non-limiting example, pancreatic alpha may be reprogrammed into beta cells for treating autoimmune diseases and diabetes. Transcription factors including Pdx1 and MafA can be used to reprogram mouse alpha cells into beta cells. See, e.g., Xiao et al., Cell Stem Cell. 2018 Jan. 4; 22(1):78-90.e4.

Additional non-limiting examples of transdifferentiation inducing factors for production of various cell types may be found in Cieslar-Pobuda et al., Biochim Biophys Acta Mol Cell Res. 2017 July; 1864(7):1359-1369, which is herein incorporated by reference in its entirety. See e.g., Table 4 of Cieslar-Pobuda et al., Biochim Biophys Acta Mol Cell Res. 2017 July; 1864(7):1359-1369.

Induction of OCT4, SOX2, KLF4, or a combination thereof may increase the efficiency of trandifferentiation of cells by at least 1%, at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000%, including all values in between, as compared to a control. The efficiency of transdifferentiation may be measured by any suitable method including comparing the percentage of cells that were transdifferentiated when OCT4, SOX2, KLF4, or a combination thereof was activated as compared to control cells in which OCT4, SOX2, KLF4, or a combination thereof was not activated.

These and other aspects of the present invention will be further appreciated upon consideration of the following Examples, which are intended to illustrate certain particular embodiments of the invention but are not intended to limit its scope, as defined by the claims.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Figure 2:
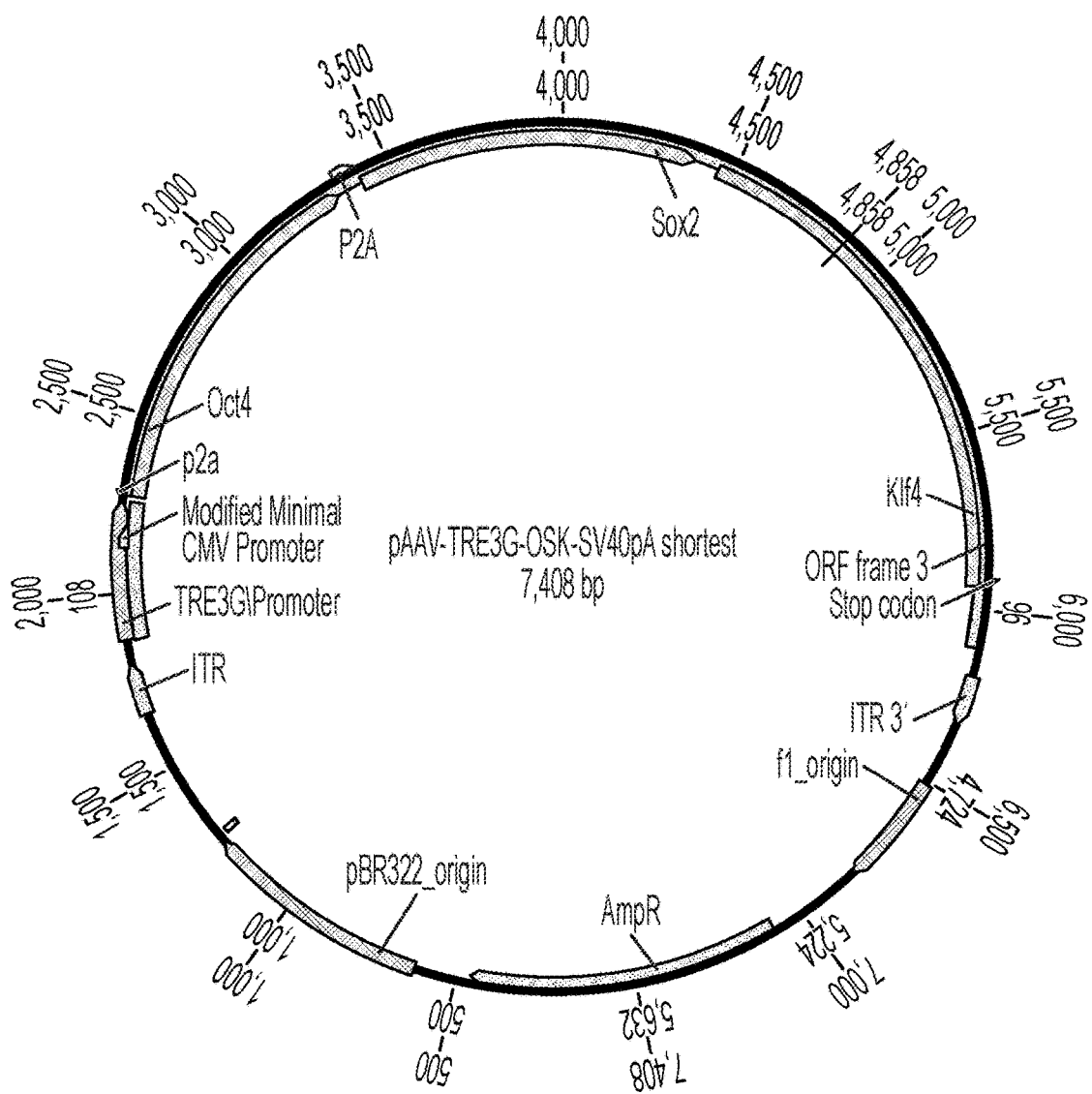
FIG. 2 is a vector map of TRE3G-OSK-SV40 pA, an AAV vector encoding OSK. Features including the location of sequences encoding OCT4, SOX2, and KLF4 and inverted terminal repeat sequences (ITRs) are indicated.
Figure 3:
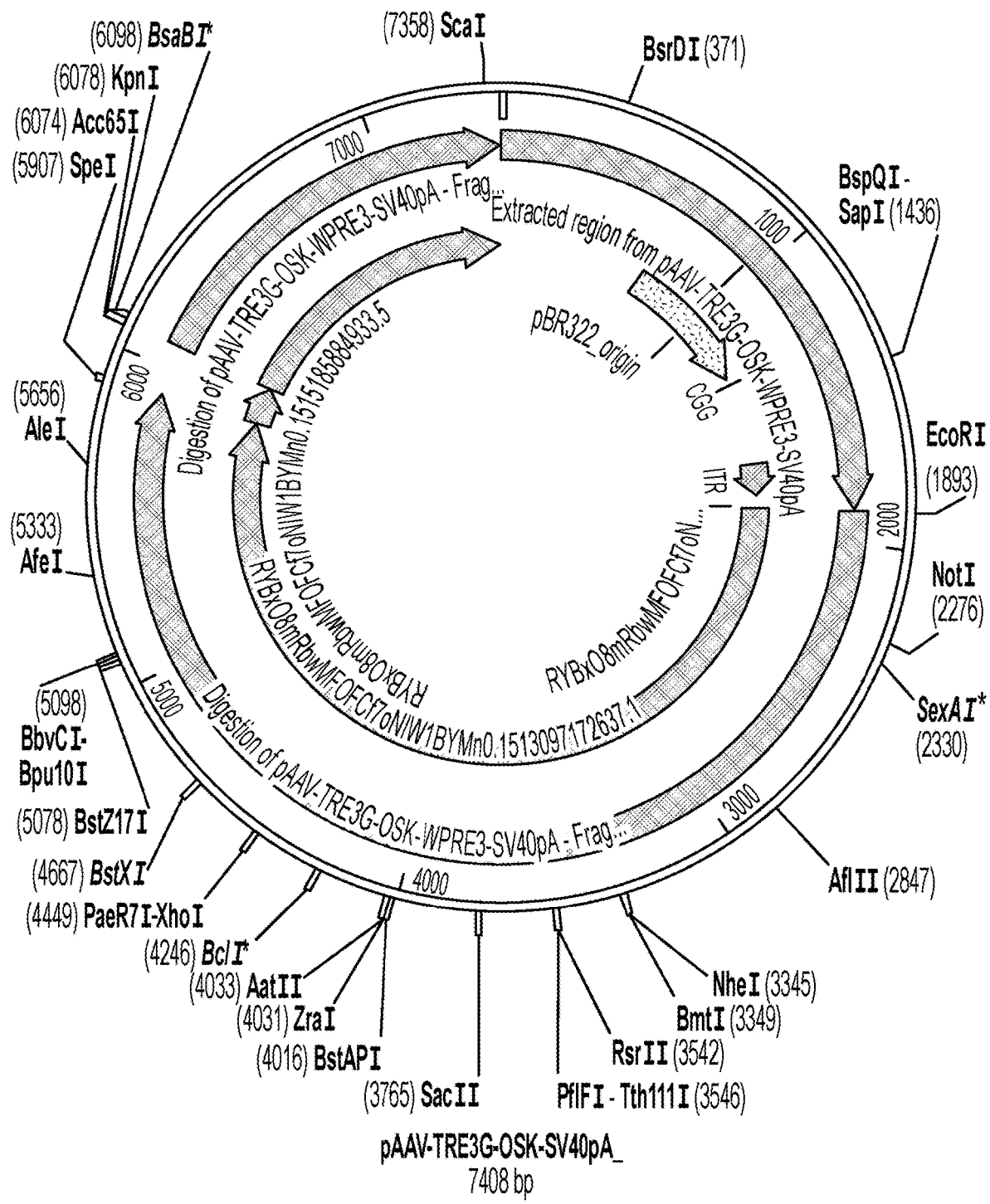
FIG. 3 is a vector map showing the location of restriction enzyme digestion sites in TRE3G-OSK-SV40 pA.

Example 1: Development of an Adenovirus-Associated Virus (AAV) Vector for Inducible Expression of OCT4, SOX2, and KLF4 (OSK) in Mammalian Cells An AAV vector that is capable of expressing OCT4, SOX2, and KLF4 in mammalian cells was developed as described herein. As shown in FIG. 1, such a vector comprises a TRE3G promoter (SEQ ID NO: 7), nucleic acids (e.g., engineered nucleic acids) encoding OCT4, SOX2, KLF4, and an SV40 polyA (SV40 pA) terminator sequence (SEQ ID NO: 8). This vector will be referred to as TRE3G-OSK-SV40 pA. Nucleic acid (e.g., engineered nucleic acid) sequences encoding self-cleaving peptides (T2A, a 2A peptide, SEQ ID NO: 9) were used to separate the nucleic acids (e.g., engineered nucleic acids) encoding OCT4, SOX2, and KLF4. As shown in FIG. 2, the entire vector is 7,408 base pairs in length and two inverted terminal repeats (ITRs) flank the OSK sequences. The restriction enzyme digestion sites in the vector are depicted in FIG. 3. A schematic mapping the features shown in the vector maps of FIGS. 4A-4AL onto the nucleic acid (e.g., engineered nucleic acid) sequence of the vector is shown in FIGS. 2-3. The restriction enzyme cut sites are shown in Table 3 below. As shown in FIGS. 5A-5D, the open reading frame (ORF frame 3) encoding OSK and intervening 2A peptides (T2A peptides) is 3,610 base pairs.

TABLE 3

Restriction Enzyme Cut Sites in the TRE3G-OSK-SV40pA vector.

| Enzymes | Sites | Location |
| --- | --- | --- |
| AatII | 1 | 4033 |
| Acc65I | 1 | 6074 |
| AfeI | 1 | 5333 |
| AflII | 1 | 2847 |
| AleI | 1 | 5656 |
| BbvCI | 1 | 5098 |
| BclI | 1* | 4246* |
| BmtI | 1 | 3349 |
| Bpu10I | 1 | 5098 |
| BsaBI | 1* | 6098* |
| BspQI | 1 | 1436 |
| BsrDI | 1 | 371 |
| BstAPI | 1 | 4016 |
| BstXI | 1 | 4667 |
| BstZ17I | 1 | 5078 |
| EcoRI | 1 | 1893 |
| KpnI | 1 | 6078 |
| NheI | 1 | 3345 |
| NotI | 1 | 2276 |
| PaeR7I | 1 | 4449 |
| PflFI | 1 | 3546 |
| RsrII | 1 | 3542 |
| SacII | 1 | 3765 |
| SapI | 1 | 1436 |
| ScaI | 1 | 7358 |
| SexAI | 1* | 2330* |
| SpeI | 1 | 5907 |
| Tth111I | 1 | 3546 |
| XhoI | 1 | 4449 |
| ZraI | 1 | 4031 |

Figure 4E:
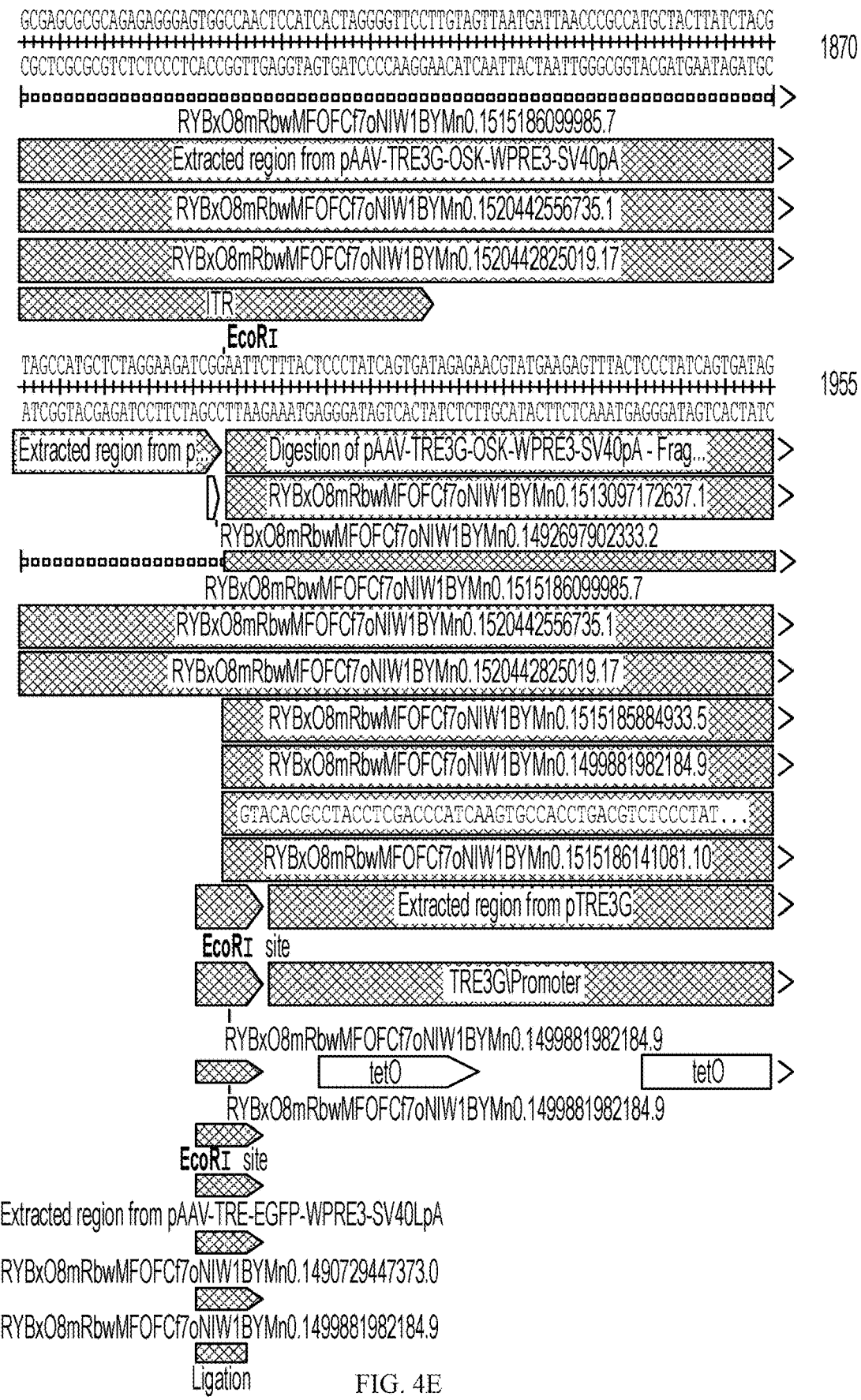
FIGS. 4A-4AL include a series of schematics mapping the features shown in FIGS. 2 and 3 onto the nucleic acid (e.g., engineered nucleic acid) sequence of TRE3G-OSK-SV40 pA.
Figure 4F:
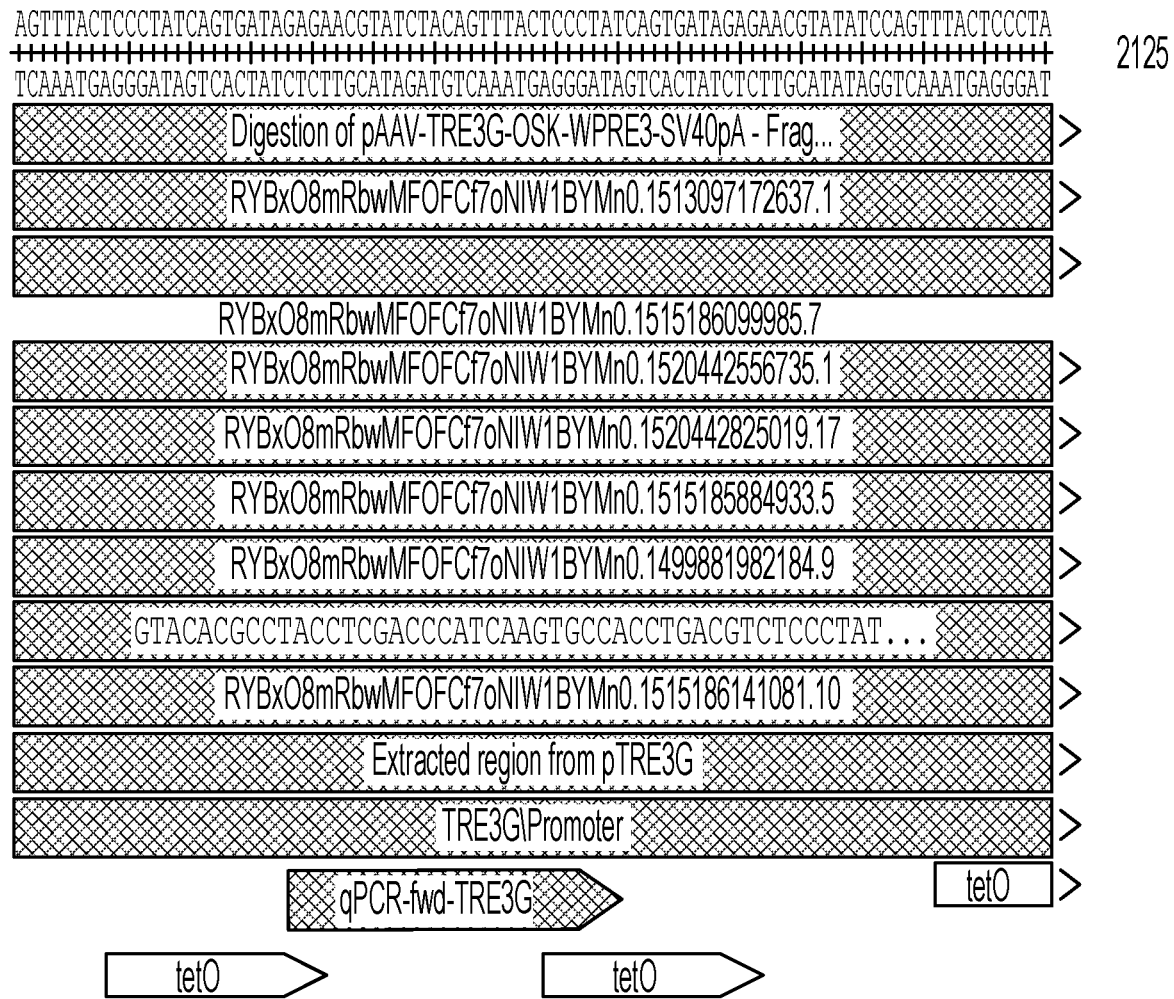
Figure 4G:
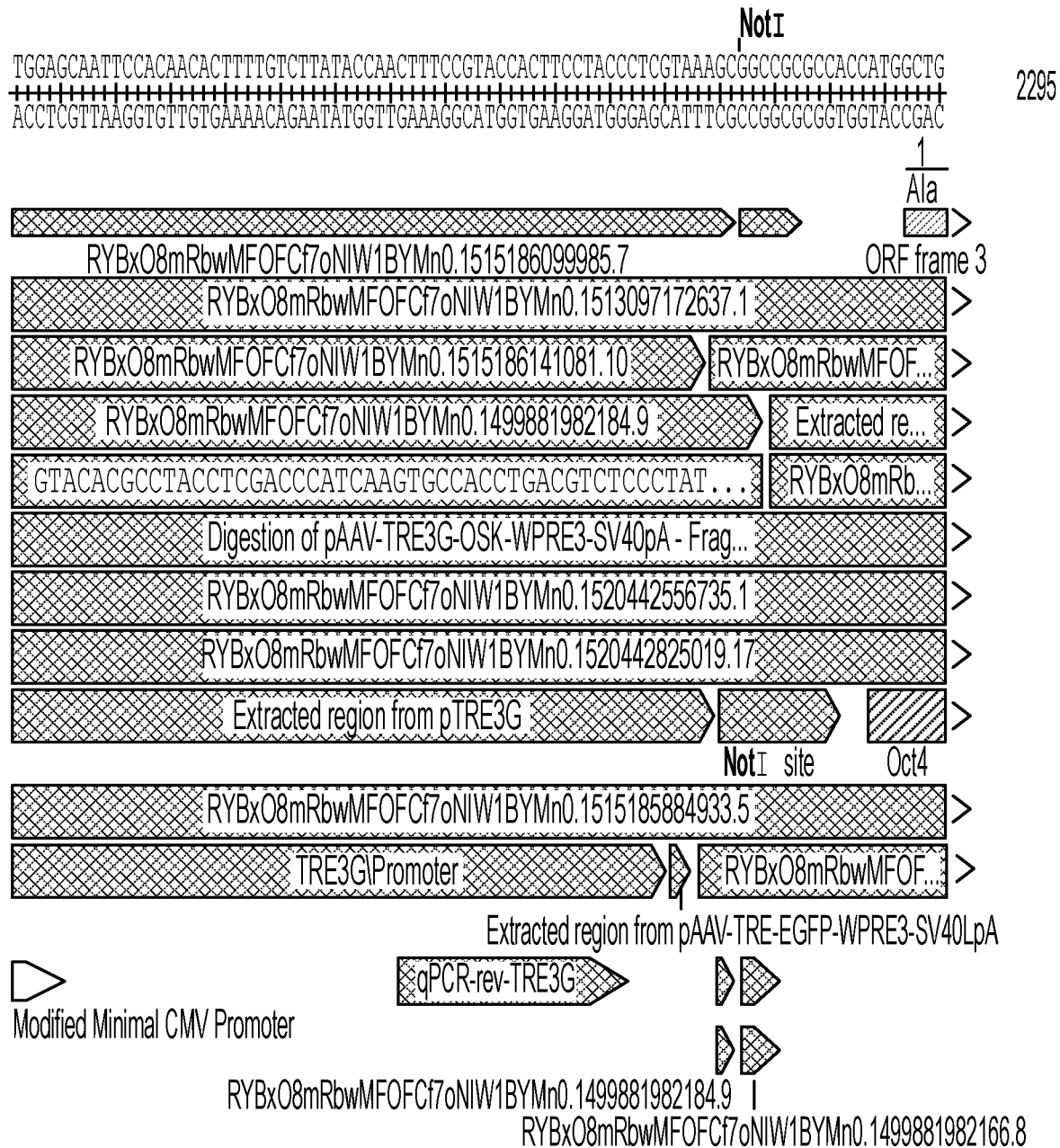
Figure 4H:
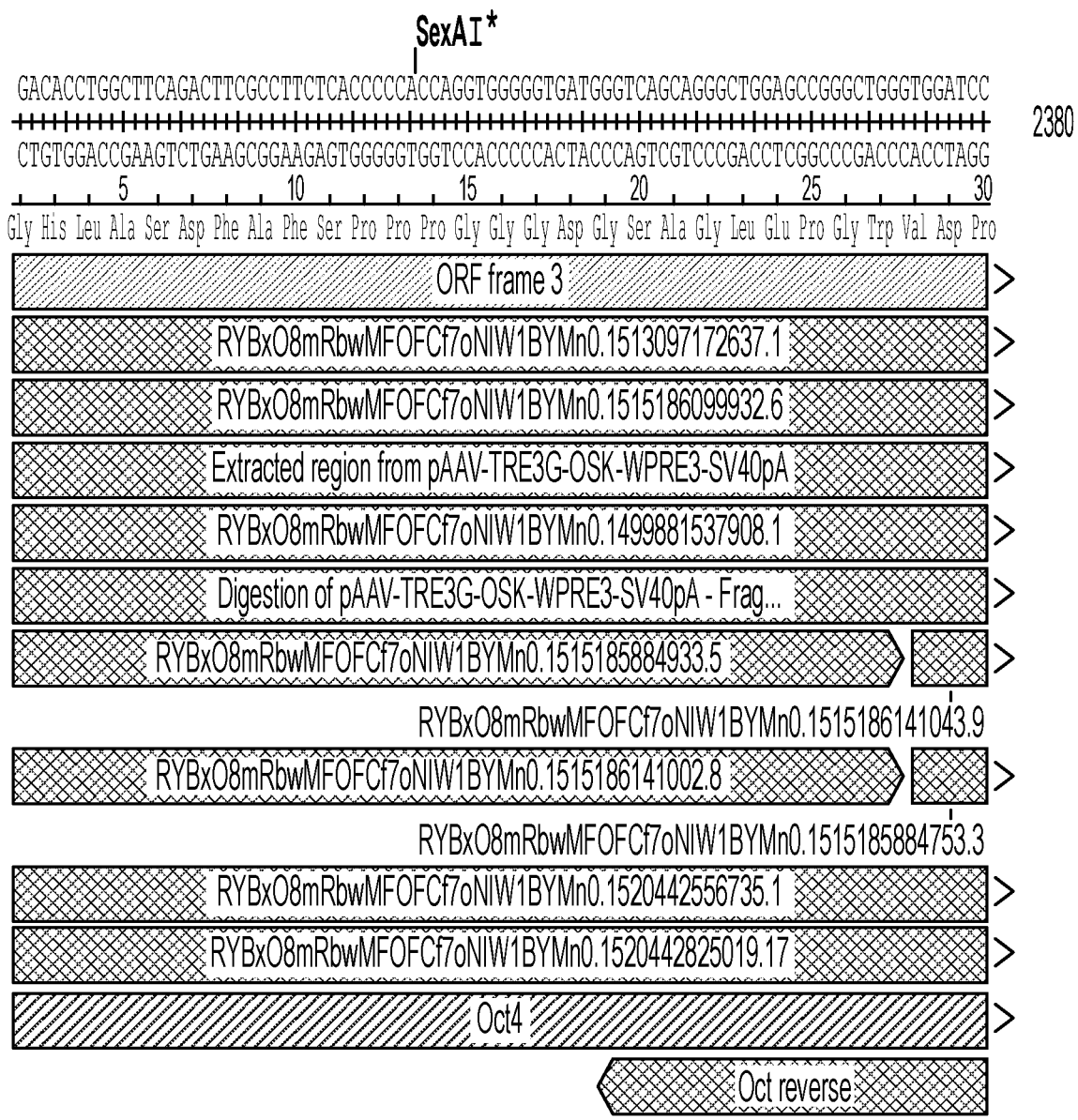
Figure 4H:
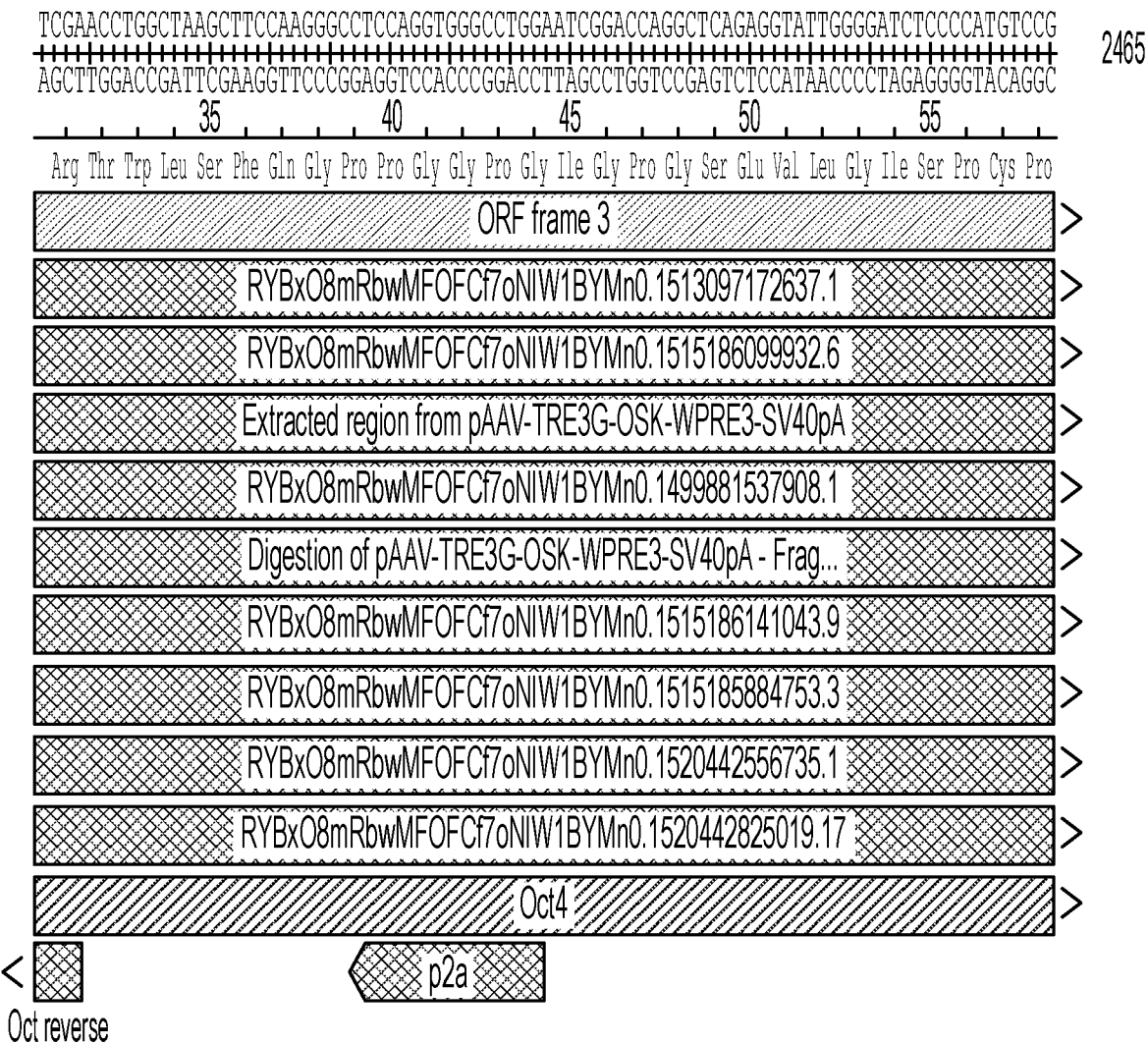
Figure 4M:
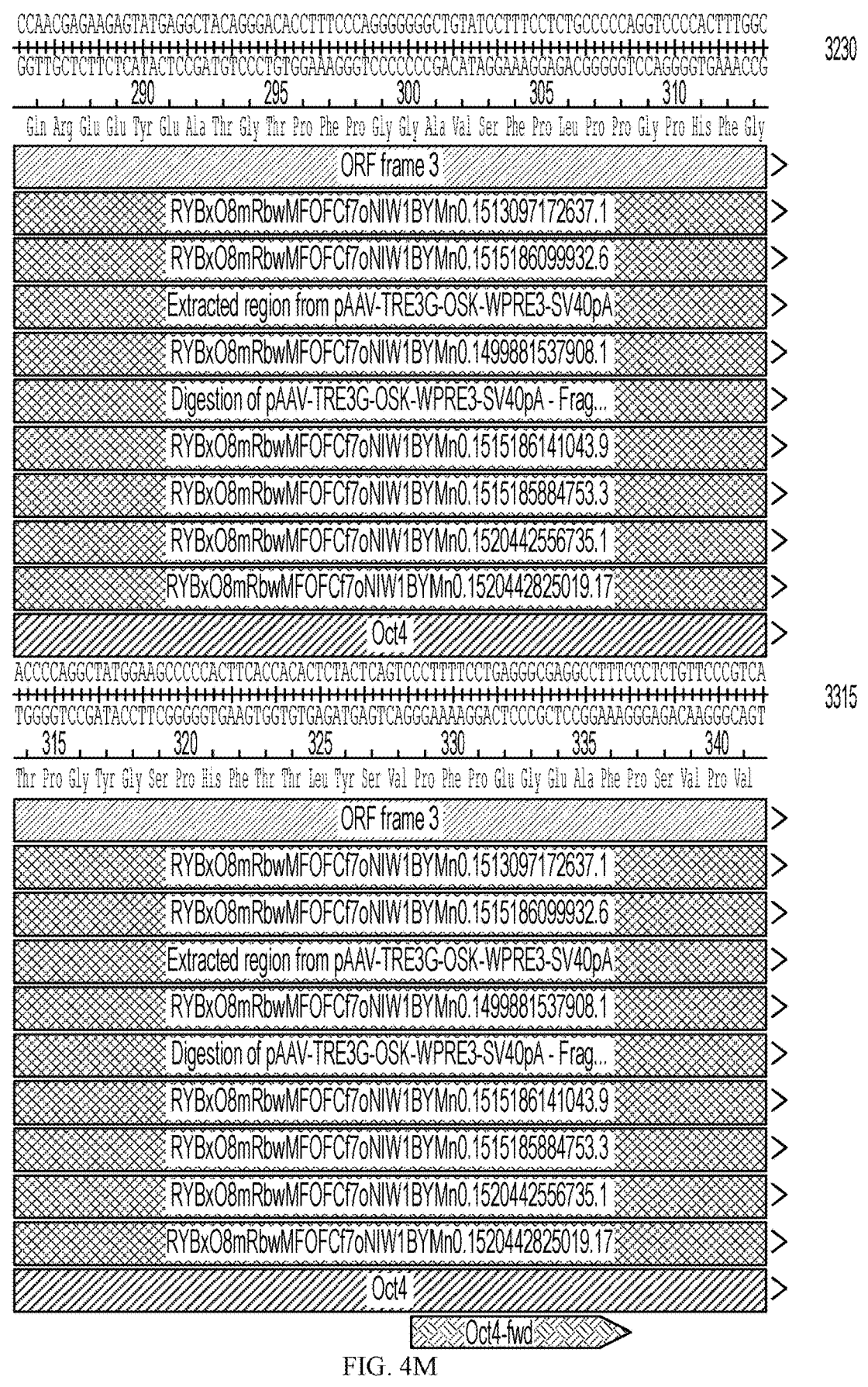
Figure 4N:
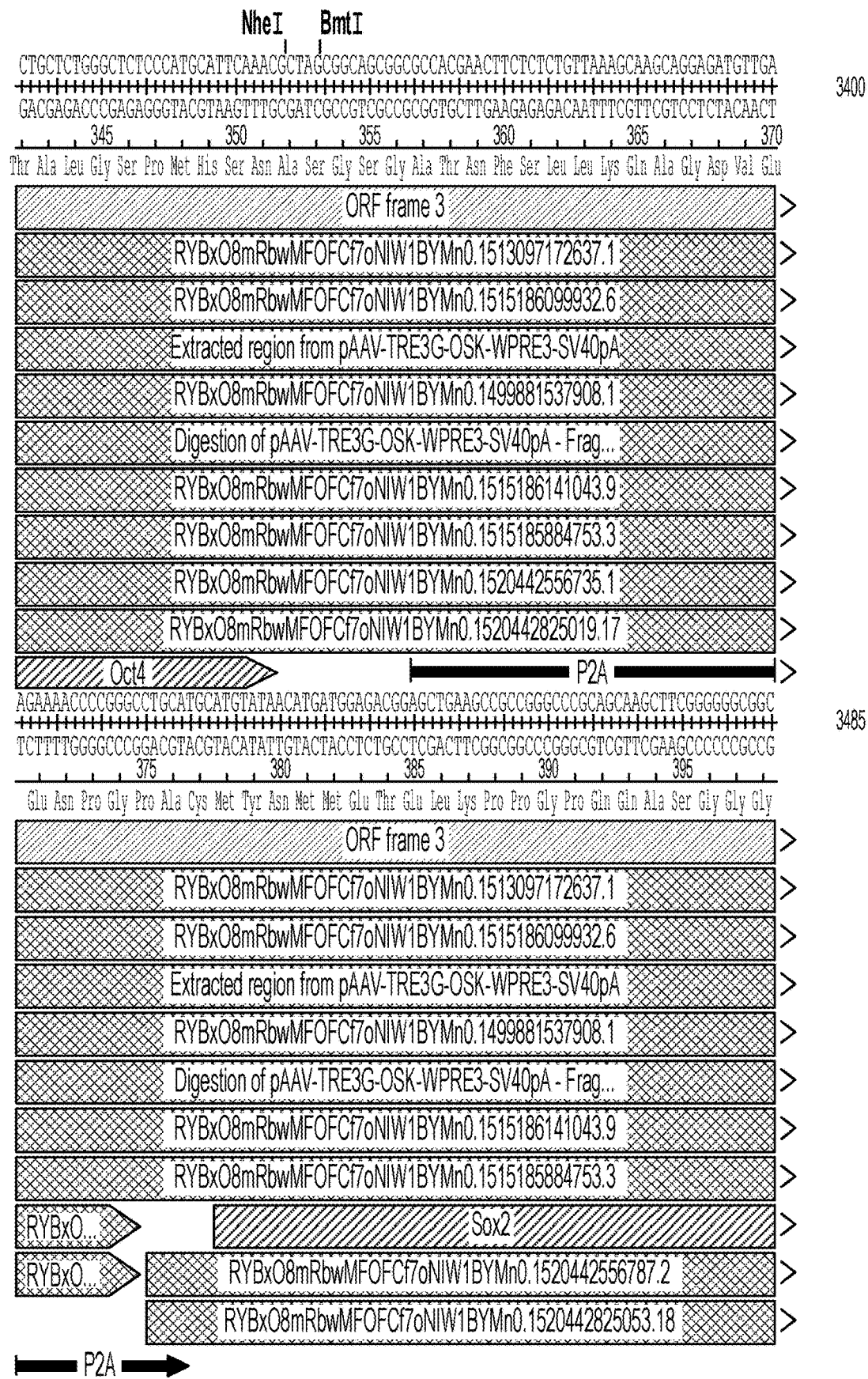
Figure 4O:
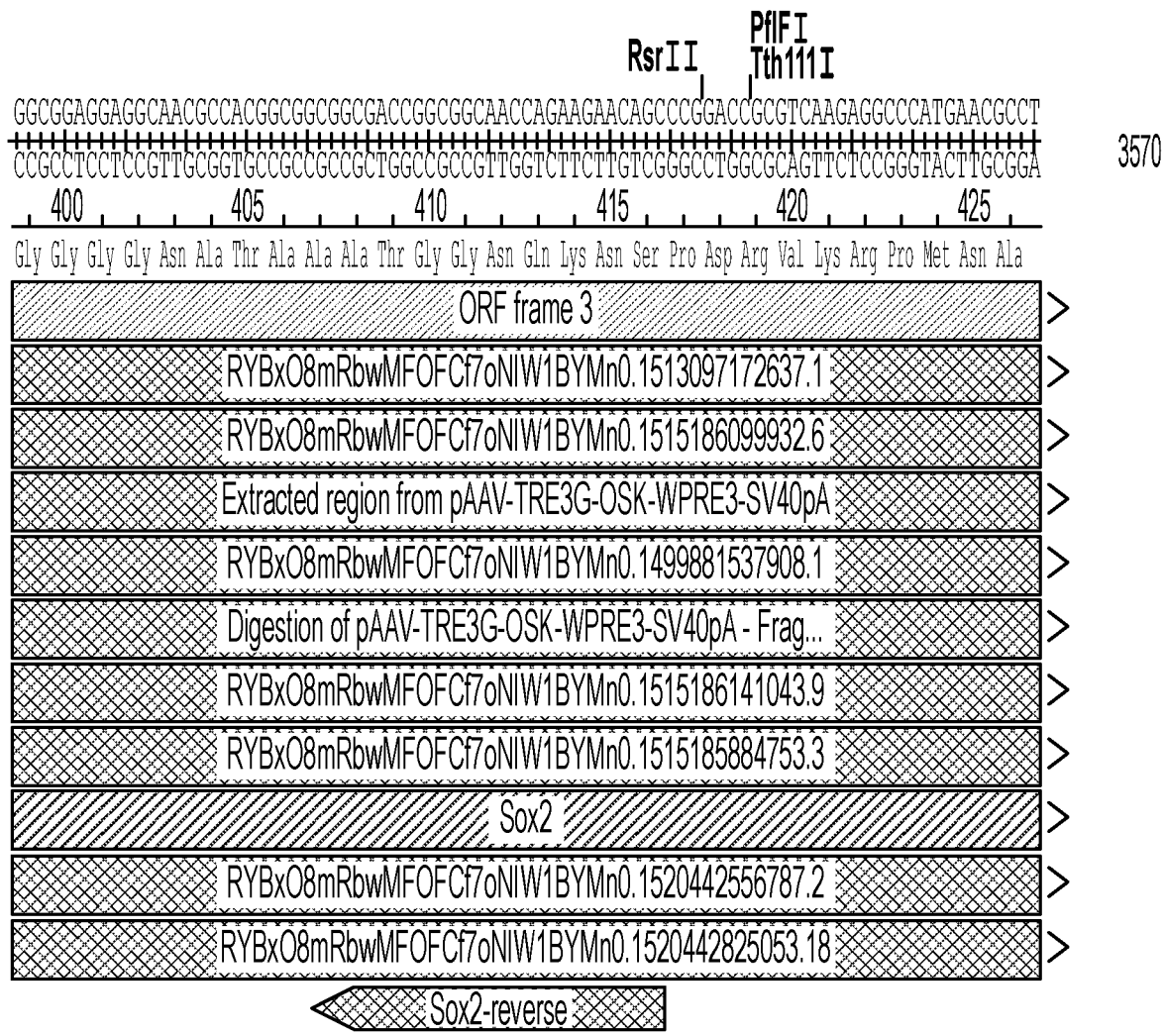
Figure 4R:
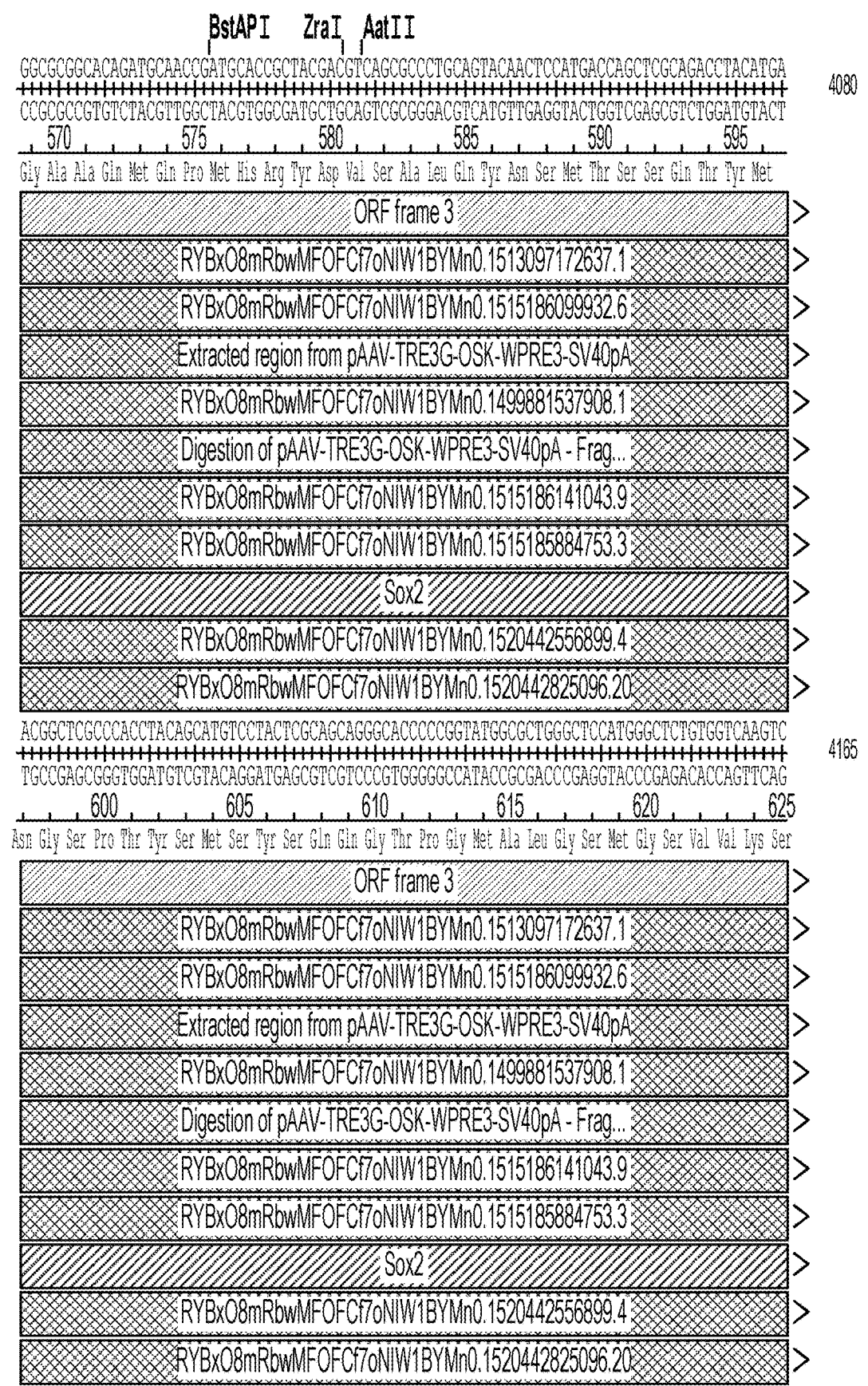
Figure 4T:
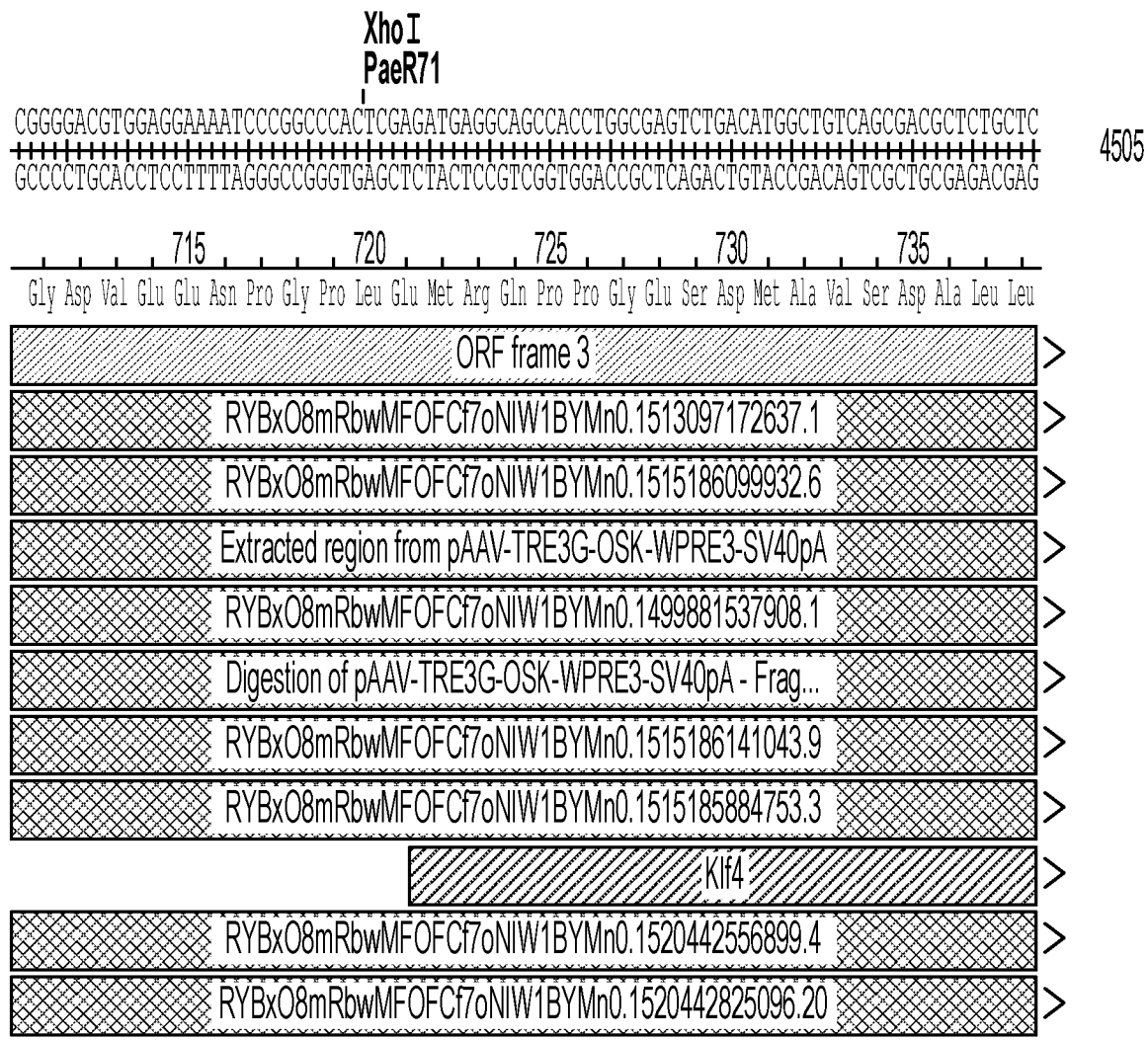
Figure 4W:
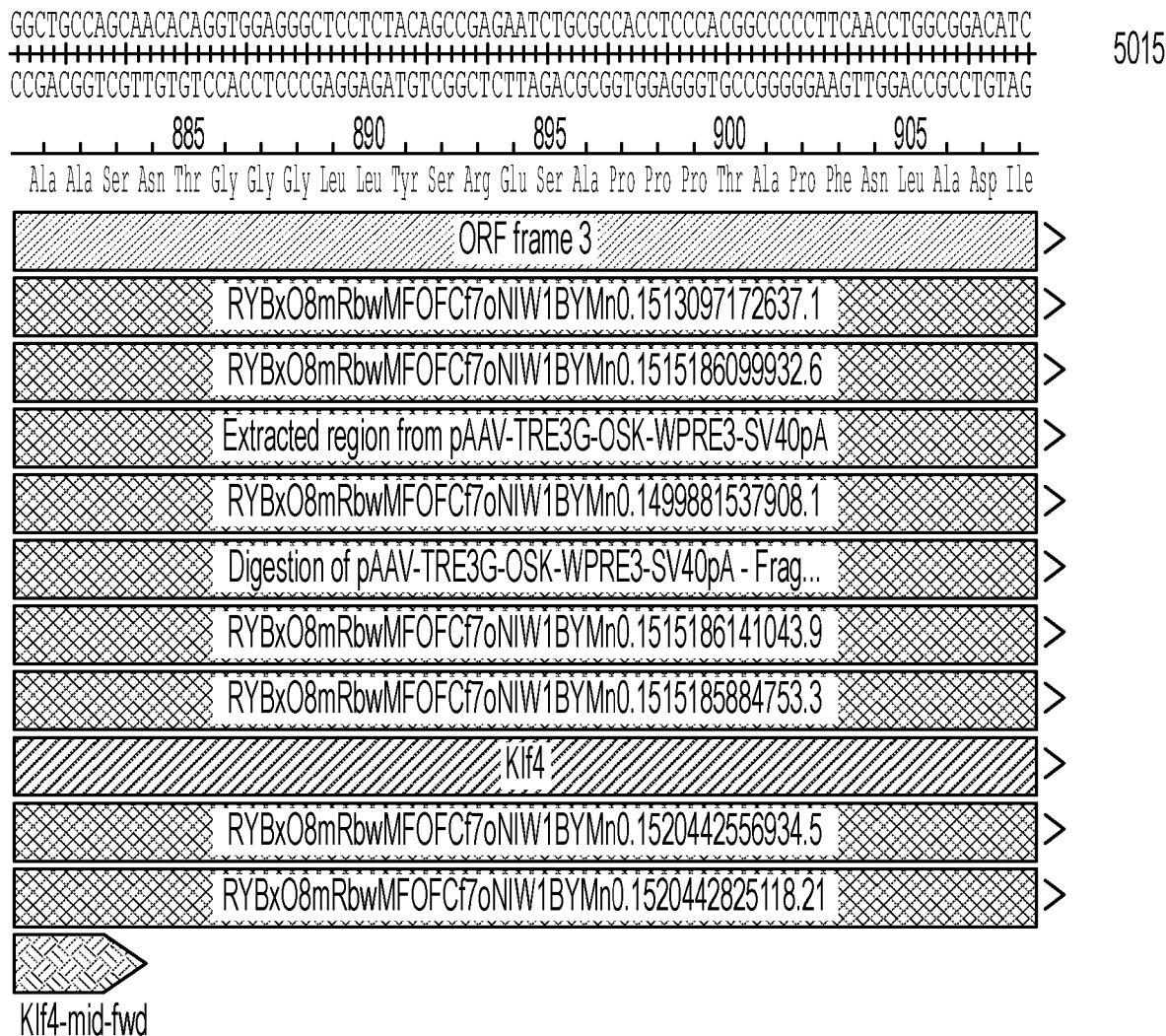
Figure 4X:
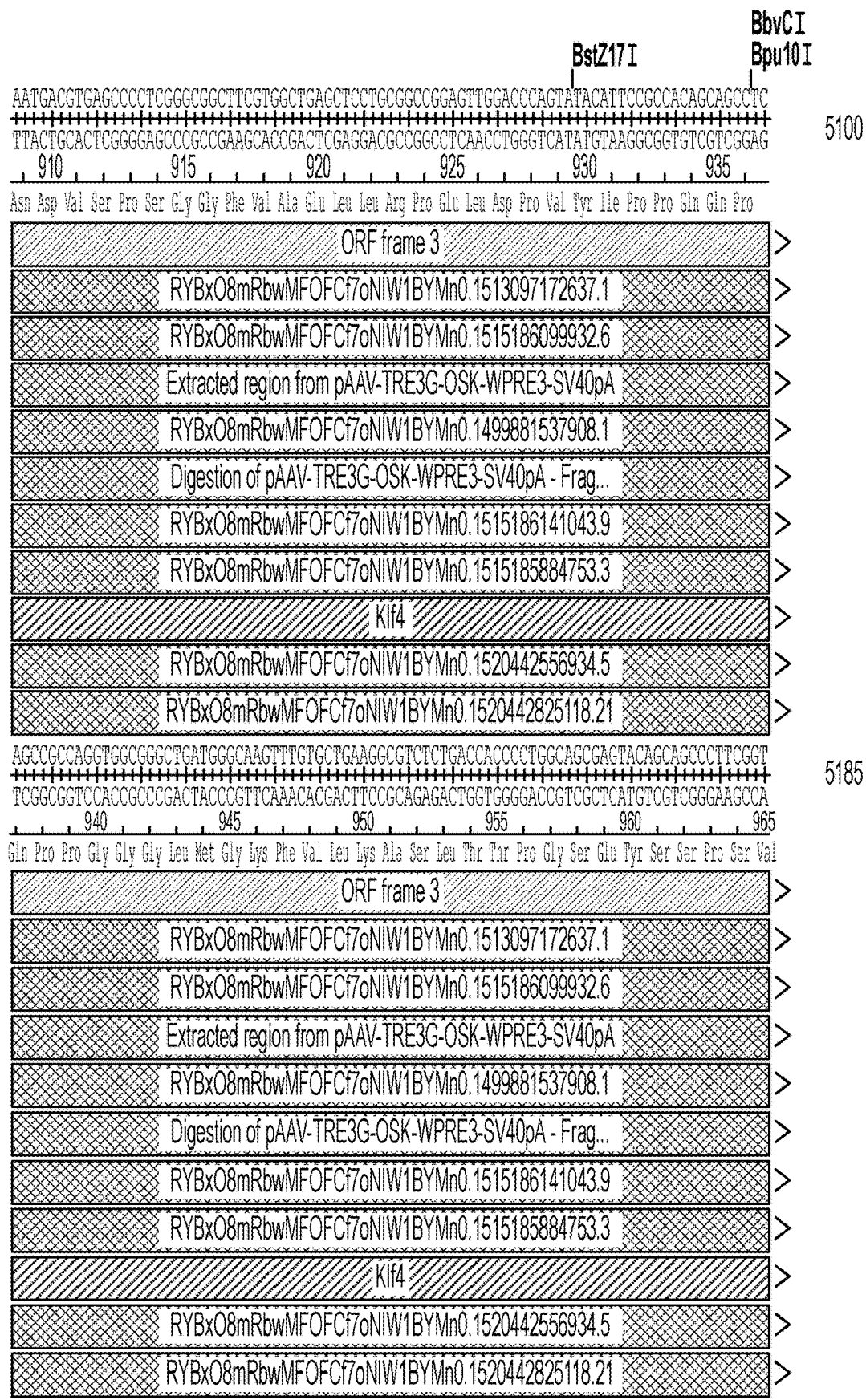
Figure 4A:
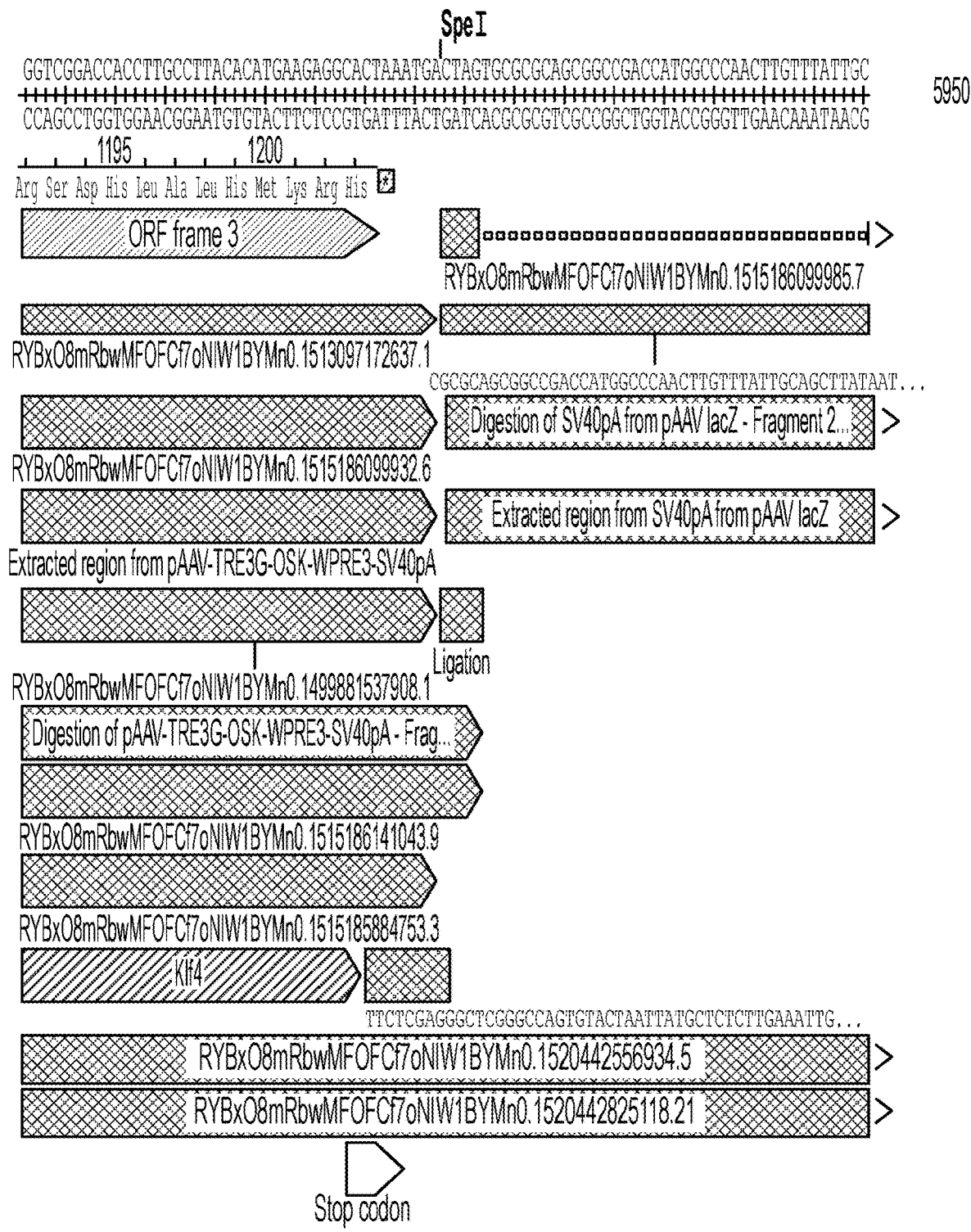
Figure 4A:
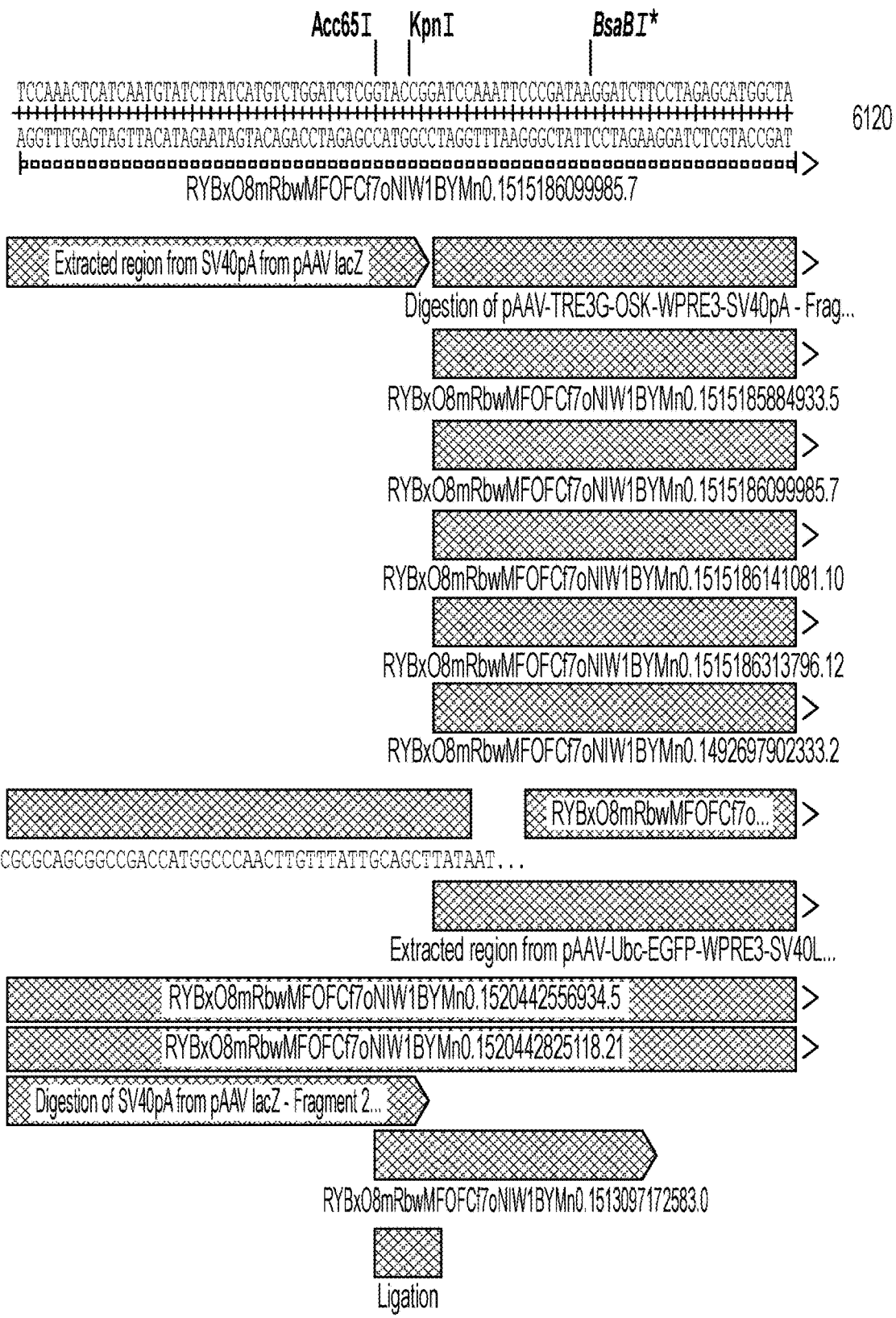
Figure 17:
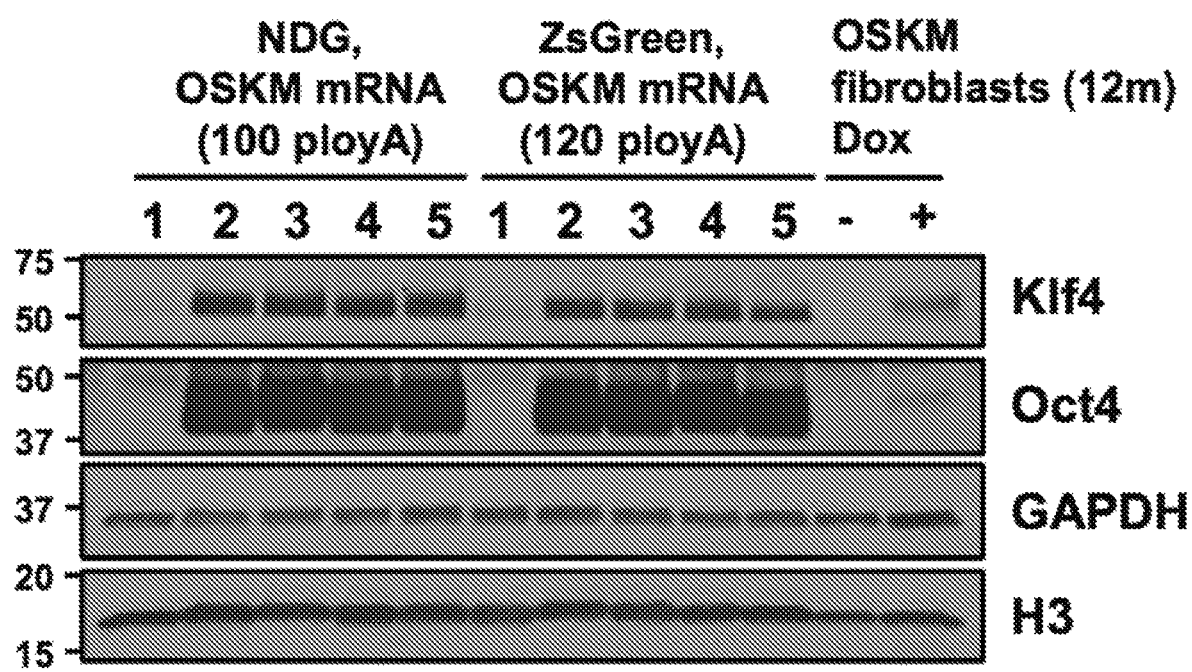
FIG. 17 is a western blot showing that administration of modified mRNA encoding OCT4, SOX2, and KLF4 induced expression of KLF4 and OCT4 in mouse cells. Antibodies against KLF4, OCT4, GAPDH, and H3 were used to detect indicated proteins.
Figure 18:
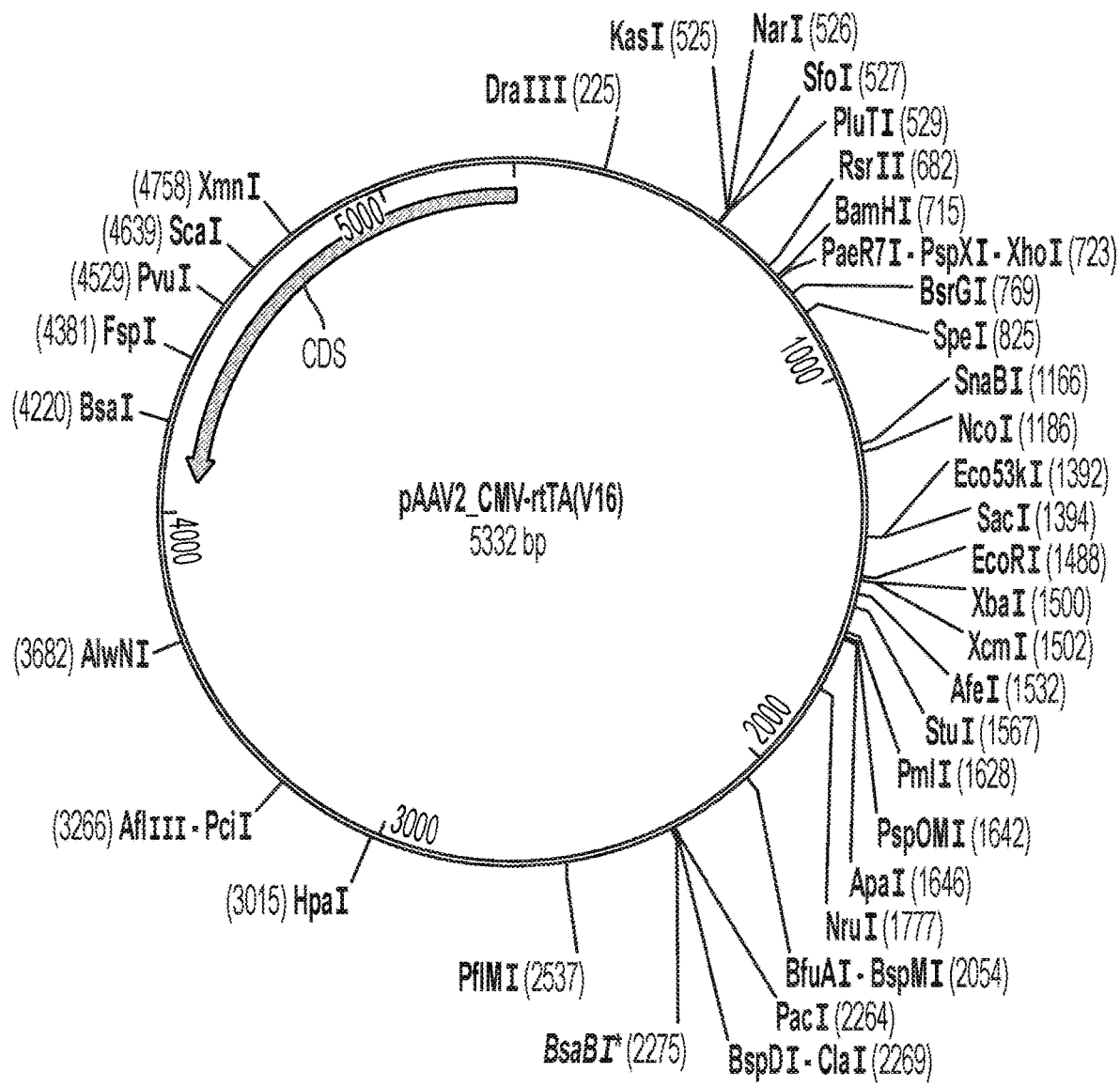
FIG. 18 is a vector map of pAAV2_CMV_rtTA (VP16) (SEQ ID NO: 31). This vector is a non-limiting example of a vector encoding rtTA.
Figure 19:
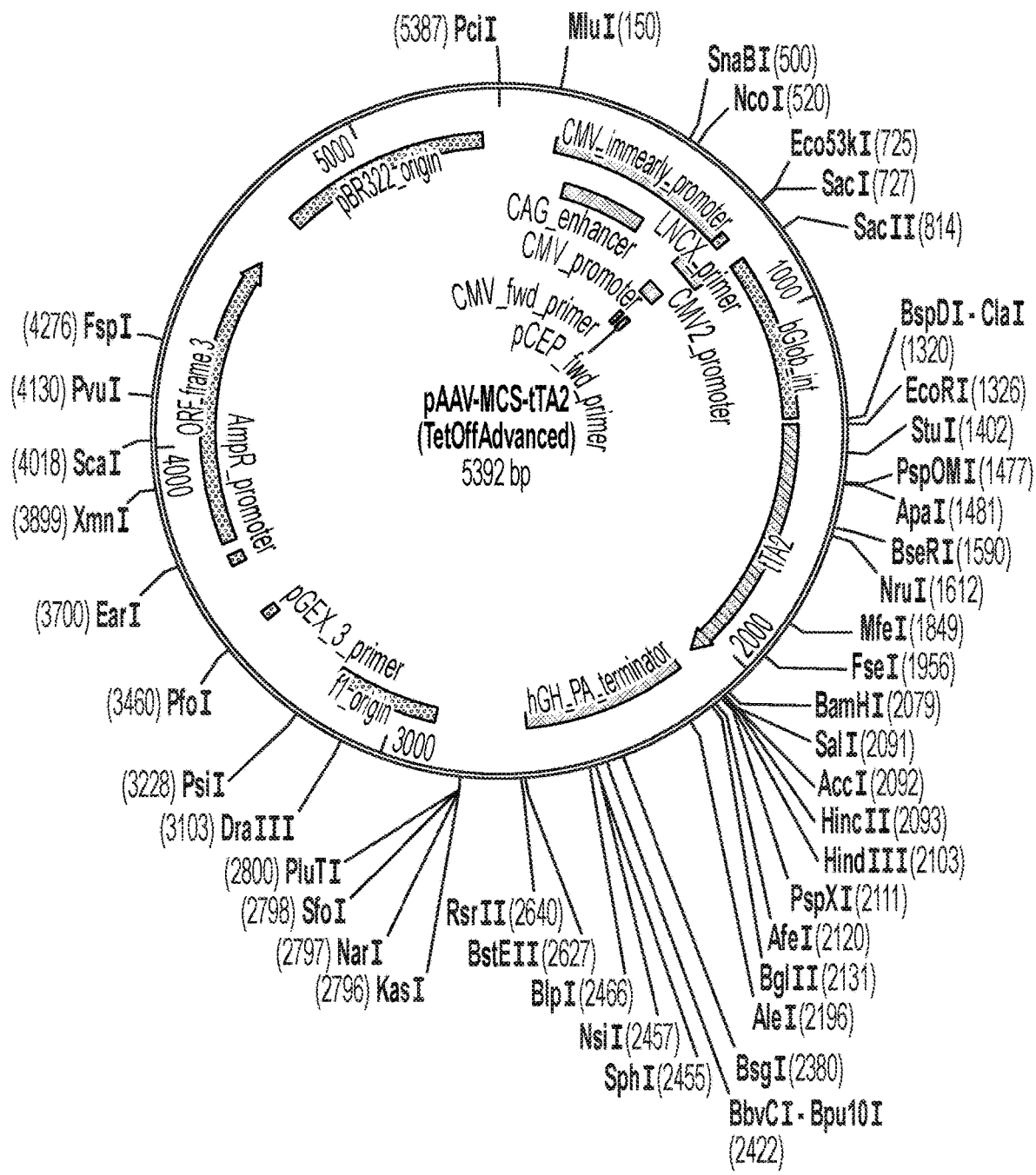
FIG. 19 is a vector map of pAAV-MCS-tTA2 (or CAG-tTA) (SEQ ID NO: 32). This vector is a non-limiting example of a vector encoding tTA under a CAG promoter.
Figure 20:
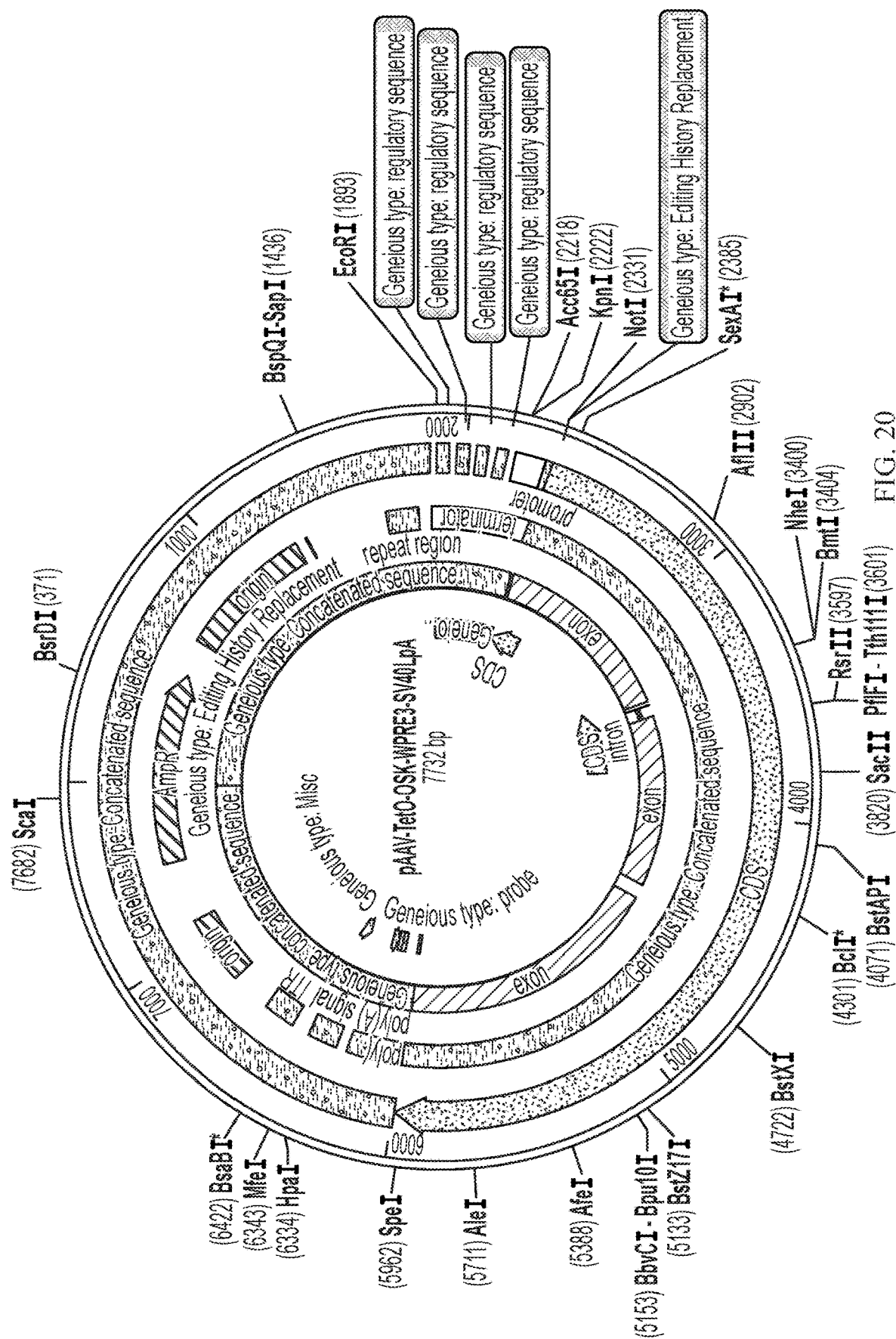
FIG. 20 is a vector map of p-AAV-TetO-OSK-WPRE3-SV50LpA (TRE2-OSK, pAAV-TRE2-OSK-SV40LpA, or TRE2-OSK) (SEQ ID NO: 33). This vector is a non-limiting example of an AAV vector comprising a nucleic acid (e.g., engineered nucleic acid) sequence that is greater than 4.7 kb between the two ITRs in the vector.

The vector shown in FIGS. 3 and 4A-4AL was cloned using routine methods. Briefly, a TRE3G promoter sequence (SEQ ID NO: 7) from Clonetech was synthesized using flanking restriction sites, primers were designed to clone OSK out of a TetO-FUW-OSKM plasmid, and a stop codon was added. To make the vector shorter, a short SV40 sequence was synthesized with flanking restriction cut sites. Whereas conventional AAV vectors encoding OSK is over the packaging limit of AAV, could only be packaged into AAV9 capsid with low titer (less than $2 \times 10^{12}$ particles per viral prep), and the low titer virus is not functional due to possible truncation as shown in FIG. 17. The vector depicted in FIGS. 3 and 4A-4AL produced virus with more than $2 \times 10^{12}$ viral partial per prep or $1 \times 10^{13}$ per mL (data not shown).

To determine whether the OSK vector could be used for inducible OSK expression in mammalian cells, the OSK vector and was packaged into different serotypes of AAV virus (AAV9 (FIG. 6A), AAV2 (FIG. 6B), and AAV.PHP.b (FIG. 6C)) using routine methods. Additional batches of AAV9 and AAV.PHP.b virus with a vector encoding rtTA3 (Tet-On system) and AAV2 virus with a vector encoding tTA (Tet-Off system) were produced. Then, mammalian 293T cells were co-infected with the OSK virus along with the same serotype of rtTA3 or tTA virus. Cells were subsequently treated with or without doxycycline (DOX) and expression of OCT4, KLF4 and the loading control H3 was determined by western blot with antibodies against OCT4, KLF4, and H3.

Figure 6A:
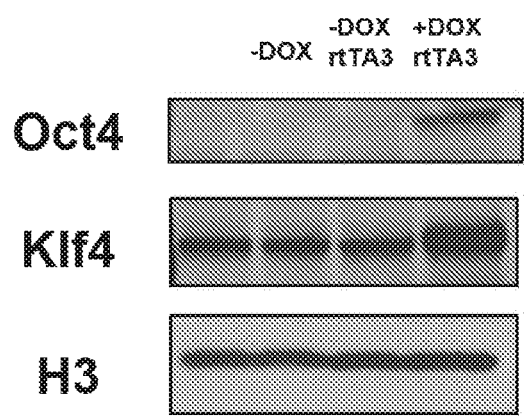
FIGS. 6A-6C include western blot data showing that different serotypes of AAVs encoding OSK (TRE3G-OSK-SV40 pA, SEQ ID NO: 16) were successfully used in a doxycycline (DOX)-inducible system to control OSK expression in 293T cells. OCT4, KLF4, and H3 expression were detected with antibodies. H3 refers to histone 3 and is a loading control.
Figure 6B:
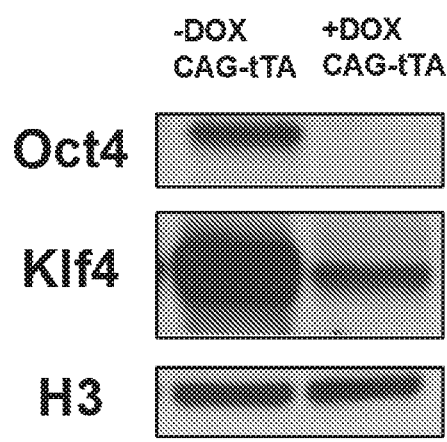
Figure 6C:
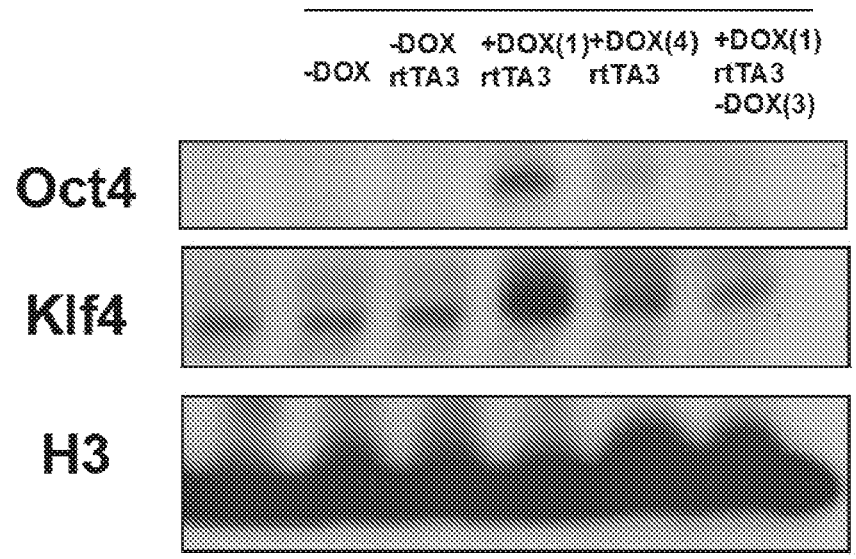

As shown with the Tet-On system in FIG. 6A, doxycycline treatment increased OCT4 and KLF4 expression in 293T cells infected with AAV9 viruses encoding OSK and rtTA3. The OSK expression could also be controlled with a Tet-Off system. DOX treatment decreased OCT4 and KLF4 expression in 293T cells infected with OSK AAV2 and AAV2 with a vector driving tTA expression under a constitutive CAG promoter (FIG. 6B). Furthermore, OSK expression could be tightly controlled even after stimulation of transgene expression. As shown in the fourth lane of FIG. 6C, one day of DOX treatment is sufficient to increase OCT4 and KLF4 expression in 293T cells infected with TRE3G-OSK-SV40 pA AAV.PHP.b virus and with Ubc-rTtA3-p2a-mkate AAV.PHP.b virus. Removal of DOX for three days after one day of DOX treatment, however, returns OCT4 and KLF4 expression back to uninduced levels (last lane of FIG. 6C). The Ubc-rtTA3-p2a-mkate vector comprises a constitutive Ubc promoter that drives expression of rtTA3, a self-cleaving 2A peptide, and a far-red fluorescent protein (mKate).

Therefore, an AAV vector that allows for controlled expression of OSK in mammalian cells (e.g., in vivo) was developed. Furthermore, the AAV vector was packaged into different AAV serotypes that successfully delivered a functional vector into 293T cells.

Figure 7A:
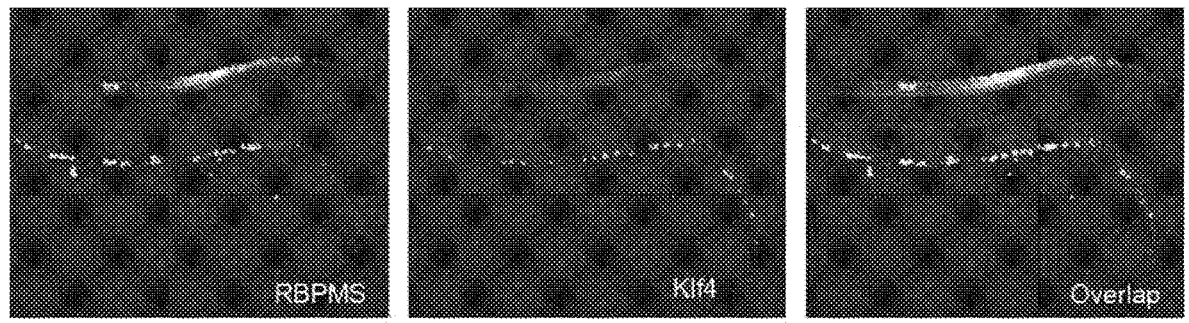
FIGS. 7A-7F include data showing that AAV encoding OSK induced partial reprogramming and promoted regeneration of optic nerves after nerve crush in an inducible manner.

Example 2: AAV Encoding OSK Promoted Optic Nerve Regeneration and Survival of Retina Ganglion Cells (RGCs) Nerves after Nerve Crush in an Inducible Manner To determine whether OSK could be delivered by AAV and inducibly expressed in vivo, AAV virus with the TRE-OSK-SV40 vector and AAV virus encoding tTA under the CAG constitutive promoter were produced through routine methods and injected into the retina of mice. Next, an optical coherence tomography (OCT) section was stained with antibody against RBPMS to identify retina ganglion cells (RGCs) and with an antibody against KLF4 to detect KLF4 expression. As shown in FIG. 7A, KLF4 was expressed in RGCs (RBPMS-positive cells), which suggested that the vectors were functional.

Figure 7B:
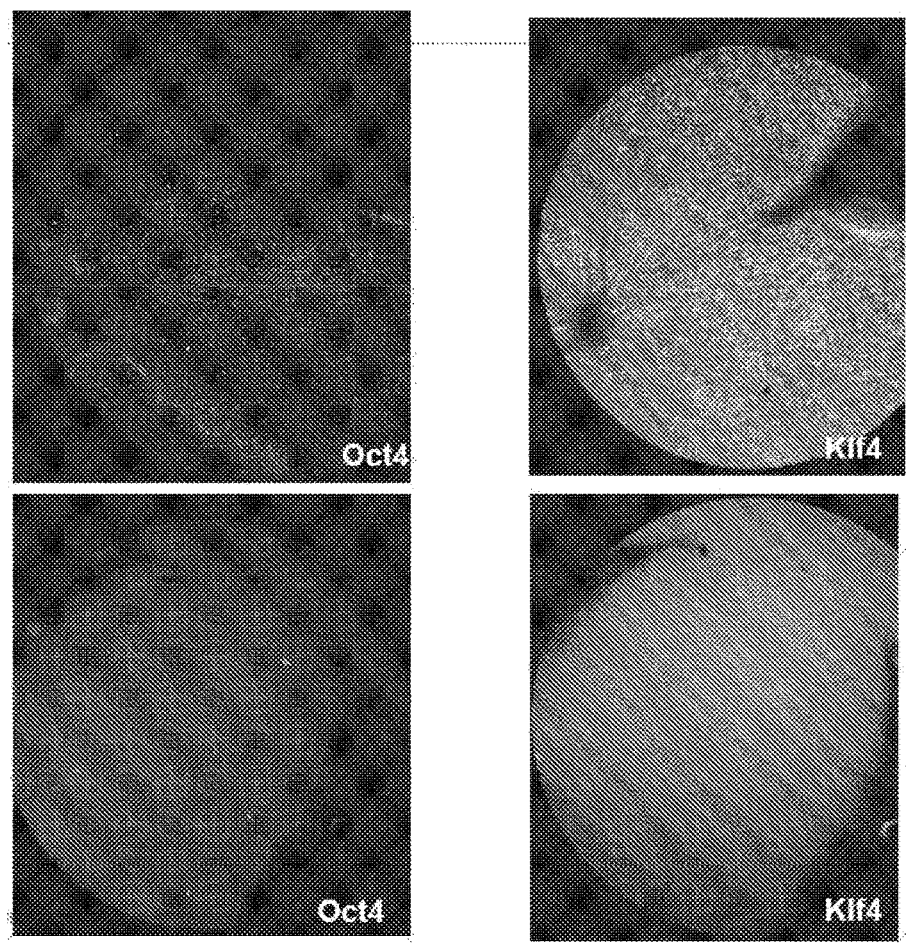

The inducibility of the system was also tested in vivo. In the absence of DOX treatment, OCT4 and KLF4 were expressed in the mouse retina as determined by whole retina mount staining (FIG. 7B, top). After four days of DOX treatment, however, OCT4 and KLF4 staining was significantly reduced, indicating that expression from the TRE-OSK-SV40 vector was turned off (FIG. 7B, bottom). Therefore, OSK vector expression could be tightly controlled.

Figure 7C:
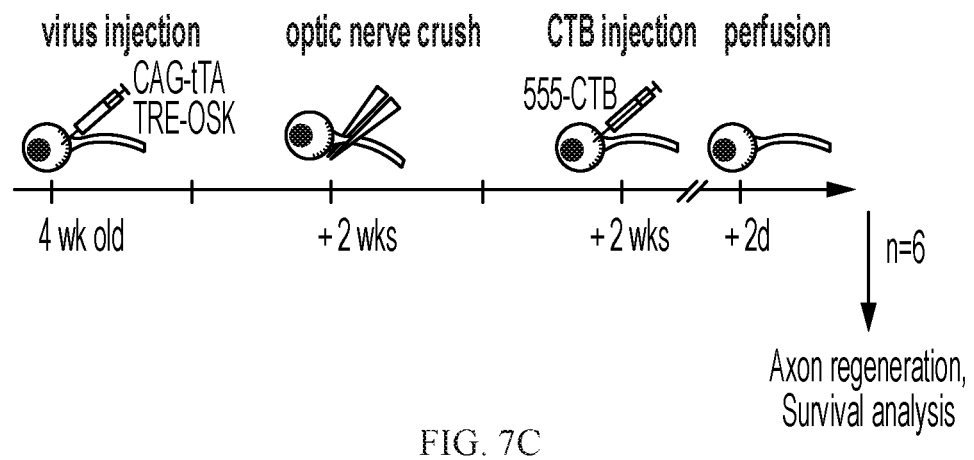

To determine whether inducible OSK expression could induce partial reprogramming and promote regeneration following nerve damage, AAV virus with the TRE-OSK-SV40 vector and AAV virus encoding tTA under the CAG constitutive promoter were injected into the retina of 4-week old mice (n=6) as shown in the experimental timeline provided in FIG. 7C. As a control, a separate cohort of mice (n=2) were only injected with the OSK virus. Mechanical damage was induced through optic nerve crush in both cohorts two weeks after virus injection. To trace axon regeneration by fluorescent microscopy of the optic nerve, fluorescently labeled cholera toxin β-subunit (CTB) was intraocularly injected into mice and perfusion was performed two days after CTB injection. Axon regeneration and axon survival analysis was subsequently conducted.

Figure 7D:
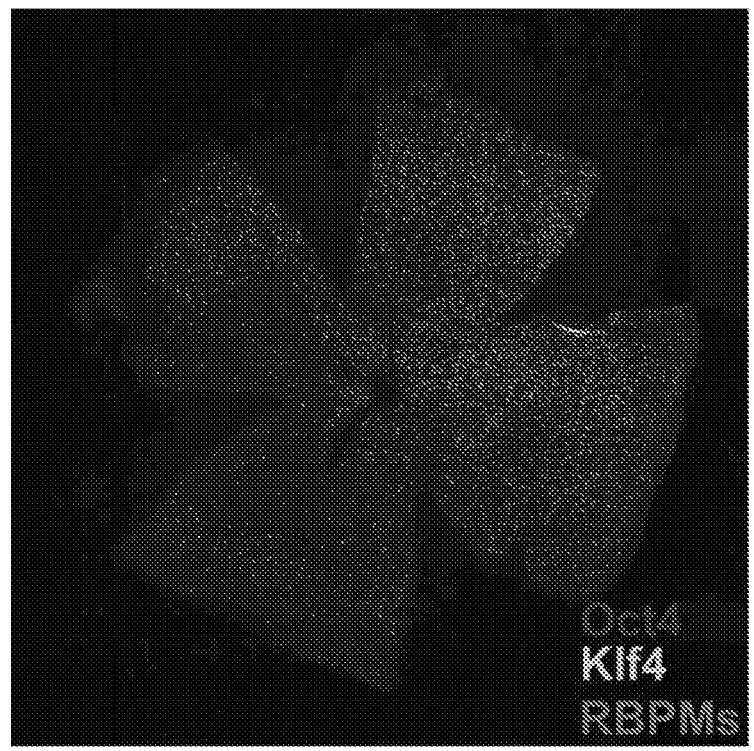
Figure 7E:
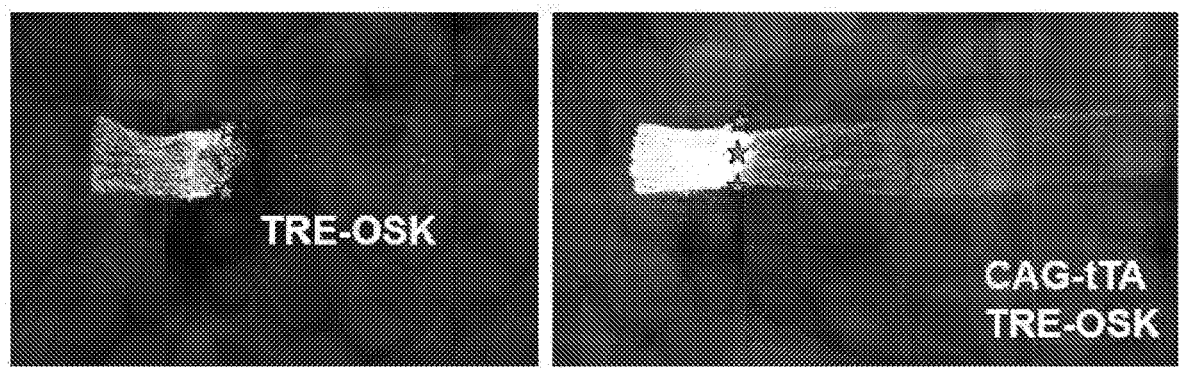
Figure 7F:
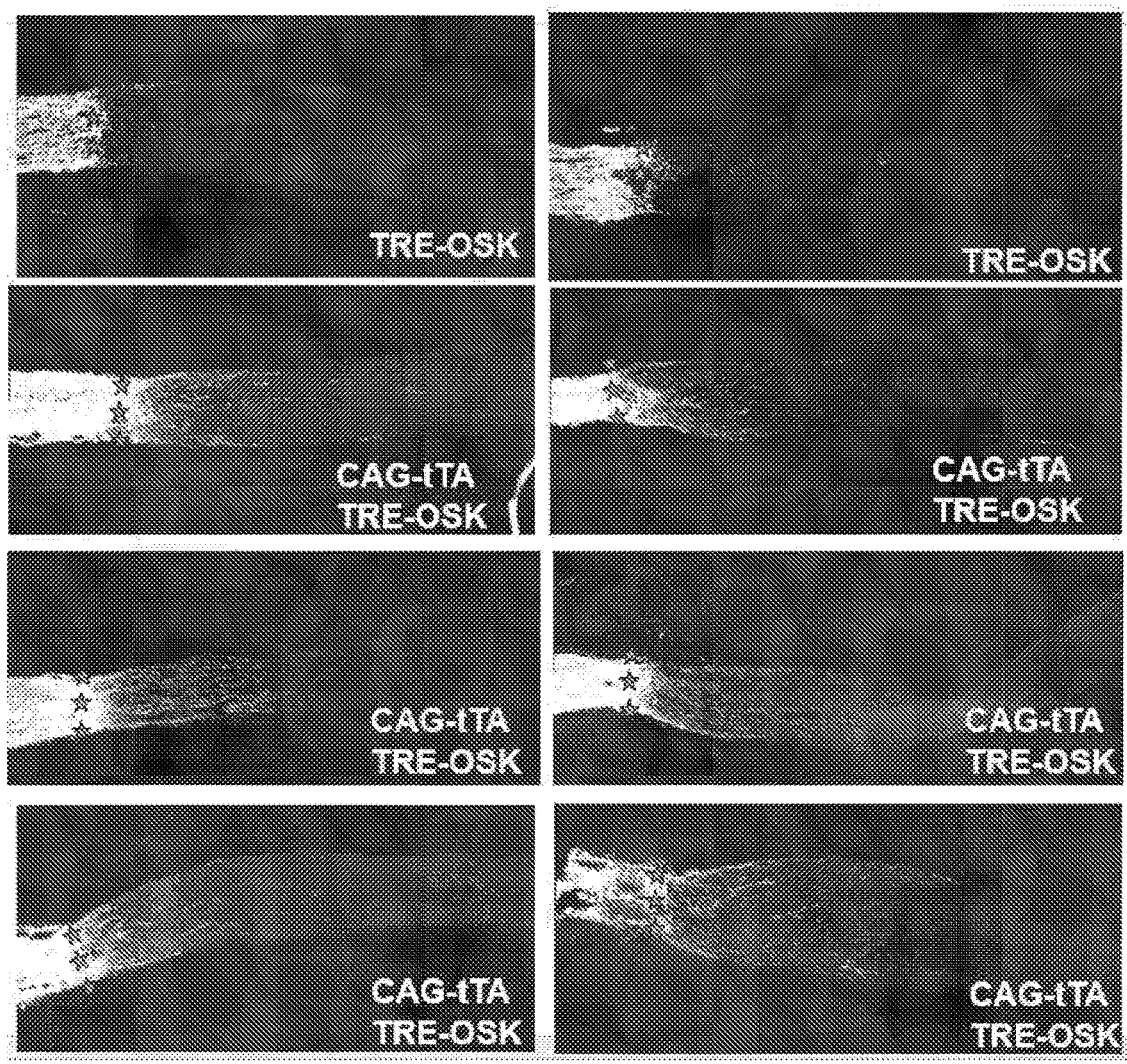

Axon regeneration was determined by estimating the number of axons per nerve. As shown in FIG. 7D, co-administration of OSK and tTA virus significantly promoted optic nerve regeneration away from the site of the optic nerve crush compared to administration of OSK virus alone. This effect was also visually apparent when comparing the fluorescence intensity of optic nerves from mice receiving both OSK and tTA virus compared to mice receiving OSK virus alone. The fluorescence intensity of optic nerves from mice receiving both viruses was higher than that of mice receiving OSK virus alone, indicating that nerve regeneration was higher with combination treatment (FIGS. 7E-7F).

Figure 8A:
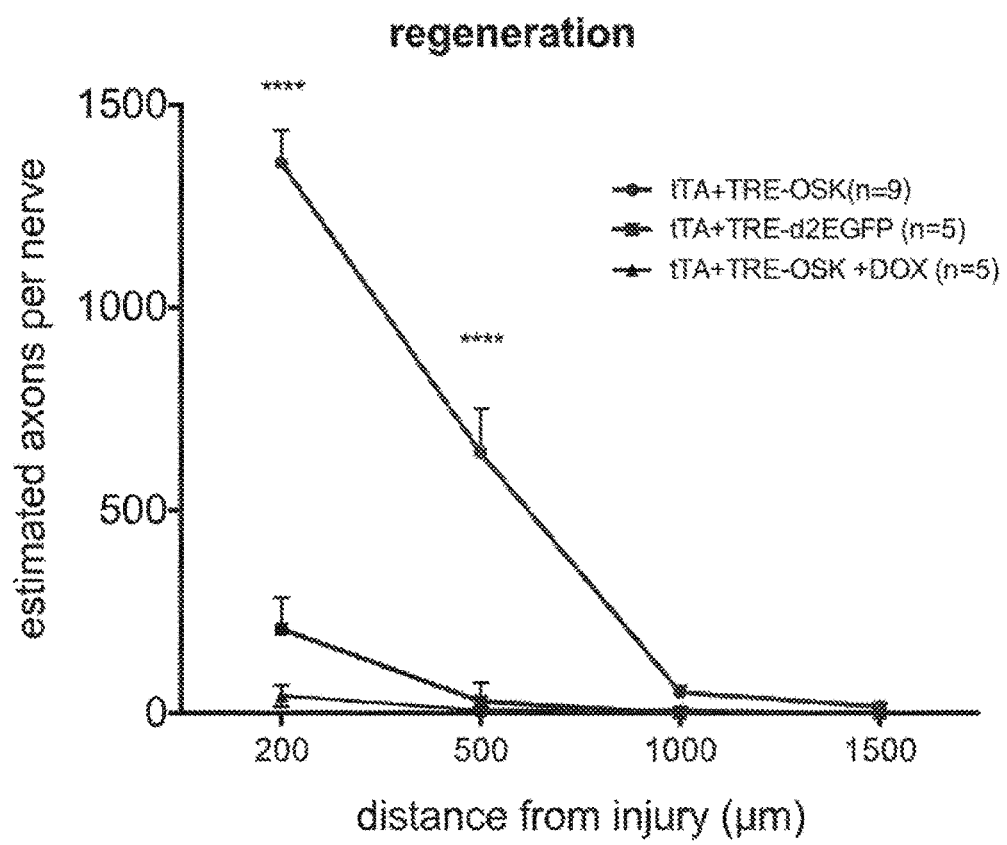
FIGS. 8A-8G shows administration of virus encoding OSK improved RGC axon regeneration after nerve crush injury.
Figure 8B:
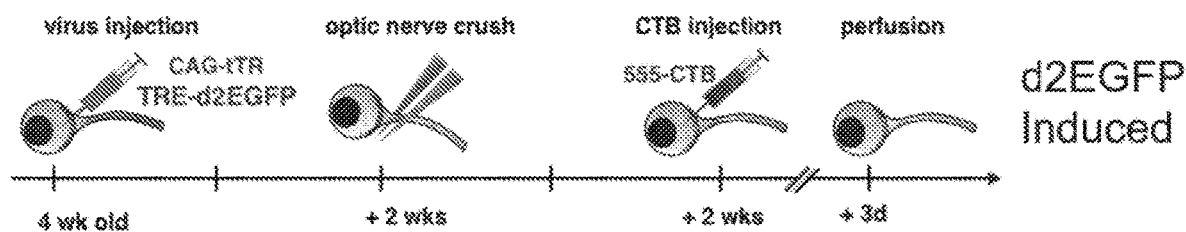
Figure 8C:
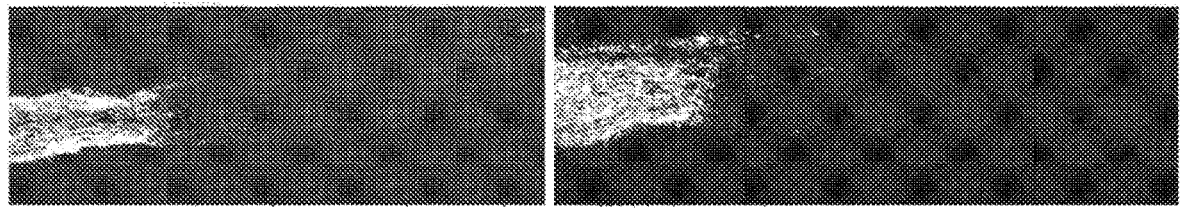
Figure 8D:
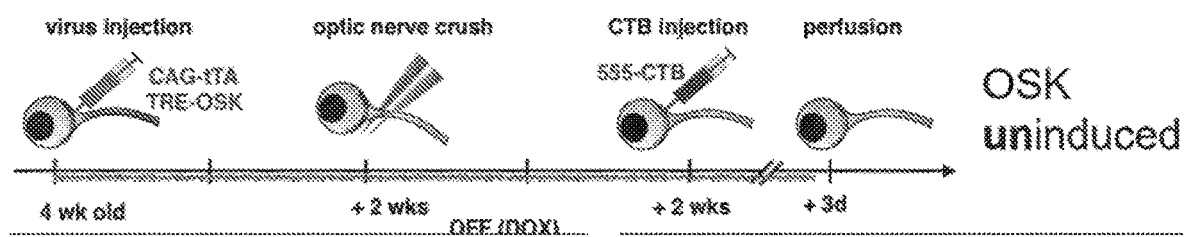
Figure 8E:
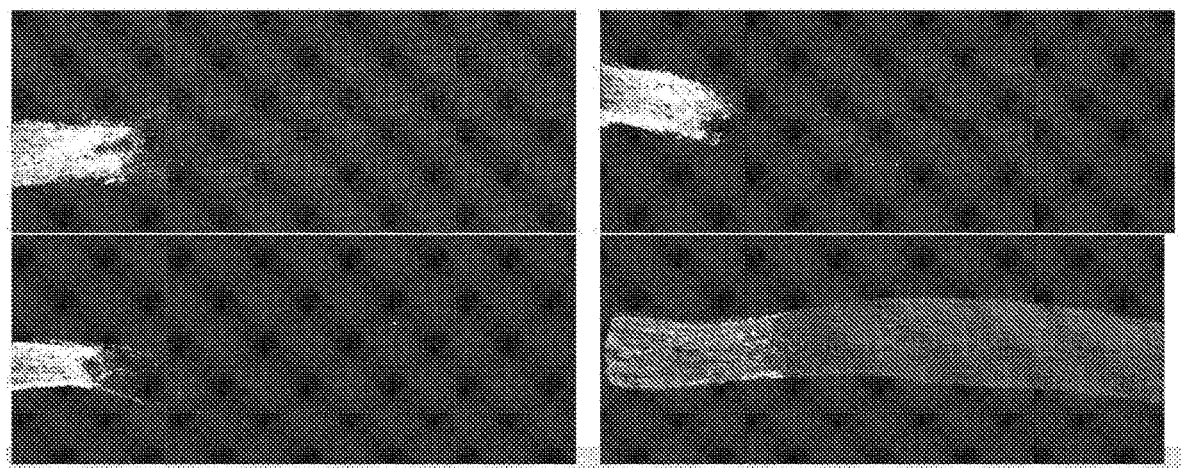
Figure 8F:
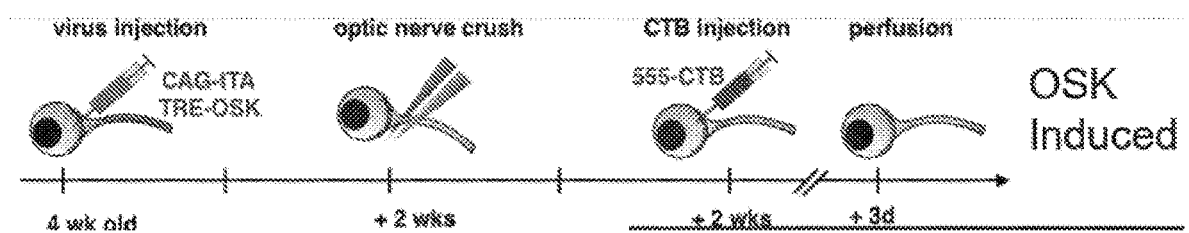
Figure 8G:
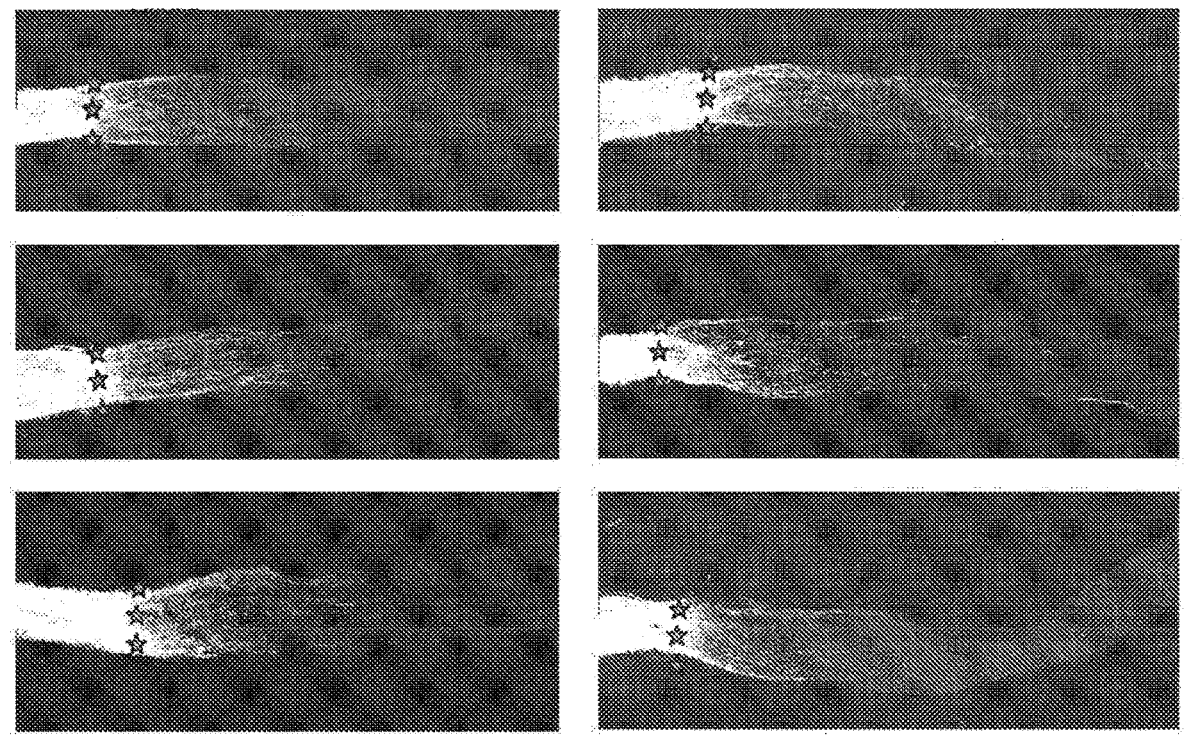

To show that the observed axon regeneration after crush injury was specifically mediated by OSK, an axon regeneration experiment was used to compare the effects of tTA virus in combination with (1) TRE-OSK virus with no DOX treatment, (2) TRE-d2EGFP virus with no DOX treatment, and (3) TRE-OSK virus with DOX treatment. The experimental timeline of treatments (1)-(3) are indicated in FIGS. 8B, 8D, and 8F, respectively. Fluorescently-labeled CTB was used to visualize axons. As shown in FIGS. 8A and 8G, the extent of optic nerve regeneration in mice in which OSK expression was induced (mice receiving OSK and tTA viruses in the absence of DOX) was very significant at 200 µm and 500 µm from crush site. In contrast, even when d2EGFP expression was induced (mice receiving d2EGFP and tTA viruses in the absence of DOX), minimal regeneration was observed (FIG. 8A and FIG. 8C). Notably, axon regeneration was dependent on induction of OSK expression. When mice were treated with DOX to inhibit OSK expression as outlined in FIG. 8D, administration of tTA and OSK viruses did not induce axon regeneration (FIG. 8A). The intensity of CTB-labeled axons in these DOX-treated mice were similar to mice receiving control d2EGFP virus (compare FIG. 8E with FIG. 8C). Therefore, administration of an AAV-based inducible OSK expression system could be used to promote regeneration following optic nerve damage.

Figure 9A:
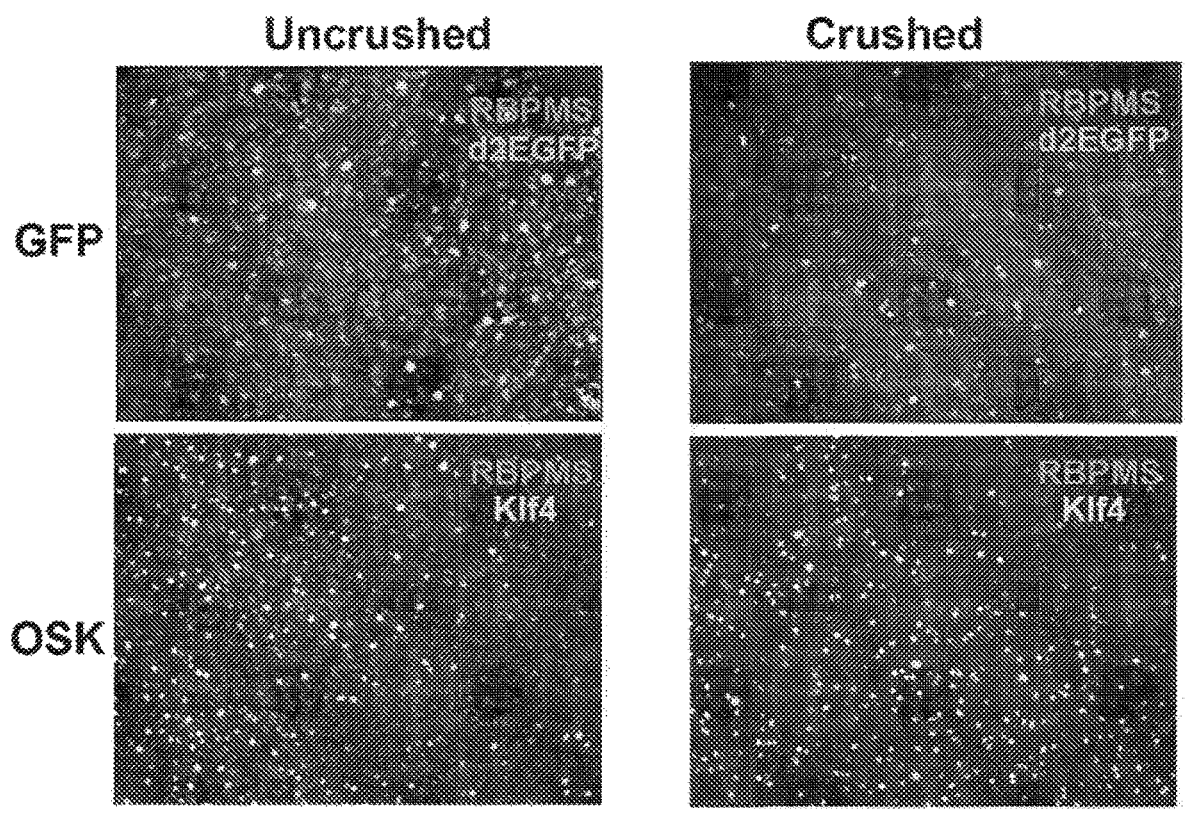
FIGS. 9A-9D show OSK-infected RGCs have a higher survival rate compared to cells not infected with OSK virus following nerve crush.
Figure 9B:
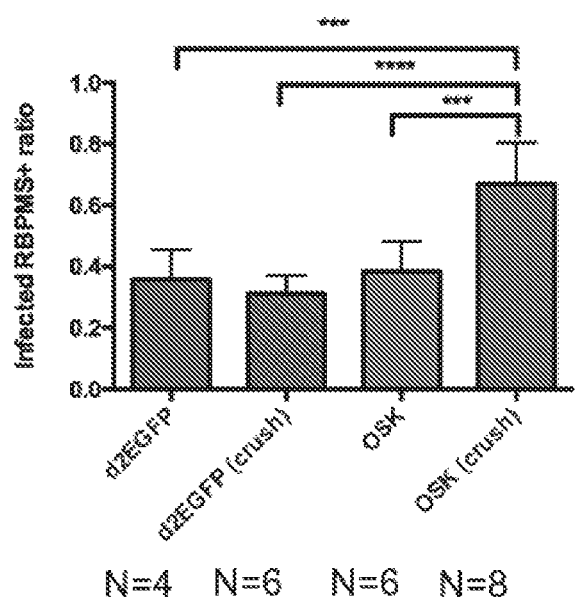
Figure 9C:
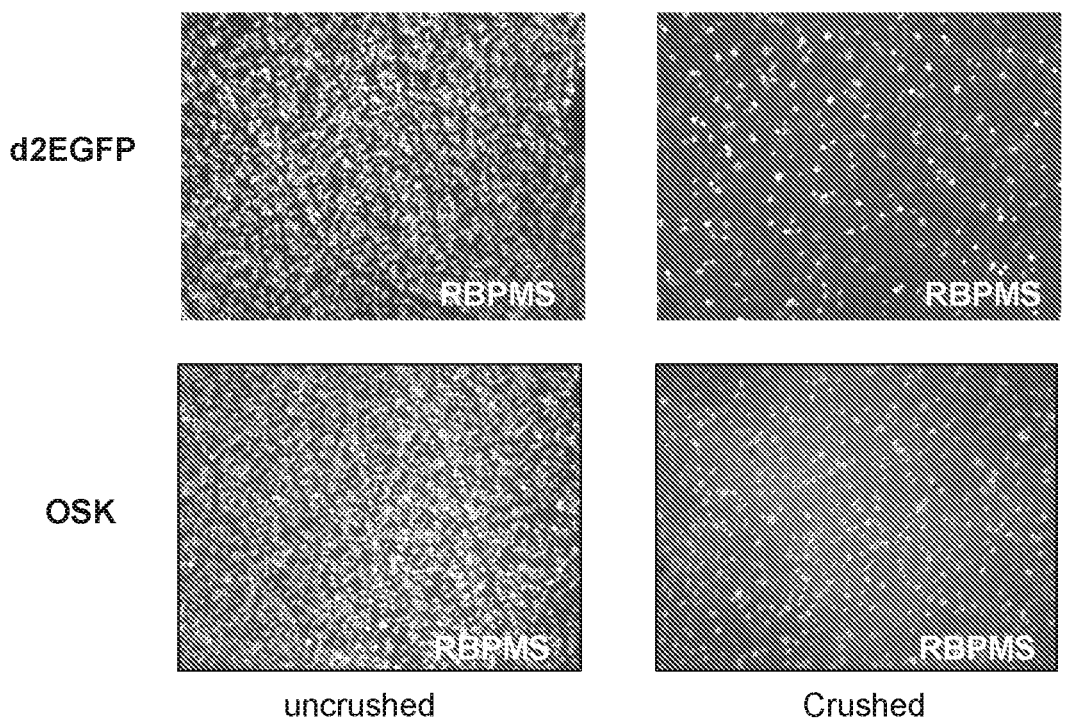
Figure 9D:
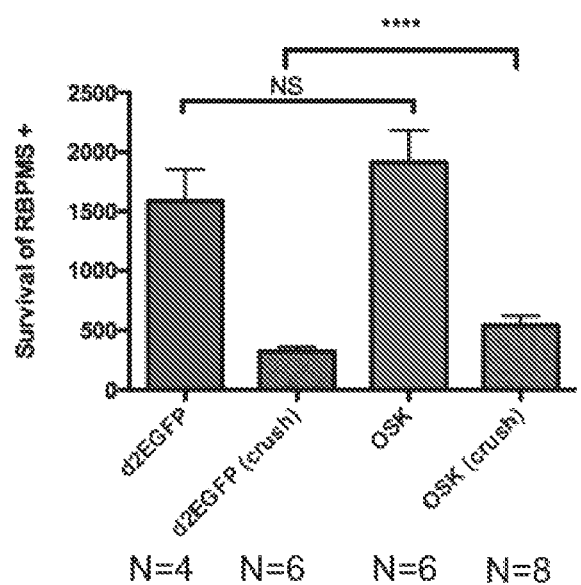
Figure 10A:
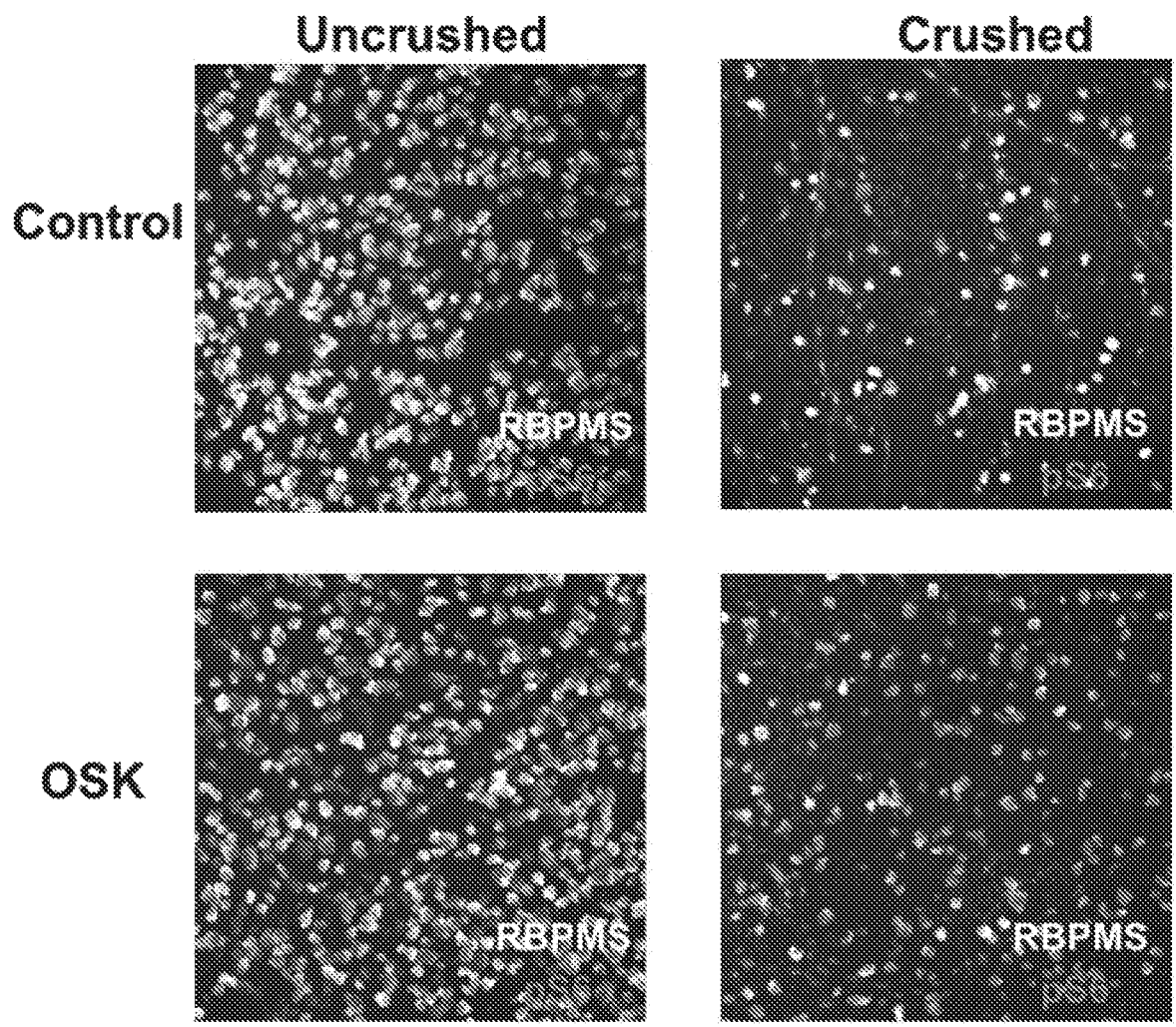
FIGS. 10A-10B show that OSK-mediated regeneration and protection is independent of mTOR activation.
Figure 10B:
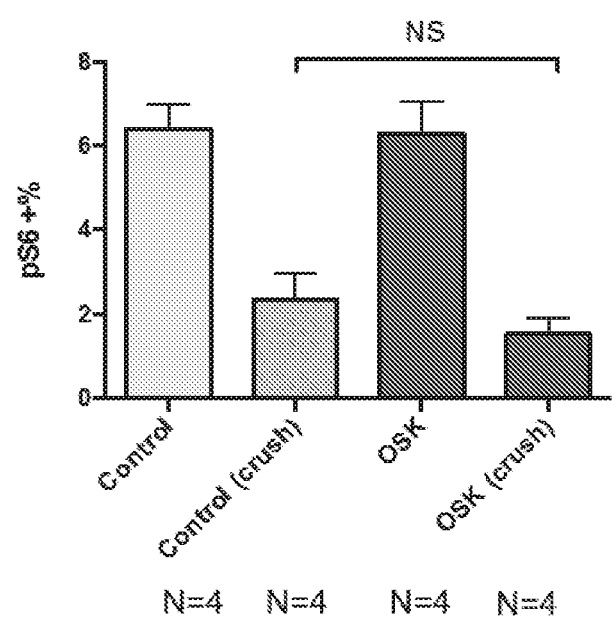

The effect of OSK on the survival rate of retina ganglion cells (RGCs) was also assessed. As shown in FIGS. 9A-9D, OSK significantly increases RGC survival rate. RGCs (RBPMS positive cells) that were infected with OSK and tTA virus (green) or uninfected with both (red) shown following optic nerve crush, OSK-infected RGC had 3 times higher survival rate (54% vs 18%) after crush compared to cells without OSK infection, quantification from a series of pictures like shown (FIG. 9A). Therefore, the percentage of RBPMS-positive cells expressing KLF4 (OSK-infected cells) was lower than 40% before crush, but significantly increased to around 70% following optic nerve crush due to its higher survival rate. While the percentage of d2EGFP-infected cells maintained at 35-40% after crush. This indicates a strong cell protection effect from OSK expression (FIG. 9B). As shown in FIG. 9C, in d2EGFP or OSK plus CAG-tTA (SEQ ID NO: 32) AAV infected retina, there is no significant difference in RGC number (RBPMs positive) without uncrushed, but after crush there is clearly more RGCs survived when they infected with OSK and CAG-tTA compared to those infected with d2EGFP and CAG-tTA. FIG. 9D shows the quantification of survived RGC numbers from each group. Though lower than 40% cells infected with both OSK and CAG-tTA AAV, it increases the total survival RGC number compared to d2EGFP (542 compared to 323).

mTOR activation has reported as a pathway for optic nerve regeneration (Parker et al., Science, 322(5903), 963-966 November 2008). To determine whether OSK expression activated the mTOR pathway, control and OSK virus-infected cells were imaged using antibodies against RBPMS and phosphorylated S6 (pS6) in the absence of damage (uncrushed) and after damage (crushed). Representative images of the staining is shown in FIG. 10A, and as quantified in FIG. 10B, the percentage of pS6-positive cells was not significantly different between control cells and OSK-infected cells following optic nerve crush.

Figure 11A:
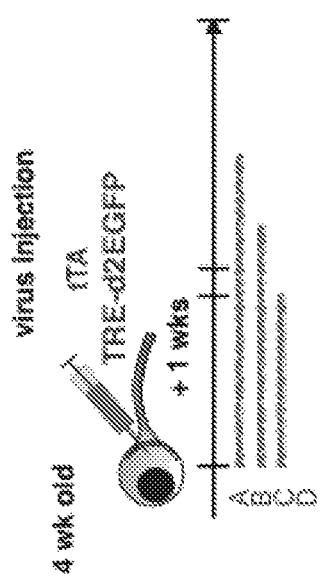
Figure 11B:
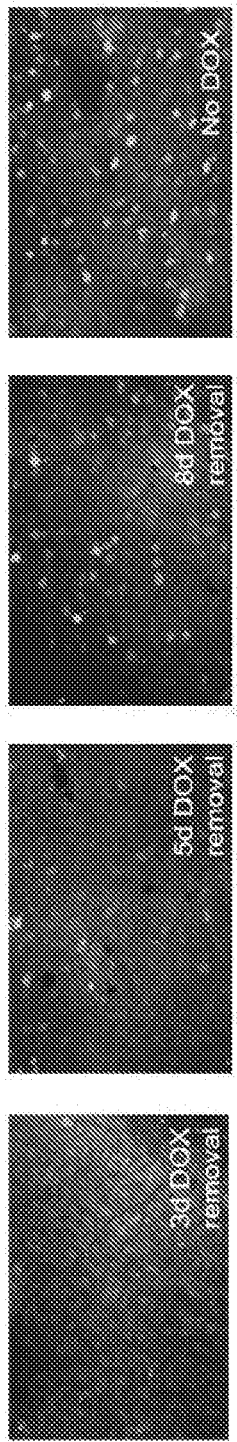

Example 3. An AAV Tet-on System Induces Faster Gene Expression Compared to an AAV Tet-Off System in Retinal Cells after Nerve Crush To compare the rate of gene expression between AAV-based Tet-On and Tet-Off systems, TRE-d2EGFP virus and (1) virus encoding tTA (Tet-Off) or (2) virus encoding rtTA (Tet-On) were administered into the retina of 4-week old mice. In the Tet-Off system, mice were given DOX starting from virus injection and DOX was removed for 3 days, 5 days or 8 days (FIG. 11A). As a control, a cohort of mice in the Tet-Off system were given no DOX. Approximately 8 days of DOX removal was needed to induce the same level of GFP expression as no DOX treatment in the Tet-Off system (FIG. 11B). In the Tet-On system, mice were treated as indicated in FIG. 11C. GFP expression was observed after only 2 days of DOX treatment in the Tet-On system (FIG. 11D). Therefore, a shorter period of time was needed to induce transgene expression in mice retina infected with an AAV-based Tet-On system compared to infection with an AAV-based Tet-Off system.

Figure 13B:
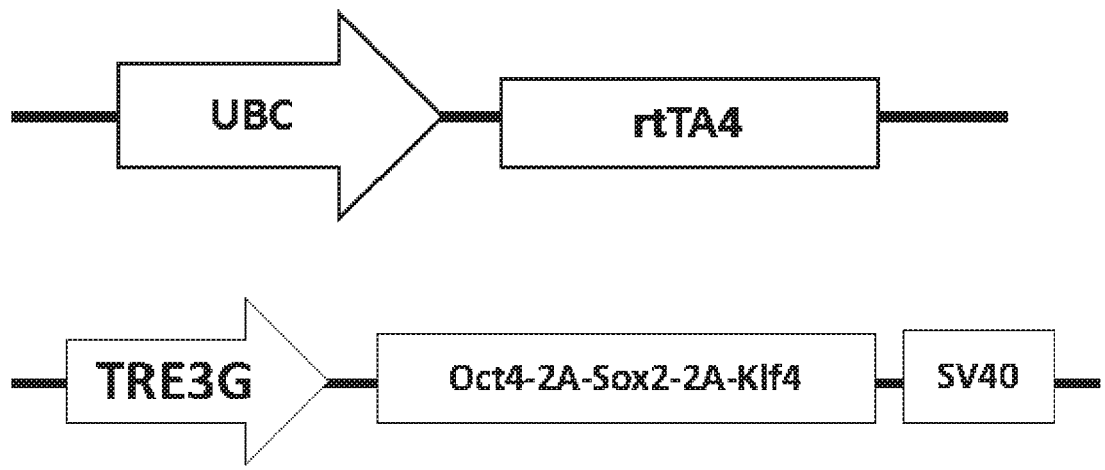
Figure 13C:
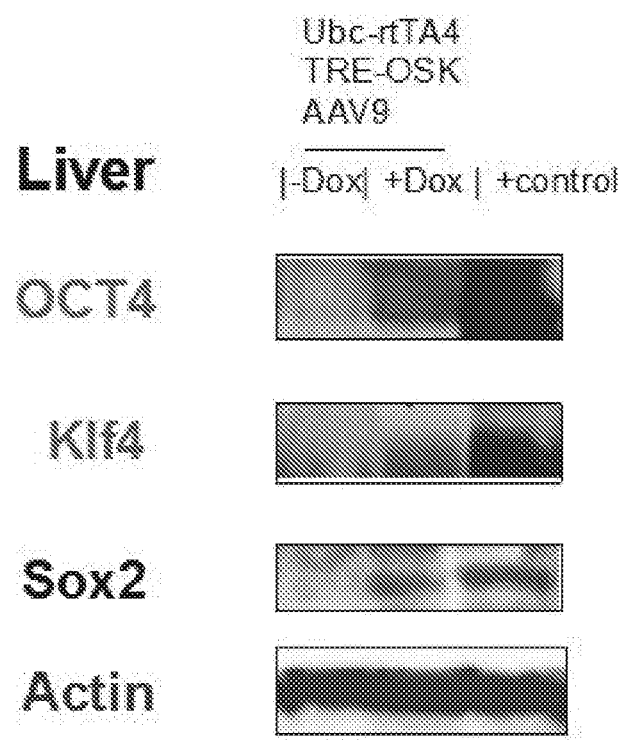
Figure 14:
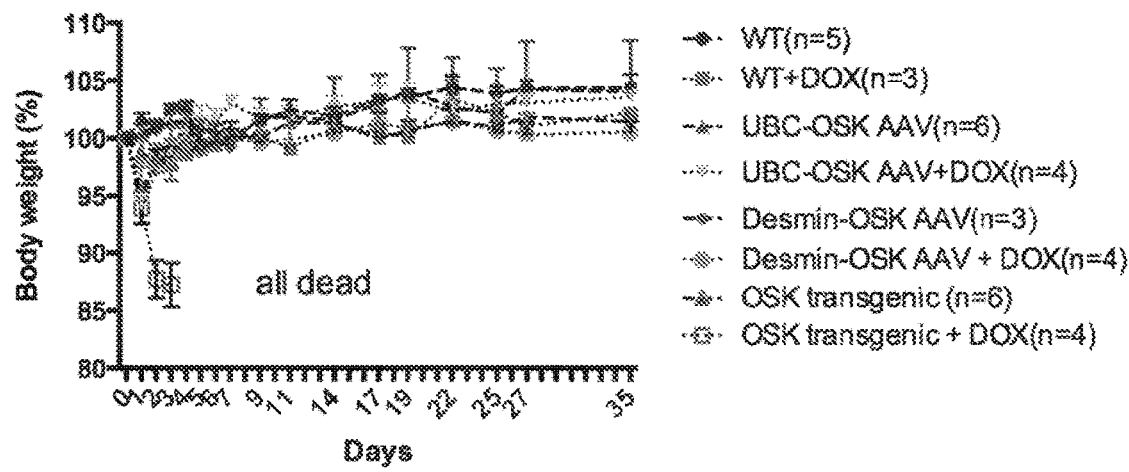
FIG. 14 is a graph comparing the body weights of mice under various treatments as indicated. WT indicates wild-type mice without exogenous OSK expression. All dead indicates that OSK transgenic mice treated with doxycycline were all dead.

Example 4: An AAV Vector Encoding Mutant Reverse Tetracycline Transactivator (rtTA) Showed Low Leakiness in the Liver of Mice and Low Toxicity As shown in FIGS. 13A-13C, OCT4, SOX2, and KLF4 through AAV9 delivery (TRE-OSK with UBC-rtTA4) can be successfully induced in liver of the mice with DOX treatment, shown with both western blot and immune staining. While mice with transgene of OCT4, SOX2, KLF4 died after 2 days-induction from doxycycline water (FIG. 14) due to generalized cytological and architectural dysplasia in the intestinal epithelium, expression from the OCT4, SOX2, and KLF4 AAV described herein did not cause toxicity or teratoma in vivo even with continuous expression through doxycycline administration in their drinking water. No teratoma or body weight loss were detected for three months when AAV9 encoding these three transcription factors were delivered to the entire body of mice (FIG. 14).

Figure 15A:
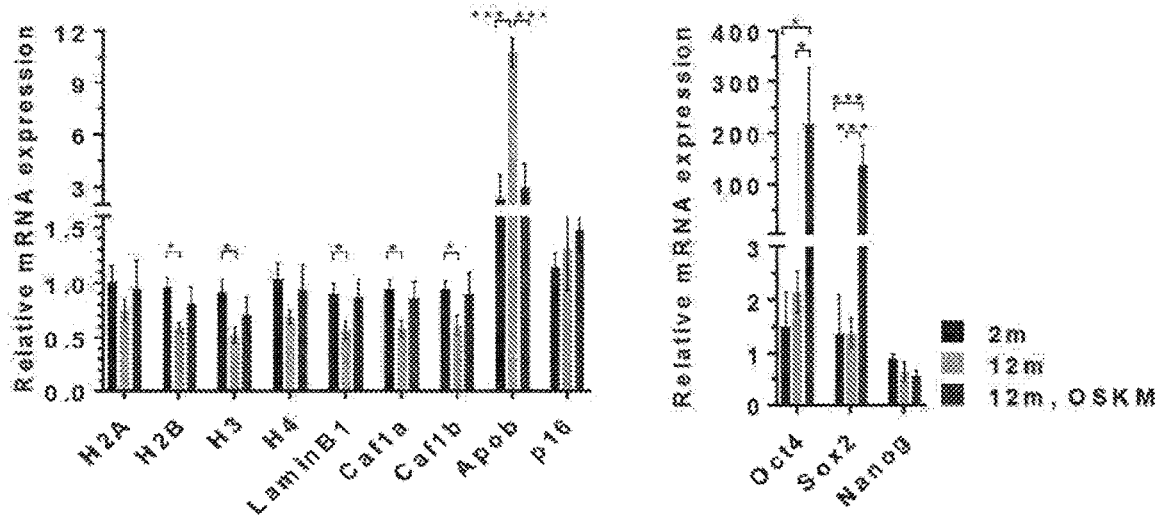
FIGS. 15A-15B include data showing that induction of OCT4, KLF4, and SOX2 expression reversed aging of mice ear fibroblasts as indicated by expression of histone and Chaf (Chromatin assembly factor) genes but did not induce Nanog expression. The asterisk (*) indicates endogenous KLF4 expression from the 293T cell line.
Figure 15B:
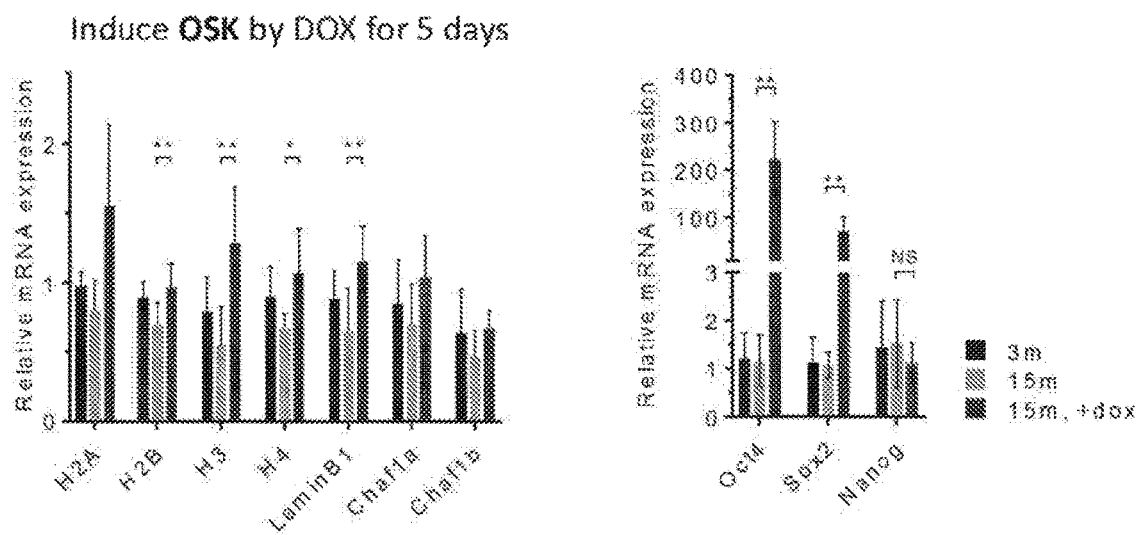

Example 5: Expression of OCT4, SOX2, and KLF4 Induced Partial Reprogramming in Mice FIGS. 15A-15B show that the expression of histone and Chaf (Chromatin assembly factor) genes declined during aging in ear fibroblasts from aged mice (12 months or 15 months) compared to those from young mice, short term of OSKM (3 days) or OSK expression (5 days) induction reset their gene expression level to young state, without making them into stem cell (e.g., Nanog was not been turned on).

Figure 16:
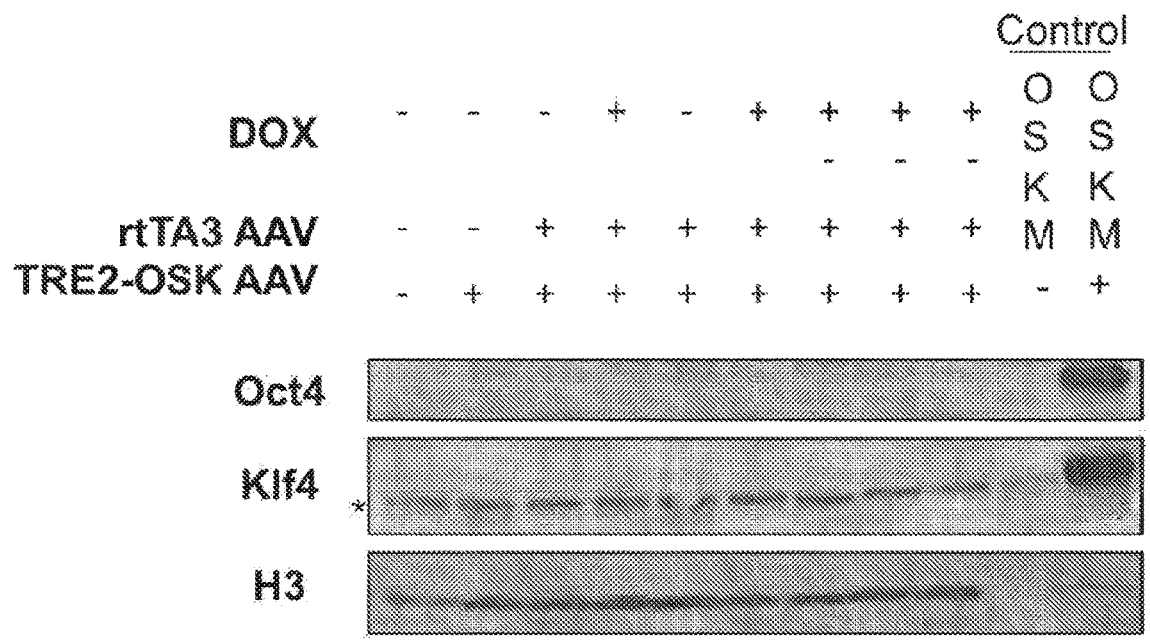
FIG. 16 is a western blot showing that an AAV vector comprising a nucleic acid (e.g., engineered nucleic acid) sequence that is greater than 4.7 kb between the two ITRs in the vector has low viral titer when incorporated into an AAV and produces non-functional AAV. The TRE2-OSK vector is provided as SEQ ID NO: 33. Expression of OCT4, KLF4 and H3 was detected using antibodies. H3 is shown as a loading control. Asterisk (*) indicates endogenous Klf4 from 293T cell line.

Conventional AAV vectors encoding OSK is over the packaging limit of AAV (e.g., 4.7 Kb), could only be packaged into AAV9 capsid with low titer (less than $2\times10^{12}$ particles per viral prep), and the low titer virus is not functional (e.g., no overexpression of OCT4 or KLF4 was detected) due to possible truncation as shown in FIG. 16.

Figure 12:
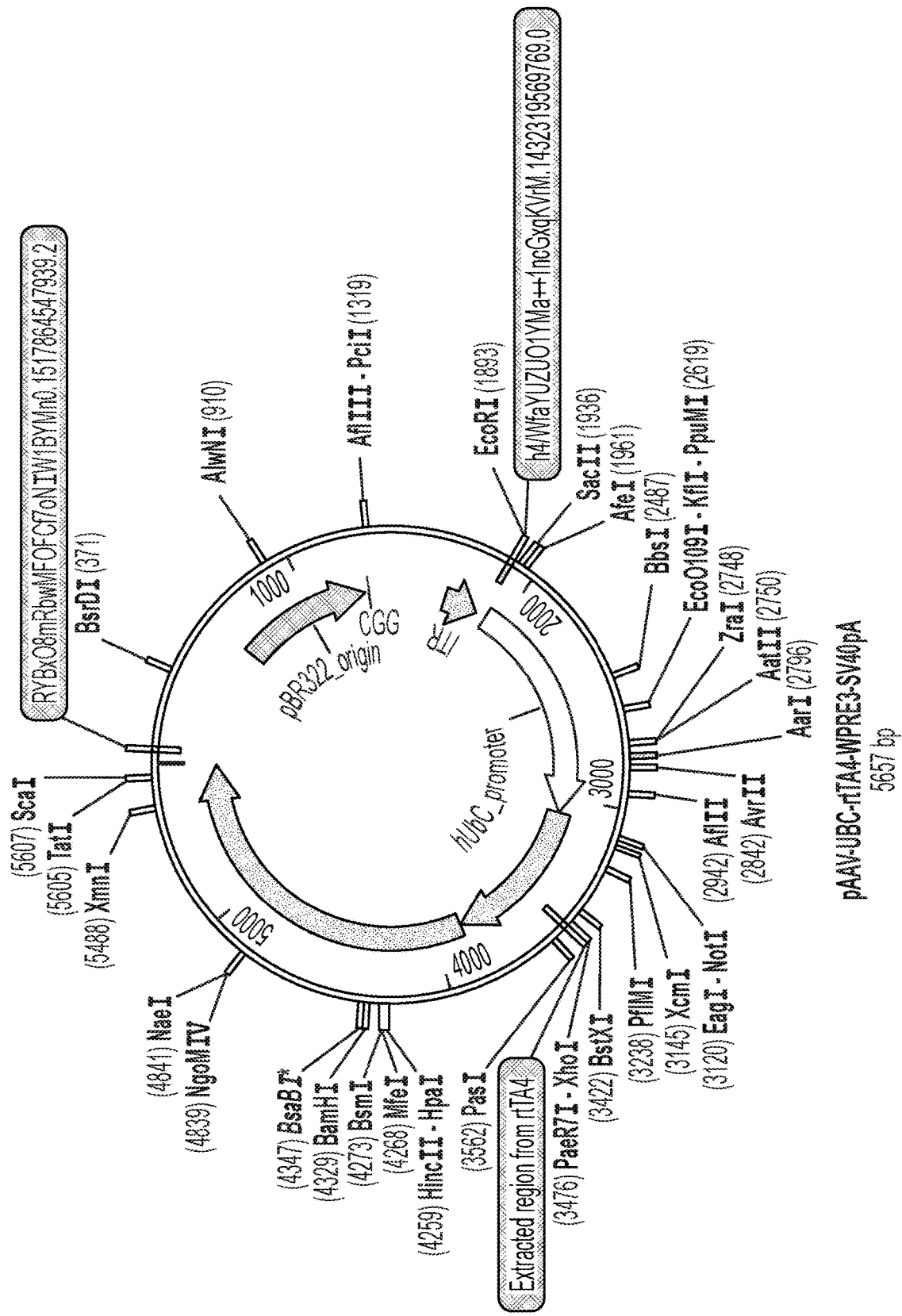
FIG. 12 is a vector map showing features in an adeno-associated virus (AAV) vector encoding reverse tetracycline-transactivator 4 (rtTA4). Ubc is a constitutive promoter that is operably linked to the nucleic acid (e.g., engineered nucleic acid) encoding rtTA4. SV40 pA is an SV40-derived terminator sequence. The sequence of this vector is provided in SEQ ID NO: 17.

Example 6: An AAV Vector Encoding Mutant Reverse Tetracycline Transactivator (rtTA) Showed Low Leakiness in the Liver of Mice A Tet-On system comprising rtTA4 (SEQ ID NO: 13) was also tested in vivo using recombinant AAV9 viruses. Two AAV vectors comprising components shown in FIG. 13B were used. AAV virus encoding rtTA4 operably linked to a UBC promoter (pAAV-UBC-rtTA4-WPRE3-SV40 pA vector is provided as SEQ ID NO: 17 and an exemplary vector map of SEQ ID NO: 17 is provided in FIG. 12) and AAV virus encoding an AAV TRE3G-OSK-SV40 pA vector (SEQ ID NO: 16) with a vector map depicted in FIG. 3 were administered to mice. Mice were treated without doxycycline or with doxycycline and liver samples were collected. As shown in the immunofluorescence images of FIG. 13A, in the absence of doxycycline, KLF4 expression was not detectable in the liver. When mice were treated with doxycycline through their drinking water, KLF4 expression was detected in the liver (FIG. 13A). These results were also evident by western blot using antibodies against OCT4, KLF4, and SOX2 to determine expression of these protein (FIG. 13C). Actin was used as a loading control (FIG. 13C). OCT4, KLF4, and SOX2 were only detected in the liver when mice were treated with doxycycline (FIG. 13C).

Example 7. Modified mRNAs Encoding OCT4, SOX2, and KLF4(OSK) Induced Expression of OSK in Mouse Fibroblasts Mouse fibroblasts were successfully transfected with modified mRNA encoding OCT4, SOX2, KLF4, and c-MYC (OSKM). Lipofectamine™ MessengerMAX™ Transfection Reagent from Invitrogen was used to transfect the modified mRNAs. The modifications were complete substitution of either 5-methylcytidine (5mC) for cytidine or pseudouridine (psi) for uridine. See, e.g., Warren et al., Cell Stem Cell. 2010 Nov. 5; 7(5):618-30; Mandal et al., Nat Protoc. 2013 March; 8(3):568-82. The dose of each RNA that was used is provided in Table 4 below. The numbers 1-5 in the first column of Table 4 correspond to the numbers 1-5 in FIG. 17.

TABLE 4

Doses of mRNA administered.

| | | mRNA (µg) | | | | |
|---|---|---|---|---|---|---|
| | NDG | O | S | K | M | Total |
| 1 | 0 | 0 | 0 | 0 | 0 | 0 |
| 2 | 1X | 0.2 | 0.6 | 0.2 | 0.2 | 0.2 | 1.4 |
| 3 | 2X | 0.4 | 1.2 | 0.4 | 0.4 | 0.4 | 2.8 |
| 4 | 4X | 0.8 | 2.4 | 0.8 | 0.8 | 0.8 | 5.6 |
| 5 | 6X | 1.2 | 3.6 | 1.2 | 1.2 | 1.2 | 8.4 |

A western blot was used to confirm that administration of the modified mRNA induced expression of protein in the mouse fibroblasts. As shown in FIG. 17, transfection of OSK modified mRNA into mouse fibroblasts cells to induce expression of OCT4, KLF4, and SOX2 protein (NDG and zsGreen are modified mRNA that express green fluorescent protein to indicate the efficiency of transfection).

This example shows that delivery of RNA (e.g., mRNA, modified RNA, modified mRNA, etc.) encoding OCT4, KLF4, and SOX2 to mouse cells is feasible. These findings may be extended to in vivo delivery of mRNA encoding OCT4, KLF4, and SOX2. As an example, for in vivo muscle delivery, electroporation, is used. As an example, for liver and other internal organ delivery, nanoparticles comprising RNA encoding OCT4, KLF4, and SOX2, nanoparticles are used. See, e.g., Dong et al., Nano Lett. 2016 Feb. 10; 16(2):842-8.

Example 8. Chemical Reprogramming of Cells

A non-limiting of a protocol to chemically reprogram a mouse embryonic fibroblast to an induced pluripotent stem cell is provided below. A similar protocol may be found at Zhao et al., Cell. 2015 Dec. 17; 163(7):1678-91. FIG. 21 shows the results after using the protocol provided below.

Stage 1
   100 ng/ml bFGF
   0.5 mM VPA,
   20 µM CHIR99021,
   10 µM 616452,
   5 µM tranylcypromine,
   50 µM forskolin,
   0.05 µM AM580
   5 µM EPZ004777
   On day 12, the cells were trypsinized, harvested and then re-plated at 50,000-200,000 cells per well of a 6-well plate (1:10-15)
   During days 12-16, concentrations of bFGF, CHIR, and forskolin were reduced to 25 ng/ml, 10 µM, and 10 µM, respectively.
   On day 16, XEN-like epithelial colonies were formed and the culture was changed into stage 2 medium Stage 2
   25 ng/ml bFGF,
   0.5 mM VPA,
   10 µM CHIR99021,
   10 µM 616452,
   5 µM tranylcypromine,
   10 µM forskolin,
   0.05 µM AM580,
   0.05 µM DZNep,
   0.5 µM 5-aza-dC,
   5 µM SGC0946
   On day 28, the culture was transferred into stage 3 medium.

Stage 3
   N2B27-2iL medium
   3 µM CHIR99021,
   1 µM PD0325901,
   1,000 U/ml LIF
   After another 8-12 days, 2i-competent, ESC-like, and GFP-positive (if using pOct4-GFP reporter) CiPSC colonies emerged and were then picked up for expansion and characterization.

Example 9. Expression of OCT4, SOX2, and KLF4 Improved Axon Regeneration in Adult and Aged Mice after Optic Nerve Crush Injury The Tet-Off system depicted in FIG. 22, top panel was used to determine whether a vector encoding TRE-OSK-SV40 (SEQ ID NO: 16) could be used to promote optic nerve axon regeneration in adult (3 month old) and aged (12 month old) mice.

AAV2 virus with the TRE-OSK-SV40 vector and AAV2 virus encoding tTA under the CAG constitutive promoter were injected into the retina of 1 month old, 3 month old, or 12 month old mice (n=5-9), similar to the experimental timeline provided in FIG. 7C. As a control, a separate cohort of 1 month old mice (n=5-6) were injected with AAV2 virus with a AAV2 vector TRE-d2EGFP-SV40 and the AAV2 virus encoding tTA. Mechanical damage was induced through optic nerve crush in both cohorts two weeks after virus injection. To trace axon regeneration by fluorescent microscopy of the optic nerve, fluorescently labeled cholera toxin β-subunit (CTB) was intraocularly injected into mice two weeks after optic nerve crush injury and perfusion was performed two days after CTB injection. Axon regeneration analysis was subsequently conducted.

Figure 23A:
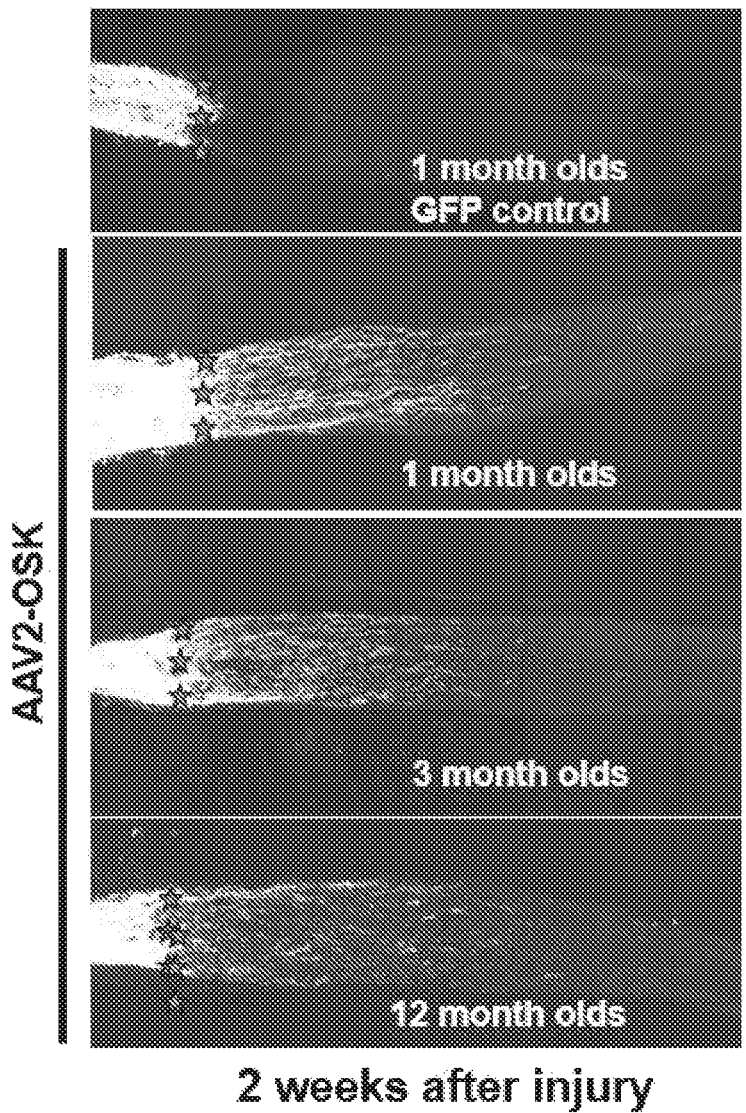
FIGS. 23A-23C include data showing that administration of AAV2 virus encoding OCT4, SOX2, and KLF4 improved axon regeneration and RGC survival in adult and aged mice two weeks after optic nerve crush.
Figure 23B:
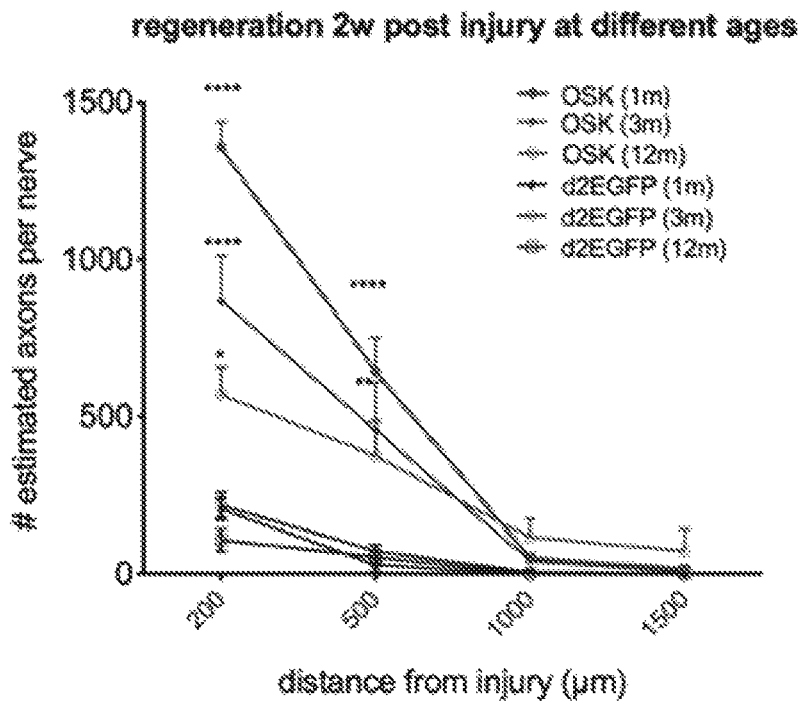
Figure 23C:
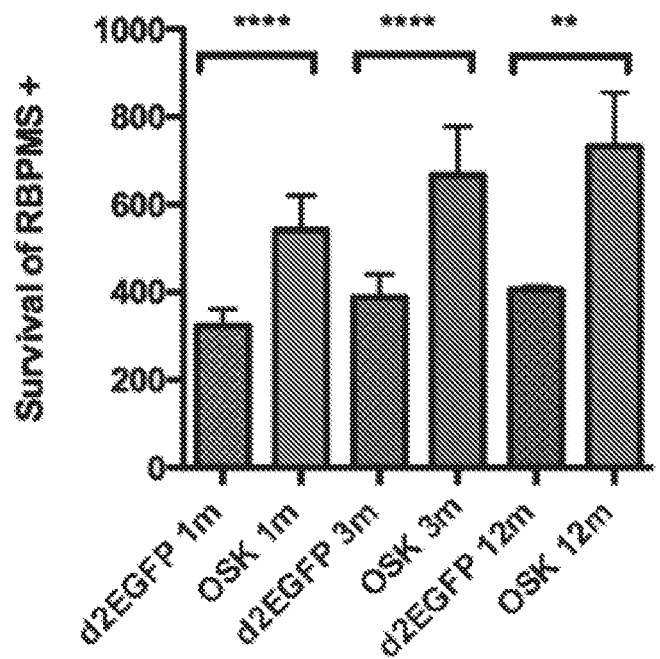

As shown in FIGS. 23A-23B, administration of AAV2 virus encoding OSK increased the number of estimated axons per nerve in 1 month old (young), 3 month old (adult), and 12 month old (aged) mice relative to administration of control virus encoding d2EGFP. Furthermore, TRE-OSK virus also increased the survival of RGCs after optic nerve injury in adult (3 month old) and aged (12 month old) mice compared to control GFP (FIG. 23C). Therefore, OSK expression surprisingly promoted axon regeneration and RGC survival after nerve crush injury in young, adult, and aged mice.

Figure 24A:
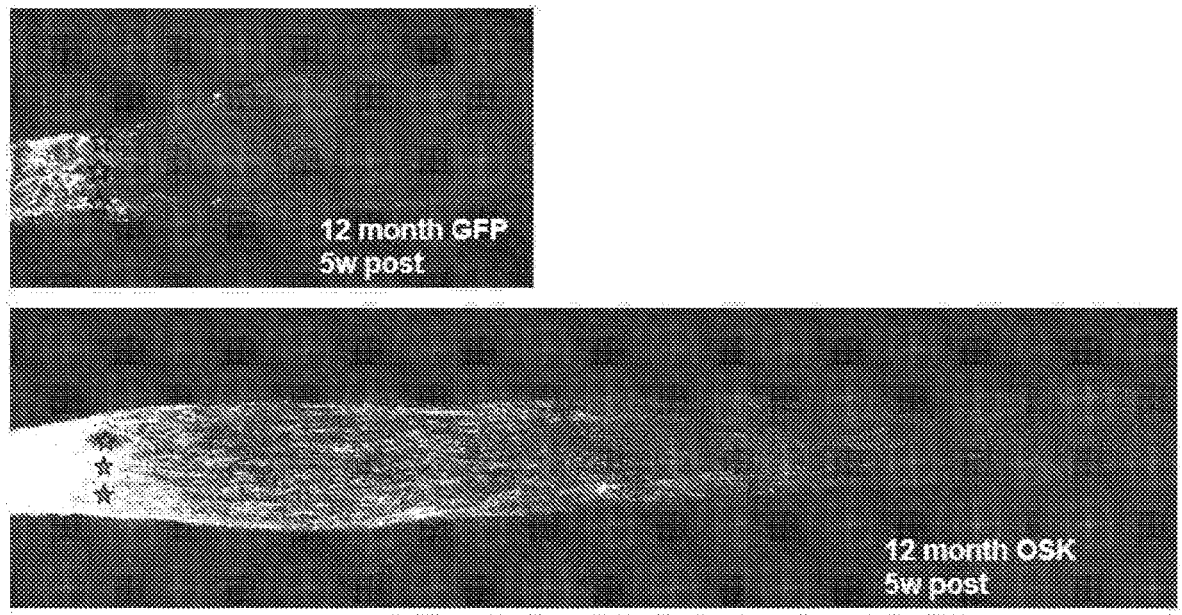
FIGS. 24A-24B include data showing that increasing the time of reprogramming from two weeks to five weeks improved regeneration in aged mice.
Figure 24B:
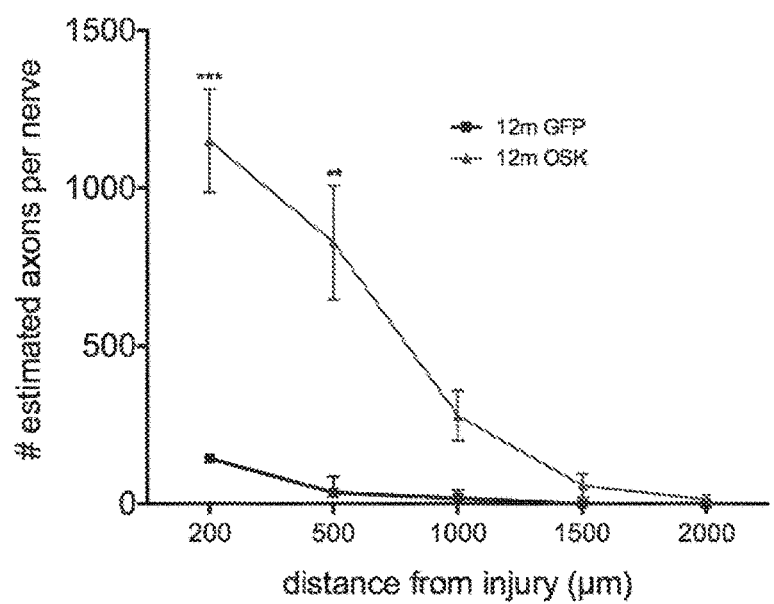

Next, the impact of the length of time of OSK expression on axon regeneration in aged mice was determined. Mice were administered tTA virus and either TRE-OSK virus or TRE-GFP virus 2 weeks prior to optic nerve crush. Then, fluorescently labeled cholera toxin β-subunit (CTB) was intraocularly injected into mice that were five weeks instead of two weeks after optic nerve crush injury. As shown in FIGS. 24A-24B, increasing the length of time of post-injury OSK expression to five weeks increased the number of estimated axons per nerve in the 12 month old mice compared to two weeks post-injury of OSK expression in FIG. 23B. In contrast, increasing the length of time of post injury GFP expression had no effect on axon regeneration (compare results with GFP in FIGS. 24A-24B with those shown in FIGS. 23A-23B). Therefore, the data suggests that a longer time of OSK expression may be beneficial in promoting axon regeneration and RGC survival after nerve crush injury in aged mice.

Figure 25A:
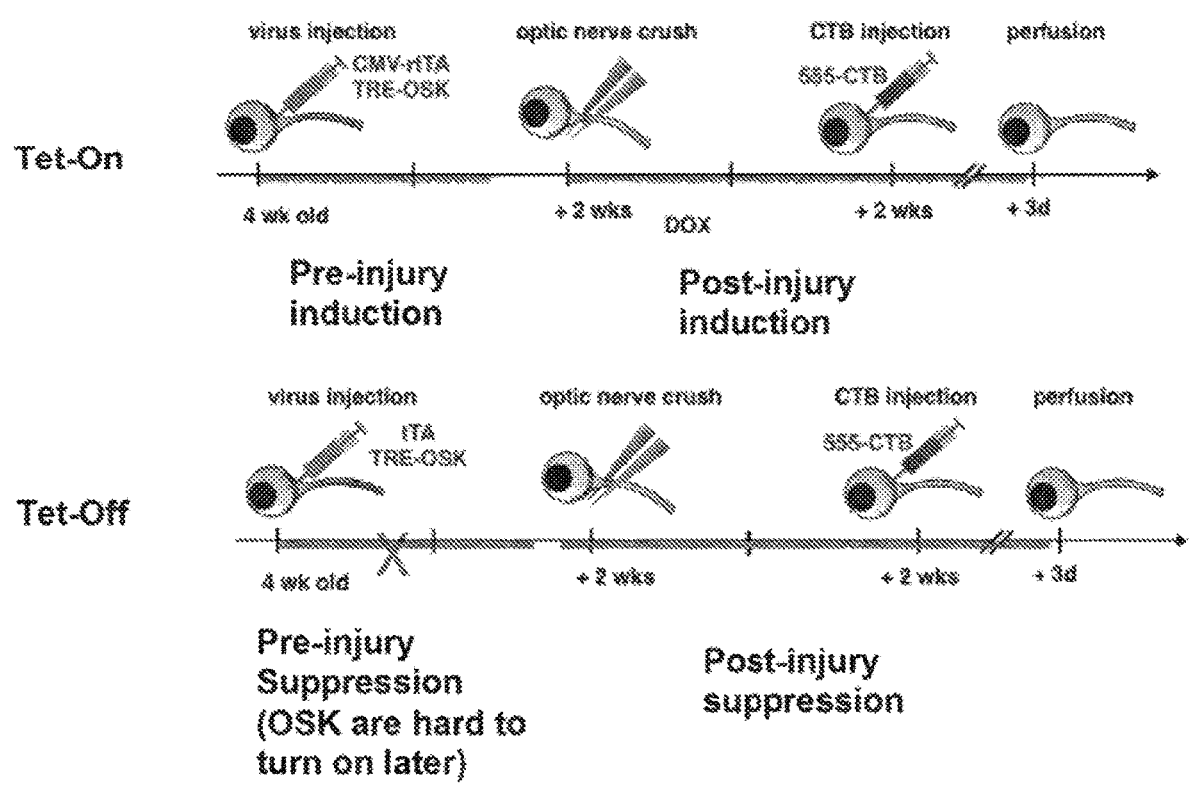
FIGS. 25A-25C include data showing that induction of OSK expression using Tet-On and Tet-Off systems even after optic nerve crush injury improved regeneration and RGC cell survival in mice.

Example 10. Induction of OSK Expression Following Optic Nerve Crush Injury Increased Axon Regeneration and RGC Survival in Mice It was also determined whether induction of OSK expression after optic nerve crush injury would promote axon regeneration and RGC survival. Both the Tet-On and Tet-Off systems depicted in the panel of FIG. 22 were used. In the Tet-On system, AAV virus with the TRE-OSK-SV40 vector and AAV virus encoding rtTA under the CMV constitutive promoter were produced through routine methods and injected into the retina of mice. As depicted in FIG. 25A, in the Tet-On system (top panel), OSK expression was induced by giving mice doxycycline either prior to optic nerve crush injury or after optic nerve crush injury. A cohort of mice were not treated with doxycycline as a control (no induction). In the Tet-Off system, AAV virus with the TRE-OSK-SV40 vector and AAV virus encoding tTA under the CAG constitutive promoter were produced through routine methods and injected into the retina of mice. As depicted in FIG. 25A, in the Tet-Off system (bottom panel), OSK expression was suppressed after optic nerve crush injury. Fluorescently labeled cholera toxin β-subunit (CTB) injection was used to visualize axons.

Figure 25B:
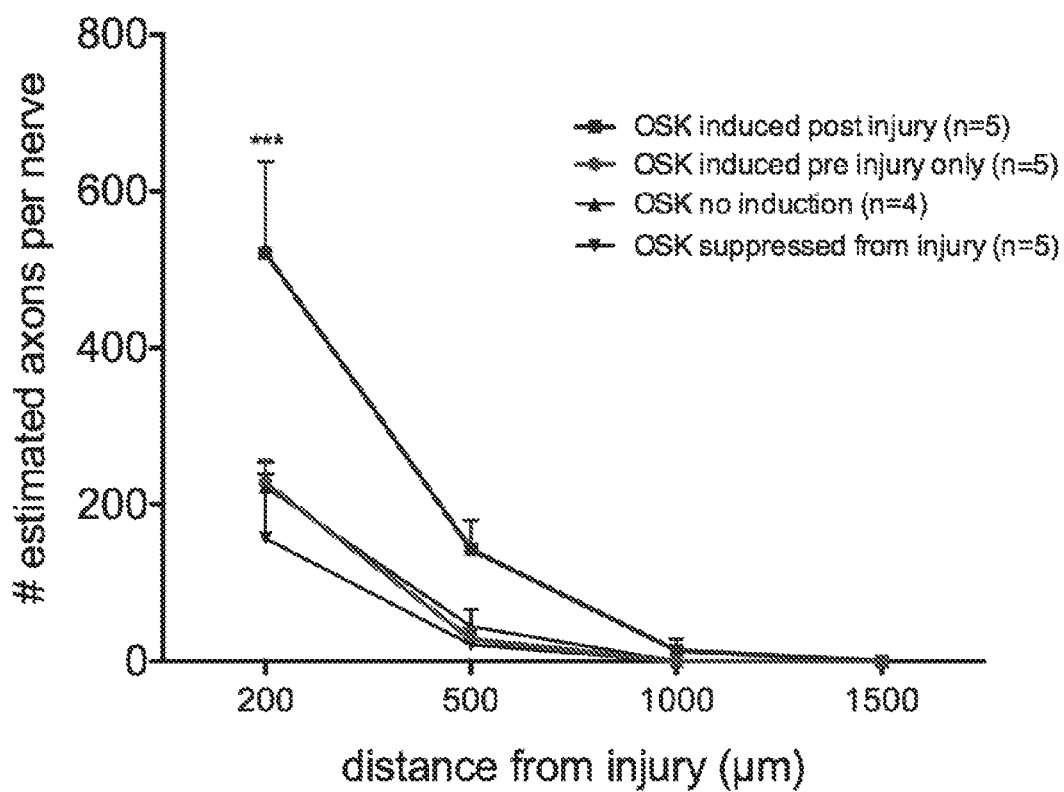
Figure 25C:
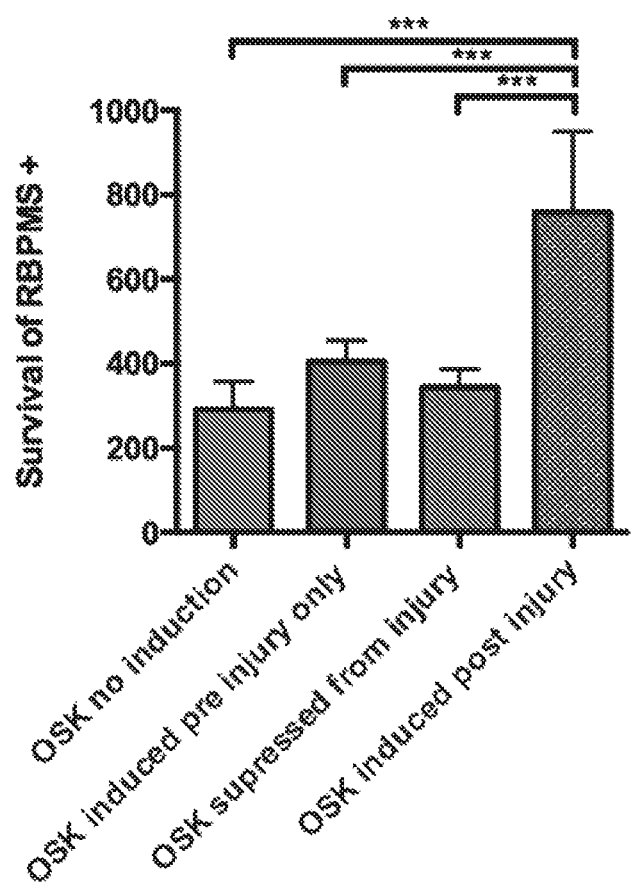

As shown in FIG. 25B, induction of OSK expression post injury through Tet-On system significantly increased the number of estimated axons per nerve compared to no induction of OSK or induction of OSK prior to injury (pre-injury) only through either Tet-On or Tet-Off system. Furthermore, induction of OSK expression post injury significantly increased the survival of RBPMS+ cells compared to no induction of OSK expression or compared to OSK induction pre-injury only through either Tet-On or Tet-Off system (FIG. 25C). Therefore, the Tet-On system depicted in FIG. 25A, top panel, allowed for temporal control of OSK expression and induction of OSK after optic nerve crush injury promoted axon regeneration and RGC survival. Without being bound by a particular theory, induction of OCT4, KLF4, and SOX2 expression using a Tet-Off system following an injury may promote regeneration when recovery from an injury does not require immediate expression of OCT4, KLF4, and/or SOX2.

Figure 26A:
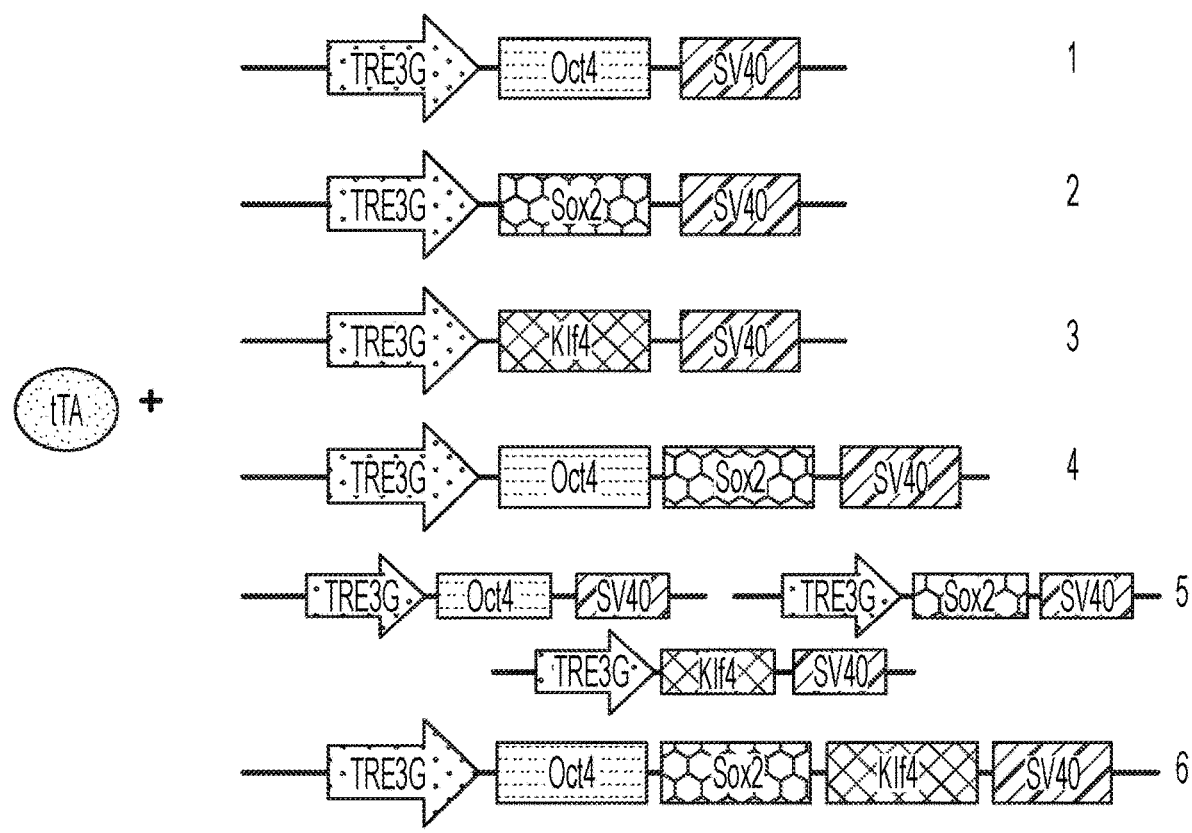
FIGS. 26A-26E include data showing that expression of OSK from a single transcript improved axon regeneration and retina ganglion cell (RGC) survival two weeks after optic nerve crush injury compared to expression of OCT4, SOX2, and KLF4 from separate transcripts.

Example 11. Superior Effect of OCT4, SOX2, and KLF4 (OSK) Expression from a Single Transcript Compared to Individual Transcripts in Promoting Axon Regeneration This example explored the effect of expressing OCT4, SOX2, and KLF4 under one promoter as compared to expression of OCT4, SOX2, KLF4 alone or in combination under separate promoters. AAV virus encoding tTA under the CAG constitutive promoter and AAV virus or viruses encoding (1) OCT4 under the TRE promoter, (2) SOX2 under a TRE promoter, (3) KLF4 under a TRE promoter, (4) OCT4 and SOX2 under one TRE promoter, (5) OCT4, SOX2, and KLF4 each under separate promoters, or (6) OCT4, SOX2, and KLF4 under the same promoter were injected into the retina of mice. A schematic showing the various vectors used in this study is shown in FIG. 26A. Optic nerve crush injury was induced 2 weeks after virus administration. Fluorescently labeled cholera toxin (β-subunit (CTB) injection 2 weeks after optic nerve crush was used to image axons.

Figure 26B:
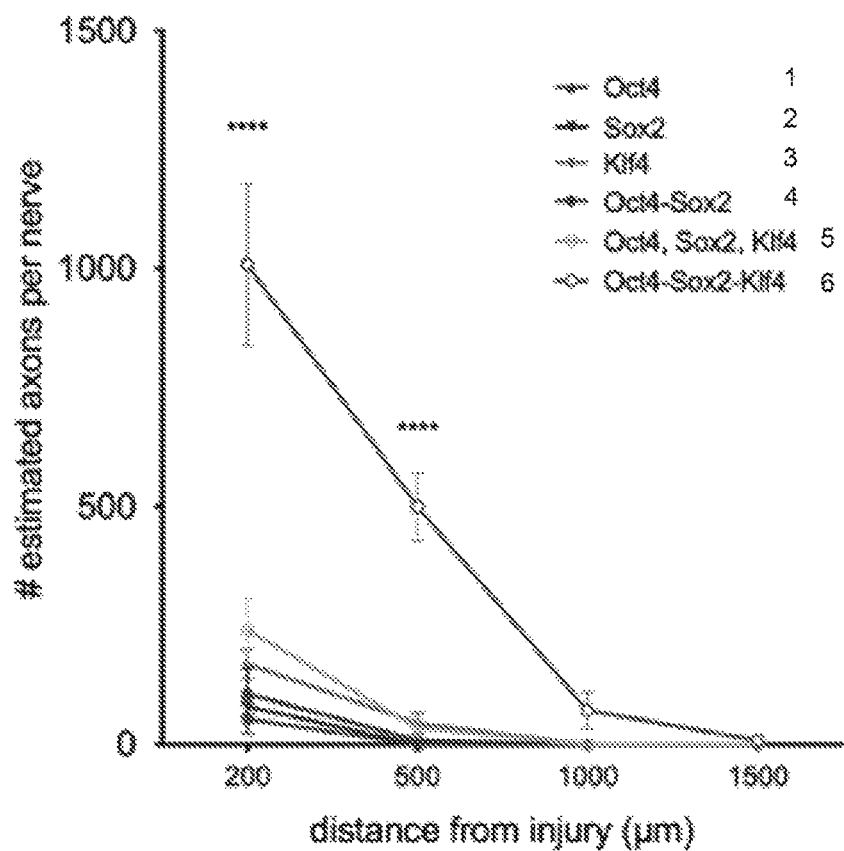

As shown in FIG. 26B, when all three transcription factors (OSK) were expressed under one promoter, the number of estimated axons per nerve was at least four times higher than when OCT4, SOX2, and KLF4 were each expressed under a separate promoter (e.g., compare OCT4, SOX2, KLF4 (5), and OCT4-SOX2-KLF4 (6) results). Similarly, the number of estimated axons per nerve was also at least four times higher when OSK was expressed on a single transcript than when OCT4, SOX2, and KLF4 expression alone (FIG. 26B) (e.g., compare OCT4 (1), SOX2 (2), and KLF4 (3) with OCT4-SOX2-KLF4 (6) results). The increase in axon regeneration was likely attributed to expression of all three transcription factors (OSK) under one promoter, as expression of OCT4 and SOX2 under one promoter did not significantly increase the number of estimated axons per nerve relative to expression of each transcription factor alone (FIG. 26B) (e.g., compare OCT4-SOX2 (4) with OCT4-SOX2-KLF4 (6) results).

Figure 26C:
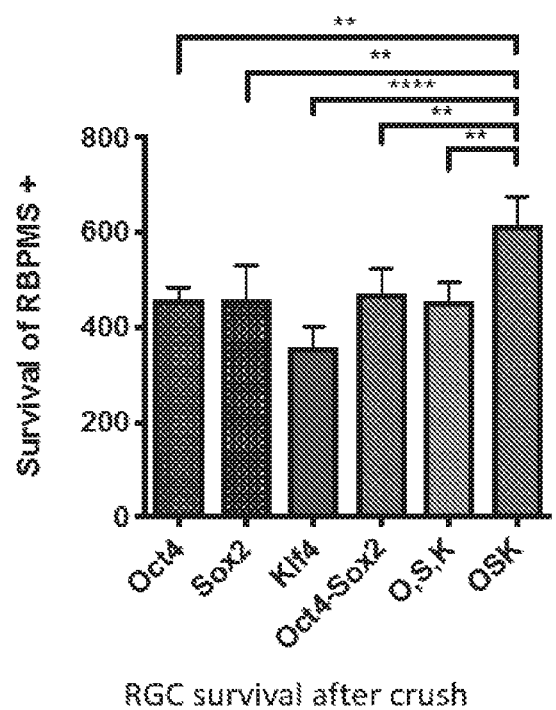

Analysis of retina ganglion cell (RGC) survival was also conducted by quantifying RBPMS+ cells. As shown in FIG. 26C, expression of OSK from one promoter increased the survival of RBPMS+ cells relative to expression of OCT4, SOX2, or KLF4 alone and relative to expression of OCT4 and SOX2 under one promoter. Expression of OSK from one promoter also increased the survival of RBPMS+ cells relative to expression of OCT4, SOX2, or KLF4 from separate vectors in separate viruses.

Figure 26D:
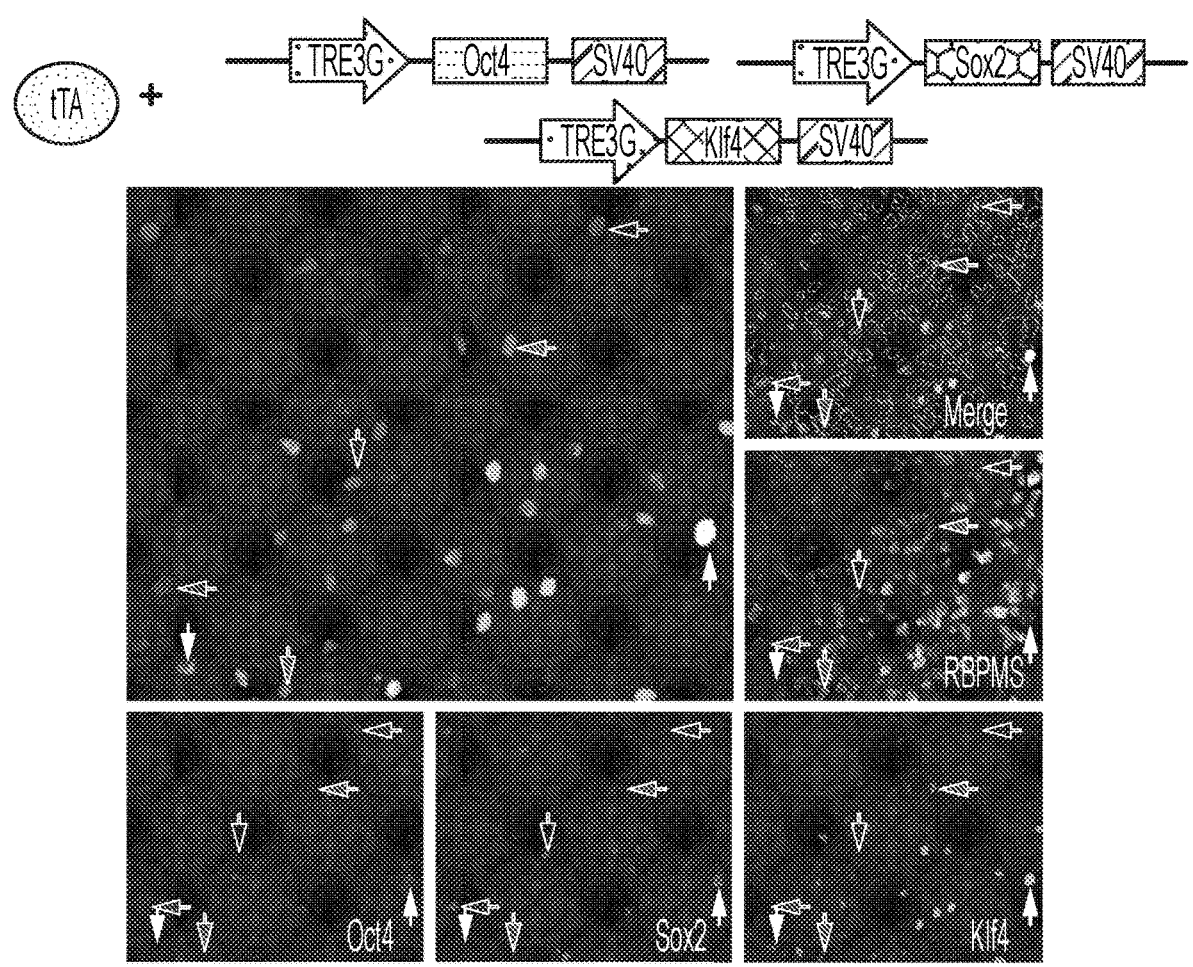
Figure 26E:
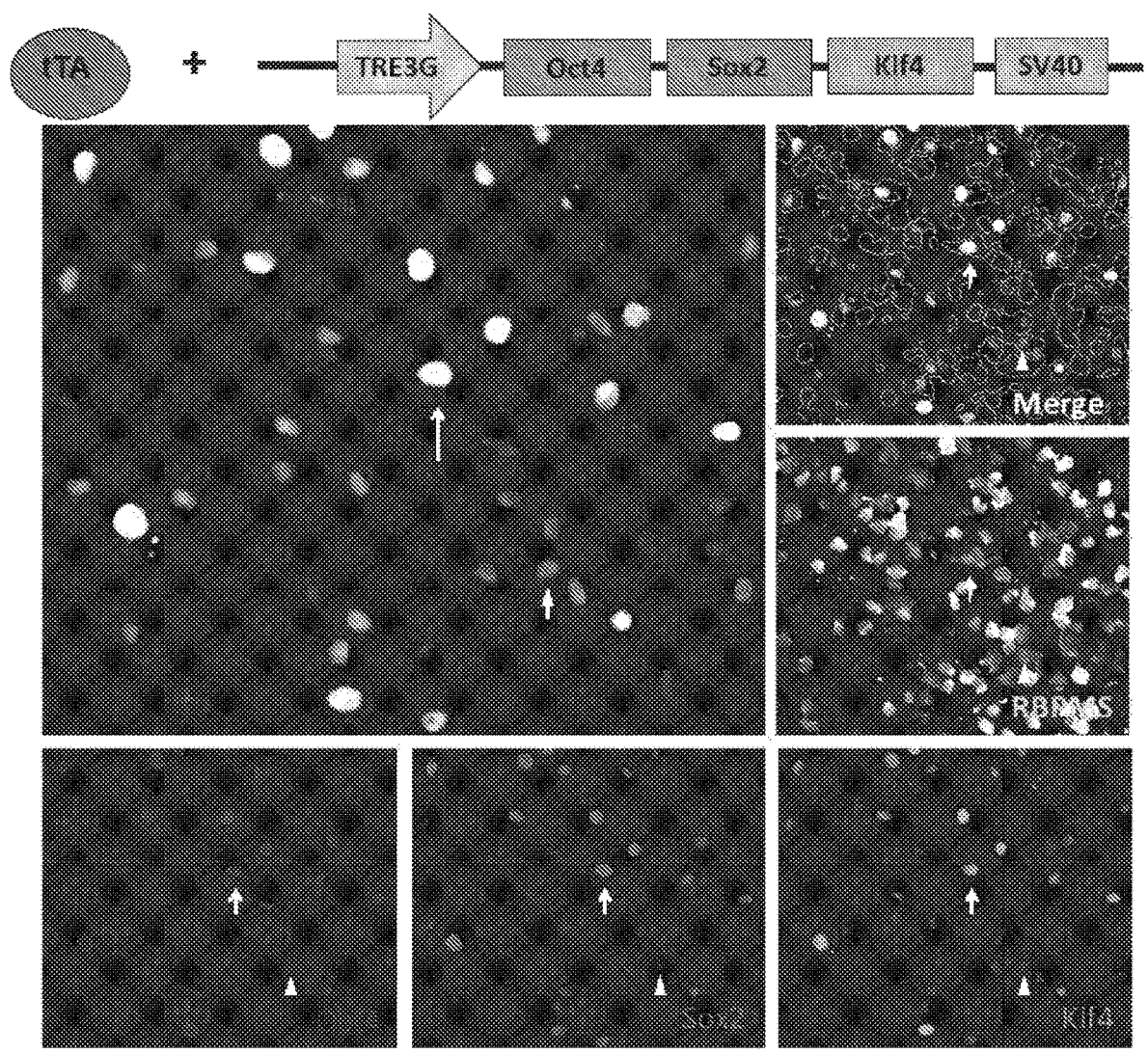

As shown by the fluorescence staining depicted in FIG. 26D, expression of OCT4, SOX2, and KLF4 in separate vectors in separate viruses resulted in a heterogeneous population of RGCs. Some cells only expressed OCT4, SOX2, or KLF4. Some cells expressed a combination of only two out of the three transcription factors and only a few three-factor positive RGCs were detected (white color cell in the bottom right corner of the top left panel in FIG. 26D). In contrast, as shown in FIG. 26E, expression of OCT4, SOX2, and KLF4 from a single vector resulted in a more homogenous population. All of the cells expressed all three of the OSK transcription factors (white color cells in the top left panel). Even in cells that were not pure white, expression of all three transcription factors were detected as shown in FIG. 26E, suggesting that the results were due to differences in staining intensity for the three transcription factors.

Therefore, this example shows that expression of OCT4, SOX2, and KLF4 using one promoter had greater therapeutic effect (e.g., increased axon regeneration and a greater survival of retina ganglion cells) compared to expression of each transcription factor alone, expression of all three transcription factors under separate promoters, or expression of only two of the transcription factors (e.g., OCT4 and SOX2) under one promoter.

Example 12. Knockdown of Tet1 or Tet2 Abrogated OSK-Induced Axon Regeneration Following Optic Nerve Crush Injury This example determined the effect of knocking down DNA demethylases Tet1 and Tet2 on OSK-induced axon regeneration. A Tet-Off system was used. AAV2 of CAG-tTA+TRE-OSK-SV40 were injected into mice through intravitreal injection two weeks before crush together with AAV2 of U6-shRNA. Mice were one month old with four mice in each group.

Addgene AAV plasmids encoding shRNA sequences were used. Control shRNA comprised the sequence 5'-GTTCA-GATGTGCGGCGAGT-3' (plasmid #85741 from Addgene). mTET1 (Tet1 shRNA) comprised the sequence 5'-GCT-CATGGAGACTAGGTTTGG-3' (plasmid #85742 from Addgene). mTet2 (Tet2 shRNA) comprised the sequence 5'-GGATGTAAGTTTGCCAGAAGC-3' (Plasmid #85743 from Addgene).

Figure 27:
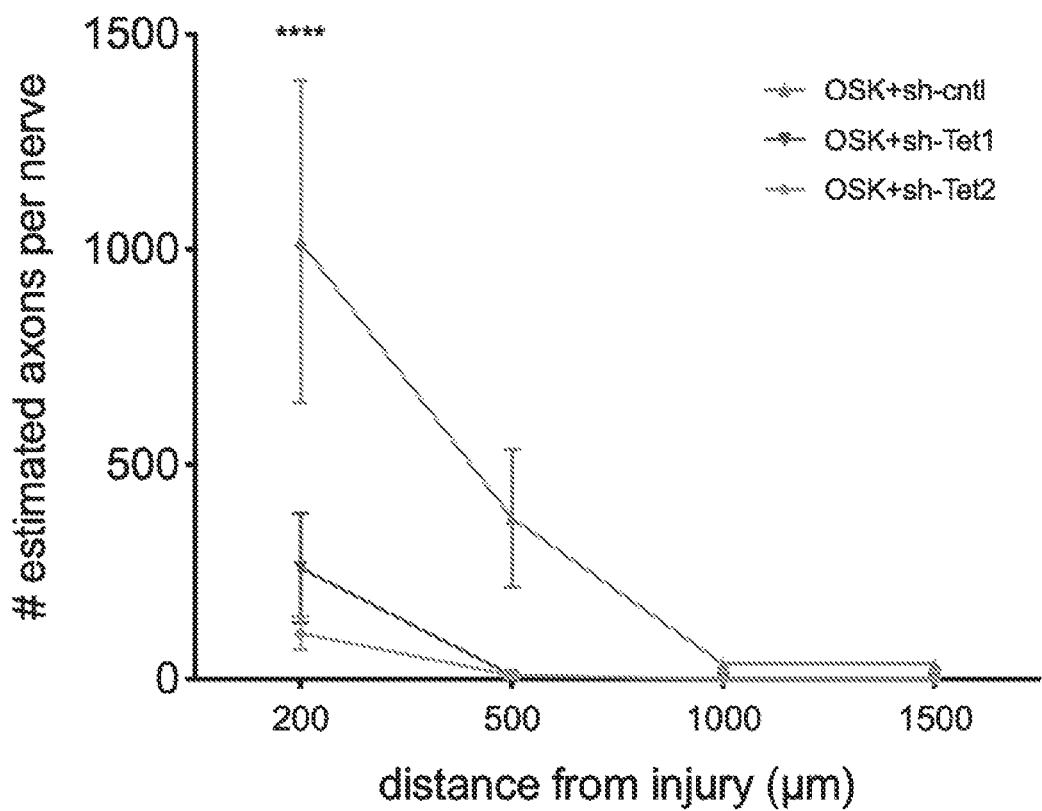
FIG. 27 is a chart showing that Tet1 and Tet2 DNA demethylases play a role in OSK-induced regeneration. The number of estimated axons per nerve after optic nerve crush was quantified in mice receiving (1) OSK virus and a short hairpin control, (2) OSK virus and a short hairpin against Tet1, or (3) OSK virus and a short hairpin against Tet2.

As shown in FIG. 27, knockdown of either Tet1 or Tet2 significantly reduced the number of estimated axons per nerve in animals also treated with OSK virus and subjected to optic nerve crush injury compared to the control hairpin (sh-cntl).

These results suggest that Tet DNA methylases may be involved in OSK-induced axon regeneration and overexpression of Tet (e.g., Tet1 or Tet2) alone or in combination with OSK expression may promote regeneration.

As a non-limiting example, mTet3 comprising the sequence 5'-GCTCCAACGAGAAGCTATTTG-3' (Plasmid #85740 from Addgene) may be used to knockdown Tet3.

Example 13. Expression of OSK Reversed Age-Related Decline in Visual Acuity and Reversed Age-Related Decline in Retina Ganglion Cell (RGC) Function To determine whether age-related visual acuity loss may be reversed with OSK expression, an optomotor response (OMR) assay was conducted on adult mice (3 month old mice) and aged mice (12 month old and 18 month old mice). OMR is a reflexive head movement used to assess visual acuity. To induce OMR, individual mice are placed on a platform in the middle of an arena surrounded by computer monitors displaying stripes. The rotation of the striped pattern elicits mouse head tracking in the same direction by reflexive neck movements. Tracking is monitored by two independent masked observers. Visual acuity is quantified by increasing the spatial frequency of the stripes until an OMR cannot be elicited.

Mice were retinally injected with AAV virus encoding tTA and AAV virus encoding TRE-OSK in the absence of doxycycline (OSK induction condition). In this Tet-Off system, OSK is expressed from a single promoter in the absence of doxycycline. As controls, age-matched mice were administered virus encoding virus encoding rtTA and virus TRE-OSK in the absence of doxycycline (uninduced control, ctl). In the control Tet-On system, OSK expression requires doxycycline treatment. Adult mice (3 month old (3 m)) were also used as a control. An OMR study was conducted to measure the spatial frequency threshold one month after virus injection.

Figure 28:
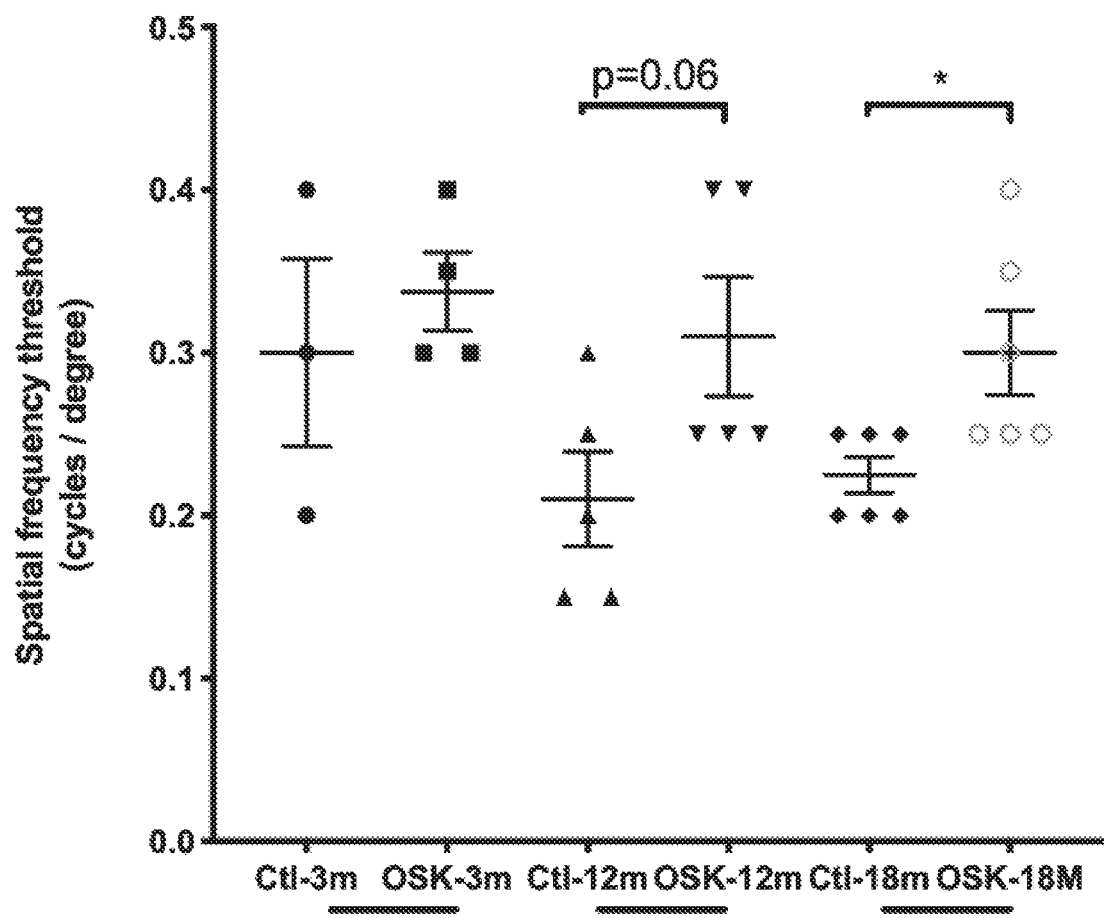
FIG. 28 includes data showing that expression of OSK using a Tet-Off system reversed age-related visual acuity loss in aged mice one month post injection of AAV virus encoding TRE-OSK and AAV virus encoding tTA.

As shown in FIG. 28, in the absence of OSK expression (control (ctl) condition) the aged mice (12 month old and 18 month old mice) had vision loss compared to the adult mice (3 month old mice). The decrease in the spatial frequency threshold for the aged mice relative to the 3 month old mice indicated vision loss in the absence of OSK expression. When OSK was expressed, however, the spatial frequency threshold on average increased for the 12 month old and 18 month old mice relative to no OSK expression. Furthermore, the spatial frequency thresholds for the 12 month old and 18 month old mice with OSK expression were similar to that of the 3 month old control mice in the presence and absence of OSK expression. These results demonstrate that induction of OSK expression reversed age-related vision loss in mice.

To determine whether age-related decline in retina ganglion cell (RGC) function could also be reversed by OSK treatment, electrical waves from RGCs were measured using pattern electroretinograms (pattern ERGs or pERGs). In pERG assays, a checkerboard light and dark pattern stimulus is projected via electrodes placed on the cornea of mice of various ages (3 month old, 12 month old, or 18 month old mice). A contrast reversing pattern is displayed with no overall change in luminance. Electrical waves generated from the RGCs are then measured.

Mice were retinally injected with AAV virus encoding tTA and AAV virus encoding TRE-OSK in the absence of doxycycline (OSK induction condition). In this Tet-Off system, OSK is expressed from a single promoter in the absence of doxycycline. As controls, age-matched mice were administered virus encoding virus encoding rtTA and virus TRE-OSK in the absence of doxycycline (uninduced control, ctl). In the control Tet-On system, OSK expression requires doxycycline treatment. Adult mice (3 month old (3 m)) were also used as a control. A pERG study was conducted to measure the amplitude of the electrical waves in the RGCs following the pattern stimulus one month after virus injection.

Figure 29:
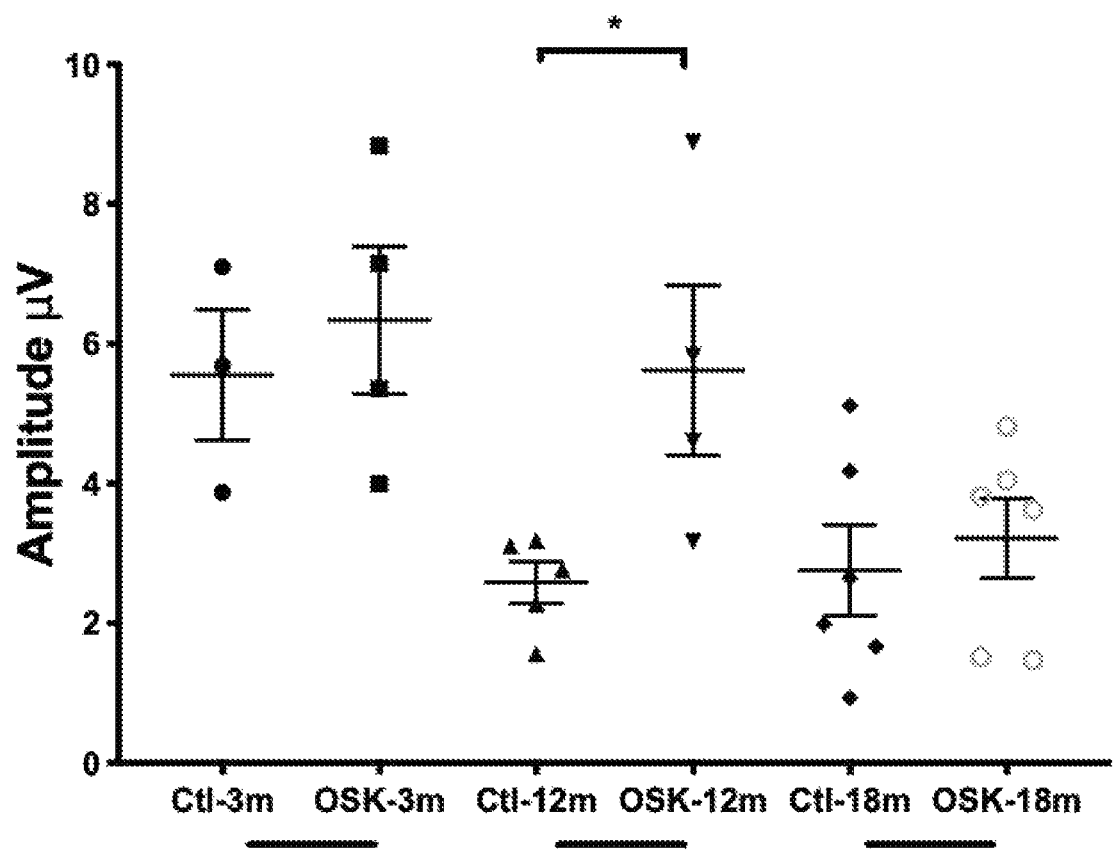
FIG. 29 includes data showing that expression of OSK reversed age-related decline in retina ganglion cell (RGC) function in aged mice.

As shown in FIG. 29, electrical waves generated from RGCs declined in aged mice (3 month old mice compared to 12 month old and 18 month old mice) in the absence of OSK expression (ctl condition). In contrast, administration of AAV virus encoding tTA and AAV virus encoding TRE-OSK in the absence of doxycycline (OSK induction condition) restored RGC electrical waves in 12 month old mice. For 18 month old mice, however, RGC function was likely not restored because corneal opacity blocked the pattern stimulus. These results suggest that expression of OSK improved RGC function in aged (12 month old) mice.

Therefore, this example demonstrates that induction of OSK expression can improve vision acuity and RGC function that is caused by aging.

Figure 30A:
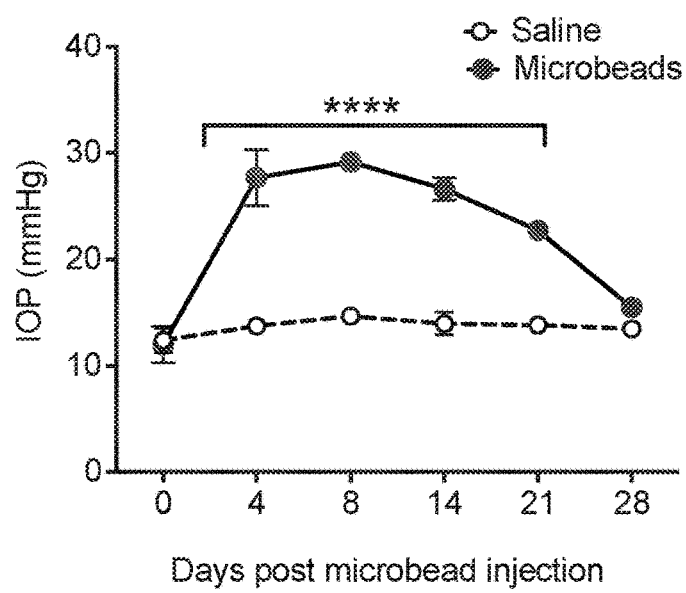
FIGS. 30A-30E include data showing that expression of OSK improved glaucoma-induced declines in visual acuity and RGC function in one month-old mice.
Figure 30B:
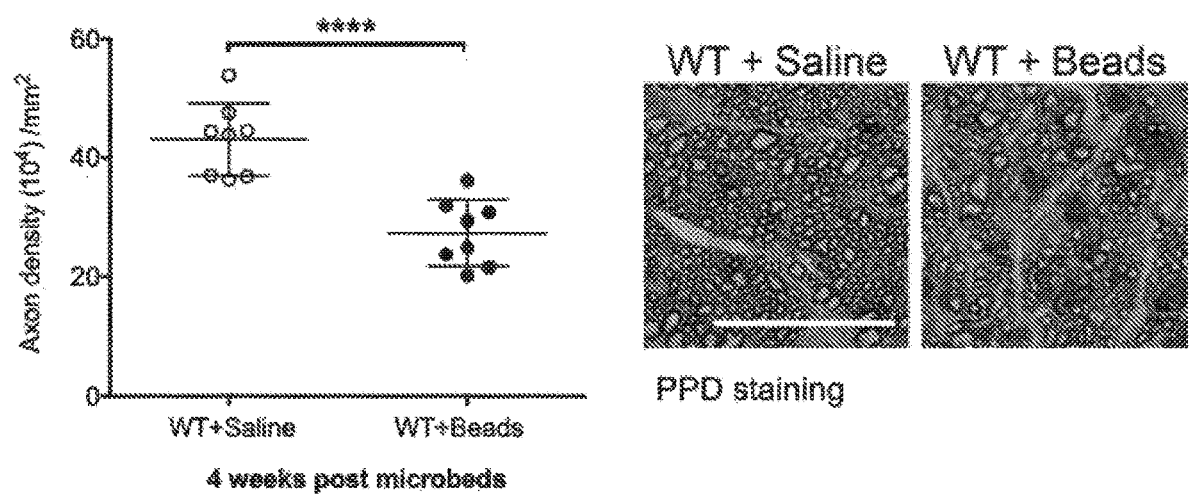
Figure 30C:
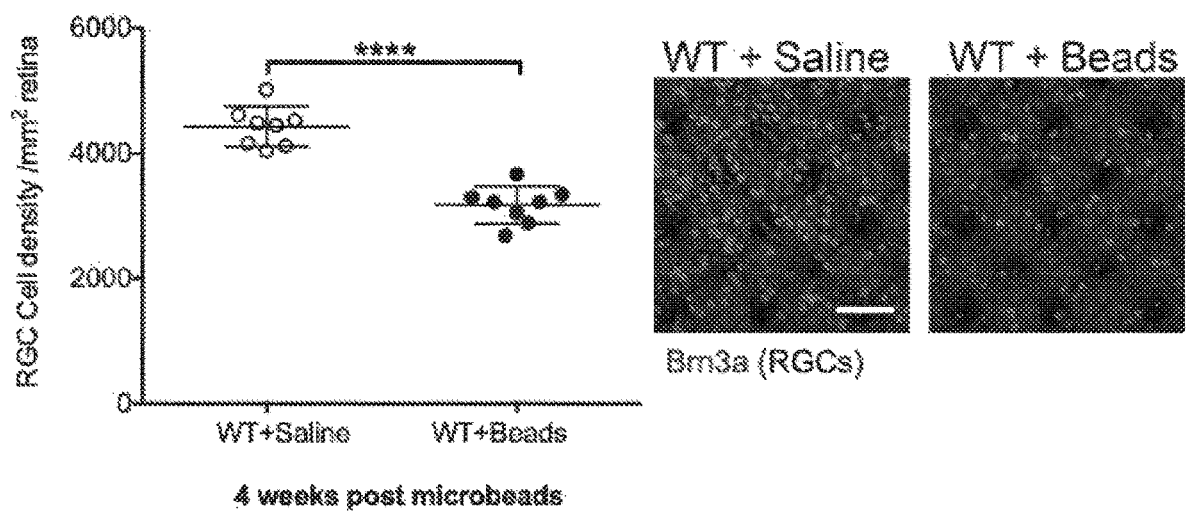

Example 14. Expression of OSK Reversed Glaucoma-Induced Decline in Visual Acuity and Reversed Glaucoma-Induced Decline in Retina Ganglion Cell (RGC) Function To determine whether OSK expression could be used to reverse glaucoma-induced declines in visual acuity and RGC function, a mouse model of glaucoma was used. Chronic elevation of intraocular pressure (IOP) was induced unilaterally in adult C57BL/6J mice by injecting polystyrene microbeads to the anterior chamber. IOP was measured in the first four weeks. As shown in FIG. 30A, microbead injection increased IOP 4-21 days after microbead injection. Axon density was quantified using p-phenylenediamine (PPD) staining (FIG. 30B). FIG. 30C includes a chart quantifying RGC cell density (left panel) using Brn3a staining (shown, for example, on the right). FIGS. 30B-30C show that 4 weeks after microbeads injection into the anterior chamber of the eye, there was significant loss of axon density and RGC density in wild-type (WT) mice that were not treated with AAV virus encoding TRE-OSK.

In these experiments, glaucoma was induced with microbead injection and then three weeks later, OMR and pERG assays were conducted (pre AAV injection measurements in FIGS. 30D-30E). Then, mice were divided into two treatment groups. One group of mice were retinally injected with AAV virus encoding rtTA and AAV virus encoding TRE-OSK in the absence of tetracycline (OSK AAV OFF) or with AAV virus encoding tTA and AAV virus encoding TRE-OSK (OSK AAV ON). Four weeks post AAV virus injection, OMR and pERG assays were conducted again (4 w post AAV) measurements in FIGS. 30D-30E). As a control, experiments were also conducted with injection of saline instead of microbeads (no glaucoma control).

Figure 30D:
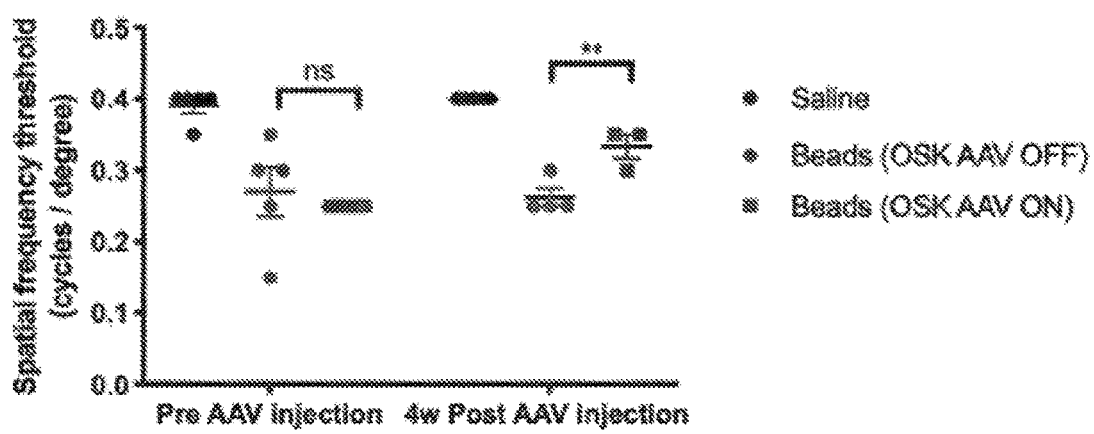

As shown in FIG. 30D, induction of OSK expression (OSK AAV ON) increased the spatial frequency threshold compared to no induction of OSK expression (OSK AAV OFF) for mice with glaucoma (mice injected with microbeads). These results suggest that induction of OSK expression can improve glaucoma-related vision loss.

Figure 30E:
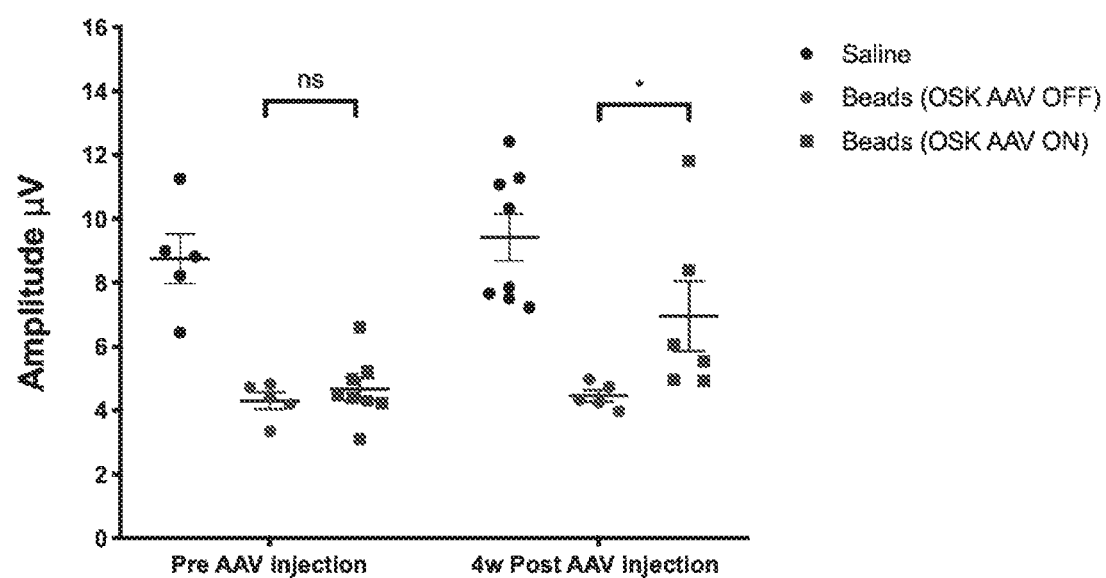

As shown in FIG. 30E, induction of OSK expression restored the electrical wave amplitude in mice with microbead-induced glaucoma. These results suggest that induction of OSK expression can also reverse glaucoma-related decline in RGC function.

Therefore, induction of OSK expression can improve the symptoms induced by glaucoma.

Example 15. Expression of Human OSK Promoted Survival of Human Neurons and Axon Regrowth Following Vincristine-Induced Neuronal Damage To determine whether expression of human OCT4, human KLF4, and human SOX2 (human OSK) could protect human neuronal cells and regenerate axons in vitro, a neurite regeneration assay was used as described below. SH-SY5Y cells, which are human neuroblastoma cells, were differentiated into neurons and were transduced with a AAV.DJ vector encoding human OCT4, human KLF4, and human SOX2 under a Tet-inducible promoter (using a Tet-Off system). In the OSK Off condition, OSK expression was not induced in cells. In the OSK On condition, OSK expression was induced in cells. Five days after transduction, vincristine (VCS) was used to induce neurite degeneration. Cells were treated with VCS for 24 hours or 48 hours. A schematic of a treatment timeline (with 24 hour VCS treatment) is provided in the left portion of FIG. 31A. VCS is a chemotherapy drug that disrupts microtubules. It is often used in vitro to determine whether treatments maintain and/or promote cellular function (e.g., neuronal function) after damage. As described herein, VCS was used determine the effect of OSK treatment on neuronal survival and axon regrowth. After VCS treatment, cells were grown in differentiation medium and neurite outgrowth was assayed.

Figure 31A:
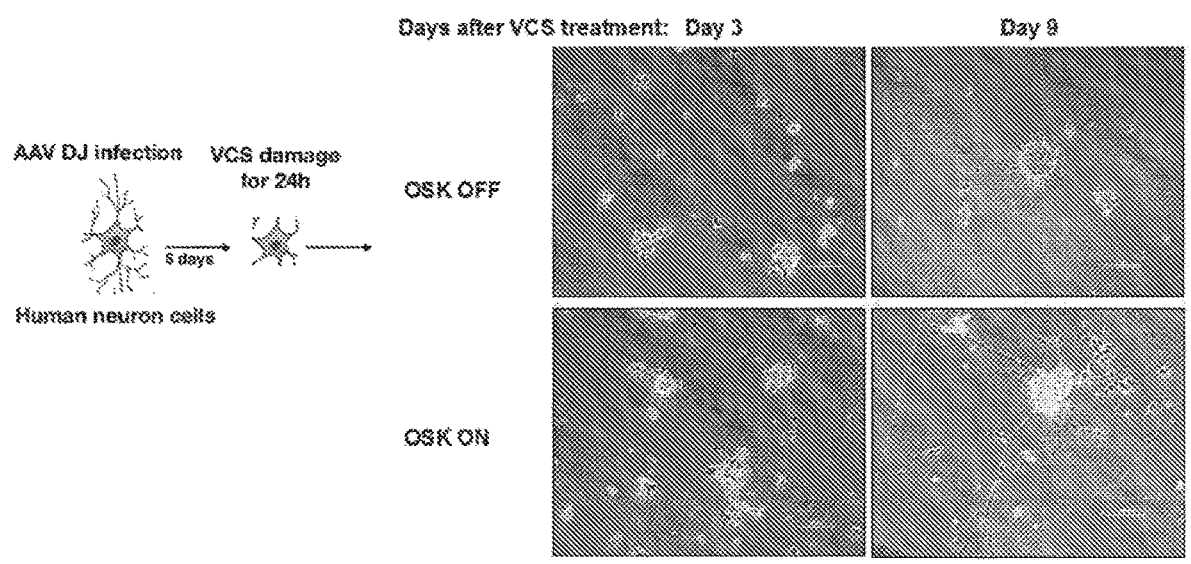
FIGS. 31A-31C include data showing that expression of OSK promoted neuronal survival and axon regeneration of human SH-SY5Y neuronal cells following vincristine (VCS)-induced damage.
Figure 31B:
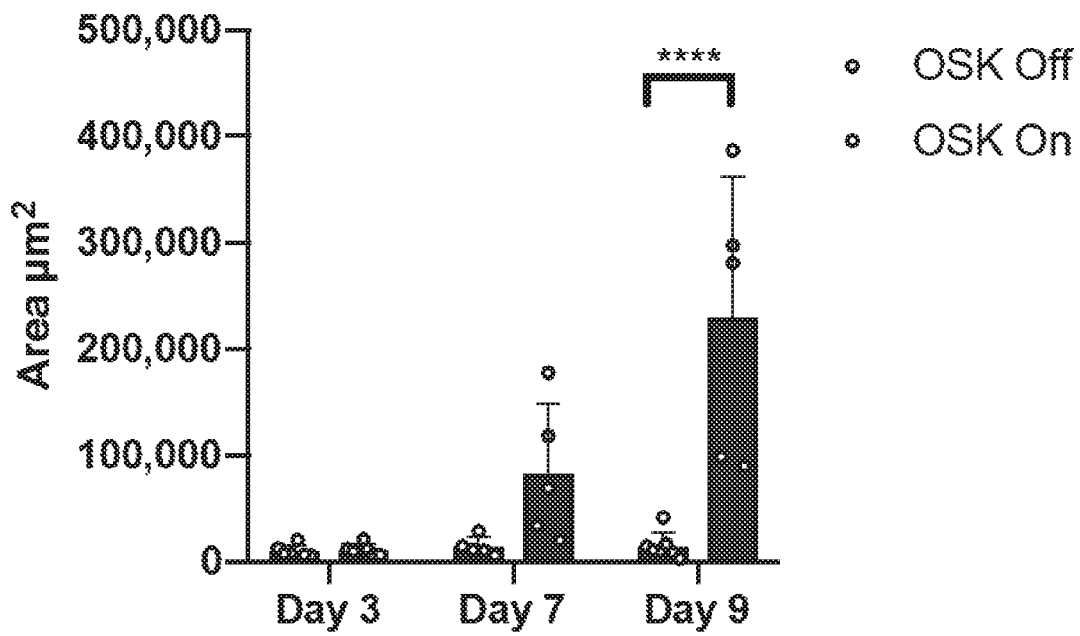
Figure 31C:
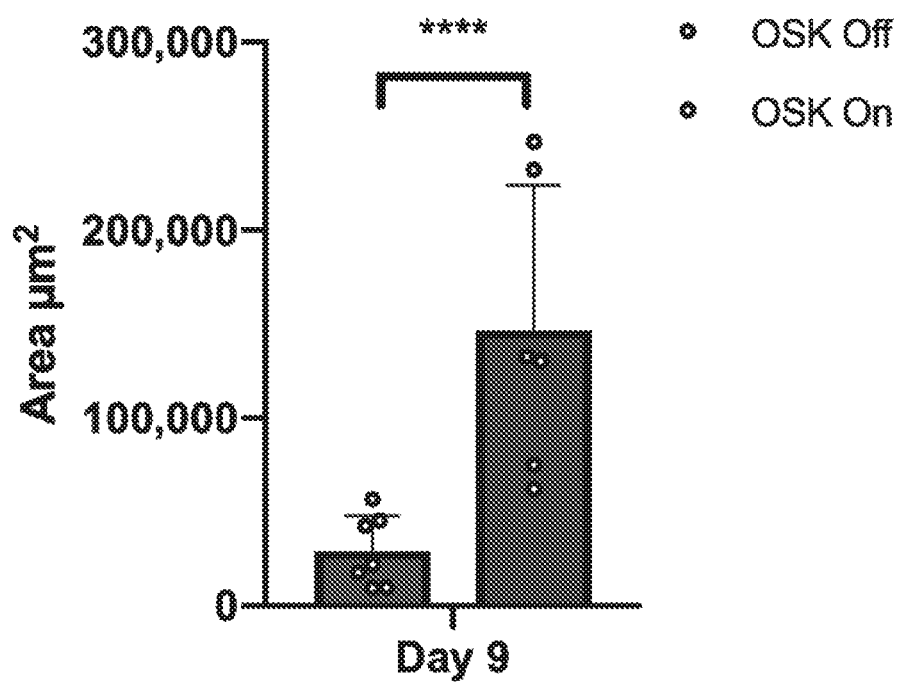

In FIG. 31A, cells were assayed for neuronal outgrowth nine days after cells were treated with VCS for 24 hours. Cells in which OSK expression was induced (OSK On condition) showed increased neuronal survival and axon outgrowth relative to cells in which OSK expression was not induced (OSK Off condition) (FIG. 31A). Quantification of neuronal cell area similarly showed that OSK expression increased the cell area of neurons by at least 8 times compared to no OSK expression (FIG. 31B). Similar results were also observed with 48 hours of VCS treatment (FIG. 31C).

These results show that expression of human OSK protected human neuron cells against VCS-induced neuron degeneration.

Methods

Cell Culture and Differentiation Protocol

SH-SY5Y neuroblastoma cells were obtained from the American Tissue Culture Collection (ATCC, CRL-2266) and maintained according to ATCC recommendations. The cells were cultured in a 1:1 mixture of Eagle's Minimum Essential Medium (EMEM, ATCC, 30-2003) and F12 medium (ThermoFisher Scientific, 11765054), supplemented with 10% fetal bovine serum (FBS, Sigma, F0926) and 1× penicillin/streptomycin (ThermoFisher Scientific, 15140122). Cells were cultured at 37° C. with 5% $CO_2$ and 3% $O_2$. Cells were passaged at ~80% confluency.

SH-SY5Y cells were differentiated into neurons as previously described (Encinas et al., J Neurochem. 2000 September; 75(3):991-1003; Shipley et al., J Vis Exp. 2016 Feb. 17; (108):53193), with some modifications. Briefly, 1 day after plating, cells started to be differentiated in EMEM/F12 medium (1:1) containing 2.5% FBS, lx penicillin/streptomycin, and 10 µM all-trans retinoic acid (ATRA, Stemcell Technologies, 72264) (Differentiation Medium 1) for 3 days, followed by treating the cells in EMEM/F12 (1:1) containing 1% FBS, 1× penicillin/streptomycin, and 10 µM ATRA (Differentiation Medium 2) for 3 days. Cells were then split into 35 mm cell culture plates coated with poly-D-lysine (ThermoFisher Scientific, A3890401). One day after splitting, neurons were matured in serum-free neurobasal/B27 plus culture medium (ThermoFisher Scientific, A3653401) containing 1×Glutamax (ThermoFisher Scientific, 35050061), 1×penicillin/streptomycin, and 50 ng/ml BDNF (Alomone labs) (Differentiation Medium 3) for at least 5 days.

Neurite Regeneration Assay

The differentiated neurons from SH-SY5Y cells were transduced with AAV.DJ vectors at 10 genome copy per cell. Five days after transduction, 100 nM vincristine (Sigma, V8879) was added to the cells for 24 hours or 48 hours to induce neurite degeneration. After vincristine treatment, neurons were washed in PBS twice and fresh differentiation medium was added back to the plates. Neurons were followed for neurite outgrowth for up to 2 weeks.

Figure 36A:
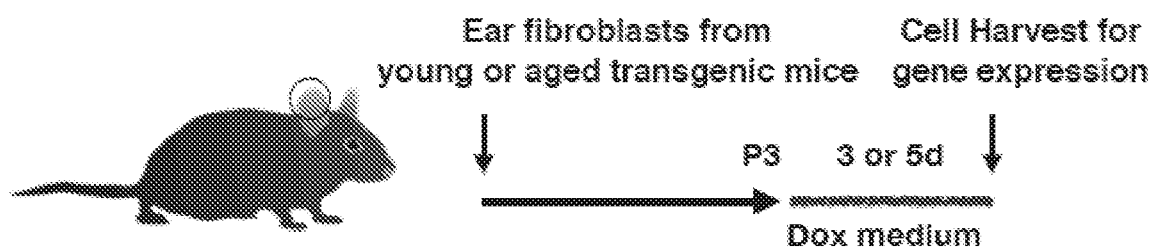
Figure 36B:
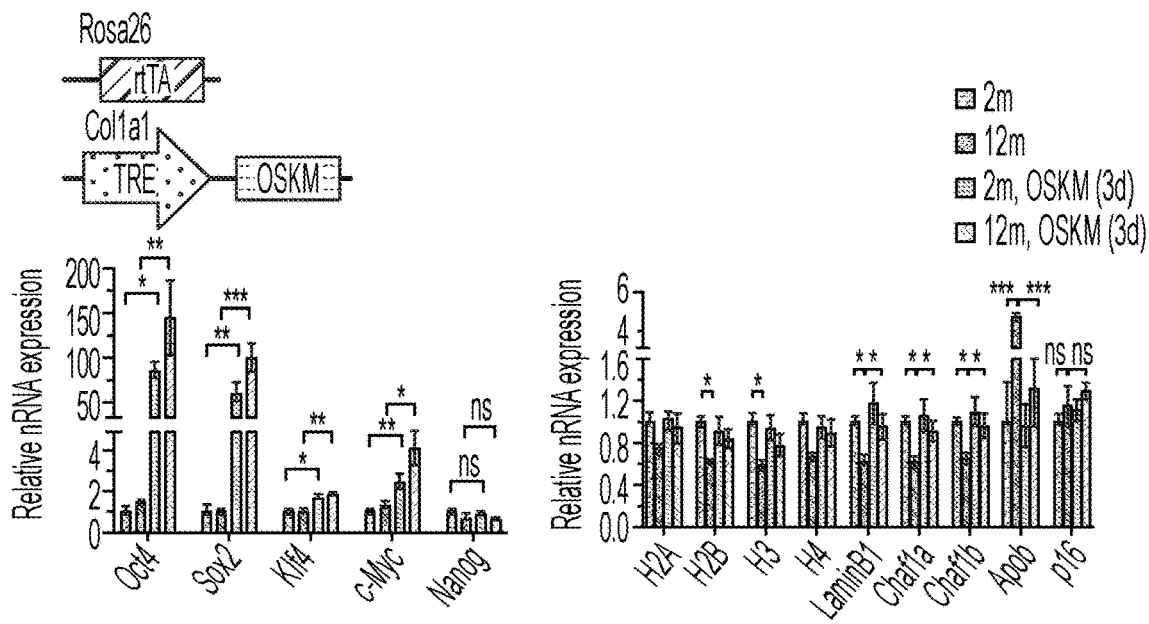
Figure 36C:
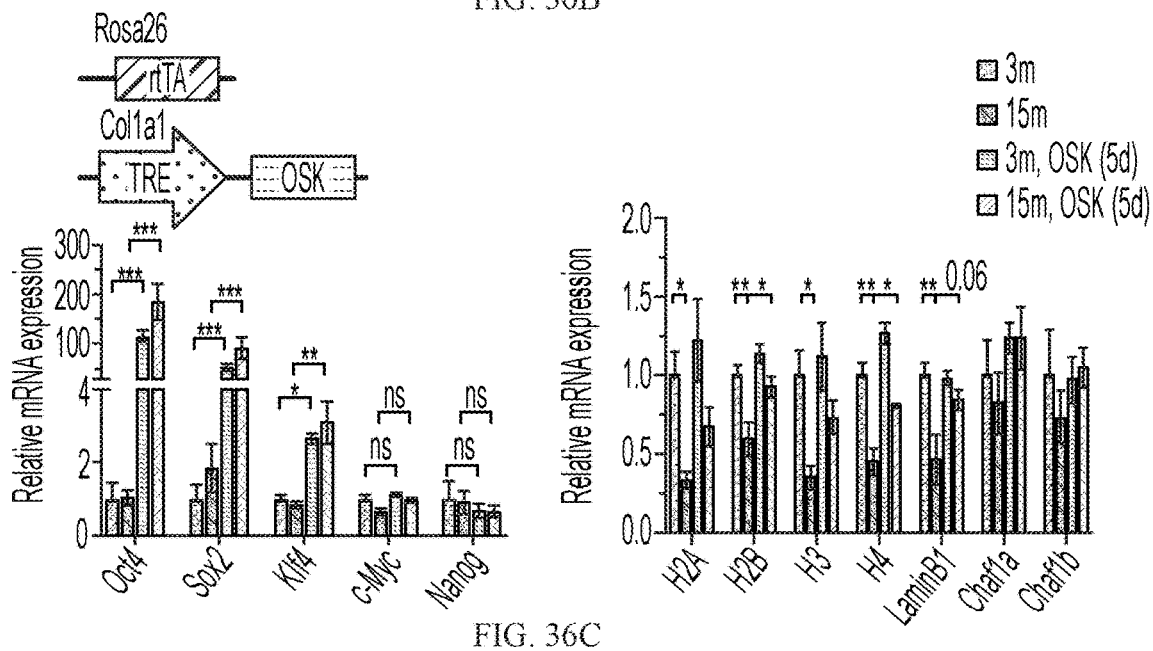

Example 16. Recovery from Injury and Restoration of Vision by Tet-Dependent Resetting of the Epigenetic Clock To determine whether mammalian cells might retain a faithful copy of epigenetic information from earlier in life, it was tested whether the three gene combination of OSK was sufficient to reset age. The three-gene OSK combination into fibroblasts from old mice and measured its effect on RNA levels of genes known to be altered with age, such as H2A, H2B, LaminB1, and Chaf1b. OSK treatment of fibroblasts from old mice restored youthful gene expression patterns, similar to what OSKM does, with no apparent loss of cellular identity or the induction of Nanog, an early embryonic transcription factor that can induce teratomas (FIG. 36A-36C).

Figure 32A:
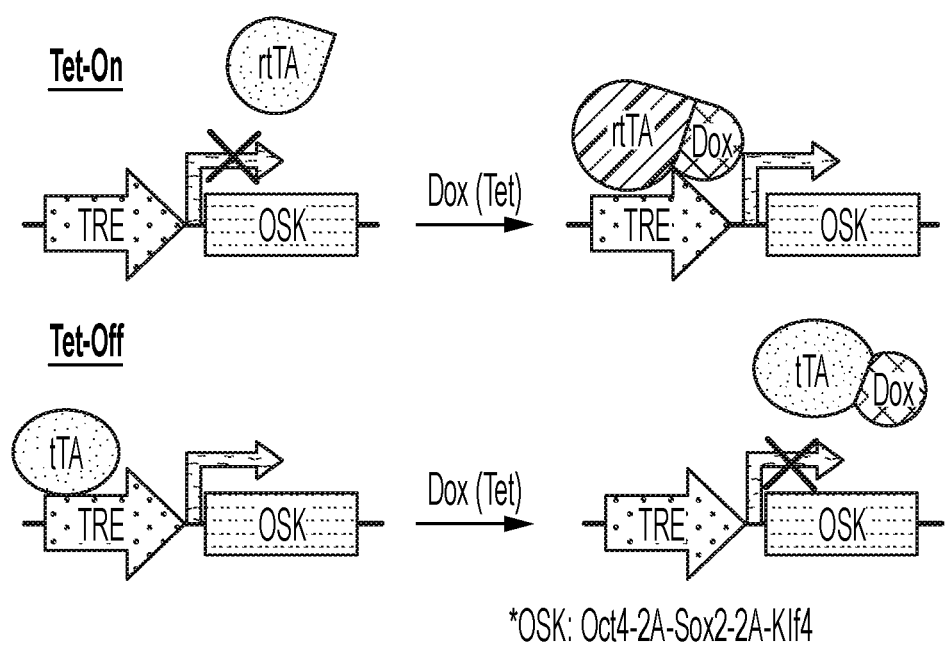
FIGS. 32A-32G show that partial reprogramming with AAV-delivered polycistronic OSK is non-toxic and induces CNS axon regeneration.
Figure 32B:
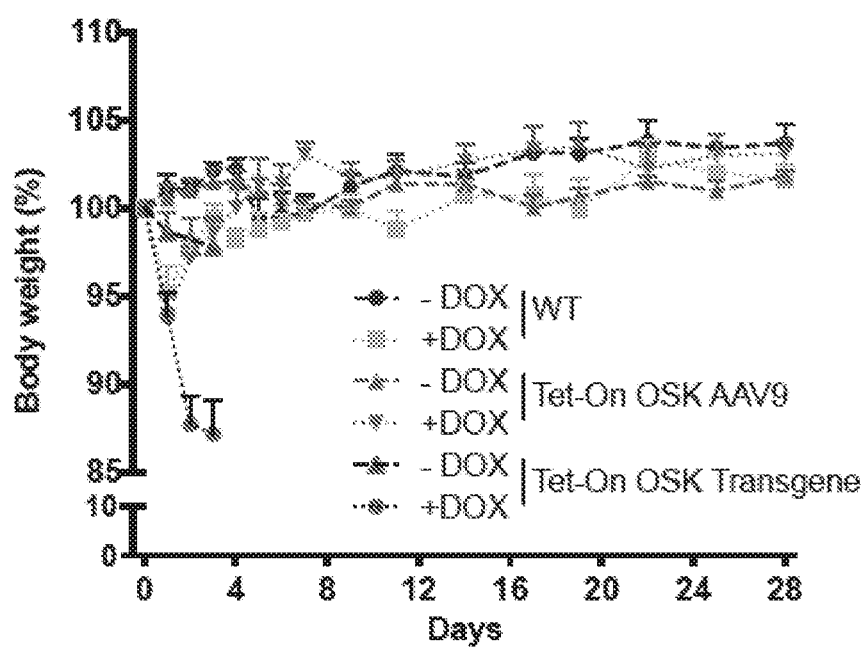
Figure 36D:
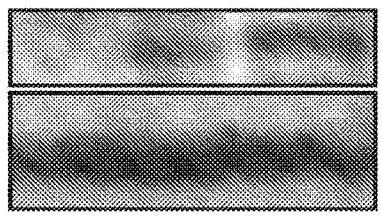
Figure 36E:
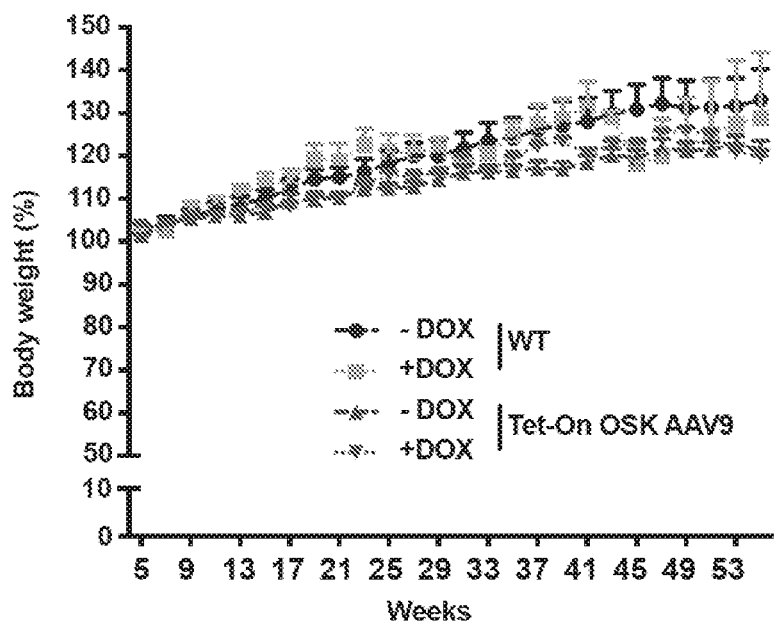
Figure 36F:
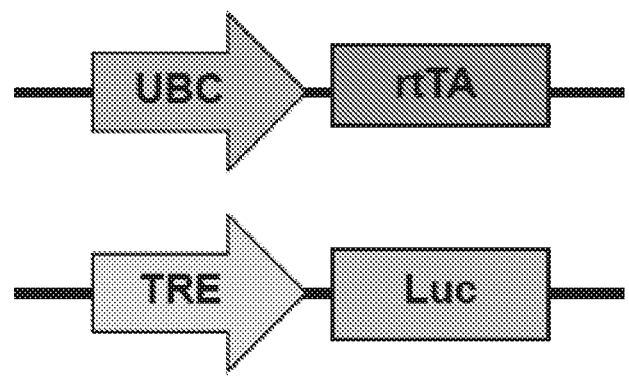
Figure 36G:
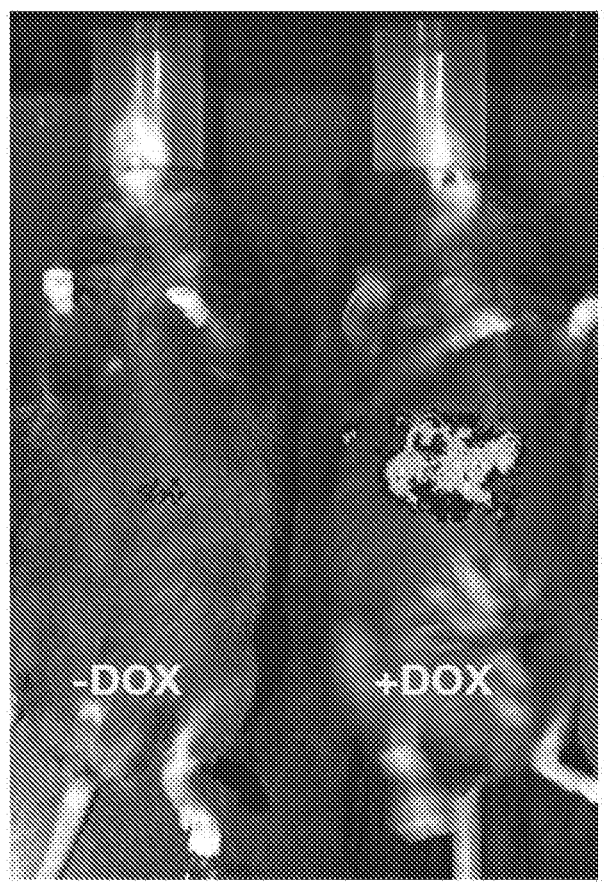

To deliver and control OSK expression in vivo, a tightly regulated Tet-ON and Tet-OFF adeno-associated viral (AAV) vector system was developed to accommodate all three reprogramming genes in one viral particle (Smalley et al., First AAV gene therapy poised for landmark approval. Nat Biotechnol, 2017. 35(11): p. 998-999; Senis et al., AAV vector-mediated in vivo reprogramming into pluripotency. Nat Commun, 2018. 9(1): p. 2651) (FIG. 32A). First, to test if induction of OSK AAVs caused toxicity in vivo, 5-month-old C57BL/6J mice were infected with rtTA and TRE-OSK AAV9s and induced expression to levels comparable to those of transgenic mice (FIG. 36D). Surprisingly, continuous induction of OSK for over a year had no discernable negative effect on the mice for over a year (FIG. 32B and FIG. 36E). Without being bound by a particular theory, there was ostensibly no discernable negative effect on the mice because high-level expression in the intestine was avoided (FIGS. 36F-36H), thus avoiding the dysplasia and weight loss seen in other studies, including Abad et al., Nature 502, 340-345, doi:10.1038/nature12586 (2013).

Figure 32C:
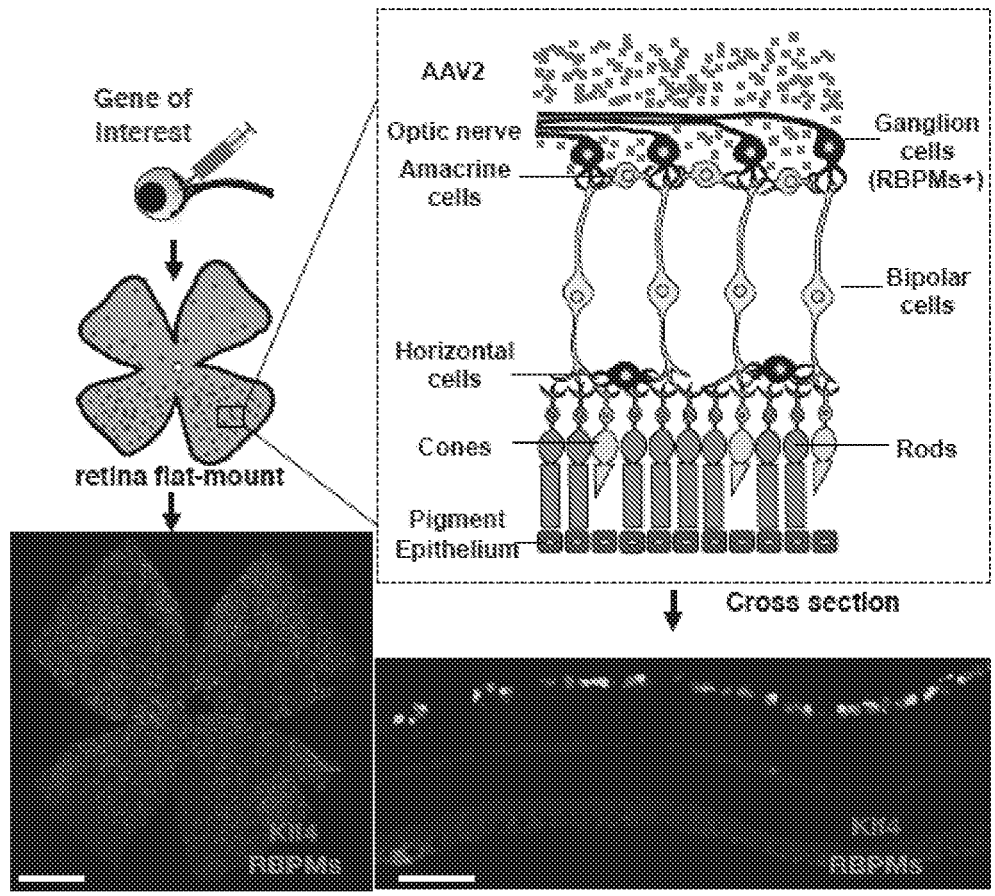
Figure 32D:
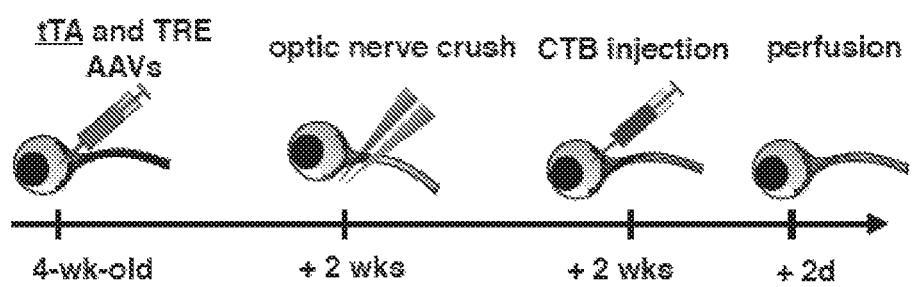
Figure 37A:
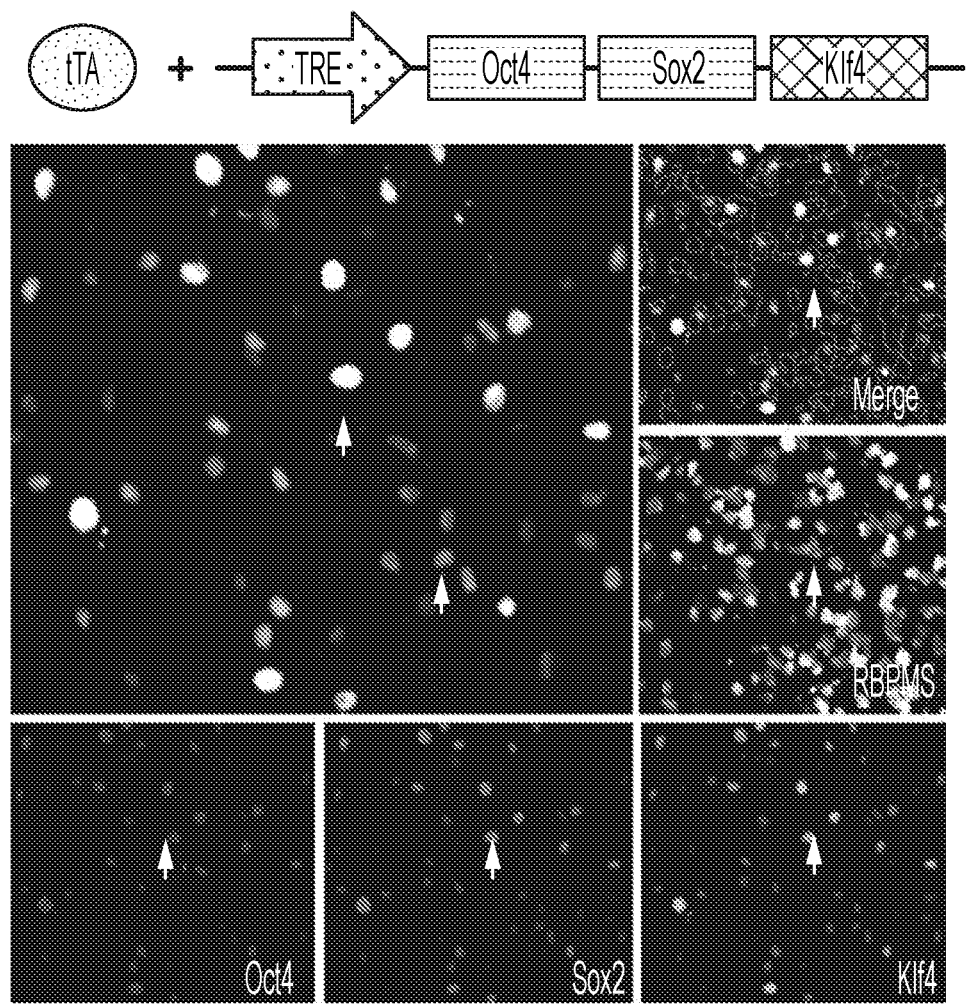
Figure 37C:
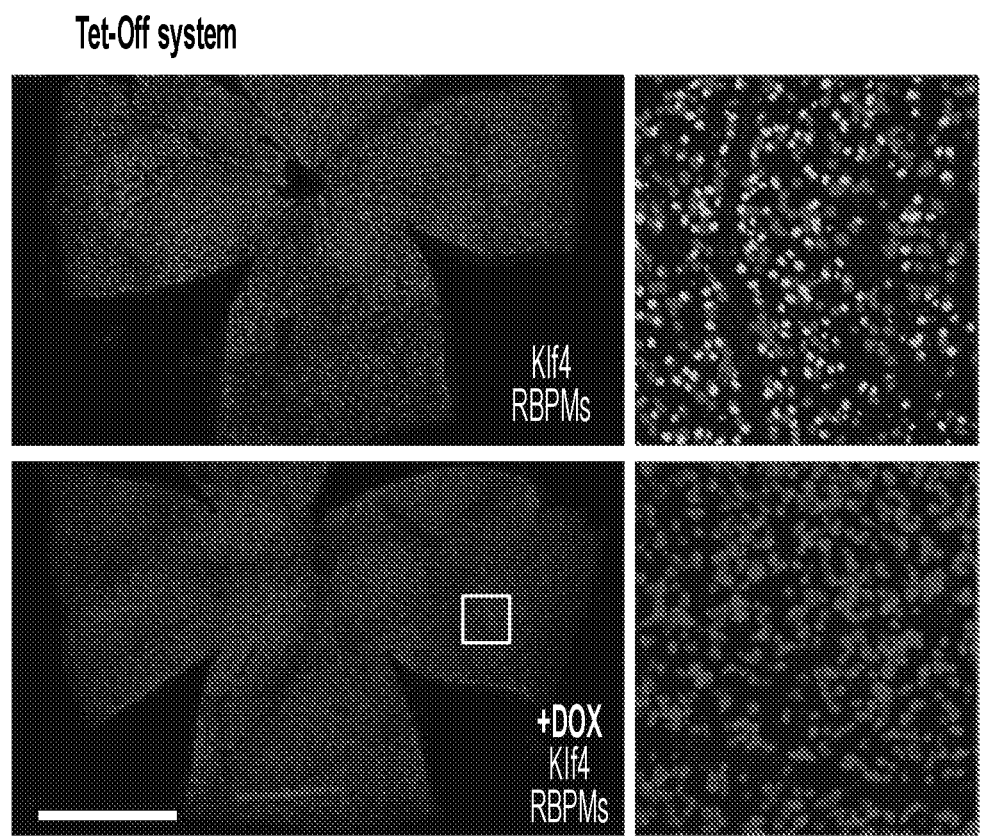

Almost all species experience a decline in regenerative potential during ageing. In mammals, one of the first systems to lose this potential is the central nervous system (CNS). A canonical CNS cell type, the retinal ganglion cell, projects an axon away from the retina towards the brain, forming the optic nerve. During embryogenesis and in neonates, RGCs can regenerate if damaged, but this capacity is soon lost (Goldberg et al., Science, 2002. 296(5574): p. 1860-4). Over time, as organisms age, the overall function and resilience of the CNS continues to decline (Geoffroy et al., Cell Rep, 2016. 15(2): p. 238-46). To explore whether it is possible to restore an early epigenetic profile in adult RGCs, OSK expression was induced in a nerve crush injury model in adult mice of various ages. The Tet-Off system (Tet-Off tTA-AAV2) carrying OSK, either in separate AAVs or in the same AAV, was injected into the vitreous body, resulting in efficient, selective, and doxycycline-responsive gene expression in RGCs. As a negative control, a group of mice were also treated with doxycycline to repress the AAVs (FIG. 32C and FIG. 37C). Two weeks post-injection, optic nerve crush was performed, and, two weeks after that, axon length and optic nerve density were calculated (FIG. 32D).

Figure 32E:
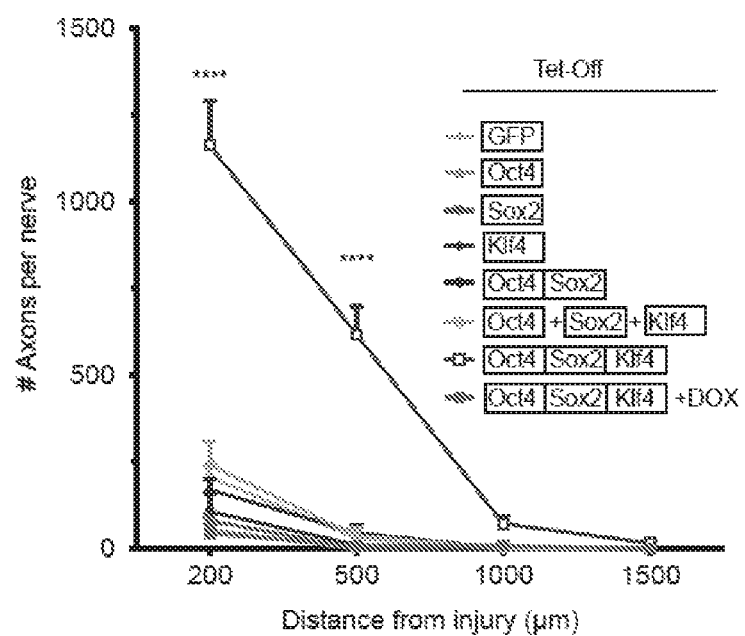
Figure 32F:
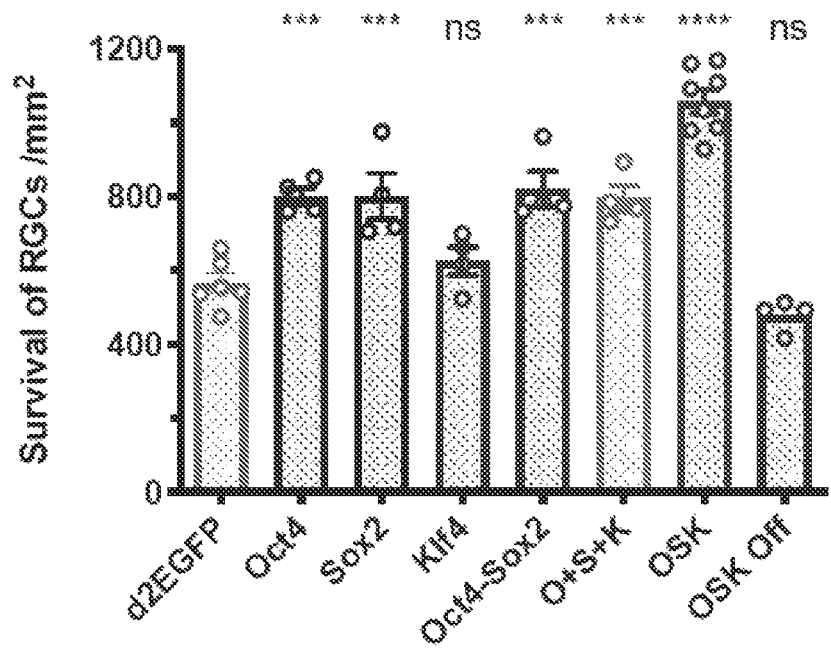
Figure 32G:
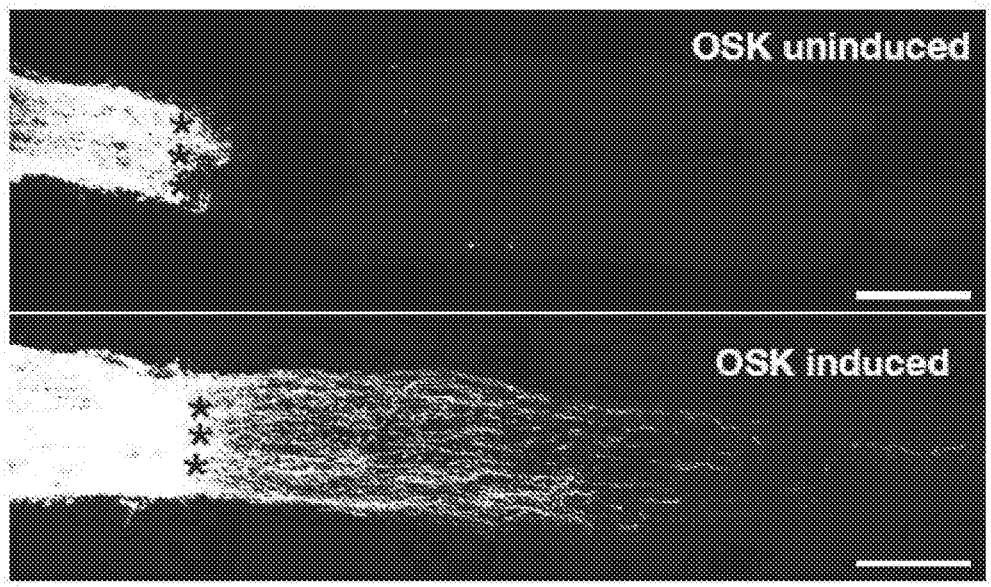
Figure 37D:
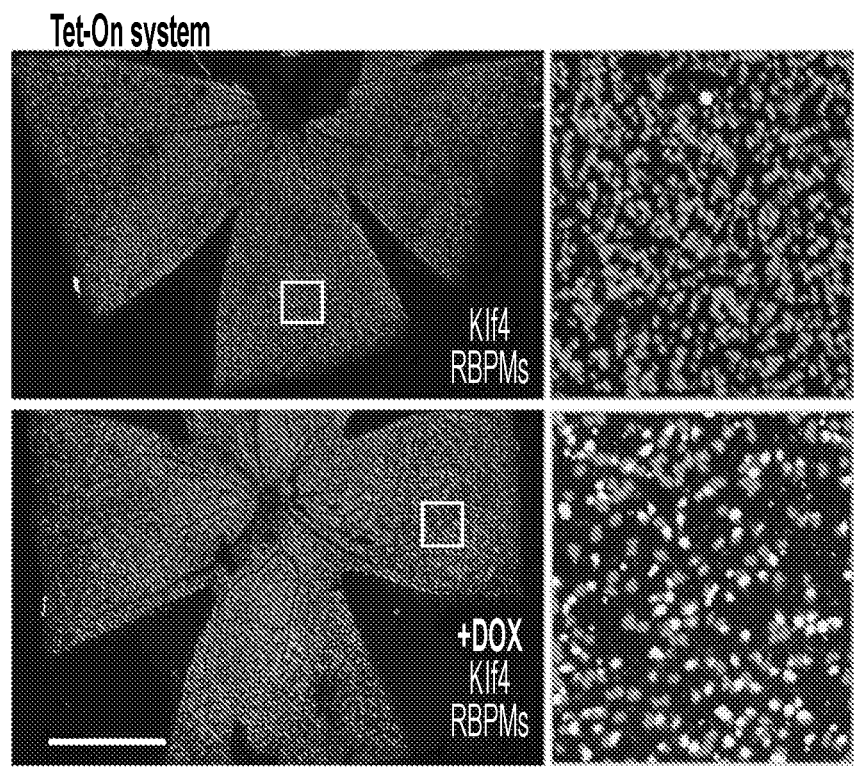
Figure 38A:
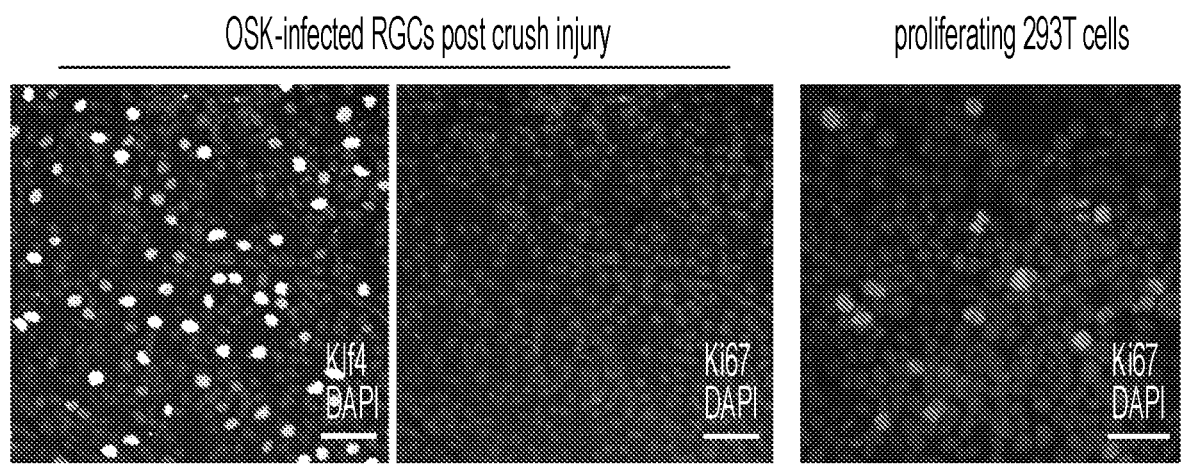
FIGS. 38A-38C show that OSK induces long-term axon regeneration post injury without RGC proliferation.
Figure 38B:
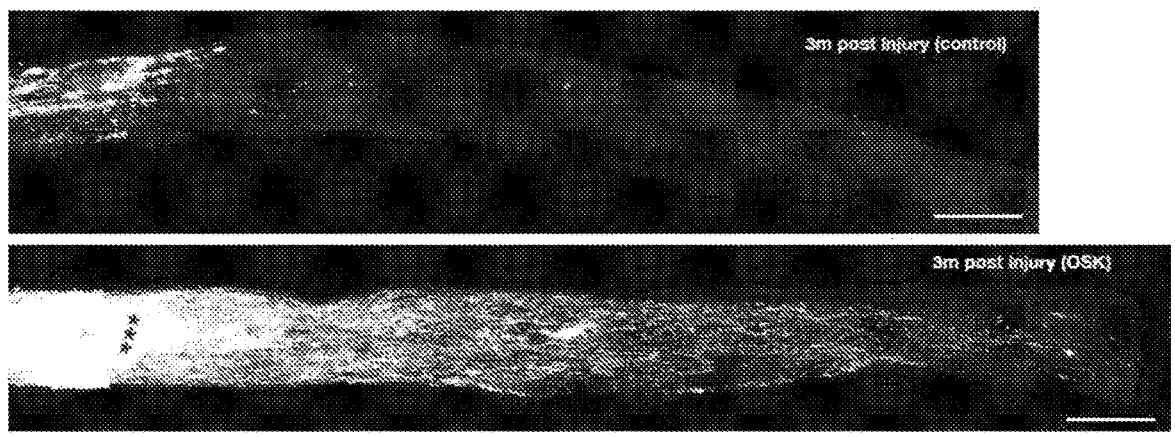
Figure 38C:
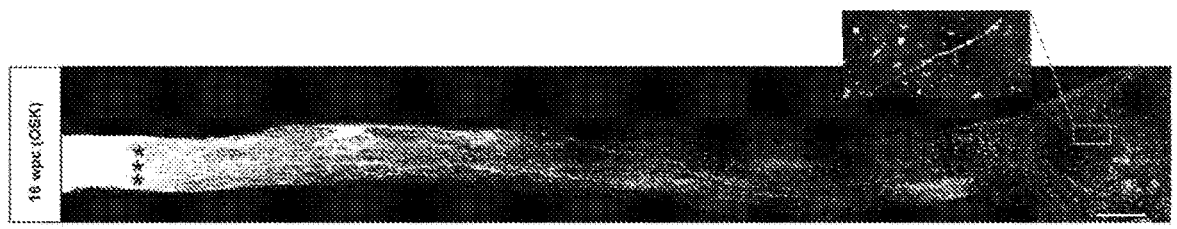

Induction of the polycistronic OSK-AAV2 caused a significant increase in RGC survival and long-distance axonal regeneration (FIG. 32E and FIG. 37D) without any sign of RGC proliferation (FIG. 38A). In contrast, when introduced on separate AAVs, OCT4, SOX2, KLF4 had no effect on regenerative capacity (FIG. 32E), ostensibly due to the lower frequency of co-infection (FIG. 37A and FIG. 37B). Because Klf4 can repress axonal growth (Moore et al., Science, 2009. 326(5950): p. 298-301; Qin et al., Nat Commun, 2013. 4: p. 2633), OCT4, SOX2, and KLF4 were also individually and a dual-cistron of Oct4 and Sox2 was tested. No regenerative effect, however, was observed in the absence of Klf4. Remarkably, if poly-cistronic OSK was induced for 3-months, RGC axon fibers extended all the way to the chiasm, a distance of over 3 mm (FIG. 38B). Indeed, when polycistronic OSK was induced for 12-16 weeks, regenerating RGC axon fibers further extended into the chiasm (5 mm away from crush site), where optic nerve connects to brain (FIGS. 38B-38C).

Figure 39A:
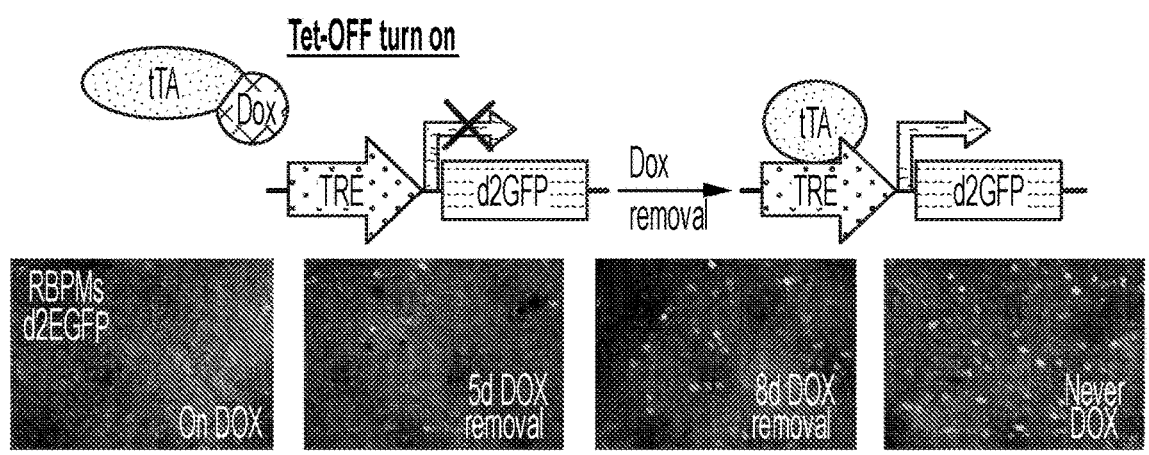
FIGS. 39A-39D show Tet-On system has better turn on rate and OSK transduced RGCs have higher survival rate.
Figure 39B:
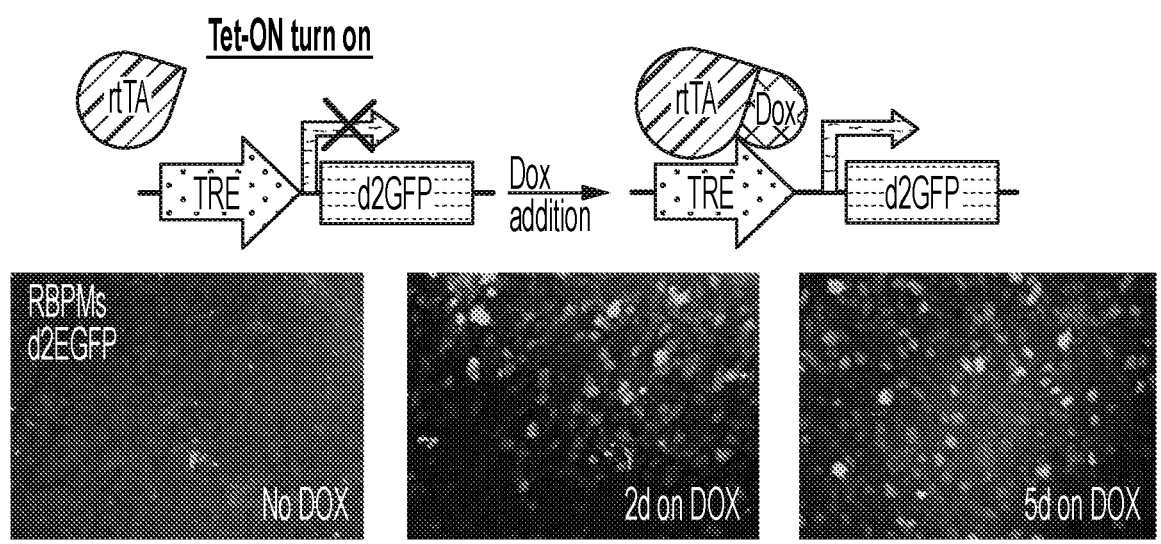
Figure 39C:
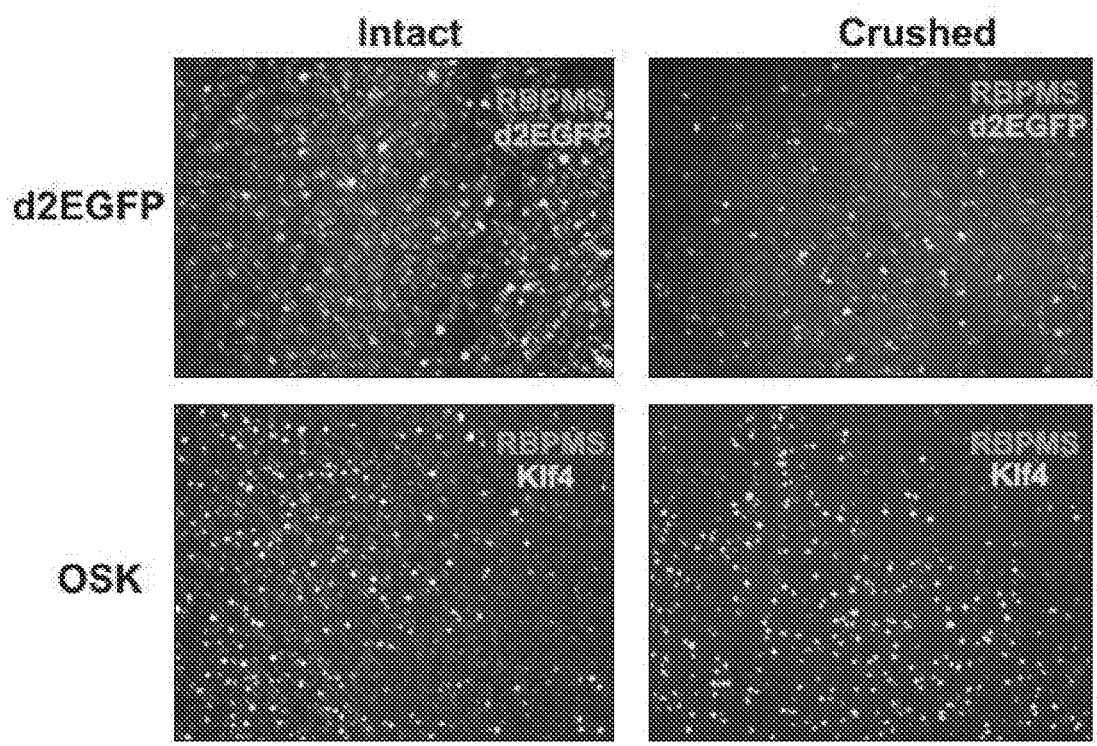
Figure 39D:
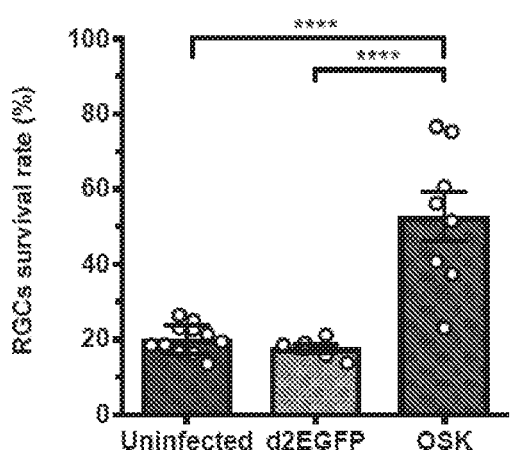
Figure 40A:
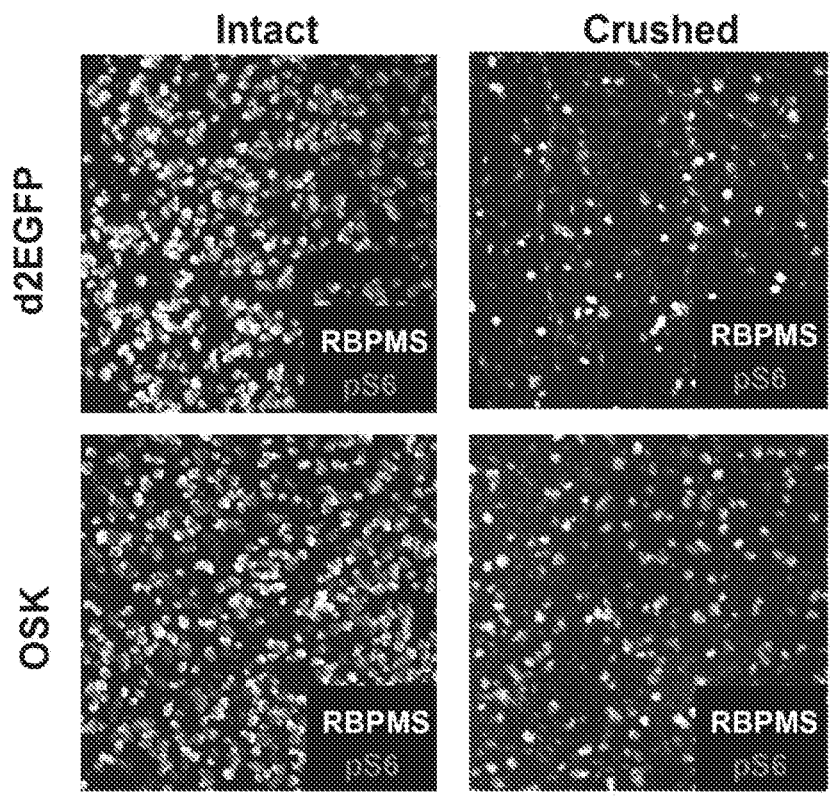
FIGS. 40A-40F show identification of epigenetic mechanism underlying OSK effect.
Figure 40B:
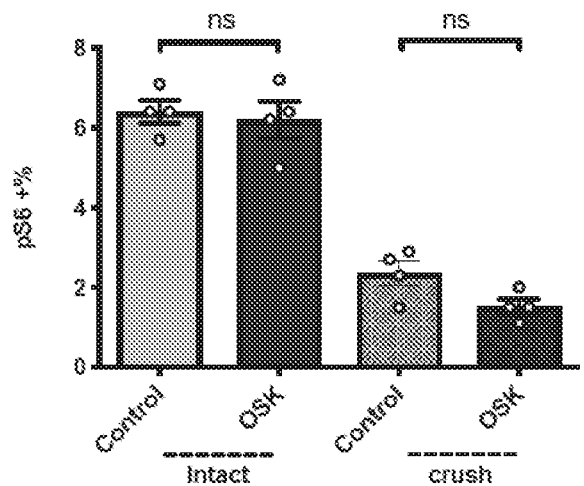
Figure 40C:
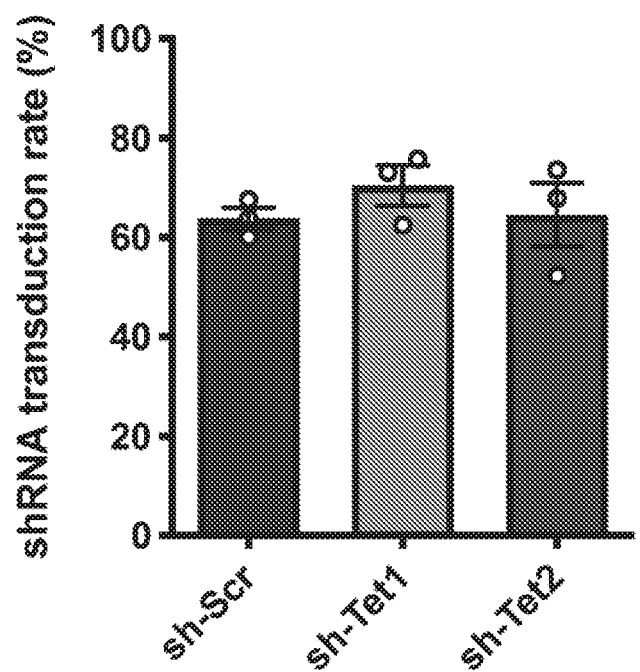
Figure 40D:
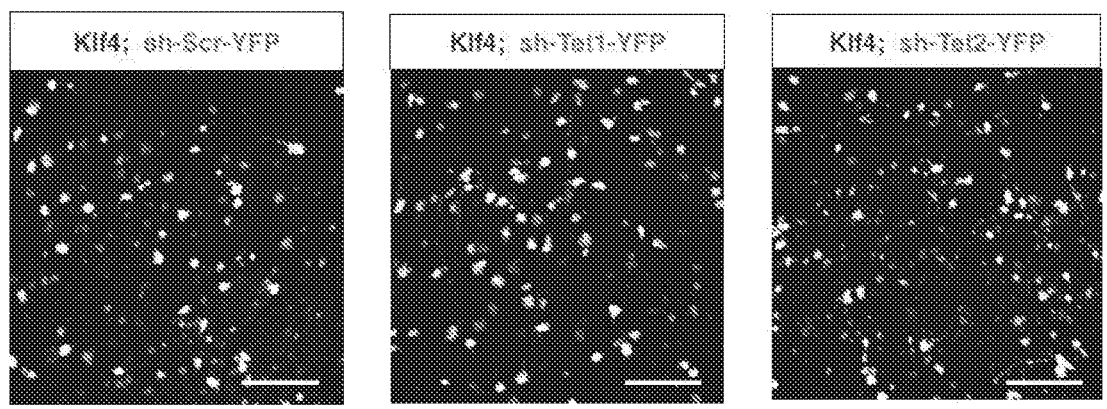
Figure 40E:
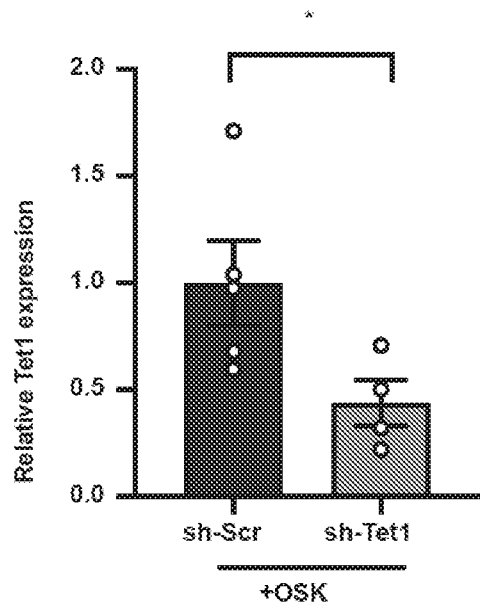
Figure 40F:
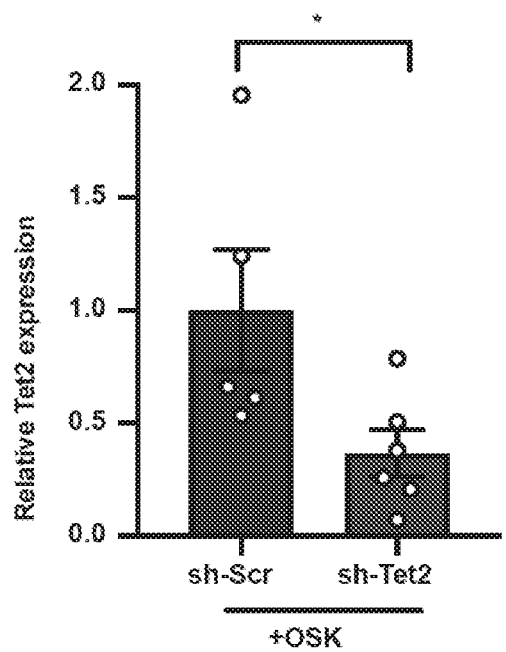

Next, the requisite timing of OSK expression was tested to promote neuronal survival and regeneration. For these experiments, the Tet-On AAV system was utilized due to its rapid on-rate (FIG. 37D and FIGS. 39A-39B). Significant improvement in axon regeneration only occurred when OSK expression was induced after injury and the longer OSK was induced, the greater distance the neurons extended, with no increase in the total number of RGCs (FIGS. 33B, 33C, and 33D). By co-staining for OSK and performing neuronal counts, survival rate was estimated to be 2.5-3 times of uninfected or GFP-infected RGCs (52 vs. 17%-20%) (FIGS. 39C and 39D), suggesting OSK effect is cell-intrinsic. The Pten-mTOR-S6K pathway, previously shown to improve neuronal survival in vivo, was not activated in OSK-infected cells post-injury (FIG. 40A and FIG. 40B), indicating a new pathway might be involved.

Figure 45A:
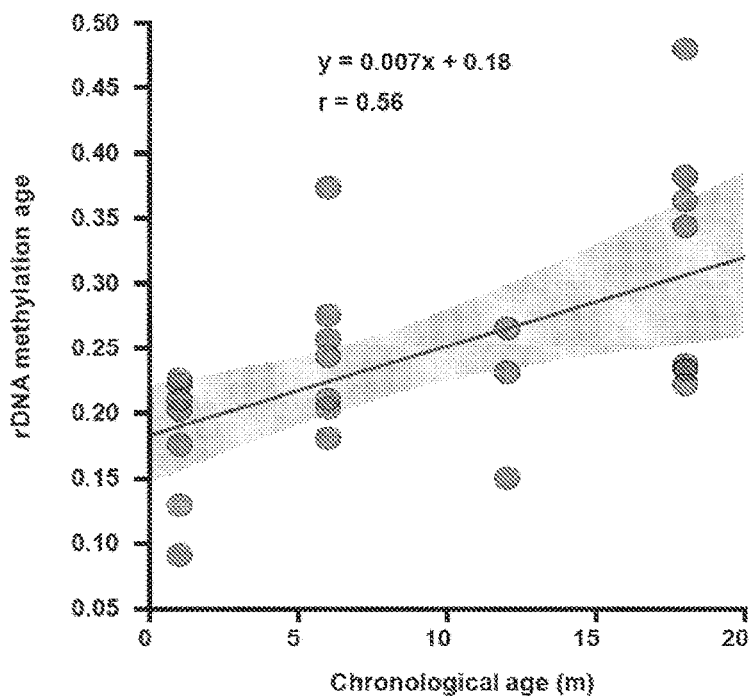
FIGS. 45A-45C show methylation clock analysis of mouse RGCs and human neurons.
Figure 45B:
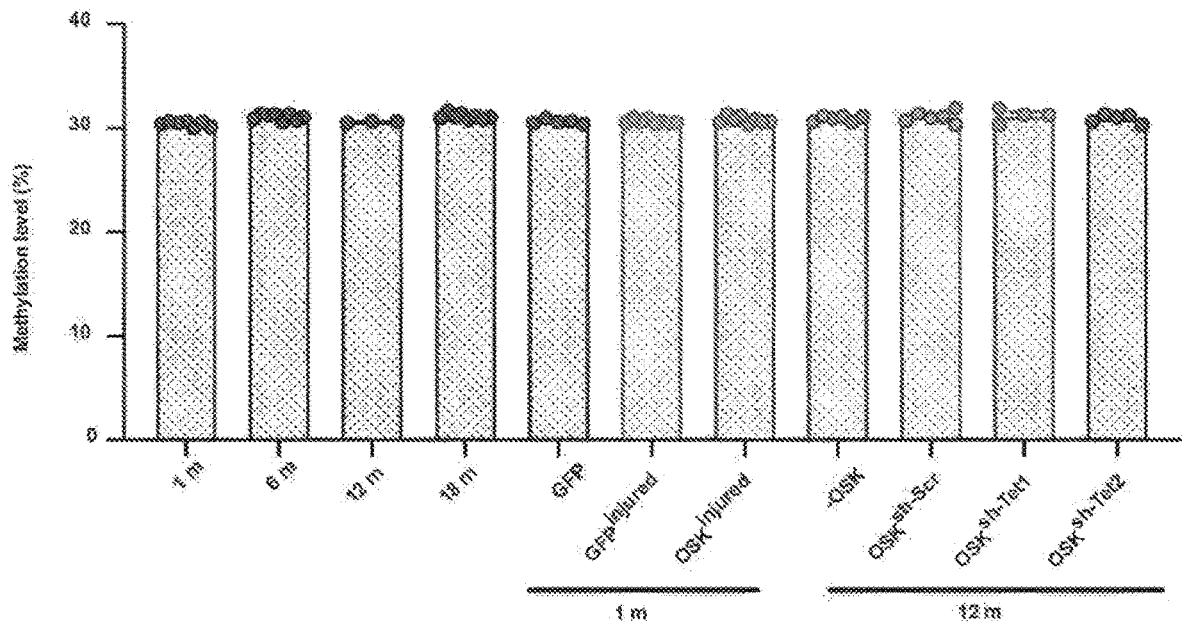

It was determined whether neuronal injury advanced epigenomic age and whether OSK's benefits were due to the preservation of a younger epigenome. Genomic DNA from RGCs was FACS-isolated before injury or 4-days after injury in the presence or absence of OSK induction, and subjected reduced-representation bisulfite sequencing (RRBS-Seq). Without being bound by a particular theory, rDNAme clock (Wang et al., Genome Res 29, 325-333, doi:10.1101/gr.241745.118 (2019)) provided the best site coverage (70/72 CpG sites) relative to other available mouse clocks (Meer et al., Elife 7, doi:10.7554/eLife.40675 (2018); Thompson et al., Aging (Albany NY) 10, 2832-2854, doi: 10.18632/aging.101590 (2018)) and its age estimate remained highly correlated with chronological age of RGCs (FIG. 45A and Methods). In the absence of global methylation changes, injured RGCs experienced an acceleration of the epigenetic clockand OSK expression counteracted this effect (FIG. 33K and FIG. 45B).

It was determined whether that the effect of OSK on neuronal survival and regeneration occurred by restoring a younger epigenome. If so, these effects should be dependent on the reversal of the epigenetic clock, which would require the removal of methyl groups from DNA via the activity of Ten-Eleven-Translocation (TET) dioxygenases. Previously characterized AAVs expressing short-hairpin RNAs against Tet1 and Tet2 (sh-Tet1 and sh-Tet2) (Guo et al., Cell 145, 423-434, doi:10.1016/j.cell.2011.03.022 (2011); Yu et al., Nat Neurosci 18, 836-843, doi:10.1038/nn.4008 (2015); Weng et al., Neuron 94, 337-346.e336, doi:10.1016/j.neuron.2017.03.034 (2017)) were utilized, and the transduction rate and knockdown efficiency in vivo was validated (FIGS. 40C-40F). Knockdown of either Tet1 or Tet2 (sh-Tet1 and sh-Tet2 AAV2, at 1/5 titer of OSK AAV), which transduced around 70% of OSK positive cells (FIGS. 40C and 40D), efficiently blocked OSK from regenerating axons and improved RGC survival (FIGS. 33E and 33F).

Figure 33A:
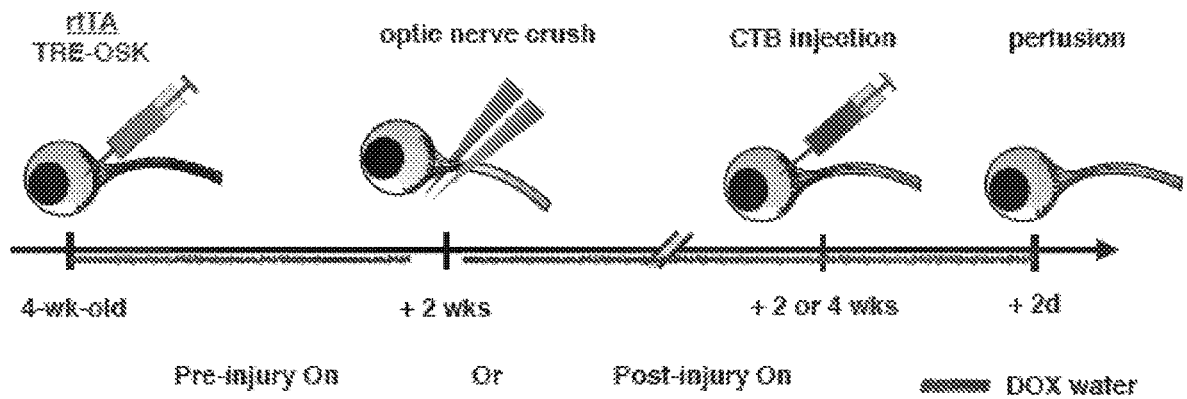
Figure 33B:
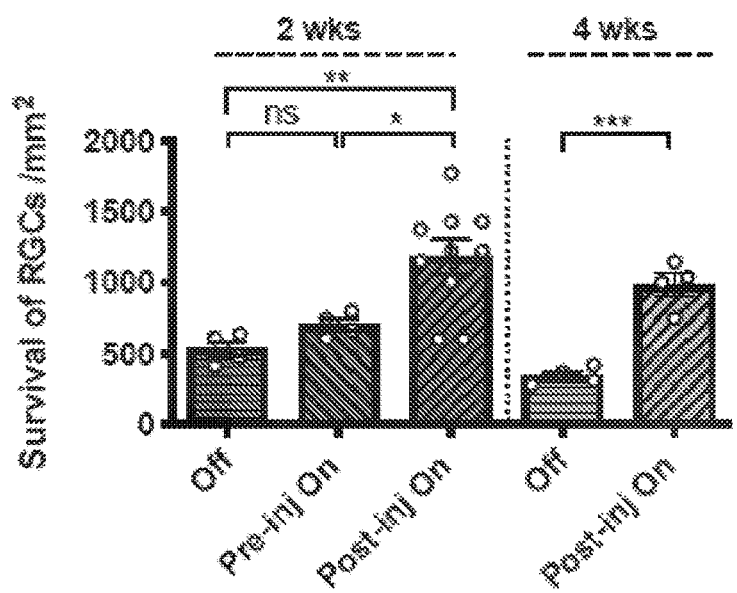
Figure 33C:
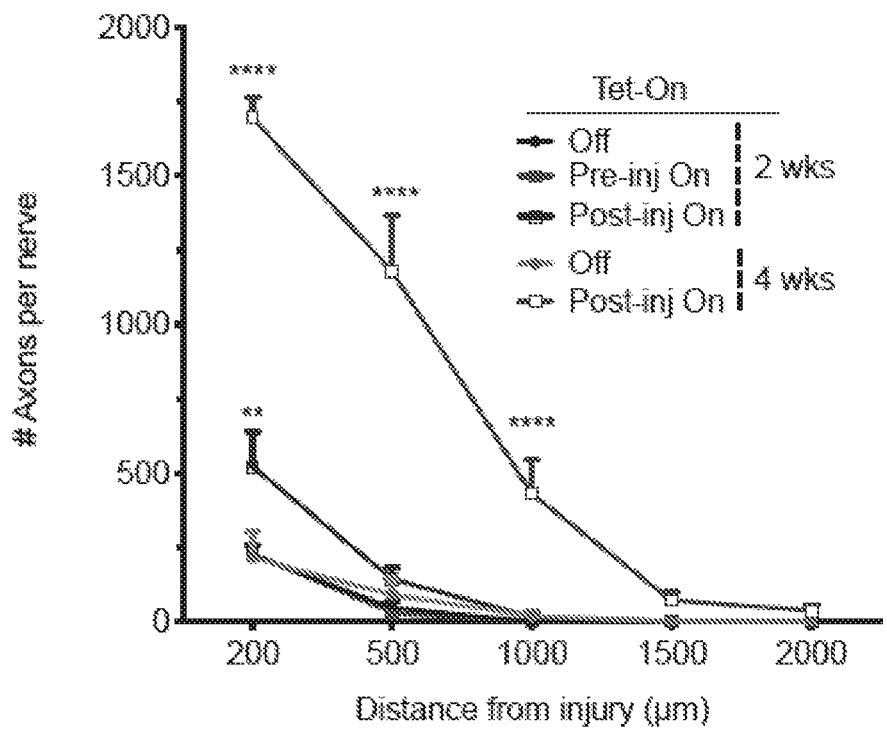
Figure 33D:
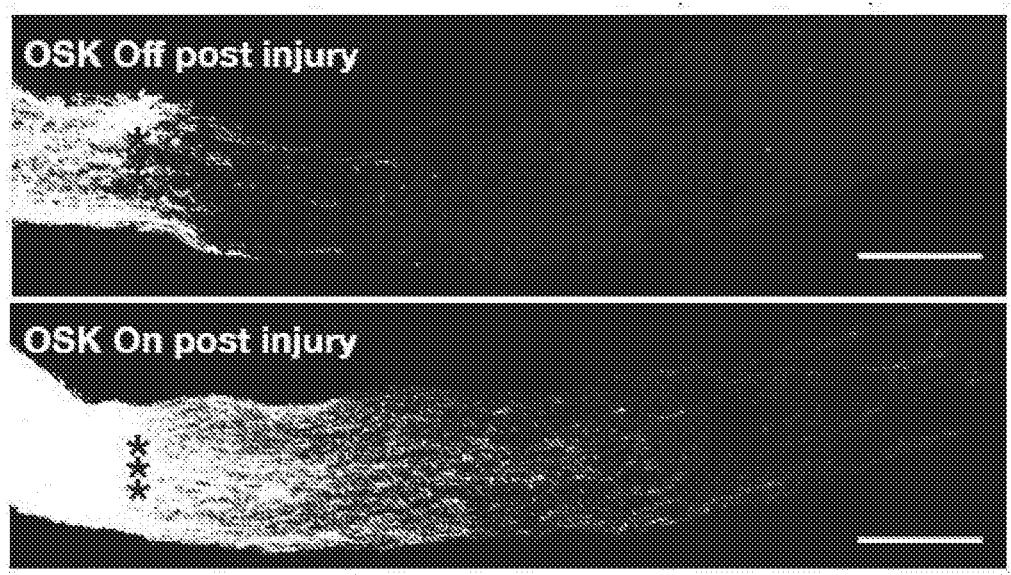
Figure 33E:
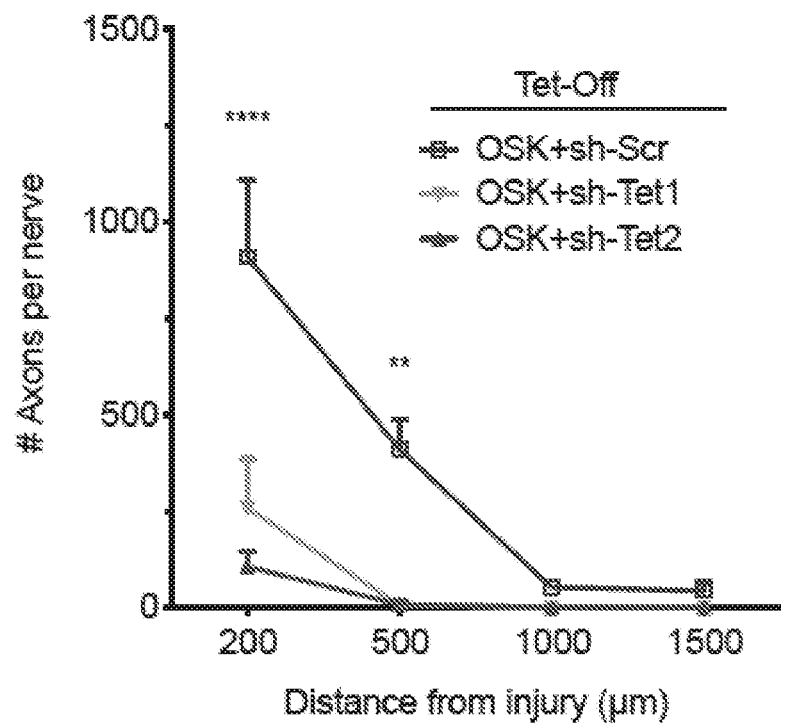
Figure 33F:
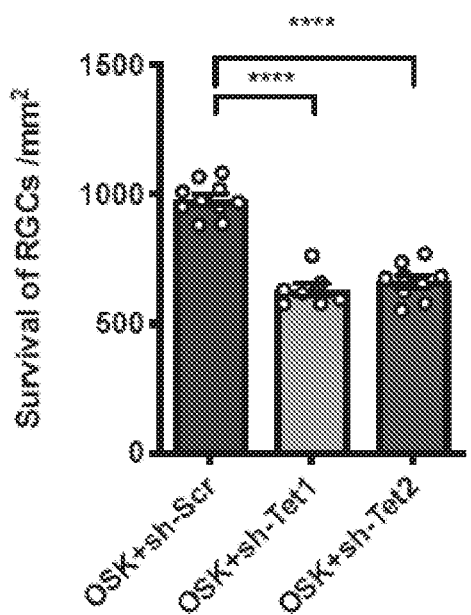

To test whether neuronal rejuvenation by OSK is specific for mouse RGCs, axon regeneration assays were performed in human neurons in vitro (FIG. 33G). Human neuroblastoma SH-SY5Y cells were differentiated into neurons and transduced them with AAV-DJ vectors to express OSK (FIG.

Figure 33I:
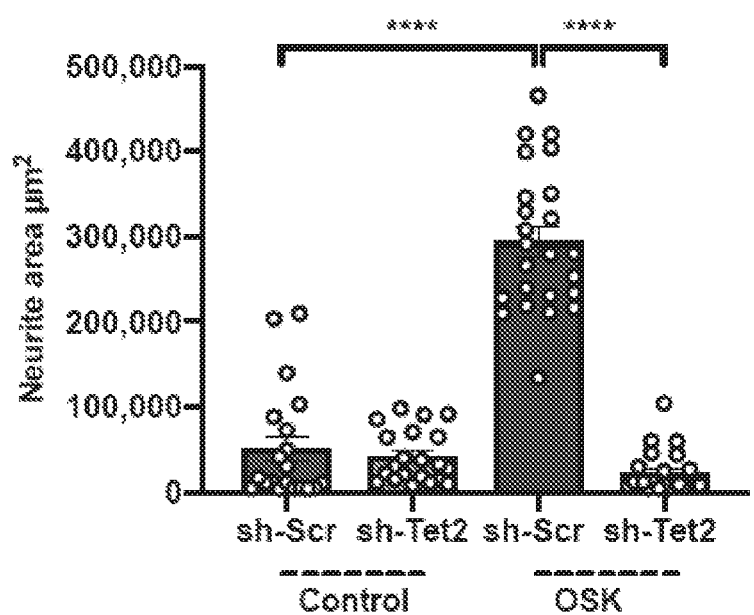
Figure 33J:
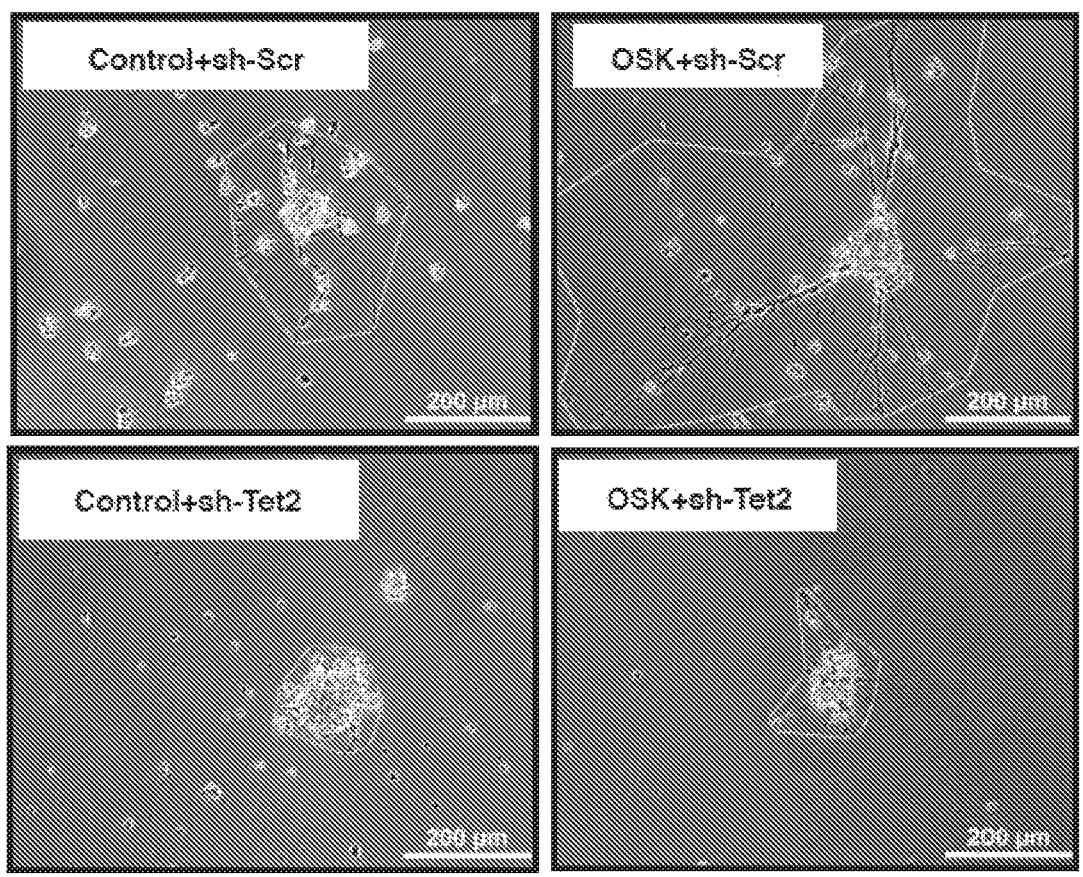
Figure 33K:
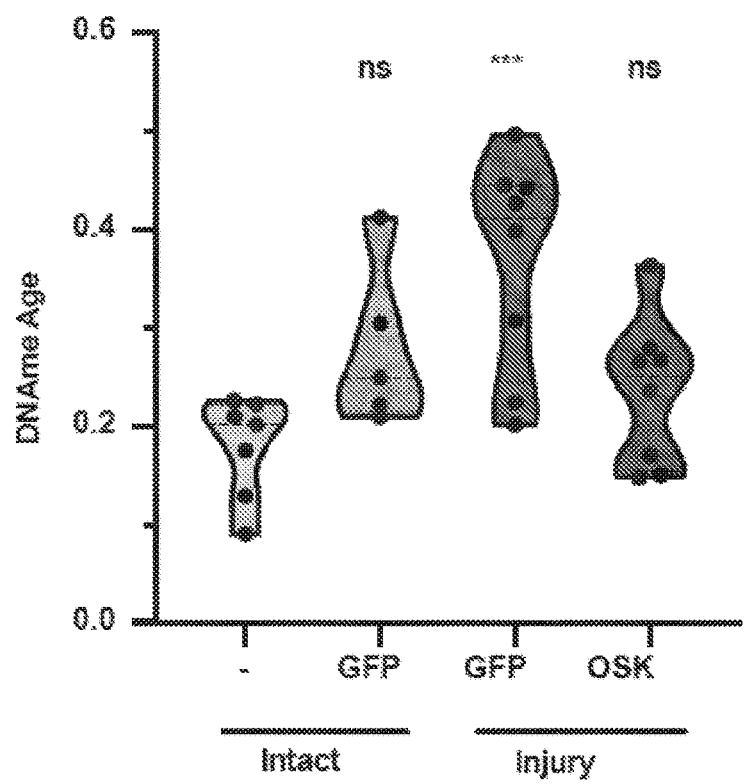
Figure 41A:
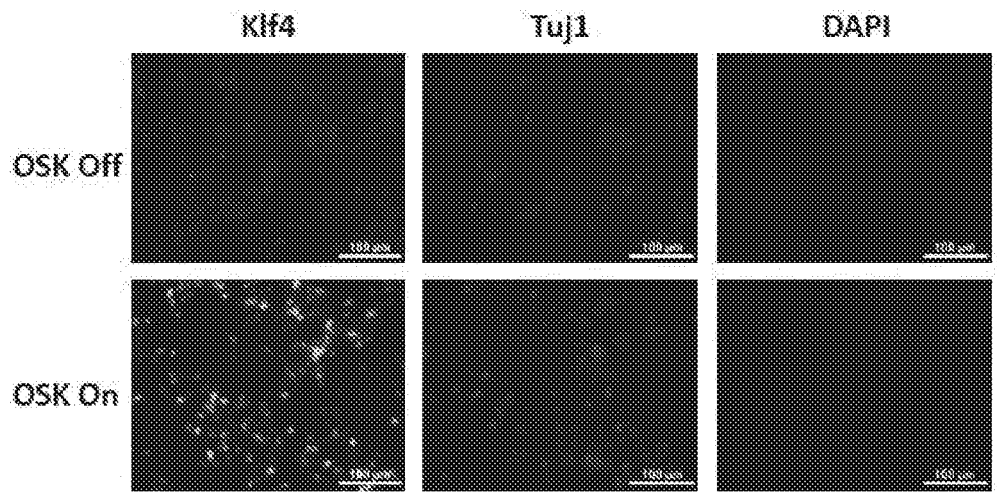
FIGS. 41A-41K show that OSK robustly induces human neuron axon regeneration independent of mTOR pathway.
Figure 41B:
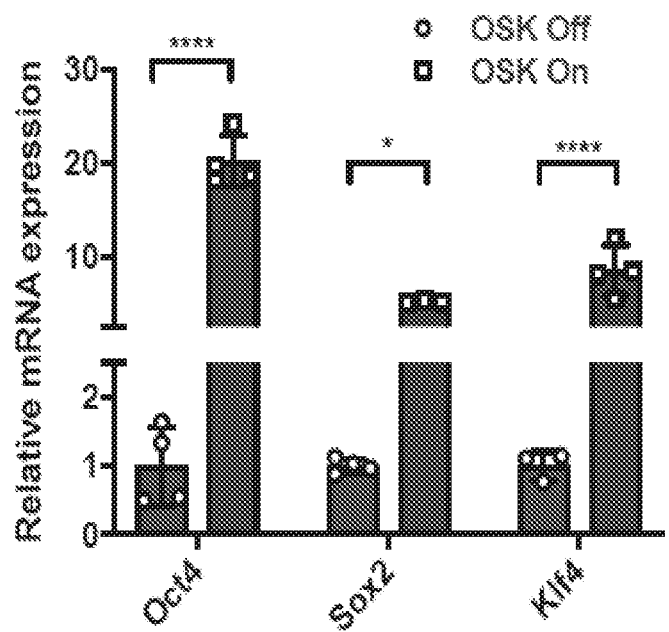
Figure 41C:
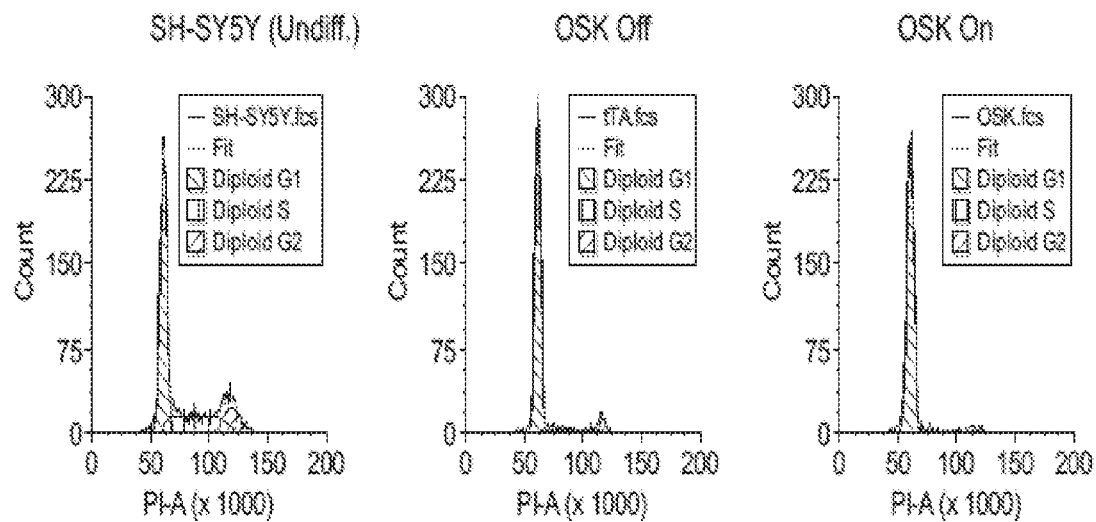
Figure 41D:
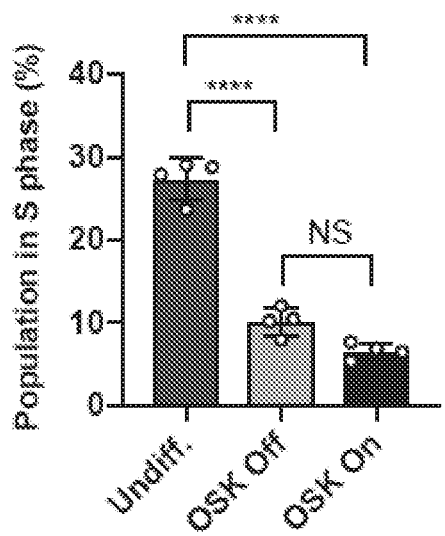
Figure 41E:
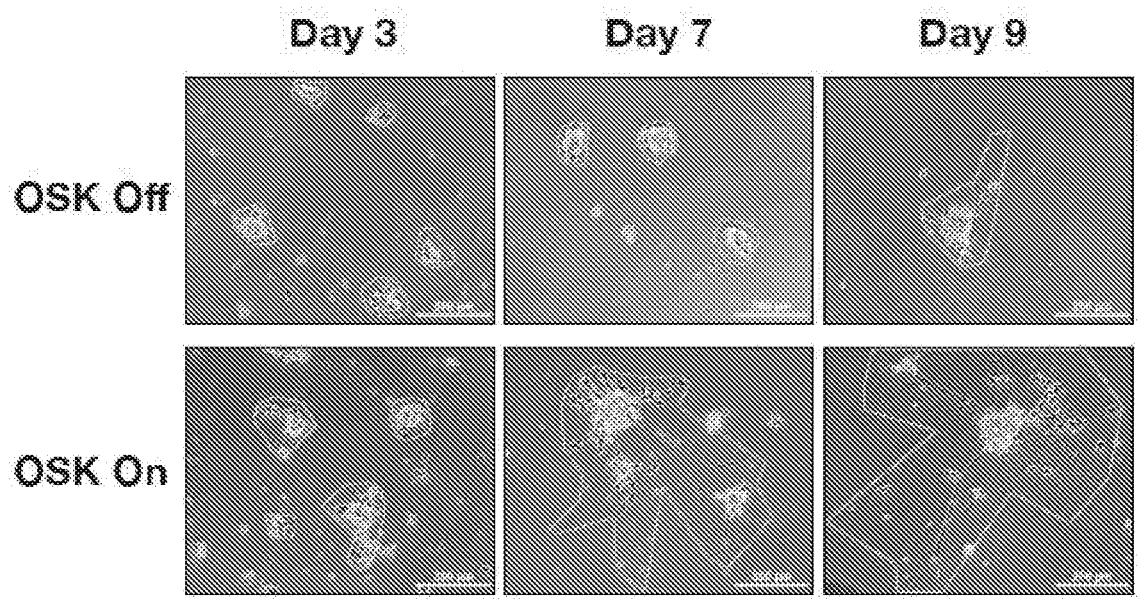
Figure 41F:
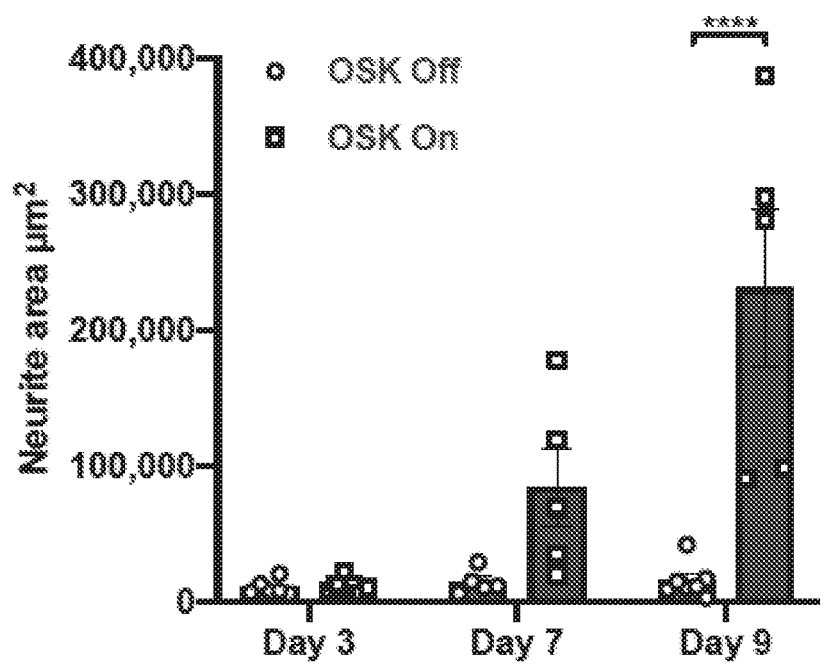
Figure 41G:
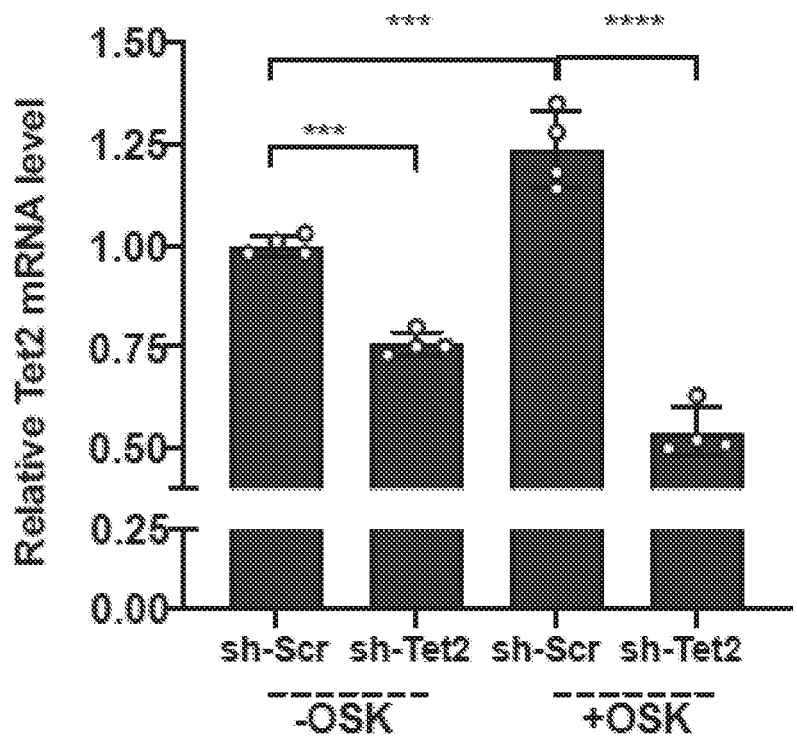
Figure 41H:
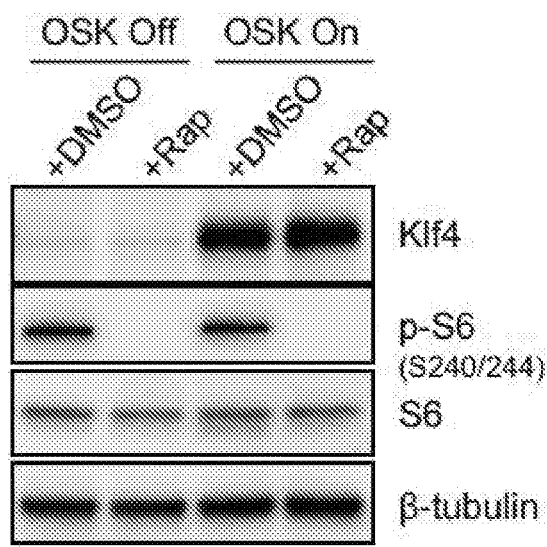
Figure 41I:
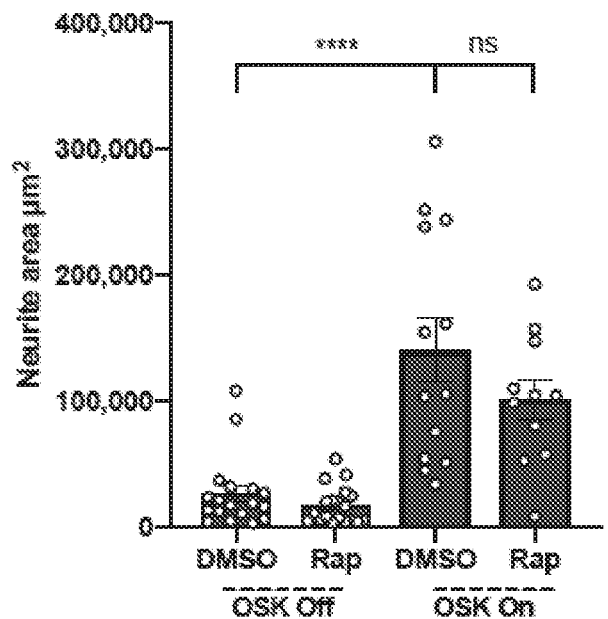
Figure 41J:
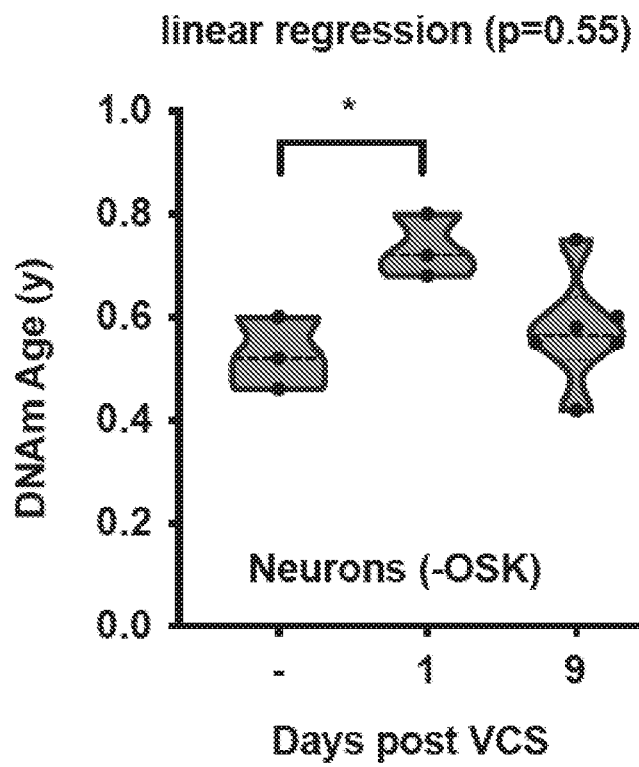
Figure 41K:
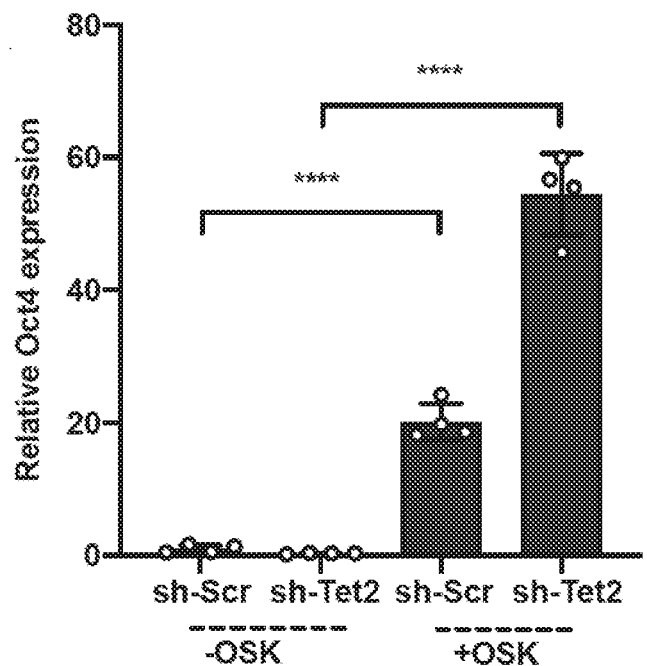
Figure 45C:
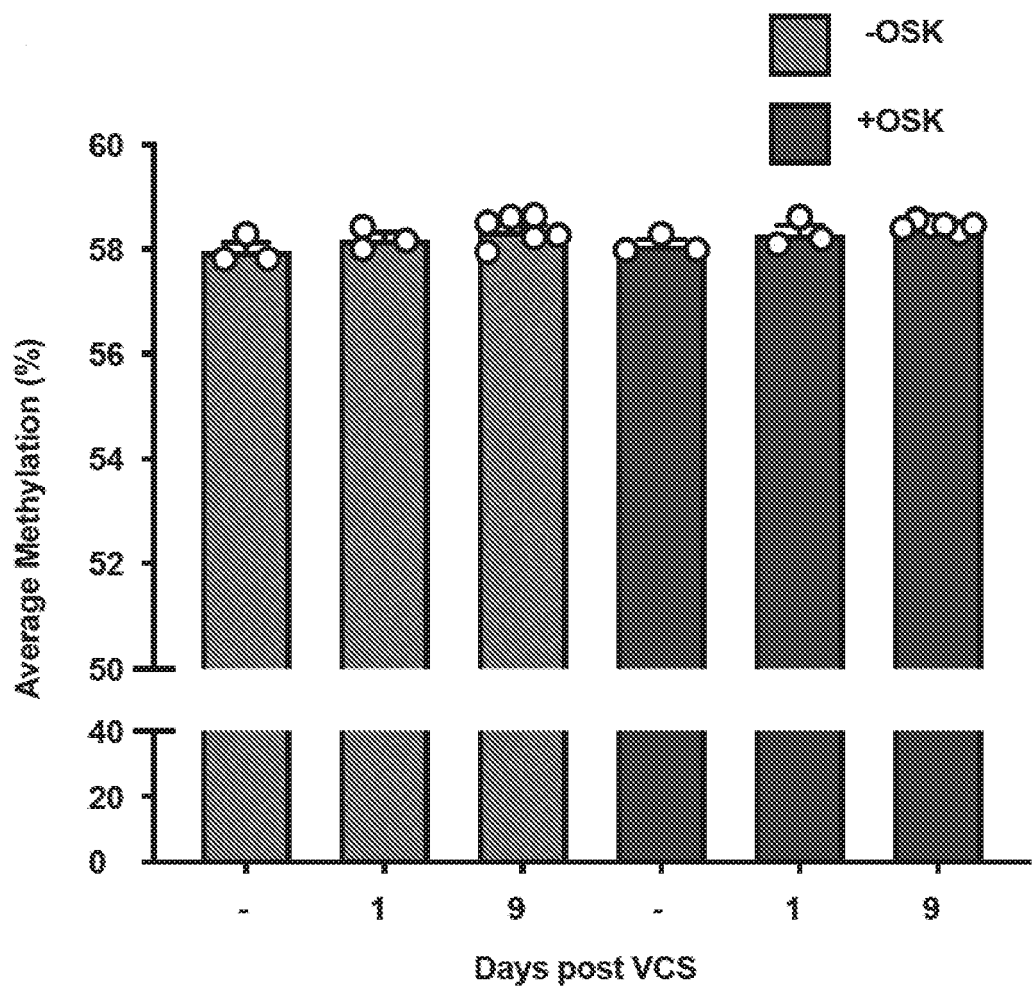

33G, FIG. 41A, and FIG. 41B). Similar to mouse RGCs in vivo (FIG. 38A), OSK did not induce cell proliferation (FIGS. 41C-41D). Axon degeneration was then induced by a 24 hour treatment with vincristine (VCS), a chemotherapeutic agent, and cells were then allowed to recover for 9 days. The epigenetic clock of these neurons were measured using the skin and blood cell clock (Horvath and Raj, Nat Rev Genet. 2018 June; 19(6):371-384). Similarly, DNA methylation age is significantly increased after VCS damage in human neurons (FIG. 41J), and OSK expression not only prevented this increase of DNA methylation age, but also restored a younger DNA methylation age without a global reduction of DNA methylation (FIG. 33H, bottom panel and FIG. 45C). DNAmAge is significantly decreased with experiment day 9 post VCS damage in OSK treated cells, but not in cells not treated by OSK (FIG. 33H). At Day 9 post damage, the neurite area was 15-fold greater in the rejuvenated OSK-transduced cells than controls (FIG. 41E and FIG. 41F) and the recovery from damage was dependent on the Tet2 demethylase (FIG. 33I, FIG. 33J, and FIG. 41G), even in presence of high OSK expression (FIG. 41K) but not the mTOR-S6K pathway, paralleling mouse retinal ganglia cells (FIG. 41H and FIG. 41I). Thus, the ability of OSK to reprogram neurons and promote axon growth is cell intrinsic, conserved in mammals, and requires epigenetic rejuvenation through DNA demethylation. This process is referred to herein as the recovery of information via epigenetic reprogramming, or "REVIVER" for short.

Figure 34A:
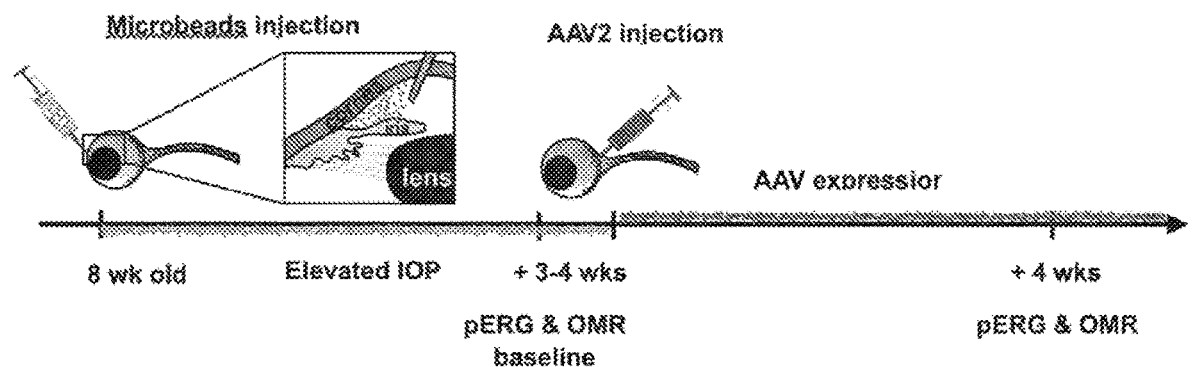
FIGS. 34A-34H show the reversal of glaucoma by OSK AAV treatment.
Figure 34B:
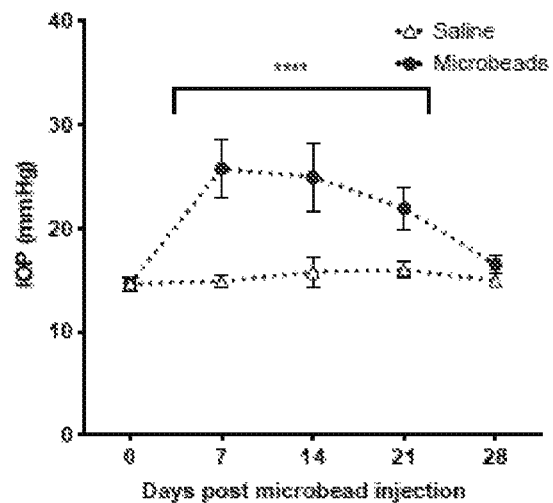
Figure 34C:
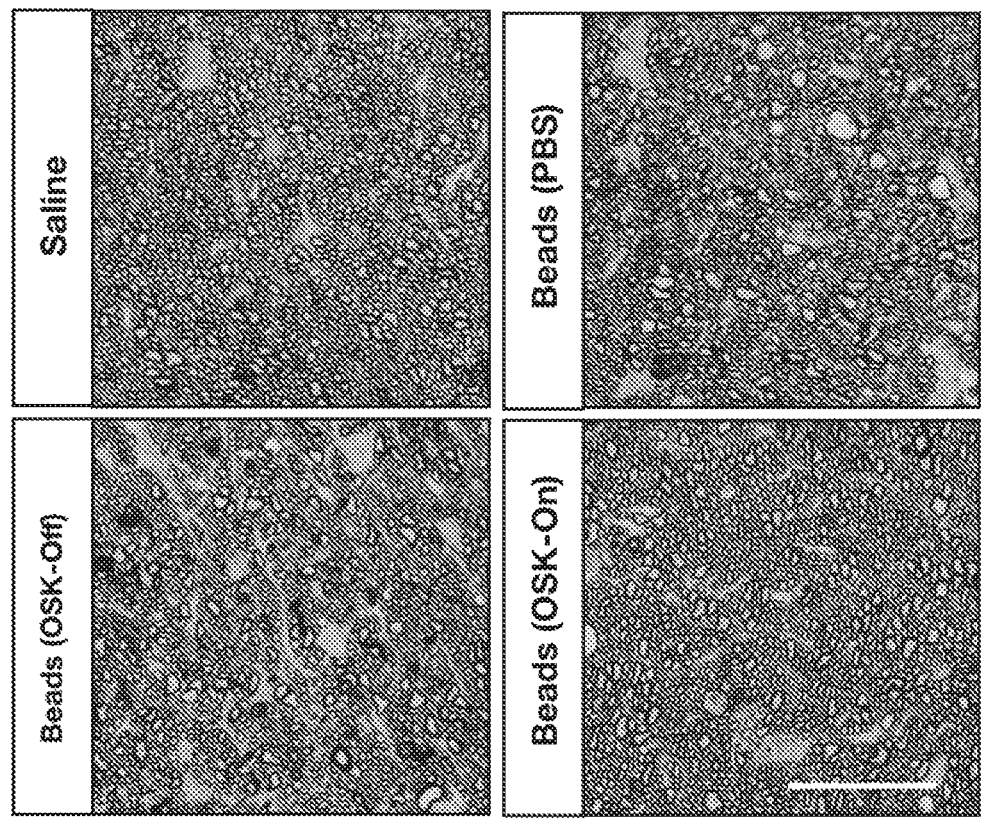
Figure 34D:
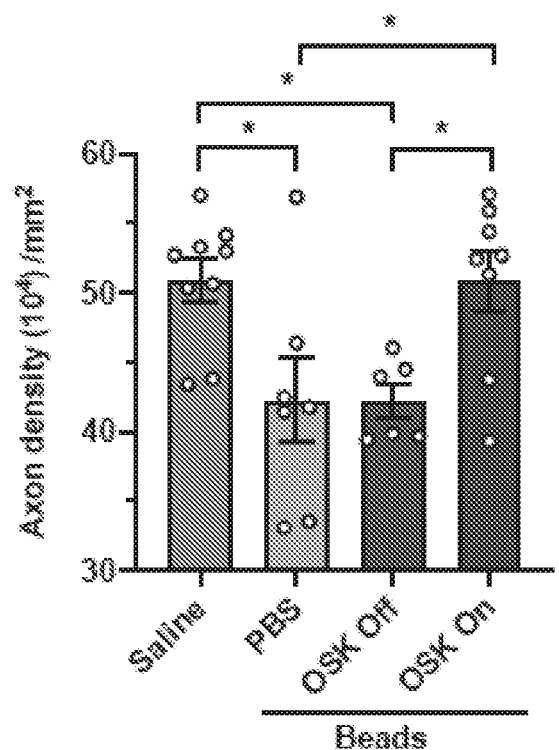
Figure 42A:
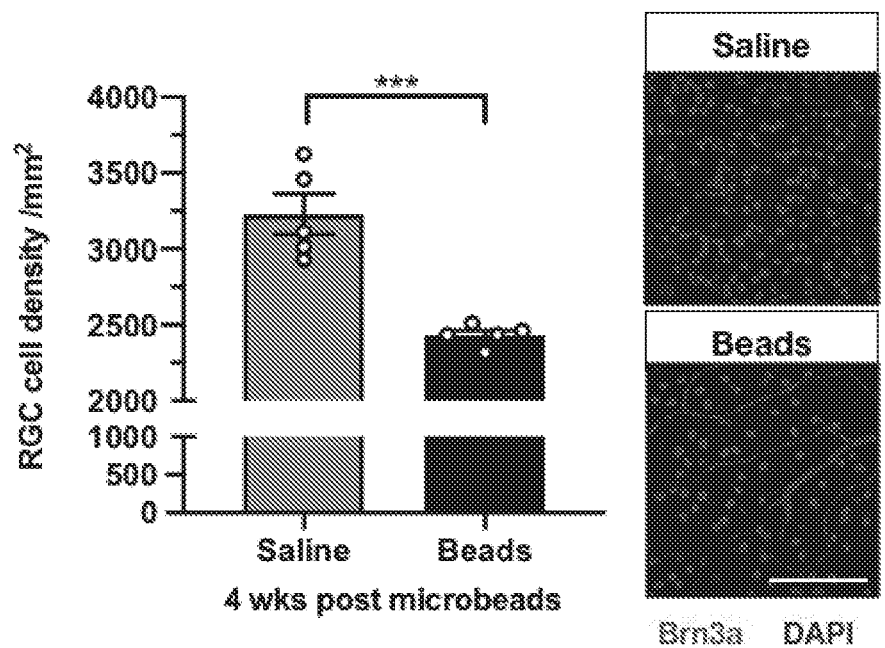
FIGS. 42A-42C show the effect of OSK in a Microbead-induced mouse model.
Figure 42B:
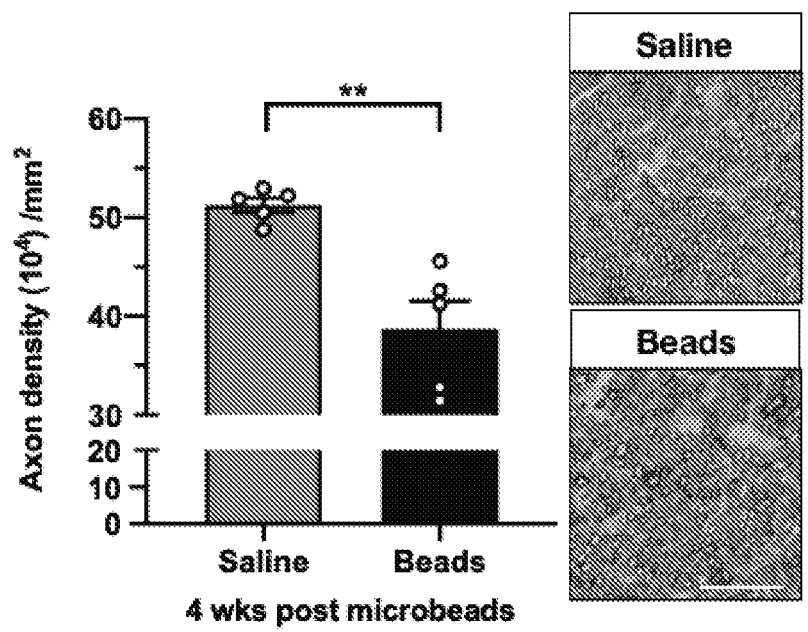
Figure 42C:
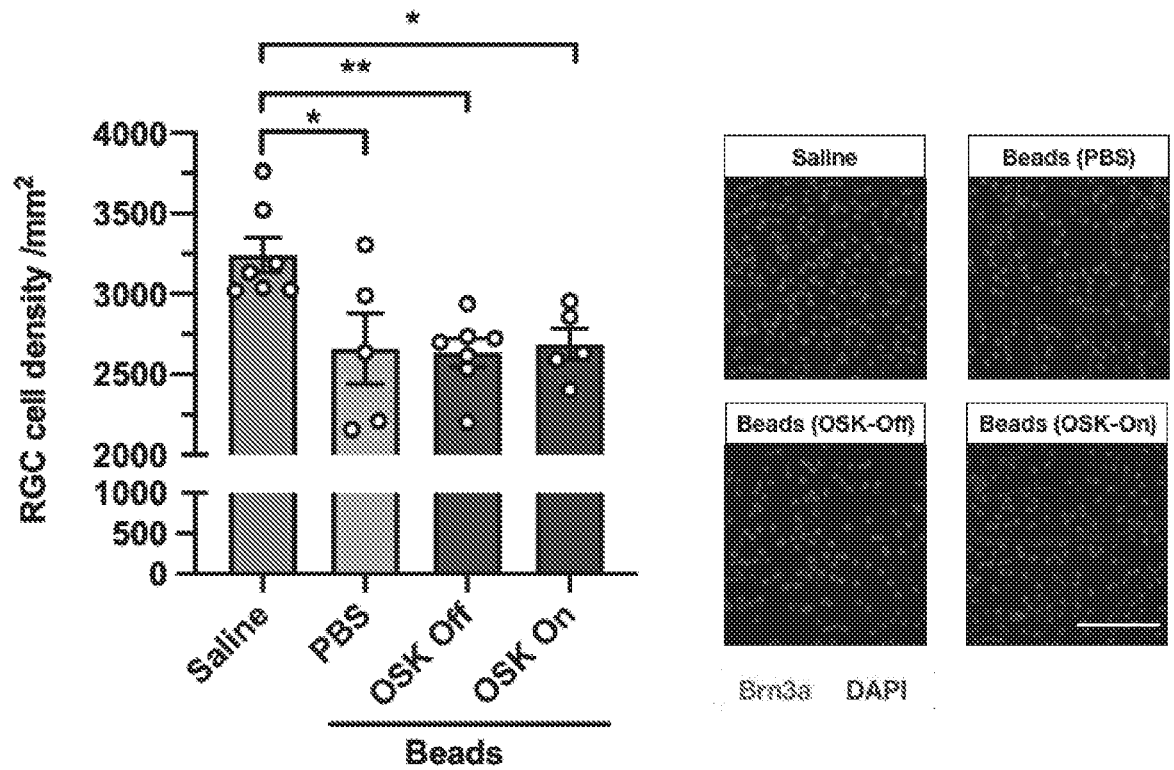

Glaucoma, a progressive loss of RGCs and their axons, most often due to increased intraocular pressure, is a leading cause of age-related blindness worldwide. Although some treatments can slow down disease progression, it is currently not possible to restore vision once it has been lost. Given the ability of OSK to regenerate axons after acute nerve damage, we decided to test whether REVIVER treatment could restore the function of RGCs in a chronic setting like glaucoma (FIG. 34A). Elevated intraocular pressure (IOP) was induced unilaterally for 4-21 days by injection of microbeads into the anterior chamber. OSK AAVs or PBS were then injected intravitreally, and express at a time point when glaucomatous damage was established, with a significant decrease in RGCs and axonal density (FIG. 34B, FIG. 42A, and FIG. 42B) (Krishnan et al., J Immunol, 2016. 197(12): p. 4626-4638). At four weeks post-AAV injection, OSK-On treated mice presented with a significant increase in axon density when compared to PBS and OSK-Off treated mice. The increased axon density observed was equivalent to the axon density in the saline-only, non-glaucomatous mice (FIGS. 34C and 34D), and was not associated with proliferation of RGCs (FIG. 42C).

Figure 34E:
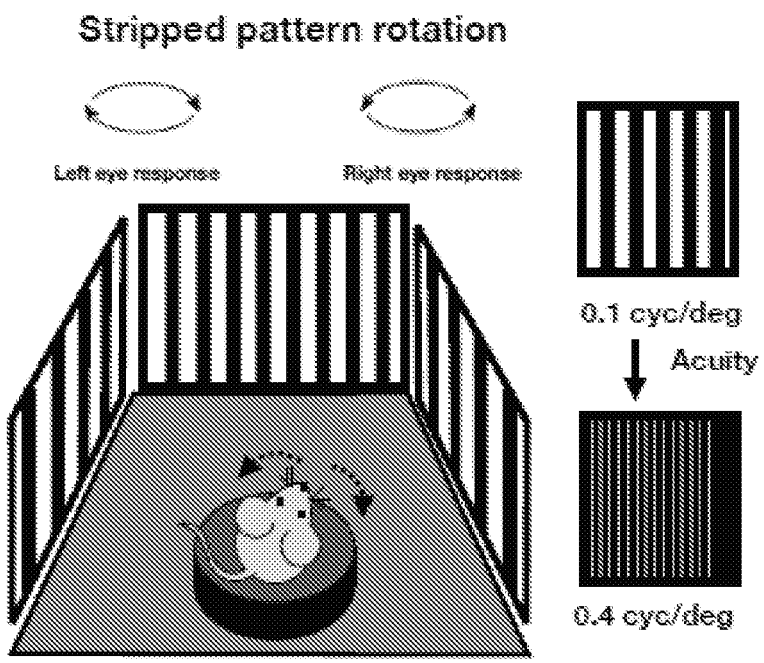
Figure 34F:
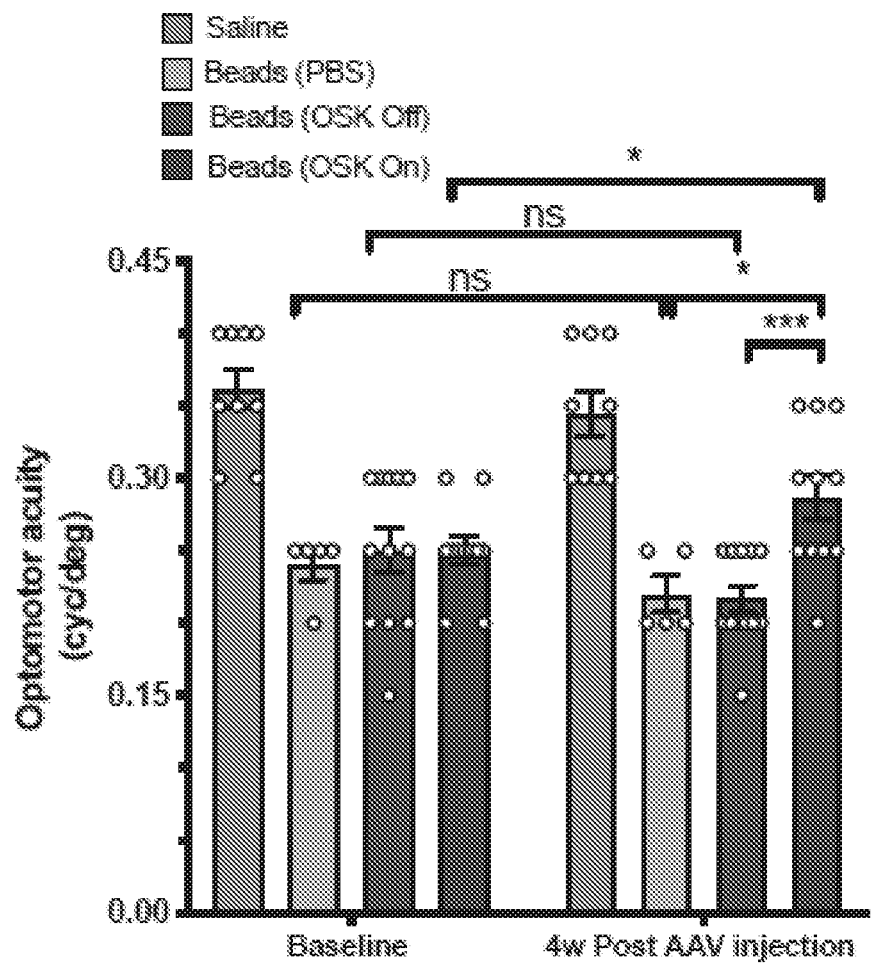
Figure 34G:
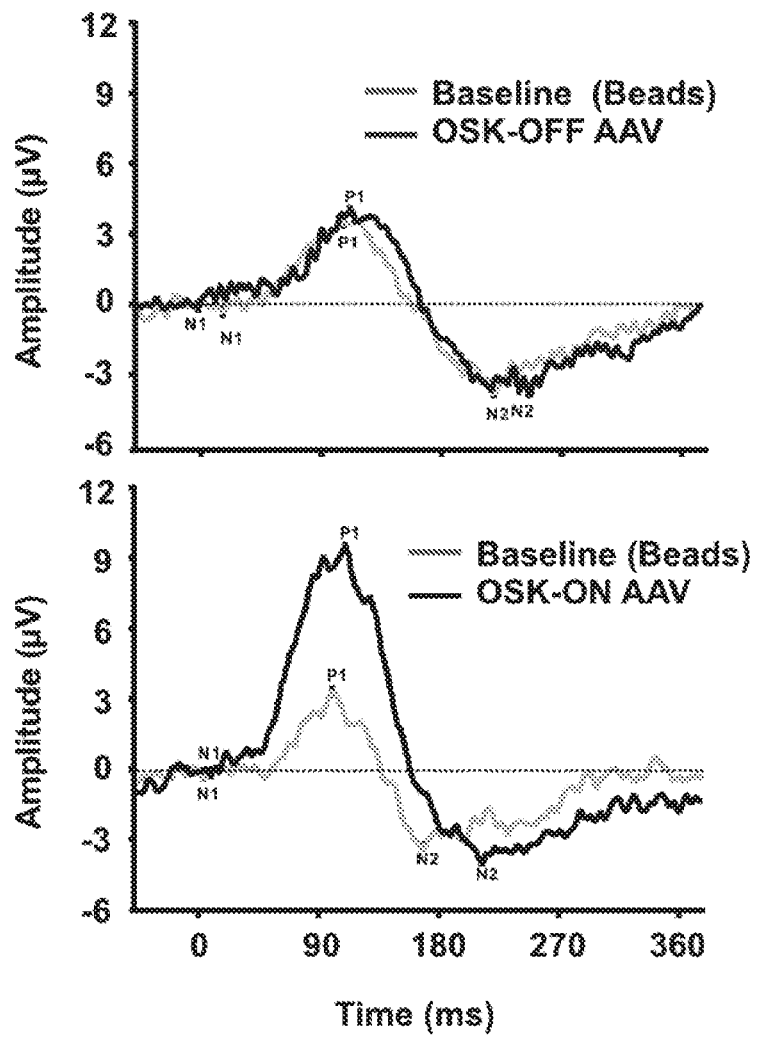
Figure 34H:
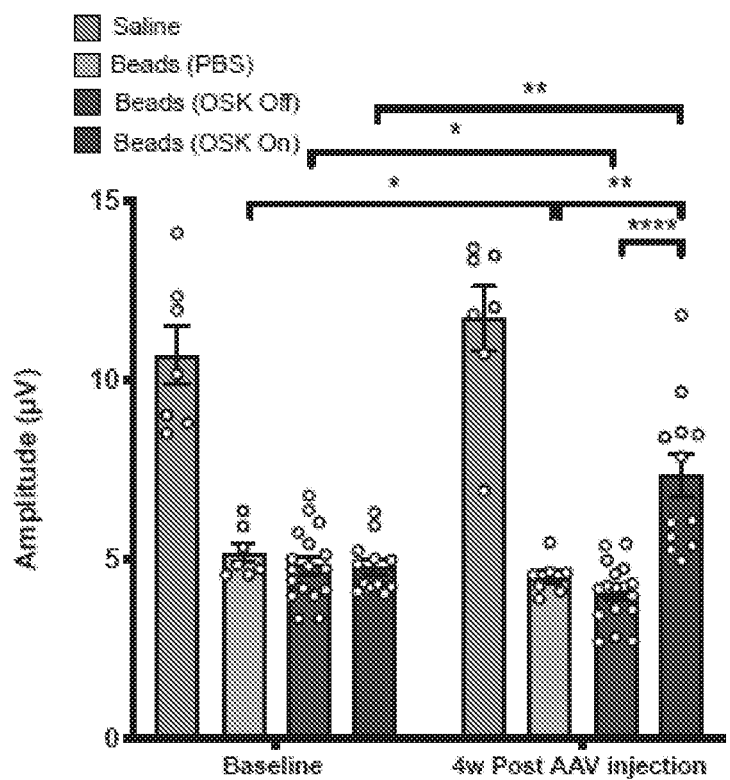

To determine whether the increased axon density observed in OSK treated mice coincided with increased vision, a behavior assay, optomotor response (OMR), was used (FIG. 34E) to track the visual acuity of each mouse. Compared to mice that received either PBS or the OSK-Off AAV, OSK treatment significantly increased visual acuity relative to the pre-treatment baseline measurement, restoring more than half of the vision loss (FIG. 34F). A readout of electrical waves generated by RGCs in response to a reversing contrast checkerboard pattern, known as Pattern electroretinogram response (pERG) analysis, showed that OSK treatment significantly improved RGC function relative to the pre-treatment baseline measurements, as well as, compared with either PBS or OSK-Off AAV treated mice (FIGS. 34G and H). Without being bound by a particular theory, treatment with OSK AAV, as shown herein, may be the first treatment to reverse vision loss in any glaucoma model. Notably, OSK reversed vision loss in a glaucoma model.

Given the ability of OSK to induce axon regeneration following optic nerve crush and to restore vision after glaucomatous damage in young mice, it was determined whether OSK could also restore vision loss associated with physiological aging and regenerate axons following optic nerve injury in aged mice. This is particularly important since a recently reported retinal rod photoreceptor regenerative approach that was successful when treating young mice was significantly diminished when treating older mice (Yao, K., et al., Restoration of vision after de novo genesis of rod photoreceptors in mammalian retinas. Nature, 2018. 560 (7719): p. 484-488).

Figure 35A:
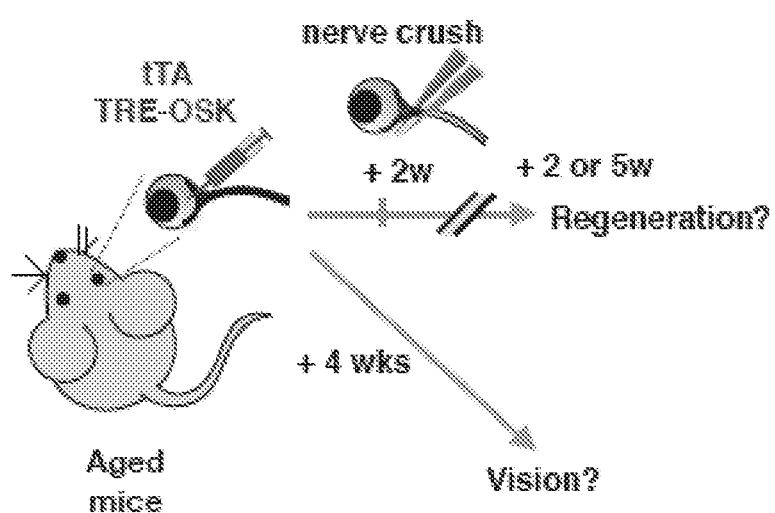
FIGS. 35A-35I show that OSK AAV induces axon regeneration and restores visual function in aged mice.
Figure 35B:
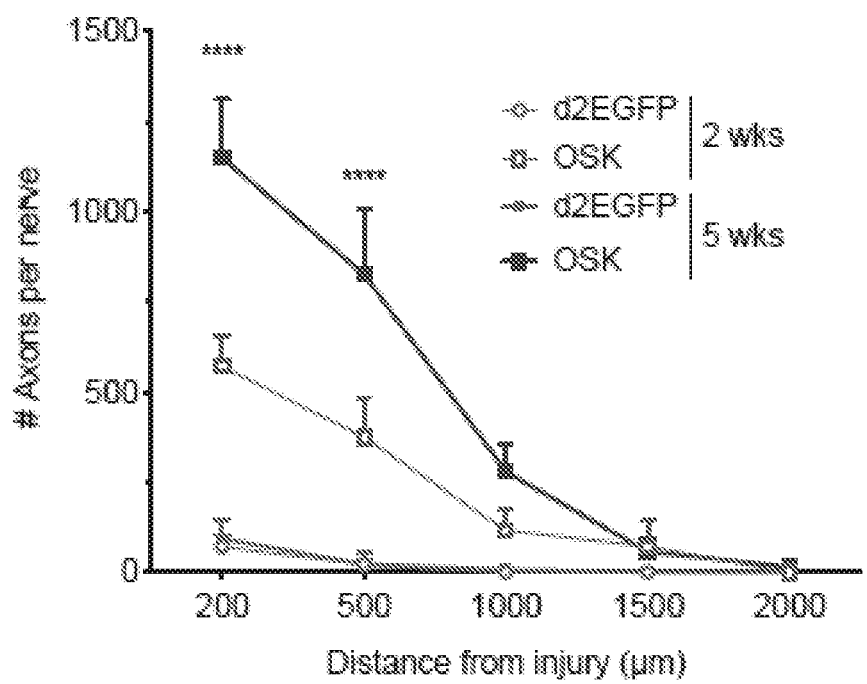
Figure 35C:
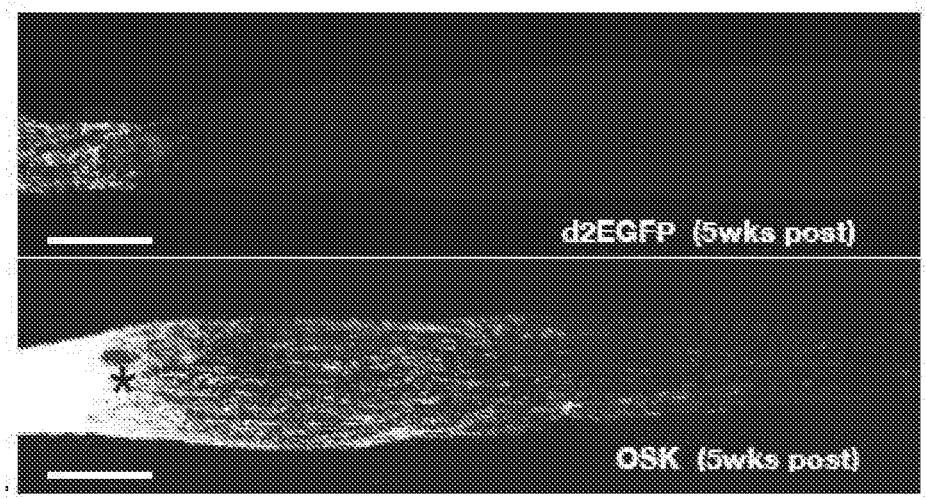
Figure 43A:
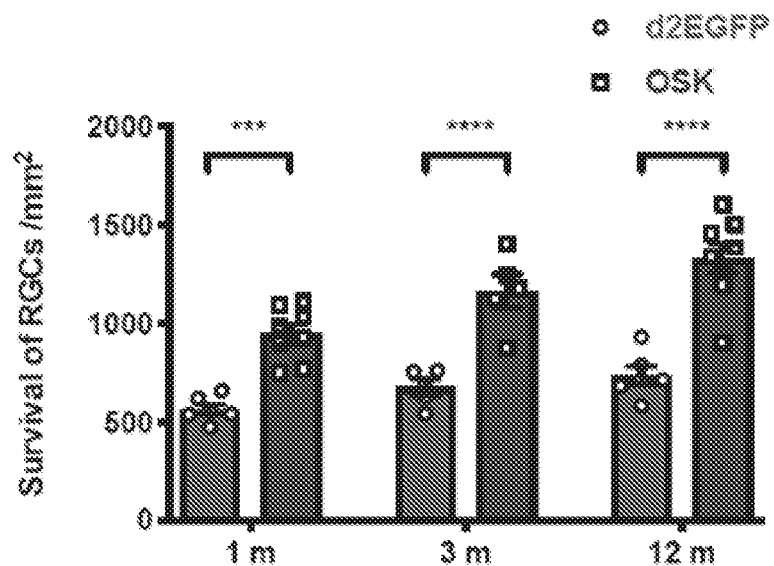
FIG. 43A-43G show the effect of OSK in aged mice.
Figure 43B:
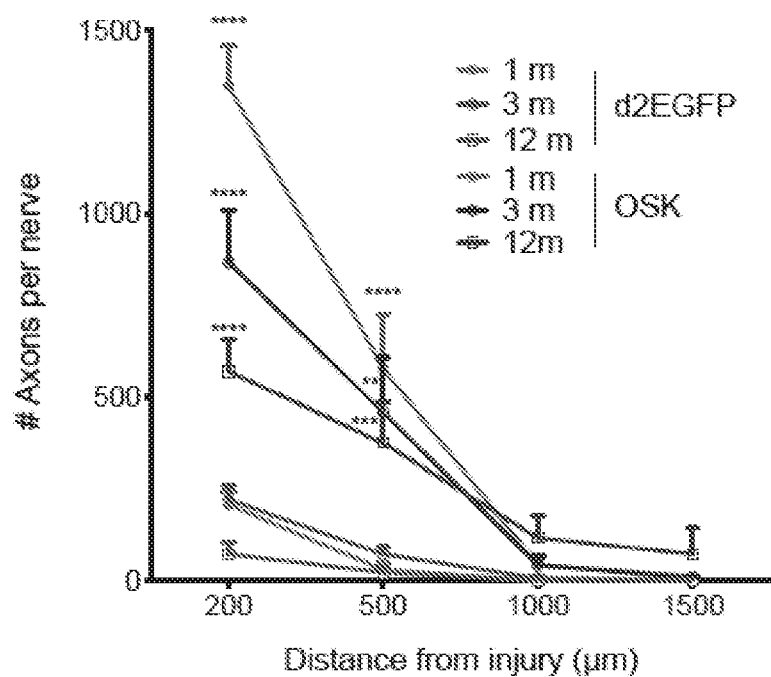

To determine whether OSK AAV treatment could induce axon regeneration in aging mice, the optic nerve crush injury model was performed on 12-month-old mice using the same protocol as in FIG. 32D with the experimental design shown (FIG. 35A). In aged mice, OSK AAV treatment for two weeks post-injury showed doubled RGC survival, similar to that observed in young mice (FIG. 43A). Though the axon regeneration is slightly less than young mice at two weeks post injury (FIG. 43B), OSK AAV treatment in aged mice for five weeks post-injury showed a significant increase in axon regeneration (FIGS. 35B and 35C), similar to that observed in young mice. These data indicate that aging does not diminish the effectiveness of OSK AAV treatment in inducing axon regeneration following an optic nerve crush injury.

Figure 35D:
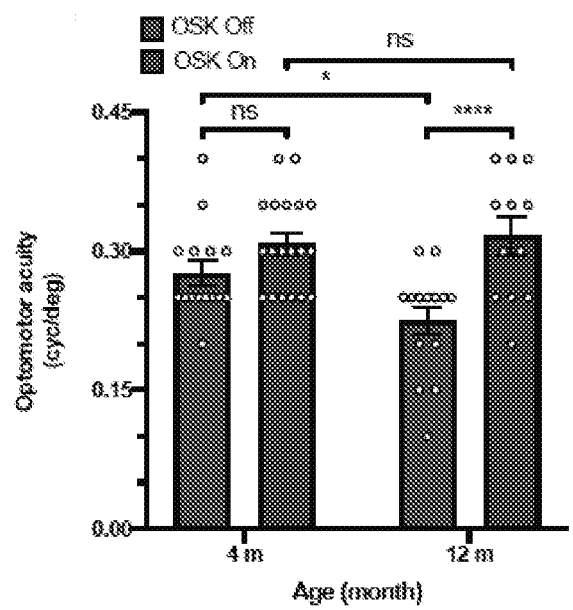
Figure 43C:
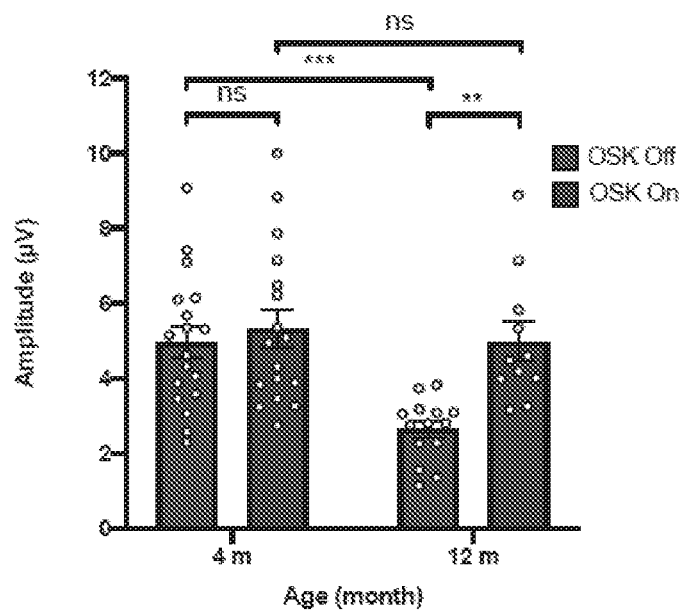
Figure 43D:
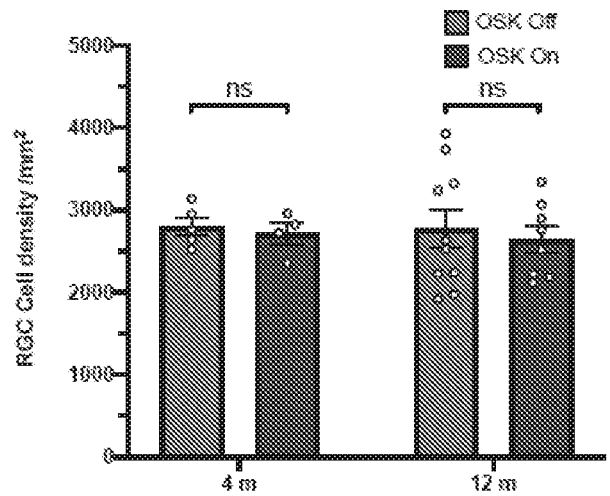
Figure 43E:
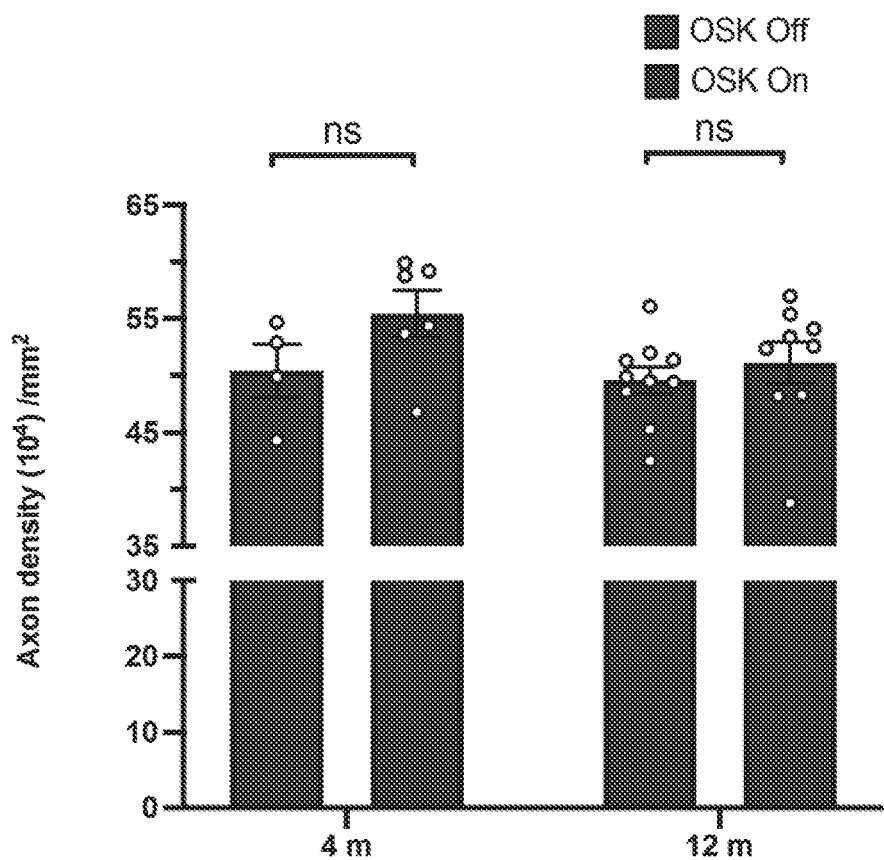
Figure 43F:
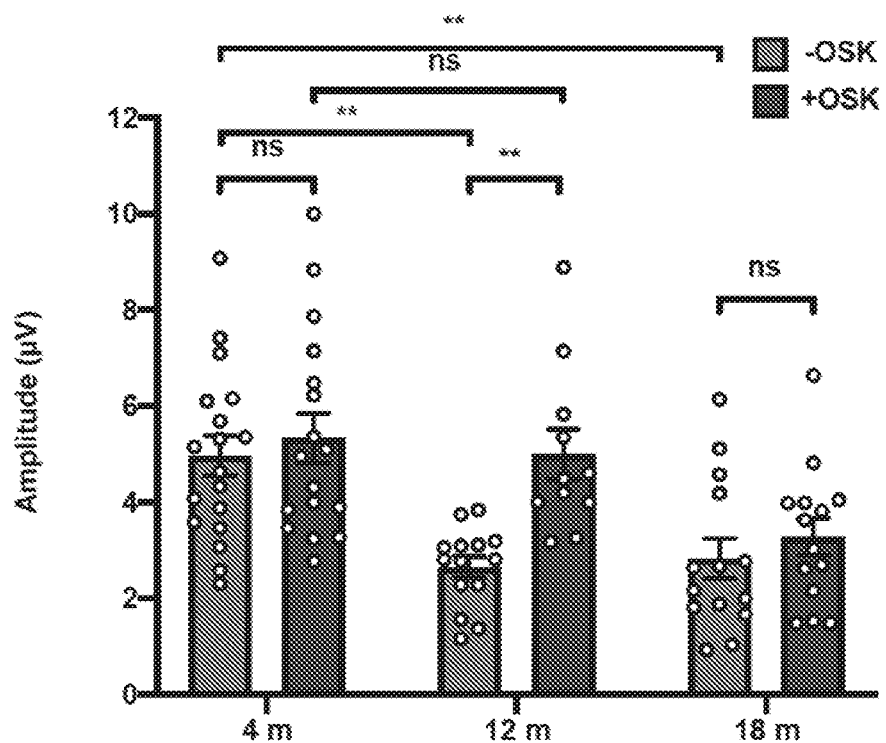
Figure 43G:
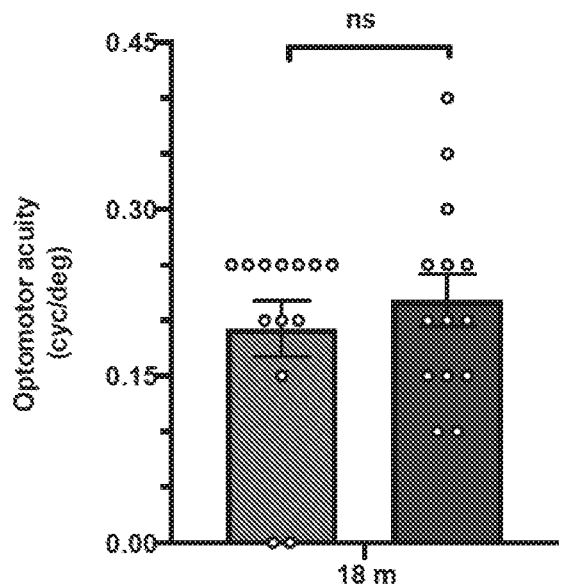

To test whether OSK treatment could reverse vision loss associated with physiological aging, 4- and 12-month-old mice received intravitreal injections of OSK-Off or OSK-On AAV. As expected, at one year of age, mice showed a significant reduction in visual acuity and RGC function as measured by OMR and pERG, which was restored by OSK AAV treatment (FIG. 35D and FIG. 43C). Such restoration was not observed in 18 month-old mice (FIG. 43F-43G) likely due to spontaneous corneal opacity developed at this age (McClellan et al., Am J Pathol 184, 631-643, doi: 10.1016/j.ajpath.2013.11.019 (2014)), suggesting the restoration effect is specifically contributed by AAV-infected RGC layer.

Figure 35E:
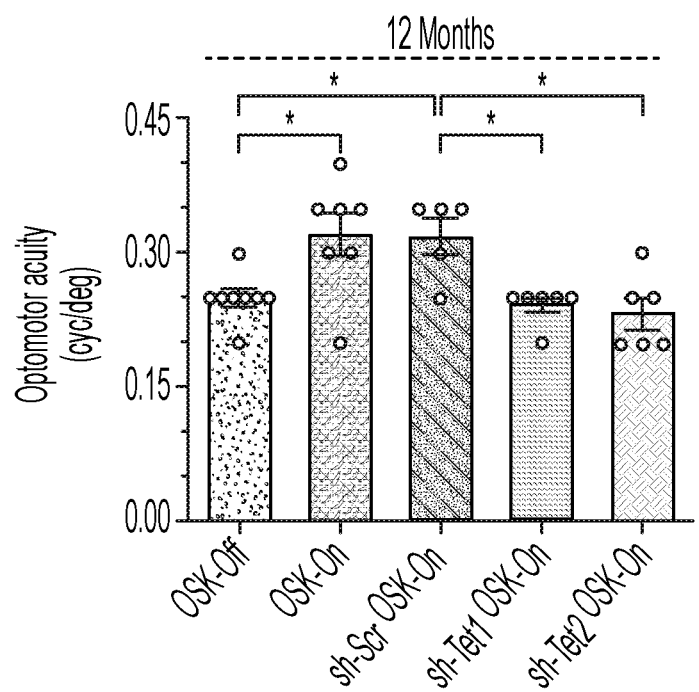
Figure 35F:
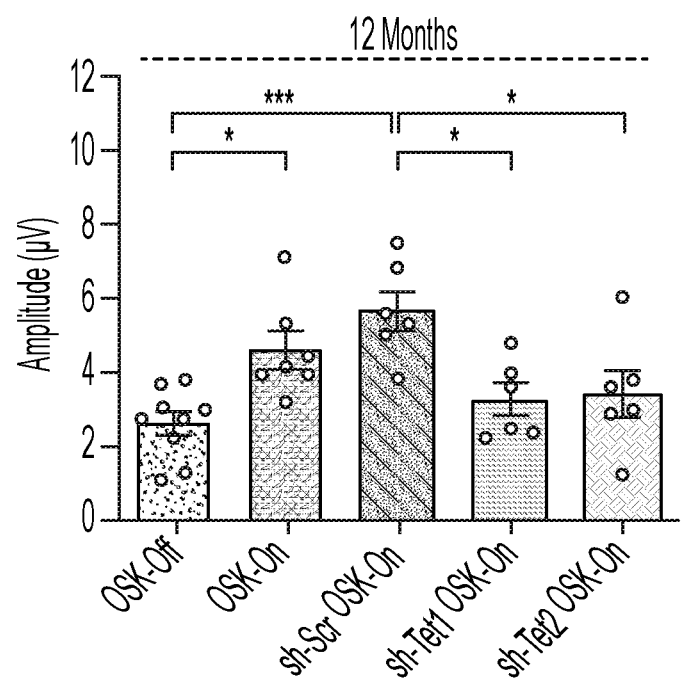

Next, it was determined whether restoration of youthful transcriptome by OSK indicates a youthful epigenome and thus would requires Tet enzymes. Remarkably, Tet1 or Tet2 knockdown completely blocked the rejuvenation effect of OSK-On AAV treatment as measured by both OMR and pERG analyses (FIG. 35E and FIG. 35F), consistent with DNA methylation as the key process for vision restoration. Notably, there is no obvious RGC and axon density increase by OSK in aged mice (FIG. 43D and FIG. 43E), suggesting functional improvement of existing RGCs. The rDNA methylation age of FACS-sorted RGCs from 12 month-old mice was measured. OSK AAV expression for 4 weeks significantly decreased the DNA methylation age and Tet1 and Tet2 knockdown blocked such rejuvenation (FIG. 35I). Together, these results demonstrate that Tet-dependent in vivo reprogramming can restore youthful gene expression patterns, reverse the DNA methylation clock, and restore the function and regenerative capacity of a complex tissue.

To further determine whether Tet2 knockout can block the effect of OSK on axon regeneration, mouse OSK and Tet2 conditional knockout mice (B6; 129S-Tet2tm1.1Iaai/J) were used. Mouse eyes were injected with (1) AAV-CRE (Tet2 cKO); (2) AAV-tTA+AAV-TRE-OSK: OSK (Tet2 WT); or (3) AAV-tTA+AAV-TRE-OSK+AAV-CRE: OSK (Tet2 cKO). After two weeks, optic nerve crush was conducted.

Figure 46A:
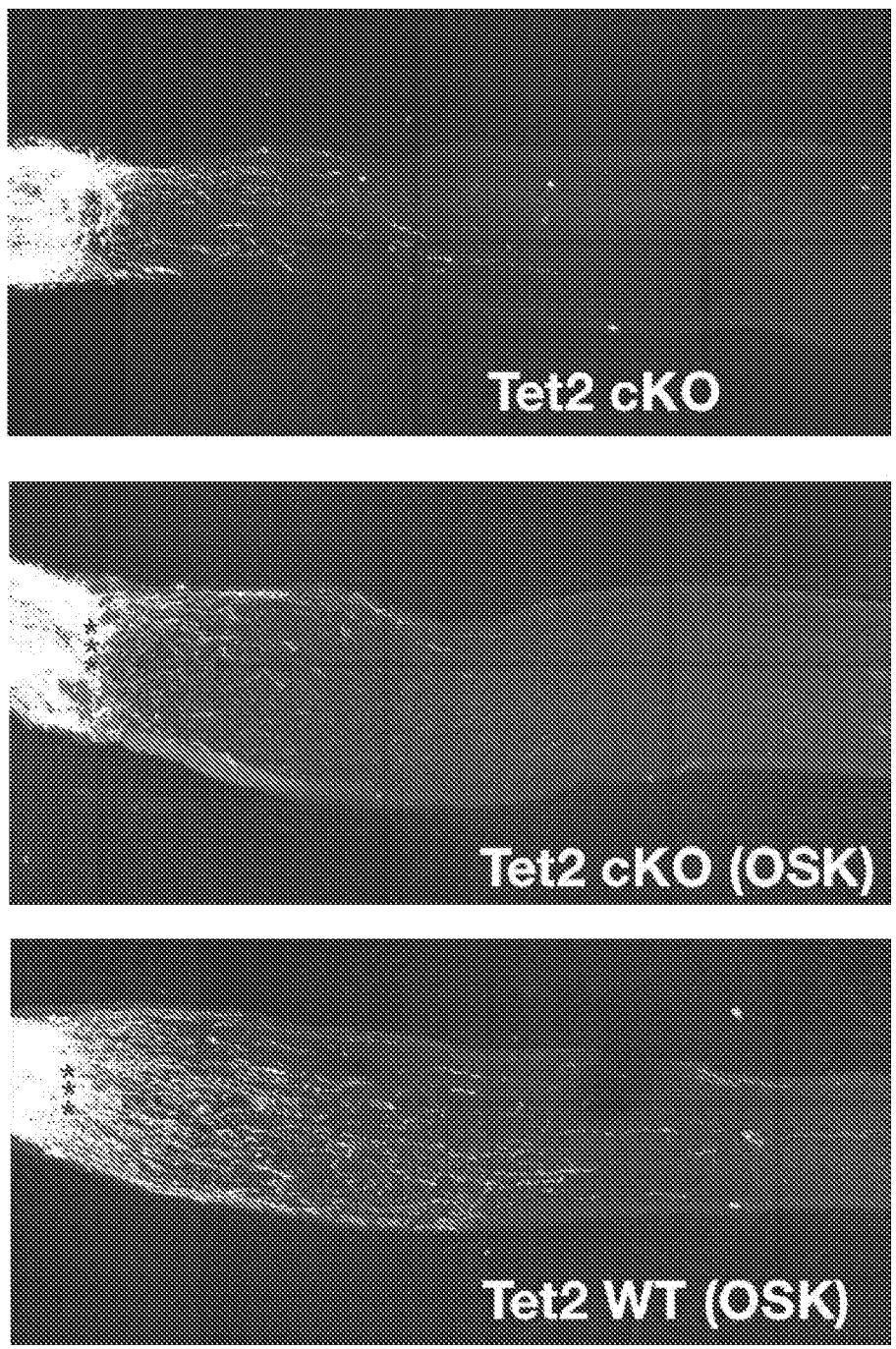
FIGS. 46A-46B show that OSK mediates axon regeneration in a Tet2-dependent manner. A Tet2 conditional knockout mouse was used. Mouse eyes were injected with (1) AAV-CRE (Tet2 cKO); (2) AAV-tTA+AAV-TRE-OSK: OSK (Tet2 WT); or (3) AAV-tTA+AAV-TRE-OSK+AAV-CRE: OSK (Tet2 cKO). Axon regeneration was assayed after optic nerve crush.
Figure 46B:
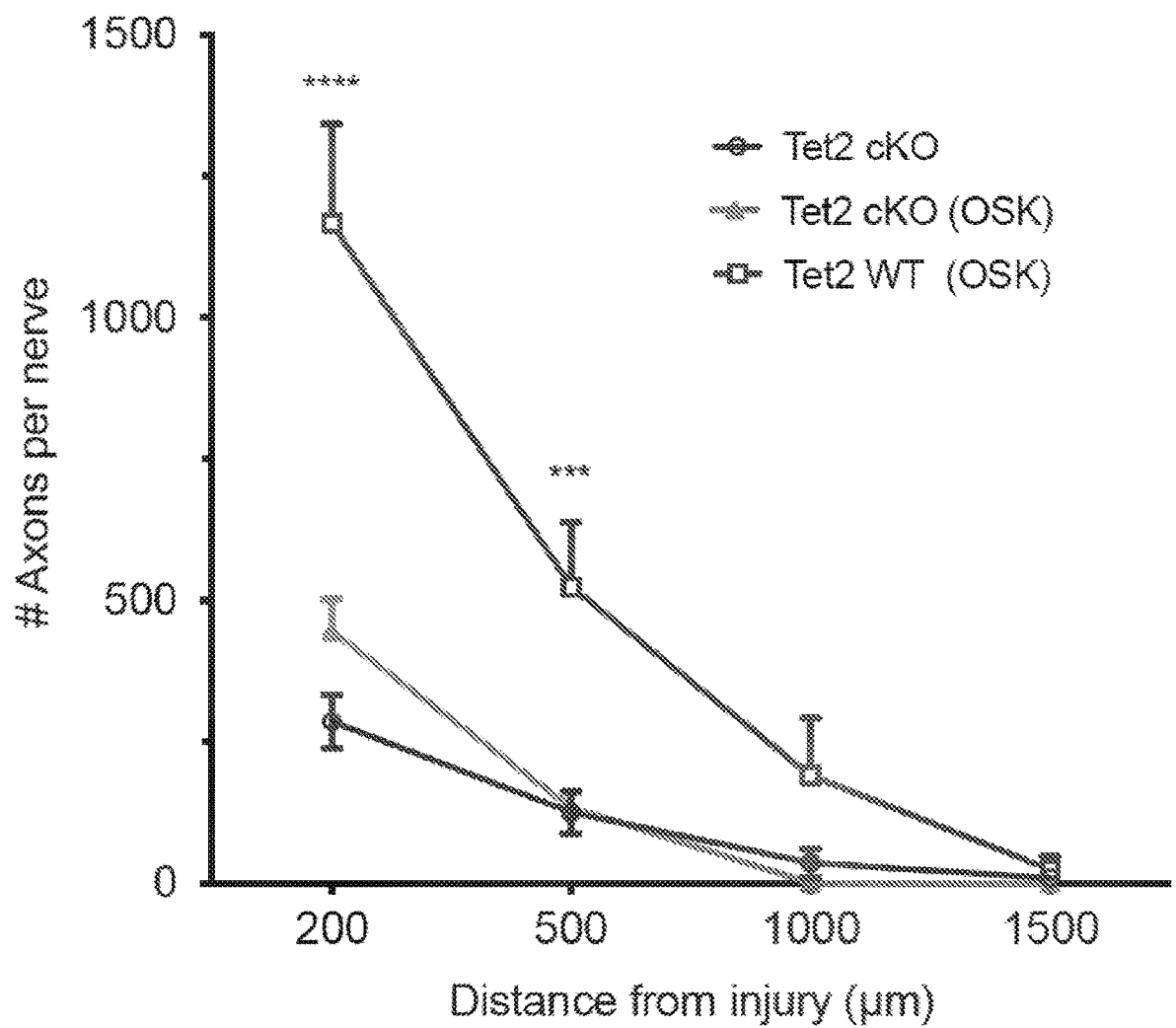

CTB was administered two weeks after optic nerve crush and mice were sacrificed two days after CTB administration to determine the extent of axon regeneration following injury. As shown in FIGS. 46A-46B, the number of axons per nerve up to at least 500 μm from the injury site was significantly higher in Tet2 wild-type mice that were administered OSK as compared to Tet2 knockout mice that were administered OSK. These results suggest that OSK-mediated axon regeneration is Tet2-dependent.

Figure 44A:
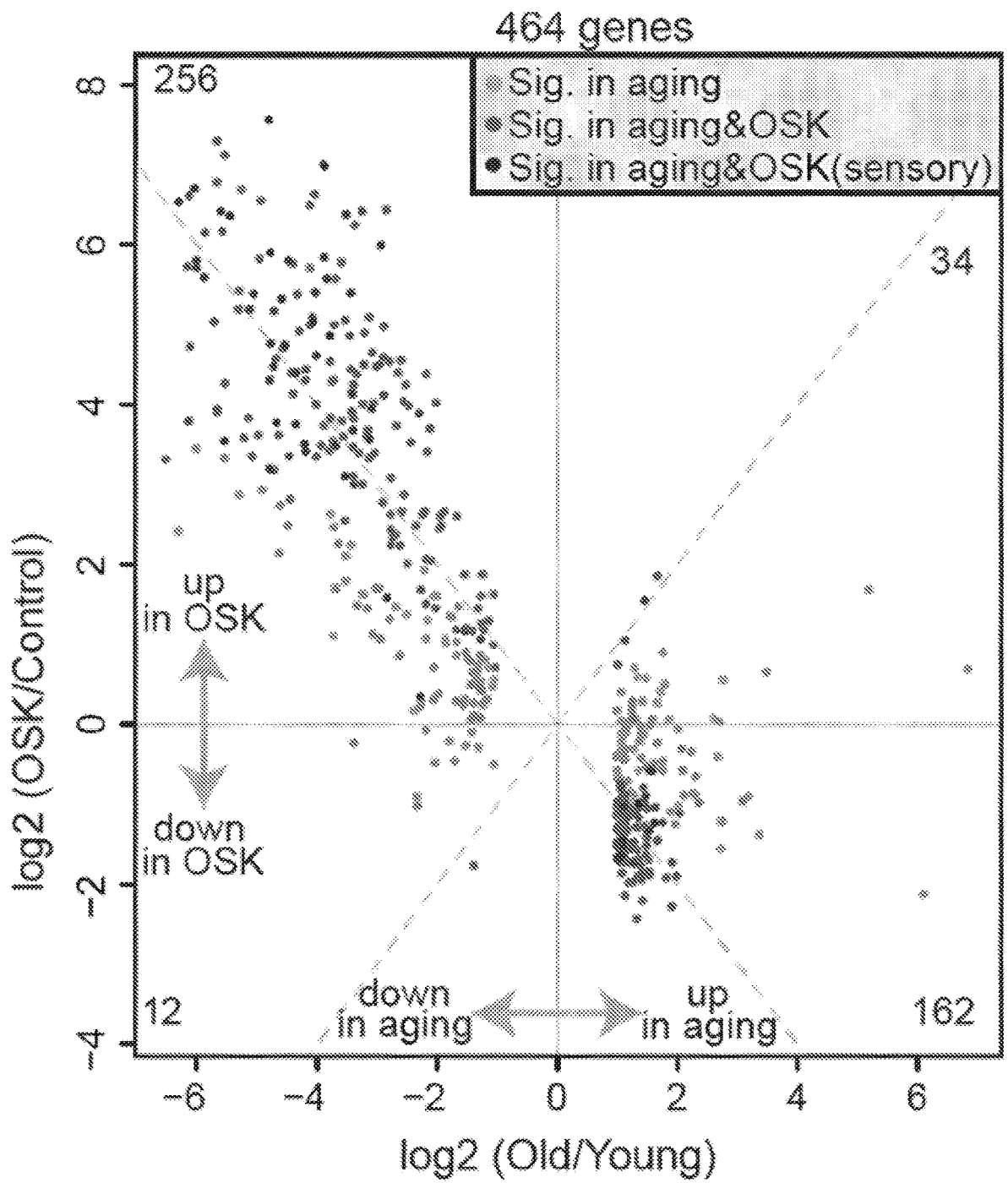
FIGS. 44A-44D show RNA-seq analysis of genes that reset their expression by Reviver treatment.
Figure 44B:
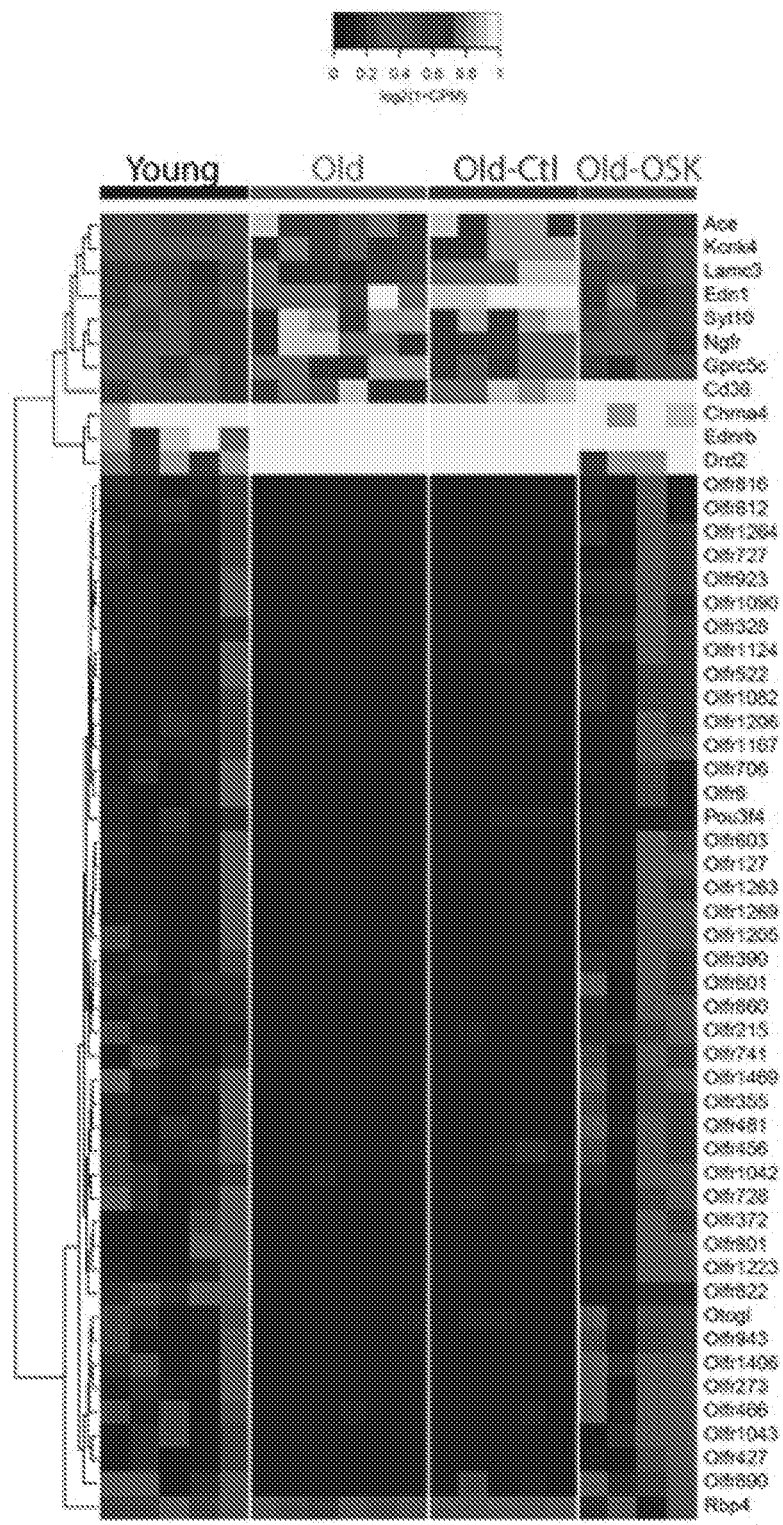
Figure 44C:
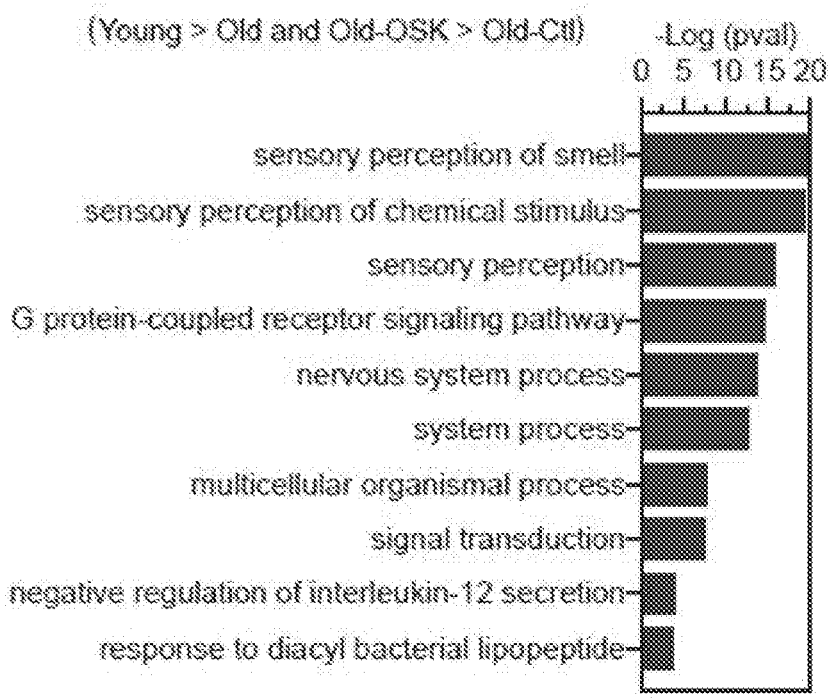
Figure 44D:
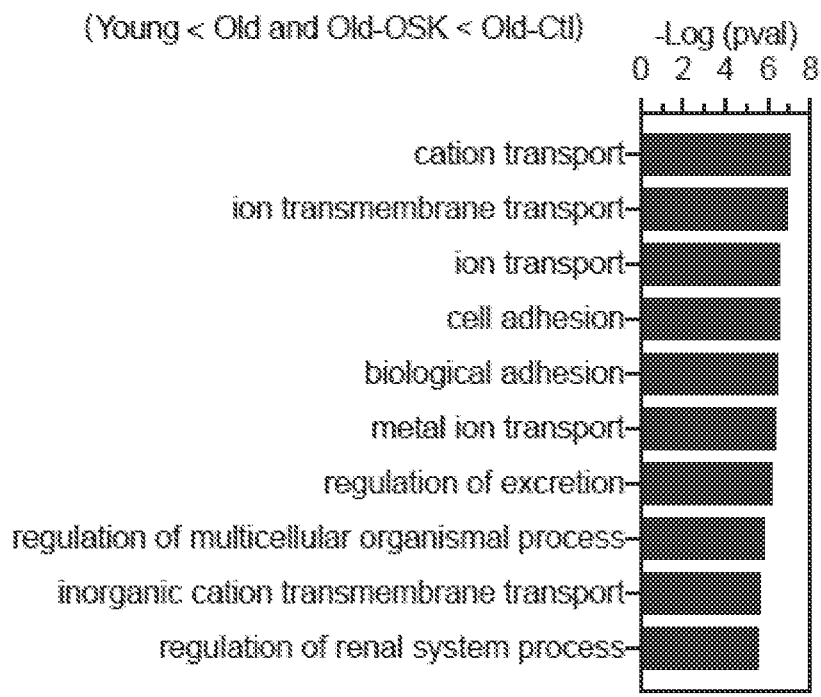

In order to determine the effect of reprogramming on the transcriptome in the retina, FACS-purified RGCs from intact old mice (12 month) and those that were either treated with empty control AAV (TRE-OSK) or OSK-On (tTA+TRE-OSK) were analyzed by genome-wide RNA-seq. Compared to RGCs from intact young mice (5 month), 464 genes were identified that were differentially-expressed during ageing (FIG. 35G, FIG. 35I, FIG. 44A, and Table 5) and not induced by empty AAV alone. Of these, 268 genes were downregulated during aging which were enriched in sensory perception genes (FIG. 35I), suggesting a decline of signaling receptors/sensory function during aging (FIGS. 44B and 44C). Interestingly, 116 of these genes appear uncharacterized, lacking an official gene name. The other 196 genes that are slightly up-regulated during aging are enriched of ion transporter genes (FIG. 44D).

Figure 35G:
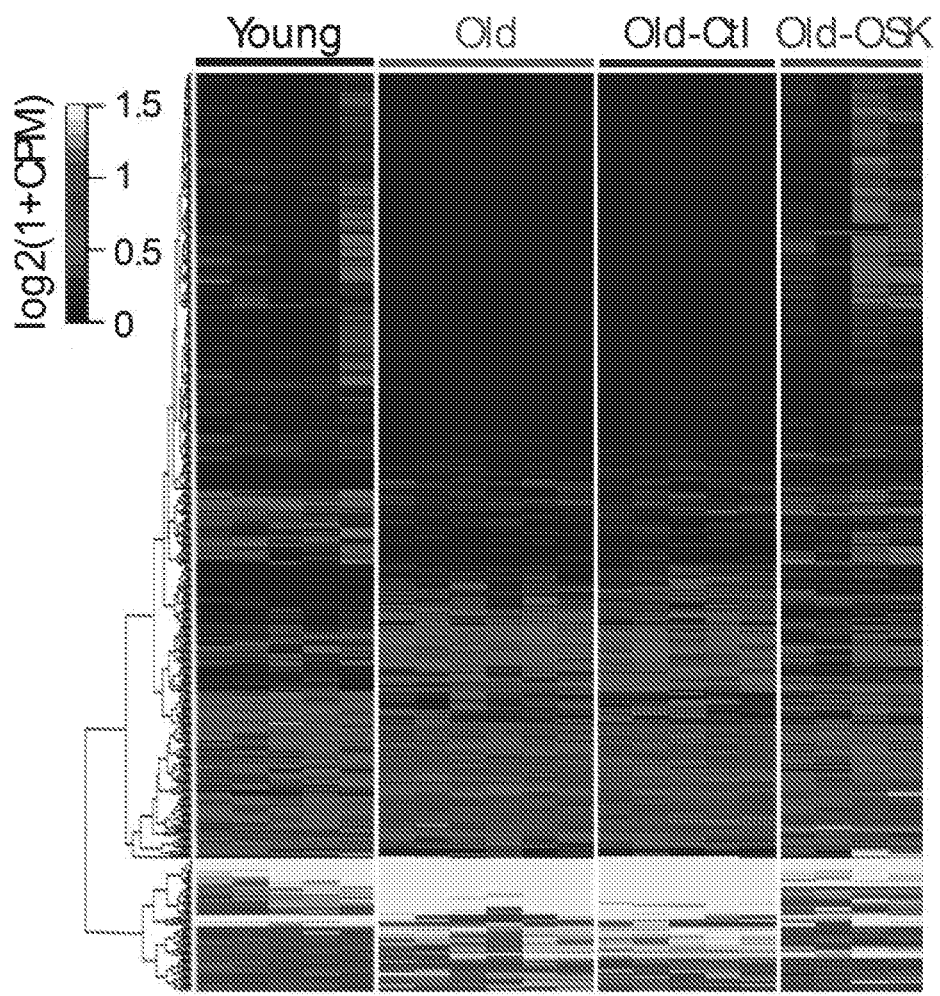
Figure 35H:
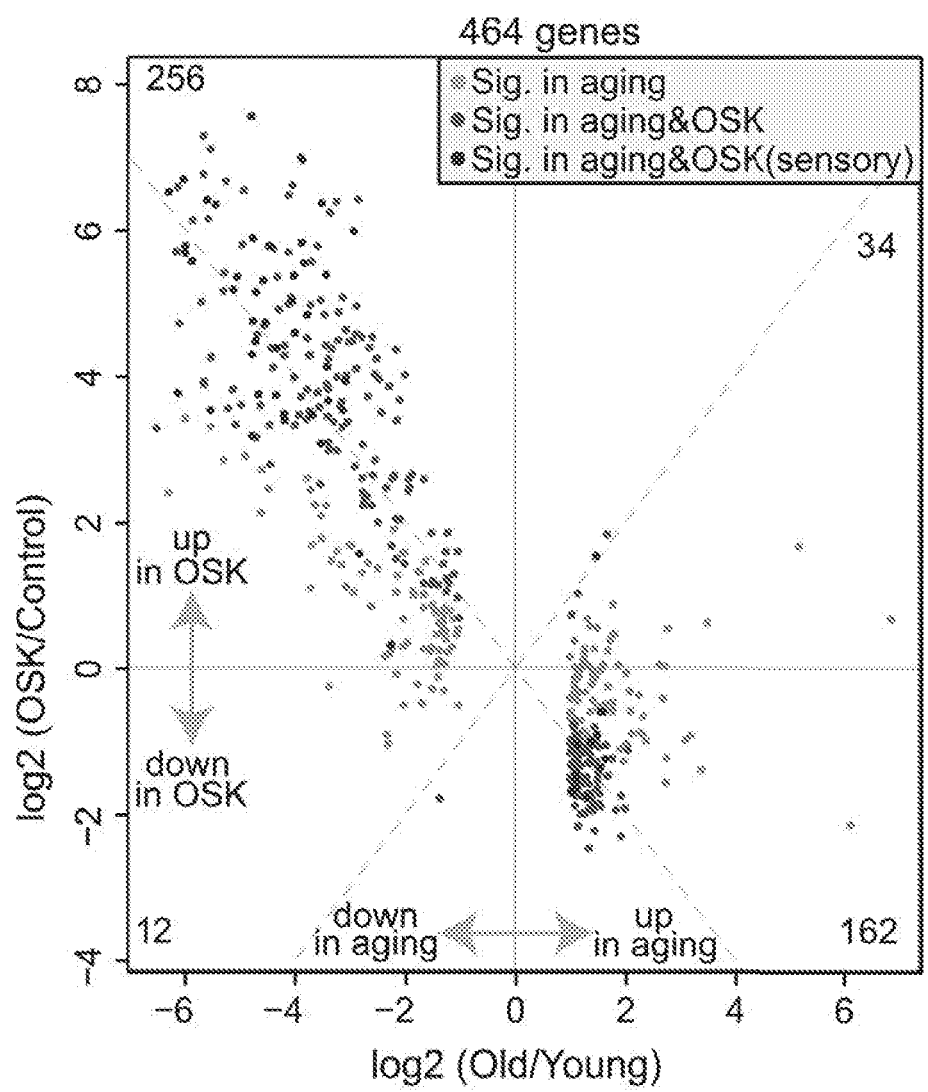
Figure 35I:
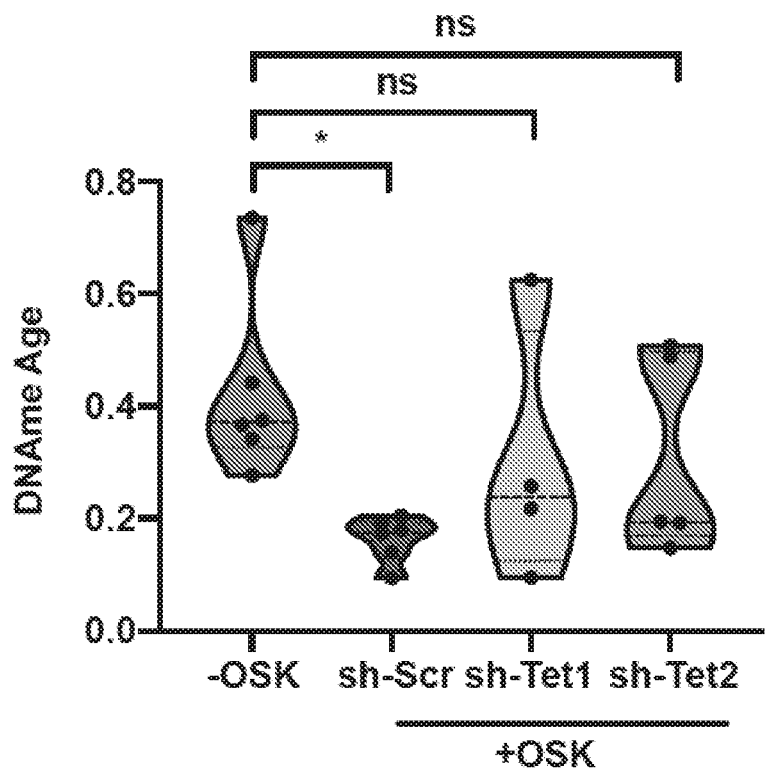

Remarkably, consistent with OSK resetting the epigenomic landscape, the vast majority (90%, 418) of the 464 genes that change in expression during aging were restored towards youthful levels after treatment (FIGS. 35G and 35H). Together, these results demonstrate that Tet-dependent in vivo reprogramming can restore youthful gene expression patterns, reverse the epigenetic clock, and restore the function of a tissue as complex as the retina.

Post-mitotic neurons in the central nervous system are some of the first cells in the body to lose their ability or regenerate. In this study, it was shown that in vivo reprogramming of aged neurons can reverse epigenetic age and allow them to regenerate and function as though they were young again. The requirement of the DNA demethylases Tet1 and Tet2 for this process indicates that DNA methylation at clock sites are not merely an indicator of ageing, but an active participant in it. It was concluded that mammalian cells retain a set of original epigenetic information, in the same way Shannon's observer stores information to ensure the recovery of lost information at a later time (SHANNON, C. E., *A Mathematical Theory of Communication*. The Bell System Technical Journal, 1948. 27: p. 379-423). How cells are able to find and remove the appropriate DNA methylation moieties and restore youthful gene expression patterns is still an open question, but even in the absence of this knowledge, our data indicate that the reversal of epigenetic age could be an effective translational strategy, not just to restore vision, but to give other tissues the ability to recover from injury and resist age-related decline.

TABLE 5

Genes that were differentially expressed during ageing in mice RGCs.

| Downregulated genes | Upregulated Genes |
|---|---|
| 1700031P21Rik | 0610040J01Rik |
| 1810053B23Rik | 1700080N15Rik |
| 2900045O20Rik | 2900064F13Rik |
| 2900060B14Rik | 4833417C18Rik |
| 4921504E06Rik | 4921522P10Rik |
| 4930402F11Rik | 4930447C04Rik |
| 4930453C13Rik | 4930488N15Rik |
| 4930455B14Rik | Ace |
| 4930500H12Rik | Ackr1 |
| 4930549P19Rik | Acot10 |
| 4930555B11Rik | Acvr1 |
| 4930556J02Rik | Adamts17 |
| 4932442E05Rik | Adra1b |
| 4933431K23Rik | AI504432 |
| 4933438K21Rik | Best3 |
| 6720475M21Rik | Boc |
| 9830132P13Rik | Cadm3 |
| A430010J10Rik | Cand2 |
| A530064D06Rik | Ccl9 |
| A530065N20Rik | Cd14 |
| Abcb5 | Cd36 |
| Abhd17c | Cfh |
| AC116759.2 | Chrm3 |
| AC131705.1 | Chrna4 |
| AC166779.3 | Cntn4 |
| Acot12 | Cracr2b |
| Adig | Cryaa |
| Akr1cl | CT573017.2 |
| Ankrd1 | Cyp26a1 |
| Asb15 | Cyp27a1 |
| Atp2c2 | D330050G23Rik |
| AU018091 | D930007P13Rik |
| AW822073 | Ddo |
| Btnl10 | Dgkg |
| C130093G08Rik | Dlk2 |
| C730027H18Rik | Dnaja1-ps |
| Ccdc162 | Drd2 |
| Chil6 | Dsel |
| Col26a1 | Dytn |
| Corin | Ecscr |
| Crls1 | Edn1 |
| Cybrd1 | Ednrb |
| Cyp2d12 | Efemp1 |
| Cyp7a1 | Elfn2 |
| D830005E20Rik | Epha10 |
| Dlx3 | Ephx1 |
| Dnah14 | Erbb4 |
| Dsc3 | Fam20a |
| Dthd1 | Fbxw21 |
| Eid2 | Ffar4 |
| Eps8l1 | Flt4 |
| EU599041 | Fmod |
| Fam90a1a | Foxp4 |
| Fancf | Fzd7 |
| Fau-ps2 | Gabrd |
| Fezf1 | Galnt15 |
| Gja5 | Galnt18 |
| Gm10248 | Gfra2 |
| Gm10513 | Ggt1 |
| Gm10635 | Gm10416 |
| Gm10638 | Gm14964 |
| Gm10718 | Gm17634 |
| Gm10722 | Gm2065 |
| Gm10800 | Gm32352 |
| Gm10801 | Gm33172 |
| Gm11228 | Gm34280 |
| Gm11251 | Gm35853 |
| Gm11264 | Gm36298 |
| Gm11337 | Gm36356 |
| Gm11368 | Gm36937 |
| Gm11485 | Gm3898 |
| Gm11693 | Gm42303 |
| Gm12793 | Gm42484 |
| Gm13050 | Gm42537 |
| Gm13066 | Gm42743 |
| Gm13323 | Gm43151 |
| Gm13339 | Gm43843 |
| Gm13346 | Gm44545 |
| Gm13857 | Gm44722 |
| Gm14387 | Gm45516 |
| Gm14770 | Gm45532 |

TABLE 5-continued

Genes that were differentially expressed during ageing in mice RGCs.

| Downregulated genes | Upregulated Genes |
|---|---|
| Gm15638 | Gm47494 |
| Gm16072 | Gm47982 |
| Gm16161 | Gm47989 |
| Gm16181 | Gm48398 |
| Gm17200 | Gm48495 |
| Gm17791 | Gm48593 |
| Gm18025 | Gm48958 |
| Gm18757 | Gm49089 |
| Gm18795 | Gm49326 |
| Gm18848 | Gm49331 |
| Gm19719 | Gm49760 |
| Gm20121 | Gm5796 |
| Gm20356 | Gm6374 |
| Gm2093 | Gm7276 |
| Gm21738 | Gm8237 |
| Gm21940 | Gm9796 |
| Gm22933 | Gm9954 |
| Gm24000 | Gpr75 |
| Gm24119 | Gprc5c |
| Gm25394 | Grid2ip |
| Gm26555 | Gsg1l2 |
| Gm27047 | Hapln4 |
| Gm28262 | Hcn3 |
| Gm28530 | Hcn4 |
| Gm29295 | Hhatl |
| Gm29825 | Hs6st2 |
| Gm29844 | Htr3a |
| Gm3081 | Il1rap |
| Gm32051 | Il1rapl2 |
| Gm32122 | Inka1 |
| Gm33056 | Kbtbd12 |
| Gm33680 | Kcnj11 |
| Gm34354 | Kcnk4 |
| Gm34643 | Kdelc2 |
| Gm3551 | Klhl33 |
| Gm36660 | Lamc3 |
| Gm36948 | Lilra5 |
| Gm37052 | Lman1l |
| Gm37142 | Lrfn2 |
| Gm37262 | Lrrc38 |
| Gm37535 | Lrrn4cl |
| Gm37569 | Ltc4s |
| Gm37589 | Mansc1 |
| Gm37647 | Mir344c |
| Gm37648 | Msr1 |
| Gm37762 | Mycbpap |
| Gm38058 | Myoc |
| Gm38069 | Ngfr |
| Gm38137 | Nipal2 |
| Gm38218 | Olfr1372-ps1 |
| Gm39139 | Otop3 |
| Gm42535 | P2rx5 |
| Gm42680 | P2ry12 |
| Gm42895 | P4ha2 |
| Gm42994 | Pcdha12 |
| Gm43027 | Pcdha2 |
| Gm43158 | Pcdhac2 |
| Gm43288 | Pcdhb18 |
| Gm43366 | Pcdhb5 |
| Gm44044 | Pcsk2os1 |
| Gm44081 | Pcsk6 |
| Gm44187 | Perp |
| Gm44280 | Pkp1 |
| Gm44535 | Plxna4 |
| Gm45338 | Prickle2 |
| Gm45644 | Qsox1 |
| Gm45740 | Rapgef4os2 |
| Gm46555 | Rbp4 |
| Gm46565 | Rcn3 |
| Gm4742 | Sec14l5 |
| Gm47485 | Sel1l3 |
| Gm47853 | Serpinh1 |
| Gm47992 | Sgpp2 |
| Gm48225 | Shisa6 |
| Gm48314 | Siah3 |
| Gm48383 | Siglech |
| Gm48673 | Slc12a4 |
| Gm48804 | Slc24a2 |
| Gm48832 | Slc2a5 |
| Gm4994 | Slc4a4 |
| Gm5487 | Slitrk3 |
| Gm5724 | Smagp |
| Gm595 | Smoc2 |
| Gm6012 | Speer4b |
| Gm6024 | Spon2 |
| Gm7669 | Sstr2 |
| Gm7730 | Sstr3 |
| Gm8043 | St3gal3 |
| Gm8953 | Stc1 |
| Gm9348 | Stc2 |
| Gm9369 | Syndig1 |
| Gm9495 | Syt10 |
| H2a12a | Thsd7a |
| Ido2 | Tlr8 |
| Igfbp1 | Tmem132a |
| Kif7 | Tmem132d |
| Klhl31 | Tmem200a |
| Lrrc31 | Tmem44 |
| Mc5r | Trpc4 |
| Mgam | Trpv4 |
| Msh4 | Unc5b |
| Mucl2 | Vgf |
| Mug1 | Vmn1r90 |
| Mybl2 | Vwc2l |
| Myh15 | Wfikkn2 |
| Nek10 | Wnt11 |
| Neurod6 | Wnt6 |
| Nr1h5 | Zeb2os |
| Olfr1042 | Zfp608 |
| Olfr1043 | Zfp976 |
| Olfr1082 | |
| Olfr1090 | |
| Olfr1124 | |
| Olfr1167 | |
| Olfr1205 | |
| Olfr1206 | |
| Olfr1223 | |
| Olfr1263 | |
| Olfr1264 | |
| Olfr1269 | |
| Olfr127 | |
| Olfr1291-ps1 | |
| Olfr1406 | |
| Olfr1469 | |
| Olfr215 | |
| Olfr273 | |
| Olfr328 | |
| Olfr355 | |
| Olfr372 | |
| Olfr390 | |
| Olfr427 | |
| Olfr456 | |
| Olfr466 | |
| Olfr481 | |
| Olfr522 | |
| Olfr6 | |
| Olfr601 | |
| Olfr603 | |
| Olfr706 | |
| Olfr727 | |
| Olfr728 | |
| Olfr741 | |
| Olfr801 | |
| Olfr812 | |
| Olfr816 | |
| Olfr822 | |
| Olfr860 | |
| Olfr890 | |
| Olfr923 | |
| Olfr943 | |

TABLE 5-continued

Genes that were differentially expressed
during ageing in mice RGCs.

| Downregulated genes | Upregulated Genes |
|---|---|
| Otogl | |
| Pi15 | |
| Pkhd1 | |
| Pkhd1l1 | |
| Platr6 | |
| Pou3f4 | |
| Prr9 | |
| Pvalb | |
| Rhag | |
| Sav1 | |
| Serpinb9b | |
| Skint1 | |
| Skint3 | |
| Skint5 | |
| Slc10a5 | |
| Slc6a4 | |
| Smok2a | |
| Tcaf3 | |
| Tomm20l | |
| Trcg1 | |
| Trdn | |
| Ugt1a6a | |
| Usp17la | |
| Vmn1r178 | |
| Vmn1r179 | |
| Vmn1r33 | |
| Vmn1r74 | |
| Vmn1r87 | |
| Vmn2r102 | |
| Vmn2r113 | |
| Vmn2r17 | |
| Vmn2r52 | |
| Vmn2r66 | |
| Vmn2r68 | |
| Vmn2r76 | |
| Vmn2r78 | |
| Wnt16 | |

Methods

Mouse Lines

C57BL6/J wild type mice are purchased from Jackson Laboratory (000664) for optic nerve crush and glaucoma model experiment. For ageing experiment, females from NIA Aged Rodent Colonies (https://www.nia.nih.gov/research/dab/aged-rodent-colonies-handbook) are used. Col1a1-tetOP-OKS-mCherry/Rosa26-M2rtTA alleles are described in Bar-Nur et al., Nat Methods, 2014. 11(11): p. 1170-6. All animal work was approved by Harvard Medical School, Boston Children's Hospital, Mass Eye and Ear Institutional animal care and use committees.

Production of AAVs

Vectors of AAV-TRE-OSK were made by cloning mouse Oct4, Sox2 and Klf4 cDNA into an AAV plasmid consisting of the a Tet Response Element (TRE3G promoter) and SV40 element. The other vectors were directly chemically synthesized. All pAAVs, as listed in Table 6, were then packaged into AAVs of serotype 2/2 or 2/9 (titers: >5×10$^{12}$ genome copies per milliliter). Adeno associated viruses were produced by Boston Children's Hospital Viral Core.

Systemical Delivery of AAV9 to Internal Organs

Expression in internal organs was achieved through retro-orbital injection of AAV9 (3×10$^{11}$ TRE-OSK plus 7×10$^{11}$ UBC-rtTA4). 1 mg/mL doxycycline was treated 3 weeks post injection continuously to induce OSK expression.

Cell Culture and Differentiation

Ear fibroblasts (EFs) were isolated from Reprogramming 4F (Jackson Laboratory 011011) or 3F (Hochedlinger lab) mice and cultured at 37° C. in DMEM (Invitrogen) containing Gluta-MAX, non-essential amino acids, and 10% fetal bovine serum (FBS). EFs of WT 4F and WT 3F mice were passaged to P3 and treated with doxycycline (2 mg/ml) for the indicated time periods in the culture medium.

SH-SY5Y neuroblastoma cells were obtained from the American Tissue Culture Collection (ATCC, CRL-2266) and maintained according to ATCC recommendations. Basically, the cells were cultured in a 1:1 mixture of Eagle's Minimum Essential Medium (EMEM, ATCC, 30-2003) and F12 medium (ThermoFisher Scientific, 11765054), supplemented with 10% fetal bovine serum (FBS, Sigma, F0926) and 1×penicillin/streptomycin (ThermoFisher Scientific, 15140122). Cells were cultured at 37° C. with 5% $CO_2$ and 3% $O_2$. Cells were passaged when reaching ~80% confluency.

SH-SY5Y cells were differentiated into neurons as previously described 1,2, with some modifications. Briefly, 1 day after plating, cells started to be differentiated in EMEM/F12 medium (1:1) containing 2.5% FBS, 1x penicillin/streptomycin, and 10 µM all-trans retinoic acid (ATRA, Stemcell Technologies, 72264) (Differentiation Medium 1) for 3 days, followed by treating the cells in EMEM/F12 (1:1) containing 1% FBS, 1×penicillin/streptomycin, and 10 µM ATRA (Differentiation Medium 2) for 3 days. Cells were then splitted into 35 mm cell culture plates coated with poly-D-lysine (ThermoFisher Scientific, A3890401). 1 day after splitting, neurons were matured in serum-free neurobasal/B27 plus culture medium (ThermoFisher Scientific, A3653401) containing 1×Glutamax (ThermoFisher Scientific, 35050061), 1×penicillin/streptomycin, and 50 ng/ml BDNF (Alomone labs) (Differentiation Medium 3) for at least 5 days.

Neurite Regeneration Assay

The differentiated neurons from SH-SY5Y cells were transduced with AAV.DJ vectors at 10$^6$ genome copy per cell. 5 days after transduction, 100 nM vincristine (Sigma, V8879) was added to the cells for 24 hours to induce neurite degeneration. After vincristine treatment, neurons were washed in PBS twice and fresh Differentiation medium 3 was added back to the plates. Neurons were followed for neurite outgrowth for 2-3 weeks. Phase-contrast images were taken at 100× magnification every three to four days. Neurite area was quantified using Image J.

Cell Cycle Analysis

Cells were harvested and fixed with 70% cold ethanol for 16 hours at 4° C. After fixation, cells were washed twice with PBS, followed by incubation with PBS containing 50 g/mL propidium iodide (Biotium, 40017) and 100 µg/mL RNase A (Omega) for 1 hour at room temperature. PI stained samples were analyzed on BD LSR II analyzer, and only single cells were gated for analysis. Cell cycle profiles were analyzed using FCS Express 6 (De Novo Software).

Human Neuron Methylation Studies and Epigenetic Clock

DNA was extracted from cells using the Zymo Quick DNA mini-prep plus kit (D4069) according to the manufacturer's instructions and DNA methylation levels were measured on Illumina 850 EPIC arrays according to the manufacturer's instructions. The Illumina BeadChip (EPIC) measures bisulfite-conversion-based, single-CpG resolution DNAm levels at different CpG sites in the human genome. These data were generated by following the standard protocol of Illumina methylation assays, which quantifies methylation levels by the 3 value using the ratio of intensities between methylated and un-methylated alleles. Specifically, the 3 value is calculated from the intensity of the methylated (M corresponding to signal A) and un-methylated (U corresponding to signal B) alleles, as the ratio of fluorescent signals 3=Max(M,0)/[Max(M,0)+ Max(U,0)+100]. Thus, 3 values range from 0 (completely un-methylated) to 1 (completely methylated). We used the "noob" normalization method, which is implemented in the "minfi" R package (Triche et al., NAR 2013, Fortin et al., Bioinformatics 2017). The mathematical algorithm and available software underlying the skin & blood clock (based on 391 CpGs) is presented in Horvath et al., Aging 2018.

AAV2 Virus Intravitreal Injection

For intravitreal injection, adult animals were anesthetized with ketamine/xylazine (100/10 mg/kg) and then AAV (1-3 µl) was injected intravitreally, just posterior to the limbus-parallel conjunctival vessels, with a fine glass pipette attached to the Hamilton syringe using plastic tubing. In elevated IOP model, mice received a 1 µl intravitreal injection between 3-4 weeks post microbead injection.

Optic Nerve Crush

For optic nerve crush in anesthetized animals, the optic nerve was accessed intraorbitally and crushed using a pair of Dumont #5 forceps (FST), two weeks after AAV injection. Alexa-conjugated cholera toxin beta subunit (CTB-555, 1 mg/ml; 1-2 µl) injection was performed 2-3 days before euthanasia to trace regenerating RGC axons. More detailed surgical methods were described by Park et al., Science, 2008. 322(5903): p. 963-6.

In Vivo Doxycycline Induction or Suppression

Induction of Tet-On system or suppression of Tet-Off system in the retina were performed by administration of doxycycline hyclate (2 mg/ml) (Sigma) in the drinking water. Induction of Tet-On system in the whole body were performed by administration of doxycycline (1 mg/ml) (USP grade, MP Biomedicals 0219895505) in the drinking water.

Axon Regeneration Quantification

Number of regenerating axons in the optic nerve was estimated by counting the number of CTB-labeled axons at different distances from the crush site as described previously (Park, K. K., et al., *Promoting axon regeneration in the adult CNS by modulation of the PTEN/mTOR pathway*. Science, 2008. 322(5903): p. 963-6).

Whole-Mount Optic Nerve Preparation

Optic nerves and connecting chiasm were dehydrated in methanol for 5 min, then incubated overnight with Visikol® HISTO-1™. Next day nerves were transferred to Visikol® HISTO-2™ and then incubated for 3 hr. Finally, optic nerves and connecting chiasm were mounted with Visikol® HISTO-2™

Immunofluorescence

Whole-mount retinas were blocked with horse serum 4° C. overnight then incubated at 4° C. for 3 days with primary antibodies: Mouse anti-Oct4 (1:100, BD bioscience, 611203), Rabbit anti-Sox2 (1:100, Cell signaling, 14962), Goat anti-Klf4 (1:100, R&D system, AF3158), Rabbit anti-Brn3a (1:200, EMD Millipore, MAB1585), and Guinea pig anti-RBPMS (1:400, Raygene custom order A008712 to peptide GGKAEKENTPSEANLQEEEVRC) diluted in PBS, BSA (3%) Triton X-100 (0.5%). Then, tissues were incubated at 4° C. overnight with appropriate Alexa Fluor conjugate secondary antibodies (Alexa 405, 488, 567, 674; Invitrogen) diluted with the same blocking solution as the primary antibodies, generally used at 1:400 final dilution. For section staining, primary overnight at 4° C. and then secondary at room temperature for 2 h. Sections or whole-mount retinas were mounted with VECTASHIELD Antifade Mounting Medium.

Western Blot

SDS-PAGE and western blot analysis was performed according to standard procedures and detected with the ECL detection kit. Antibody used: Rabbit anti-Sox2 (1:100, EMD Millipore, AB5603), Mouse anti-Klf4 (1:1000, ReproCell, 09-0021), Rabbit anti-p-S6 (5240/244) (1:1000, CST, 2215), Mouse anti-S6 (1:1000, CST, 2317), Mouse anti-β-Tubulin (1:1000, Sigma-Aldrich, 05-661), Mouse anti-β-Actin-Peroxidase antibody (1:20,000, Sigma-Aldrich, A3854).

RGCs Survival and Phospho-S6 Signal

RBPMS-positive cells in the ganglion layer were counted using a fluorescent microscope after immunostaining whole-mount retinas with anti-RBPMs antibodies. A total of four random fields per retina were enumerated. The average number per field was determined, and the percentages of viable RGCs were obtained by comparing the values determined from the uninjured contralateral retinas. In the same condition, after phospho-S6 staining, the densities of phopsho-S6-positive RGCs were obtained by comparing the value from the uninjured contralateral retinas.

RGC Enrichment

Retinas were fresh dissected and dissociated in AMES media using papain, then triturated carefully and stained with Thy1.2-PE-Cy7 anti-body (Invitrogen 25-0902-81) and Calcine Blue live-dead cell stain, then flow sorted on a BD FACS Aria using an 130 µm nozzle to collect over 10,000 Thy1.2+ and Clacine blue+ cells (1-2% of total events). Freezed cells were sent to Genewiz for RNA extraction and ultra low input RNA-seq sequencing, or to Zymo research for DNA extraction and ultra low input RRBS sequencing.

Classic RRBS Library Preparation

DNA was extracted using Quick-DNA Plus Kit Microprep Kit. 2-10 ng of starting input genomic DNA was digested with 30 units of MspI (NEB). Fragments were ligated to pre-annealed adapters containing 5'-methyl-cytosine instead of cytosine according to Illumina's specified guidelines. Adaptor-ligated fragments 50 bp in size were recovered using the DNA Clean & Concentrator™-5 (Cat #: D4003). The fragments were then bisulfite-treated using the EZ DNA Methylation-Lightning™ Kit (Cat #: D5030). Preparative-scale PCR was performed and the resulting products were purified with DNA Clean & Concentrator™-5 (Cat #: D4003) for sequencing on an Illumina HiSeq using 2×125 bp PE.

DNA Methylation Age Analysis of Mouse RGC

Reads were filtered using trim galore v0.4.1 and mapped to the mouse genome GRCm38 using Bismark v0.15.0. Methylation counts on both positions of each CpG site were combined. Only CpG sites covered in all samples were considered for analysis. This resulted in total of 708156 sites. For the rDNA methylation clock reads were mapped to BK000964 and the coordinates were adjusted accordingly (Wang et al., Genome Res 29, 325-333, doi:10.1101/gr.241745.118 (2019)). 70/72 sites were covered for rDNA clock, compared to 102/435 sites of whole lifespan multi-tissue clock (Meer et al., Elife 7, doi:10.7554/eLife.40675 (2018)), or 248/582 and 77,342/193,651 sites (ridge) of two entire lifespan multi-tissue clocks (Thompson et al., Aging (Albany NY) 10, 2832-2854, doi:10.18632/aging.101590 (2018)).

Microbead-Induced Mouse Model of Elevated IOP

Mice were anesthetized by intraperitoneal injection of a mixture of ketamine (100 mg/kg; Ketaset; Fort Dodge Animal Health, Fort Dodge, IA) and xylazine (9 mg/kg; TranquiVed; Vedco, Inc., St. Joseph, MO) supplemented by topical application of proparacaine (0.5%; Bausch & Lomb, Tampa, FL). Elevation of IOP was induced unilaterally by injection of polystyrene microbeads (FluoSpheres; Invitrogen, Carlsbad, CA; 15-m diameter) to the anterior chamber of the right eye of each animal under a surgical microscope, as previously reported (Krishnan et al., J Immunol, 2016. 197(12): p. 4626-4638). Briefly, microbeads were prepared at a concentration of $5.0 \times 10^6$ beads/mL in sterile physiologic saline. The right cornea was gently punctured near the center using a sharp glass micropipette (World Precision Instruments Inc., Sarasota, FL). A 2 μL volume of microbeads was injected through the preformed hole into the anterior chamber followed by injection of an air bubble via the micropipette connected with a Hamilton syringe. Any mice that developed signs of inflammation (clouding of the cornea, edematous cornea etc) were excluded from the study.

IOP (Intraocular Pressure) Measurements

IOPs were measured with a rebound TonoLab tonometer (Colonial Medical Supply, Espoo, Finland), as previously described (Krishnan et al., J Immunol, 2016. 197(12): p. 4626-4638; Mukai et al., PLoS One, 2019. 14(1): p. e0208713). Mice were anesthetized by 3% isoflurane in 100% oxygen (induction) followed by 1.5% isoflurane in 100% oxygen (maintenance) delivered with a precision vaporizer. IOP measurement was initiated within 2 to 3 min after the loss of a toe pinch reflex or tail pinch response. Anesthetized mice were placed on a platform and the tip of the pressure sensor was placed approximately ⅛ inch from the central cornea. Average IOP was displayed automatically after 6 measurements after elimination of the highest and lowest values. The machine-generated mean was considered as one reading, and six readings were obtained for each eye. All IOPs were taken at the same time of day (between 10:00 and 12:00 hours) due to the variation of IOP throughout the day.

Optomotor Response

Visual acuity of mice was measured using an optomotor re-flex-based spatial frequency threshold test (Gao et al., Am J Pathol, 2016. 186(4): p. 985-1005; Sun et al., Glia, 2013. 61(8): p. 1218-1235). Mice would be able to freely move and were placed on a pedestal located in the center of an area formed by four computer monitors arranged in a quadrangle. The monitors displayed a moving vertical black and white sinusoidal grating pattern. A blinded observer, unable to see the direction of the moving bars, monitored the tracking behavior of the mouse. Tracking was considered positive when there was a movement of the head (motor response) to the direction of the bars or rotation of the body in the direction concordant with the stimulus. Each eye would be tested separately depending on the direction of rotation of the grating. The staircase method was used to determine the spatial frequency start from 0.15 to 0.40 cycles/deg, the interval is 0.05 cycles/deg. Rotation speed (12°/s) and contrast (100%) were kept constant. Responses were measured before and after treatment by individuals blinded to the group of the animal and the treatment.

Pattern Electroretinogram (pERG)

Mice were anesthetized with ketamine/xylazine (100 mg/kg and 20 mg/kg) and the pupils dilated with one drop of 1% tropicamide ophthalmic solution. The mice were placed on a built-in warming plate (Celeris, Full-Field and Pattern Stimulation for the rodent model), that maintained the body temperature at 37 C and kept under dim red light throughout the procedure. The visual stimuli of a black and white reversing checkerboard pattern with a check size of 1° was displayed on light guide electrode-stimulators placed directly on the ocular surface of both eyes and centered with the pupil. The visual stimuli were presented at 98% contrast and constant mean luminance of 50 $cd/m^2$, spatial frequency:0.05 cyc/deg; temporal frequency:1 Hz. A total of 300 complete contrast reversals of pERG were repeated twice in each eye and the 600 cycles were segmented and averaged and recorded. The averaged PERGs were analyzed to evaluate the peak to trough N1 to P1 (positive wave) amplitude.

Quantification of Optic Nerve Axons

For quantification of axons, optic nerves were dissected and fixed overnight in Karnovsky's reagent (50% in phosphate buffer). Semi-thin cross-sections of the nerve were taken at 1.0 mm posterior to the globe and stained with 1% p-phenylenediamine (PPD) for evaluation by light microscopy. Optic nerve cross sections were imaged at 60× magnification using a Nikon microscope (Eclipse E800, Nikon, Japan) with the DPController software (Olympus, Japan) and 6-8 non-overlapping photomicrographs were taken to cover the entire area of each optic nerve cross-section. Using ImageJ (Version 2.0.0-rc-65/1.51u), a 100 μM×100 μM square was placed on each 60× image and all axons within the square (0.01 $mm^2$) were counted using the threshold and analyze particles function in image J as previously described (Krishnan et al., J Immunol, 2016. 197(12): p. 4626-4638; Mukai et al., PLoS One, 2019. 14(1): p. e0208713; Gao et al., Am J Pathol, 2016. 186(4): p. 985-1005). Damaged axons stain darkly with PPD and are not counted. The average axon counts in the 6-8 images were used to calculate the axon density per square millimeter of optic nerve. Individuals blinded to the experimental groups performed all axon counts.

Quantification of Retinal Ganglion Cells

For ganglion cell counting, images of whole mount retinas were acquired using a 63× oil immersion objective of the Leica TCS SP5 confocal microscope (Leica Microsystems). The retinal whole mount was divided into four quadrants and three to four images (248.53 μm by 248.53 μm in size) were taken from the midperipheral and peripheral regions of each quadrant, for a total of twelve to sixteen images per retina. were taken from the midperipheral and peripheral regions (4 images per quadrant). The images were obtained as z-stacks (0.5 m) and all Brn3a positive cells in the ganglion cell layer of each image were counted manually as previously described (Gao et al., Am J Pathol, 2016. 186(4): p. 985-1005). Briefly, RGCs were counted using the "Cell Counter" plugin (fiji.sc/Cell_Counter) in Fiji is Just ImageJ software (ImageJ Fiji, version 2.0.0-rc-69/1.52n). Each image was loaded into Fiji and a color counter type was chosen to mark all Brn3a stained RGCs within each image (0.025 $mm^2$). The average number of RGCs in the 12 to sixteen images were used to calculate the RGC density per square millimeter of retina. Two individuals blinded to the experimental groups performed all RGC counts.

Total RNA Extraction and Sample QC

Total RNA was extracted following the Trizol Reagent User Guide (Thermo Fisher Scientific). 1 ul 10 mg/ml Glycogen was added to the supernatant to increase RNA recovery. RNA was quantified using Qubit 2.0 Fluorometer (Life Technologies, Carlsbad, CA, USA) and RNA integrity was checked with TapeStation (Agilent Technologies, Palo Alto, CA, USA) to see if the concentration met the requirements.

Ultra-Low Input RNA Library Preparation and Multiplexing

RNA samples were quantified using Qubit 2.0 Fluorometer (Life Technologies, Carlsbad, CA, USA) and RNA integrity was checked with 2100 TapeStation (Agilent Technologies, Palo Alto, CA, USA). RNA library preparations, sequencing reactions, and initial bioinformatics analysis were conducted at GENEWIZ, LLC. (South Plainfield, NJ, USA). SMART-Seq v4 Ultra Low Input Kit for Sequencing was used for full-length cDNA synthesis and amplification (Clontech, Mountain View, CA), and Illumina Nextera XT library was used for sequencing library preparation. Briefly, cDNA was fragmented and adaptor was added using Transposase, followed by limited-cycle PCR to enrich and add index to the cDNA fragments. The final library was assessed with Qubit 2.0 Fluorometer and Agilent TapeStation.

Sequencing 2×150 bp PE

The sequencing libraries were multiplexed and clustered on two lanes of a flowcell. After clustering, the flowcell were loaded on the Illumina HiSeq instrument according to manufacturer's instructions. The samples were sequenced using a 2×150 Paired End (PE) configuration. Image analysis and base calling were conducted by the HiSeq Control Software (HCS) on the HiSeq instrument. Raw sequence data (.bcl files) generated from Illumina HiSeq were be converted into fastq files and de-multiplexed using Illumina bcl2fastq v. 2.17 program. One mis-match was allowed for index sequence identification. RNA-seq analysis Paired-end reads were aligned with hisat2 D.1.0 to the Ensembl GRCm38 primary assembly using splice junctions from the Ensembl release 84 annotation. Paired read counts were quantified using featureCounts v1.6.4 using reads with a MAPQ>h20. Differentially-expressed genes for each pairwise comparison were identified with edgeR v3.26, testing only genes with at least 0.1 counts-per-million (CPM) in at least three samples. Gene ontology analysis of differentially-expressed genes was performed with AmiGO v2.5.12. Age-associated sensory perception genes were extracted from the mouse Sensory Perception (GO:0007600) category the Gene Ontology database, including genes that were differentially expressed (q<=0.05) in 12 versus 5 month old mice, excluding genes that were induced by the Control virus alone (q<=0.1).

TABLE 6

AAV vectors used in Example 16

| Vector | qPCR Primer for measuring titer | Source |
| --- | --- | --- |
| pAAV-TRE-Oct4 | TRE3G | Disclosed herein |
| pAAV-TRE-Sox2 | TRE3G | Disclosed herein |
| pAAV-TRE-Klf4 | TRE3G | Disclosed herein |
| pAAV-TRE-Oct4-Sox2 | TRE3G | Disclosed herein |
| pAAV-TRE-OSK | TRE3G | Disclosed herein |
| pAAV-TRE-d2EGFP | TRE3G | Disclosed herein |
| pAAV-CMV-rtTAV16 | WPRE | Disclosed herein |
| pAAV-CAG-tTA | hGH | Disclosed herein |
| pAAV-sh-Scr-YFP | WPRE | Plasmid #85741 |
| pAAV-Sh-Tet1-YFP | WPRE | Plasmid #85742 |
| pAAV-sh-Tet2-YFP | WPRE | Plasmid #85743 |

TABLE 7

Primers

| Primer name | Sequence | SEQ ID NO: |
| --- | --- | --- |
| TRE3G F | AACGTATCTACAGTTTACTCCCTATC | 53 |
| TRE3G R | GGTAGGAAGTGGTACGGAAAG | 54 |
| WPRE F | CACTGACAATTCCGTGGTGT | 55 |
| WPRE R | GAGATCCGACTCGTCTGAGG | 56 |
| hGH F | TGGGAAGACAACCTGTAGGG | 57 |
| hGH R | TGAAACCCCGTCTCTACCAA | 58 |

TABLE 8

Primers used for RT-PCR

| Gene | Primer sequence | SEQ ID NO: |
| --- | --- | --- |
| mOct4 F | ACA TCG CCA ATC AGC TTG G | 59 |
| mOct4 R | AGA ACC ATA CTC GAA CCA CAT CC | 60 |
| mSox2 F | ACA GAT GCA ACC GAT GCA CC | 61 |
| mSox2 R | TGG AGT TGT ACT GCA GGG CG | 62 |
| mKlf4 F | GTGCCCCGACTAACCGTTG | 63 |
| mKlf4 R | GTCGTTGAACTCCTCGGTCT | 64 |
| mMyc F | ATGCCCCTCAACGTGAACTTC | 65 |
| mMyc R | CGCAACATAGGATGGAGAGCA | 66 |
| mHist1 h2a F | GCG ACA ACA AGA AGA CGC GCA T | 67 |
| mHist1 h2a R | CTG GAT GTT GGG CAG GAC GCC | 68 |
| mHist1 h2b F | AAG AAG GAC GGC AAG AAG CGC A | 69 |
| mHist1 h2b R | CGC TCG AAG ATG TCG TTC ACG A | 70 |
| mHIST1 H3.1/H3.2 F | GAA GAA GCC TCA CCG CTA CCG | 71 |
| mHIST1 H3.1/H3.2 R | GGT TGG TGT CCT CAA ACA GAC CC | 72 |
| mHist1 h4 F | AAC ATC CAG GGC ATC ACC AAG C | 73 |
| mHist1 h4 R | GTT CTC CAG GAA CAC CTT CAG C | 74 |
| mLmnb1 F | CCG GCC TCA AGG CTC TCT A | 75 |
| mLmnb1 R | TGC CGC CTC ATA CTC TCG AA | 76 |
| mActb F | AGT GTG ACG TTG ACA TCC GT | 77 |
| mActb R | TGC TAG GAG CCA GAG CAG TA | 78 |
| mNanog F | TCTTCCTGGTCCCCACAGTTT | 79 |
| mNanog R | GCAAGAATAGTTCTCGGGATGAA | 80 |
| mChaf1a R | GTG TCT TCC TCA ACT TTC TCC TTG G | 81 |
| mChaf1a F | CGC GGA CAG CCG CGG CCG TGG ATT GC | 82 |
| mChaf1b R | GGC TCC TTG CTG TCA TTC ATC TTC CAC | 83 |
| mChaf1b F | CAC CGC CGT CAG GAT CTG GAA GTT GG | 84 |
| mLmnb1 F | CCG GCC TCA AGG CTC TCT A | 85 |
| mLmnb1 R | TGC CGC CTC ATA CTC TCG AA | 86 |
| mTet1 F | TCAAGCAATGGACCACTGGG | 87 |
| mTet1 R | TCTCCATGAGCTCCCTGACA | 88 |
| mTet2 F | ACT CCT GGT GAA CAA AGT CAG A | 89 |
| mTet2 R | CAT CCC TGA GAG CTC TTG CC | 90 |
| mGAPDH F | CCA ATG TGT CCG TCG TGG ATC T | 91 |
| mGAPDH R | GTT GAA GTC GCA GGA GAC AAC C | 92 |

TABLE 8-continued

Primers used for RT-PCR

| Gene | Primer sequence | SEQ ID NO: |
|---|---|---|
| mp16 (Cdkn2a) F | ACA TCA AGA CAT CGT GCG ATA TT | 93 |
| mp16 (Cdkn2a) R | CCA GCG GTA CAC AAA GAC CA | 94 |
| mApob F | AAG CAC CTC CGA AAG TAC GTG | 95 |
| mApob R | CTC CAG CTC TAC CTT ACA GTT GA | 96 |
| hTet2 F | GATAGAACCAACCATGTTGAGGG | 97 |
| hTet2 R | TGGAGCTTTGTAGCCAGAGGT | 98 |
| hActb F | CACCATTGGCAATGAGCGGTTC | 99 |
| hActb R | AGGTCTTTGCGGATGTCCACGT | 100 |

Example 17. Non-Limiting Examples of Sequences

```
Nucleotide sequence encoding Mus Musculus OCT4 (no stop codon)
(SEQ ID NO: 1):
ATGGCTGGACACCTGGCTTCAGACTTCGCCTTCTCACCCCCACCAGGTGGGGGTG

ATGGGTCAGCAGGGCTGGAGCCGGGCTGGGTGGATCCTCGAACCTGGCTAAGCT

TCCAAGGGCCTCCAGGTGGGCCTGGAATCGGACCAGGCTCAGAGGTATTGGGGA

TCTCCCCATGTCCGCCCGCATACGAGTTCTGCGGAGGGATGGCATACTGTGGACC

TCAGGTTGGACTGGGCCTAGTCCCCCAAGTTGGCGTGGAGACTTTGCAGCCTGAG

GGCCAGGCAGGAGCACGAGTGGAAAGCAACTCAGAGGGAACCTCCTCTGAGCCC

TGTGCCGACCGCCCCAATGCCGTGAAGTTGGAGAAGGTGGAACCAACTCCCGAG

GAGTCCCAGGACATGAAAGCCCTGCAGAAGGAGCTAGAACAGTTTGCCAAGCTG

CTGAAGCAGAAGAGGATCACCTTGGGGTACACCCAGGCCGACGTGGGGCTCACC

CTGGGCGTTCTCTTTGGAAAGGTGTTCAGCCAGACCACCATCTGTCGCTTCGAGG

CCTTGCAGCTCAGCCTTAAGAACATGTGTAAGCTGCGGCCCCTGCTGGAGAAGTG

GGTGGAGGAAGCCGACAACAATGAGAACCTTCAGGAGATATGCAAATCGGAGA

CCCTGGTGCAGGCCCGGAAGAGAAAGCGAACTAGCATTGAGAACCGTGTGAGGT

GGAGTCTGGAGACCATGTTTCTGAAGTGCCCGAAGCCCTCCCTACAGCAGATCAC

TCACATCGCCAATCAGCTTGGGCTAGAGAAGGATGTGGTTCGAGTATGGTTCTGT

AACCGGCGCCAGAAGGGCAAAAGATCAAGTATTGAGTATTCCCAACGAGAAGAG

TATGAGGCTACAGGGACACCTTTCCCAGGGGGGCTGTATCCTTTCCTCTGCCCC

CAGGTCCCCACTTTGGCACCCCAGGCTATGGAAGCCCCCACTTCACCACACTCTA

CTCAGTCCCTTTTCCTGAGGGCGAGGCCTTTCCCTCTGTTCCCGTCACTGCTCTGG

GCTCTCCCATGCATTCAAAC

Amino acid sequence encoding Mus Musculus OCT 4 (SEQ ID NO: 2):
MAGHLASDFAFSPPPGGGDGSAGLEPGWVDPRTWLSFQGPPGGPGIGPGSEVLGISP

CPPAYEFCGGMAYCGPQVGLGLVPQVGVETLQPEGQAGARVESNSEGTSSEPCADR

PNAVKLEKVEPTPEESQDMKALQKELEQFAKLLKQKRITLGYTQADVGLTLGVLFG

KVFSQTTICRFEALQLSLKNMCKLRPLLEKWVEEADNNENLQEICKSETLVQARKRK

RTSIENRVRWSLETMFLKCPKPSLQQITHIANQLGLEKDVVRVWFCNRRQKGKRSSI

EYSQREEYEATGTPFPGGAVSFPLPPGPHFGTPGYGSPHFTTLYSVPFPEGEAFPSVPV

TALGSPMHSN
```

-continued

Nucleotide sequence encoding Mus Musculus SOX2 (no stop codon)
(SEQ ID NO: 3):
ATGTATAACATGATGGAGACGGAGCTGAAGCCGCCGGGCCCGCAGCAAGCTTCG

GGGGGCGGCGGCGGAGGAGGCAACGCCACGGCGGCGGCGACCGGCGGCAACCA

GAAGAACAGCCCGGACCGCGTCAAGAGGCCCATGAACGCCTTCATGGTATGGTC

CCGGGGGCAGCGGCGTAAGATGGCCCAGGAGAACCCCAAGATGCACAACTCGG

AGATCAGCAAGCGCCTGGGCGCGGAGTGGAAACTTTTGTCCGAGACCGAGAAGC

GGCCGTTCATCGACGAGGCCAAGCGGCTGCGCGCTCTGCACATGAAGGAGCACC

CGGATTATAAATACCGGCCGCGGCGGAAAACCAAGACGCTCATGAAGAAGGATA

AGTACACGCTTCCCGGAGGCTTGCTGGCCCCCGGCGGGAACAGCATGGCGAGCG

GGGTTGGGGTGGGCGCCGGCCTGGGTGCGGGCGTGAACCAGCGCATGGACAGCT

ACGCGCACATGAACGGCTGGAGCAACGGCAGCTACAGCATGATGCAGGAGCAG

CTGGGCTACCCGCAGCACCCGGGCCTCAACGCTCACGGCGCGGCACAGATGCAA

CCGATGCACCGCTACGACGTCAGCGCCCTGCAGTACAACTCCATGACCAGCTCGC

AGACCTACATGAACGGCTCGCCCACCTACAGCATGTCCTACTCGCAGCAGGGCA

CCCCCGGTATGGCGCTGGGCTCCATGGGCTCTGTGGTCAAGTCCGAGGCCAGCTC

CAGCCCCCCCGTGGTTACCTCTTCCTCCCACTCCAGGGCGCCCTGCCAGGCCGGG

GACCTCCGGGACATGATCAGCATGTACCTCCCCGGCGCCGAGGTGCCGGAGCCC

GCTGCGCCCAGTAGACTGCACATGGCCCAGCACTACCAGAGCGGCCCGGTGCCC

GGCACGGCCATTAACGGCACACTGCCCCTGTCGCACATG

Amino acid sequence encoding Mus Musculus SOX2 (translated)
(SEQ ID NO: 4)
MYNMMETELKPPGPQQASGGGGGGNATAAATGGNQKNSPDRVKRPMNAFMVW

SRGQRRKMAQENPKMHNSEISKRLGAEWKLLSETEKRPFIDEAKRLRALHMKEHPD

YKYRPRRKTKTLMKKDKYTLPGGLLAPGGNSMASGVGVGAGLGAGVNQRMDSYA

HMNGWSNGSYSMMQEQLGYPQHPGLNAHGAAQMQPMHRYDVSALQYNSMTSSQ

TYMNGSPTYSMSYSQQGTPGMALGSMGSVVKSEASSSPPVVTSSSHSRAPCQAGDL

RDMISMYLPGAEVPEPAAPSRLHMAQHYQSGPVPGTAINGTLPLSHM

Nucleotide sequence encoding Mus Musculus KLF4 (no stop codon)
(SEQ ID NO: 5):
ATGAGGCAGCCACCTGGCGAGTCTGACATGGCTGTCAGCGACGCTCTGCTCCCGT

CCTTCTCCACGTTCGCGTCCGGCCCGGCGGGAAGGGAGAAGACACTGCGTCCAG

CAGGTGCCCCGACTAACCGTTGGCGTGAGGAACTCTCTCACATGAAGCGACTTCC

CCCACTTCCCGGCCGCCCCTACGACCTGGCGGCGACGGTGGCCACAGACCTGGA

GAGTGGCGGAGCTGGTGCAGCTTGCAGCAGTAACAACCCGGCCCTCCTAGCCCG

GAGGGAGACCGAGGAGTTCAACGACCTCCTGGACCTAGACTTTATCCTTTCCAAC

TCGCTAACCCACCAGGAATCGGTGGCCGCCACCGTGACCACCTCGGCGTCAGCTT

CATCCTCGTCTTCCCCAGCGAGCAGCGGCCCTGCCAGCGCGCCCTCCACCTGCAG

CTTCAGCTATCCGATCCGGGCCGGGGTGACCCGGGCGTGGCTGCCAGCAACAC

AGGTGGAGGGCTCCTCTACAGCCGAGAATCTGCGCCACCTCCCACGGCCCCCTTC

AACCTGGCGGACATCAATGACGTGAGCCCTCGGGCGGCTTCGTGGCTGAGCTC

CTGCGGCCGGAGTTGGACCCAGTATACATTCCGCCACAGCAGCCTCAGCCGCCA

GGTGGCGGGCTGATGGGCAAGTTTGTGCTGAAGGCGTCTCTGACCACCCCTGGCA

GCGAGTACAGCAGCCCTTCGGTCATCAGTGTTAGCAAAGGAAGCCCAGACGGCA

```
GCCACCCCGTGGTAGTGGCGCCCTACAGCGGTGGCCCGCCGCGCATGTGCCCCA

AGATTAAGCAAGAGGCGGTCCCGTCCTGCACGGTCAGCCGGTCCCTAGAGGCCC

ATTTGAGCGCTGGACCCCAGCTCAGCAACGGCCACCGGCCCAACACACACGACT

TCCCCCTGGGGCGGCAGCTCCCCACCAGGACTACCCCTACACTGAGTCCCGAGG

AACTGCTGAACAGCAGGGACTGTCACCCTGGCCTGCCTCTTCCCCCAGGATTCCA

TCCCCATCCGGGGCCCAACTACCCTCCTTTCCTGCCAGACCAGATGCAGTCACAA

GTCCCCTCTCTCCATTATCAAGAGCTCATGCCACCGGGTTCCTGCCTGCCAGAGG

AGCCCAAGCCAAAGAGGGGAAGAAGGTCGTGGCCCCGGAAAAGAACAGCCACC

CACACTTGTGACTATGCAGGCTGTGGCAAAACCTATACCAAGAGTTCTCATCTCA

AGGCACACCTGCGAACTCACACAGGCGAGAAACCTTACCACTGTGACTGGGACG

GCTGTGGGTGGAAATTCGCCCGCTCCGATGAACTGACCAGGCACTACCGCAAAC

ACACAGGGCACCGGCCCTTTCAGTGCCAGAAGTGCGACAGGGCCTTTTCCAGGT

CGGACCACCTTGCCTTACACATGAAGAGGCAC
```

Amino acid sequence encoding Mus Musculus KLF4 (translated):
(SEQ ID NO: 6):
```
MRQPPGESDMAVSDALLPSFSTFASGPAGREKTLRPAGAPTNRWREELSHMKRLPPL

PGRPYDLAATVATDLESGGAGAACSSNNPALLARRETEEFNDLLDLDFILSNSLTHQE

SVAATVTTSASASSSSSPASSGPASAPSTCSFSYPIRAGGDPGVAASNTGGGLLYSRES

APPPTAPFNLADINDVSPSGGFVAELLRPELDPVYIPPQQPQPPGGGLMGKFVLKASL

TTPGSEYSSPSVISVSKGSPDGSHPVVVAPYSGGPPRMCPKIKQEAVPSCTVSRSLEAH

LSAGPQLSNGHRPNTHDFPLGRQLPTRTTPTLSPEELLNSRDCHPGLPLPPGFHPHPGP

NYPPFLPDQMQSQVPSLHYQELMPPGSCLPEEPKPKRGRRSWPRKRTATHTCDYAG

CGKTYTKSSHLKAHLRTHTGEKPYHCDWDGCGWKFARSDELTRHYRKHTGHRPFQ

CQKCDRAFSRSDHLALHMKRH
```

TRE3G promoter sequence (non-limiting example of a TRE promoter)
(SEQ ID NO: 7):
```
TTTACTCCCTATCAGTGATAGAGAACGTATGAAGAGTTTACTCCCTATCAGTGAT

AGAGAACGTATGCAGACTTTACTCCCTATCAGTGATAGAGAACGTATAAGGAGT

TTACTCCCTATCAGTGATAGAGAACGTATGACCAGTTTACTCCCTATCAGTGATA

GAGAACGTATCTACAGTTTACTCCCTATCAGTGATAGAGAACGTATATCCAGTTT

ACTCCCTATCAGTGATAGAGAACGTATAAGCTTTAGGCGTGTACGGTGGGCGCCT

ATAAAAGCAGAGCTCGTTTAGTGAACCGTCAGATCGCCTGGAGCAATTCCACAA

CACTTTTGTCTTATACCAACTTTCCGTACCACTTCCTACCCTCGTAAA
```

SV40-derived terminator sequence (SEQ ID NO: 8):
```
TGCGCGCAGCGGCCGACCATGGCCCAACTTGTTTATTGCAGCTTATAATGGTTAC

AAATAAAGCAATAGCATCACAAATTTCACAAATAAAGCATTTTTTTCACTGCATT

CTAGTTGTGGTTTGTCCAAACTCATCAATGTATCTTATCATGTCTGGATCTCGGTA

CCG
```

T2A sequence (SEQ ID NO: 9): GSGEGRGSLLTCGDVEENPGP

Nucleotide sequence encoding rtTA3(with 2 VP16 domain at 3' end)
(SEQ ID NO: 10):
```
ATGTCTAGGCTGGACAAGAGCAAAGTCATAAACGGAGCTCTGGAATTACTCAAT

GGTGTCGGTATCGAAGGCCTGACGACAAGGAAACTCGCTCAAAAGCTGGGAGTT

GAGCAGCCTACCCTGTACTGGCACGTGAAGAACAAGCGGGCCCTGCTCGATGCC
```

```
CTGCCAATCGAGATGCTGGACAGGCATCATACCCACTTCTGCCCCCTGGAAGGCG

AGTCATGGCAAGACTTTCTGCGGAACAACGCCAAGTCATACCGCTGTGCTCTCCT

CTCACATCGCGACGGGGCTAAAGTGCATCTCGGCACCCGCCCAACAGAGAAACA

GTACGAAACCCTGGAAAATCAGCTCGCGTTCCTGTGTCAGCAAGGCTTCTCCCTG

GAGAACGCACTGTACGCTCTGTCCGCCGTGGGCCACTTTACACTGGGCTGCGTAT

TGGAGGAACAGGAGCATCAAGTAGCAAAAGAGGAAAGAGAGACACCTACCACC

GATTCTATGCCCCCACTTCTGAGACAAGCAATTGAGCTGTTCGACCGGCAGGGAG

CCGAACCTGCCTTCCTTTTCGGCCTGGAACTAATCATATGTGGCCTGGAGAAACA

GCTAAAGTGCGAAAGCGGCGGGCCGACCGACGCCCTTGACGATTTTGACTTAGA

CATGCTCCCAGCCGATGCCCTTGACGATTTTGACCTTGACATGCTCCCCGGGTAA

Amino acid sequence encoding rtTA3 (SEQ ID NO: 11):
MSRLDKSKVINGALELLNGVGIEGLTTRKLAQKLGVEQPTLYWHVKNKRALLDALP

IEMLDRHHTHFCPLEGESWQDFLRNNAKSYRCALLSHRDGAKVHLGTRPTEKQYET

LENQLAFLCQQGFSLENALYALSAVGHFTLGCVLEEQEHQVAKEERETPTTDSMPPL

LRQAIELFDRQGAEPAFLFGLELIICGLEKQLKCESGGPTDALDDFDLDMLPADALDD

FDLDMLPG

Nucleotide sequence encoding rtTA4 (with 3 VP16 domain at 3' end)
(SEQ ID NO: 12):
ATGTCCCGCTTGGATAAGAGCAAGGTAATAAATAGCGCACTCGAACTCCTCAAC

GGCGTGGGCATCGAAGGTCTGACTACTCGAAAGCTCGCCCAGAAATTGGGTGTG

GAGCAACCTACATTGTATTGGCATGTCAAGAACAAAAGAGCCCTGCTGGACGCT

CTTCCTATTGAAATGCTTGACAGGCATCACACTCATTCCTGCCCCCTTGAGGTCG

AGAGTTGGCAAGATTTTCTCCGAAACAATGCAAAGTCCTACCGCTGCGCACTTTT

GTCCCATAGGGATGGAGCAAAAGTGCACCTGGGAACCAGGCCAACAGAGAAAC

AATACGAGACTCTCGAGAACCAGTTGGCTTTCTTGTGCCAACAGGGGTTCTCACT

TGAAAATGCCCTTTACGCACTGTCAGCCGTTGGACATTTTACCCTGGGGTGCGTT

CTTGAGGAGCAAGAACATCAGGTTGCTAAGGAGGAGCGCGAGACTCCAACCACT

GATTCTATGCCACCTTTGCTGAAACAGGCCATTGAACTTTTCGATAGACAGGGTG

CTGAACCTGCCTTTCTCTTCGGGTTGGAGCTGATTATTTGTGGTCTCGAAAAACA

GCTGAAATGTGAAAGTGGTGGCCCTACTGACGCCCTCGATGATTTCGACCTGGAT

ATGCTGCCAGCCGATGCACTTGATGATTTCGATTTGGATATGCTTCCAGCCGACG

CACTGGACGACTTCGATTTGGACATGCTTCCCGGTTAA

Amino acid sequence encoding rtTA4 (SEQ ID NO: 13):
MSRLDKSKVINSALELLNGVGIEGLTTRKLAQKLGVEQPTLYWHVKNKRALLDALPI

EMLDRHHTHSCPLEVESWQDFLRNNAKSYRCALLSHRDGAKVHLGTRPTEKQYETL

ENQLAFLCQQGFSLENALYALSAVGHFTLGCVLEEQEHQVAKEERETPTTDSMPPLL

KQAIELFDRQGAEPAFLFGLELIICGLEKQLKCESGGPTDALDDFDLDMLPADALDDF

DLDMLPADALDDFDLDMLPG

Nucleotide sequence encoding M2-rtTA (SEQ ID NO: 14):
ATGCCTTTGTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGCAACGTG

GCGTGGTGTGCACTGTGTTTGCTGACGCAACCCCCACTGGTTGGGGCATTGCCAC

CACCTGTCAGCTCCTTTCCGGGACTTTCGCTTTCCCCCTCCCTATTGCCACGGCGG
```

-continued

AACTCATCGCCGCCTGCCTTGCCCGCTGCTGGACAGGGGCTCGGCTGTTGGGCAC

TGACAATTCCGTGGTGTTGTCGGGAAATCATCGTCCTTTCCTTGGCTGCTCGCCT

GTGTTGCCACCTGGATTCTGCGCGGGACGTCCTTCTGCTACGTCCCTTCGGCCCTC

AATCCAGCGGACCTTCCTTCCCGCGGCCTGCTGCCGGCTCTGCGGCCTCTTCCGC

GTCTTCGCCTTCGCCCTCAGACGAGTCGGATCTCCCTTTGGGCCGCCTCCCCGCAT

CGATACCGTCGACCTCGAGACCTAGAAAAACATGGAGCAATCACAAGTAGCAAT

ACAGCAGCTACCAATGCTGATTGTGCCTGGCTAGAAGCACAAGAGGAGGAGGAG

GTGGGTTTTCCAGTCACACCTCAGGTACCTTTAAGACCAATGACTTACAAGGCAG

CTGTAGATCTTAGCCACTTTTTAAAAGAAAAGGGGGGACTGGAAGGGCTAATTC

ACTCCCAACGAAGACAAGATATCCTTGATCTGTGGATCTACCACACACAAGGCTA

CTTCCCTGATTGGCAGAACTACACACCAGGGCCAGGGATCAGATATCCACTGAC

CTTTGGATGGTGCTACAAGCTAGTACCAGTTGAGCAAGAGAAGGTAGAAGAAGC

CAATGAAGGAGAGAACACCCGCTTGTTACACCCTGTGAGCCTGCATGGGATGGA

TGACCCGGAGAGAGAAGTATTAGAGTGGAGGTTTGACAGCCGCCTAGCATTTCA

TCACATGGCCCGAGAGCTGCATCCGGACTGTACTGGGTCTCTCTGGTTAGACCAG

ATCTGA

Amino acid sequence encoding M2-rtTA (SEQ ID NO: 15):
MPLYHAIASRMAFIFSSLYKSWLLSLYEELWPVVRQRGVVCTVFADATPTGWGIATT

CQLLSGTFAFPLPIATAELIAACLARCWTGARLLGTDNSVVLSGKSSSFPWLLACVAT

WILRGTSFCYVPSALNPADLPSRGLLPALRPLPRLRLRPQTSRISLWAASPHRYRRPR

DLEKHGAITSSNTAATNADCAWLEAQEEEEVGFPVTPQVPLRPMTYKAAVDLSHFL

KEKGGLEGLIHSQRRQDILDLWIYHTQGYFPDWQNYTPGPGIRYPLTFGWCYKLVPV

EQEKVEEANEGENTRLLHPVSLHGMDDPEREVLEWRFDSRLAFHHMARELHPDCTG

SLWLDQI

Nucleic acid sequence of pAAV-TRE3G-OSK-SV40pA, TRE-OSK-SV40, or
TRE3G-OSK-SV40pA vector (SEQ ID NO: 16):
TTATGCAGTGCTGCCATAACCATGAGTGATAACACTGCGGCCAACTTACTTCTGA

CAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTAT

TAACTGGCGAACTACTTACTCTAGCTTCCCGGCAACAATTAATAGACTGGATGGA

GGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

-continued

```
CATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACAC
CGAACTGAGATACCTACAGCGTGAGCTATGAGAAAGCGCCACGCTTCCCGAAGG
GAGAAAGGCGGACAGGTATCCGGTAAGCGGCAGGGTCGGAACAGGAGAGCGCA
CGAGGGAGCTTCCAGGGGAAACGCCTGGTATCTTTATAGTCCTGTCGGGTTTCG
CCACCTCTGACTTGAGCGTCGATTTTTGTGATGCTCGTCAGGGGGCGGAGCCTA
TGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAG
TCAGTGAGCGAGGAAGCGGAAGAGCGCCCAATACGCAAACCGCCTCTCCCCGCG
CGTTGGCCGATTCATTAATGCAGCTGGCACGACAGGTTTCCCGACTGGAAAGCGG
GCAGTGAGCGCAACGCAATTAATGTGAGTTAGCTCACTCATTAGGCACCCCAGG
CTTTACACTTTATGCTTCCGGCTCGTATGTTGTGTGGAATTGTGAGCGGATAACA
ATTTCACACAGGAAACAGCTATGACCATGATTACGCCAGATTTAATTAAGGCCTT
AATTAGGCTGCGCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGG
AGTGGCCAACTCCATCACTAGGGGTTCCTTGTAGTTAATGATTAACCCGCCATGC
TACTTATCTACGTAGCCATGCTCTAGGAAGATCGGAATTCTTTACTCCCTATCAGT
GATAGAGAACGTATGAAGAGTTTACTCCCTATCAGTGATAGAGAACGTATGCAG
ACTTTACTCCCTATCAGTGATAGAGAACGTATAAGGAGTTTACTCCCTATCAGTG
ATAGAGAACGTATGACCAGTTTACTCCCTATCAGTGATAGAGAACGTATCTACAG
TTTACTCCCTATCAGTGATAGAGAACGTATATCCAGTTTACTCCCTATCAGTGATA
GAGAACGTATAAGCTTTAGGCGTGTACGGTGGGCGCCTATAAAAGCAGAGCTCG
TTTAGTGAACCGTCAGATCGCCTGGAGCAATTCCACAACACTTTTGTCTTATACC
AACTTTCCGTACCACTTCCTACCCTCGTAAAGCGGCCGCGCCACCATGGCTGGAC
ACCTGGCTTCAGACTTCGCCTTCTCACCCCCACCAGGTGGGGGTGATGGGTCAGC
AGGGCTGGAGCCGGGCTGGGTGGATCCTCGAACCTGGCTAAGCTTCCAAGGGCC
TCCAGGTGGGCCTGGAATCGGACCAGGCTCAGAGGTATTGGGGATCTCCCCATGT
CCGCCCGCATACGAGTTCTGCGGAGGGATGGCATACTGTGGACCTCAGGTTGGA
CTGGGCCTAGTCCCCCAAGTTGGCGTGGAGACTTTGCAGCCTGAGGGCCAGGCA
GGAGCACGAGTGGAAAGCAACTCAGAGGGAACCTCCTCTGAGCCCTGTGCCGAC
CGCCCCAATGCCGTGAAGTTGGAGAAGGTGGAACCAACTCCCGAGGAGTCCCAG
GACATGAAAGCCCTGCAGAAGGAGCTAGAACAGTTTGCCAAGCTGCTGAAGCAG
AAGAGGATCACCTTGGGGTACACCCAGGCCGACGTGGGGCTCACCCTGGGCGTT
CTCTTTGGAAAGGTGTTCAGCCAGACCACCATCTGTCGCTTCGAGGCCTTGCAGC
TCAGCCTTAAGAACATGTGTAAGCTGCGGCCCCTGCTGGAGAAGTGGGTGGAGG
AAGCCGACAACAATGAGAACCTTCAGGAGATATGCAAATCGGAGACCCTGGTGC
AGGCCCGGAAGAGAAAGCGAACTAGCATTGAGAACCGTGTGAGGTGGAGTCTGG
AGACCATGTTTCTGAAGTGCCCGAAGCCCTCCCTACAGCAGATCACTCACATCGC
```

-continued

```
CAATCAGCTTGGGCTAGAGAAGGATGTGGTTCGAGTATGGTTCTGTAACCGGCGC

CAGAAGGGCAAAAGATCAAGTATTGAGTATTCCCAACGAGAAGAGTATGAGGCT

ACAGGGACACCTTTCCCAGGGGGGCTGTATCCTTTCCTCTGCCCCAGGTCCCC

ACTTTGGCACCCCAGGCTATGGAAGCCCCACTTCACCACACTCTACTCAGTCCC

TTTTCCTGAGGGCGAGGCCTTTCCCTCTGTTCCCGTCACTGCTCTGGGCTCTCCCA

TGCATTCAAACGCTAGCGGCAGCGGCGCCACGAACTTCTCTCTGTTAAAGCAAGC

AGGAGATGTTGAAGAAAACCCCGGGCCTGCATGCATGTATAACATGATGGAGAC

GGAGCTGAAGCCGCCGGGCCCGCAGCAAGCTTCGGGGGGCGGCGGCGGAGGAG

GCAACGCCACGGCGGCGGCGACCGGCGGCAACCAGAAGAACAGCCCGGACCGC

GTCAAGAGGCCCATGAACGCCTTCATGGTATGGTCCCGGGGGCAGCGGCGTAAG

ATGGCCCAGGAGAACCCCAAGATGCACAACTCGGAGATCAGCAAGCGCCTGGGC

GCGGAGTGGAAACTTTTGTCCGAGACCGAGAAGCGGCCGTTCATCGACGAGGCC

AAGCGGCTGCGCGCTCTGCACATGAAGGAGCACCCGGATTATAAATACCGGCCG

CGGCGGAAAACCAAGACGCTCATGAAGAAGGATAAGTACACGCTTCCCGGAGGC

TTGCTGGCCCCCGGCGGGAACAGCATGGCGAGCGGGGTTGGGGTGGGCGCCGGC

CTGGGTGCGGGCGTGAACCAGCGCATGGACAGCTACGCGCACATGAACGGCTGG

AGCAACGGCAGCTACAGCATGATGCAGGAGCAGCTGGGCTACCCGCAGCACCCG

GGCCTCAACGCTCACGGCGCGGCACAGATGCAACCGATGCACCGCTACGACGTC

AGCGCCCTGCAGTACAACTCCATGACCAGCTCGCAGACCTACATGAACGGCTCG

CCCACCTACAGCATGTCCTACTCGCAGCAGGGCACCCCCGGTATGGCGCTGGGCT

CCATGGGCTCTGTGGTCAAGTCCGAGGCCAGCTCCAGCCCCCCCGTGGTTACCTC

TTCCTCCCACTCCAGGGCGCCCTGCCAGGCCGGGGACCTCCGGGACATGATCAGC

ATGTACCTCCCCGGCGCCGAGGTGCCGGAGCCCGCTGCGCCCAGTAGACTGCAC

ATGGCCCAGCACTACCAGAGCGGCCCGGTGCCCGGCACGGCCATTAACGGCACA

CTGCCCCTGTCGCACATGGCATGCGGCTCCGGCGAGGGCAGGGGAAGTCTTCTA

ACATGCGGGACGTGGAGGAAAATCCCGGCCCACTCGAGATGAGGCAGCCACCT

GGCGAGTCTGACATGGCTGTCAGCGACGCTCTGCTCCCGTCCTTCTCCACGTTCG

CGTCCGGCCCGGCGGGAAGGGAGAAGACACTGCGTCCAGCAGGTGCCCCGACTA

ACCGTTGGCGTGAGGAACTCTCTCACATGAAGCGACTTCCCCCACTTCCCGGCCG

CCCCTACGACCTGGCGGCGACGGTGGCCACAGACCTGGAGAGTGGCGGAGCTGG

TGCAGCTTGCAGCAGTAACAACCCGGCCCTCCTAGCCCGGAGGGAGACCGAGGA

GTTCAACGACCTCCTGGACCTAGACTTTATCCTTTCCAACTCGCTAACCCACCAG

GAATCGGTGGCCGCCACCGTGACCACCTCGGCGTCAGCTTCATCCTCGTCTTCCC

CAGCGAGCAGCGGCCCTGCCAGCGCGCCCTCCACCTGCAGCTTCAGCTATCCGAT

CCGGGCCGGGGTGACCCGGGCGTGGCTGCCAGCAACACAGGTGGAGGGCTCCT

CTACAGCCGAGAATCTGCGCCACCTCCCACGGCCCCCTTCAACCTGGCGGACATC

AATGACGTGAGCCCCTCGGGCGGCTTCGTGGCTGAGCTCCTGCGGCCGGAGTTGG

ACCCAGTATACATTCCGCCACAGCAGCCTCAGCCGCCAGGTGGCGGGCTGATGG

GCAAGTTTGTGCTGAAGGCGTCTCTGACCACCCCTGGCAGCGAGTACAGCAGCC

CTTCGGTCATCAGTGTTAGCAAAGGAAGCCCAGACGGCAGCCACCCCGTGGTAG

TGGCGCCCTACAGCGGTGGCCCGCCGCGCATGTGCCCCAAGATTAAGCAAGAGG
```

-continued

```
CGGTCCCGTCCTGCACGGTCAGCCGGTCCCTAGAGGCCCATTTGAGCGCTGGACC

CCAGCTCAGCAACGGCCACCGGCCCAACACACACGACTTCCCCCTGGGGCGGCA

GCTCCCCACCAGGACTACCCCTACACTGAGTCCCGAGGAACTGCTGAACAGCAG

GGACTGTCACCCTGGCCTGCCTCTTCCCCCAGGATTCCATCCCCATCCGGGGCCC

AACTACCCTCCTTTCCTGCCAGACCAGATGCAGTCACAAGTCCCCTCTCTCCATT

ATCAAGAGCTCATGCCACCGGGTTCCTGCCTGCCAGAGGAGCCCAAGCCAAAGA

GGGGAAGAAGGTCGTGGCCCCGGAAAAGAACAGCCACCCACACTTGTGACTATG

CAGGCTGTGGCAAAACCTATACCAAGAGTTCTCATCTCAAGGCACACCTGCGAA

CTCACACAGGCGAGAAACCTTACCACTGTGACTGGGACGGCTGTGGGTGGAAAT

TCGCCCGCTCCGATGAACTGACCAGGCACTACCGCAAACACACAGGGCACCGGC

CCTTTCAGTGCCAGAAGTGCGACAGGGCCTTTTCCAGGTCGGACCACCTTGCCTT

ACACATGAAGAGGCACTAAATGACTAGTGCGCGCAGCGGCCGACCATGGCCCAA

CTTGTTTATTGCAGCTTATAATGGTTACAAATAAAGCAATAGCATCACAAATTTC

ACAAATAAAGCATTTTTTTCACTGCATTCTAGTTGTGGTTTGTCCAAACTCATCAA

TGTATCTTATCATGTCTGGATCTCGGTACCGGATCCAAATTCCCGATAAGGATCTT

CCTAGAGCATGGCTACGTAGATAAGTAGCATGGCGGGTTAATCATTAACTACAA

GGAACCCCTAGTGATGGAGTTGGCCACTCCCTCTCTGCGCGCTCGCTCGCTCACT

GAGGCCGGGCGACCAAAGGTCGCCCGACGCCCGGGCTTTGCCCGGGCGGCCTCA

GTGAGCGAGCGAGCGCGCAGCCTTAATTAACCTAATTCACTGGCCGTCGTTTTAC

AACGTCGTGACTGGGAAAACCCTGGCGTTACCCAACTTAATCGCCTTGCAGCACA

TCCCCCTTTCGCCAGCTGGCGTAATAGCGAAGAGGCCCGCACCGATCGCCCTTCC

CAACAGTTGCGCAGCCTGAATGGCGAATGGGACGCGCCCTGTAGCGGCGCATTA

AGCGCGGCGGGTGTGGTGGTTACGCGCAGCGTGACCGCTACACTTGCCAGCGCC

CTAGCGCCCGCTCCTTTCGCTTTCTTCCCTTCCTTTCTCGCCACGTTCGCCGGCTTT

CCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTG

GACTCTTGTTCCAAACTGGAACAACACTCAACCCTATCTCGGTCTATTCTTTTGAT

TTATAAGGGATTTTGCCGATTTCGGCCTATTGGTTAAAAAATGAGCTGATTTAAC

AAAAATTTAACGCGAATTTTAACAAAATATTAACGTTTATAATTTCAGGTGGCAT

CTTTCGGGGAAATGTGCGCGGAACCCCTATTTGTTTATTTTTCTAAATACATTCAA

ATATGTATCCGCTCATGAGACAATAACCCTGATAAATGCTTCAATAATATTGAAA

AAGGAAGAGTATGAGTATTCAACATTTCCGTGTCGCCCTTATTCCCTTTTTTGCGG

CATTTTGCCTTCCTGTTTTTGCTCACCCAGAAACGCTGGTGAAAGTAAAAGATGC

TGAAGATCAGTTGGGTGCACGAGTGGGTTACATCGAACTGGATCTCAATAGTGGT

AAGATCCTTGAGAGTTTTCGCCCCGAAGAACGTTTTCCAATGATGAGCACTTTTA

AAGTTCTGCTATGTGGCGCGGTATTATCCCGTATTGACGCCGGGCAAGAGCAACT

CGGTCGCCGCATACACTATTCTCAGAATGACTTGGTTGAGTACTCACCAGTCACA

GAAAAGCATCTTACGGATGGCATGACAGTAAGAGAA
```

-continued

Nucleic acid sequence of pAAV-UBC-rtTA4-WPRE3-SV40pA vector
(SEQ ID NO: 17):
TTATGCAGTGCTGCCATAACCATGAGTGATAACACTGCGGCCAACTTACTTCTGA

CAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTAT

TAACTGGCGAACTACTTACTCTAGCTTCCCGGCAACAATTAATAGACTGGATGGA

GGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGGTTTCG

CCACCTCTGACTTGAGCGTCGATTTTTGTGATGCTCGTCAGGGGGCGGAGCCTA

TGGAAAAACGCCAGCAACGCGGCCTTTTTACGGTTCCTGGCCTTTTGCTGGCCTT

TTGCTCACATGTTCTTTCCTGCGTTATCCCCTGATTCTGTGGATAACCGTATTACC

GCCTTTGAGTGAGCTGATACCGCTCGCCGCAGCCGAACGACCGAGCGCAGCGAG

TCAGTGAGCGAGGAAGCGGAAGAGCGCCCAATACGCAAACCGCCTCTCCCCGCG

CGTTGGCCGATTCATTAATGCAGCTGGCACGACAGGTTTCCCGACTGGAAAGCGG

GCAGTGAGCGCAACGCAATTAATGTGAGTTAGCTCACTCATTAGGCACCCCAGG

CTTTACACTTTATGCTTCCGGCTCGTATGTTGTGTGGAATTGTGAGCGGATAACA

ATTTCACACAGGAAACAGCTATGACCATGATTACGCCAGATTTAATTAAGGCCTT

AATTAGGCTGCGCGCTCGCTCGCTCACTGAGGCCGCCCGGGCAAAGCCCGGGCG

TCGGGCGACCTTTGGTCGCCCGGCCTCAGTGAGCGAGCGAGCGCGCAGAGAGGG

AGTGGCCAACTCCATCACTAGGGGTTCCTTGTAGTTAATGATTAACCCGCCATGC

TACTTATCTACGTAGCCATGCTCTAGGAAGATCGGAATTCCTGATCTGGCCTCCG

CGCCGGGTTTTGGCGCCTCCCGCGGGCGCCCCCCTCCTCACGGCGAGCGCTGCCA

CGTCAGACGAAGGGCGCAGCGAGCGTCCTGATCCTTCCGCCCGGACGCTCAGGA

CAGCGGCCCGCTGCTCATAAGACTCGGCCTTAGAACCCAGTATCAGCAGAAGG

ACATTTTAGGACGGGACTTGGGTGACTCTAGGGCACTGGTTTTCTTTCCAGAGAG

CGGAACAGGCGAGGAAAAGTAGTCCCTTCTCGGCGATTCTGCGGAGGGATCTCC

-continued

```
GTGGGGCGGTGAACGCCGATGATTATATAAGGACGCGCCGGGTGTGGCACAGCT

AGTTCCGTCGCAGCCGGGATTTGGGTCGCGGTTCTTGTTTGTGGATCGCTGTGAT

CGTCACTTGGTGAGTAGCGGGCTGCTGGGCTGGCCGGGGCTTTCGTGGCCGCCGG

GCCGCTCGGTGGGACGGAAGCGTGTGGAGAGACCGCCAAGGGCTGTAGTCTGGG

TCCGCGAGCAAGGTTGCCCTGAACTGGGGGTTGGGGGGAGCGCAGCAAAATGGC

GGCTGTTCCCGAGTCTTGAATGGAAGACGCTTGTGAGGCGGGCTGTGAGGTCGTT

GAAACAAGGTGGGGGGCATGGTGGGCGGCAAGAACCCAAGGTCTTGAGGCCTTC

GCTAATGCGGGAAAGCTCTTATTCGGGTGAGATGGGCTGGGGCACCATCTGGGG

ACCCTGACGTGAAGTTTGTCACTGACTGGAGAACTCGGTTTGTCGTCTGTTGCGG

GGGCGGCAGTTATGCGGTGCCGTTGGGCAGTGCACCCGTACCTTTGGGAGCGCG

CGCCTCGTCGTGTCGTGACGTCACCCGTTCTGTTGGCTTATAATGCAGGGTGGGG

CCACCTGCCGGTAGGTGTGCGGTAGGCTTTTCTCCGTCGCAGGACGCAGGGTTCG

GGCCTAGGGTAGGCTCTCCTGAATCGACAGGCGCCGGACCTCTGGTGAGGGGAG

GGATAAGTGAGGCGTCAGTTTCTTTGGTCGGTTTTATGTACCTATCTTCTTAAGTA

GCTGAAGCTCCGGTTTTGAACTATGCGCTCGGGGTTGGCGAGTGTGTTTTGTGAA

GTTTTTTAGGCACCTTTTGAAATGTAATCATTTGGGTCAATATGTAATTTTCAGTG

TTAGACTAGTAAATTGTCCGCTAAATTCTGGCCGTTTTTGGCTTTTTTGTTAGACG

AAGCGGCCGCATTAAACGCCACCATGTCCCGCTTGGATAAGAGCAAGGTAATAA

ATAGCGCACTCGAACTCCTCAACGGCGTGGGCATCGAAGGTCTGACTACTCGAA

AGCTCGCCCAGAAATTGGGTGTGGAGCAACCTACATTGTATTGGCATGTCAAGA

ACAAAAGAGCCCTGCTGGACGCTCTTCCTATTGAAATGCTTGACAGGCATCACAC

TCATTCCTGCCCCCTTGAGGTCGAGAGTTGGCAAGATTTTCTCCGAAACAATGCA

AAGTCCTACCGCTGCGCACTTTTGTCCCATAGGGATGGAGCAAAAGTGCACCTGG

GAACCAGGCCAACAGAGAAACAATACGAGACTCTCGAGAACCAGTTGGCTTTCT

TGTGCCAACAGGGGTTCTCACTTGAAAATGCCCTTTACGCACTGTCAGCCGTTGG

ACATTTTACCCTGGGGTGCGTTCTTGAGGAGCAAGAACATCAGGTTGCTAAGGAG

GAGCGCGAGACTCCAACCACTGATTCTATGCCACCTTTGCTGAAACAGGCCATTG

AACTTTTCGATAGACAGGGTGCTGAACCTGCCTTTCTCTTCGGGTTGGAGCTGAT

TATTTGTGGTCTCGAAAAACAGCTGAAATGTGAAAGTGGTGGCCCTACTGACGCC

CTCGATGATTTCGACCTGGATATGCTGCCAGCCGATGCACTTGATGATTTCGATTT

GGATATGCTTCCAGCCGACGCACTGGACGACTTCGATTTGGACATGCTTCCCGGT

TAAACTAGTCTAGCAATCAACCTCTGGATTACAAAATTTGTGAAAGATTGACTGG

TATTCTTAACTATGTTGCTCCTTTTACGCTATGTGGATACGCTGCTTTAATGCCTTT

GTATCATGCTATTGCTTCCCGTATGGCTTTCATTTTCTCCTCCTTGTATAAATCCTG

GTTAGTTCTTGCCACGGCGGAACTCATCGCCGCCTGCCTTGCCCGCTGCTGGACA

GGGGCTCGGCTGTTGGGCACTGACAATTCCGTGGTGTTTATTTGTGAAATTTGTG

ATGCTATTGCTTTATTTGTAACCATTCTAGCTTTATTTGTGAAATTTGTGATGCTA

TTGCTTTATTTGTAACCATTATAAGCTGCAATAAACAAGTTAACAACAACAATTG

CATTCATTTTATGTTTCAGGTTCAGGGGGAGATGTGGGAGGTTTTTTAAAGCGGG

GGATCCAAATTCCCGATAAGGATCTTCCTAGAGCATGGCTACGTAGATAAGTAGC
```

-continued

```
ATGGCGGGTTAATCATTAACTACAAGGAACCCCTAGTGATGGAGTTGGCCACTCC

CTCTCTGCGCGCTCGCTCGCTCACTGAGGCCGGGCGACCAAAGGTCGCCCGACGC

CCGGGCTTTGCCCGGGCGGCCTCAGTGAGCGAGCGAGCGCGCAGCCTTAATTAA

CCTAATTCACTGGCCGTCGTTTTACAACGTCGTGACTGGGAAAACCCTGGCGTTA

CCCAACTTAATCGCCTTGCAGCACATCCCCCTTTCGCCAGCTGGCGTAATAGCGA

AGAGGCCCGCACCGATCGCCCTTCCCAACAGTTGCGCAGCCTGAATGGCGAATG

GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGGCTCCCT

TTAGGGTTCCGATTTAGTGCTTTACGGCACCTCGACCCCAAAAAACTTGATTAGG

GTGATGGTTCACGTAGTGGGCCATCGCCCTGATAGACGGTTTTTCGCCCTTTGAC

GTTGGAGTCCACGTTCTTTAATAGTGGACTCTTGTTCCAAACTGGAACAACACTC

AACCCTATCTCGGTCTATTCTTTTGATTTATAAGGGATTTTGCCGATTTCGGCCTA

TTGGTTAAAAAATGAGCTGATTTAACAAAAATTTAACGCGAATTTTAACAAAATA

TTAACGTTTATAATTTCAGGTGGCATCTTTCGGGGAAATGTGCGCGGAACCCCTA

TTTGTTTATTTTTCTAAATACATTCAAATATGTATCCGCTCATGAGACAATAACCC

TGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAG

AAACGCTGGTGAAAGTAAAAGATGCTGAAGATCAGTTGGGTGCACGAGTGGGTT

ACATCGAACTGGATCTCAATAGTGGTAAGATCCTTGAGAGTTTTCGCCCCGAAGA

ACGTTTTCCAATGATGAGCACTTTTAAAGTTCTGCTATGTGGCGCGGTATTATCCC

GTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGT

AAGAGAA
```

UBC promoter sequence (SEQ ID NO: 18):
```
GATCTGGCCTCCGCGCCGGGTTTTGGCGCCTCCCGCGGGCGCCCCCCTCCTCACG

GCGAGCGCTGCCACGTCAGACGAAGGGCGCAGCGAGCGTCCTGATCCTTCCGCC

CGGACGCTCAGGACAGCGGCCCGCTGCTCATAAGACTCGGCCTTAGAACCCCAG

TATCAGCAGAAGGACATTTTAGGACGGGACTTGGGTGACTCTAGGGCACTGGTTT

TCTTTCCAGAGAGCGGAACAGGCGAGGAAAAGTAGTCCCTTCTCGGCGATTCTGC

GGAGGGATCTCCGTGGGCGGTGAACGCCGATGATTATATAAGGACGCGCCGGG

TGTGGCACAGCTAGTTCCGTCGCAGCCGGGATTTGGGTCGCGGTTCTTGTTTGTG

GATCGCTGTGATCGTCACTTGGTGAGTAGCGGGCTGCTGGGCTGGCCGGGGCTTT

CGTGGCCGCCGGGCCGCTCGGTGGGACGGAAGCGTGTGGAGAGACCGCCAAGG

GCTGTAGTCTGGGTCCGCGAGCAAGGTTGCCCTGAACTGGGGGTTGGGGGAGC

GCAGCAAAATGGCGGCTGTTCCCGAGTCTTGAATGGAAGACGCTTGTGAGGCGG

GCTGTGAGGTCGTTGAAACAAGGTGGGGGGCATGGTGGGCGGCAAGAACCCAAG

GTCTTGAGGCCTTCGCTAATGCGGGAAAGCTCTTATTCGGGTGAGATGGGCTGGG

GCACCATCTGGGGACCCTGACGTGAAGTTTGTCACTGACTGGAGAACTCGGTTTG

TCGTCTGTTGCGGGGGCGGCAGTTATGCGGTGCCGTTGGGCAGTGCACCCGTACC

TTTGGGAGCGCGCGCCTCGTCGTGTCGTGACGTCACCCGTTCTGTTGGCTTATAAT
```

```
GCAGGGTGGGGCCACCTGCCGGTAGGTGTGCGGTAGGCTTTTCTCCGTCGCAGGA

CGCAGGGTTCGGGCCTAGGGTAGGCTCTCCTGAATCGACAGGCGCCGGACCTCT

GGTGAGGGGAGGGATAAGTGAGGCGTCAGTTTCTTTGGTCGGTTTTATGTACCTA

TCTTCTTAAGTAGCTGAAGCTCCGGTTTTGAACTATGCGCTCGGGGTTGGCGAGT

GTGTTTTGTGAAGTTTTTTAGGCACCTTTTGAAATGTAATCATTTGGGTCAATATG

TAATTTTCAGTGTTAGACTAGTAAATTGTCCGCTAAATTCTGGCCGTTTTTGGCTT

TTTTGTTAGAC

Tet-O sequence (SEQ ID NO: 19):
TCCCTATCAGTGATAGAGA

Nucleic acid sequence encoding minimal CMV promoter (SEQ ID NO: 20):
GCTTTAGGCGTGTACGGTGGGCGCCTATAAAAGCAGAGCTCGTTTAGTGAACCGT
CAGATCGCCTGGA Nucleic acid sequence encoding WPRE (SEQ ID NO: 21):
AATCAACCTCTGGATTACAAAATTTGTGAAAGATTGACTGGTATTCTT

AACTATGTTGCTCCTTTTACGCTATGTGGATACGCTGCTTTAATGCCTTTGTATCA

TGCTATTGCTTCCCGTATGGCTTTCATTTTCTCCTCCTTGTATAAATCCTGGTTAGT

TCTTGCCACGGCGGAACTCATCGCCGCCTGCCTTGCCCGCTGCTGGACAGGGGCT

CGGCTGTTGGGCACTGACAATTCCGTGGTGTT

Nucleic acid sequence encoding inverted terminal repeat sequence
(SEQ ID NO: 22):
CCTTAATTAGGCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCAGAGA

GGGAGTGGCCAACTCCATCACTAGGGGTTCCT

Nucleic acid sequence of a TRE2 promoter (a non-limiting example of a TRE
promoter) (SEQ ID NO: 23):
AATTCGTACACGCCTACCTCGACCCATCAAGTGCCACCTGACGTCTCCCTATCAG

TGATAGAGAAGTCGACACGTCTCGAGCTCCCTATCAGTGATAGAGAAGGTACGT

CTAGAACGTCTCCCTATCAGTGATAGAGAAGTCGACACGTCTCGAGCTCCCTATC

AGTGATAGAGAAGGTACGTCTAGAACGTCTCCCTATCAGTGATAGAGAAGTCGA

CACGTCTCGAGCTCCCTATCAGTGATAGAGAAGGTACGTCTAGAACGTCTCCCTA

TCAGTGATAGAGAAGTCGACACGTCTCGAGCTCCCTATCAGTGATAGAGAAGGT

ACCCCCTATATAAGCAGAGCTCGTTTAGTGAACCGTCAGATCGCCTGGAGACGCC

ATCCACGCTGTTTTGACCTCCATAGAAGACACCGGGACCGATCCAGCCTGGATCG

C

Nucleic acid sequence of P tight promoter (a non-limiting example of a TRE
promoter) (SEQ ID NO: 24):
GAGTTTACTCCCTATCAGTGATAGAGAACGTATGTCGAGTTTACTCCCTATCAGT

GATAGAGAACGATGTCGAGTTTACTCCCTATCAGTGATAGAGAACGTATGTCGA

GTTTACTCCCTATCAGTGATAGAGAACGTATGTCGAGTTTACTCCCTATCAGTGA

TAGAGAACGTATGTCGAGTTTATCCCTATCAGTGATAGAGAACGTATGTCGAGTT

TACTCCCTATCAGTGATAGAGAACGTATGTCGAGGTAGGCGTGTACGGTGGGAG

GCCTATATAAGCAGAGCTCGTTTAGTGAACCGTCAGATCGCC

Nucleic acid sequence encoding TetR (SEQ ID NO: 25):
ATGGCTAGATTAGATAAAAGTAAAGTGATTAACAGCGCATTAGAGCTGCTTAAT

GAGGTCGGAATCGAAGGTTTAACAACCCGTAAACTCGCCCAGAAGCTAGGTGTA

GAGCAGCCTACATTGTATTGGCATGTAAAAAATAAGCGGGCTTTGCTCGACGCCT
```

-continued
TAGCCATTGAGATGTTAGATAGGCACCATACTCACTTTTGCCCTTTAGAAGGGGA

AAGCTGGCAAGATTTTTTACGTAATAACGCTAAAAGTTTTAGATGTGCTTTACTA

AGTCATCGCGATGGAGCAAAAGTACATTTAGGTACACGGCCTACAGAAAAACAG

TATGAAACTCTCGAAAATCAATTAGCCTTTTTATGCCAACAAGGTTTTTCACTAG

AGAATGCATTATATGCACTCAGCGCTGTGGGGCATTTTACTTTAGGTTGCGTATT

GGAAGATCAAGAGCATCAAGTCGCTAAAGAAGAAAGGGAAACACCTACTACTG

ATAGTATGCCGCCATTATTACGACAAGCTATCGAATTATTTGATCACCAAGGTGC

AGAGCCAGCCTTCTTATTCGGCCTTGAATTGATCATATGCGGATTAGAAAAACAA

CTTAAATGTGAAAGTGGG

Amino acid sequence encoding TetR (SEQ ID NO: 26):
MARLDKSKVINSALELLNEVGIEGLTTRKLAQKLGVEQPTLYWHVKNKRALLDALA

IEMLDRHHTHFCPLEGESWQDFLRNNAKSFRCALLSHRDGAKVHLGTRPTEKQYET

LENQLAFLCQQGFSLENALYALSAVGHFTLGCVLEDQEHQVAKEERETPTTDSMPPL

LRQAIELFDHQGAEPAFLFGLELIICGLEKQLKCESG

Nucleic acid sequence encoding TetR-Krab (SEQ ID NO: 27)
ATGGCTAGATTAGATAAAAGTAAAGTGATTAACAGCGCATTAGAGCTGCTTAAT

GAGGTCGGAATCGAAGGTTTAACAACCCGTAAACTCGCCCAGAAGCTAGGTGTA

GAGCAGCCTACATTGTATTGGCATGTAAAAAATAAGCGGGCTTTGCTCGACGCCT

TAGCCATTGAGATGTTAGATAGGCACCATACTCACTTTTGCCCTTTAGAAGGGGA

AAGCTGGCAAGATTTTTTACGTAATAACGCTAAAAGTTTTAGATGTGCTTTACTA

AGTCATCGCGATGGAGCAAAAGTACATTTAGGTACACGGCCTACAGAAAAACAG

TATGAAACTCTCGAAAATCAATTAGCCTTTTTATGCCAACAAGGTTTTTCACTAG

AGAATGCATTATATGCACTCAGCGCTGTGGGGCATTTTACTTTAGGTTGCGTATT

GGAAGATCAAGAGCATCAAGTCGCTAAAGAAGAAAGGGAAACACCTACTACTG

ATAGTATGCCGCCATTATTACGACAAGCTATCGAATTATTTGATCACCAAGGTGC

AGAGCCAGCCTTCTTATTCGGCCTTGAATTGATCATATGCGGATTAGAAAAACAA

CTTAAATGTGAAAGTGGGTCGCCAAAAAAGAAGAGAAAGGTCGACGGCGGTGGT

GCTTTGTCTCCTCAGCACTCTGCTGTCACTCAAGGAAGTATCATCAAGAACAAGG

AGGGCATGGATGCTAAGTCACTAACTGCCTGGTCCCGGACACTGGTGACCTTCAA

GGATGTATTTGTGGACTTCACCAGGGAGGAGTGGAAGCTGCTGGACACTGCTCA

GCAGATCGTGTACAGAAATGTGATGCTGGAGAACTATAAGAACCTGGTTTCCTTG

GGTTATCAGCTTACTAAGCCAGATGTGATCCTCCGGTTGGAGAAGGGAGAAGAG

CCCTGGCTGGTGGAGAGAGAAATTCACCAAGAGACCCATCCTGATTCAGAGACT

GCATTTGAAATCAAATCATCAGTTTAA

Amino acid sequence encoding TetR-KRAB (SEQ ID NO: 28):
MARLDKSKVINSALELLNEVGIEGLTTRKLAQKLGVEQPTLYWHVKNKRALLDALA

IEMLDRHHTHFCPLEGESWQDFLRNNAKSFRCALLSHRDGAKVHLGTRPTEKQYET

LENQLAFLCQQGFSLENALYALSAVGHFTLGCVLEDQEHQVAKEERETPTTDSMPPL

LRQAIELFDHQGAEPAFLFGLELIICGLEKQLKCESGSPKKKRKVDGGGALSPQHSAV

TQGSIIKNKEGMDAKSLTAWSRTLVTFKDVFVDFTREEWKLLDTAQQIVYRNVMLE

NYKNLVSLGYQLTKPDVILRLEKGEEPWLVEREIHQETHPDSETAFEIKSSV

Desmin promoter (SEQ ID NO: 29):
ACCTTGCTTCCTAGCTGGGCCTTTCCTTCTCCTCTATAAATACCAGCTCTGGTATT

TCGCCTTGGCAGCTGTTGCTGCTAGGGAGACGGCTGGCTTGACATGCATCTCCTG

ACAAAACACAAACCCGTGGTGTGAGTGGGTGTGGGCGGTGTGAGTAGGGGGATG

AATCAGAGAGGGGGCGAGGGAGACAGGGGCGCAGGAGTCAGGCAAAGGCGATG

CGGGGGTGCGACTACACGCAGTTGGAAACAGTCGTCAGAAGATTCTGGAAACTA

TCTTGCTGGCTATAAACTTGAGGGAAGCAGAAGGCCAACATTCCTCCCAAGGGA

AACTGAGGCTCAGAGTTAAAACCCAGGTATCAGTGATATGCATGTGCCCCGGCC

AGGGTCACTCTCTGACTAACCGGTACCTACCCTACAGGCCTACCTAGAGACTCTT

TTGAAAGGATGGTAGAGACCTGTCCGGGCTTTGCCCACAGTCGTTGGAAACCTCA

GCATTTTCTAGGCAACTTGTGCGAATAAAACACTTCGGGGGTCCTTCTTGTTCATT

CCAATAACCTAAAACCTCTCCTCGGAGAAAATAGGGGGCCTCAAACAAACGAAA

TTCTCTAGCCCGCTTTCCCCAGGATAAGGCAGGCATCCAAATGGAAAAAAAGGG

GCCGGCCGGGGTCTCCTGTCAGCTCCTTGCCCTGTGAAACCCAGCAGGCCTGCC

TGTCTTCTGTCCTCTTGGGGCTGTCCAGGGGCGCAGGCCTCTTGCGGGGGAGCTG

GCCTCCCCGCCCCCTCGCCTGTGGCCGCCCTTTTCCTGGCAGGACAGAGGGATCC

TGCAGCTGTCAGGGGAGGGGCGCCGGGGGGTGATGTCAGGAGGGCTACAAATAG

TGCAGACAGCTAAGGGGCTCCGTCACCCATCTTCACATCCACTCCAGCCGGCTGC

CCGCCCGCTGCCTCCTCTGTGCGTCCGCCCAGCCAGCCTCGTCCACGCC

Desmin-rtTA4 vector (SEQ ID NO: 30):
TTATGCAGTGCTGCCATAACCATGAGTGATAACACTGCGGCCAACTTACTTCTGA

CAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTAT

TAACTGGCGAACTACTTACTCTAGCTTCCCGGCAACAATTAATAGACTGGATGGA

GGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGGTTTCG

-continued

```
CCACCTCTGACTTGAGCGTCGATTTTTGTGATGCTCGTCAGGGGGGCGGAGCCTA
TGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAG
TCAGTGAGCGAGGAAGCGGAAGAGCGCCCAATACGCAAACCGCCTCTCCCCGCG
CGTTGGCCGATTCATTAATGCAGCTGGCACGACAGGTTTCCCGACTGGAAAGCGG
GCAGTGAGCGCAACGCAATTAATGTGAGTTAGCTCACTCATTAGGCACCCCAGG
CTTTACACTTTATGCTTCCGGCTCGTATGTTGTGTGGAATTGTGAGCGGATAACA
ATTTCACACAGGAAACAGCTATGACCATGATTACGCCAGATTTAATTAAGGCCTT
AATTAGGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGG
AGTGGCCAACTCCATCACTAGGGGTTCCTTGTAGTTAATGATTAACCCGCCATGC
TACTTATCTACGTAGCCATGCTCTAGGAAGATCGGAATTCCTAGATCTACCTTGC
TTCCTAGCTGGGCCTTTCCTTCTCCTCTATAAATACCAGCTCTGGTATTTCGCCTT
GGCAGCTGTTGCTGCTAGGGAGACGGCTGGCTTGACATGCATCTCCTGACAAAAC
ACAAACCCGTGGTGTGAGTGGGTGTGGGCGGTGTGAGTAGGGGGATGAATCAGA
GAGGGGGCGAGGGAGACAGGGGCGCAGGAGTCAGGCAAAGGCGATGCGGGGGT
GCGACTACACGCAGTTGGAAACAGTCGTCAGAAGATTCTGGAAACTATCTTGCTG
GCTATAAACTTGAGGGAAGCAGAAGGCCAACATTCCTCCCAAGGGAAACTGAGG
CTCAGAGTTAAAACCCAGGTATCAGTGATATGCATGTGCCCCGGCCAGGGTCACT
CTCTGACTAACCGGTACCTACCCTACAGGCCTACCTAGAGACTCTTTTGAAAGGA
TGGTAGAGACCTGTCCGGGCTTTGCCCACAGTCGTTGGAAACCTCAGCATTTTCT
AGGCAACTTGTGCGAATAAAACACTTCGGGGTCCTTCTTGTTCATTCCAATAAC
CTAAAACCTCTCCTCGGAGAAAATAGGGGGCCTCAAACAAACGAAATTCTCTAG
CCCGCTTTCCCCAGGATAAGGCAGGCATCCAAATGGAAAAAAAGGGGCCGGCCG
GGGGTCTCCTGTCAGCTCCTTGCCCTGTGAAACCCAGCAGGCCTGCCTGTCTTCT
GTCCTCTTGGGGCTGTCCAGGGGCGCAGGCCTCTTGCGGGGGAGCTGGCCTCCCC
GCCCCCTCGCCTGTGGCCGCCCTTTTCCTGGCAGGACAGAGGGATCCTGCAGCTG
TCAGGGGAGGGCGCCGGGGGGTGATGTCAGGAGGGCTACAAATAGTGCAGAC
AGCTAAGGGGCTCCGTCACCCATCTTCACATCCACTCCAGCCGGCTGCCCGCCCG
CTGCCTCCTCTGTGCGTCCGCCCAGCCAGCCTCGTCCACGCCAAGCTTGCGGCCG
CATTAAACGCCACCATGTCCCGCTTGGATAAGAGCAAGGTAATAAATAGCGCAC
TCGAACTCCTCAACGGCGTGGGCATCGAAGGTCTGACTACTCGAAAGCTCGCCC
AGAAATTGGGTGTGGAGCAACCTACATTGTATTGGCATGTCAAGAACAAAAGAG
CCCTGCTGGACGCTCTTCCTATTGAAATGCTTGACAGGCATCACACTCATTCCTGC
CCCCTTGAGGTCGAGAGTTGGCAAGATTTTCTCCGAAACAATGCAAAGTCCTACC
GCTGCGCACTTTTGTCCCATAGGGATGGAGCAAAAGTGCACCTGGGAACCAGGC
CAACAGAGAAACAATACGAGACTCTCGAGAACCAGTTGGCTTTCTTGTGCCAAC
AGGGGTTCTCACTTGAAAATGCCCTTTACGCACTGTCAGCCGTTGGACATTTTAC
CCTGGGGTGCGTTCTTGAGGAGCAAGAACATCAGGTTGCTAAGGAGGAGCGCGA
```

```
GACTCCAACCACTGATTCTATGCCACCTTTGCTGAAACAGGCCATTGAACTTTTC

GATAGACAGGGTGCTGAACCTGCCTTTCTCTTCGGGTTGGAGCTGATTATTTGTG

GTCTCGAAAAACAGCTGAAATGTGAAAGTGGTGGCCCTACTGACGCCCTCGATG

ATTTCGACCTGGATATGCTGCCAGCCGATGCACTTGATGATTTCGATTTGGATAT

GCTTCCAGCCGACGCACTGGACGACTTCGATTTGGACATGCTTCCCGGTTAAACT

AGTCTAGCAATCAACCTCTGGATTACAAAATTTGTGAAAGATTGACTGGTATTCT

TAACTATGTTGCTCCTTTTACGCTATGTGGATACGCTGCTTTAATGCCTTTGTATC

ATGCTATTGCTTCCCGTATGGCTTTCATTTTCTCCTCCTTGTATAAATCCTGGTTAG

TTCTTGCCACGGCGGAACTCATCGCCGCCTGCCTTGCCCGCTGCTGGACAGGGGC

TCGGCTGTTGGGCACTGACAATTCCGTGGTGTTTATTTGTGAAATTTGTGATGCTA

TTGCTTTATTTGTAACCATTCTAGCTTTATTTGTGAAATTTGTGATGCTATTGCTTT

ATTTGTAACCATTATAAGCTGCAATAAACAAGTTAACAACAACAATTGCATTCAT

TTTATGTTTCAGGTTCAGGGGGAGATGTGGGAGGTTTTTTAAAGCGGGGGATCCA

AATTCCCGATAAGGATCTTCCTAGAGCATGGCTACGTAGATAAGTAGCATGGCG

GGTTAATCATTAACTACAAGGAACCCCTAGTGATGGAGTTGGCCACTCCCTCTCT

GCGCGCTCGCTCGCTCACTGAGGCCGGGCGACCAAAGGTCGCCCGACGCCCGGG

CTTTGCCCGGGCGGCCTCAGTGAGCGAGCGAGCGCGCAGCCTTAATTAACCTAAT

TCACTGGCCGTCGTTTTACAACGTCGTGACTGGGAAAACCCTGGCGTTACCCAAC

TTAATCGCCTTGCAGCACATCCCCCTTTCGCCAGCTGGCGTAATAGCGAAGAGGC

CCGCACCGATCGCCCTTCCCAACAGTTGCGCAGCCTGAATGGCGAATGGGACGC

GCCCTGTAGCGGCGCATTAAGCGCGGCGGGTGTGGTGGTTACGCGCAGCGTGAC

CGCTACACTTGCCAGCGCCCTAGCGCCCGCTCCTTTCGCTTTCTTCCCTTCCTTTC

TCGCCACGTTCGCCGGCTTTCCCCGTCAAGCTCTAAATCGGGGGCTCCCTTTAGG

GTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGG

AGTCCACGTTCTTTAATAGTGGACTCTTGTTCCAAACTGGAACAACACTCAACCC

TATCTCGGTCTATTCTTTTGATTTATAAGGGATTTTGCCGATTTCGGCCTATTGGT

TAAAAAATGAGCTGATTTAACAAAAATTTAACGCGAATTTTAACAAAATATTAAC

GTTTATAATTTCAGGTGGCATCTTTCGGGGAAATGTGCGCGGAACCCCTATTTGT

TTATTTTTCTAAATACATTCAAATATGTATCCGCTCATGAGACAATAACCCTGATA

AATGCTTCAATAATATTGAAAAAGGAAGAGTATGAGTATTCAACATTTCCGTGTC

GCCCTTATTCCCTTTTTTGCGGCATTTTGCCTTCCTGTTTTTGCTCACCCAGAAACG

CTGGTGAAAGTAAAAGATGCTGAAGATCAGTTGGGTGCACGAGTGGGTTACATC

GAACTGGATCTCAATAGTGGTAAGATCCTTGAGAGTTTTCGCCCCGAAGAACGTT

TTCCAATGATGAGCACTTTTAAAGTTCTGCTATGTGGCGCGGTATTATCCCGTATT

GACGCCGGGCAAGAGCAACTCGGTCGCCGCATACACTATTCTCAGAATGACTTG

GTTGAGTACTCACCAGTCACAGAAAAGCATCTTACGGATGGCATGACAGTAAGA

GAA pAAV2_CMV_rtTA(V16) (SEQ ID NO: 31):
AAATTGTAAACGTTAATATTTTGTTAAAATTCGCGTTAAATTTTTGTTAAATCAGC

TCATTTTTTAACCAATAGGCCGAAATCGGCAAAATCCCTTATAAATCAAAAGAAT
```

-continued

```
AGCCCGAGATAGGGTTGAGTGTTGTTCCAGTTTGGAACAAGAGTCCACTATTAAA

GAACGTGGACTCCAACGTCAAAGGGCGAAAAACCGTCTATCAGGGCGATGGCCC

ACTACGTGAACCATCACCCAAATCAAGTTTTTTGGGGTCGAGGTGCCGTAAAGCA

CTAAATCGGAACCCTAAAGGGAGCCCCCGATTTAGAGCTTGACGGGGAAAGCCG

GCGAACGTGGCGAGAAAGGAAGGGAAGAAAGCGAAAGGAGCGGGCGCTAGGGC

GCTGGCAAGTGTAGCGGTCACGCTGCGCGTAACCACCACACCCGCCGCGCTTAA

TGCGCCGCTACAGGGCGCGTACTATGGTTGCTTTGACGTATGCGGTGTGAAATAC

CGCACAGATGCGTAAGGAGAAAATACCGCATCAGGCGCCCCTGCAGGCAGCTGC

GCGCTCGCTCGCTCACTGAGGCCGCCCGGGCAAAGCCCGGGCGTCGGGCGACCT

TTGGTCGCCCGGCCTCAGTGAGCGAGCGAGCGCGCAGAGAGGGAGTGGCCAACT

CCATCACTAGGGGTTCCTGCGGCCGCTCGGTCCGCACGATCTCAATTCGGCCATT

ACGGCCGGATCCGGCTCGAGGAGCTTGGCCCATTGCATACGTTGTATCCATATCA

TAATATGTACATTTATATTGGCTCATGTCCAACATTACCGCCATGTTGACATTGAT

TATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAA

TAGGGACTTTCCATTGACGTCAATGGGTGGAGTATTTACGCTAAACTGCCCACTT

GGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTA

CTTGGCAGTACATCTACGTATTAGTCATCGCTATTACCATGGTGATGCGGTTTTGG

CAGTACATCAATGGGCGTGGATAGCGGTTTGACTCACGGGGATTTCCAAGTCTCC

ACCCCATTGACGTCAATGGGAGTTTGTTTTGGCACCAAAATCAACGGGACTTTCC

AAAATGTCGTAACAACTCCGCCCCATTGACGCAAATGGGCGGTAGGCGTGTACG

GTGGGAGGTCTATATAAGCAGAGCTCGTTTAGTGAACCGTCAGATCGCCTGGAG

ACGCCATCCACGCTGTTTTGACCTCCATAGAAGACACCGGGACCGATCCAGCCTC

CGCGGCCCCGAATTCACCATGTCTAGACTGGACAAGAGCAAAATCATAAACAGC

GCTCTGGAATTACTCAATGGAGTCGGTATCGAAGGCCTGACGACAAGGAAACTC

GCTCAAAAGCTGGGAGTTGAGCAGCCTACCCTGTACTGGCACGTGAAGAACAAG

CGGGCCCTGCTCGATGCCCTGCCAATCGAGATGCTGGACAGGCATCATACCCAC

AGCTGCCCCTGGAAGGCGAGTCATGGCAAGACTTTCTGCGGAACAACGCCAAG

TCATACCGCTGTGCTCTCCTCTCACATCGCGACGGGGCTAAAGTGCATCTCGGCA

CCCGCCCAACAGAGAAACAGTACGAAACCCTGGAAAATCAGCTCGCGTTCCTGT

GTCAGCAAGGCTTCTCCCTGGAGAACGCACTGTACGCTCTGTCCGCCGTGGGCCA

CTTTACACTGGGCTGCGTATTGGAGGAACAGGAGCATCAAGTAGCAAAAGAGGA

AAGAGAGACACCTACCACCGATTCTATGCCCCCACTTCTGAAGCAAGCAATTGA

GCTGTTCGACCGGCAGGGAGCCGAACCTGCCTTCCTTTTCGGCCTGGAACTAATC

ATATGTGGCCTGGAGAAACAGCTAAAGTGCGAAAGCGGCGGGCCGACCGACGCC

CTTGACGATTTTGACTTAGACATGCTCCCAGCCGATGCCCTTGACGACTTTGACCT

TGATATGCTGCCTGCTGACGCTCTTGACGATTTTGACCTTGACATGCTCCCCGGGT

AACTAAGTAAGGATCATCTTAATTAAATCGATAAGGATCTGGCCGCCTCGGCCTA

ATCAACCTCTGGATTACAAAATTTGTGAAAGATTGACTGGTATTCTTAACTATGT
```

-continued

```
TGCTCCTTTTACGCTATGTGGATACGCTGCTTTAATGCCTTTGTATCATGCTATTG

CTTCCCGTATGGCTTTCATTTTCTCCTCCTTGTATAAATCCTGGTTGCTGTCTCTTT

ATGAGGAGTTGTGGCCCGTTGTCAGGCAACGTGGCGTGGTGTGCACTGTGTTTGC

TGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGC

CCGCTGCTGGACAGGGGCTCGGCTGTTGGGCACTGACAATTCCGTGGTGTTGTCG

GGGAAATCATCGTCCTTTCCTTGGCTGCTCGCCTGTGTTGCCACCTGGATTCTGCG

CGGGACGTCCTTCTGCTACGTCCCTTCGGCCCTCAATCCAGCGGACCTTCCTTCCC

GCGGCCTGCTGCCGGCTCTGCGGCCTCTTCCGCGTCTTCGCCTTCGCCCTCAGAC

GAGTCGGATCTCCCTTTGGGCCGCCTCCCCGCCAGACATGATAAGATACATTGAT

GAGTTTGGACAAACCACAACTAGAATGCAGTGAAAAAAATGCTTTATTTGTGAA

ATTTGTGATGCTATTGCTTTATTTGTAACCATTATAAGCTGCAATAAACAAGTTAA

CAACAACAATTGCATTCATTTTATGTTTCAGGTTCAGGGGGAGATGTGGGAGGTT

TTTTAAAGCAAGTAAAACCTCTACAAATGTGGTAACTAGCGCGTGCGGCCGCAG

GAACCCCTAGTGATGGAGTTGGCCACTCCCTCTCTGCGCGCTCGCTCGCTCACTG

AGGCCGGGCGACCAAAGGTCGCCCGACGCCCGGGCTTTGCCCGGGCGGCCTCAG

TGAGCGAGCGAGCGCGCAGCTGCCTGCAGGACATGTGAGCAAAAGGCCAGCAA

AAGGCCAGGAACCGTAAAAAGGCCGCGTTGCTGGCGTTTTTCCATAGGCTCCGCC

CCCCTGACGAGCATCACAAAAATCGACGCTCAAGTCAGAGGTGGCGAAACCCGA

CAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGCG

TGGCGCTTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTAT

CCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGA

GTTCTTGAAGTGGTGGCCTAACTACGGCTACACTAGAAGGACAGTATTTGGTATC

TGCGCTCTGCTGAAGCCAGTTACCTTCGGAAAAAGAGTTGGTAGCTCTTGATCCG

GCAAACAAACCACCGCTGGTAGCGGTGGTTTTTTTGTTTGCAAGCAGCAGATTAC

GCGCAGAAAAAAAGGATCTCAAGAAGATCCTTTGATCTTTTCTACGGGGTCTGAC

GCTCAGTGGAACGAAAACTCACGTTAAGGGATTTTGGTCATGAGATTATCAAAA

AGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACC

TATCTCAGCGATCTGTCTATTTCGTTCATCCATAGTTGCCTGACTCCCCGTCGTGT

AGATAACTACGATACGGGAGGGCTTACCATCTGGCCCCAGTGCTGCAATGATAC

CGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTAT

TAATTGTTGCCGGGAAGCTAGAGTAAGTAGTTCGCCAGTTAATAGTTTGCGCAAC

GTTGTTGCCATTGCTACAGGCATCGTGGTGTCACGCTCGTCGTTTGGTATGGCTTC

ATTCAGCTCCGGTTCCCAACGATCAAGGCGAGTTACATGATCCCCCATGTTGTGC

AAAAAAGCGGTTAGCTCCTTCGGTCCTCCGATCGTTGTCAGAAGTAAGTTGGCCG
```

-continued

CAGTGTTATCACTCATGGTTATGGCAGCACTGCATAATTCTCTTACTGTCATGCCA

TCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGC

GCCACATAGCAGAACTTTAAAAGTGCTCATCATTGGAAAACGTTCTTCGGGGCGA

AAACTCTCAAGGATCTTACCGCTGTTGAGATCCAGTTCGATGTAACCCACTCGTG

CACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTT

GAATACTCATACTCTTCCTTTTTCAATATTATTGAAGCATTTATCAGGGTTATTGT

CTCATGAGCGGATACATATTTGAATGTATTTAGAAAAATAAACAAATAGGGGTTC

CGCGCACATTTCCCCGAAAAGTGCCACCTGACGTCTAAGAAACCATTATTATCAT

GACATTAACCTATAAAAATAGGCGTATCACGAGGCCCTTTCGTCTCGCGCGTTTC

GGTGATGACGGTGAAAACCTCTGACACATGCAGCTCCCGGAGACGGTCACAGCT

TGTCTGTAAGCGGATGCCGGGAGCAGACAAGCCCGTCAGGGCGCGTCAGCGGGT

GTTGGCGGGTGTCGGGGCTGGCTTAACTATGCGGCATCAGAGCAGATTGTACTGA

GAGTGCACCATA

CAG-tTA (SEQ ID NO: 32):
CCTGCAGGCAGCTGCGCGCTCGCTCGCTCACTGAGGCCGCCCGGGCAAAGCCCG

GGCGTCGGGCGACCTTTGGTCGCCCGGCCTCAGTGAGCGAGCGAGCGCGCAGAG

AGGGAGTGGCCAACTCCATCACTAGGGGTTCCTGCGGCCGCACGCGTGGAGCTA

GTTATTAATAGTAATCAATTACGGGGTCATTAGTTCATAGCCCATATATGGAGTT

CCGCGTTACATAACTTACGGTAAATGGCCCGCCTGGCTGACCGCCCAACGACCCC

CGCCCATTGACGTCAATAATGACGTATGTTCCCATAGTAACGTCAATAGGGACTT

TCCATTGACGTCAATGGGTGGAGTATTTACGGTAAACTGCCCACTTGGCAGTACA

TCAAGTGTATCATATGCCAAGTACGCCCCCTATTGACGTCAATGACGGTAAATGG

CCCGCCTGGCATTATGCCCAGTACATGACCTTATGGGACTTTCCTACTTGGCAGT

ACATCTACGTATTAGTCATCGCTATTACCATGGTGATGCGGTTTTGGCAGTACAT

CAATGGGCGTGGATAGCGGTTTGACTCACGGGGATTTCCAAGTCTCCACCCCATT

GACGTCAATGGGAGTTTGTTTTGCACCAAAATCAACGGGACTTTCCAAAATGTCG

TAACAACTCCGCCCCATTGACGCAAATGGGCGGTAGGCGTGTACGGTGGGAGGT

CTATATAAGCAGAGCTCGTTTAGTGAACCGTCAGATCGCCTGGAGACGCCATCCA

CGCTGTTTTGACCTCCATAGAAGACACCGGGACCGATCCAGCCTCCGCGGATTCG

AATCCCGGCCGGGAACGGTGCATTGGAACGCGGATTCCCCGTGCCAAGAGTGAC

GTAAGTACCGCCTATAGAGTCTATAGGCCCACAAAAAATGCTTTCTTCTTTTAAT

ATACTTTTTGTTTATCTTATTTCTAATACTTTCCCTAATCTCTTTCTTTCAGGGCA

ATAATGATACAATGTATCATGCCTCTTTGCACCATTCTAAAGAATAACAGTGATA

ATTTCTGGGTTAAGGCAATAGCAATATTTCTGCATATAAATATTTCTGCATATAA

ATTGTAACTGATGTAAGAGGTTTCATATTGCTAATAGCAGCTACAATCCAGCTAC

CATTCTGCTTTTATTTTATGGTTGGGATAAGGCTGGATTATTCTGAGTCCAAGCTA

GGCCCTTTTGCTAATCATGTTCATACCTCTTATCTTCCTCCCACAGCTCCTGGGCA

ACGTGCTGGTCTGTGTGCTGGCCCATCACTTTGGCAAAGAATTGGGATTCGAACA

TCGATTGAATTCATGTCTAGACTGGACAAGAGCAAAGTCATAAACTCTGCTCTGG

-continued

```
AATTACTCAATGAAGTCGGTATCGAAGGCCTGACGACAAGGAAACTCGCTCAAA

AGCTGGGAGTTGAGCAGCCTACCCTGTACTGGCACGTGAAGAACAAGCGGGCCC

TGCTCGATGCCCTGGCAATCGAGATGCTGGACAGGCATCATACCCACTTCTGCCC

CCTGGAAGGCGAGTCATGGCAAGACTTTCTGCGGAACAACGCCAAGTCATTCCG

CTGTGCTCTCCTCTCACATCGCGACGGGGCTAAAGTGCATCTCGGCACCCGCCCA

ACAGAGAAACAGTACGAAACCCTGGAAAATCAGCTCGCGTTCCTGTGTCAGCAA

GGCTTCTCCCTGGAGAACGCACTGTACGCTCTGTCCGCCGTGGGCCACTTTACAC

TGGGCTGCGTATTGGAGGATCAGGAGCATCAAGTAGCAAAAGAGGAAAGAGAG

ACACCTACCACCGATTCTATGCCCCCACTTCTGAGACAAGCAATTGAGCTGTTCG

ACCATCAGGGAGCCGAACCTGCCTTCCTTTTCGGCCTGGAACTAATCATATGTGG

CCTGGAGAAACAGCTAAAGTGCGAAAGCGGCGGGCCGGCCGACGCCCTTGACGA

TTTTGACTTAGACATGCTCCCAGCCGATGCCCTTGACGACTTTGACCTTGATATGC

TGCCTGCTGACGCTCTTGACGATTTTGACCTTGACATGCTCCCCGGATGAGGATC

CTCTAGAGTCGACCTGCAGAAGCTTGCCTCGAGCAGCGCTGCTCGAGAGATCTAC

GGGTGGCATCCCTGTGACCCCTCCCCAGTGCCTCTCCTGGCCCTGGAAGTTGCCA

CTCCAGTGCCCACCAGCCTTGTCCTAATAAAATTAAGTTGCATCATTTTGTCTGAC

TAGGTGTCCTTCTATAATATTATGGGTGGAGGGGGGTGGTATGGAGCAAGGGG

CAAGTTGGGAAGACAACCTGTAGGGCCTGCGGGGTCTATTGGGAACCAAGCTGG

AGTGCAGTGGCACAATCTTGGCTCACTGCAATCTCCGCCTCCTGGGTTCAAGCGA

TTCTCCTGCCTCAGCCTCCCGAGTTGTTGGGATTCCAGGCATGCATGACCAGGCT

CAGCTAATTTTTGTTTTTTTGGTAGAGACGGGGTTTCACCATATTGGCCAGGCTGG

TCTCCAACTCCTAATCTCAGGTGATCTACCCACCTTGGCCTCCCAAATTGCTGGG

ATTACAGGCGTGAACCACTGCTCCCTTCCCTGTCCTTCTGATTTTGTAGGTAACCA

CGTGCGGACCGAGCGGCCGCAGGAACCCCTAGTGATGGAGTTGGCCACTCCCTC

TCTGCGCGCTCGCTCGCTCACTGAGGCCGGGCGACCAAAGGTCGCCCGACGCCC

GGGCTTTGCCCGGGCGGCCTCAGTGAGCGAGCGAGCGCGCAGCTGCCTGCAGGG

GCGCCTGATGCGGTATTTTCTCCTTACGCATCTGTGCGGTATTTCACACCGCATAC

GTCAAAGCAACCATAGTACGCGCCCTGTAGCGGCGCATTAAGCGCGGCGGGTGT

GGTGGTTACGCGCAGCGTGACCGCTACACTTGCCAGCGCCCTAGCGCCCGCTCCT

TTCGCTTTCTTCCCTTCCTTTCTCGCCACGTTCGCCGGCTTTCCCCGTCAAGCTCTA

AATCGGGGGCTCCCTTTAGGGTTCCGATTTAGTGCTTTACGGCACCTCGACCCCA

AAAAACTTGATTTGGGTGATGGTTCACGTAGTGGGCCATCGCCCTGATAGACGGT

TTTTCGCCCTTTGACGTTGGAGTCCACGTTCTTTAATAGTGGACTCTTGTTCCAAA

CTGGAACAACACTCAACCCTATCTCGGGCTATTCTTTTGATTTATAAGGGATTTTG

CCGATTTCGGCCTATTGGTTAAAAAATGAGCTGATTTAACAAAAATTTAACGCGA

ATTTTAACAAAATATTAACGTTTACAATTTTATGGTGCACTCTCAGTACAATCTGC

TCTGATGCCGCATAGTTAAGCCAGCCCCGACACCCGCCAACACCCGCTGACGCG

CCCTGACGGGCTTGTCTGCTCCCGGCATCCGCTTACAGACAAGCTGTGACCGTCT

CCGGGAGCTGCATGTGTCAGAGGTTTTCACCGTCATCACCGAAACGCGCGAGAC

GAAAGGGCCTCGTGATACGCCTATTTTTATAGGTTAATGTCATGATAATAATGGT

TTCTTAGACGTCAGGTGGCACTTTTCGGGGAAATGTGCGCGGAACCCCTATTTGT
```

TTATTTTTCTAAATACATTCAAATATGTATCCGCTCATGAGACAATAACCCTGATA
AATGCTTCAATAATATTGAAAAAGGAAGAGTATGAGTATTCAACATTTCCGTGTC
GCCCTTATTCCCTTTTTTGCGGCATTTTGCCTTCCTGTTTTTGCTCACCCAGAAACG
CTGGTGAAAGTAAAAGATGCTGAAGATCAGTTGGGTGCACGAGTGGGTTACATC
GAACTGGATCTCAACAGCGGTAAGATCCTTGAGAGTTTTCGCCCCGAAGAACGTT
TTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTG
GTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTC
TGACAACGATCGGAGGACCGAAGGAGCTAACCGCTTTTTTGCACAACATGGGGG
ATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAAC
TATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGG
TTTATTGCTGATAAATCTGGAGCCGGTGAGCGTGGGTCTCGCGGTATCATTGCAG
CACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCAC
TGATTAAGCATTGGTAACTGTCAGACCAAGTTTACTCATATATACTTTAGATTGA
TTTAAAACTTCATTTTTAATTTAAAAGGATCTAGGTGAAGATCCTTTTTGATAATC
TCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCT
TGCAAACAAAAAAACCACCGCTACCAGCGGTGGTTTGTTTGCCGGATCAAGAGC
TACCAACTCTTTTTCCGAAGGTAACTGGCTTCAGCAGAGCGCAGATACCAAATAC
TGTCCTTCTAGTGTAGCCGTAGTTAGGCCACCACTTCAAGAACTCTGTAGCACCG
CCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGC
GGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGCGGAG
CCTATGGAAAAACGCCAGCAACGCGGCCTTTTTACGGTTCCTGGCCTTTTGCTGG
CCTTTTGCTCACATGT pAAV-Tet-O-OSK-SV40LpA (or pAAV-TRE2-OSK-SV40LpA)
(SEQ ID NO: 33):
TTATGCAGTGCTGCCATAACCATGAGTGATAACACTGCGGCCAACTTACTTCTGA
CAACGATCGGAGGACCGAAGGAGCTAACCGCTTTTTTGCACAACATGGGGGATC
ATGTAACTCGCCTTGATCGTTGGGAACCGGAGCTGAATGAAGCCATACCAAACG
ACGAGCGTGACACCACGATGCCTGTAGTAATGGTAACAACGTTGCGCAAACTAT
TAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTT

-continued
```
ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGGTTTCG

CCACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCCTT

TTGCTCACATGTTCTTTCCTGCGTTATCCCCTGATTCTGTGGATAACCGTATTACC

GCCTTTGAGTGAGCTGATACCGCTCGCCGCAGCCGAACGACCGAGCGCAGCGAG

TCAGTGAGCGAGGAAGCGGAAGAGCGCCCAATACGCAAACCGCCTCTCCCCGCG

CGTTGGCCGATTCATTAATGCAGCTGGCACGACAGGTTTCCCGACTGGAAAGCGG

GCAGTGAGCGCAACGCAATTAATGTGAGTTAGCTCACTCATTAGGCACCCCAGG

CTTTACACTTTATGCTTCCGGCTCGTATGTTGTGTGGAATTGTGAGCGGATAACA

ATTTCACACAGGAAACAGCTATGACCATGATTACGCCAGATTTAATTAAGGCCTT

AATTAGGCTGCGCGCTCGCTCGCTCACTGAGGCCGCCCGGGCAAAGCCCGGGCG

TCGGGCGACCTTTGGTCGCCCGGCCTCAGTGAGCGAGCGAGCGCGCAGAGAGGG

AGTGGCCAACTCCATCACTAGGGGTTCCTTGTAGTTAATGATTAACCCGCCATGC

TACTTATCTACGTAGCCATGCTCTAGGAAGATCGGAATTCGTACACGCCTACCTC

GACCCATCAAGTGCCACCTGACGTCTCCCTATCAGTGATAGAGAAGTCGACACGT

CTCGAGCTCCCTATCAGTGATAGAGAAGGTACGTCTAGAACGTCTCCCTATCAGT

GATAGAGAAGTCGACACGTCTCGAGCTCCCTATCAGTGATAGAGAAGGTACGTC

TAGAACGTCTCCCTATCAGTGATAGAGAAGTCGACACGTCTCGAGCTCCCTATCA

GTGATAGAGAAGGTACGTCTAGAACGTCTCCCTATCAGTGATAGAGAAGTCGAC

ACGTCTCGAGCTCCCTATCAGTGATAGAGAAGGTACCCCTATATAAGCAGAGCT

CGTTTAGTGAACCGTCAGATCGCCTGGAGACGCCATCCACGCTGTTTTGACCTCC

ATAGAAGACACCGGGACCGATCCAGCCTGGATCGCGGCCGCGCCACCATGGCTG

GACACCTGGCTTCAGACTTCGCCTTCTCACCCCCACCAGGTGGGGGTGATGGGTC

AGCAGGGCTGGAGCCGGGCTGGGTGGATCCTCGAACCTGGCTAAGCTTCCAAGG

GCCTCCAGGTGGGCCTGGAATCGGACCAGGCTCAGAGGTATTGGGGATCTCCCC

ATGTCCGCCCGCATACGAGTTCTGCGGAGGGATGGCATACTGTGGACCTCAGGTT
```

-continued

```
GGACTGGGCCTAGTCCCCCAAGTTGGCGTGGAGACTTTGCAGCCTGAGGGCCAG

GCAGGAGCACGAGTGGAAAGCAACTCAGAGGGAACCTCCTCTGAGCCCTGTGCC

GACCGCCCCAATGCCGTGAAGTTGGAGAAGGTGGAACCAACTCCCGAGGAGTCC

CAGGACATGAAAGCCCTGCAGAAGGAGCTAGAACAGTTTGCCAAGCTGCTGAAG

CAGAAGAGGATCACCTTGGGGTACACCCAGGCCGACGTGGGGCTCACCCTGGGC

GTTCTCTTTGGAAAGGTGTTCAGCCAGACCACCATCTGTCGCTTCGAGGCCTTGC

AGCTCAGCCTTAAGAACATGTGTAAGCTGCGGCCCCTGCTGGAGAAGTGGGTGG

AGGAAGCCGACAACAATGAGAACCTTCAGGAGATATGCAAATCGGAGACCCTGG

TGCAGGCCCGGAAGAGAAAGCGAACTAGCATTGAGAACCGTGTGAGGTGGAGTC

TGGAGACCATGTTTCTGAAGTGCCCGAAGCCCTCCCTACAGCAGATCACTCACAT

CGCCAATCAGCTTGGGCTAGAGAAGGATGTGGTTCGAGTATGGTTCTGTAACCGG

CGCCAGAAGGGCAAAAGATCAAGTATTGAGTATTCCCAACGAGAAGAGTATGAG

GCTACAGGGACACCTTTCCCAGGGGGGCTGTATCCTTTCCTCTGCCCCCAGGTC

CCCACTTTGGCACCCCAGGCTATGGAAGCCCCCACTTCACCACACTCTACTCAGT

CCCTTTTCCTGAGGGCGAGGCCTTTCCCTCTGTTCCCGTCACTGCTCTGGGCTCTC

CCATGCATTCAAACGCTAGCGGCAGCGGCGCCACGAACTTCTCTCTGTTAAAGCA

AGCAGGAGATGTTGAAGAAAACCCCGGGCCTGCATGCATGTATAACATGATGGA

GACGGAGCTGAAGCCGCCGGGCCCGCAGCAAGCTTCGGGGGGCGGCGGCGGAG

GAGGCAACGCCACGGCGGCGGCGACCGGCGGCAACCAGAAGAACAGCCCGGAC

CGCGTCAAGAGGCCCATGAACGCCTTCATGGTATGGTCCCGGGGGCAGCGGCGT

AAGATGGCCCAGGAGAACCCCAAGATGCACAACTCGGAGATCAGCAAGCGCCTG

GGCGCGGAGTGGAAACTTTTGTCCGAGACCGAGAAGCGGCCGTTCATCGACGAG

GCCAAGCGGCTGCGCGCTCTGCACATGAAGGAGCACCCGGATTATAAATACCGG

CCGCGGCGGAAAACCAAGACGCTCATGAAGAAGGATAAGTACACGCTTCCCGGA

GGCTTGCTGGCCCCCGGCGGGAACAGCATGGCGAGCGGGGTTGGGGTGGGCGCC

GGCCTGGGTGCGGGCGTGAACCAGCGCATGGACAGCTACGCGCACATGAACGGC

TGGAGCAACGGCAGCTACAGCATGATGCAGGAGCAGCTGGGCTACCCGCAGCAC

CCGGGCCTCAACGCTCACGGCGCGGCACAGATGCAACCGATGCACCGCTACGAC

GTCAGCGCCCTGCAGTACAACTCCATGACCAGCTCGCAGACCTACATGAACGGC

TCGCCCACCTACAGCATGTCCTACTCGCAGCAGGGCACCCCCGGTATGGCGCTGG

GCTCCATGGGCTCTGTGGTCAAGTCCGAGGCCAGCTCCAGCCCCCCGTGGTTAC

CTCTTCCTCCCACTCCAGGGCGCCCTGCCAGGCCGGGGACCTCCGGGACATGATC

AGCATGTACCTCCCCGGCGCCGAGGTGCCGGAGCCCGCTGCGCCCAGTAGACTG

CACATGGCCCAGCACTACCAGAGCGGCCCGGTGCCCGGCACGGCCATTAACGGC

ACACTGCCCCTGTCGCACATGGCATGCGGCTCCGGCGAGGGCAGGGGAAGTCTT

CTAACATGCGGGGACGTGGAGGAAAATCCCGGCCCACTCGAGATGAGGCAGCCA

CCTGGCGAGTCTGACATGGCTGTCAGCGACGCTCTGCTCCCGTCCTTCTCCACGT

TCGCGTCCGGCCCGGCGGGAAGGGAGAAGACACTGCGTCCAGCAGGTGCCCCGA

CTAACCGTTGGCGTGAGGAACTCTCTCACATGAAGCGACTTCCCCCACTTCCCGG

CCGCCCCTACGACCTGGCGGCGACGGTGGCCACAGACCTGGAGAGTGGCGGAGC
```

-continued

```
TGGTGCAGCTTGCAGCAGTAACAACCCGGCCCTCCTAGCCCGGAGGGAGACCGA
GGAGTTCAACGACCTCCTGGACCTAGACTTTATCCTTTCCAACTCGCTAACCCAC
CAGGAATCGGTGGCCGCCACCGTGACCACCTCGGCGTCAGCTTCATCCTCGTCTT
CCCCAGCGAGCAGCGGCCCTGCCAGCGCGCCCTCCACCTGCAGCTTCAGCTATCC
GATCCGGGCCGGGGGTGACCCGGGCGTGGCTGCCAGCAACACAGGTGGAGGGCT
CCTCTACAGCCGAGAATCTGCGCCACCTCCCACGGCCCCCTTCAACCTGGCGGAC
ATCAATGACGTGAGCCCCTCGGGCGGCTTCGTGGCTGAGCTCCTGCGGCCGGAGT
TGGACCCAGTATACATTCCGCCACAGCAGCCTCAGCCGCCAGGTGGCGGGCTGA
TGGGCAAGTTTGTGCTGAAGGCGTCTCTGACCACCCCTGGCAGCGAGTACAGCA
GCCCTTCGGTCATCAGTGTTAGCAAAGGAAGCCCAGACGGCAGCCACCCCGTGG
TAGTGGCGCCCTACAGCGGTGGCCCGCCGCGCATGTGCCCCAAGATTAAGCAAG
AGGCGGTCCCGTCCTGCACGGTCAGCCGGTCCCTAGAGGCCCATTTGAGCGCTGG
ACCCCAGCTCAGCAACGGCCACCGGCCCAACACACACGACTTCCCCCTGGGGCG
GCAGCTCCCCACCAGGACTACCCCTACACTGAGTCCCGAGGAACTGCTGAACAG
CAGGGACTGTCACCCTGGCCTGCCTCTTCCCCCAGGATTCCATCCCCATCCGGGG
CCCAACTACCCTCCTTTCCTGCCAGACCAGATGCAGTCACAAGTCCCCTCTCTCC
ATTATCAAGAGCTCATGCCACCGGGTTCCTGCCTGCCAGAGGAGCCCAAGCCAA
AGAGGGGAAGAAGGTCGTGGCCCCGGAAAAGAACAGCCACCCACACTTGTGACT
ATGCAGGCTGTGGCAAAACCTATACCAAGAGTTCTCATCTCAAGGCACACCTGCG
AACTCACACAGGCGAGAAACCTTACCACTGTGACTGGGACGGCTGTGGGTGGAA
ATTCGCCCGCTCCGATGAACTGACCAGGCACTACCGCAAACACACAGGGCACCG
GCCCTTTCAGTGCCAGAAGTGCGACAGGGCCTTTTCCAGGTCGGACCACCTTGCC
TTACACATGAAGAGGCACTAAATGACTAGTCTAGCAATCAACCTCTGGATTACAA
AATTTGTGAAAGATTGACTGGTATTCTTAACTATGTTGCTCCTTTTACGCTATGTG
GATACGCTGCTTTAATGCCTTTGTATCATGCTATTGCTTCCCGTATGGCTTTCATT
TTCTCCTCCTTGTATAAATCCTGGTTAGTTCTTGCCACGGCGGAACTCATCGCCGC
CTGCCTTGCCCGCTGCTGGACAGGGGCTCGGCTGTTGGGCACTGACAATTCCGTG
GTGTTTATTTGTGAAATTTGTGATGCTATTGCTTTATTTGTAACCATTCTAGCTTTA
TTTGTGAAATTTGTGATGCTATTGCTTTATTTGTAACCATTATAAGCTGCAATAAA
CAAGTTAACAACAACAATTGCATTCATTTTATGTTTCAGGTTCAGGGGGAGATGT
GGGAGGTTTTTTAAAGCGGGGGATCCAAATTCCCGATAAGGATCTTCCTAGAGCA
TGGCTACGTAGATAAGTAGCATGGCGGGTTAATCATTAACTACAAGGAACCCCT
AGTGATGGAGTTGGCCACTCCCTCTCTGCGCGCTCGCTCGCTCACTGAGGCCGGG
CGACCAAAGGTCGCCCGACGCCCGGGCTTTGCCCGGCGGCCTCAGTGAGCGAG
CGAGCGCGCAGCCTTAATTAACCTAATTCACTGGCCGTCGTTTTACAACGTCGTG
ACTGGGAAAACCCTGGCGTTACCCAACTTAATCGCCTTGCAGCACATCCCCCTTT
CGCCAGCTGGCGTAATAGCGAAGAGGCCCGCACCGATCGCCCTTCCCAACAGTT
GCGCAGCCTGAATGGCGAATGGGACGCGCCCTGTAGCGGCGCATTAAGCGCGGC
GGGTGTGGTGGTTACGCGCAGCGTGACCGCTACACTTGCCAGCGCCCTAGCGCCC
GCTCCTTTCGCTTTCTTCCCTTCCTTTCTCGCCACGTTCGCCGGCTTTCCCCGTCAA
GCTCTAAATCGGGGGCTCCCTTTAGGGTTCCGATTTAGTGCTTTACGGCACCTCG
```

-continued

ACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGT

TCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTT

AACGCGAATTTTAACAAAATATTAACGTTTATAATTTCAGGTGGCATCTTTCGGG

GAAATGTGCGCGGAACCCCTATTTGTTTATTTTTCTAAATACATTCAAATATGTAT

CCGCTCATGAGACAATAACCCTGATAAATGCTTCAATAATATTGAAAAAGGAAG

AGTATGAGTATTCAACATTTCCGTGTCGCCCTTATTCCCTTTTTTGCGGCATTTTG

CCTTCCTGTTTTTGCTCACCCAGAAACGCTGGTGAAAGTAAAAGATGCTGAAGAT

CAGTTGGGTGCACGAGTGGGTTACATCGAACTGGATCTCAATAGTGGTAAGATCC

TTGAGAGTTTTCGCCCCGAAGAACGTTTTCCAATGATGAGCACTTTTAAAGTTCT

GCTATGTGGCGCGGTATTATCCCGTATTGACGCCGGGCAAGAGCAACTCGGTCGC

CGCATACACTATTCTCAGAATGACTTGGTTGAGTACTCACCAGTCACAGAAAAGC

ATCTTACGGATGGCATGACAGTAAGAGAA

VP64, 4 repeats of VP16 (SEQ ID NO: 34) (Non-limiting example of a
transactivation domain):
GAGGCCAGCGGTTCCGGACGGGCTGACGCATTGGACGATTTTGATCTGGATATGC

TGGGAAGTGACGCCCTCGATGATTTTGACCTTGACATGCTTGGTTCGGATGCCCT

TGATGACTTTGACCTCGACATGCTCGGCAGTGACGCCCTTGATGATTTCGACCTG

GACATGCTGATTAACTCTAGA

P65 (SEQ ID NO: 35) (Non-limiting example of a transactivation domain):
AGCCAGTACCTGCCCGACACCGACGACCGGCACCGGATCGAGGAAAAGCGGAA

GCGGACCTACGAGACATTCAAGAGCATCATGAAGAAGTCCCCCTTCAGCGGCCC

CACCGACCCTAGACCTCCACCTAGAAGAATCGCCGTGCCCAGCAGATCCAGCGC

CAGCGTGCCAAAACCTGCCCCCCAGCCTTACCCCTTCACCAGCAGCCTGAGCACC

ATCAACTACGACGAGTTCCCTACCATGGTGTTCCCCAGCGGCCAGATCTCTCAGG

CCTCTGCTCTGGCTCCAGCCCCTCCTCAGGTGCTGCCTCAGGCTCCTGCTCCTGCA

CCAGCTCCAGCCATGGTGTCTGCACTGGCTCAGGCACCAGCACCCGTGCCTGTGC

TGGCTCCTGGACCTCCACAGGCTGTGGCTCCACCAGCCCCTAAACCTACACAGGC

CGGCGAGGGCACACTGTCTGAAGCTCTGCTGCAGCTGCAGTTCGACGACGAGGA

TCTGGGAGCCCTGCTGGGAAACAGCACCGATCCTGCCGTGTTCACCGACCTGGCC

AGCGTGGACAACAGCGAGTTCCAGCAGCTGCTGAACCAGGGCATCCCTGTGGCC

CCTCACACCACCGAGCCCATGCTGATGGAATACCCCGAGGCCATCACCCGGCTC

GTGACAGGCGCTCAGAGGCCTCCTGATCCAGCTCCTGCCCCTCTGGGAGCACCAG

GCCTGCCTAATGGACTGCTGTCTGGCGACGAGGACTTCAGCTCTATCGC

CGATATGGATTTCTCAGCCTTGCTG

RTA (SEQ ID NO: 36) (Non-limiting example of a transactivation domain):
CGGGATTCCAGGGAAGGGATGTTTTTGCCGAAGCCTGAGGCCGGCTCCGCTATTA

GTGACGTGTTTGAGGGCCGCGAGGTGTGCCAGC CAAAACGAA TCCGGCCA

TTTCATCCTCCAGGAAGTCCATGGGCCAACCGCCCACTCCCCGCCAGCCTCGCAC

CAACACCAACCGGTCCAGTACATGAGCCAGTCGGGTCACTGACCCCGGCACCAG

TCCC

-continued

TCAGCCACTGGATCCAGCGCCCGCAGTGACTCCCGAGGCCAGTCACCTGTTGGA

GGATCCCGATGAAGAGACGAGCCAGGCTGTCAAAGCCCTTCGGGAGATGGCCGA

TACTGTGATTCCCCAGAAGGAA GAGGCTGCAA TCTGTGGCCAAA

TGGACCTTTCCCA TCCGCCCCCAAGGGGCCA TCTGGA TGAGCT

GACAACCACACTTGAGTCCA

TGACCGAGGATCTGAACCTGGACTCACCCCTGACCCCGGAATTGAACGAGATTCT

GGATACCTTCCTGAACGACGAGTGCCTCTTGCATGCCATGCATATCAGCACAGGA

C TGTCCA TCTTCGACACA TCTCTGTTT

MPH MS2-P65-HSF1 (SEQ ID NO: 37) (Non-limiting example of a
transactivation domain):
GCTTCAAACTTTACTCAGTTCGTGCTCGTGGACAATGGTGGGACAGGGGATGTGA

CAGTGGCTCCTTCTAATTTCGCTAATGGGGTGGCAGAGTGGATCAGCTCCAACTC

ACGGAGCCAGGCCTACAAGGTGACATGCAGCGTCAGGCAGTCTAGTGCCCAGAA

GAGAAAGTATACCATCAAGGTGGAGGTCCCCAAAGTGGCTACCCAGACAGTGGG

CGGAGTCGAACTGCCTGTCGCCGCTTGGAGGTCCTACCTGAACATGGAGCTCACT

ATCCCAATTTTCGCTACCAATTCTGACTGTGAACTCATCGTGAAGGCAATGCAGG

GGCTCCTCAAAGACGGTAATCCTATCCCTTCCGCCATCGCCGCTAACTCAGGTAT

CTACAGCGCTGGAGGAGGTGGAAGCGGAGGAGGAGGAAGCGGAGGAGGAGGTA

GCGGACCTAAGAAAAAGAGGAAGGTGGCGGCCGCTGGATCCCCTTCAGGGCAGA

TCAGCAACCAGGCCCTGGCTCTGGCCCCTAGCTCCGCTCCAGTGCTGGCCCAGAC

TATGGTGCCCTCTAGTGCTATGGTGCCTCTGGCCCAGCCACCTGCTCCAGCCCCT

GTGCTGACCCCAGGACCACCCCAGTCACTGAGCGCTCCAGTGCCCAAGTCTACAC

AGGCCGGCGAGGGGACTCTGAGTGAAGCTCTGCTGCACCTGCAGTTCGACGCTG

ATGAGGACCTGGGAGCTCTGCTGGGGAACAGCACCGATCCCGGAGTGTTCACAG

ATCTGGCCTCCGTGGACAACTCTGAGTTTCAGCAGCTGCTGAATCAGGGCGTGTC

CATGTCTCATAGTACAGCCGAACCAATGCTGATGGAGTACCCCGAAGCCATTACC

CGGCTGGTGACCGGCAGCCAGCGGCCCCCCGACCCCGCTCCAACTCCCCTGGGA

ACCAGCGGCCTGCCTAATGGGCTGTCCGGAGATGAAGACTTCTCAAGCATCGCTG

ATATGGACTTTAGTGCCCTGCTGTCACAGATTTCCTCTAGTGGGCAGGGAGGAGG

TGGAAGCGGCTTCAGCGTGGACACCAGTGCCCTGCTGGACCTGTTCAGCCCCTCG

GTGACCGTGCCCGACATGAGCCTGCCTGACCTTGACAGCAGCCTGGCCAGTATCC

AAGAGCTCCTGTCTCCCCAGGAGCCCCCCAGGCCTCCCGAGGCAGAGAACAGCA

GCCCGGATTCAGGGAAGCAGCTGGTGCACTACACAGCGCAGCCGCTGTTCCTGC

TGGACCCCGGCTCCGTGGACACCGGGAGCAACGACCTGCCGGTGCTGTTTGAGC

TGGGAGAGGGCTCCTACTTCTCCGAAGGGGACGGCTTCGCCGAGGACCCCACCA

TCTCCCTGCTGACAGGCTCGGAGCCTCCCAAAGCCAAGGACCCCACTGTCTCC

OCT4-2A-SOX2-2A-KLF4 (non-limiting example of nucleic acid sequence
encoding human OCT4, human SOX2, and human KLF4, each separated by a 2A peptide)
(SEQ ID NO: 38):
ATGGCGGGACACCTGGCTTCGGATTTCGCCTTCTCGCCCCCTCCAGGTGGTGGAG

GTGATGGGCCAGGGGGGCCGGAGCCGGGCTGGGTTGATCCTCGGACCTGGCTAA

GCTTCCAAGGCCCTCCTGGAGGGCCAGGAATCGGGCCGGGGGTTGGGCCAGGCT

CTGAGGTGTGGGGGATTCCCCCATGCCCCCCGCCGTATGAGTTCTGTGGGGGGAT

-continued

```
GGCGTACTGTGGGCCCCAGGTTGGAGTGGGGCTAGTGCCCCAAGGCGGCTTGGA

GACCTCTCAGCCTGAGGGCGAAGCAGGAGTCGGGGTGGAGAGCAACTCCGATGG

GGCCTCCCCGGAGCCCTGCACCGTCACCCCTGGTGCCGTGAAGCTGGAGAAGGA

GAAGCTGGAGCAAAACCCGGAGGAGTCCCAGGACATCAAAGCTCTGCAGAAAG

AACTCGAGCAATTTGCCAAGCTCCTGAAGCAGAAGAGGATCACCCTGGGATATA

CACAGGCCGATGTGGGGCTCACCCTGGGGGTTCTATTTGGGAAGGTATTCAGCCA

AACGACCATCTGCCGCTTTGAGGCTCTGCAGCTTAGCTTCAAGAACATGTGTAAG

CTGCGGCCCTTGCTGCAGAAGTGGGTGGAGGAAGCTGACAACAATGAAAATCTT

CAGGAGATATGCAAAGCAGAAACCCTCGTGCAGGCCCGAAAGAGAAAGCGAAC

CAGTATCGAGAACCGAGTGAGAGGCAACCTGGAGAATTTGTTCCTGCAGTGCCC

GAAACCCACACTGCAGCAGATCAGCCACATCGCCCAGCAGCTTGGGCTCGAGAA

GGATGTGGTCCGAGTGTGGTTCTGTAACCGGCGCCAGAAGGGCAAGCGATCAAG

CAGCGACTATGCACAACGAGAGGATTTTGAGGCTGCTGGGTCTCCTTTCTCAGGG

GGACCAGTGTCCTTTCCTCTGGCCCCAGGGCCCCATTTTGGTACCCCAGGCTATG

GGAGCCCTCACTTCACTGCACTGTACTCCTCGGTCCCTTTCCCTGAGGGGGAAGC

CTTTCCCCCTGTCTCTGTCACCACTCTGGGCTCTCCCATGCATTCAAACGCTAGCG

GCAGCGGCGCCACGAACTTCTCTCTGTTAAAGCAAGCAGGAGATGTTGAAGAAA

ACCCCGGGCCTGCATGCATGTACAACATGATGGAGACGGAGCTGAAGCCGCCGG

GCCCGCAGCAAACTTCGGGGGCGGCGGCGGCAACTCCACCGCGGCGGCGGCCG

GCGGCAACCAGAAAAACAGCCCGGACCGCGTCAAGCGGCCCATGAATGCCTTCA

TGGTGTGGTCCCGCGGGCAGCGGCGCAAGATGGCCCAGGAGAACCCCAAGATGC

ACAACTCGGAGATCAGCAAGCGCCTGGGCGCCGAGTGGAAACTTTTGTCGGAGA

CGGAGAAGCGGCCGTTCATCGACGAGGCTAAGCGGCTGCGAGCGCTGCACATGA

AGGAGCACCCGGATTATAAATACCGGCCCCGGCGGAAAACCAAGACGCTCATGA

AGAAGGATAAGTACACGCTGCCCGGCGGGCTGCTGGCCCCCGGCGGCAATAGCA

TGGCGAGCGGGGTCGGGGTGGGCGCCGGCCTGGGCGCGGGCGTGAACCAGCGC

ATGGACAGTTACGCGCACATGAACGGCTGGAGCAACGGCAGCTACAGCATGATG

CAGGACCAGCTGGGCTACCCGCAGCACCCGGGCCTCAATGCGCACGGCGCAGCG

CAGATGCAGCCCATGCACCGCTACGACGTGAGCGCCCTGCAGTACAACTCCATG

ACCAGCTCGCAGACCTACATGAACGGCTCGCCCACCTACAGCATGTCCTACTCGC

AGCAGGGCACCCCTGGCATGGCTCTTGGCTCCATGGGTTCGGTGGTCAAGTCCGA

GGCCAGCTCCAGCCCCCCTGTGGTTACCTCTTCCTCCCACTCCAGGGCGCCCTGC

CAGGCCGGGGACCTCCGGGACATGATCAGCATGTATCTCCCCGGCGCCGAGGTG

CCGGAACCCGCCGCCCCCAGCAGACTTCACATGTCCCAGCACTACCAGAGCGGC

CCGGTGCCCGGCACGGCCATTAACGGCACACTGCCCCTCTCACACATGGCATGCG

GCTCCGGCGAGGGCAGGGGAAGTCTTCTAACATGCGGGGACGTGGAGGAAAATC

CCGGCCCACTCGAGATGGCTGTCAGCGACGCGCTGCTCCCATCTTTCTCCACGTT

CGCGTCTGGCCCGGCGGGAAGGGAGAAGACACTGCGTCAAGCAGGTGCCCCGAA

TAACCGCTGGCGGGAGGAGCTCTCCCACATGAAGCGACTTCCCCCAGTGCTTCCC

GGCCGCCCCTATGACCTGGCGGCGGCGACCGTGGCCACAGACCTGGAGAGCGGC

GGAGCCGGTGCGGCTTGCGGCGGTAGCAACCTGGCGCCCCTACCTCGGAGAGAG
```

-continued

ACCGAGGAGTTCAACGATCTCCTGGACCTGGACTTTATTCTCTCCAATTCGCTGA

CCCATCCTCCGGAGTCAGTGGCCGCCACCGTGTCCTCGTCAGCGTCAGCCTCCTC

TTCGTCGTCGCCGTCGAGCAGCGGCCCTGCCAGCGCGCCCTCCACCTGCAGCTTC

ACCTATCCGATCCGGGCCGGGAACGACCCGGGCGTGGCGCCGGGCGGCACGGGC

GGAGGCCTCCTCTATGGCAGGGAGTCCGCTCCCCCTCCGACGGCTCCCTTCAACC

TGGCGGACATCAACGACGTGAGCCCCTCGGGCGGCTTCGTGGCCGAGCTCCTGC

GGCCAGAATTGGACCCGGTGTACATTCCGCCGCAGCAGCCGCAGCCGCCAGGTG

GCGGGCTGATGGGCAAGTTCGTGCTGAAGGCGTCGCTGAGCGCCCCTGGCAGCG

AGTACGGCAGCCCGTCGGTCATCAGCGTCAGCAAAGGCAGCCCTGACGGCAGCC

ACCCGGTGGTGGTGGCGCCCTACAACGGCGGGCCGCCGCGCACGTGCCCCAAGA

TCAAGCAGGAGGCGGTCTCTTCGTGCACCCACTTGGGCGCTGGACCCCCTCTCAG

CAATGGCCACCGGCCGGCTGCACACGACTTCCCCCTGGGGCGGCAGCTCCCCAG

CAGGACTACCCCGACCCTGGGTCTTGAGGAAGTGCTGAGCAGCAGGGACTGTCA

CCCTGCCCTGCCGCTTCCTCCCGGCTTCCATCCCCACCCGGGGCCCAATTACCCAT

CCTTCCTGCCCGATCAGATGCAGCCGCAAGTCCCGCCGCTCCATTACCAAGAGCT

CATGCCACCCGGTTCCTGCATGCCAGAGGAGCCCAAGCCAAAGAGGGGAAGACG

ATCGTGGCCCCGGAAAAGGACCGCCACCCACACTTGTGATTACGCGGGCTGCGG

CAAAACCTACACAAAGAGTTCCCATCTCAAGGCACACCTGCGAACCCACACAGG

TGAGAAACCTTACCACTGTGACTGGGACGGCTGTGGATGGAAATTCGCCCGCTCA

GATGAACTGACCAGGCACTACCGTAAACACACGGGGCACCGCCCGTTCCAGTGC

CAAAAATGCGACCGAGCATTTTCCAGGTCGGACCACCTCGCCTTACACATGAAG

AGGCATTTT

OCT4-2A-SOX2-2A-KLF4 (non-limiting example of an amino acid sequence
encoding human OCT4, human SOX2, and human KLF4, each separated by a 2A peptide)
(SEQ ID NO: 39):
MAGHLASDFAFSPPPGGGGDGPGGPEPGWVDPRTWLSFQGPPGGPGIGPGVGPGSE

VWGIPPCPPPYEFCGGMAYCGPQVGVGLVPQGGLETSQPEGEAGVGVESNSDGASP

EPCTVTPGAVKLEKEKLEQNPEESQDIKALQKELEQFAKLLKQKRITLGYTQADVGL

TLGVLFGKVFSQTTICRFEALQLSFKNMCKLRPLLQKWVEEADNNENLQEICKAETL

VQARKRKRTSIENRVRGNLENLFLQCPKPTLQQISHIAQQLGLEKDVVRVWFCNRRQ

KGKRSSSDYAQREDFEAAGSPFSGGPVSFPLAPGPHFGTPGYGSPHFTALYSSVPFPE

GEAFPPVSVTTLGSPMHSNASGSGATNFSLLKQAGDVEENPGPACMYNMMETELKP

PGPQQTSGGGGGNSTAAAAGGNQKNSPDRVKRPMNAFMVWSRGQRRKMAQENPK

MHNSEISKRLGAEWKLLSETEKRPFIDEAKRLRALHMKEHPDYKYRPRRKTKTLMK

KDKYTLPGGLLAPGGNSMASGVGVGAGLGAGVNQRMDSYAHMNGWSNGSYSMM

QDQLGYPQHPGLNAHGAAQMQPMHRYDVSALQYNSMTSSQTYMNGSPTYSMSYS

QQGTPGMALGSMGSVVKSEASSSPPVVTSSSHSRAPCQAGDLRDMISMYLPGAEVPE

PAAPSRLHMSQHYQSGPVPGTAINGTLPLSHMACGSGEGRGSLLTCGDVEENPGPLE

MAVSDALLPSFSTFASGPAGREKTLRQAGAPNNRWREELSHMKRLPPVLPGRPYDL

AAATVATDLESGGAGAACGGSNLAPLPRRETEEFNDLLDLDFILSNSLTHPPESVAAT

VSSSASASSSSSPSSSGPASAPSTCSFTYPIRAGNDPGVAPGGTGGGLLYGRESAPPPT

APFNLADINDVSPSGGFVAELLRPELDPVYIPPQQPQPPGGGLMGKFVLKASLSAPGS

EYGSPSVISVSKGSPDGSHPVVVAPYNGGPPRTCPKIKQEAVSSCTHLGAGPPLSNGH

RPAAHDFPLGRQLPSRTTPTLGLEEVLSSRDCHPALPLPPGFHPHPGPNYPSFLPDQM

QPQVPPLHYQELMPPGSCMPEEPKPKRGRRSWPRKRTATHTCDYAGCGKTYTKSSH

LKAHLRTHTGEKPYHCDWDGCGWKFARSDELTRHYRKHTGHRPFQCQKCDRAFSR

SDHLALHMKRHF

Human OCT4 nucleic acid sequence (non-limiting example of a nucleic acid
sequence encoding human OCT4) (SEQ ID NO: 40):
ATGGCGGGACACCTGGCTTCGGATTTCGCCTTCTCGCCCCCTCCAGGTGGTGGAG

GTGATGGGCCAGGGGGGCCGGAGCCGGGCTGGGTTGATCCTCGGACCTGGCTAA

GCTTCCAAGGCCCTCCTGGAGGGCCAGGAATCGGGCCGGGGGTTGGGCCAGGCT

CTGAGGTGTGGGGGATTCCCCCATGCCCCCCGCCGTATGAGTTCTGTGGGGGGAT

GGCGTACTGTGGGCCCCAGGTTGGAGTGGGGCTAGTGCCCCAAGGCGGCTTGGA

GACCTCTCAGCCTGAGGGCGAAGCAGGAGTCGGGGTGGAGAGCAACTCCGATGG

GGCCTCCCCGGAGCCCTGCACCGTCACCCCTGGTGCCGTGAAGCTGGAGAAGGA

GAAGCTGGAGCAAAACCCGGAGGAGTCCCAGGACATCAAAGCTCTGCAGAAAG

AACTCGAGCAATTTGCCAAGCTCCTGAAGCAGAAGAGGATCACCCTGGGATATA

CACAGGCCGATGTGGGGCTCACCCTGGGGGTTCTATTTGGGAAGGTATTCAGCCA

AACGACCATCTGCCGCTTTGAGGCTCTGCAGCTTAGCTTCAAGAACATGTGTAAG

CTGCGGCCCTTGCTGCAGAAGTGGGTGGAGGAAGCTGACAACAATGAAAATCTT

CAGGAGATATGCAAAGCAGAAACCCTCGTGCAGGCCCGAAAGAGAAAGCGAAC

CAGTATCGAGAACCGAGTGAGAGGCAACCTGGAGAATTTGTTCCTGCAGTGCCC

GAAACCCACACTGCAGCAGATCAGCCACATCGCCCAGCAGCTTGGGCTCGAGAA

GGATGTGGTCCGAGTGTGGTTCTGTAACCGGCGCCAGAAGGGCAAGCGATCAAG

CAGCGACTATGCACAACGAGAGGATTTTGAGGCTGCTGGGTCTCCTTTCTCAGGG

GGACCAGTGTCCTTTCCTCTGGCCCCAGGGCCCCATTTTGGTACCCCAGGCTATG

GGAGCCCTCACTTCACTGCACTGTACTCCTCGGTCCCTTTCCCTGAGGGGGAAGC

CTTTCCCCCTGTCTCTGTCACCACTCTGGGCTCTCCCATGCATTCAAAC

Human OCT4 amino acid sequence (non-limiting example of an amino acid
sequence encoding human OCT4) (SEQ ID NO: 41):
MAGHLASDFAFSPPPGGGGDGPGGPEPGWVDPRTWLSFQGPPGGPGIGPGVGPGSE

VWGIPPCPPPYEFCGGMAYCGPQVGVGLVPQGGLETSQPEGEAGVGVESNSDGASP

EPCTVTPGAVKLEKEKLEQNPEESQDIKALQKELEQFAKLLKQKRITLGYTQADVGL

TLGVLFGKVFSQTTICRFEALQLSFKNMCKLRPLLQKWVEEADNNENLQEICKAETL

VQARKRKRTSIENRVRGNLENLFLQCPKPTLQQISHIAQQLGLEKDVVRVWFCNRRQ

KGKRSSSDYAQREDFEAAGSPFSGGPVSFPLAPGPHFGTPGYGSPHFTALYSSVPFPE

GEAFPPVSVTTLGSPMHSN

Human SOX2 nucleic acid sequence (non-limiting example of a nucleic acid
sequence encoding human SOX2) (SEQ ID NO: 42):
ATGTACAACATGATGGAGACGGAGCTGAAGCCGCCGGGCCCGCAGCAAACTTCG

GGGGGCGGCGGCGGCAACTCCACCGCGGCGGCGGCCGGCGGCAACCAGAAAAA

CAGCCCGGACCGCGTCAAGCGGCCCATGAATGCCTTCATGGTGTGGTCCCGCGG

GCAGCGGCGCAAGATGGCCCAGGAGAACCCCAAGATGCACAACTCGGAGATCA

GCAAGCGCCTGGGCGCCGAGTGGAAACTTTTGTCGGAGACGGAGAAGCGGCCGT

-continued
TCATCGACGAGGCTAAGCGGCTGCGAGCGCTGCACATGAAGGAGCACCCGGATT

ATAAATACCGGCCCCGGCGGAAAACCAAGACGCTCATGAAGAAGGATAAGTACA

CGCTGCCCGGCGGGCTGCTGGCCCCCGGCGGCAATAGCATGGCGAGCGGGGTCG

GGGTGGGCGCCGGCCTGGGCGCGGGCGTGAACCAGCGCATGGACAGTTACGCGC

ACATGAACGGCTGGAGCAACGGCAGCTACAGCATGATGCAGGACCAGCTGGGCT

ACCCGCAGCACCCGGGCCTCAATGCGCACGGCGCAGCGCAGATGCAGCCCATGC

ACCGCTACGACGTGAGCGCCCTGCAGTACAACTCCATGACCAGCTCGCAGACCT

ACATGAACGGCTCGCCCACCTACAGCATGTCCTACTCGCAGCAGGGCACCCCTG

GCATGGCTCTTGGCTCCATGGGTTCGGTGGTCAAGTCCGAGGCCAGCTCCAGCCC

CCCTGTGGTTACCTCTTCCTCCCACTCCAGGGCGCCCTGCCAGGCCGGGGACCTC

CGGGACATGATCAGCATGTATCTCCCCGGCGCCGAGGTGCCGGAACCCGCCGCC

CCCAGCAGACTTCACATGTCCCAGCACTACCAGAGCGGCCCGGTGCCCGGCACG

GCCATTAACGGCACACTGCCCCTCTCACACATG

Human SOX2 amino acid sequence (non-limiting example of an amino acid
sequence encoding human SOX2) (SEQ ID NO: 43):
MYNMMETELKPPGPQQTSGGGGGNSTAAAAGGNQKNSPDRVKRPMNAFMVWSRG

QRRKMAQENPKMHNSEISKRLGAEWKLLSETEKRPFIDEAKRLRALHMKEHPDYKY

RPRRKTKTLMKKDKYTLPGGLLAPGGNSMASGVGVGAGLGAGVNQRMDSYAHMN

GWSNGSYSMMQDQLGYPQHPGLNAHGAAQMQPMHRYDVSALQYNSMTSSQTYM

NGSPTYSMSYSQQGTPGMALGSMGSVVKSEASSSPPVVTSSSHSRAPCQAGDLRDMI

SMYLPGAEVPEPAAPSRLHMSQHYQSGPVPGTAINGTLPLSHM

Human KLF4 (non-limiting example of a nucleotide sequence encoding human
KLF4) (SEQ ID NO: 44):
ATGGCTGTCAGCGACGCGCTGCTCCCATCTTTCTCCACGTTCGCGTCTGGCCCGG

CGGGAAGGGAGAAGACACTGCGTCAAGCAGGTGCCCCGAATAACCGCTGGCGG

GAGGAGCTCTCCCACATGAAGCGACTTCCCCCAGTGCTTCCCGGCCGCCCCTATG

ACCTGGCGGCGGCGACCGTGGCCACAGACCTGGAGAGCGGCGGAGCCGGTGCG

GCTTGCGGCGGTAGCAACCTGGCGCCCCTACCTCGGAGAGAGACCGAGGAGTTC

AACGATCTCCTGGACCTGGACTTTATTCTCTCCAATTCGCTGACCCATCCTCCGGA

GTCAGTGGCCGCCACCGTGTCCTCGTCAGCGTCAGCCTCCTCTTCGTCGTCGCCG

TCGAGCAGCGGCCCTGCCAGCGCGCCCTCCACCTGCAGCTTCACCTATCCGATCC

GGGCCGGGAACGACCCGGGCGTGGCGCCGGGCGGCACGGGCGGAGGCCTCCTCT

ATGGCAGGGAGTCCGCTCCCCCTCCGACGGCTCCCTTCAACCTGGCGGACATCAA

CGACGTGAGCCCCTCGGGCGGCTTCGTGGCCGAGCTCCTGCGGCCAGAATTGGA

CCCGGTGTACATTCCGCCGCAGCAGCCGCAGCCGCCAGGTGGCGGGCTGATGGG

CAAGTTCGTGCTGAAGGCGTCGCTGAGCGCCCCTGGCAGCGAGTACGGCAGCCC

GTCGGTCATCAGCGTCAGCAAAGGCAGCCCTGACGGCAGCCACCCGGTGGTGGT

GGCGCCCTACAACGGCGGGCCGCCGCGCACGTGCCCCAAGATCAAGCAGGAGGC

GGTCTCTTCGTGCACCCACTTGGGCGCTGGACCCCCTCTCAGCAATGGCCACCGG

CCGGCTGCACACGACTTCCCCCTGGGGCGGCAGCTCCCCAGCAGGACTACCCCG

ACCCTGGGTCTTGAGGAAGTGCTGAGCAGCAGGGACTGTCACCCTGCCCTGCCG

CTTCCTCCCGGCTTCCATCCCCACCCGGGGCCCAATTACCCATCCTTCCTGCCCGA

TCAGATGCAGCCGCAAGTCCCGCCGCTCCATTACCAAGAGCTCATGCCACCCGGT

```
TCCTGCATGCCAGAGGAGCCCAAGCCAAAGAGGGGAAGACGATCGTGGCCCCGG

AAAAGGACCGCCACCCACACTTGTGATTACGCGGGCTGCGGCAAAACCTACACA

AAGAGTTCCCATCTCAAGGCACACCTGCGAACCCACACAGGTGAGAAACCTTAC

CACTGTGACTGGGACGGCTGTGGATGGAAATTCGCCCGCTCAGATGAACTGACC

AGGCACTACCGTAAACACACGGGGCACCGCCCGTTCCAGTGCCAAAAATGCGAC

CGAGCATTTTCCAGGTCGGACCACCTCGCCTTACACATGAAGAGGCATTTT
```

Human KLF4 (non-limiting example of an amino acid sequence encoding human
KLF4) (SEQ ID NO: 45):
```
MAVSDALLPSFSTFASGPAGREKTLRQAGAPNNRWREELSHMKRLPPVLPGRPYDL

AAATVATDLESGGAGAACGGSNLAPLPRRETEEFNDLLDLDFILSNSLTHPPESVAAT

VSSSASASSSSSPSSSGPASAPSTCSFTYPIRAGNDPGVAPGGTGGGLLYGRESAPPPT

APFNLADINDVSPSGGFVAELLRPELDPVYIPPQQPQPPGGGLMGKFVLKASLSAPGS

EYGSPSVISVSKGSPDGSHPVVVAPYNGGPPRTCPKIKQEAVSSCTHLGAGPPLSNGH

RPAAHDFPLGRQLPSRTTPTLGLEEVLSSRDCHPALPLPPGFHPHPGPNYPSFLPDQM

QPQVPPLHYQELMPPGSCMPEEPKPKRGRRSWPRKRTATHTCDYAGCGKTYTKSSH

LKAHLRTHTGEKPYHCDWDGCGWKFARSDELTRHYRKHTGHRPFQCQKCDRAFSR

SDHLALHMKRHF
```

Human RCVRN (recoverin) promoter (non-limiting example of a human RCVRN
(recoverin) promoter) (SEQ ID NO: 46):
```
ATTTTAATCTCACTAGGGTTCTGGGAGCACCCCCCCCCACCGCTCCCGCCCTCCA

CAAAGCTCCTGGGCCCCTCCTCCCTTCAAGGATTGCGAAGAGCTGGTCGCAAATC

CTCCTAAGCCACCAGCATCTCGGTCTTCAGCTCACACCAGCCTTGAGCCCAGCCT

GCGGCCAGGGGACCACGCACGTCCCACCCACCCAGCGACTCCCCAGCCGCTGCC

CACTCTTCCTCACTCA
```

RSV promoter (non-limiting example of a RSV promoter)
(SEQ ID NO: 47):
```
AATGTAGTCTTATGCAATACTCTTGTAGTCTTGCAACATGGTAACGATGAGTTAG

CAACATGCCTTACAAGGAGAGAAAAAGCACCGTGCATGCCGATTGGTGGAAGTA

AGGTGGTACGATCGTGCCTTATTAGGAAGGCAACAGACGGGTCTGACATGGATT

GGACGAACCACTGAATTGCCGCATTGCAGAGATATTGTATTTAAGTGCCTAGCTC

GATACATAAAC
```

CMV promoter (non-limiting example of a CMV promoter)
(SEQ ID NO: 48):
```
CATTGATTATTGACTAGTTATTAATAGTAATCAATTACGGGGTCATTAGTTCATA

GCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTA

ACGCCAATAGGGACTTTCCATTGACGTCAATGGGTGGACTATTTACGGTAAACTG

CCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGAC

TTTCCTACTTGGCAGTACATCTACGTATTAGTCATCGCTATTACCATGGTGATGCG

GTTTTGGCAGTACATCAATGGGCGTGGATAGCGGTTTGACTCACGGGGATTTCCA

AGTCTCCACCCCATTGACGTCAATGGGAGTTTGTTTTGGCACCAAAATCAACGGG
```

-continued
```
ACTTTCCAAAATGTCGTAACAACTCCGCCCCATTGACGCAAATGGGCGGTAGGCG

TGTACGGTGGGAGGTCTATATAAGCAGAGCTGGTTTAGTGAACCGTCAGATCCGC

TAGAGATCCGC
```

EFS promoter (non-limiting example of an EFS promoter)
(SEQ ID NO: 49):
```
TCGAGTGGCTCCGGTGCCCGTCAGTGGGCAGAGCGCACATCGCCCACAGTCCCC

GAGAAGTTGGGGGGAGGGGTCGGCAATTGAACCGGTGCCTAGAGAAGGTGGCG

CGGGGTAAACTGGGAAAGTGATGTCGTGTACTGGCTCCGCCTTTTTCCCGAGGGT

GGGGGAGAACCGTATATAAGTGCAGTAGTCGCCGTGAACGTTCTTTTTCGCAACG

GGTTTGCCGCCAGAACACAGGTGTCGTGACCGCGG
```

Human GRK1 (rhodopsin kinase) promoter (non-limiting example of a human
promoter) (SEQ ID NO: 50):
```
Gggccccagaagcctggtggttgtttgtccttctcaggggaaaagtgaggcggccccttggaggaaggggccgg gcagaatgatctaatcggattccaagcagctcaggggattgtcttttctagcaccttcttgccactcctaagcgtcctccgtgaccccgg ctgggatttcgcctggtgctgtgtcagccccggtctcccaggggcttcccagtggtccccaggaaccctcgacagggcccggtctctc tcgtccagcaagggcagggacgggccacaggccaagggc
```

Human CRX (cone rod homeobox transcription factor) promoter (non-limiting
example of a human CRX promoter) (SEQ ID NO: 51):
```
Gcctgtagccttaatctctcctagcaggggtttgggggaggaggaggagaaagaaagggcccttatggctga gacacaatgacccagccacaaggagggattaccgggcg
```

Human NRL promoter (neural retina leucine zipper transcription factor enhancer
upstream of the human TK terminal promoter) (non-limiting example of a human NRL
promoter) (SEQ ID NO: 52):
```
Aggtaggaagtggcctttaactccatagaccctatttaaacagcttcggacaggtttaaacatctccttggataattcct agtatccctgttcccactcctactcagggatgatagctctaagaggtgttaggggattaggctgaaaatgtaggtcacccctcagccatc tgggaactagaatgagtgagagaggagagaggggcagagacacacacattcgcatattaaggtgacgcgtgtggcctcgaacacc gagcgaccctgcagcgacccgcttaa
```

Human red opsin promoter (hred promoter) (SEQ ID NO: 101):
```
Gatccggttccaggcctcggccctaaatagtctccctgggctttcaagagaaccacatgagaaaggaggattcggg ctctgagcagtttcaccacccaccccccagtctgcaaatcctgaccccgtgggtccacctgccccaaaggcggacgcaggacagtaga agggaacagagaacacataaacacagagagggccacagcggctcccacagtcaccgccaccacctggcggggatgggtgggc gtctgagtttggttcccagcaaatccctctgagccgcccttgcgggctcgcctcaggagcaggggagcaagaggtgggaggaggag gtctaagtcccaggcccaattaagagatcaggtagtgtagggtttgggagcttttaaggtgaagaggcccgggctgatcccacaggcc agtataaagcgccgtgaccctcaggtgatgcgccagggccggctgccgtcggggacagggctttccatagc
```

Human rhodopsin promoter (rho promoter) (SEQ ID NO: 102):
```
Agttaatgattaacccgccatgctacttatctacgtagccatgctctaggaagatcggaattcgcccttaagctagcag atcttccccacctagccacctggcaaactgctccttctctcaaaggcccaaacatggcctcccagactgcaaccccccaggcagtcagg ccctgtctccacaacctcacagccaccctggacggaatctgcttcttcccacatttgagtcctcctcagccctgagctcctctgggcag ggctgtttctttccatctttgtattcccaggggcctgcaaataaatgtttaatgaacgaacaagagagtgaattccaattccatgcaacaag gattgggctcctgggccctaggctatgtgtctggcaccagaaacggaagctgcaggttgcagcccctgccctcatggagctcctcctg tcagaggagtgtggggactggatgactccagaggtaacttgtggggaacgaacaggtaaggggctgtgtgacgagatgagagact gggagaataaaccagaaagtctctagctgtccagaggacatagcacagaggcccatggtccctatttcaaacccaggccaccagact gagctgggaccttgggacagacaagtcatgcagaagttaggggaccttctcctcccttttcctggatggatcctgagtaccttctcctcc ctgacctcaggcacctcctagtgtcaccaggcccctcttagaagccaattaggccctcagtactgcagcggggattaatatgattatga acaccccaatctcccagatgctgattcagccaggagcttaggaggggggaggtcactttataagggtctgggggggtcagaacccag agtcatcccctgaattctgca
```

Mouse cone arrestin promoter (mcar promoter) (SEQ ID NO: 103):
Ggacacccattaggctacatggtctattattaccataggacctaggcctaggcttaggcaccagggcactgga tccccccaaccctcccatacacatacacatgtgcactcgtgcactcaacccagcacaggataatgttcattcttgacctttccacatac atctggctatgactctctcttatctacaataaatctcctccactatacttaggagcagttatgacttcactactacttattattattcattcagt aacatcatcagaatcccctagctctggcctacctcctcagtaacaatcagctgatccctggccactaatctgtactcactaatctgttttcca aactcttggcccctgagctaattatagcagtgcttcatgccacccaccccaacccctattcttgttctctgactcccactaatctacacattca gaggattgtggatataagaggctggaggccagcttagcaaccagagctggagg Human rhodopsin kinase promoter (hrk promoter) (SEQ ID NO: 104):
Gggcccccagaagcctggtggttgtttgtccttctcaggggaaaagtgaggcggcccttggaggaagggccgg gcagaatgatctaatcggattccaagcagctcaggggattgtcttttttctagcaccttcttgccactcctaagcgtcctccgtgaccccgg ctgggatttagcctggtgctgtgtcagccccggtctcccaggggcttcccagtggtccccaggaaccctcgacagggcccggtctctc tcgtccagcaagggcagggacgggccacaggccaagggc TRE-human OSK-SV40 (SEQ ID NO: 105):
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGGCG

ATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGC

GGAGCCTATGGAAAAACGCCAGCAACGCGGCCTTTTTACGGTTCCTGGCCTTTTG

CTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCGCCT

CTCCCCGCGCGTTGGCCGATTCATTAATGCAGCTGGCACGACAGGTTTCCCGACT

GGAAAGCGGGCAGTGAGCGCAACGCAATTAATGTGAGTTAGCTCACTCATTAGG

-continued

```
CACCCCAGGCTTTACACTTTATGCTTCCGGCTCGTATGTTGTGTGGAATTGTGAGC

GGATAACAATTTCACACAGGAAACAGCTATGACCATGATTACGCCAGATTTAATT

AAGGCCTTAATTAGGCTGCGCGCTCGCTCGCTCACTGAGGCCGCCCGGGCAAAG

CCCGGGCGTCGGGCGACCTTTGGTCGCCCGGCCTCAGTGAGCGAGCGAGCGCGC

AGAGAGGGAGTGGCCAACTCCATCACTAGGGGTTCCTTGTAGTTAATGATTAACC

CGCCATGCTACTTATCTACGTAGCCATGCTCTAGGAAGATCGGAATTCTTTACTC

CCTATCAGTGATAGAGAACGTATGAAGAGTTTACTCCCTATCAGTGATAGAGAAC

GTATGCAGACTTTACTCCCTATCAGTGATAGAGAACGTATAAGGAGTTTACTCCC

TATCAGTGATAGAGAACGTATGACCAGTTTACTCCCTATCAGTGATAGAGAACGT

ATCTACAGTTTACTCCCTATCAGTGATAGAGAACGTATATCCAGTTTACTCCCTAT

CAGTGATAGAGAACGTATAAGCTTTAGGCGTGTACGGTGGGCGCCTATAAAAGC

AGAGCTCGTTTAGTGAACCGTCAGATCGCCTGGAGCAATTCCACAACACTTTTGT

CTTATACCAACTTTCCGTACCACTTCCTACCCTCGTAAAGCGGCCGCGCCACCAT

GGCGGGACACCTGGCTTCGGATTTCGCCTTCTCGCCCCCTCCAGGTGGTGGAGGT

GATGGGCCAGGGGGGCCGGAGCCGGGCTGGGTTGATCCTCGGACCTGGCTAAGC

TTCCAAGGCCCTCCTGGAGGGCCAGGAATCGGGCCGGGGTTGGGCCAGGCTCT

GAGGTGTGGGGGATTCCCCCATGCCCCCCGCCGTATGAGTTCTGTGGGGGGATGG

CGTACTGTGGGCCCCAGGTTGGAGTGGGGCTAGTGCCCCAAGGCGGCTTGGAGA

CCTCTCAGCCTGAGGGCGAAGCAGGAGTCGGGGTGGAGAGCAACTCCGATGGGG

CCTCCCCGGAGCCCTGCACCGTCACCCCTGGTGCCGTGAAGCTGGAGAAGGAGA

AGCTGGAGCAAAACCCGGAGGAGTCCCAGGACATCAAAGCTCTGCAGAAAGAA

CTCGAGCAATTTGCCAAGCTCCTGAAGCAGAAGAGGATCACCCTGGGATATACA

CAGGCCGATGTGGGGCTCACCCTGGGGGTTCTATTTGGGAAGGTATTCAGCCAAA

CGACCATCTGCCGCTTTGAGGCTCTGCAGCTTAGCTTCAAGAACATGTGTAAGCT

GCGGCCCTTGCTGCAGAAGTGGGTGGAGGAAGCTGACAACAATGAAAATCTTCA

GGAGATATGCAAAGCAGAAACCCTCGTGCAGGCCCGAAAGAGAAAGCGAACCA

GTATCGAGAACCGAGTGAGAGGCAACCTGGAGAATTTGTTCCTGCAGTGCCCGA

AACCCACACTGCAGCAGATCAGCCACATCGCCCAGCAGCTTGGGCTCGAGAAGG

ATGTGGTCCGAGTGTGGTTCTGTAACCGGCGCCAGAAGGGCAAGCGATCAAGCA

GCGACTATGCACAACGAGAGGATTTTGAGGCTGCTGGGTCTCCTTTCTCAGGGGG

ACCAGTGTCCTTTCCTCTGGCCCCAGGGCCCCATTTTGGTACCCCAGGCTATGGG

AGCCCTCACTTCACTGCACTGTACTCCTCGGTCCCTTTCCCTGAGGGGAAGCCT

TTCCCCCTGTCTCTGTCACCACTCTGGGCTCTCCCATGCATTCAAACGCTAGCGGC

AGCGGCGCCACGAACTTCTCTCTGTTAAAGCAAGCAGGAGATGTTGAAGAAAAC

CCCGGGCCTGCATGCATGTACAACATGATGGAGACGGAGCTGAAGCCGCCGGGC

CCGCAGCAAACTTCGGGGGGCGGCGGCGGCAACTCCACCGCGGCGGCGGCCGGC

GGCAACCAGAAAAACAGCCCGGACCGCGTCAAGCGGCCCATGAATGCCTTCATG

GTGTGGTCCCGCGGGCAGCGGCGCAAGATGGCCCAGGAGAACCCCAAGATGCAC

AACTCGGAGATCAGCAAGCGCCTGGGCGCCGAGTGGAAACTTTTGTCGGAGACG

GAGAAGCGGCCGTTCATCGACGAGGCTAAGCGGCTGCGAGCGCTGCACATGAAG

GAGCACCCGGATTATAAATACCGGCCCCGGCGGAAAACCAAGACGCTCATGAAG
```

-continued

```
AAGGATAAGTACACGCTGCCCGGCGGGCTGCTGGCCCCCGGCGGCAATAGCATG
GCGAGCGGGGTCGGGTGGGCGCCGGCCTGGGCGCGGGCGTGAACCAGCGCAT
GGACAGTTACGCGCACATGAACGGCTGGAGCAACGGCAGCTACAGCATGATGCA
GGACCAGCTGGGCTACCCGCAGCACCCGGGCCTCAATGCGCACGGCGCAGCGCA
GATGCAGCCCATGCACCGCTACGACGTGAGCGCCCTGCAGTACAACTCCATGAC
CAGCTCGCAGACCTACATGAACGGCTCGCCCACCTACAGCATGTCCTACTCGCAG
CAGGGCACCCCTGGCATGGCTCTTGGCTCCATGGGTTCGGTGGTCAAGTCCGAGG
CCAGCTCCAGCCCCCCTGTGGTTACCTCTTCCTCCCACTCCAGGGCGCCCTGCCA
GGCCGGGGACCTCCGGGACATGATCAGCATGTATCTCCCCGGCGCCGAGGTGCC
GGAACCCGCCGCCCCCAGCAGACTTCACATGTCCCAGCACTACCAGAGCGGCCC
GGTGCCCGGCACGGCCATTAACGGCACACTGCCCCTCTCACACATGGCATGCGG
CTCCGGCGAGGGCAGGGGAAGTCTTCTAACATGCGGGGACGTGGAGGAAAATCC
CGGCCCACTCGAGATGGCTGTCAGCGACGCGCTGCTCCCATCTTTCTCCACGTTC
GCGTCTGGCCCGGCGGGAAGGGAGAAGACACTGCGTCAAGCAGGTGCCCCGAAT
AACCGCTGGCGGAGGAGCTCTCCCACATGAAGCGACTTCCCCCAGTGCTTCCCG
GCCGCCCCTATGACCTGGCGGCGGCGACCGTGGCCACAGACCTGGAGAGCGGCG
GAGCCGGTGCGGCTTGCGGCGGTAGCAACCTGGCGCCCCTACCTCGGAGAGAGA
CCGAGGAGTTCAACGATCTCCTGGACCTGGACTTTATTCTCTCCAATTCGCTGAC
CCATCCTCCGGAGTCAGTGGCCGCCACCGTGTCCTCGTCAGCGTCAGCCTCCTCT
TCGTCGTCGCCGTCGAGCAGCGGCCCTGCCAGCGCGCCCTCCACCTGCAGCTTCA
CCTATCCGATCCGGGCCGGGAACGACCCGGGCGTGGCGCCGGGCGGCACGGGCG
GAGGCCTCCTCTATGGCAGGGAGTCCGCTCCCCCTCCGACGGCTCCCTTCAACCT
GGCGGACATCAACGACGTGAGCCCCTCGGGCGGCTTCGTGGCCGAGCTCCTGCG
GCCAGAATTGGACCCGGTGTACATTCCGCCGCAGCAGCCGCAGCCGCCAGGTGG
CGGGCTGATGGGCAAGTTCGTGCTGAAGGCGTCGCTGAGCGCCCCTGGCAGCGA
GTACGGCAGCCCGTCGGTCATCAGCGTCAGCAAAGGCAGCCCTGACGGCAGCCA
CCCGGTGGTGGTGGCGCCCTACAACGGCGGGCCGCCGCGCACGTGCCCCAAGAT
CAAGCAGGAGGCGGTCTCTTCGTGCACCCACTTGGGCGCTGGACCCCCTCTCAGC
AATGGCCACCGGCCGGCTGCACACGACTTCCCCCTGGGGCGGCAGCTCCCCAGC
AGGACTACCCCGACCCTGGGTCTTGAGGAAGTGCTGAGCAGCAGGGACTGTCAC
CCTGCCCTGCCGCTTCCTCCCGGCTTCCATCCCCACCCGGGGCCCAATTACCCATC
CTTCCTGCCCGATCAGATGCAGCCGCAAGTCCCGCCGCTCCATTACCAAGAGCTC
ATGCCACCCGGTTCCTGCATGCCAGAGGAGCCCAAGCCAAAGAGGGGAAGACGA
TCGTGGCCCCGGAAAAGGACCGCCACCCACACTTGTGATTACGCGGGCTGCGGC
AAAACCTACACAAAGAGTTCCCATCTCAAGGCACACCTGCGAACCCACACAGGT
GAGAAACCTTACCACTGTGACTGGGACGGCTGTGGATGGAAATTCGCCCGCTCA
GATGAACTGACCAGGCACTACCGTAAACACACGGGGCACCGCCCGTTCCAGTGC
CAAAAATGCGACCGAGCATTTTCCAGGTCGGACCACCTCGCCTTACACATGAAG
AGGCATTTTTAAATGACTAGTGCGCGCAGCGGCCGACCATGCCCAACTTGTTTA
TTGCAGCTTATAATGGTTACAAATAAAGCAATAGCATCACAAATTTCACAAATAA
```

-continued

AGCATTTTTTTCACTGCATTCTAGTTGTGGTTTGTCCAAACTCATCAATGTATCTT

ATCATGTCTGGATCTCGGTACCGGATCCAAATTCCCGATAAGGATCTTCCTAGAG

CATGGCTACGTAGATAAGTAGCATGGCGGGTTAATCATTAACTACAAGGAACCC

CTAGTGATGGAGTTGGCCACTCCCTCTCTGCGCGCTCGCTCGCTCACTGAGGCCG

GGCGACCAAAGGTCGCCCGACGCCCGGGCTTTGCCCGGGCGGCCTCAGTGAGCG

AGCGAGCGCGCAGCCTTAATTAACCTAATTCACTGGCCGTCGTTTTACAACGTCG

TGACTGGGAAAACCCTGGCGTTACCCAACTTAATCGCCTTGCAGCACATCCCCCT

TTCGCCAGCTGGCGTAATAGCGAAGAGGCCCGCACCGATCGCCCTTCCCAACAG

TTGCGCAGCCTGAATGGCGAATGGGACGCGCCCTGTAGCGGCGCATTAAGCGCG

GCGGGTGTGGTGGTTACGCGCAGCGTGACCGCTACACTTGCCAGCGCCCTAGCG

CCCGCTCCTTTCGCTTTCTTCCCTTCCTTTCTCGCCACGTTCGCCGGCTTTCCCCGT

CAAGCTCTAAATCGGGGGCTCCCTTTAGGGTTCCGATTTAGTGCTTTACGGCACC

TCGACCCCAAAAAACTTGATTAGGGTGATGGTTCACGTAGTGGGCCATCGCCCTG

ATAGACGGTTTTTCGCCCTTTGACGTTGGAGTCCACGTTCTTTAATAGTGGACTCT

TGTTCCAAACTGGAACAACACTCAACCCTATCTCGGTCTATTCTTTTGATTTATAA

GGGATTTTGCCGATTTCGGCCTATTGGTTAAAAAATGAGCTGATTTAACAAAAAT

TTAACGCGAATTTTAACAAAATATTAACGTTTATAATTTCAGGTGGCATCTTTCG

GGGAAATGTGCGCGGAACCCCTATTTGTTTATTTTTCTAAATACATTCAAATATGT

ATCCGCTCATGAGACAATAACCCTGATAAATGCTTCAATAATATTGAAAAAGGA

AGAGTATGAGTATTCAACATTTCCGTGTCGCCCTTATTCCCTTTTTTGCGGCATTT

TGCCTTCCTGTTTTTGCTCACCCAGAAACGCTGGTGAAAGTAAAAGATGCTGAAG

ATCAGTTGGGTGCACGAGTGGGTTACATCGAACTGGATCTCAATAGTGGTAAGAT

CCTTGAGAGTTTTCGCCCCGAAGAACGTTTTCCAATGATGAGCACTTTTAAAGTT

CTGCTATGTGGCGCGGTATTATCCCGTATTGACGCCGGGCAAGAGCAACTCGGTC

GCCGCATACACTATTCTCAGAATGACTTGGTTGAGTACTCACCAGTCACAGAAAA

GCATCTTACGGATGGCATGACAGTAAGAGAA

EFS-human OSK-SV40 (SEQ ID NO: 106):
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

-continued

```
AGCTACCAACTCTTTTTCCGAAGGTAACTGGCTTCAGCAGAGCGCAGATACCAAA
TACTGTCCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGC
AGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTC
CCGAAGGGAGAAAGGCGGACAGGTATCCGGTAAGCGGCAGGGTCGGAACAGGA
GAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGC
GGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACC
GTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGCCT
CTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGG
CACCCCAGGCTTTACACTTTATGCTTCCGGCTCGTATGTTGTGTGGAATTGTGAGC
GGATAACAATTTCACACAGGAAACAGCTATGACCATGATTACGCCAGATTTAATT
AAGGCCTTAATTAGGCTGCGCGCTCGCTCGCTCACTGAGGCCGCCCGGGCAAAG
CCCGGGCGTCGGGCGACCTTTGGTCGCCCGGCCTCAGTGAGCGAGCGAGCGCGC
AGAGAGGGAGTGGCCAACTCCATCACTAGGGGTTCCTTGTAGTTAATGATTAACC
CGCCATGCTACTTATCTACGTAGCCATGCTCTAGGAAGATCGGAATTCTCGAGTG
GCTCCGGTGCCCGTCAGTGGGCAGAGCGCACATCGCCCACAGTCCCCGAGAAGT
TGGGGGGAGGGGTCGGCAATTGAACCGGTGCCTAGAGAAGGTGGCGCGGGGTA
AACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGC
CGCCAGAACACAGGTGTCGTGACGCGGGCGGCCGCGCCACCATGGCGGGACACC
TGGCTTCGGATTTCGCCTTCTCGCCCCCTCCAGGTGGTGGAGGTGATGGGCCAGG
GGGGCCGGAGCCGGGCTGGGTTGATCCTCGGACCTGGCTAAGCTTCCAAGGCCC
TCCTGGAGGGCCAGGAATCGGGCCGGGGGTTGGGCCAGGCTCTGAGGTGTGGGG
GATTCCCCCATGCCCCCGCCGTATGAGTTCTGTGGGGGATGGCGTACTGTGGG
CCCCAGGTTGGAGTGGGCTAGTGCCCCAAGGCGGCTTGGAGACCTCTCAGCCT
GAGGGCGAAGCAGGAGTCGGGGTGGAGAGCAACTCCGATGGGCCTCCCCGGA
GCCCTGCACCGTCACCCCTGGTGCCGTGAAGCTGGAGAAGGAGAAGCTGGAGCA
AAACCCGGAGGAGTCCCAGGACATCAAAGCTCTGCAGAAAGAACTCGAGCAATT
TGCCAAGCTCCTGAAGCAGAAGAGGATCACCCTGGGATATACACAGGCCGATGT
GGGGCTCACCCTGGGGGTTCTATTTGGGAAGGTATTCAGCCAAACGACCATCTGC
CGCTTTGAGGCTCTGCAGCTTAGCTTCAAGAACATGTGTAAGCTGCGGCCCTTGC
TGCAGAAGTGGGTGGAGGAAGCTGACAACAATGAAAATCTTCAGGAGATATGCA
AAGCAGAAACCCTCGTGCAGGCCCGAAAGAGAAAGCGAACCAGTATCGAGAAC
CGAGTGAGAGGCAACCTGGAGAATTTGTTCCTGCAGTGCCCGAAACCCACACTG
CAGCAGATCAGCCACATCGCCCAGCAGCTTGGGCTCGAGAAGGATGTGGTCCGA
```

-continued

```
GTGTGGTTCTGTAACCGGCGCCAGAAGGGCAAGCGATCAAGCAGCGACTATGCA

CAACGAGAGGATTTTGAGGCTGCTGGGTCTCCTTTCTCAGGGGACCAGTGTCCT

TTCCTCTGGCCCCAGGGCCCCATTTTGGTACCCCAGGCTATGGGAGCCCTCACTT

CACTGCACTGTACTCCTCGGTCCCTTTCCCTGAGGGGAAGCCTTTCCCCCTGTCT

CTGTCACCACTCTGGGCTCTCCCATGCATTCAAACGCTAGCGGCAGCGGCGCCAC

GAACTTCTCTCTGTTAAAGCAAGCAGGAGATGTTGAAGAAAACCCCGGGCCTGC

ATGCATGTACAACATGATGGAGACGGAGCTGAAGCCGCCGGGCCCGCAGCAAAC

TTCGGGGGGCGGCGGCGGCAACTCCACCGCGGCGGCGGCCGGCGGCAACCAGA

AAAACAGCCCGGACCGCGTCAAGCGGCCCATGAATGCCTTCATGGTGTGGTCCC

GCGGGCAGCGGCGCAAGATGGCCCAGGAGAACCCCAAGATGCACAACTCGGAG

ATCAGCAAGCGCCTGGGCGCCGAGTGGAAACTTTTGTCGGAGACGGAGAAGCGG

CCGTTCATCGACGAGGCTAAGCGGCTGCGAGCGCTGCACATGAAGGAGCACCCG

GATTATAAATACCGGCCCCGGCGGAAAACCAAGACGCTCATGAAGAAGGATAAG

TACACGCTGCCCGGCGGGCTGCTGGCCCCGGCGGCAATAGCATGGCGAGCGGG

GTCGGGGTGGGCGCCGGCCTGGGCGCGGGCGTGAACCAGCGCATGGACAGTTAC

GCGCACATGAACGGCTGGAGCAACGGCAGCTACAGCATGATGCAGGACCAGCTG

GGCTACCCGCAGCACCCGGGCCTCAATGCGCACGGCGCAGCGCAGATGCAGCCC

ATGCACCGCTACGACGTGAGCGCCCTGCAGTACAACTCCATGACCAGCTCGCAG

ACCTACATGAACGGCTCGCCCACCTACAGCATGTCCTACTCGCAGCAGGGCACCC

CTGGCATGGCTCTTGGCTCCATGGGTTCGGTGGTCAAGTCCGAGGCCAGCTCCAG

CCCCCCTGTGGTTACCTCTTCCTCCCACTCCAGGGCGCCCTGCCAGGCCGGGGAC

CTCCGGGACATGATCAGCATGTATCTCCCCGGCGCCGAGGTGCCGGAACCCGCC

GCCCCCAGCAGACTTCACATGTCCCAGCACTACCAGAGCGGCCCGGTGCCCGGC

ACGGCCATTAACGGCACACTGCCCCTCTCACACATGGCATGCGGCTCCGGCGAG

GGCAGGGGAAGTCTTCTAACATGCGGGGACGTGGAGGAAAATCCCGGCCCACTC

GAGATGGCTGTCAGCGACGCGCTGCTCCCATCTTTCTCCACGTTCGCGTCTGGCC

CGGCGGGAAGGGAGAAGACACTGCGTCAAGCAGGTGCCCCGAATAACCGCTGG

CGGGAGGAGCTCTCCCACATGAAGCGACTTCCCCCAGTGCTTCCCGGCCGCCCCT

ATGACCTGGCGGCGGCGACCGTGGCCACAGACCTGGAGAGCGGCGGAGCCGGTG

CGGCTTGCGGCGGTAGCAACCTGGCGCCCCTACCTCGGAGAGAGACCGAGGAGT

TCAACGATCTCCTGGACCTGGACTTTATTCTCTCCAATTCGCTGACCCATCCTCCG

GAGTCAGTGGCCGCCACCGTGTCCTCGTCAGCGTCAGCCTCCTCTTCGTCGTCGC

CGTCGAGCAGCGGCCCTGCCAGCGCGCCCTCCACCTGCAGCTTCACCTATCCGAT

CCGGGCCGGGAACGACCCGGGCGTGGCGCCGGGCGGCACGGGCGGAGGCCTCCT

CTATGGCAGGGAGTCCGCTCCCCCTCCGACGGCTCCCTTCAACCTGGCGGACATC

AACGACGTGAGCCCCTCGGGCGGCTTCGTGGCCGAGCTCCTGCGGCCAGAATTG

GACCCGGTGTACATTCCGCCGCAGCAGCCGCAGCCGCCAGGTGGCGGGCTGATG

GGCAAGTTCGTGCTGAAGGCGTCGCTGAGCGCCCCTGGCAGCGAGTACGGCAGC

CCGTCGGTCATCAGCGTCAGCAAAGGCAGCCCTGACGGCAGCCACCCGGTGGTG

GTGGCGCCCTACAACGGCGGGCCGCCGCGCACGTGCCCCAAGATCAAGCAGGAG
```

-continued

```
GCGGTCTCTTCGTGCACCCACTTGGGCGCTGGACCCCCTCTCAGCAATGGCCACC

GGCCGGCTGCACACGACTTCCCCCTGGGGCGGCAGCTCCCCAGCAGGACTACCC

CGACCCTGGGTCTTGAGGAAGTGCTGAGCAGCAGGGACTGTCACCCTGCCCTGC

CGCTTCCTCCCGGCTTCCATCCCCACCCGGGGCCCAATTACCCATCCTTCCTGCCC

GATCAGATGCAGCCGCAAGTCCCGCCGCTCCATTACCAAGAGCTCATGCCACCC

GGTTCCTGCATGCCAGAGGAGCCCAAGCCAAAGAGGGGAAGACGATCGTGGCCC

CGGAAAAGGACCGCCACCCACACTTGTGATTACGCGGGCTGCGGCAAAACCTAC

ACAAAGAGTTCCCATCTCAAGGCACACCTGCGAACCCACACAGGTGAGAAACCT

TACCACTGTGACTGGGACGGCTGTGGATGGAAATTCGCCCGCTCAGATGAACTG

ACCAGGCACTACCGTAAACACACGGGGCACCGCCCGTTCCAGTGCCAAAAATGC

GACCGAGCATTTTCCAGGTCGGACCACCTCGCCTTACACATGAAGAGGCATTTTT

AAATGACTAGTGCGCGCAGCGGCCGACCATGGCCCAACTTGTTTATTGCAGCTTA

TAATGGTTACAAATAAAGCAATAGCATCACAAATTTCACAAATAAAGCATTTTTT

TCACTGCATTCTAGTTGTGGTTTGTCCAAACTCATCAATGTATCTTATCATGTCTG

GATCTCGGTACCGGATCCAAATTCCCGATAAGGATCTTCCTAGAGCATGGCTACG

TAGATAAGTAGCATGGCGGGTTAATCATTAACTACAAGGAACCCCTAGTGATGG

AGTTGGCCACTCCCTCTCTGCGCGCTCGCTCGCTCACTGAGGCCGGGCGACCAAA

GGTCGCCCGACGCCCGGGCTTTGCCCGGGCGGCCTCAGTGAGCGAGCGAGCGCG

CAGCCTTAATTAACCTAATTCACTGGCCGTCGTTTTACAACGTCGTGACTGGGAA

AACCCTGGCGTTACCCAACTTAATCGCCTTGCAGCACATCCCCCTTTCGCCAGCT

GGCGTAATAGCGAAGAGGCCCGCACCGATCGCCCTTCCCAACAGTTGCGCAGCC

TGAATGGCGAATGGGACGCGCCCTGTAGCGGCGCATTAAGCGCGGCGGGTGTGG

TGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAA

ATCGGGGGCTCCCTTTAGGGTTCCGATTTAGTGCTTTACGGCACCTCGACCCCAA

AAAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAAC

TGGAACAACACTCAACCCTATCTCGGTCTATTCTTTTGATTTATAAGGGATTTTGC

CGATTTCGGCCTATTGGTTAAAAAATGAGCTGATTTAACAAAAATTTAACGCGAA

TTTTAACAAAATATTAACGTTTATAATTTCAGGTGGCATCTTTCGGGGAAATGTG

CGCGGAACCCCTATTTGTTTATTTTTCTAAATACATTCAAATATGTATCCGCTCAT

GAGACAATAACCCTGATAAATGCTTCAATAATATTGAAAAAGGAAGAGTATGAG

TATTCAACATTTCCGTGTCGCCCTTATTCCCTTTTTTGCGGCATTTTGCCTTCCTGT

TTTTGCTCACCCAGAAACGCTGGTGAAAGTAAAAGATGCTGAAGATCAGTTGGG

TGCACGAGTGGGTTACATCGAACTGGATCTCAATAGTGGTAAGATCCTTGAGAGT

TTTCGCCCCGAAGAACGTTTTCCAATGATGAGCACTTTTAAAGTTCTGCTATGTG

GCGCGGTATTATCCCGTATTGACGCCGGGCAAGAGCAACTCGGTCGCCGCATAC

ACTATTCTCAGAATGACTTGGTTGAGTACTCACCAGTCACAGAAAAGCATCTTAC

GGATGGCATGACAGTAAGAGAA
```

TRE-Fluc-SV40 (SEQ ID NO: 107):
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGGCG

ATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGC

GGAGCCTATGGAAAAACGCCAGCAACGCGGCCTTTTTACGGTTCCTGGCCTTTTG

CTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCGCCT

CTCCCCGCGCGTTGGCCGATTCATTAATGCAGCTGGCACGACAGGTTTCCCGACT

GGAAAGCGGGCAGTGAGCGCAACGCAATTAATGTGAGTTAGCTCACTCATTAGG

CACCCCAGGCTTTACACTTTATGCTTCCGGCTCGTATGTTGTGTGGAATTGTGAGC

GGATAACAATTTCACACAGGAAACAGCTATGACCATGATTACGCCAGATTTAATT

AAGGCCTTAATTAGGCTGCGCGCTCGCTCGCTCACTGAGGCCGCCCGGGCAAAG

CCCGGGCGTCGGGCGACCTTTGGTCGCCCGGCCTCAGTGAGCGAGCGAGCGCGC

AGAGAGGGAGTGGCCAACTCCATCACTAGGGGTTCCTTGTAGTTAATGATTAACC

CGCCATGCTACTTATCTACGTAGCCATGCTCTAGGAAGATCGGAATTCTTTACTC

CCTATCAGTGATAGAGAACGTATGAAGAGTTTACTCCCTATCAGTGATAGAGAAC

GTATGCAGACTTTACTCCCTATCAGTGATAGAGAACGTATAAGGAGTTTACTCCC

TATCAGTGATAGAGAACGTATGACCAGTTTACTCCCTATCAGTGATAGAGAACGT

ATCTACAGTTTACTCCCTATCAGTGATAGAGAACGTATATCCAGTTTACTCCCTAT

CAGTGATAGAGAACGTATAAGCTTTAGGCGTGTACGGTGGGCGCCTATAAAAGC

-continued

```
AGAGCTCGTTTAGTGAACCGTCAGATCGCCTGGAGCAATTCCACAACACTTTTGT
CTTATACCAACTTTCCGTACCACTTCCTACCCTCGTAAAGCGGCCGCATGGAAGA
CGCCAAAAACATAAAGAAAGGCCCGGCGCCATTCTATCCGCTGGAAGATGGAAC
CGCTGGAGAGCAACTGCATAAGGCTATGAAGAGATACGCCCTGGTTCCTGGAAC
AATTGCTTTTACAGATGCACATATCGAGGTGGACATCACTTACGCTGAGTACTTC
GAAATGTCCGTTCGGTTGGCAGAAGCTATGAAACGATATGGGCTGAATACAAAT
CACAGAATCGTCGTATGCAGTGAAAACTCTCTTCAATTCTTTATGCCGGTGTTGG
GCGCGTTATTTATCGGAGTTGCAGTTGCGCCCGCGAACGACATTTATAATGAACG
TGAATTGCTCAACAGTATGGGCATTTCGCAGCCTACCGTGGTGTTCGTTTCCAAA
AAGGGGTTGCAAAAAATTTTGAACGTGCAAAAAAAGCTCCCAATCATCCAAAAA
ATTATTATCATGGATTCTAAAACGGATTACCAGGGATTTCAGTCGATGTACACGT
TCGTCACATCTCATCTACCTCCCGGTTTTAATGAATACGATTTTGTGCCAGAGTCC
TTCGATAGGGACAAGACAATTGCACTGATCATGAACTCCTCTGGATCTACTGGTC
TGCCTAAAGGTGTCGCTCTGCCTCATAGAACTGCCTGCGTGAGATTCTCGCATGC
CAGAGATCCTATTTTTGGCAATCAAATCATTCCGGATACTGCGATTTTAAGTGTT
GTTCCATTCCATCACGGTTTTGGAATGTTTACTACACTCGGATATTTGATATGTGG
ATTTCGAGTCGTCTTAATGTATAGATTTGAAGAAGAGCTGTTTCTGAGGAGCCTT
CAGGATTACAAGATTCAAAGTGCGCTGCTGGTGCCAACCCTATTCTCCTTCTTCG
CCAAAAGCACTCTGATTGACAAATACGATTTATCTAATTTACACGAAATTGCTTC
TGGTGGCGCTCCCCTCTCTAAGGAAGTCGGGGAAGCGGTTGCCAAGAGGTTCCAT
CTGCCAGGTATCAGGCAAGGATATGGGCTCACTGAGACTACATCAGCTATTCTGA
TTACACCCGAGGGGATGATAAACCGGGCGCGGTCGGTAAAGTTGTTCCATTTTT
TGAAGCGAAGGTTGTGGATCTGGATACCGGGAAAACGCTGGGCGTTAATCAAAG
AGGCGAACTGTGTGTGAGAGGTCCTATGATTATGTCCGGTTATGTAAACAATCCG
GAAGCGACCAACGCCTTGATTGACAAGGATGGATGGCTACATTCTGGAGACATA
GCTTACTGGGACGAAGACGAACACTTCTTCATCGTTGACCGCCTGAAGTCTCTGA
TTAAGTACAAAGGCTATCAGGTGGCTCCCGCTGAATTGGAATCCATCTTGCTCCA
ACACCCCAACATCTTCGACGCAGGTGTCGCAGGTCTTCCCGACGATGACGCCGGT
GAACTTCCCGCCGCCGTTGTTGTTTTGGAGCACGGAAAGACGATGACGGAAAAA
GAGATCGTGGATTACGTCGCCAGTCAAGTAACAACCGCGAAAAAGTTGCGCGGA
GGAGTTGTGTTTGTGGACGAAGTACCGAAAGGTCTTACCGGAAAACTCGACGCA
AGAAAAATCAGAGAGATCCTCATAAAGGCCAAGAAGGGCGGAAAGATCGCCGT
GTAAACTAGTGCGCGCAGCGGCCGACCATGGCCCAACTTGTTTATTGCAGCTTAT
AATGGTTACAAATAAAGCAATAGCATCACAAATTTCACAAATAAAGCATTTTTT
CACTGCATTCTAGTTGTGGTTTGTCCAAACTCATCAATGTATCTTATCATGTCTGG
ATCTCGGTACCGGATCCAAATTCCCGATAAGGATCTTCCTAGAGCATGGCTACGT
AGATAAGTAGCATGGCGGGTTAATCATTAACTACAAGGAACCCCTAGTGATGGA
GTTGGCCACTCCCTCTCTGCGCGCTCGCTCGCTCACTGAGGCCGGGCGACCAAAG
GTCGCCCGACGCCCGGGCTTTGCCCGGGCGGCCTCAGTGAGCGAGCGAGCGCGC
AGCCTTAATTAACCTAATTCACTGGCCGTCGTTTTACAACGTCGTGACTGGGAAA
ACCCTGGCGTTACCCAACTTAATCGCCTTGCAGCACATCCCCCTTTCGCCAGCTG
```

```
GCGTAATAGCGAAGAGGCCCGCACCGATCGCCCTTCCCAACAGTTGCGCAGCCT

GAATGGCGAATGGGACGCGCCCTGTAGCGGCGCATTAAGCGCGGCGGGTGTGGT

GGTTACGCGCAGCGTGACCGCTACACTTGCCAGCGCCCTAGCGCCCGCTCCTTTC

GCTTTCTTCCCTTCCTTTCTCGCCACGTTCGCCGGCTTTCCCCGTCAAGCTCTAAA

TCGGGGGCTCCCTTTAGGGTTCCGATTTAGTGCTTTACGGCACCTCGACCCCAAA

AAACTTGATTAGGGTGATGGTTCACGTAGTGGGCCATCGCCCTGATAGACGGTTT

TTCGCCCTTTGACGTTGGAGTCCACGTTCTTTAATAGTGGACTCTTGTTCCAAACT

GGAACAACACTCAACCCTATCTCGGTCTATTCTTTTGATTTATAAGGGATTTTGCC

GATTTCGGCCTATTGGTTAAAAAATGAGCTGATTTAACAAAAATTTAACGCGAAT

TTTAACAAAATATTAACGTTTATAATTTCAGGTGGCATCTTTCGGGGAAATGTGC

GCGGAACCCCTATTTGTTTATTTTTCTAAATACATTCAAATATGTATCCGCTCATG

AGACAATAACCCTGATAAATGCTTCAATAATATTGAAAAAGGAAGAGTATGAGT

ATTCAACATTTCCGTGTCGCCCTTATTCCCTTTTTTGCGGCATTTTGCCTTCCTGTT

TTTGCTCACCCAGAAACGCTGGTGAAAGTAAAAGATGCTGAAGATCAGTTGGGT

GCACGAGTGGGTTACATCGAACTGGATCTCAATAGTGGTAAGATCCTTGAGAGTT

TTCGCCCCGAAGAACGTTTTCCAATGATGAGCACTTTTAAAGTTCTGCTATGTGG

CGCGGTATTATCCCGTATTGACGCCGGGCAAGAGCAACTCGGTCGCCGCATACA

CTATTCTCAGAATGACTTGGTTGAGTACTCACCAGTCACAGAAAAGCATCTTACG

GATGGCATGACAGTAAGAGAA shRNA against mouse KDM1a (SEQ ID NO: 108):
CACAAGTCAAACCTTTAT shRNA against human Tet1-1 (SEQ ID NO: 109):
GGACGTAATCCAGAAAGAAGA shRNA against human Tet1-2 (SEQ ID NO: 110):
TTGTGCCTCTGGAGGTTATAA shRNA against human Tet3-1 (SEQ ID NO: 111):
GGAAATAAAGGCTGGTGAAGG shRNA against human Tet3-2 (SEQ ID NO: 112):
GAAAGATGAAGGTCCATATTA shRNA against mouse Tet1-2 (SEQ ID NO: 113):
GCAGATGGCCGTGACACAAAT shRNA against mouse Tet1-1 (SEQ ID NO: 114):
GCTCATGGAGACTAGGTTTGG shRNA against both mouse and human Tet2 (SEQ ID NO: 115):
GGATGTAAGTTTGCCAGAAGC shRNA against mouse Tet3 (SEQ ID NO: 116):
GCTCCAACGAGAAGCTATTTG shRNA against scramble sequence (no target in genome) (SEQ ID NO: 117):
GTTCAGATGTGCGGCGAGT Amino acid sequence encoding P2A (SEQ ID NO: 118):
GSGATNFSLLKQAGDVEENPGP Nucleic acid sequence encoding P2A (SEQ ID NO: 119):
GGCAGCGGCGCCACGAACTTCTCTCTGTTAAAGCAAGCAGGAGATGTT
GAAGAAAACCCCGGGCCT
```

-continued

Nucleic acid sequence encoding T2A (SEQ ID NO: 120)
GGCTCCGGCGAGGGCAGGGGAAGTCTTCTAACATGCGGGGACGTGGA

GGAAAATCCCGGCCCA. (SEQ ID NO: 120)

SEQ ID NO: 121:
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGGCG

ATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGC

GGAGCCTATGGAAAAACGCCAGCAACGCGGCCTTTTTACGGTTCCTGGCCTTTTG

CTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCGCCT

CTCCCCGCGCGTTGGCCGATTCATTAATGCAGCTGGCACGACAGGTTTCCCGACT

GGAAAGCGGGCAGTGAGCGCAACGCAATTAATGTGAGTTAGCTCACTCATTAGG

CACCCCAGGCTTTACACTTTATGCTTCCGGCTCGTATGTTGTGTGGAATTGTGAGC

GGATAACAATTTCACACAGGAAACAGCTATGACCATGATTACGCCAGATTTAATT

AAGGCCTTAATTAGGCTGCGCGCTCGCTCGCTCACTGAGGCCGCCCGGGCAAAG

CCCGGGCGTCGGGCGACCTTTGGTCGCCCGGCCTCAGTGAGCGAGCGAGCGCGC

AGAGAGGGAGTGGCCAACTCCATCACTAGGGGTTCCTTGTAGTTAATGATTAACC

CGCCATGCTACTTATCTACGTAGCCATGCTCTAGGAAGATCGGAATTCTTTACTC

CCTATCAGTGATAGAGAACGTATGAAGAGTTTACTCCCTATCAGTGATAGAAC

GTATGCAGACTTTACTCCCTATCAGTGATAGAGAACGTATAAGGAGTTTACTCCC

TATCAGTGATAGAGAACGTATGACCAGTTTACTCCCTATCAGTGATAGAGAACGT

-continued

```
ATCTACAGTTTACTCCCTATCAGTGATAGAGAACGTATATCCAGTTTACTCCCTAT

CAGTGATAGAGAACGTATAAGCTTTAGGCGTGTACGGTGGGCGCCTATAAAAGC

AGAGCTCGTTTAGTGAACCGTCAGATCGCCTGGAGCAATTCCACAACACTTTTGT

CTTATACCAACTTTCCGTACCACTTCCTACCCTCGTAAAGCGGCCGCGCCACCAT

GGCGGGACACCTGGCTTCGGATTTCGCCTTCTCGCCCCCTCCAGGTGGTGGAGGT

GATGGGCCAGGGGGCCGGAGCCGGGCTGGGTTGATCCTCGGACCTGGCTAAGC

TTCCAAGGCCCTCCTGGAGGGCCAGGAATCGGGCCGGGGGTTGGGCCAGGCTCT

GAGGTGTGGGGGATTCCCCCATGCCCCCCGCCGTATGAGTTCTGTGGGGGGATGG

CGTACTGTGGGCCCCAGGTTGGAGTGGGGCTAGTGCCCCAAGGCGGCTTGGAGA

CCTCTCAGCCTGAGGGCGAAGCAGGAGTCGGGGTGGAGAGCAACTCCGATGGGG

CCTCCCCGGAGCCCTGCACCGTCACCCCTGGTGCCGTGAAGCTGGAGAAGGAGA

AGCTGGAGCAAAACCCGGAGGAGTCCCAGGACATCAAAGCTCTGCAGAAAGAA

CTCGAGCAATTTGCCAAGCTCCTGAAGCAGAAGAGGATCACCCTGGGATATACA

CAGGCCGATGTGGGGCTCACCCTGGGGGTTCTATTTGGGAAGGTATTCAGCCAAA

CGACCATCTGCCGCTTTGAGGCTCTGCAGCTTAGCTTCAAGAACATGTGTAAGCT

GCGGCCCTTGCTGCAGAAGTGGGTGGAGGAAGCTGACAACAATGAAAATCTTCA

GGAGATATGCAAAGCAGAAACCCTCGTGCAGGCCCGAAAGAGAAAGCGAACCA

GTATCGAGAACCGAGTGAGAGGCAACCTGGAGAATTTGTTCCTGCAGTGCCCGA

AACCCACACTGCAGCAGATCAGCCACATCGCCCAGCAGCTTGGGCTCGAGAAGG

ATGTGGTCCGAGTGTGGTTCTGTAACCGGCGCCAGAAGGGCAAGCGATCAAGCA

GCGACTATGCACAACGAGAGGATTTTGAGGCTGCTGGGTCTCCTTTCTCAGGGGG

ACCAGTGTCCTTTCCTCTGGCCCCAGGGCCCCATTTTGGTACCCCAGGCTATGGG

AGCCCTCACTTCACTGCACTGTACTCCTCGGTCCCTTTCCCTGAGGGGGAAGCCT

TTCCCCCTGTCTCTGTCACCACTCTGGGCTCTCCCATGCATTCAAACGCTAGCGGC

AGCGGCGCCACGAACTTCTCTCTGTTAAAGCAAGCAGGAGATGTTGAAGAAAAC

CCCGGGCCTGCATGCATGTACAACATGATGGAGACGGAGCTGAAGCCGCCGGGC

CCGCAGCAAACTTCGGGGGGCGGCGGCGGCAACTCCACCGCGGCGGCGGCCGGC

GGCAACCAGAAAAACAGCCCGGACCGCGTCAAGCGGCCCATGAATGCCTTCATG

GTGTGGTCCCGCGGGCAGCGGCGCAAGATGGCCCAGGAGAACCCCAAGATGCAC

AACTCGGAGATCAGCAAGCGCCTGGGCGCCGAGTGGAAACTTTTGTCGGAGACG

GAGAAGCGGCCGTTCATCGACGAGGCTAAGCGGCTGCGAGCGCTGCACATGAAG

GAGCACCCGGATTATAAATACCGGCCCCGGCGGAAAACCAAGACGCTCATGAAG

AAGGATAAGTACACGCTGCCCGGCGGGCTGCTGGCCCCCGGCGGCAATAGCATG

GCGAGCGGGTCGGGGTGGGCGCCGGCCTGGGCGCGGGCGTGAACCAGCGCAT

GGACAGTTACGCGCACATGAACGGCTGGAGCAACGGCAGCTACAGCATGATGCA

GGACCAGCTGGGCTACCCGCAGCACCCGGGCCTCAATGCGCACGGCGCAGCGCA

GATGCAGCCCATGCACCGCTACGACGTGAGCGCCCTGCAGTACAACTCCATGAC

CAGCTCGCAGACCTACATGAACGGCTCGCCCACCTACAGCATGTCCTACTCGCAG

CAGGGCACCCCTGGCATGGCTCTTGGCTCCATGGGTTCGGTGGTCAAGTCCGAGG

CCAGCTCCAGCCCCCCTGTGGTTACCTCTTCCTCCCACTCCAGGGCGCCCTGCCA
```

-continued

```
GGCCGGGGACCTCCGGGACATGATCAGCATGTATCTCCCCGGCGCCGAGGTGCC

GGAACCCGCCGCCCCCAGCAGACTTCACATGTCCCAGCACTACCAGAGCGGCCC

GGTGCCCGGCACGGCCATTAACGGCACACTGCCCCTCTCACACATGGCATGCGG

CTCCGGCGAGGGCAGGGGAAGTCTTCTAACATGCGGGGACGTGGAGGAAAATCC

CGGCCCACTCGAGATGGCTGTCAGCGACGCGCTGCTCCCATCTTTCTCCACGTTC

GCGTCTGGCCCGGCGGGAAGGGAGAAGACACTGCGTCAAGCAGGTGCCCCGAAT

AACCGCTGGCGGGAGGAGCTCTCCCACATGAAGCGACTTCCCCCAGTGCTTCCCG

GCCGCCCCTATGACCTGGCGGCGGCGACCGTGGCCACAGACCTGGAGAGCGGCG

GAGCCGGTGCGGCTTGCGGCGGTAGCAACCTGGCGCCCCTACCTCGGAGAGAGA

CCGAGGAGTTCAACGATCTCCTGGACCTGGACTTTATTCTCTCCAATTCGCTGAC

CCATCCTCCGGAGTCAGTGGCCGCCACCGTGTCCTCGTCAGCGTCAGCCTCCTCT

TCGTCGTCGCCGTCGAGCAGCGGCCCTGCCAGCGCGCCCTCCACCTGCAGCTTCA

CCTATCCGATCCGGGCCGGGAACGACCCGGGCGTGGCGCCGGGCGGCACGGGCG

GAGGCCTCCTCTATGGCAGGGAGTCCGCTCCCCCTCCGACGGCTCCCTTCAACCT

GGCGGACATCAACGACGTGAGCCCCTCGGGCGGCTTCGTGGCCGAGCTCCTGCG

GCCAGAATTGGACCCGGTGTACATTCCGCCGCAGCAGCCGCAGCCGCCAGGTGG

CGGGCTGATGGGCAAGTTCGTGCTGAAGGCGTCGCTGAGCGCCCCTGGCAGCGA

GTACGGCAGCCCGTCGGTCATCAGCGTCAGCAAAGGCAGCCCTGACGGCAGCCA

CCCGGTGGTGGTGGCGCCCTACAACGGCGGGCCGCCGCGCACGTGCCCCAAGAT

CAAGCAGGAGGCGGTCTCTTCGTGCACCCACTTGGGCGCTGGACCCCCTCTCAGC

AATGGCCACCGGCCGGCTGCACACGACTTCCCCCTGGGGCGGCAGCTCCCCAGC

AGGACTACCCCGACCCTGGGTCTTGAGGAAGTGCTGAGCAGCAGGGACTGTCAC

CCTGCCCTGCCGCTTCCTCCCGGCTTCCATCCCCACCCGGGGCCCAATTACCCATC

CTTCCTGCCCGATCAGATGCAGCCGCAAGTCCCGCCGCTCCATTACCAAGAGCTC

ATGCCACCCGGTTCCTGCATGCCAGAGGAGCCCAAGCCAAAGAGGGGAAGACGA

TCGTGGCCCCGGAAAAGGACCGCCACCCACACTTGTGATTACGCGGGCTGCGGC

AAAACCTACACAAAGAGTTCCCATCTCAAGGCACACCTGCGAACCCACACAGGT

GAGAAACCTTACCACTGTGACTGGGACGGCTGTGGATGGAAATTCGCCCGCTCA

GATGAACTGACCAGGCACTACCGTAAACACACGGGGCACCGCCCGTTCCAGTGC

CAAAAATGCGACCGAGCATTTTCCAGGTCGGACCACCTCGCCTTACACATGAAG

AGGCATTTTTAAATGACTAGTGCGCGCAGCGGCCGACCATGGCCCAACTTGTTTA

TTGCAGCTTATAATGGTTACAAATAAAGCAATAGCATCACAAATTTCACAAATAA

AGCATTTTTTTCACTGCATTCTAGTTGTGGTTTGTCCAAACTCATCAATGTATCTT

ATCATGTCTGGATCTCGGTACCGGATCCAAATTCCCGATAAGGATCTTCCTAGAG

CATGGCTACGTAGATAAGTAGCATGGCGGGTTAATCATTAACTACAAGGAACCC

CTAGTGATGGAGTTGGCCACTCCCTCTCTGCGCGCTCGCTCGCTCACTGAGGCCG

GGCGACCAAAGGTCGCCCGACGCCCGGGCTTTGCCCGGGCGGCCTCAGTGAGCG

AGCGAGCGCGCAGCCTTAATTAACCTAATTCACTGGCCGTCGTTTTACAACGTCG

TGACTGGGAAAACCCTGGCGTTACCCAACTTAATCGCCTTGCAGCACATCCCCCT

TTCGCCAGCTGGCGTAATAGCGAAGAGGCCCGCACCGATCGCCCTTCCCAACAG

TTGCGCAGCCTGAATGGCGAATGGGACGCGCCCTGTAGCGGCGCATTAAGCGCG
```

GCGGGTGTGGTGGTTACGCGCAGCGTGACCGCTACACTTGCCAGCGCCCTAGCG

CCCGCTCCTTTCGCTTTCTTCCCTTCCTTTCTCGCCACGTTCGCCGGCTTTCCCCGT

CAAGCTCTAAATCGGGGGCTCCCTTTAGGGTTCCGATTTAGTGCTTTACGGCACC

TCGACCCCAAAAAACTTGATTAGGGTGATGGTTCACGTAGTGGGCCATCGCCCTG

ATAGACGGTTTTTCGCCCTTTGACGTTGGAGTCCACGTTCTTTAATAGTGGACTCT

TGTTCCAAACTGGAACAACACTCAACCCTATCTCGGTCTATTCTTTTGATTTATAA

GGGATTTTGCCGATTTCGGCCTATTGGTTAAAAAATGAGCTGATTTAACAAAAAT

TTAACGCGAATTTTAACAAAATATTAACGTTTATAATTTCAGGTGGCATCTTTCG

GGGAAATGTGCGCGGAACCCCTATTTGTTTATTTTTCTAAATACATTCAAATATGT

ATCCGCTCATGAGACAATAACCCTGATAAATGCTTCAATAATATTGAAAAAGGA

AGAGTATGAGTATTCAACATTTCCGTGTCGCCCTTATTCCCTTTTTTGCGGCATTT

TGCCTTCCTGTTTTTGCTCACCCAGAAACGCTGGTGAAAGTAAAAGATGCTGAAG

ATCAGTTGGGTGCACGAGTGGGTTACATCGAACTGGATCTCAATAGTGGTAAGAT

CCTTGAGAGTTTTCGCCCCGAAGAACGTTTTCCAATGATGAGCACTTTTAAAGTT

CTGCTATGTGGCGCGGTATTATCCCGTATTGACGCCGGGCAAGAGCAACTCGGTC

GCCGCATACACTATTCTCAGAATGACTTGGTTGAGTACTCACCAGTCACAGAAAA

GCATCTTACGGATGGCATGACAGTAAGAGAA

Thy1.2 promoter (RGC-specific) (SEQ ID NO: 122):
AATTCAGAGACCGGGAACCAAACTAGCCTTTAAAAAACATAAGTACA

GGAGCCAGCAAGATGGCTCAGTGGGTAAAGGTGCCTACCAGCAAGCCTGACAGC

CTGAGTTCAGTCCCCACGAACTACGTGGTAGGAGAGGACCAACCAACTCTGGAA

ATCTGTTCTGCAAACACATGCTCACACACACACACACAAATAGTATAAACAATTT

TAAATTTCATTTAAAAATAATTTGTAAACAAAATCATTAGCACAGGTTTTAGAAA

GAGCCTCTTGGTGACATCAAGTTGATGCTGTAGATGGGGTATCATTCCTGAGGAC

CCAAAACCGGGTCTCAGCCTTTCCCCATTCTGAGAGTTCTCTCTTTTCTCAGCCAC

TAGCTGAAGAGTAGAGTGGCTCAGCACTGGGCTCTTGAGTTCCCAAGTCCTACAA

CTGGTCAGCCTGACTACTAACCAGCCATGAAGAAACAAGGAGTGGATGGGCTGA

GTCTGCTGGGATGGGAGTGGAGTTAGTAAGTGGCCATGGATGTAATGACCCCAG

CAATGCTGGCTAGAAGGCATGCCTCCTTTCCTTGTCTGGAGACGGAACGGGAGG

GATCATCTTGTACTCACAGAAGGGAGAACATTCTAGCTGGTTGGGCCAAAATGTG

CAAGTTCACCTGGAGGTGGTGGTGCATGCTTTTAACTCCAGTACTCAGGAGGCAG

GGCCAGGTGGATCTCTGTGAGTTCAAGACCAGCCTGCACTATGGAGAGAGTTTTG

GGACAGCCAGAGTTACACAGAAAAATCCTGGTGGAAAATCTGAAAGAAAGAGA

GAAAGAAAGAAAGAAAGGAAGAAAGAAAGAAAGAGTGGCAGGCAGGCA

GGCAGGAGGAAGGAAGGAAGGAAGGAAGGAAGGAAGGAAGGAAGGAAGGAAA

ATAGGTGCGACTTCAAGATCCGGAGTTACAAGCAGAATGCACTGTTTCCCTAACA

GGGCCAAGTGTTTTGAGTAACTGAAGGTGGGCATGATGCCTGGGAAGCAGAAAC

AAGCCAGGCAGATGCACCCCTTGCCTTGCTTCCGAAGGGCTGCAGTAGCATGGA

AAACATGGAAAACAACCAATCCATTCCCTTTGCTGATATAACAGGCTCCAAAGCC

AAAACCTGTCACTGGAGGCTCAAGAGCAGATCTCCAGCCAAGAGGCAAAGGAAT

GGGGGAAGCTGGAGGGCCTCCCTCTGGTTATCCAGGCTTCTGAAGGTTCAAGCA

-continued

```
AAGAAAGGGTTACAACCTTAAAAGGAGAGCGTCCCGGGGTATGGGTAGAAGACT

GCTCCACCCCGACCCCCAGGGTCCCTAACCGTCTTTTCCCTGGGCGAGTCAGCCC

AATCACAGGACTGAGAGTGCCTCTTTAGTAGCAGCAAGCCACTTCGGACACCCA

AATGGAACACCTCCAGTCAGCCCTCGCCGACCACCCCACCCCCTCCATCCTTTTC

CCTCAGCCTCCGATTGGCTGAATCTAGAGTCCCTCCCTGCTCCCCCCTCTCTCCCC

ACCCCTGGTGAAAACTGCGGGCTTCAGCGCTGGGTGCAGCAACTGGAGGCGTTG

GCGCACCAGGAGGAGGCTGCAGCTAGGGGAGTCCAGGTGAGAGCAGGCCGACG

GGAGGGACCCGCACATGCAAGGACCGCCGCAGGGCGAGGATGCAAGCCTTCCCC

AGCTACAGTTTTGGGAAAGGATACCAGGGCGCTCCTATATGGGGCGCGGGAAC

TGGGGAAAGAAGGTGCTCCCAGGTCGAGGTGGGAGAGGAAGGCAGTGCGGGGT

CACGGGCTTTCTCCCTGCTAACGGACGCTTTCGAAGAGTGGGTGCCGGAGGAGA

ACCATGAGGAAGGACATCAAGGACAGCCTTTGGTCCCCAAGCTCAAATCGCTTT

AGTGGTGCGAATAGAGGGAGGAGGTGGGTGGCAAACTGGAGGGAGTCCCCAGC

GGGTGACCTCGTGGCTGGCTGGGTGCGGGGCACCGCAGGTAAGAAAACCGCAAT

GTTGCGGGAGGGGACTGGGTGGCAGGCGCGGGGGAGGGGAAAGCTAGAAAGGA

TGCGAGGGAGCGGAGGGGGGAGGGAGCGGGAGAATCTCAACTGGTAGAGGAAG

ATTAAAATGAGGAAATAGCATCAGGGTGGGGTTAGCCAAGCCGGGCCTCAGGGA

AAGGGCGCAAAGTTTGTCTGGGTGTGGGCTTAGGTGGGCTGGGTATGAGATTCG

GGGCGCCGAAAACACTGCTGCGCCTCTGCCAAATCACGCTACCCCTGTATCTAGT

TCTGCCAGGCTTCTCCAGCCCCAGCCCCAATTCTTTTCTCTAGTGTTCCCCCTTCC

CTCCCCTGAATCTCAAGCCCACACTCCCTCCTCCATAACCCACTGTTATCAAATCT

AAGTCATTTGCCACCCAACAACCATCAGGAGGCGGAAGCAGACGGGAGGAGTTT

GAGATCAACTTGGGCTACATCACGAGTTCCAGGCTCACCAAGGCTTCTTAAGGAG

ACCTTGTCTCTAAAATTAATTAATTAATTAATAGTCCCCTTTCTCTGCCACA

GAACCTTGGGATCTGGCTCCTGGTCGCAGCTCCCCCCACCCCAGGCTGACATTCA

CTGCCATAGCCCATCCGGAAATCCTAGTCTATTTCCCCATGGATCTTGAACTGCA

GAGAGAATGGCAGAGTGGCCCGCCCTGTGCAAAGGATGTTCCTAGCCTAGGTGG

AGCTCGCGAACTCGCAGACTGTGCCTCTCTTGGGCAAGGACAGGCTAGACAGCC

TGCCGGTGTGTTGAGCTAGGGCACTGTGGGAAGGCAGAGAACCTGTGCAGGGC

AGCAATGAACACAGGACCAGAAAACTGCAGCCCTAGGAACACTCAAGAGCTGG

CCATTTGCAAGCATCTCTGGCCTCCGTGCTTCTCACTCATGTCCCATGTCTTATAC

AGGCCTCTGTGGCACCTCGCTTGCCTGATCTCATCCCTAGCCGTTAAGCTTTCTGC

ATGACTTATCACTTGGGGCATAATGCTGGATACCTACCATTTTCTTAGACCCCATC

AAAATCCTATTTGAGTGTACGGTTCGGAGAACCTCATTTATCCGGTAAATGTCTT

TTACTCTGCTCTCAGGGAGCTGAGGCAGGACATCCTGAGATACATTGGGAGAGG

AGATACAGTTTCAATAAAATAATAGGTTGGGTGGAGGTACATGCCTATAATGCC

ACCACTCAGGAAATGGTGGCAGCTTCGTGAGTTTGAGGCCAACCCAAGAAACAT

AGTGAAACCCTGTCAGTAAATAAGTAAGCAAGTATTTGAGTATCTACTATATGCT

AGGGCTGACCTGGACATTAGGGGTCATCTTCTGAACAAACTAGTGCTTGAGGGA

GGTATTTGGGGTTTTTGTTTGTTTAATGGATCTGAATGAGTTCCAGAGACTGGCTA
```

-continued

```
CACAGCGATATGACTGAGCTTAACACCCCTAAAGCATACAGTCAGACCAATTAG

ACAATAAAAGGTATGTATAGCTTACCAAATAAAAAAATTGTATTTTCAAGAGAG

TGTCTGTCTGTGTAGCCCTGGCTGTTCTTGAACTCACTCTGTAGACCAGGCTGGCC

TGGAAATCCATCTGCCTGCCTCTGCCTCTCTGCCTCTCTGCCTCTCTGCCTCTCT

CTGCCTCTCTCTGCCTCTCTCTGCCCCTCTCTGCCCCTCTCTGCCCCTCTCTGCCGC

CCTCTGCCTTTTGCCCTCTGCCCTCTGTTCTCTGGCCTCTGCCCTCTGCCCTCTGGC

CTCTGGCCTCTGCCTCTGCCTCTTGAGTGCTGGAATCAAAGGTGTGAGCTCTGTA

GGTCTTAAGTTCCAGAAGAAAGTAATGAAGTCACCCAGCAGGGAGGTGCTCAGG

GACAGCACAGACACACACCCAGGACATAGGCTCCCACTTCCTTGGCTTTCTCTGA

GTGGCAAAGGACCTTAGGCAGTGTCACTCCCTAAGAGAAGGGGATAAAGAGAGG

GGCTGAGGTATTCATCATGTGCTCCGTGGATCTCAAGCCCTCAAGGTAAATGGGG

ACCCACCTGTCCTACCAGCTGGCTGACCTGTAGCTTTCCCCACCACAGAATCCAA

GTCGGAACTCTTGGCACCTAGAGGATCTCGAGGTCCTTCCTCTGCAGAGGTCTTG

CTTCTCCCGGTCAGCTGACTCCCTCCCCAAGTCCTTCAAATATCTCAGAACATGG

GGAGAAACGGGGACCTTGTCCCTCCTAAGGAACCCCAGTGCTGCATGCCATCAT

CCCCCCCACCCTCGCCCCCACCCCCGCCACTTCTCCCTCCATGCATACCACTAGCT

GTCATTTTGTACTCTGTATTTATTCCAGGGCTGCTTCTGATTATTTAGTTTGTTCTT

TCCCTGGAGACCTGTTAGAACATAAGGGCGTATGGTGGGTAGGGGAGGCAGGAT

ATCAGTCCCTGGGGCGAGTTCCTCCCTGCCAACCAAGCCAGATGCCTGAAAGAG

ATATGGATGAGGGAAGTTGGACTGTGCCTGTACCTGGTACAGTCATACTCTGTTG

AAAGAATCATCGGGGAGGGGGGGGGGCTCAAGAGGGGAGAGCTCTGCTGAGCC

TTTGTGGACCATCCAATGAGGATGAGGGCTTAGATTCTACCAGGTCATTCTCAGC

CACCACACACAAGCGCTCTGCCATCACTGAAGAAGCCCCCTAGGGCTCTTGGGC

CAGGGCACACTCAGTAAAGATGCAGGTTCAGTCAGGGAATGATGGGGAAAGGG

GTAGGAGGTGGGGAGGGATCACCCCCTCCTCTAAAACACGAGCCTGCTGTCTC

CAAAGGCCTCTGCCTGTAGTGAGGGTGGCAGAAGAAGACAAGGAGCCAGAACTC

TGACTCCAGGATCTAAGTCCGTGCAGGAAGGGGATCCTAGAACCATCTGGTTGG

ACCCAGCTTACCAAGGGAGAGCCTTTATTCTTCTTTCCCTTGCCCCTCTGTGCCAG

CCCCTCTTGCTGTCCCTGATCCCCCAGACAGCGAGAGTCTTGCAACCTGCCTCTTC

CAAGACCTCCTAATCTCAGGGGCAGGCGGTGGAGTGAGATCCGGCGTGCACACT

TTTTGGAAGATAGCTTTCCCAAGGATCCTCTCCCCCACTGGCAGCTCTGCCTGTCC

CATCACCATGTATAATACCACCACTGCTACAGCATCTCACCGAGGAAAGAAAAC

TGCACAATAAAACCAAGCCTCTGGAGTGTGTCCTGGTGTCTGTCTCTTCTGTGTCC

TGGCGTCTGTCTCTTCTGTGTTCTTCCAAGGTCAGAAACAAAAACCACACACTTC

AACCTGGATGGCTCGGCTGAGCACTTCTGTGTGCAGAAGGTCCAACCAGACTCTG

GGGTACCCCGGCCCTCCCTATTCCCTTGCCTCCTGTCTCCCGCTTTTTATAGCTCC

CTATGCTGGGCTTCTCTGGAGAGTGAAATCTTTGCCCAAATCAATGCGCATTCTC

TCTGCTGAGTCATCTGGCGACAGCAGTTGAGTTCACCCGCCAACACATGGGCCCA

GCTATGTAGCCGAACCCTGGCTCTGGAAGTGCCAGGGACTTTGTGCATAAGTATG

TACCATGCCTTTTTTCACAGTCCTAGCTCTGCAGAAGTGCAGCCTGAAGGCCTG

TCTGCTGAGAGGACATGCCCTGGAGCCCTGAAACAGGCACAGTGGGAGGAGGAA
```

-continued

```
CGGAGGATGACAGGCATCAGGCCCTCAGTCCAAAAGCAACCACTTGAGAATGGG

CTGGAGTACGAAACATGGGGTCCCGTCCCTGGATCCCTCCTCAAAGAGTAATAA

GTAAAATATAAACAGGTACCCCAGGCCGTTCTGGGTTTGGGTTGTAATGGGATCC

ATTTGCAGAGAACTATTGAGACAGCCCAGCCGTACTGTGACAGGCAATGTGGGG

GAGGAGGTTGAATCACTTGGTATTTAGCATGAATAGAATAATTCCCTGAACATTT

TTCTTAAACATCCATATCTAAATTACCACCACTCGCTCCCAGTCTTCCTGCCTTTG

CGCCAGCCTCCTGTCTGGCCATGCCTGAAGAAGGCTGGAGAAGCCACCCACCTC

AGGCCATGACACTGCCAGCCACTTGGCAGGTGCAGCCAAACCTGAGCTGTCCCA

GAAAGGGACATTCTCAAGACCCAGGCACCCTGATCAGCACTGACTTGGAGCTAC

AAGTGTCATGCCAGAAAAGTCTCTAAGAAAACCTTTTCAGGGAAAAGGGGGTGA

CTCAACACCGGGCAAGTTTGGGAAGCCCCACCCTTCGAGTGATGGAAGAGCAGA

TAGGAAGCCTCAGAAGAGAGACACCGGCACCCAGGTAACGTTCCTCATGTGGTC

TCTGTCACACTAGGTGCTCTTCCCTGGACATCTCCGTGACCACACTCTCAGTTCTT

AGGGAGATGCGGGTGCTCTCTGAGGCTATCTCAGAGTTGCAGATTCTGAGGCCTA

GAGTGACTACAGTCAGCCTAGGAAGCCACAGAGGACTGTGGACCAGGAGGGCA

GAAGAGGAGAAGGGAAGAAAAACCATCAGATAGGACTTGCAATGAAACTAACC

CAAGACAATCATAATGCAGACAGGAATGTTAAAGGCGTTCAGCAGC
```

ADDITIONAL EMBODIMENTS

Embodiment 1. A method comprising:
inducing in a cell, tissue, organ and/or subject:
  (i) OCT4 expression;
  (ii) SOX2 expression; and
  (iii) KLF4 expression;
in the absence of inducing c-MYC expression.

Embodiment 2. The method of embodiment 1, wherein OCT4 expression is induced by administering:
  (i) a first engineered nucleic acid encoding OCT4 or encoding a Cas9 fusion protein (CRISPR activator) and a guide RNA sequence targeting promoter or enhancer at endogenous locus of Oct4, optionally wherein the first nucleic acid (e.g., engineered nucleic acid) comprises RNA and/or DNA;
  (ii) a chemical agent that induces OCT4 expression;
  (iii) an antibody that induces OCT4 expression; or
  (iv) an engineered protein encoding OCT4,
optionally wherein OCT4 comprises a sequence that is at least 70% identical to SEQ ID NO: 2 or SEQ ID NO: 41.

Embodiment 3. The method of any one of embodiments 1-2, wherein SOX2 expression comprises administering:
  (v) a second engineered nucleic acid encoding SOX2 encoding a Cas9 fusion protein (CRISPR activator) and a guide RNA sequence targeting promoter or enhancer at endogenous locus of SOX2, wherein the second engineered nucleic acid comprises RNA and/or DNA;
  (vi) a chemical agent that induces SOX2 expression;
  (vii) an antibody that induces SOX2 expression; or
  (viii) an engineered protein encoding SOX2,
optionally wherein SOX2 comprises a sequence that is at least 70% identical to SEQ ID NO: 4 or SEQ ID NO: 43.

Embodiment 4. The method of any one of embodiments 1-3, wherein KLF4 expression comprises administering:
  (ix) a third engineered nucleic acid encoding KLF4 encoding a Cas9 fusion protein (CRISPR activator) and a guide RNA sequence targeting promoter or enhancer at endogenous locus of KLF4, wherein the third nucleic acid (e.g., engineered nucleic acid) comprises RNA and/or DNA;
  (ix) a chemical agent that induces KLF4 expression;
  (xi) an antibody that induces KLF4 expression; or
  (xii) an engineered protein encoding KLF4,
optionally wherein KLF4 comprises a sequence that is at least 70% identical to SEQ ID NO: 6 or SEQ ID NO: 45.

Embodiment 5. The method of any one of embodiments 2-4, wherein said first, second, third engineered nucleic acids, or a combination thereof are present on an expression vector or are not present on an expression vector, optionally wherein the first, second, third engineered nucleic acids are mRNA or plasmid DNA.

Embodiment 6. The method of embodiment 5, wherein two or three of said first, second and third engineered nucleic acids are present in the same expression vector.

Embodiment 7. The method of any one of embodiments 1-5, wherein said first, second and third engineered nucleic acids are present in separate expression vectors.

Embodiment 8. The method of any one of embodiments 5-7, wherein said expression vector(s) include an inducible promoter operably linked to the first, second, third engineered nucleic acids, or a combination thereof, optionally wherein said method further comprises administering an inducing agent.

Embodiment 9. The method of embodiment 8 wherein said promoter comprises a tetracycline response element (TRE).

Embodiment 10. The method of embodiment 9, wherein administration of the inducing agent comprises administering a protein or a fourth engineered nucleic acid encoding the inducing agent, optionally wherein the fourth engineered nucleic acid is introduced simultaneously as the first, second, and third engineered nucleic acids.

Embodiment 11. The method of embodiment 10, wherein the fourth engineered nucleic acid is present on a separate expression vector from the first, second, and third engineered nucleic acids.

Embodiment 12. The method of embodiment 10, wherein the fourth engineered nucleic acid is present on the same expression vector with at least one of the first, second, and third engineered nucleic acids.

Embodiment 13. The method of any one of embodiments 9-12, wherein the inducing agent is capable of inducing expression of the first, second, third engineered nucleic acids, or a combination thereof from the inducible promoter in the presence of a tetracycline and the method further comprises administering tetracycline and/or removing tetracycline, optionally wherein the tetracycline is doxycycline.

Embodiment 14. The method of embodiment 13, wherein the inducing agent is reverse tetracycline-controlled transactivator (rtTA).

Embodiment 15. The method of embodiment 14, wherein the rtTA is M2-rtTA or rtTA3.

Embodiment 16. The method of embodiment 15, wherein the M2-rtTA comprises an amino acid sequence that is at least 70% identical to SEQ ID NO: 15 or the rtTA3 comprises an amino acid sequence that is at least 70% identical to SEQ ID NO: 11.

Embodiment 17. The method of any one of embodiments 9-12, wherein the inducing agent is capable of inducing expression of the first, second, third engineered nucleic acids, or a combination thereof from the inducible promoter in the absence of a tetracycline, optionally wherein the tetracycline is doxycycline.

Embodiment 18. The method of embodiment 17, wherein the inducing agent is a temperature, a chemical, a pH, a nucleic acid, a protein, optionally wherein the protein is a tetracycline-controlled transactivator (tTA).

Embodiment 19. The method of any one of embodiments embodiment 11 or 13-18, wherein the first, second, and third engineered nucleic acids are present in a first expression vector and the fourth engineered nucleic acid is present in a second expression vector.

Embodiment 20. The method of any one of embodiments 9-19, wherein the promoter is a TRE3G, a TRE2 promoter, or a P tight promoter, optionally, wherein the promoter comprises a engineered nucleic acid sequence that is at least 70% identical to SEQ ID NO: 7, optionally, wherein the promoter comprises a engineered nucleic acid sequence that is at least 70% identical to SEQ ID NO: 23, and optionally wherein the promoter comprises a sequence that is at least 70% identical to SEQ ID NO: 24.

Embodiment 21. The method of any one of embodiments 1-7 or 10-20, wherein said expression vector(s) comprise a constitutive promoter operably linked to the first, second, third, fourth engineered nucleic acids, or any combination thereof.

Embodiment 22. The method of embodiment 21, wherein the constitutive promoter is operably linked to the fourth engineered nucleic acid but not to the first, second, or third engineered nucleic acids, optionally wherein the constitutive promoter is CP1, CMV, EF1 alpha, SV40, PGK1, Ubc, human beta actin, CAG, Ac5, polyhedrin, TEF1, GDS, CaM3 5S, Ubi, H1, and U6 promoter, or a tissue-specific promoter.

Embodiment 23. The method of embodiment 19-22, wherein the first expression vector comprises the sequence provided in SEQ ID NO: 16, optionally wherein the second expression vector comprises the sequence provided in SEQ ID NO: 31 or SEQ ID NO: 32.

Embodiment 24. The method of any one of embodiments 2-23, wherein at least one of (i)-(xii) is delivered in a viral vector or is delivered without a viral vector, wherein the viral vector is selected from the group consisting of a lentivirus, a retrovirus, an adenovirus, alphavirus, vaccinia virus, and an adeno-associated virus (AAV) vector, optionally wherein delivery without a viral vector comprises administration of a naked nucleic acid, electroporation, use of a nanoparticle, or use of liposomes.

Embodiment 25. The method of any one of embodiments 19-24, wherein the first expression vector is a first viral vector, and the second expression vector is a viral vector, optionally wherein the first and second viral vectors are AAV vectors.

Embodiment 26. The method of any one of embodiments 1-25 wherein at least one engineered nucleic acid comprises an SV40-derived sequence including a sequence that is at least 70% identical to SEQ ID NO: 8.

Embodiment 27. The methods of any one of embodiments 1-26, wherein OCT4, KLF4, or SOX2 is a mammalian protein.

Embodiment 28. The method of any one of embodiments 1-27, wherein the cell or tissue is in a subject, wherein the subject has a condition, is suspected of having a condition, or at risk for a condition, optionally wherein the condition is selected from the group consisting of ocular disease, aging, cancer, musculoskeletal disease, age-related disease, a disease affecting a non-human animal and neurodegenerative disease.

Embodiment 29. The method of any one of embodiments 1-28, wherein the method further comprises regulating: cellular reprogramming, tissue repair, tissue survival, tissue regeneration, tissue growth, tissue function, organ regeneration, organ survival, organ function, disease, or any combination thereof, optionally wherein regulating comprises inducing cellular reprogramming, reversing aging, improving tissue function, improving organ function, tissue repair, tissue survival, tissue regeneration, tissue growth, promoting angiogenesis, treating a disease, reducing scar formation, reducing the appearance of aging, promoting organ regeneration, promoting organ survival, altering the taste and quality of agricultural products derived from animals, treating a disease, or any combination thereof, ex vivo or in vitro and optionally wherein treating a disease comprises inducing expression of OCT4, KLF4, and/or SOX2 prior to the onset of disease or wherein treating a disease a disease comprises inducing expression of OCT4, KLF4, and/or SOX2 after the onset of disease.

Embodiment 30. The method of embodiment 29, wherein the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine, optionally wherein the tissue is damaged or the tissue may be considered healthy but suboptimal for performance or survival in current or future conditions.

Embodiment 31. The method of any one of embodiments 1-30, wherein the engineered nucleic acid further comprises a self-cleaving peptide, optionally wherein the self-cleaving peptide is a 2A peptide that is at least 70% identical to SEQ ID NO: 9.

Embodiment 32. The method of any one of embodiments 1-31, wherein the engineered nucleic acid further comprises inverted terminal repeats (ITRs) flanking the first nucleic acid, the second nucleic acid, the third nucleic acid, or a combination thereof, optionally, wherein the distance between the ITRs is 4.7 kb or less.

Embodiment 33. An expression vector comprising:
(i) a first engineered nucleic acid encoding OCT4;
(ii) a second engineered nucleic acid encoding SOX2; and
(iii) a third engineered nucleic acid encoding KLF4;
in the absence of an engineered nucleic acid capable of expressing c-MYC.

Embodiment 34. The expression vector of embodiment 33, wherein the OCT4 protein comprises a sequence that is at least 70% identical to SEQ ID NO: 2 or SEQ ID NO: 41.

Embodiment 35. The expression vector of any one of embodiments 33-34, wherein the SOX2 protein comprises a sequence that is at least 70% identical to SEQ ID NO: 4 or SEQ ID NO: 43.

Embodiment 36. The expression vector of any one of embodiments 33-35, wherein the KLF4 protein comprises a sequence that is at least 70% identical to SEQ ID NO: 6 or SEQ ID NO: 45.

Embodiment 37. The expression vector of any one of embodiments 33-36, further comprising an inducible promoter operably linked to the first, second, third engineered nucleic acids, or any combination thereof.

Embodiment 38. The expression vector of embodiment 37, wherein an inducing agent is capable of inducing expression of the first, second, third engineered nucleic acids, or any combination thereof from the inducible promoter in the presence of a tetracycline, optionally wherein the tetracycline is doxycycline.

Embodiment 39. The expression vector of embodiment 38, wherein the inducing agent is reverse tetracycline-controlled transactivator (rtTA).

Embodiment 40. The expression vector of embodiment 39, wherein the rtTA is M2-rtTA or rtTA3.

Embodiment 41. The expression vector of embodiment 40, wherein the M2-rtTA comprises an amino acid sequence that is at least 70% identical to SEQ ID NO: 15 or the rtTA3 comprises an amino acid sequence that is at least 70% identical to SEQ ID NO: 11.

Embodiment 42. The expression vector of any one of embodiments 38-41, wherein the inducing agent is capable of inducing expression of the first, second, third engineered nucleic acids, or any combination thereof from the inducible promoter in the absence of a tetracycline, optionally, wherein the tetracycline is doxycycline.

Embodiment 43. The expression vector of embodiment 42, wherein the inducing agent is a tetracycline-controlled transactivator (tTA).

Embodiment 44. The expression vector of any one of embodiments 37-43, wherein the inducible promoter comprises a tetracycline-responsive element (TRE), optionally, wherein the promoter is a TRE3G promoter comprising a engineered nucleic acid sequence that is at least 70% identical to SEQ ID NO: 7, optionally, wherein the promoter comprises a engineered nucleic acid sequence that is at least 70% identical to SEQ ID NO: 23, and optionally wherein the promoter comprises a sequence that is at least 70% identical to SEQ ID NO: 24.

Embodiment 45. The expression vector of any one of embodiments 33-36, wherein said expression vector(s) comprise a constitutive promoter operably linked to the first, second, third engineered nucleic acids, or a combination thereof.

Embodiment 46. The expression vector of any one of embodiments 33-44, wherein the expression vector comprises the sequence provided in SEQ ID NO: 16.

Embodiment 47. The expression vector of any one of embodiments 33-46, wherein the expression vector is a viral vector, wherein the viral vector is selected from the group consisting of a lentivirus, alphavirus, vaccinia virus, a herpes virus, a retrovirus, an adenovirus, and an adeno-associated virus (AAV) vector.

Embodiment 48. The expression vector of any one of embodiments 33-47, wherein at least one engineered nucleic acid comprises an SV40-derived sequence including a sequence that is at least 70% identical to SEQ ID NO: 8.

Embodiment 49. The expression vectors of any one of embodiments 33-48, wherein OCT4, KLF4, or SOX2 is a mammalian protein.

Embodiment 50. The expression vector of any one of embodiments 33-49, wherein the expression vector further comprises a self-cleaving peptide, optionally wherein the self-cleaving peptide is 2A peptide, optionally wherein the 2A peptide comprises a sequence that is at least 70% identical to SEQ ID NO: 9.

Embodiment 51. The expression vector of any one of embodiments 37-44 and 46-50, wherein the expression vector comprises one inducible promoter.

Embodiment 52. The expression vector of any one of embodiments 45-50, wherein the expression vector comprises one constitutive promoter.

Embodiment 53. The expression vector of any one of embodiments 33-52, wherein the engineered nucleic acid further comprises inverted terminal repeats (ITRs) flanking the first nucleic acid, the second nucleic acid, the third nucleic acid, or a combination thereof.

Embodiment 54. The expression vector of embodiment 32, wherein the distance between the ITRs is 4.7 kb or less.

Embodiment 55. A recombinant virus comprising the expression vector of any one of embodiments 47-54, optionally wherein the recombinant virus is a retrovirus, an adenovirus, an AAV, alphavirus, vaccinia virus, a herpes virus, or a lentivirus.

Embodiment 56. An engineered cell produced by any one of the methods of embodiments 1-32, 63-66, 70-75, 81, and 85-87, optionally wherein the engineered cell comprises the expression vector of any one of embodiments 33-54.

Embodiment 57. A composition comprising the, expression vector of any one of embodiments 33-54, the recombinant virus of embodiment 55, the engineered cell of embodiment 56, a chemical agent that is capable of inducing OCT4, KLF4, and/or SOX2 expression, an engineered protein selected from the group consisting of OCT4, KLF4, and/or SOX2, an antibody capable of inducing expression of OCT4, KLF4, and/or SOX2, optionally wherein the composition comprises a pharmaceutically acceptable carrier.

Embodiment 58. The composition of embodiment 57, further comprising a second expression vector encoding an inducing agent, a second protein encoding an inducing agent, or a second recombinant virus encoding an inducing agent, optionally wherein the second expression vector is an AAV vector and/or the second recombinant virus is an AAV.

Embodiment 59. The composition of embodiment 58, wherein the inducing agent is reverse tetracycline transactivator (rtTA) or tetracycline transactivator (tTA).

Embodiment 60. The composition of any one of embodiments 58-59, wherein the inducing agent is encoded by a viral vector, optionally, wherein the viral vector is selected from the group consisting of a lentiviral vector, an adenoviral vector, an adeno-associated viral vector, and a retroviral vector.

Embodiment 61. The composition of embodiment 60, wherein the viral vector encoding the inducing agent comprises a sequence set forth in SEQ ID NO: 31 or SEQ ID NO: 32.

Embodiment 62. A kit comprising the expression vector of any one of embodiments 33-54, recombinant virus of embodiment 55, the engineered cell of embodiment 56, a chemical agent that is capable of inducing OCT4, KLF4, and/or SOX2 expression, an engineered protein selected from the group consisting of OCT4, KLF4, and/or SOX2, an antibody capable of inducing expression of OCT4, KLF4, and/or SOX2, or the composition of any one of embodiments 56-61.

Embodiment 63. A method of producing an engineered cell comprising the method of any one of embodiments 1-32, thereby producing the engineered cell.

Embodiment 64. The method of embodiment 63, wherein the engineered cell is an induced pluripotent stem cell.

Embodiment 65. The method of any one of embodiments 63-64, wherein the engineered cell is the cell of embodiment 56.

Embodiment 66. A method of producing an engineered cell, comprising the method of any one of embodiments 1-32 and 63-65, wherein the engineered cell is produced ex vivo.

Embodiment 67. The method of any one of embodiments 63-66, further comprising generating an engineered tissue or engineered organ.

Embodiment 68. The method of any one of embodiments 66-67, further comprising administering the engineered cell, engineered tissue, and/or engineered organ to a subject in need thereof, optionally wherein the cell, tissue, and/or organ is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine cell.

Embodiment 69. The method of any one of embodiments 63-68, wherein the method further comprises treating a disease, optionally wherein the disease is selected from the group consisting of acute injuries, neurodegenerative diseases, chronic diseases, proliferative diseases, ocular disease, cardiovascular diseases, genetic diseases, inflammatory diseases, autoimmunue diseases, neurological diseases, hematological diseases, painful conditions, psychiatric disorders, metabolic disorders, chronic diseases, cancers, aging, age-related diseases, and diseases affecting any tissue in a subject, optionally wherein the disease is an ocular disease.

Embodiment 70. A method comprising:
(i) activating OCT4;
(ii) activating SOX2; and
(iii) activating KLF4;
in a cell, tissue, organ, and/or subject and in the absence of activating c-Myc.

Embodiment 71. The method of embodiment 71, wherein the activating in any one of (i)-(iii) comprises administering an antibody, protein, nucleic acid, or chemical agent.

Embodiment 72. The method of any one of embodiments 72, wherein the nucleic acid, antibody, protein, and/or chemical agent replaces OCT4, SOX2, and/or KLF4.

Embodiment 73. The method of embodiment 72, wherein the replacing comprises promoting cellular reprogramming.

Embodiment 74. The method of any one of embodiments 70-73, wherein activating of any one of (i)-(iii) comprises replacing OCT4, SOX2, and/or KLF4, selected from the group consisting of an antibody, a protein, a nucleic acid, and a chemical agent.

Embodiment 75. The method of embodiment 74, wherein the replacing of OCT4, SOX2, and/or KLF4 comprises administering a nucleic acid and/or protein encoding Tet1, NR5A-2, Sall4, E-cadherin, NKX3-1, NANOG, and/or Tet2.

Embodiment 76. The method of any one of embodiments 1-32 and 70-75, wherein the subject is healthy.

Embodiment 77. The method of any one of embodiments 1-32 and 70-76, wherein the subject is a pediatric subject.

Embodiment 78. The method of any one of embodiments 1-32 and 70-76, wherein the subject is an adult subject.

Embodiment 79. The method of any one of embodiments 28-32 and 70-78, wherein the subject has, is suspected of having, or at risk for glaucoma.

Embodiment 80. The method of any one of embodiments 28-32 and 70-79, wherein the subject has, is suspected of having, or at risk for age-related decline in visual acuity, and/or retinal function.

Embodiment 81. A method comprising administering a nucleic acid and/or protein encoding Tet1 or Tet2 to a cell, tissue, organ, and/or subject.

Embodiment 82. The method of embodiment 81, wherein the subject has a disease.

Embodiment 83. The method of embodiment 82, wherein the disease is selected from acute injuries, neurodegenerative diseases, chronic diseases, proliferative diseases, ocular disease, cardiovascular diseases, genetic diseases, inflammatory diseases, autoimmunue diseases, neurological diseases, hematological diseases, painful conditions, psychiatric disorders, metabolic disorders, chronic diseases, cancers, aging, age-related diseases, and diseases affecting any tissue in a subject.

Embodiment 84. The method of embodiment 83, wherein the disease is an ocular disease.

Embodiment 85. The method of any one of embodiments 1-32 and 63-84, further comprising activating an enhancer of reprogramming in the cell, tissue, organ and/or subject.

Embodiment 86. The method of any one of embodiments 1-32 and 63-85, further comprising inhibiting a barrier of reprogramming in the cell, tissue, organ and/or subject.

Embodiment 87. The method of embodiment 86, wherein the barrier of reprogramming is a DNA methyltransferase (DNMT) in the cell, tissue, organ and/or subject.

Embodiment 88. A method comprising:
inducing in a subject:
(i) OCT4 expression;
(ii) SOX2 expression; and
(iii) KLF4 expression;
in the absence of inducing c-MYC expression, wherein the subject has been treated with a chemotherapy drug.

Embodiment 89. The method of embodiment 89, wherein the chemotherapy drug is vincristine (VCS).

Embodiment 90. A method comprising inducing in a cell, tissue, organ, and/or subject:
(i) OCT4 expression;
(ii) SOX2 expression; and
(iii) KLF4 expression;
wherein OCT4, SOX2, and KLF4 is encoded by a nucleic acid and expression of OCT4, SOX2, and/or KLF4 is induced from a single promoter.

Embodiment 91. A method comprising:
inducing in a cell, tissue, organ and/or subject:
(i) OCT4 expression;
(ii) SOX2 expression;
(iii) KLF4 expression; or
(iv) any combination of (i)-(iii),
in the absence of inducing c-MYC expression.

Embodiment 92. The method of embodiment 91, wherein the combination of (i)-(iii) comprises (i) and (ii); (i) and (iii); (ii) and (iii); or (i), (ii), and (iii).

Embodiment 93. An expression vector comprising:
(i) a first engineered nucleic acid encoding OCT4;
(ii) a second engineered nucleic acid encoding SOX2;
(iii) a third engineered nucleic acid encoding KLF4; or
(iv) any combination of (i)-(iii),
in the absence of an engineered nucleic acid capable of inducing c-MYC expression.

Embodiment 94. The expression vector of embodiment 93, wherein the combination of (i)-(iii) comprises (i) and (ii); (i) and (iii); (ii) and (iii); or (i), (ii), and (iii).

Embodiment 95. A recombinant virus comprising the expression vector of any one of embodiments 47-54 and 93-94, optionally wherein the recombinant virus is a retrovirus, an adenovirus, an AAV, alphavirus, vaccinia virus, a herpes virus, or a lentivirus.

Embodiment 96. An engineered cell produced by any one of the methods of embodiments 1-32, 63-66, 70-75, 81, 85-87, and 91-92, optionally wherein the engineered cell comprises the expression vector of any one of embodiments 33-54 and 93-94.

Embodiment 97. A composition comprising the expression vector of any one of embodiments 33-54 and 93-94, the recombinant virus of embodiment 55 or embodiment 95, the engineered cell of embodiment 56 or 96, a chemical agent that is capable of inducing expression of OCT4; KLF4; SOX2; or any combination thereof, an engineered protein selected from the group consisting of OCT4; KLF4; SOX2; or any combination thereof, an antibody capable of inducing expression of OCT4; KLF4; SOX2; or any combination thereof, optionally wherein the composition comprises a pharmaceutically acceptable carrier.

Embodiment 98. A kit comprising the expression vector of any one of embodiments 33-54 and 93-94, recombinant virus of embodiment 55 or 95, the engineered cell of embodiment 56 or 96, a chemical agent that is capable of inducing expression of OCT4; KLF4; SOX2; or any combination thereof, an engineered protein selected from the group consisting of OCT4; KLF4; SOX2; or any combination thereof, an antibody capable of inducing expression of OCT4; KLF4; SOX2; or any combination thereof, or the composition of any one of embodiments 56-61 or 97.

Embodiment 99. A method of producing an engineered cell comprising the method of any one of embodiments 1-32 and 91-92, thereby producing the engineered cell.

Embodiment 100. A method of producing an engineered cell, comprising the method of any one of embodiments 1-32, 63-65, 91-92, and 99, wherein the engineered cell is produced in vivo.

Embodiment 101. A method of producing an engineered cell, comprising the method of any one of embodiments 1-32, 63-65, 91-92, and 99, wherein the engineered cell is produced ex vivo.

Embodiment 102. A method comprising:
(i) activating OCT4;
(ii) activating SOX2;
(iii) activating KLF4; or
(iv) any combination of (i)-(iii),
in a cell, tissue, organ, subject, or any combination thereof, and in the absence of activating c-Myc above endogenous levels.

Embodiment 103. The method of embodiment 102, wherein the combination of (i)-(iii) comprises (i) and (ii); (i) and (iii); (ii) and (iii); or (i), (ii), and (iii).

Embodiment 104. A method comprising:
inducing in a subject:
(i) OCT4 expression;
(ii) SOX2 expression;
(iii) KLF4 expression; or
(iv) any combination of (i)-(iii),
in the absence of inducing c-MYC expression, wherein the subject has been treated with a chemotherapy drug.

Embodiment 105. The method of embodiment 104, wherein the combination of (i)-(iii) comprises (i) and (ii); (i) and (iii); (ii) and (iii); or (i), (ii), and (iii).

Embodiment 106. A method comprising inducing in a cell, tissue, organ, subject, or any combination thereof:
(i) OCT4 expression;
(ii) SOX2 expression;
(iii) KLF4 expression; or
(iv) any combination of (i)-(iii),
wherein OCT4, SOX2, KLF4, or any combination thereof is encoded by a nucleic acid and expression of OCT4, SOX2, KLF4, or any combination thereof is induced from a single promoter.

Embodiment 107. The method of embodiment 106, wherein the combination of (i)-(iii) comprises (i) and (ii); (i) and (iii); (ii) and (iii); or (i), (ii), and (iii).

Embodiment 108. The method of any one of embodiments 1-32, 68-92, or 102-107 wherein the subject is a human.

Embodiment 109. The method of any one of embodiments 1-32, 68-92, or 102-108, wherein the method does not induce teratoma formation.

Embodiment 110. The method of any one of embodiments 1-32, 68-92, or 102-109, wherein the method does not induce tumor formation or tumor growth.

Embodiment 111. The method of embodiment 110, wherein the method reduces tumor formation or tumor growth.

Embodiment 112. The method of any one of embodiments 1-32, 68-92, or 102-111, wherein the method increases visual acuity in the subject.

Embodiment 113. The method of any one of embodiments 1-32, 68-92, or 102-112, wherein the method does not induce cancer.

Embodiment 114. The method of any one of embodiments 1-32, 68-92, or 102-113, wherein the method does not induce glaucoma.

Embodiment 115. The method of any one of embodiments 1-32, 68-92, or 102-114, wherein the method reverses the epigenetic clock of the cell, the tissue, the organ, the subject, or any combination thereof.

Embodiment 116. The method of embodiment 115, wherein the epigenetic clock is determined using a DNA methylation-based (DNAm) age estimator.

Embodiment 117. The method of any one of embodiments 1-32, 68-92, or 102-116, wherein the method alters the expression of one or more genes associated with ageing.

Embodiment 118. The method of embodiment 117, wherein the method reduces expression of one or more genes associated with ageing.

Embodiment 119. The method of embodiment 118, wherein the method reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Ccl9, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnaja1-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galnt18, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg1l2, Hapln4, Hcn3, Hcn4, Hhatl, Hs6st2, Htr3a, Il1rap, Il1rapl2, Inka1, Kbtbd12, Kcnj11, Kcnk4, Kdelc2, Klhl33, Lamc3, Lilra5, Lman1l, Lrfn2, Lrrc38, Lrrn4cl, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sel1l3, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof.

Embodiment 120. The method of embodiment 119, wherein the gene is a sensory gene.

Embodiment 121. The method of any one of embodiments 118-120, wherein the gene is Ace, Kcnk4, Lamc3, Edn1, Syt10, Ngfr, Gprc5c, Cd36, Chrna4, Ednrb, Drd2, or a combination thereof.

Embodiment 122. The method of embodiment 117, wherein the method increases expression of one or more genes associated with ageing.

Embodiment 123. The method of any one of embodiments 1-32, 68-92, 102-122, wherein the method increases expression of 1700031P21Rik, 1810053B23Rik, 2900045O20Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1cl, Ankrd1, Asb15, Atp2c2, AU018091, AW822073, Btnl10, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps8l1, EU599041, Fam90a1a, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2al2a, Ido2, Igfbp1, Kif7, Klhl31, Lrrc31, Mc5r, Mgam, Msh4, Mucl2, Mug1, Mybl2, Myhl5, Nek10, Neurod6, Nr1h5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otogl, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Treg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Embodiment 124. The method of embodiment 123, wherein the method increases expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otogl, Olfr943, Olfr1406, Olfr273, Olfr466, Olfr1043, Olfr427, Olfr890, Rbp4, or any combination thereof.

Embodiment 125. A method of reprogramming comprising rejuvenating the epigenetic clock of a cell, tissue, organ, subject, or any combination thereof.

Embodiment 126. The method of embodiment 125, wherein rejuvenating the epigenetic clock of a cell, tissue, organ, subject, or any combination thereof comprises introducing, activating, and/or expressing OCT4, KLF4, SOX2, or any combination thereof.

Embodiment 127. The method of any one of embodiments 126, wherein the epigenetic clock of a cell, tissue, organ, subject, or any combination thereof is rejuvenated to that of a young cell, tissue, organ, subject, or any combination thereof.

Embodiment 128. The method of any one of embodiments 125-127, wherein rejuvenating the epigenetic clock comprises altering expression of one or more genes associated with ageing in the cell, tissue, organ, subject, or the combination thereof.

Embodiment 129. The method of embodiment 128, wherein the method comprises reducing expression of one or more genes associated with ageing.

Embodiment 130. The method of embodiment 129, wherein the method comprises reducing expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Ccl9, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnaja1-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galnt18, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg1l2, Hapln4, Hcn3, Hcn4, Hhatl, Hs6st2, Htr3a, Il1rap, Il1rapl2, Inka1, Kbtbd12, Kcnj11, Kcnk4, Kdelc2, Klhl33, Lamc3, Lilra5, Lman1l, Lrfn2, Lrrc38, Lrrn4cl, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec14l5, Sel1l3, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof.

Embodiment 131. The method of embodiment 128-130, wherein the one or more genes is one or more sensory genes.

Embodiment 132. The method of any one of embodiments 128-131, wherein the gene is Ace, Kcnk4, Lamc3, Edn1, Syt10, Ngfr, Gprc5c, Cd36, Chrna4, Ednrb, Drd2, or a combination thereof.

Embodiment 133. The method of any one of embodiments 128-132, wherein the method comprises increasing expression of one or more genes associated with ageing.

Embodiment 134. The method of embodiment 133, wherein the method increases expression of 1700031P21Rik, 1810053B23Rik, 2900045O20Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1cl, Ankrd1, Asb15, Atp2c2, AU018091, AW822073, Btnl10, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps8l1, EU599041, Fam90a1a, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2al2a, Ido2, Igfbp1, Kif7, Klhl31, Lrrc31, Mc5r, Mgam, Msh4, Mucl2, Mug1, Mybl2, Myhl5, Nek10, Neurod6, Nr1h5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otogl, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Tregl, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Embodiment 135. The method of any one of embodiments 133-134, wherein the method comprises increasing expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otogl, Olfr943, Olfr1406, Olfr273, Olfr466, Olfr1043, Olfr427, Olfr890, Rbp4, or any combination thereof.

Embodiment 136. A method of reprogramming comprising altering the expression of one or more genes associated with ageing.

Embodiment 137. The method of embodiment 136, comprising increasing expression of OCT4, KLF4, SOX2, or any combination thereof.

Embodiment 138. The method of any one of embodiments 136-137, wherein the method rejuvenates the epigenetic clock of a cell, tissue, organ, subject, or any combination thereof.

Embodiment 139. The method of any one of embodiments embodiment 136-138, wherein the method comprises reducing expression of one or more genes associated with ageing.

Embodiment 140. The method of embodiment 139, wherein the method reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Ccl9, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnaja1-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galnt18, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg1l2, Hapln4, Hcn3, Hcn4, Hhatl, Hs6st2, Htr3a, Il1rap, Il1rapl2, Inka1, Kbtbd12, Kcnj11, Kcnk4, Kdelc2, Klhl33, Lamc3, Lilra5, Lman1l, Lrfn2, Lrrc38, Lrrn4cl, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec14l5, Sel1l3, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof.

Embodiment 141. The method of any one of embodiments 136-140, wherein the one or more genes is one or more sensory genes.

Embodiment 142. The method of any one of embodiments 136-140, wherein the gene is Ace, Kcnk4, Lamc3, Edn1, Syt10, Ngfr, Gprc5c, Cd36, Chrna4, Ednrb, Drd2, or a combination thereof.

Embodiment 143. The method of any one of embodiments embodiment 136-142, wherein the method comprises increasing expression of one or more genes associated with ageing.

Embodiment 144. The method of embodiment 143, wherein the method comprises increasing expression of 1700031P21Rik, 1810053B23Rik, 2900045020Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1cl, Ankrd1, Asb15, Atp2c2, AU018091, AW822073, Btnl10, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps8l1, EU599041, Fam90a1a, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2al2a, Ido2, Igfbp1, Kif7, Klhl31, Lrrc31, Mc5r, Mgam, Msh4, Mucl2, Mug1, Mybl2, Myhl5, Nek10, Neurod6, Nr1h5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otogl, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Embodiment 145. The method of embodiment 144, wherein the method comprises increasing expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otogl, Olfr943, Olfr1406, Olfr273, Olfr466, Olfr1043, Olfr427, Olfr890, Rbp4, or any combination thereof.

Embodiment 146. A method comprising resetting the transcriptional profile of old cells in vitro.

Embodiment 147. A method comprising resetting the transcriptional profile of old cells in vivo.

Embodiment 148. A method comprising inducing in a subject:
  (i) OCT4 expression;
  (ii) SOX2 expression; and/or
  (iii) KLF4 expression;
in the absence of inducing c-MYC expression, wherein the subject has, is at risk for, or is suspected of having a condition that increases the DNA methylation-based age of a cell, of a tissue, and/or of an organ within the subject, as compared to a control cell, a control tissue, and/or of a control organ of a control subject that does not have the condition.

Embodiment 149. The method of embodiment 148, wherein the method reduces the DNA methylation-based age of the cell, the tissue, the organ, and/or the subject.

Embodiment 150. A method of transdifferentiation comprising inducing in one type of cell:
  (i) OCT4 expression;
  (ii) SOX2 expression;
  (iii) KLF4 expression; and
  (iv) expression of a lineage determining factor,
wherein (i)-(iii) are expressed from a single vector, thereby transdifferentiating the cell into another cell type.

Embodiment 151. A method of transdifferentiation comprising inducing in a cell:
  (i) OCT4 expression;
  (ii) SOX2 expression; and
  (iii) KLF4 expression; and
reducing expression of a lineage determining factor, wherein (i)-(iii) are expressed from a single vector.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method of treating glaucoma in a subject in need thereof comprising administering to an eye of the subject an adeno-associated virus (AAV) vector comprising a polynucleotide encoding OCT4, SOX2, and KLF4 operably linked to a promoter, flanked by inverted terminal repeat sequence (ITR) sequences, wherein the vector does not encode c-Myc and does not encode Nanog.

2. The method of claim 1, wherein the vector is administered by intravitreal injection.

3. The method of claim 1, wherein the vector is administered by sub-retinal injection.

4. The method of claim 1, wherein the vector is an AAV2 vector.

5. The method of claim 1, wherein the vector is an AAV9 vector.

6. The method of claim 1, wherein the vector is an AAV.PHP.b vector.

7. The method of claim 1, wherein the promoter comprises a comprises a tetracycline response element (TRE).

8. The method of claim 7, wherein the promoter is a TRE3G promoter.

9. The method of claim 8, wherein the polynucleotide comprises nucleic acid elements in the following order:
   a. a first inverted terminal repeat sequence (ITR) sequence;
   b. a TRE3G promoter sequence;
   c. a multicistronic open reading frame encoding, in any order, OCT4, SOX2, and KLF4;
   d. an SV-40-derived terminator sequence; and
   e. a second inverted terminal repeat (ITR) sequence.

10. The method of claim 8, wherein the TRE3G promoter comprises a minimal CMV promoter sequence.

11. The method of claim 10, wherein the TRE3G promoter comprises a polynucleotide sequence at least 90% identical to SEQ ID NO: 7.

12. The method of claim 7, wherein the method further comprises administering a second AAV vector comprising a second polynucleotide encoding a reverse tetracycline transactivator (rtTA) operably linked to a promoter, flanked by inverted terminal repeat sequence (ITR) sequences; and administering a tetracycline.

13. The method of claim 1, wherein:
   i) OCT4 comprises an amino acid sequence having at least 90% identity to SEQ ID NO: 41;
   ii) SOX2 comprises an amino acid sequence having at least 90% identity to SEQ ID NO: 43; and
   iii) KLF4 comprises an amino acid sequence having at least 90% identity to SEQ ID NO: 45.

14. The method of claim 1, wherein:
   i) OCT4 comprises the amino acid sequence of SEQ ID NO: 41;
   ii) SOX2 comprises the amino acid sequence of SEQ ID NO: 43; and
   iii) KLF4 comprises the amino acid sequence of SEQ ID NO: 45.

15. The method of claim 1, wherein the polynucleotide comprises a polynucleotide sequence that is at least 90% identical to SEQ ID NO: 38 or a polynucleotide sequence that is at least 90% identical to SEQ ID NO: 121.

16. A method of rejuvenating an optic nerve in a subject in need thereof comprising administering to an eye of the subject an adeno-associated virus (AAV) vector comprising a polynucleotide encoding OCT4, SOX2, and KLF4 operably linked to a promoter, flanked by inverted terminal repeat sequence (ITR) sequences, wherein the vector does not encode c-Myc and does not encode Nanog.

17. The method of claim 16, wherein the vector is administered by intravitreal injection.

18. The method of claim 16, wherein the vector is administered by sub-retinal injection.

19. The method of claim 16, wherein the vector is an AAV2 vector.

20. The method of claim 16, wherein the vector is an AAV9 vector.

21. The method of claim 16, wherein the vector is an AAV.PHP.b vector.

22. The method of claim 16, wherein the promoter comprises a comprises a tetracycline response element (TRE).

23. The method of claim 22, wherein the promoter is a TRE3G promoter.

24. The method of claim 23, wherein the polynucleotide comprises nucleic acid elements in the following order:
   a. a first inverted terminal repeat sequence (ITR) sequence;
   b. a TRE3G promoter sequence;
   c. a multicistronic open reading frame encoding, in any order, OCT4, SOX2, and KLF4;
   d. an SV-40-derived terminator sequence; and
   e. a second inverted terminal repeat (ITR) sequence.

25. The method of claim 23, wherein the TRE3G promoter comprises a minimal CMV promoter sequence.

26. The method of claim 25, wherein the TRE3G promoter comprises a polynucleotide sequence at least 90% identical to SEQ ID NO: 7.

27. The method of claim 22, wherein the method further comprises administering a second AAV vector comprising a second polynucleotide encoding a reverse tetracycline transactivator (rtTA) operably linked to a promoter, flanked by inverted terminal repeat sequence (ITR) sequences; and administering a tetracycline.

28. The method of claim 16, wherein:
i) OCT4 comprises an amino acid sequence having at least 90% identity to SEQ ID NO: 41;
ii) SOX2 comprises an amino acid sequence having at least 90% identity to SEQ ID NO: 43; and
iii) KLF4 comprises an amino acid sequence having at least 90% identity to SEQ ID NO: 45.

29. The method of claim 16, wherein:
i) OCT4 comprises the amino acid sequence of SEQ ID NO: 41;
ii) SOX2 comprises the amino acid sequence of SEQ ID NO: 43; and
iii) KLF4 comprises the amino acid sequence of SEQ ID NO: 45.

30. The method of claim 16, wherein the polynucleotide comprises a polynucleotide sequence that is at least 90% identical to SEQ ID NO: 38 or a polynucleotide sequence that is at least 90% identical to SEQ ID NO: 121.

31. A method of treating damage to retinal ganglion cells in optic neuropathy in a subject in need thereof comprising administering to an eye of the subject an adeno-associated virus (AAV) vector comprising a polynucleotide encoding OCT4, SOX2, and KLF4 operably linked to a promoter, flanked by inverted terminal repeat sequence (ITR) sequences, wherein the vector does not encode c-Myc and does not encode Nanog.

32. A method of treating decline in retinal ganglion cell function in a subject suffering from age-related visual acuity loss comprising administering to an eye of the subject an adeno-associated virus (AAV) vector comprising a polynucleotide encoding OCT4, SOX2, and KLF4 operably linked to a promoter, flanked by inverted terminal repeat sequence (ITR) sequences, wherein the vector does not encode c-Myc and does not encode Nanog.

33. The method of claim 31 or 32, wherein the vector is administered by intravitreal injection.

34. The method of claim 31 or 32, wherein the vector is administered by sub-retinal injection.

35. The method of claim 31 or 32, wherein the vector is an AAV2 vector.

36. The method of claim 31 or 32, wherein the vector is an AAV9 vector.

37. The method of claim 31 or 32, wherein the vector is an AAV.PHP.b vector.

38. The method of claim 31 or 32, wherein the promoter comprises a comprises a tetracycline response element (TRE).

39. The method of claim 38, wherein the promoter is a TRE3G promoter.

40. The method of claim 39, wherein the polynucleotide comprises nucleic acid elements in the following order:
a. a first inverted terminal repeat sequence (ITR) sequence;
b. a TRE3G promoter sequence;
c. a multicistronic open reading frame encoding, in any order, OCT4, SOX2, and KLF4;
d. an SV-40-derived terminator sequence; and
e. a second inverted terminal repeat (ITR) sequence.

41. The method of claim 39, wherein the TRE3G promoter comprises a minimal CMV promoter sequence.

42. The method of claim 41, wherein the TRE3G promoter comprises a polynucleotide sequence at least 90% identical to SEQ ID NO: 7.

43. The method of claim 38, wherein the method further comprises administering a second AAV vector comprising a second polynucleotide encoding a reverse tetracycline transactivator (rtTA) operably linked to a promoter, flanked by inverted terminal repeat sequence (ITR) sequences; and administering a tetracycline.

44. The method of claim 31 or 32, wherein:
i) OCT4 comprises an amino acid sequence having at least 90% identity to SEQ ID NO: 41;
ii) SOX2 comprises an amino acid sequence having at least 90% identity to SEQ ID NO: 43; and
iii) KLF4 comprises an amino acid sequence having at least 90% identity to SEQ ID NO: 45.

45. The method of claim 44, wherein:
i) OCT4 comprises the amino acid sequence of SEQ ID NO: 41;
ii) SOX2 comprises the amino acid sequence of SEQ ID NO: 43; and
iii) KLF4 comprises the amino acid sequence of SEQ ID NO: 45.

46. The method of claim 31 or 32, wherein the polynucleotide comprises a polynucleotide sequence that is at least 90% identical to SEQ ID NO: 38 or a polynucleotide sequence that is at least 90% identical to SEQ ID NO: 121.

47. An adeno-associated virus (AAV) vector comprising a polynucleotide encoding OCT4, SOX2, and KLF4, flanked by inverted terminal repeats (ITRs), wherein the AAV vector does not encode c-Myc and does not encode Nanog, wherein the polynucleotide comprises nucleic acid elements in the following order:
a. a first inverted terminal repeat sequence (ITR) sequence;
b. a TRE3G promoter sequence;
c. a multicistronic open reading frame encoding, in any order, OCT4, SOX2, and KLF4;
d. an SV-40-derived terminator sequence; and
e. a second inverted terminal repeat (ITR) sequence.

48. The AAV vector of claim 47, wherein the AAV vector is an AAV2 vector.

49. The AAV vector of claim 47, wherein the AAV vector is an AAV9 vector.

50. The AAV vector of claim 47, wherein the AAV vector is an AAV.PHP.b vector.

51. The AAV vector of claim 47, wherein:
i) OCT4 comprises an amino acid sequence having at least 90% identity to SEQ ID NO: 41;
ii) SOX2 comprises an amino acid sequence having at least 90% identity to SEQ ID NO: 43; and
iii) KLF4 comprises an amino acid sequence having at least 90% identity to SEQ ID NO: 45.

52. The AAV vector of claim 51, wherein the AAV vector is an AAV2 vector.

53. The AAV vector of claim 51, wherein the AAV vector is an AAV9 vector.

54. The AAV vector of claim 51, wherein the AAV vector is an AAV.PHP.b vector.

55. The AAV vector of claim 47, wherein:
i) OCT4 comprises the amino acid sequence of SEQ ID NO: 41;
ii) SOX2 comprises the amino acid sequence of SEQ ID NO: 43; and
iii) KLF4 comprises the amino acid sequence of SEQ ID NO: 45.

56. The AAV vector of claim 55, wherein the AAV vector is an AAV2 vector.

57. The AAV vector of claim 55, wherein the AAV vector is an AAV9 vector.

58. The AAV vector of claim 55, wherein the AAV vector is an AAV.PHP.b vector.

59. The AAV vector of claim 47, wherein the AAV vector also does not encode homologs of c-Myc, and does not encode homologs of Nanog.

60. An adeno-associated virus (AAV) vector comprising a polynucleotide encoding OCT4, SOX2, and KLF4, but not c-Myc and not Nanog, the polynucleotide comprising nucleic acid elements in the following order:
   a. a first inverted terminal repeat sequence (ITR) sequence;
   b. a TRE3G promoter sequence;
   c. an OCT4 sequence;
   d. a P2A cleavage sequence;
   e. a SOX2 sequence;
   f. a T2A cleavage sequence;
   g. a KLF4 sequence;
   h. an SV-40-derived terminator sequence; and
   i. a second inverted terminal repeat (ITR) sequence.

61. The AAV vector of claim 60, wherein the AAV vector is an AAV2 vector.

62. The AAV vector of claim 60, wherein the AAV vector is an AAV9 vector.

63. The AAV vector of claim 60, wherein the AAV vector is an AAV.PHP.b vector.

64. The AAV vector of claim 60, wherein:
   i) OCT4 comprises an amino acid sequence having at least 90% identity to SEQ ID NO: 41;
   ii) SOX2 comprises an amino acid sequence having at least 90% identity to SEQ ID NO: 43; and
   iii) KLF4 comprises an amino acid sequence having at least 90% identity to SEQ ID NO: 45.

65. The AAV vector of claim 60, wherein:
   i) OCT4 comprises the amino acid sequence of SEQ ID NO: 41;
   ii) SOX2 comprises the amino acid sequence of SEQ ID NO: 43; and
   iii) KLF4 comprises the amino acid sequence of SEQ ID NO: 45.

66. The AAV vector of claim 60, wherein the AAV vector also does not encode homologs of c-Myc, and does not encode homologs of Nanog.

* * * * *

UNITED STATES PATENT AND TRADEMARK OFFICE
CERTIFICATE OF CORRECTION

PATENT NO. : 12,274,733 B2
APPLICATION NO. : 17/280384
DATED : April 15, 2025
INVENTOR(S) : David A. Sinclair et al.

It is certified that error appears in the above-identified patent and that said Letters Patent is hereby corrected as shown below:

On the Title Page

In item (60), Related U.S. Application Data, the text:
"Provisional application No. 62/880,448, filed on Jul. 30, 2019,"
Should be replaced with:
-- Provisional application No. 62/880,488, filed on Jul. 30, 2019, --.

In the Claims

In Claim 32, at Column 393, Line 38, the text:
"KLF4operably"
Should be replaced with:
-- KLF4 operably --.

In Claim 35, at Column 393, Line 47, the text:
"AAV2vector"
Should be replaced with:
-- AAV2 vector --.

In Claim 36, at Column 393, Line 49, the text:
"AAV9vector"
Should be replaced with:
-- AAV9 vector --.

In Claim 48, at Column 394, Line 43, the text:
"AAV2vector"
Should be replaced with:
-- AAV2 vector --.

Signed and Sealed this
Eighth Day of July, 2025

Coke Morgan Stewart
*Acting Director of the United States Patent and Trademark Office*

CERTIFICATE OF CORRECTION (continued)
U.S. Pat. No. 12,274,733 B2

In Claim 49, at Column 394, Line 45, the text:
"AAV9vector"
Should be replaced with:
-- AAV9 vector --.

In Claim 52, at Column 394, Line 56, the text:
"AAV2vector"
Should be replaced with:
-- AAV2 vector --.

In Claim 53, at Column 394, Line 58, the text:
"AAV9vector"
Should be replaced with:
-- AAV9 vector --.

In Claim 61, at Column 396, Line 2, the text:
"AAV2vector"
Should be replaced with:
-- AAV2 vector --.

In Claim 62, at Column 396, Line 4, the text:
"AAV9vector"
Should be replaced with:
-- AAV9 vector --.